(12) United States Patent
Bender et al.

(10) Patent No.: US 6,635,641 B2
(45) Date of Patent: Oct. 21, 2003

(54) AMIDE COMPOUNDS AND PHARMACEUTICAL COMPOSITIONS FOR INHIBITING PROTEIN KINASES, AND METHODS FOR THEIR USE

(75) Inventors: Steven Lee Bender, Oceanside, CA (US); Dilip Bhumralkar, San Diego, CA (US); Michael Raymond Collins, San Diego, CA (US); Stephen James Cripps, San Diego, CA (US); Judith Gail Deal, Wildomar, CA (US); Lei Jia, San Diego, CA (US); Mitchell David Nambu, San Diego, CA (US); Cynthia Louise Palmer, La Mesa, CA (US); Zhengwei Peng, San Diego, CA (US); Michael David Varney, Solana Beach, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/764,306

(22) Filed: Jan. 19, 2001

(65) Prior Publication Data

US 2002/0103203 A1 Aug. 1, 2002

Related U.S. Application Data

(60) Provisional application No. 60/177,059, filed on Jan. 21, 2000.

(51) Int. Cl.[7] .................. C07D 241/18; C07D 403/12; A61K 31/497; A61K 31/4965

(52) U.S. Cl. ................ 514/247; 544/224; 544/238; 544/408; 544/410; 544/236; 544/237; 544/353; 544/354; 514/252.01; 514/248; 514/255.05; 514/252.1; 548/263.2; 548/366.1; 548/375; 546/139; 546/141; 546/153; 546/181; 546/329; 546/339; 546/345; 546/118; 546/119

(58) Field of Search .................. 544/224, 238, 544/408, 410, 236, 237, 353, 354; 514/252.01, 248, 247, 255.05, 252.1; 548/263.2, 366.1, 375; 546/139, 141, 149, 153, 181, 329, 339, 345, 118, 119

(56) References Cited

U.S. PATENT DOCUMENTS

| | | | |
|---|---|---|---|
| 3,862,958 A | 1/1975 | Ruechardt et al. | 534/558 |
| 4,500,340 A | 2/1985 | Becker et al. | 504/263 |
| 4,826,987 A | 5/1989 | Nielsen et al. | 546/152 |
| 5,612,360 A | 3/1997 | Boyd et al. | 514/303 |
| 5,621,082 A | 4/1997 | Xiong et al. | 435/194 |
| 5,733,920 A | 3/1998 | Mansuri et al. | 514/252.02 |
| 6,020,336 A | 2/2000 | Lavielle et al. | 514/252.11 |
| 6,046,205 A | 4/2000 | Lavielle et al. | 514/255.05 |

FOREIGN PATENT DOCUMENTS

| | | |
|---|---|---|
| EP | 0666 270 A2 | 8/1995 |
| EP | 0 731 385 | 9/1996 |
| EP | 0 731 385 | 11/1996 |
| EP | 0767172 | 4/1997 |
| EP | 0 767 172 | 4/1997 |
| JP | 63030563 A2 | 2/1998 |
| WO | WO 94/14780 | 7/1994 |
| WO | WO 96/14843 | 5/1996 |
| WO | WO 96/23783 | 8/1996 |

(List continued on next page.)

OTHER PUBLICATIONS

Merenmies, J., Parada, L.F., Henkemeyer, M., Cell Growth & Differentiation, 8, 3–10 (1997).
Folkman, Nature Med., 1, 27–31 (1995).

(List continued on next page.)

*Primary Examiner*—Mukund J. Shah
*Assistant Examiner*—Kahsay Habte
(74) *Attorney, Agent, or Firm*—Joseph F. Reidy; Bryan C. Zielinski; Peter C. Richardson

(57) ABSTRACT

Amide compounds represented by the formula:

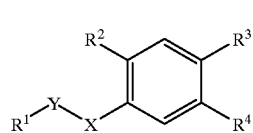

I wherein:

$R^1$ is a moiety represented by the formula

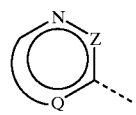

where X is selected from the group consisting of $CH_2$, O, S, and NH; and Y is selected from the group consisting of $CH_2$, O, and S, provided that at least one of X and Y is $CH_2$, or X and Y together with the bond there-between form a cyclopropyl; are described. These compounds and pharmaceutical compositions containing them modulate and/or inhibit the activity of certain protein kinases and are capable of mediating tyrosine kinase signal transduction in order to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, neovascular glaucoma, rheumatoid arthritis, and psoriasis, by administering effective amounts of such compounds.

11 Claims, No Drawings

FOREIGN PATENT DOCUMENTS

| WO | WO 96/30015 | 10/1996 |
|---|---|---|
| WO | WO 97/03967 | 2/1997 |
| WO | WO 97/16447 | 5/1997 |
| WO | WO 97/34876 | 9/1997 |
| WO | WO 97/42949 | 11/1997 |
| WO | WO 98/03487 | 1/1998 |
| WO | WO 98/17662 | 4/1998 |
| WO | WO 98/33798 | 6/1998 |
| WO | WO 98/38168 | 9/1998 |
| WO | WO 99/02162 | 1/1999 |
| WO | WO 99/15500 | 4/1999 |
| WO | WO 99/17769 | 4/1999 |
| WO | WO 99/21845 | 5/1999 |
| WO | WO 99/23077 | 5/1999 |
| WO | WO 99/24416 | 5/1999 |
| WO | WO 99/06540 | 7/1999 |
| WO | WO 99/43663 | 9/1999 |
| WO | WO 99/43675 | 9/1999 |
| WO | WO 99/43676 | 9/1999 |
| WO | WO 99/59959 | 11/1999 |

OTHER PUBLICATIONS

Strawn et al., Cancer Research, 56, 3540–3545 (1996).
Lin et al., J. Med. Chem., 15 (6), 615–618, 1972.
Rosowsky et al., J. Med. Chem., vol. 31, 763–768, 1988.
Millauer et al., Cancer Research, 56, 1615–1620 (1996).
Yoshiji et al., Cancer Research, 57, 3924–3928 (1997).
Mohammad et al., EMBO Journal, 17, 5896–5904 (1998).
Maisonpierre et al., Science, 277, 55–60 (1997).
Science, 274, 1643–1677 (1996).
Hall et al., Adv. Cancer Res., 68, 67–108 (1996).
Kamb, Trends in Genetics, 11, 136–140 (1995).
Kamb et al., Science, 264, 436–440 (1994).
Webster, Exp. Opin. Invest. Drugs, 7, 865–887 (1998).
Stover, et al., Curr. Opin. Drug Disc. Dev. 2, 274–285 (1999).
Gray et al., Curr. Med. Chem., 6, 859–875 (1999).
Sielecki, et al., J. Med. Chem., 43, 1–18 (2000).
Crews, et al., Curr. Opin. Chem Biol., 4, 47–53 (2000).
Buolamwini, Curr. Pharm. Des., 6, 379–392 (2000).
Rosania, et al., Exp. Opin. Ther. Pat., 10, 215–230 (2000).
O'Connor, Cancer Surveys, 29, 151–182 (1997).
Nurse, Cell, 91, 865–867 (1997).
Hartwell et al. Science, 266, 1821–1828 (1994).
Hartwell et al., Science, 246, 629–634 (1989).
Bunz et al., Science, 28, 1497–1501 (1998).
Winters et al., Oncogene, 17, 673–684 (1998).
Thompson, Oncogene, 15, 3025–3035 (1997).
Peng et al. Science, 277, 1501–1505 (1997).
Sanchez et al., Science, 277, 1497–1501.
Weinert, Science, 277, 1450–1451 (1997.
Walworth et al., Nataure, 363, 368–371 (1993).
Al–Khodairy et al., Molec. Biol. Cell, 5, 147–160 (1994).
Zeng, et al., Nature, 395, 507–510 (1998).
Matsuoka, Science, 282, 1893–1897 (1998).
Bolen, Oncogene, 8, 2025–2031 (1993).
McMahon et al., Current Opinion in Drug Discovery & Development, 1, 131–146 (1998).
Strawn et al., Exp. Opin. Invest. Drugs, 7, 553–573 (1998).
Adams et al., Curr. Opin, Drug Disc. Dev., 2, 96–109 (1999).
Toledo et al., Curr. Med. Chem., 6, 775–805 (1999).
Garcia–Echeverria, et al., Med. Res. Rev., 20, 28–57 (2000).
Bertolini et al., J. Med. Chem., 40, 2011–2016 (1997).
Shan, et al., J. Pharm. Sci., 86 (7), 765–767.
Bagshawe, Drug Dev. Res., 34, 220–230 (1995).
Bodor, Advances in Drug Res., 13, 224–331 (1984).
Bundgaard, Design of Prodrugs (Elsevier Press 1985).
Larsen, Design and Application of Prodrugs, drug Design and Development (Krogsgaard–Larsen et al., eds., Harwood Academic Publishers, 1991).
Lee et al., Biochem, 23, 4255 (1984).
Parast C. et al., BioChemistry, 34, 16788–16801 (1998).
Jeffrey et al., Nature, 376, 313–320 (1995).
Still et al., J. Org. Chem., 43, 2923 (1978).
J. Am. Chem. Soc. 120, 9722–23 (1998).
Forbes, et al., J. Med. Chem., 38, 2525 (1995).
J. Med. Chem., 40, 2866–2875 (1997).
Trova, M.P. et al., J. Med. Chem., 36, 580–590 (1993).
Mohammadi et al., Mol. Cell, Biol., 16, 977–989 (1996).
Rosenblatt et al., J. Mol. Biol., 230, 1317–1319 (1993).
Schang et al., J. Virol. 74, 2107–2120 (2000).
Braun–Dullaeus et al., Circulation, 98, 82–89 (1998).
Taniguchi et al., Nature Med., 5, 760–767 (1999).
Ann. Rev. Cell Dev. Biol., vol. 13, pp. 261–291 (1997).
Lukas et al., Genes and Dev., vol. 11, pp. 1479–1492 (1997).
Harper, Cancer Surv., vol. 29, pp. 91–107 (1997).
DelSal et al., Critical Rev. Oncogenesis, vol. 71, pp. 127–142 (1996).
Nobori et al., Nature, vol. 368, pp. 753–775 (1994).
Loda et al., Nature Medicine, vol. 3 (1997), pp. 231–234.
Sherr, et al., Genes Dev., vol. 13 (1999), pp. 1501–1512.
Bandara, et al., Nature Biotechnology, vol. 15 (1997), pp. 896–901.
Chen, et al., Proceedings of the National Academy of Science, USA, vol. 96 (1999) pp. 4325–4329.
Cohen, et al., Proc. Natl. Acad. Sci. U.S.A., vol. 95 (1998), pp. 14272–14277.
Sedlacek et al., Int. J. Oncol., vol. 9 (1996), pp. 1143–1168.
Schow et al., Bioorg. Med. Chem. Lett., vol. 7 (1997), pp. 2697–2702.
Grant et al., Proc. Amer. Assoc. Cancer Res., vol. 39 (1998), Abst. 1207.
Legravend et al., Bioorg. Med. Chem. Lett., vol. 8 (1998), pp. 793–798.
Gray et al., Science, vol. 281 (1998), pp. 533–538.
Chang, et al., Chemistry & Biology, vol. 6 (1999), pp. 361–375.
Ruetz et al., Proc. Amer. Assoc. Cancer Res., vol. 39 (1998), Abst. 3794.
Meyer et al., Proc. Amer. Assoc. Cancer Res., vol. 39 (1998), Abst. 3794.
Owa, et al., J. Med. Chem., vol. 42 (1999), pp. 3789–3799.
Luzzio, et all, Proc. Amer. Assoc. Cancer Res., vol. (1999), Abst. 4102.
Schultz, et al., J. Med. Chem. vol. (1999), pp. 2909–2919.
Seitz, et al., 218th ACS Natl. Mtg. (Aug. 22–26, 1999, New Orleans), Abst MEDI 316.
International Search Report from the European Patent Office for PCT Patent Application No. PCT/US01/01723, issued the EPO on Jun. 12, 2001.
Rosania, "Targeting hyperproliferative disorders with cyclin dependent kinase inhibitors" Exp. Opin. Ther. Pat., 10 (2): pp. 215–230 (2000).
Crews, "Small–molecule inhibitors of the cell cycle," Curr. Opin. Chem. Bio., 4: pp. 47–53 (2000).

Adams, "Recent progress towards the identification of selective inhibitors of serine/threonine protein kinases", *Curr. Opin. Drug Disc. Dev.* 2 (2): pp. 96–109 (1999).

Buolamwini, "Cell Cycle Molecular Targets in Novel Anticancer Drug Discovery," *Curr. Pharm. Design*, 6: pp. 379–392 (2000).

Toledo, L. "The Structure–Based Design of ATP–Site Directed Protein Kinase Inhibitors", *Current Medicinal Chemistry*, 6, pp. 775–805 (1999).

Rosowsky, "Methotrexate Analogues. 31. Meta and Ortho Isomer of Aminopterin, Compounds with a Double Bond in the Side Chain, and a Novel Analogue Modified at the α–Carbon: Chemical and in Vitro Biological Studies", *J. Med. Chem.*, 31 pp. 763–768 (1988).

Lin, "Potential Antitumor Agents. Derivatives of 3– and 5–Benzyloxy–2–formylpyridine Thiosemicarbazone", *J. Med. Chem.*, 15 (6), pp. 615–618 (1972).

De Sal, "Cell Cycle and Cancer: Critical Events at the G1 Restriction Point" *Critical Reviews in Oncogensis*, 7 (1&2): 127–142 (1996).

Walworth, "Fission yeast chk1 protein kinase links the rad checkpoint pathway to cdc2" *Nature*, 363: pp. 368–371 (1993).

Stover, "Recent advances in protein kinase inhibition: Current molecular scaffolds used for inhibitors synthesis" *Curr. Opin. Drug Disc. Dev.* vol. 2, No. 4: 274–285 (1999).

AMIDE COMPOUNDS AND PHARMACEUTICAL COMPOSITIONS FOR INHIBITING PROTEIN KINASES, AND METHODS FOR THEIR USE

This applications claims the benefit of U.S. Provisional Application Ser. No. 60/177,059, filed Jan. 21, 2000, the contents of which are hereby incorporated by reference herein.

FIELD OF THE INVENTION

This invention is directed to amide compounds that mediate and/or inhibit the activity of certain protein kinases, and to pharmaceutical compositions containing such compounds. The invention is also directed to the therapeutic or prophylactic use of such compounds and compositions, and to methods of treating cancer as well as other disease states associated with unwanted angiogenesis and/or cellular proliferation, by administering effective amounts of such compounds.

BACKGROUND OF THE INVENTION

Protein kinases are a family of enzymes that catalyze phosphorylation of the hydroxyl group of specific tyrosine, serine, or threonine residues in proteins. Typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are angiogenesis and cell-cycle control, in which protein kinases play a pivotal role; these processes are essential for the growth of solid tumors as well as for other diseases.

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies, J., Parada, L. F., Henkemeyer, M., *Cell Growth & Differentiation*, 8, 3–10 (1997). On the other hand, unwanted angiogenesis is a hallmark of several diseases, such as retinopathies, psoriasis, rheumatoid arthritis, age-related macular degeneneration, and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

VEGF-R2, which is selectively expressed on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924–3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17, 5996–5904 (1998).

TEK (also known as Tie-2) is another receptor tyrosine kinase selectively expressed on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation. Two documents described hereinafter disclose certain amide derivatives but do not disclose or teach that any of the compounds may be used for modulating or inhibiting the activity of protein kinases: WIPO International Publication No. WO 97/03967; and WIPO International Publication No. WO 96/23783.

In addition to its role in angiogenesis, protein kinases also play a crucial role in cell-cycle control. Uncontrolled cell proliferation is the insignia of cancer. Cell proliferation in response to various stimuli is manifested by a de-regulation of the cell division cycle, the process by which cells multiply and divide. Tumor cells typically have damage to the genes that directly or indirectly regulate progression through the cell division cycle.

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. See, e.g., the articles compiled in *Science*, 274, 1643–1677 (1996). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell-cycle.

It is CDK4 complexed to the D cyclins that plays a critical part in initiating the cell-division cycle from a resting or quiescent stage to one in which cells become committed to cell division. This progression is subject to a variety of growth regulatory mechanisms, both negative and positive. Aberrations in this control system, particularly those that affect the function of CDK4, have been implicated in the advancement of cells to the highly proliferative state characteristic of malignancies, particularly familial melanomas, esophageal carcinomas, and pancreatic cancers. See, e.g., Hall et al., *Adv. Cancer Res.,* 68, 67–108 (1996); Kamb, *Trends in Genetics,* 11, 136–140 (1995); Kamb et al., *Science,* 264, 436–440 (1994).

A large number of small molecule ATP-site antagonists have been identified as CDK inhibitors. (See, Webster, *Exp. Opin. Invest. Drugs,* 7, 865–887 (1998), Stover, Et al., *Curr. Opin. Drug Disc. Dev.,* 2, 274–285(1999), Gray et al., *Curr. Med. Chem.,* 6, 859–875 (1999), Sielecki, et al., *J. Med. Chem.,* 43, 1–18 (2000), Crews, et al., *Curr. Opin. Chem. Biol.,* 4, 47–53 (2000), Buolamwini, *Curr.Pharm. Des.,* 6, 379–392 (2000), and Rosania, et al., *Exp. Opin. Ther. Pat.,* 10, 215–230 (2000)). Moreover, the use of compounds as anti-proliferative therapeutic agents that inhibit CDKs is the subject of several patents and publications. For example, U.S. Pat. No. 5,621,082 to Xiong et al., discloses nucleic acid encoding an inhibitor of CDK6 and European Patent Publication No. 0 666 270 A2 describes peptides and peptide mimetics that act as inhibitors of CDK1 and CDK2. WIPO International Publication No. WO 97/16447 discloses certain analogs of chromones that are inhibitors of cyclin-dependent kinases, in particular of CDK/cyclin complexes such as CDK4/cyclin D1, which may be used for inhibiting excessive or abnormal cell proliferation, and therefore for treating cancer. WIPO International Publication No. WO 99/21845 describes 4-aminothiazole derivatives that are useful as CDK inhibitors.

There is still a need, however, for small-molecule compounds that may be readily synthesized and are effective in inhibiting one or more CDKs or CDK/cyclin complexes. Because CDK4 may serve as a general activator of cell division in most cells, and complexes of CDK4 and D-type cyclins govern the early $G_1$ phase of the cell-cycle, there is a need for effective inhibitors of CDK4, and D-type cyclin complexes thereof, for treating one or more types of tumors. Also, the pivotal roles of cyclin E/CDK2 and cyclin B/CDK1 kinases in the G1/S phase and G2/M transitions, respectively offer additional targets for therapeutic intervention in suppressing deregulated cell-cycle progression in cancer.

Another protein kinase, CHK-1, plays an important role as a checkpoint in cell-cycle progression. Checkpoints are control systems that coordinate cell-cycle progression by influencing the formation, activation and subsequent inactivation of the cyclin-dependent kinases. Checkpoints prevent cell-cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys,* 29, 151–182 (1997); Nurse, *Cell,* 91, 865–867 (1997); Hartwell et al., *Science,* 266, 1821–1828 (1994); Hartwell et al., *Science,* 246, 629–634 (1989).

One series of checkpoints monitors the integrity of the genome and, upon sensing DNA damage, these "DNA damage checkpoints" block cell-cycle progression in $G_1$ & $G_2$ phases, and slow progression through S phase. O'Connor, *Cancer Surveys,* 29, 151–182 (1997); Hartwell et al., *Science,* 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell-cycle progression in $G_1$ phase and/or induces apoptosis (programmed cell death) following DNA damage. Hartwell et al., *Science,* 266, 1821–1828 (1994). The p53 tumor suppressor has also been shown to strengthen the action of a DNA damage checkpoint in $G_2$ phase of the cell-cycle. See, e.g., Bunz et al., *Science,* 28, 1497–1501 (1998); Winters et al., *Oncogene,* 17, 673–684 (1998); Thompson, *Oncogene,* 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer killing effects of DNA-damaging agents: the $G_2$ checkpoint. The $G_2$ checkpoint is regulated by a control system that has been conserved from yeast to humans. Important in this conserved system is a kinase, CHK-1, which transduces signals from the DNA-damage sensory complex to inhibit activation of the cyclin B/Cdc2 kinase, which promotes mitotic entry. See, e.g., Peng et al., *Science,* 277, 1501–1505 (1997); Sanchez et al., *Science,* 277, 1497–1501 (1997). Inactivation of CHK-1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell,* 91, 865–867 (1997); Weinert, *Science,* 277, 1450–1451 (1997); Walworth et al., *Nature,* 363, 368–371 (1993); and Al-Khodairy et al., *Molec. Biol. Cell,* 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK-1 as a pivotal target in DNA-damage checkpoint control. The elucidation of inhibitors of this and functionally related kinases such as Cds1/CHK-2, a kinase recently discovered to cooperate with CHK-1 in regulating S phase progression (see Zeng et al., *Nature,* 395, 507–510 (1998); Matsuoka, *Science,* 282, 1893–1897 (1998)), could provide valuable new therapeutic entities for the treatment of cancer.

Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene,* 8, 2025–2031 (1993), which is incorporated herein by reference.

In addition to the protein kinases identified above, many other protein kinases have been considered to be therapeutic targets, and numerous publications disclose inhibitors of kinase activity, as reviewed in the following: McMahon et al., *Current Opinion in Drug Discovery & Development*, 1, 131–146 (1998); Strawn et al., *Exp. Opin. Invest. Drugs*, 7, 553–573 (1998); Adams et al., *Curr. Opin. Drug Disc. Dev.*, 2, 96–109 (1999), Stover et al., *Curr. Opin. Drug Disc. Dev.*, 2, 274–285 (1999), Toledo et al., *Curr. Med. Chem.*, 6, 775–805 (1999), and García-Echeverría, et al., *Med. Res. Rev.*, 20, 28–57 (2000).

There is still a need, however, for effective inhibitors of protein kinases. Moreover, as is well understood by those skilled in the art, it is desirable for kinase inhibitors to possess both high affinity for the target kinase as well as high selectivity versus other protein kinases.

SUMMARY OF THE INVENTION

Thus, an objective of the invention is to provide potent inhibitors of protein kinases. Another objective of the invention is to provide effective kinase inhibitors having a strong and selective affinity for a particular kinase.

These and other objectives of the invention, which will become apparent from the following description, have been achieved by the discovery of amide compounds, pharmaceutically acceptable prodrugs, pharmaceutically active metabolites, and pharmaceutically acceptable salts thereof (such compounds, prodrugs, metabolites and salts are collectively referred to as "agents") described below, which modulate and/or inhibit the activity of protein kinases.

Pharmaceutical compositions containing such agents are useful in treating various diseases and disorders associated with uncontrolled or unwanted angiogenesis and/or cellular proliferation, such as cancer, autoimmune diseases, viral diseases, fungal diseases, neurodegenerative disorders and cardiovascular diseases. Thus, pharmaceutical compositions containing such agents are useful in the treatment of diabetic retinopathy, neovascular glaucoma, rheumatoid arthritis, and psoriasis.

Further, the agents have advantageous properties relating to modulation and/or inhibition of the kinase activity associated with VEGF-R, FGF-R, CDK complexes (e.g., CDK1, CDK2, CDK4 and CDK6), CHK-1, TEK, and LCK. Thus, pharmaceutical compositions containing such agents are useful in the treatment of diseases and disorders mediated by kinase activity, such as cancer.

In a general aspect, the invention relates to compounds represented by the Formula I:

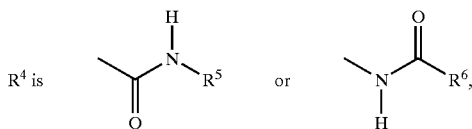

I wherein:
$R^1$ is a moiety of the formula

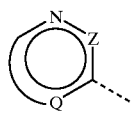

where
Z is CH or NH, and Q is a moiety such that $R^1$ is a substituted or unsubstituted monocyclic or bicyclic heteroaryl which has at least two carbon atoms in the heteroaryl ring system;

X is selected from $CH_2$, O, S, and NH;

Y is selected from $CH_2$, O, and S, provided that at least one of X and Y is $CH_2$, or X and Y together with the bond there-between form a cyclopropyl;

$R^2$ and $R^3$ are independently selected from hydrogen, methyl, halogen, trifluoromethyl, and cyano; and

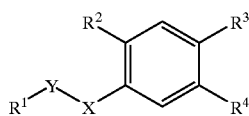

$R^4$ is where $R^5$ is a substituted or unsubstituted aryl, heteroaryl, cycloalkyl, heterocycloalkyl, O—$R^7$, $NR^8R^9$, $C_1$–$C_8$ alkyl, or monocyclic heterocycloalkyl group, $R^6$ is a substituted or unsubstituted aryl, heteroaryl, cycloalkyl, heterocycloalkyl, alkenyl, O—$R^7$, C(O)$R^7$, $NR^8R^9$, $C_2$–$C_8$ alkyl, or monocyclic heterocycloalkyl group, where $R^7$ is a substituted or unsubstituted alkyl, cycloalkyl, heterocycloalkyl, aryl, or heteroaryl, $R^8$ is hydrogen or a substituted or unsubstituted alkyl, and $R^9$ is a substituted or unsubstituted alkyl, aryl, heteroaryl, cycloalkyl, or heterocycloalkyl.

The invention is also directed to pharmaceutically acceptable prodrugs, pharmaceutically active metabolites, and pharmaceutically acceptable salts of the compounds of Formula I. Pharmaceutically acceptable salts of such active metabolites are also provided. Advantageous methods of making the compounds of the Formula I are also described.

In a preferred general embodiment, the invention relates to compounds of the Formula I wherein $R^1$ is a substituted or unsubstituted heteroaryl group selected from:

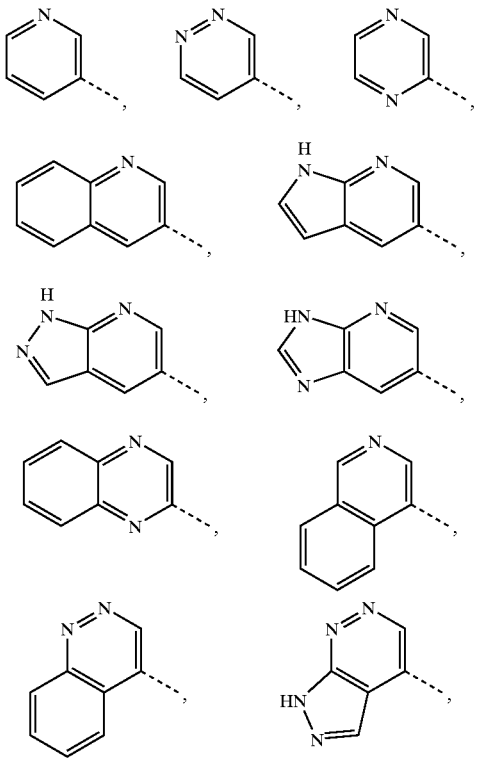

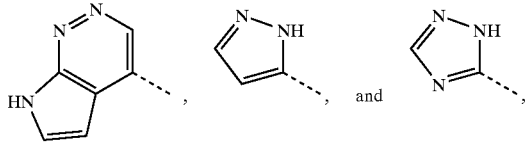

where

X is selected from CH$_2$, O, and S;

Y is selected from CH$_2$ and S, provided that at least one of X and Y is CH$_2$;

R$^2$ and R$^3$ are independently selected from hydrogen, methyl, fluorine, and chlorine; and

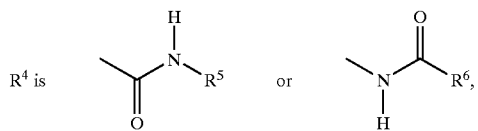

where R$^5$ is a substituted or unsubstituted aryl, heteroaryl, cycloalkyl, heterocycloalkyl, O—R$^7$, NR$^8$R$^9$, C$_1$–C$_8$ alkyl, or monocyclic heterocycloalkyl group, R$^6$ is a substituted or unsubstituted aryl, heteroaryl, cycloalkyl, heterocycloalkyl, alkenyl, O—R$^7$, C(O)R$^7$, NR$^8$R$^9$, C$_2$–C$_8$ alkyl, or monocyclic heterocycloalkyl group, where R$^7$ is a substituted or unsubstituted alkyl, cycloalkyl, heterocycloalkyl, aryl, or heteroaryl, R$^8$ is hydrogen or a substituted or unsubstituted alkyl, and R$^9$ is a substituted or unsubstituted alkyl, aryl, heteroaryl, cycloalkyl, or heterocycloalkyl.

Especially preferred are compounds represented by the Formula II:

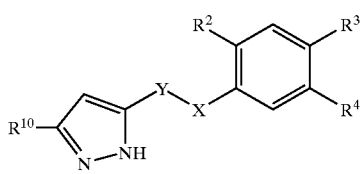

wherein:

X is selected from CH$_2$, O and S;

Y is selected from CH$_2$ and S, provided that at least one of X and Y is CH$_2$;

R$^2$ and R$^3$ are independently selected from hydrogen, methyl, fluorine, and chlorine;

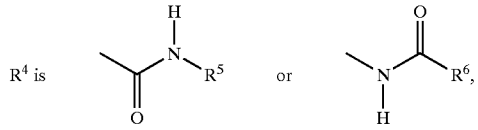

where R$^5$ and R$^6$ are each independently a substituted or unsubstituted aryl or heteroaryl; and R$^{10}$ is a substituted or unsubstituted alkenyl, aryl, heteroaryl, or NHR$^9$, where R$^9$ is a substituted or unsubstituted alkyl, aryl, heteroaryl, cycloalkyl, or heterocycloalkyl.

In another embodiment, the present invention is directed to compounds represented by the Formula III:

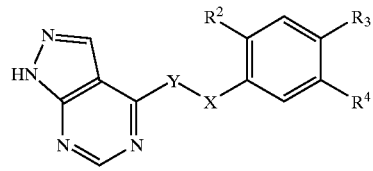

wherein:

X is selected from CH$_2$, O, S, and NH;

Y is selected from CH$_2$, O, and S, provided that at least one of X and Y is CH$_2$, or X and Y together with the bond there-between form a cyclopropyl;

R$^2$ and R$^3$ are independently selected from hydrogen, methyl, halogen, trifluoromethyl, and cyano; and

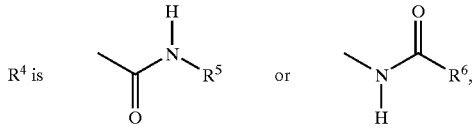

where R$^5$ is a substituted or unsubstituted aryl, heteroaryl, cycloalkyl, heterocycloalkyl, O—R$^7$, NR$^8$R$^9$, C$_1$–C$_8$ alkyl, or monocyclic heterocycloalkyl group, R$^6$ is a substituted or unsubstituted aryl, heteroaryl, cycloalkyl, heterocycloalkyl, alkenyl, O—R$^7$, C(O)R$^7$, NR$^8$R$^9$, C$_2$–C$_8$ alkyl, or monocyclic heterocycloalkyl group, where R$^7$ is a substituted or unsubstituted alkyl, cycloalkyl, heterocycloalkyl, aryl, or heteroaryl, R$^8$ is hydrogen or a substituted or unsubstituted alkyl, and R$^9$ is a substituted or unsubstituted alkyl, aryl, heteroaryl, cycloalkyl, or heterocycloalkyl; and pharmaceutically acceptable salts thereof and pharmaceutically acceptable prodrugs thereof.

In preferred embodiments of compounds of Formula III:

X is selected from CH$_2$, O, and S;

Y is selected from CH$_2$ and S, provided that at least one of X and Y is CH$_2$;

R$^2$ and R$^3$ are independently selected from hydrogen, methyl, fluorine, and chlorine; and

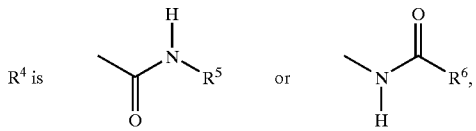

where R$^5$ and R$^6$ are each independently a substituted or unsubstituted aryl or heteroaryl.

Especially preferred are compounds represented by the Formula III, wherein:

X is CH$_2$;

Y is S;

R$^2$ and R$^3$ are independently selected from hydrogen, methyl, fluorine, and chlorine; and

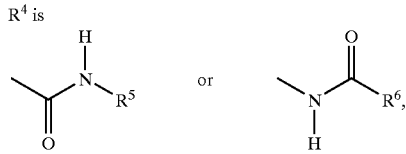

where R$^5$ and R$^6$ are each independently a substituted or unsubstituted aryl or heteroaryl.

The invention also relates to a method of modulating and/or inhibiting the kinase activity of VEGF-R, FGF-R, a CDK complex, CHK-1, TEK, and/or LCK by administering a compound of the Formula I, II, or III, or a pharmaceutically acceptable prodrug, pharmaceutically active metabolites, or pharmaceutically acceptable salt thereof. Preferably, compounds of the present invention have selective kinase activity—i.e., they possess significant activity against one specific kinase while possessing less or minimal activity against a different kinase. In one preferred embodiment of the invention, compounds of the present invention are those of Formula I, II, or III, possessing substantially higher potency against VEGF receptor tyrosine kinase than against LCK receptor tyrosine kinase. The invention is also directed to methods of modulating VEGF receptor tyrosine kinase activity without significantly modulating LCK receptor tyrosine kinase activity.

The invention also relates to pharmaceutical compositions each comprising: an effective amount of an agent selected from compounds of the Formula I, II, and III, and pharmaceutically acceptable salts, pharmaceutically active metabolites, and pharmaceutically acceptable prodrugs thereof; and a pharmaceutically acceptable carrier or vehicle for such agent.

The invention further provides methods of treating cancer as well as other disease states associated with unwanted angiogenesis and/or cellular proliferation, comprising administering effective amounts of such agents to a patient in need of such treatment.

DETAILED DESCRIPTION OF THE INVENTION AND PREFERRED EMBODIMENTS

The inventive compounds of the Formula I, II, and III are useful for mediating the activity of protein kinases. More particularly, the compounds are useful as anti-angiogenesis agents and as agents for modulating and/or inhibiting the activity of protein kinases, thus providing treatments for cancer or other diseases associated with cellular proliferation mediated by protein kinases.

The term "alkyl" as used herein refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like. The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "cycloalkyl" refers to saturated or unsaturated carbocycles having from three to twelve carbon atoms, including bicyclic and tricyclic cycloalkyl structures. Suitable cycloalkyls include cyclopropyl, cyclobutyl, cyclopentyl, cyclohexyl, cycloheptyl, and the like.

A "heterocycloalkyl" group is intended to mean a saturated or unsaturated monocyclic radical containing carbon atoms, preferably 4 or 5 ring carbon atoms, and at least one heteroatom selected from nitrogen, oxygen and sulfur.

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by one or more suitable substituents, for example, a substituent selected from a halogen (F, Cl, Br or I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

The term "alkoxy" is intended to mean the radical —O-alkyl. Illustrative examples include methoxy, ethoxy, propoxy, and the like.

The term "halogen" represents chlorine, fluorine, bromine or iodine. The term "halo" represents chloro, fluoro, bromo or iodo.

In general, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, —aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

It is understood that compounds of Formula I, II, and III may exhibit the phenomenon of tautomerism and that the formula drawings within this specification can represent only one of the possible tautomeric forms. It is to be understood that the invention encompasses any tautomeric form which modulates and/or inhibits kinase activity and is not to be limited merely to any one tautomeric form utilized within the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of the Formula I, II, and III, the invention includes pharmaceutically acceptable prodrugs, pharmaceutically active metabolites, and pharmaceutically acceptable salts of such compounds. Pharmaceutically active salts of such active metabolites are also included.

The term "pharmaceutically acceptable" means pharmacologically acceptable and substantially non-toxic to the subject being administered the cell-cycle control agent.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. See, e.g., Bertolini et al., J. Med. Chem., 40, 2011–2016 (1997); Shan, et al., J. Pharm. Sci., 86 (7), 765–767; Bagshawe, Drug Dev. Res., 34, 220–230 (1995); Bodor, Advances in Drug Res., 13, 224–331 (1984); Bundgaard, Design of Prodrugs (Elsevier Press 1985); and Larsen, Design and Application of Prodrugs, Drug Design and Development (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydrozy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tyrosine kinases. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available.

Compounds of formula I where $R^4$ is $CONHR^5$ may be prepared as shown in Scheme 1.

Scheme 1

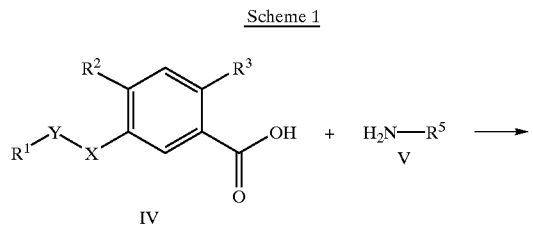

IV

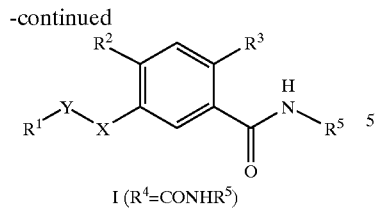

I (R⁴=CONHR⁵)

As sown in Scheme 1, carboxylic acids of formula IV are coupled to amines of formula V to give compounds of formula I (R⁴=CONHR⁵). The coupling may be carried out employing various peptide coupling reagents, for example 1-ethyl-3-(3'-dimethylaminopropyl)carbodiimide HCl (EDC), O-(7-azabenzotriazol-1-yl)-N,N,N',N'-tetramethyluronium hexafluorophosphate (HATU), or benzotriazole-1-yl-oxy-tris-pyrrolidino-phosphonium hexafluorophosphate (pyBop), in polar aprotic solvents, such as N,N-dimethylforamide (DMF) or dichloromethane. Alternatively, the acid IV may be first converted to an acid chloride by treatment with, for example, oxalyl chloride or thionyl chloride, and then, without purification, reacted with amines of formula V to give compounds of formula I (R⁴=CONHR⁵).

Compounds of formula I where $R^4$ is $NHCOR^6$ may be prepared as shown in Scheme 2.

Scheme 2

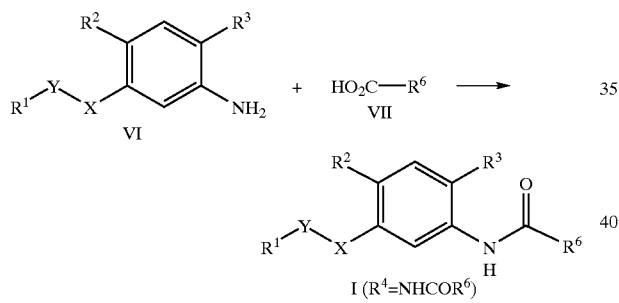

I (R⁴=NHCOR⁶)

Carboxylic acids of formula VII are coupled to amines of formula VI to give compounds of formula I (R⁴=NHCOR⁶). The coupling may be carried out employing with various peptide coupling reagents, for example EDC, HATU, or pyBOP, in polar aprotic solvents, such as DMF or dichloromethane. Alternatively, the acid VII may be first converted to an acid chloride by treatment with, for example, oxalyl chloride or thionyl chloride, and then, without purification, reacted with amines of formula VI to give compounds of formula I (R⁴=NHCOR⁶).

Compounds of formula I-a may be prepared by the reaction shown in Scheme 3.

Scheme 3

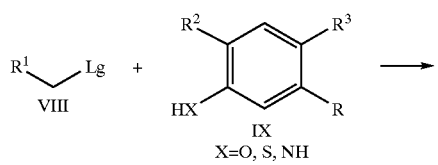

X=O, S, NH

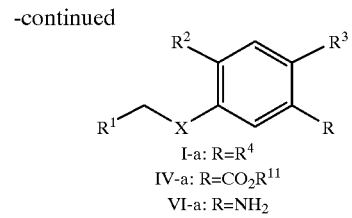

I-a: R=R⁴
IV-a: R=CO₂R¹¹
VI-a: R=NH₂

Compounds of formula IX (R=R⁴) are treated with compounds of formula VIII, where Lg is a suitable leaving group such as chloride, bromide, or mesylate, in a dipolar aprotic solvent such as acetone, DMF, or DMSO, in the presence of a suitable base, such as potassium carbonate, cesium carbonate, sodium hydride, and the like, to provide, after extractive workup and conventional purification, compounds of formula I-a. Alternatively, this reaction may be carried out in the same manner with compounds of formula XI (R=CO₂R¹¹, where R¹¹ is hydrogen or a suitable carboxylic acid protecting group, such as methyl, ethyl, or benzyl) to give compounds of formula IV-a. In addition, the reaction carried out with compounds of formula IX (R=NH₂) provides compounds of formula VI-a.

Compounds of formula I-b may be prepared by the reaction shown in Scheme 4.

Scheme 4

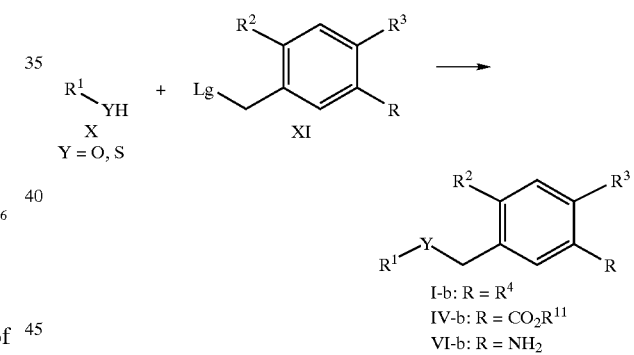

I-b: R = R⁴
IV-b: R = CO₂R¹¹
VI-b: R = NH₂

Compounds of formula XI (R=R⁴), where Lg is a suitable leaving group such as chloride, bromide, or mesylate, are treated with compounds of formula X in a dipolar aprotic solvent such as acetone, DMF, or DMSO, in the presence of a suitable base, such as potassium carbonate, cesium carbonate, sodium hydride, and the like, to provide, after extractive workup and conventional purification, compounds of formula I-b. Alternatively, this reaction may be carried out in the same manner with compounds of formula XI (R=CO₂R¹¹, where R¹¹ is hydrogen or a suitable carboxylic acid protecting group, such as methyl, ethyl, or benzyl) to give compounds of formula IV-b. In addition, the reaction carried out with compounds of formula XI (R=NH₂) provides compounds of formula VI-b.

Compounds of formula I-c may be prepared by the reaction shown in Scheme 5.

Scheme 5

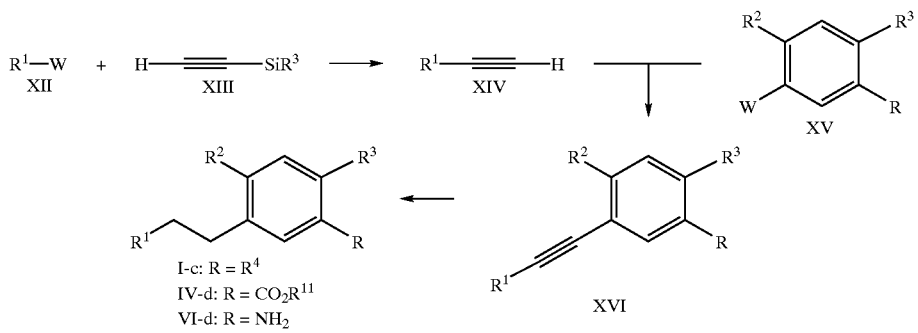

Compounds of formula XII, where W is a suitable group that can participate in a palladium-catalyzed coupling reaction such as bromide, iodide, or triflate, are allowed to react with acetylenes of formula XIII in the presence of a suitable palladium catalyst, such as dichlorobis(triphenylphosphine) palladium, and a copper catalyst, such as cuprous iodide, in the presence of a suitable base, such as piperidine, triethylamine or diisopropylethylamine, in an aprotic solvent, such as THF or DMF, at a temperature between 25° C. and 125° C., for 1 to 24 hours. After extractive work-up and conventional purification, removal of the silyl protecting group is effected with, for example, either tetrabutylammonium fluoride in THF or sodium hydroxide in methanol, to provide compounds of formula XIV.

Under similar catalyzed coupling conditions as those described above, compounds of formula XV can be reacted with those of formula XIV to yield compounds of formula XVI. Catalytic hydrogenation of alkynes of formula XVI provides compounds of formula I-c after filtration and convention purification. Typical catalytic conditions include catalysts such as palladium, rhodium, preferably palladium-on-carbon, in a suitable solvent such as $C_1$–$C_4$ alcohols, preferably ethanol.

Compounds of formula II-a may be prepared as shown in Scheme 6.

Scheme 6

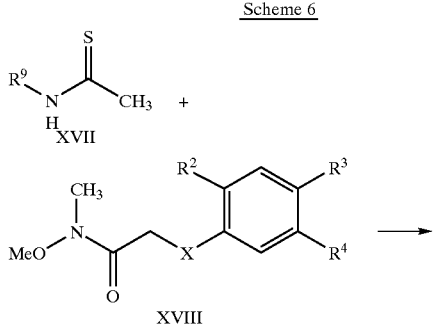

Thioamides of formula XVII are treated with two molar equivalents of a suitable strong base, such as n-butyllithium or lithium diisopropylamide, in a suitable solvent, such as THF, at −78° C. to 0° C., to give a solution of thioamide dianion, which is further treated with less than or equal to 0.5 molar equivalents of compounds of formula XVIII. Conventional aqueous work-up and purification then provides compounds of formula XIX, which upon treatment with hydrazine, preferably in the presence of acetic acid, in ethanol at 0° C. to 50° C., preferably at room temperature, provides compounds of formula II-a.

Compounds of formula I-b may be prepared as shown in Scheme 7.

Scheme 7

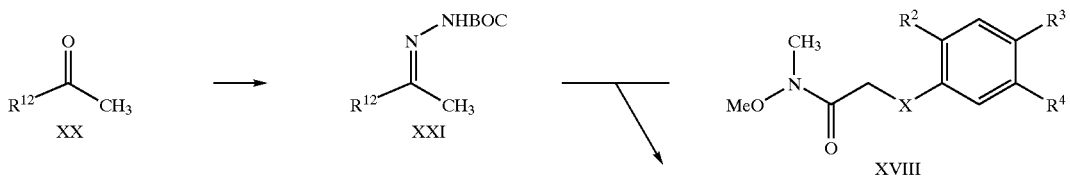

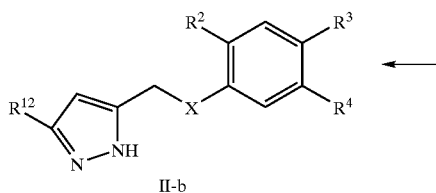

II-b

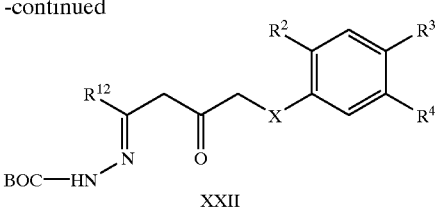

XXII

Ketones of formula XX, where $R^{12}$ is substituted or unsubstituted alkenyl, aryl, or heteroaryl, are converted to hydrazones of formula XXI by treatment with t-butyl carbazate and acetic acid in ethanol. Treatment of hydrazones of formula XXI with two molar equivalents of a suitable strong base, such as n-butyllithium or lithium diisopropylamide, in a suitable solvent, such as THF, at −78° C. to 0° C., generates a solution of hydrazone dianion, which is further treated with less than or equal to 0.5 molar equivalents of compounds of formula XVIII. Conventional aqueous work-up and purification then provides compounds of formula XXII, which upon further treatment with a suitable acid, such as trifluoroacetic acid, provides compounds of formula II-b.

Compounds of formula XVIII are prepared as shown in Scheme 8.

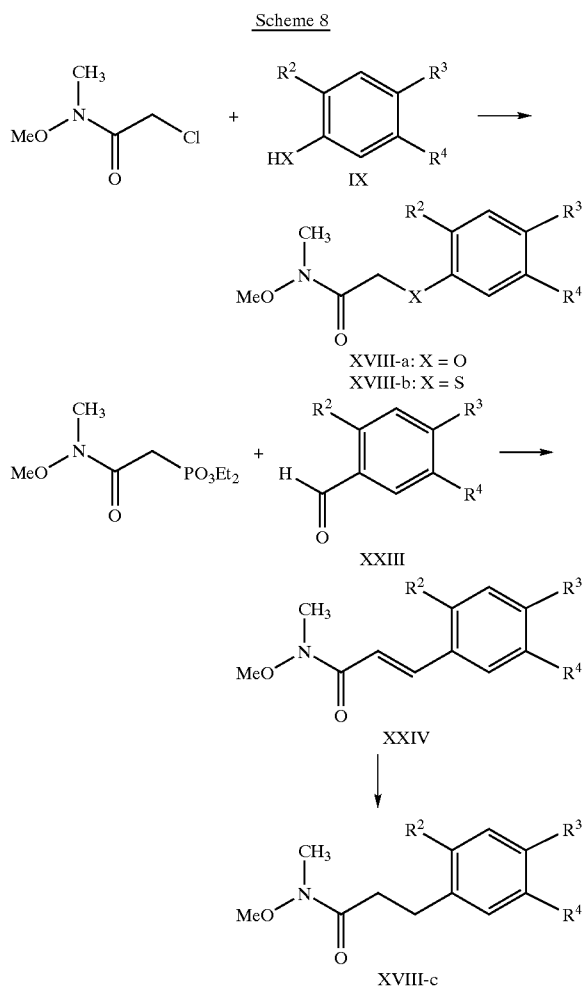

Thus, compounds of formula XVIII-a and XVIII-b are prepared by alkylation of compounds of formula IX with N-methoxy-N-methyl chloroacetamide in a like manner to that shown in Scheme 3 above. Compounds of formula XVIII-c may be prepared by (1) reaction of aldehydes of formula XXIII with the anion derived from N-methoxy-N-methyl triethylphosphonoacetamide to give unsaturated amides of formula XXIV, and (2) reduction of compounds of formula XXIV with, for example, hydrogen in the presence of palladium on carbon to provide compounds of formula XVIII-c.

Other compounds of Formula I, II, and III may be prepared in manners analogous to the general procedures described above or the detailed procedures described in the examples herein.

The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See e.g., Lee et al., Biochem, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as BSA or HAS, a multiplicity of peptides including, for example, pentapeptides, decapeptides, pentadecapeptides, and the like. The peptides or proteins can contain the desired number of amino acid residues having free amino groups in their side chains; however, other functional groups, such as mercapto (—SH) groups or hydroxyl (—OH) groups, can also be used to obtain stable linkages.

Compounds that potently regulate, modulate, or inhibit the protein kinase activity associated with receptors VEGF, FGF, CDK complexes, TEK, CHK-1, and LCK, among others, and which inhibit angiogenesis and/or cellular profileration is desirable and is one preferred embodiment of the present invention. The present invention is further directed to methods of modulating or inhibiting protein kinase activity, for example in mammalian tissue, by administering an inventive agent. The activity of the inventive compounds as modulators of protein kinase activity, such as the activity of kinases, may be measured by any of the methods available to those skilled in the art, including in vivo and/or in vitro assays. Examples of suitable assays for activity measurements include those described in Parast C. et al., BioChemistry, 37, 16788–16801 (1998); Jeffrey et al., Nature, 376, 313–320 (1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I, II, or IIII and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent is administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or soibitol, and cellulose preparations, for example, maize starch, wheat starch, rice starch, potato starch, gelatin, gum, methyl cellulose, hydroxypropylmethyl-cellulose, sodium carboxymetnylcellulose; or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the formula I, II, or III is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60° F. 254 plates and eluted with the appropriate solvent ratios (v/v), and are denoted where appropriate. The reactions were assayed by TLC and terminated as judged by the consumption of starting material.

Visualization of the TLC plates was generally done by ultraviolet visualization. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Products were purified by employing radial chromatography or flash column chromatography (Still et al., *J. Org. Chem.*, 43, 2923 (1978)), the latter using Merck grade flash silica gel (47–61 μm) and a silica gel: crude material ratio of about 20:1 to 100:1 unless otherwise stated. Hydrogenolysis was done at the pressure indicated in the examples or at ambient pressure.

$^1$H-NMR spectra were recorded on an instrument operating at 300 or 500 MHz, and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m multiplet), q (quartet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). All melting points (mp) are uncorrected.

Unless otherwise stated, the HPLC conditions are the following: Hewlett Packard ODS Hypersil (5 μm, 125×4 mm), 10% acetonitrile/0.1 M ammonium acetate from 0–2 minutes to 90% acetonitrile/0.1 M ammonium acetate at 22 minutes, 1.0 mL/minute, detection at 254 nm.

Abbreviations for reagents, equipment, and techniques are defined as follows: MTBE (methyl t-butyl ether); DMSO (dimethylsulfoxide); DIEA (diisopropylethylamine); TEA (triethylamine); AcOH (acetic acid); DMAP (4-(dimethylamino)pyridine); EDC (1-ethyl-3-(3'-dimethylaminopropyl)carbodiimide,HCl); HATU (O-(7-azabenzotriazol-1-yl)-N,N,N',N'-tetramethyluronium hexafluorophosphate); HOBt (N-hydroxybenzotriazole); PyBop (benzotriazole-1-yl-oxy-tris-pyrrolidinophosphonium hexafluorophosphate); MS (ESI) (Electrospray ionization mass spectrometry); MS (FAB) (fast atom bombardment mass spectrometry); HRMS (FAB) (high resolution fast atom bombardment mass spectrometry); HRMS (MALDI) (high resolution matrix-assisted laser desorption/ionization mass spectrometry); and APCIMS (atmospheric pressure chemical ionization mass spectrometry).

Example A-1

N-(3,4,5-Trimethoxyphenyl)-3-[(pyrazin-2-yl)sulfanylmethyl]benzamide

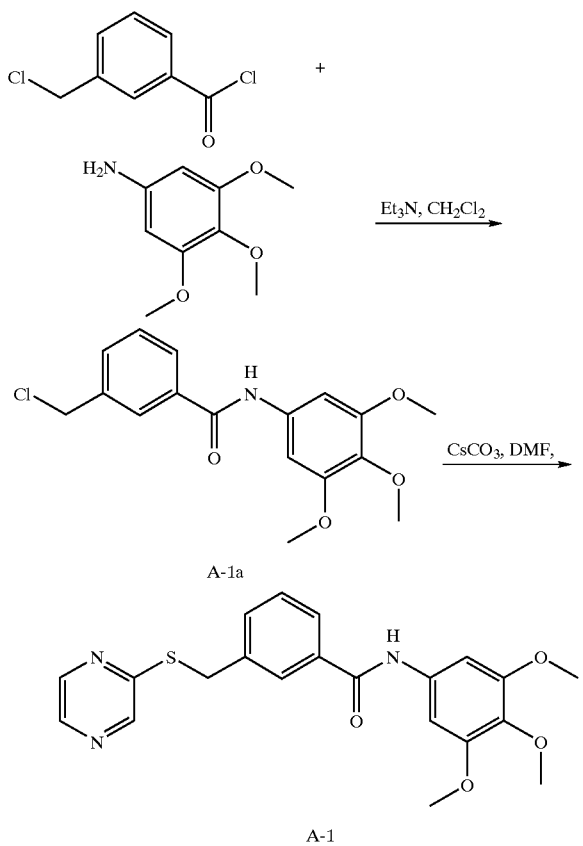

(a) To a solution of 3,4,5-trimethoxyaniline (3.0 g, 16.4 mmol) and triethylamine (2.5 mL, 18 mmol) in 100 mL dichloromethane at room temperature was added, via pipette, 3-(chloromethyl)benzoyl chloride (2.4 mL, 16.9 mmol). After stirring at room temperature for 4 h, the mixture was partitioned between chloroform (100 mL) and water (200 mL). The aqueous layer was extracted twice with chloroform (100 mL) and the combined organics were washed with brine (100 mL), dried over $NA_2SO_4$, and concentrated to dryness. The crude residue was triturated with MTBE to obtain 5.22 g (95%) of N-(3,4,5-trimethoxyphenyl)-3-(chloromethyl)benzamide, A-1a, as an off-white solid which was collected by filtration: mp 138–145° C.; $^1$H NMR (DMSO-$d_6$) δ7.98 (s, 1H), 7.89 (d, 1H, J=7.8 Hz), 7.63 (d, 1H, J=7.8 Hz), 7.52 (t, 1H, J=7.7 Hz), 7.20 (s, 2H), 4.83 (s, 2H), 3.75 (s, 6H), 3.62 (s, 3H). Anal. calc'd for $C_{17}H_{18}NO_4Cl.0.2 H_2O$: C, 60.16; H, 5.47; N, 4.13; Cl, 10.45. Found: C, 60:18; H, 5.38; N, 4.17; Cl, 10.68.

(b) To a solution of 0.112 g (1 mmol) of 2-pyrazinethiol (Specs) and N-(3,4,5-(trimethoxyphenyl)-3-(chloromethyl) benzamide, A-1a, (0.335 g, 1 mmol) in 5 mL anhydrous DMF under an argon purge was added cesium carbonate (0.814 g, 2.5 mmol). The resulting suspension was stirred at ~65° C. for 17 hr. The mixture was allowed to cool to room temperature and then was partitioned between ethyl acetate (50 mL) and water (75 mL). The aqueous layer was extracted twice with ethyl acetate (50 mL) and the combined organics were washed with brine (25 mL), dried over NA$_2$SO$_4$, and concentrated to dryness. The crude residue was purified on silica gel using a gradient of 0% to 6% methanol in 1:1 ethyl acetate:hexane as eluent to obtain N-(3,4,5-trimethoxyphenyl)-3-[(pyrazin-2-yl)sulfanylmethyl]benzamide as a pale yellow oil (0.18 g, 43%) which crystallized upon standing: mp 112–119° C.; $^1$H NMR (DMSO-d$_6$) δ10.13 (s, 1H), 8.63 (d, 1H, J=1.55 Hz), 8.53 (dd, 1H, J=2.60, 1.58 Hz), 8.36 (d, 1H, J=2.64 Hz), 8.00 (s, 1H), 7.83 (d, 1H, J=7.81 Hz), 7.64 (d, 1H, J=7.72 Hz), 7.47 (t, 1H, J=7.7 Hz), 7.21 (s, 2H), 4.56 (s, 2H), 3.77 (s, 6H), 3.65 (s, 3H). Anal. calc'd for C$_{21}$H$_{21}$N$_3$O$_4$S.0.2 MTBE: C, 61.58; H, 5.50; N, 9.79; S, 7.47. Found: C, 61.34; H, 5.43; N, 9.69; S, 7.34.

Example A-2

N-(3,4,5-Trimethoxyphenyl)-3-[(5-amino-2H-[1,2,4]triazol-3-yl)sulfanylmethyl]benzamide

A-2

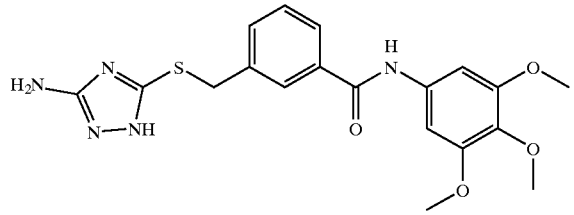

Example A-2 was prepared in a similar manner to that described for A-1, except that 3-amino-5-mercapto-1,2,4-triazole (Aldrich) was used in place of 2-pyrazinethiol in step (b): $^1$H NMR (DMSO-d$_6$) δ11.96 (br s, 1H), 10.12 (s, 1H), 7.95 (s, 1H), 7.82 (d, 1H, J=7.8 Hz), 7.59 (d, 1H, J=7.6 Hz), 7.46 (t, 1H, J=7.69 Hz), 7.23 (s, 2H), 6.05 (br s, 2H), 4.32 (s, 2H), 3.78 (s, 6H), 3.65 (s, 3H); HR MS (FAB): Calculated for C$_{19}$H$_{22}$N$_5$O$_4$S (M+H$^+$): 416.1393. Found: 416.1408. Anal. calc'd for C$_{19}$H$_{21}$N$_5$O$_4$S.0.3 EtOAc: C, 54.90; H, 5.34; N, 15.85; S, 7.26. Found: C, 54.87; H, 5.50; N, 15.71; S, 7.03.

Example A-3

N-(4-Isopropyl-3-methylphenyl)-3-[(pyrazin-2-yl)sulfanylmethyl]benzamide

A-3

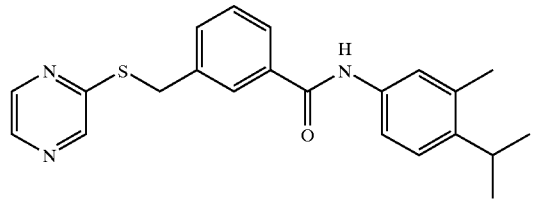

Example A-3 was prepared in a similar manner to that described for A-1, except that 3-methyl-4-isopropylaniline hydrochloride (Maybridge) was used in place of 3,4,5-trimethoxyaniline in step (a): mp 69–73° C.; $^1$H NMR (DMSO-d$_6$) δ10.07 (s, 1H), 8.62 (d, 1H, J=1.6 Hz), 8.52 (dd, 1H, J=2.6, 1.6 Hz), 8.35 (d, 1H, J=2.6 Hz), 7.99 (s, 1H), 7.83 (d, 1H, J=7.8 Hz), 7.62 (d, 1H, J=7.7 Hz), 7.56–7.51 (m, 2H), 7.46 (t, 1H, J=7.7 Hz), 7.20 (d, 1H, J=8.3 Hz), 4.55 (s, 2H), 3.10–3.05 (m, 1H), 2.69 (s, 3H), 1.17 (d, 6H, J=6.9 Hz).

Anal. calc'd for C$_{22}$H$_{23}$N$_3$OS.0.2 MTBE: C, 69.91; H, 6.48; N, 10.64; S, 8.12. Found: C, 70.03; H, 6.40; N, 10.41; S, 7.81.

Example A-4

N-(4-Isopropyl-3-methylphenyl)-3-[(5-amino-2H-[1,2,4]triazol-3-yl)sulfanylmethyl]benzamide

A-4

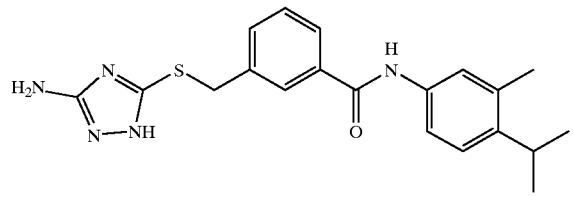

Example A-4 was prepared in a similar manner to that described for A-1, except that 3-methyl-4-isopropylaniline was used in place of 3,4,5-trimethoxyaniline in step (a), and 3-amino-5-mercapto-1,2,4-triazole was used in place of 2-pyrazinethiol in step (b): $^1$H NMR (DMSO-d$_6$) δ11.93 (br s, 1H), 10.05 (s, 1H), 7.92 (s, 1H), 7.80 (d, 1H, J=7.8 Hz), 7.57–7.51 (m, 3H), 7.43 (t, 1H, J=7.7 Hz), 7.19 (d, 1H, J=8.3 Hz), 6.02 (br s, 2H), 4.30 (s, 2H), 3.09–3.04 (m, 1H), 2.29 (s, 3H), 1.17 (d, 6H, J=6.9 Hz). Anal. calc'd for C$_{20}$H$_{23}$N$_5$OS.0.1 MTBE: C, 63.08; H, 6.25; N, 17.94; S, 8.22. Found: C, 62.78; H, 6.26; N, 17.78; S, 8.00.

Example A-5

N-(4-Isopropyl-3-methylphenyl)-3-[(1H-pyrazolo[3,4-d]pyrimidin-4-yl)sulfanylmethyl]benzamide

A-5

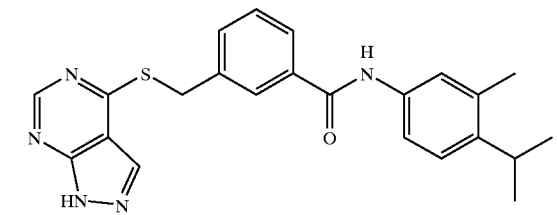

Example A-5 was prepared in a similar manner to that described for A-1, except that 3-methyl-4-isopropylaniline was used in place of 3,4,5-trimethoxyaniline in step (a), and 4-mercapto-1H-pyrazolo[3,4-d]pyrimidine was used in place of 2-pyrazinethiol in step (b): mp 187–189° C.; $^1$H NMR (DMSO-d$_6$) δ10.09 (s, 1H), 8.81 (s, 1H), 8.31 (s, 1H), 8.05 (s, 1H), 7.85 (d, 1H, J=7.9 Hz), 7.69 (d, 1H, J=7.7 Hz), 7.55–7.47 (m, 3H), 7.20 (d, 1H, J=8.4 Hz), 4.78 (s, 2H), 3.09–3.06 (m, 1H), 2.29 (s, 3H), 1.18 (d, 6H, J=6.9 Hz). Anal. calc'd for C$_{23}$H$_{23}$N$_5$OS: C, 66.16; H, 5.55; N, 16.77; S, 7.68. Found: C, 65.90; H, 5.51; N, 16.98; S, 7.40.

Example A-6

N-(2-Methylquinolin-6-yl)-3-[(pyrazin-2-yl)sulfanylmethyl]benzamide

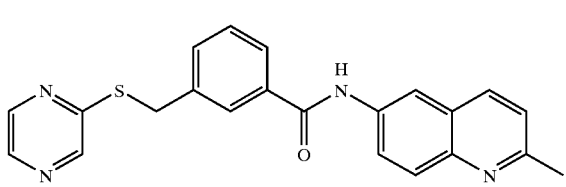

A-6

Example A-6 was prepared in a similar manner to that described for A-1, except that 6-amino-2-methylquinoline (Lancaster) was used in place of 3,4,5-trimethoxyaniline in step (a): mp 133–135° C.; $^1$H NMR (DMSO-d$_6$) δ10.51 (s, 1H), 8.63 (s, 1H), 8.53 (t, 1H, J=1.9 Hz), 8.44 (t, 1H, J=3.0 Hz), 8.35 (d, 1H, J=2.6 Hz), 8.20 (d, 1H, J=2.4 Hz), 8.04 (s, 1H), 7.96 (d, 1H, J=9.0 Hz), 7.89 (d, 2H, J=9.1 Hz), 7.66 (d, 1H, J=7.7 Hz), 7.50 (t, 1H, J=7.7 Hz), 7.38 (d, 1H, J=8.4 Hz), 4.57 (s, 2H), 2.63 (s, 3H). Anal. calc'd for C$_{22}$H$_{18}$N$_4$OS: C, 68.37; H, 4.69; N, 14.50; S, 8.30. Found: C, 68.41; H, 4.72; N, 14.52; S, 8.30.

Example A-7

N-(3-Isopropylphenyl)-3-[(pyrazin-2-yl)sulfanylmethyl]benzamide

A-7

Example A-7 was prepared in a similar manner to that described for A-1, except that 3-isopropylaniline (Maybridge) was used in place of 3,4,5-trimethoxyaniline in step (a): $^1$H NMR (DMSO-d$_6$) δ10.02 (s, 1H), 8.63 (d, 1H, J=1.6 Hz), 8.52 (dd, 1H, J=2.42, 1.5 Hz), 8.34 (d, 1H, J=2.6 Hz), 7.99 (s, 1H), 7.83 (d, 1H, J=7.7 Hz), 7.63–7.60 (m, 3H), 7.46 (t, 1H, J=7.7 Hz), 7.25 (t, 1H, J=7.8 Hz), 6.97 (d, 1H, J=7.6 Hz), 4.55 (s, 2H), 2.88–2.85 (m, 1H), 1.21 (d, 6H, J=6.9 Hz). Anal. calc'd for C$_{21}$H$_{21}$N$_3$OS.0.3 MTBE: C, 69.31; H, 6.36; N, 10.78; S, 8.22. Found: C, 69.34; H, 6.15; N, 10.54; S, 7.96.

Example A-8

N-(3,5-Dibromo-4-methylphenyl)-3-[(pyrazin-2-yl)sulfanylmethyl]benzamide

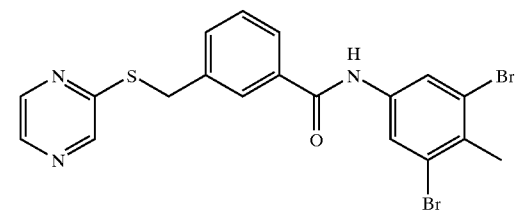

A-8

Example A-8 was prepared in a similar manner to that described for A-1, except that 3,5-dibomo-4-methylaniline (Lancaster) was used in place of 3,4,5-trimethoxyaniline in step (a): mp 119–127° C.; $^1$H NMR (DMSO-d$_6$) δ10.39 (s, 1H), 8.61 (d, 1H, J=1.30 Hz), 8.51 (t, 1H, J=2.1 Hz), 8.34 (d, 1H, J=2.61 Hz), 8.12 (s, 2H), 7.99 (s, 1H), 7.82 (d, 1H, J=7.96 Hz), 7.65 (d, 1H, J=7.73 Hz), 7.48 (t, 1H, J=7.74 Hz), 4.54 (s, 2H), 2.47 (s, 3H). Anal. calc'd for C$_{19}$H$_{15}$N$_3$$_4$S.0.25 EtOAc: C, 46.62; H, 3.33; N, 8.16; S, 6.22. Found: C, 46.33; H, 3.24; N, 7.90; S, 5.83.

Example B-1

N-(3,4,5-Trimethoxyphenyl)-3-[(1H-pyrazolo[3,4-d]pyrimidin-4-yl)sulfanylmethyl]benzamide

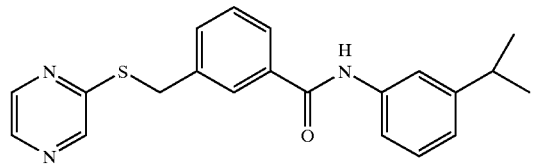

B-1

To a solution of 3,4,5-trimethoxyaniline (400 mg, 2.18 mmol) and triethylamine (0.30 mL, 2.18 mmol) in dichloromethane was added 0.31 mL (2.18 mmol) of 3-chloromethylbenzoyl chloride (Aldrich). After 10 min, the solvent was removed and the residual crude N-(3,4,5-trimethoxyphenyl)-3-(chloromethyl)benzamide, A-1a, was dissolved in DMF (10 mL) under argon. To the resulting solution was added 4-mercapto-1H-pyrazolo[3,4-d] pyrimidine (332 mg, 2.18 mmol) followed by triethylamine (0.30 mL, 2.18 mmol). The resulting solution was heated at 70° C. for 2 h, then cooled and poured into water. The solid was collected by filtration and washed with water. After air-drying, the solid was sequentially triturated with ethyl acetate/hexane and with dichloromethane, and the solid collected by filtration to provide 360 mg (37%) of N-(3,4,5-trimethoxyphenyl)-3-[(1H-pyrazolo[3,4-d]pyrimidin-4-yl)sulfanylmethyl)benzamide, B-1: $^1$H NMR (300 MHz, DMSO-$d_6$) δ14.12 (s, 1H), 10.15 (s, 1H), 8.79 (s, 1H), 8.03 (s, 1H), 7.83 (d, 1H, J=7.7 Hz), 7.68 (d, 1H, J=7.7 Hz), 7.48 (t, 1H, J=7.7 Hz), 7.20 (s, 2H), 4.77 (s, 2H), 3.75 (s, 6H), 3.62 (s, 3H). Anal. calc'd for $C_{22}H_{21}N_5O_4S.0.7 H_2O$: C, 56.93; H, 4.87; N, 15.09; S, 6.91. Found: C, 56.89; H, 4.76; N, 14.85; S, 6.91.

Example B-2

N-(3,4,5-Trimethoxyphenyl)-3-[(1H-pyrazolo[3,4-d]pyrimidin-4-yl)sulfanylmethyl]benzamide

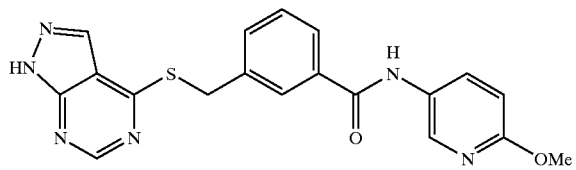

B-2

Example B-2 was prepared in a similar manner to that described for B-1, except that 5-amino-2-methoxypyridine was used in place of 3,4,5-trimethoxyaniline: $^1$H NMR (300 MHz, DMSO-$d_6$) δ14.10 (s, 1H), 10.20 (s, 1H), 8.75 (s, 1H), 8.43 (d, J=2.5 Hz, 1H), 8.25 (s, 1H), 7.95–8.00 (m, 2H), 7.81 (d, 1H, J=7.8 Hz), 7.65 (d, 1H, J=7.7 Hz), 7.41–7.46 (dd, 1H), 6.78 (d, 1H, J=8.8 Hz), 4.70 (s, 2H), 3.80 (s, 3H); APCIMS m/z 393 [M+H]$^+$.

Example B-3

N-(Quinolin-6-yl)-3-[(1H-pyrazolo[3,4-d]pyrimidin-4-yl)sulfanylmethyl]benzamide

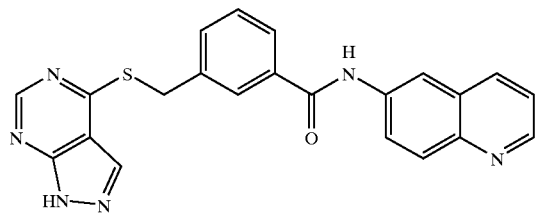

B-3

Example B-3 was prepared in a similar manner to that described for B-1, except that 6-aminoquinoline was used in place of 3,4,5-trimethoxyaniline: mp 236–240° C. (dec); $^1$H NMR (DMSO-$d_6$) δ14.15 (s, 1H), 10.60 (s, 1H), 8.80 (s, 2H), 8.52 (s, 1H), 8.34–8.29 (m, 2H), 8.10 (s, 1H), 8.05–7.98 (m, 2H), 7.91 (d, 1H, J=7.7 Hz), 7.72 (d, 1H, J=7.4 Hz), 7.54–7.48 (m, 2H), 4.79 (s, 2H). Anal. calc'd for $C_{22}H_{16}N_6OS.0.7 H_2O$: C, 62.16; H, 4.13; N, 19.77; S, 7.54. Found: C, 62.34; H, 3.83; N, 19.48; S, 7.61.

Example B-4

N-(5-Methylisoxazol-3-yl)-3-[(1H-pyrazolo[3,4-d]pyrimidin-4-yl)sulfanylmethyl]benzamide

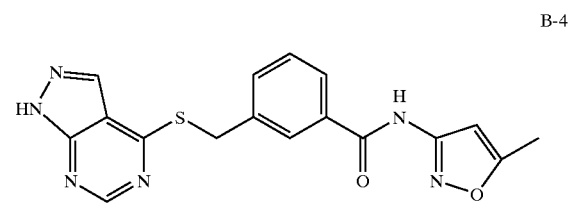

B-4

Example B-4 was prepared in a similar manner to that described for B-1, except that 3-amino-5-methylisoxazole was used in place of 3,4,5-trimethoxyaniline: $^1$H NMR (300 MHz, DMSO-$d_6$) δ13.99 (s, 1H), 11.34 (s, 1H), 8.79 (s, 1H), 8.31 (s, 1H), 8.11 (s, 1H), 7.90 (d, 1H, J=8.0 Hz), 7.72 (d, 1H, J=8.0 Hz), 7.47 (dd, 1H, J=7.5, 7.6 Hz), 6.74 (s, 1H), 4.76 (s, 2H), 2.41 (s, 3H); APCIMS m/z 367 [M+H]$^+$.

Example B-5

N-(Pyridin-4-yl)methyl-3-[(1H-pyrazolo[3,4-d]pyrimidin-4-yl)sulfanylmethyl]benzamide

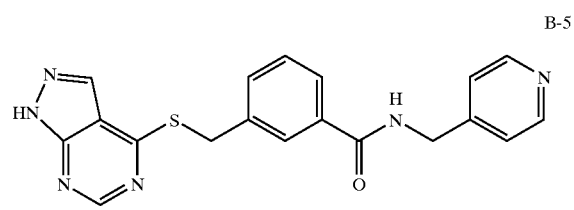

B-5

Example B-5 was prepared in a similar manner to that described for B-1, except that 4-picolylamine was used in place of 3,4,5-trimethoxyaniline: $^1$H NMR (300 MHz, DMSO-$d_6$) δ14.05 (s, 1H), 9.08–9.12 (t, 1H, J=5.8 Hz), 8.74 (s, 1H), 8.44 (d, 1H, J=5.7 Hz), 8.25 (s, 1H), 7.96 (s, 1H), 7.76 (d, 1H, J=7.9 Hz), 7.62 (d, 1H, J=7.7 Hz), 7.40 (dd, 1H, J=7.7, 7.9 Hz), 7.24 (d, 1H, J=5.7 Hz), 4.70 (s, 2H), 4.43 (d, 2H, J=5.9 Hz); APCIMS m/z 377 [M+H]$^+$.

Example B-6

N-(1,3-Benzodioxyl-5-ylmethyl)-3-[(1H-pyrazolo[3,4-d]pyrimidin-4-yl)sulfanylmethyl]benzamide

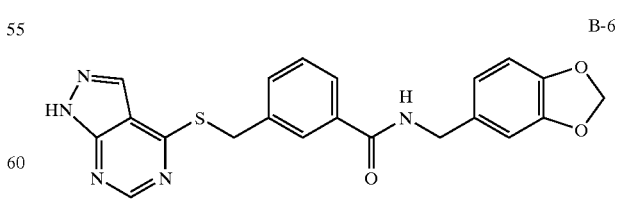

B-6

Example B-6 was prepared in a similar manner to that described for B-1, except that 3,4-(methylenedioxy)benzylamine was used in place of 3,4,5-trimethoxyaniline: $^1$H NMR (300 MHz, DMSO-$d_6$) δ14.05 (s, 1H), 8.98 (t, 1H, J=6.0 Hz), 8.78 (s, 1H), 8.30 (s, 1H), 7.99 (s, 1H), 7.77 (d, 1H, J=7.9 Hz), 7.64 (d, 1H, J=7.5 Hz), 7.42 (dd, 1H, J=7.6, 7.9 Hz), 6.84–6.87 (m, 2H), 6.78 (d, 1H, J=7.9 Hz), 5.97 (s, 2H), 4.74 (s, 2H), 4.36 (d, 2H, J=6.1 Hz); APCIMS m/z 420 [M+H]⁺.

Example B-7

N-(2-Methoxybenzyl)-3-[(1H-pyrazolo[3,4-d]pyrimidin-4-yl)sulfanylmethyl]benzamide

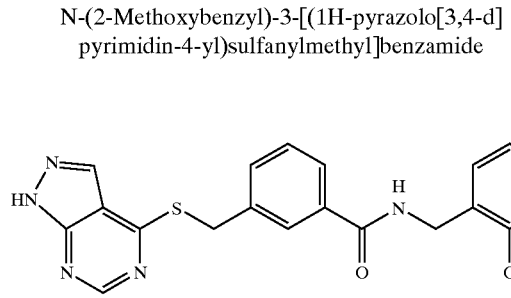

B-7

Example B-7 was prepared in a similar manner to that described for B-1, except that 2-methoxybenzylamine was used in place of 3,4,5-trimethoxyaniline: $^1$H NMR (300 MHz, DMSO-d$_6$) δ14.12 (s, 1H), 8.86 (t, 1H, J=6.0 Hz), 8.79 (s, 1H), 8.30 (s, 1H), 8.02 (s, 1H), 7.81 (d, 1H, J=7.9 Hz), 7.64 (d, 1H, J=7.6 Hz), 7.44 (dd, 1H, J=7.6, 7.9 Hz), 7.23 (m, 1H), 7.16 (d, 1H, J=7.2Hz), 6.98 (d, 1H, J=7.9Hz), 6.89 (dd, 1H, J=7.5, 6.8 Hz), 4.75 (s, 2H), 4.43 (d, 2H, J=6.1 Hz), 3.82 (s, 3H); APCIMS m/z 406 [M+H]⁺.

Example B-8

N-(2-Phenylethyl)-3-[(1H-pyrazolo[3,4-d]pyrimidin-4-yl)sulfanylmethyl]benzamide

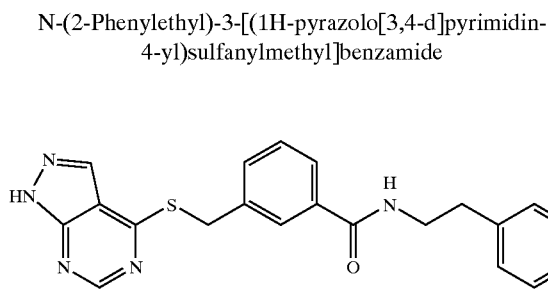

B-8

Example B-8 was prepared in a similar manner to that described for B-1, except that phenethylamine was used in place of 3,4,5-trimethoxyaniline: $^1$H NMR (300 MHz, DMSO-d$_6$) δ14.13 (s, 1H), 8.79 (s, 1H), 8.61 (t, 1H J=5.7 Hz), 8.30 (s, 1H), 7.93 (s, 1H), 7.70 (d, 1H, J=7.9 Hz), 7.62 (d, 1H, J=7.9 Hz), 7.41 (dd, 1H, J=7.6, 7.9 Hz), 7.16–7.31 (m, 5H), 4.73 (s, 2H), 3.43–3.50 (m, 2H), 2.83 (dd, 2H, J=7.2, 7.9 Hz); APCIMS m/z 390 [M+H]⁺.

Example B-9

N-(2-Methoxyphenyl)-3-[(1H-pyrazolo[3,4-d]pyrimidin-4-yl)sulfanylmethyl]benzamide

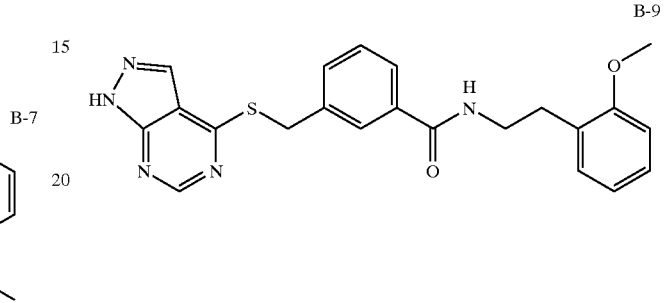

B-9

Example B-9 was prepared in a similar manner to that described for B-1, except that 2-methoxyaniline was used in place of 3,4,5-trimethoxyaniline: $^1$H NMR (300 MHz, DMSO-d$_6$) δ14.12 (s, 1H), 9.43 (s, 1H), 8.81 (s, 1H), 8.32 (s, 1H), 8.08 (s, 1H), 7.87 (d, 1H, J=7.9 Hz), 7.77 (d, 1H, J=7.5 Hz), 7.70 (d, 1H, J=7.9 Hz), 7.48 (dd, 1H, J=7.5, 7.6 Hz), 7.19 (m, 1H), 7.09 (d, 1H, J=7.2 Hz), 6.97 (dd, 1H, J=7.1, 8.0 Hz), 4.79 (s, 2H), 3.83 (s, 3H); APCIMS m/z 392 [M+H]⁺.

Example B-10

N-[3-(N-Methyl-N-phenylamino)propyl]-3-[(5-methyl-1H-1,2,4-triazol-3-yl)sulfanylmethyl]benzamide

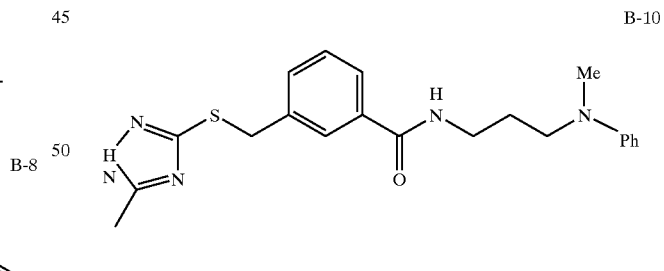

B-10

Example B-10 was prepared in a similar manner to that described for B-1, except that N-(3-aminopropyl)-N-methylaniline was used in place of 3,4,5-trimethoxyaniline, and 3-mercapto-5-methyl-1H-1,2,4-triazole was used in place of 4-mercapto-1H-pyrazolo[3,4-d]pyrimidine: $^1$H NMR (300 MHz, CD$_3$OD) δ7.80 (s, 1H), 7.68 (d, 1H, J=7.9 Hz), 7.52 (d, 1H, J=7.5 Hz), 7.38 (dd, 1H, J=7.5, 8.0 Hz), 7.15 (m, 2H), 6.74–6.77 (m, 2H), 6.64 (dd, 1H, J=7.1, 7.1 Hz), 4.36 (s, 2H), 3.41–3.45 (m, 4H), 2.93 (s, 3H), 2.38 (s, 3H), 1.85–1.96 (m, 2H); APCIMS m/z 396 [M+H]⁺.

Example B-11

N-(1,3-Benzodioxyl-5-ylmethyl)-3-[(5-methyl-1H-1,2,4-triazol-3-yl)sulfanylmethyl]benzamide

B-11

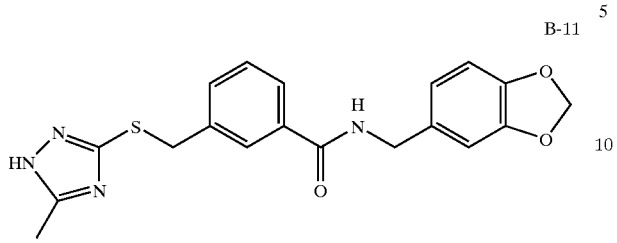

Example B-11 was prepared in a similar manner to that described for B-1, except that (3,4-methylenedioxy)benzylamine was used in place of 3,4,5-trimethoxyaniline, and 3-mercapto-5-methyl-1H-1,2,4-triazole was used in place of 4-mercapto-1H-pyrazolo[3,4-d]pyrimidine: $^1$H NMR (300 MHz, CD$_3$OD) δ7.83 (s, 1H), 7.71 (d, 1H, J=7.5 Hz), 7.52 (d, 1H, J=7.2 Hz), 7.38 (dd, 1H, J=7.50, 7.6 Hz), 6.76–6.86 (m, 3H), 5.93 (s, 2H), 4.47 (s, 2H), 4.35 (s, 2H), 2.38 (s, 3H); APCIMS m/z 383 [M+H]$^+$.

Example B-12

N-[4-cyano-3-(trifluoromethyl)phenyl]-3-[(1H-pyrazolo[3,4-d]pyrimidin-4-yl-sulfanyl)methyl]benzamide

B-12

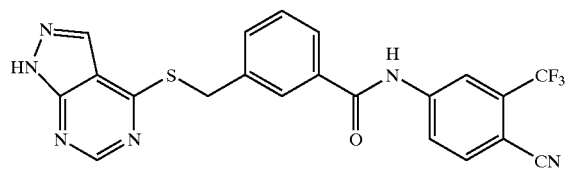

Example B-12 was prepared in a similar manner to that described for B-1, except that 4-cyano-3-trifluoromethylaniline was used in place of 3,4,5-trimethoxyaniline: $^1$H NMR (300 MHz, DMSO-d$_6$) δ14.07 (s, 1H), 10.98 (s, 1H), 8.80 (s, 1H), 8.44 (s, 1H), 8.26–8.31 (m, 2H), 8.15 (d, 1H, J=7.9 Hz), 8.08 (s, 1H), 7.89 (d, 1H, J=7.5 Hz), 7.76 (d, 1H, J=7.9 Hz), 7.53 (dd, 1H J=7.50, 7.9 Hz), 4.79 (s, 2H); APCIMS m/z 455 [M+H]$^+$.

Example B-13

N-(3,3-Diphenylpropyl)-3-{[(5-methyl-1H-1,2,4-triazol-3-yl)sulfanyl]methyl}benzamide

B-13

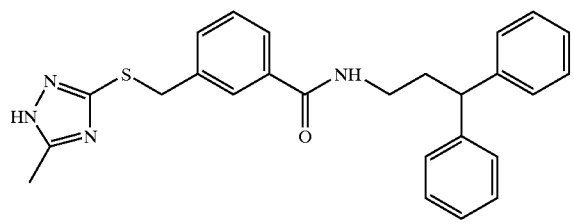

Example B-13 was prepared in a similar manner to that described for B-1, except that 3,3-diphenyl-1-propylamine was used in place of 3,4,5-trimethoxyaniline, and 3-mercapto-5-methyl-1H-1,24-triazole was used in place of 4-mercapto-1H-pyrazolo[3,4-d]pyrimidine: $^1$H NMR (300 MHz, CD$_3$OD) δ7.74 (s, 1H), 7.62 (d, 1H, J=7.6 Hz), 7.50 (d, 1H, J=7.6 Hz), 7.25–7.38 (m, 9H), 7.13–7.18 (m, 2H), 4.35 (s, 2H), 4.05 (dd, 1H, J=7.6, 7.9 Hz), 3.34–3.37 (m, 2H), 2.38 (m, 5H); APCIMS m/z 443 [M+H]$^+$.

Example B-14

3-{[(5-Methyl-1H-1,2,4-triazol-3-yl)-sulfonyl]methyl}-N-phenethylbenzamide

B-14

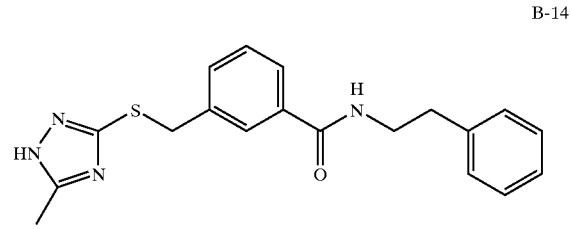

Example B-14 was prepared in a similar manner to that described for B-1, except that 2-phenylethylamine was used in place of 3,4,5-trimethoxyaniline, and 3-mercapto-5-methyl-1H-1,2,4-triazole was used in place of 4-mercapto-1H-pyrazolo[3,4-d]pyrimidine: $^1$H NMR (300 MHz, CD$_3$OD) δ7.78 (s, 1H), 7.64 (d, 1H, J=7.9 Hz), 7.51 (d, 1H, J=7.5 Hz), 7.38 (dd, 1H, J=7.5, 7.9 Hz), 7.18–7.33 (m, 5H), 4.35 (s, 2H), 3.57–3.62 (m, 2H), 2.90–2.93 (m, 2H), 2.40 (s, 3H); APCIMS m/z 353 [M+H]$^+$.

Example B-15

3-[(1H-Pyrazolo[3,4-d]pyrimidin-4-yl)sulfanylmethyl]-N(3-isopropylphenyl)-benzamide

B-15

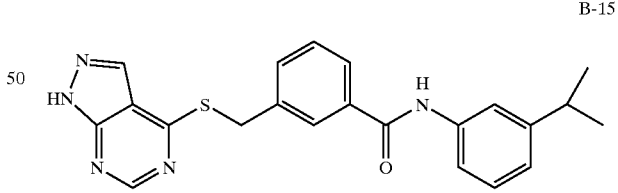

Example B-15 was prepared in a similar manner to that described for B-1, except that 3-isopropylaniline was used in place of 3,4,5-trimethoxyaniline: $^1$H NMR (300 MHz, DMSO-d$_6$) δ14.13 (s, 1H), 10.19 (s, 1H), 8.80 (s, 1H), 8.31 (s, 1H), 8.05 (s, 1H), 7.85 (d, 1H, J=7.9 Hz), 7.69 (d, 1H, J=7.9 Hz), 7.61 (m, 2H), 7.48 (dd, 1H, J=7.6, 7.6 Hz), 7.25 (dd, 1H, J=7.5, 8.0 Hz), 6.99 (d, 1H, J=7.9 Hz), 4.78 (s, 2H), 2.83–2.91 (m, 1H), 1.21 (d, 6H, J=6.0 Hz); APCIMS m/z 404 [M+H]$^+$.

Example B-16

3-[(1H-Pyrazolo[3,4-d]pyrimidin-4-yl) sulfanylmethyl]-N(3-trifluoromethyl-5-methoxyphenyl)-benzamide

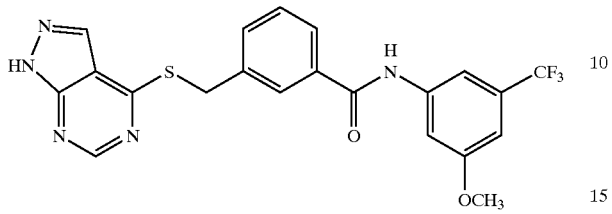

B-16

Example B-16 was prepared in a similar manner to that described for B-1, except that 3-trifluoromethyl-5-trifluoromethoxyaniline was used in place of 3,4,5-trimethoxyaniline: $^1$H NMR (300 MHz, DMSO-d$_6$) δ14.13 (s, 1H), 10.51 (s, 1H), 8.80 (s, 1H), 8.30 (s, 1H), 8.06 (s, 1H), 7.86 (d, 1H, J=7.9 Hz), 7.81 (s, 1H), 7.73 (m, 2H), 7.50 (dd, 1H, J=7.50, 8.0 Hz), 6.98 (s, 2H), 6.46–6.50 (m, 1H), 4.78 (s, 2H), 3.83 (s, 3H); APCIMS m/z 460 [M+H]$^+$.

Example B-17

3-[(1H-Pyrazolo[3,4-d]pyrimidin-4-yl) sulfanylmethyl]-N(3,5-bis-trifluoromethylphenyl)-benzamide

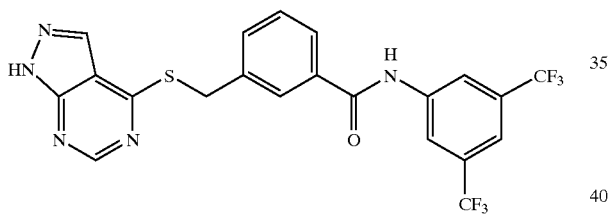

B-17

Example B-17 was prepared in a similar manner to that described for B-1, except that 3,5-bis(trifluoromethyl) aniline was used in place of 3,4,5-trimethoxyaniline: $^1$H NMR (300 MHz, DMSO-d$_6$) δ14.20 (s, 1H), 10.92 (s, 1H), 8.87 (s, 1H), 8.57 (s, 2H), 8.37 (s, 1H), 8.17 (s, 1H), 7.97 (d, 1H, J=7.9 Hz), 7.89 (s, 1H), 7.83 (d, 1H, J=7.6 Hz), 7.60 (dd, 1H, J=7.50, 8.0 Hz), 4.86 (s, 2H); APCIMS m/z 498 [M+H]$^+$.

Example B-18

3-[(1H-Pyrazolo[3,4-d]pyrimidin-4-yl) sulfanylmethyl]-N(3-t-butylpheny)-benzamide

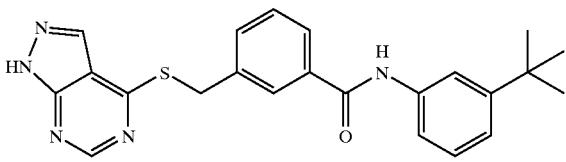

B-18

Example B-18 was prepared in a similar manner to that described for B-1, except that 3-(tert-butyl)aniline was used in place of 3,4,5-trimethoxyaniline: $^1$H NMR (300 MHz, DMSO-d$_6$) δ14.13 (s, 1H), 10.19 (s, 1H), 8.81 (s, 1H), 8.30 (s, 2H), 8.05 (s, 1H), 7.85–7.88 (d, 1H, J=7.6 Hz), 7.75 (s, 1H), 7.65–7.71 (m, 1H), 7.48 (dd, 1H, J=7.6, 7.9 Hz), 7.26 (dd, 1H, J=7.5, 8.0 Hz), 7.13 (d, 1H, J=7.9 Hz), 4.78 (s, 2H), 1.29 (s, 9H); APCIMS m/z 418 [M+H]$^+$.

Example B-19

3-[(1H-Pyrazolo[3,4-d]pyrimidin-4-yl) sulfanylmethyl]-N(4-isopropylphenyl)-benzamide

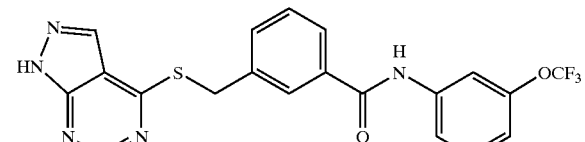

B-19

Example B-19 was prepared in a similar manner to that described for B-1, except that 4-isopropylaniline was used in place of 3,4,5-trimethoxyaniline: $^1$H NMR (300 MHz, DMSO-d$_6$) δ14.13 (s, 1H), 10.19 (s, 1H), 8.80 (s, 1H), 8.30 (s, 1H), 8.04 (s, 1H), 7.84 (d, 1H, J=7.6 Hz), 7.64–7.70 (m, 3H), 7.47 (dd, 1H, J=7.5, 8.0 Hz), 7.21 (d, 2H, J=8.3 Hz), 4.78 (s, 2H), 2.81–2.90 (m, 1H), 1.19 (d, 6H, J=6.0 Hz); APCIMS m/z 404 [M+H]$^+$.

Example B-20

3-[(1H-Pyrazolo[3,4-d]pyrimidin-4-yl) sulfanylmethyl]-N(4-trifluoromethoxyphenyl)-benzamide

B-20

Example B-20 was prepared in a similar manner to that described for B-1, except that 3-trifluoromethoxyaniline was used in place of 3,4,5-trimethoxyaniline: $^1$H NMR (300 MHz, DMSO-d$_6$) δ14.13 (s, 1H), 10.54 (s, 1H), 8.80 (s, 1H), 8.30 (s, 1H), 8.06 (s, 1H), 7.93 (s, 1H), 7.86 (d, 1H, J=7.6 Hz), 7.71–7.78 (m, 2H), 7.46–7.53 (m, 2H), 7.09 (d, 1H, J=8.3 Hz), 4.79 (s, 2H); APCIMS m/z 446 [M+H]$^+$.

Example B-21

3-[(1H-Pyrazolo[3,4-d]pyrimidin-4-yl)sulfanylmethyl]-N(3,5-dimethylphenyl)-benzamide

B-21

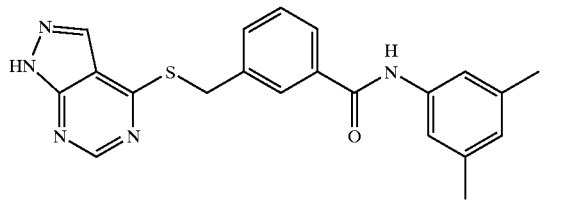

Example B-21 was prepared in a similar manner to that described for B-1, except that 3,5-dimethylaniline was used in place of 3,4,5-trimethoxyaniline: $^1$H NMR (300 MHz, DMSO-$d_6$) δ14.13 (s, 1H), 10.10 (s, 1H), 8.80 (s, 1H), 8.30 (s, 1H), 8.04 (s, 1H), 7.83–7.85 (d, 1H, J=7.5 Hz), 7.68–7.71 (d, 1H, J=7.6 Hz), 7.45–7.50 (dd, 1H, J=7.50, 7.6 Hz), 7.39 (s, 2H), 6.74 (s, 1H), 4.78 (s, 2H), 2.26 (s, 6H); APCIMS m/z 390 [M+H]$^+$.

Example B-22

3-[(1H-Pyrazolo[3,4-d]pyrimidin-4-yl)sulfanylmethyl]-N(3-(2-hydroxyethyl)phenyl)-benzamide

B-22

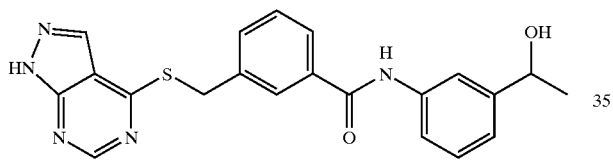

Example B-22 was prepared in a similar manner to that described for B-1, except that 3-(1-hydroxyethyl)aniline was used in place of 3,4,5-trimethoxyaniline: $^1$H NMR (300 MHz, DMSO-$d_6$) δ14.13 (s, 1H), 10.23 (s, 1H), 8.80 (s, 1H), 8.30 (s, 1H), 8.06 (m, 1H), 7.86 (d, 1H, J=7.9 Hz), 7.73 (s, 1H), 7.74–7.84 (m, 2H), 7.48 (dd, 1H, J=7.6, 7.9 Hz), 7.27 (dd, 1H, J=7.9, 8.0 Hz), 7.06 (d, 1H, J=7.9 Hz), 5.18 (d, 1H, J=3.0), 4.78 (s, 2H), 4.68 (q, 1H), 1.32 (d, 3H, J=9.0 Hz); APCIMS m/z 406 [M+H]$^+$.

Example B-23

3-[(1H-Pyrazolo[3,4-d]pyrimidin-4-yl)sulfanylmethyl]-N(4-dimethylaminophenyl)-benzamide

B-23

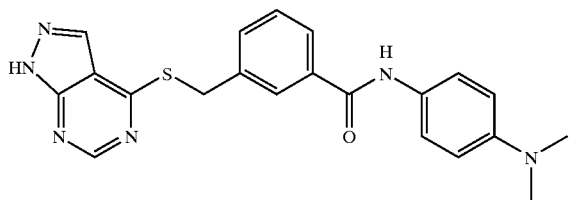

Example B-23 was prepared in a similar manner to that described for B-1, except that 4-dimethylaminoaniline was used in place of 3,4,5-trimethoxyaniline: $^1$H NMR (300 MHz, DMSO-$d_6$) 13.76 (s, 1H), 9.63 (s, 1H), 8.44 (s, 1H), 7.94 (s, 1H), 7.66 (s, 1H), 7.46 (d, 1H, J=7.9 Hz), 7.301 (d, 1H, J=7.5 Hz), 7.18 (d, 1H, J=9.0 Hz), 7.10 (dd, 1H, J=7.5, 7.6 Hz), 6.35 (d, 1H, J=9.0 Hz), 4.56 (s, 2H), 2.13 (s, 6H); APCIMS m/z 405 [M+H]$^+$.

Example B-24

3-[(1H-Pyrazolo[3,4-d]pyrimidin-4-yl)sulfanylmethyl]-N(3-trifluoromethylsulfonylphenyl)-benzamide

B-24

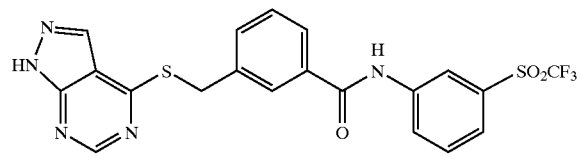

Example B-24 was prepared in a similar manner to that described for B-1, except that 3-(trifluoromethylsulfonyl)aniline was used in place of 3,4,5-trimethoxyaniline: $^1$H NMR (300 MHz, DMSO-$d_6$) δ14.13 (s, 1H), 10.83 (s, 1H), 8.80 (s, 1H), 8.66 (s, 1H), 8.35–8.39 (m, 1H), 8.30 (s, 1H), 8.09 (s, 1H), 7.90 (d, 1H, J=7.9 Hz), 7.85 (m, 2H), 7.75 (d, 1H, J=7.60), 7.53 (dd, 1H, J=7.5, 7.6 Hz), 4.79 (s, 2H); APCIMS m/z 494 [M+H]$^+$.

Example B-25

3-[(1H-Pyrazolo[3,4-d]pyrimidin-4-yl)sulfanylmethyl]-N(3-dimethylaminophenyl)-benzamide

B-25

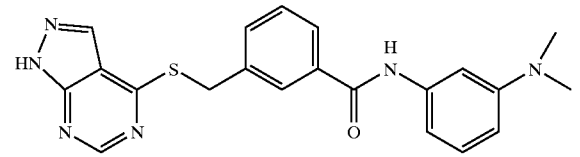

Example B-25 was prepared in a similar manner to that described for B-1, except that 3-dimethylaminoaniline was used in place of 3,4,5-trimethoxyaniline: $^1$H NMR (300 MHz, DMSO-$d_6$) 14.14 (s, 1H), 10.06 (s, 1H), 8.80 (s, 1H), 8.30 (s, 1H), 8.04 (s, 1H), 7.84 (d, 1H, J=8.0 Hz), 7.680 (d, 1H, J=7.5 Hz), 7.46 (dd, 1H, J=7.5, 7.6 Hz), 7.20 (s, 1H), 7.13 (m, 2H), 6.46–6.50 (m, 1H), 4.78 (s, 2H), 2.89 (s, 6H); APCIMS m/z 405 [M+H]$^+$.

Example B-26

(a) To an array of 40 μL of 0.25 M solution of different amines (0.01 mmol) in acetonitrile distributed in the eleven columns of a 96-well plate was added 40 μL of 0.25 M solution of triethylamine (0.01 mmol) and the array of reactions was agitated briefly. To each of the wells was added 40 μL of a 0.25 M solution of 3-(chloromethyl)benzoylchloride (0.01 mmol) in acetonitrile and the plate was agitated in a shaker at room temperature for 2 h.

(b) An 0.25 M solution of different mercapto compounds was prepared in DMF and 40 μL (0.01 mmol) and was added in eight different rows to the appropriate intermediate from step (a) above. To each reaction mixture was add approximately 8–15 mg of cesium carbonate and the reactions were heated at 60° C. on a Vortex heater for 16 h. The solvents were removed using the SpeedVac™ apparatus and the crude reaction mixtures were redissolved in DMSO and transferred using a liquid handler to a 1 mL 96-well plate to give a final theoretical concentration of 10 mM.

Example B-27

Using the general procedure described above in Example B-26, the following compounds were made (wherein for convenience, and as understood in the art, not all hydrogen atoms have been expressly indicated as bonding to each carbon and/or nitrogen atom).

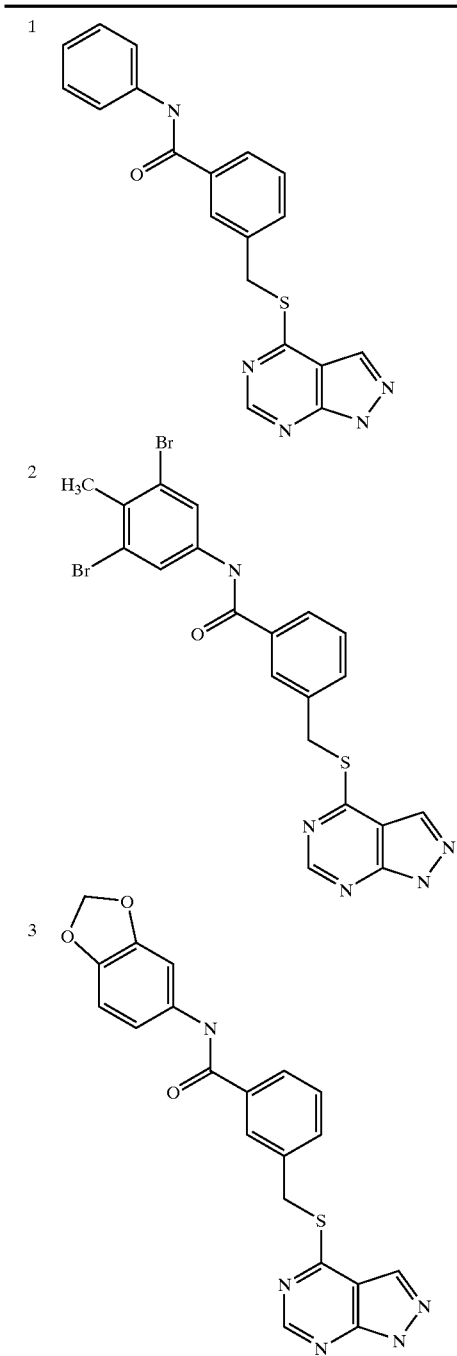
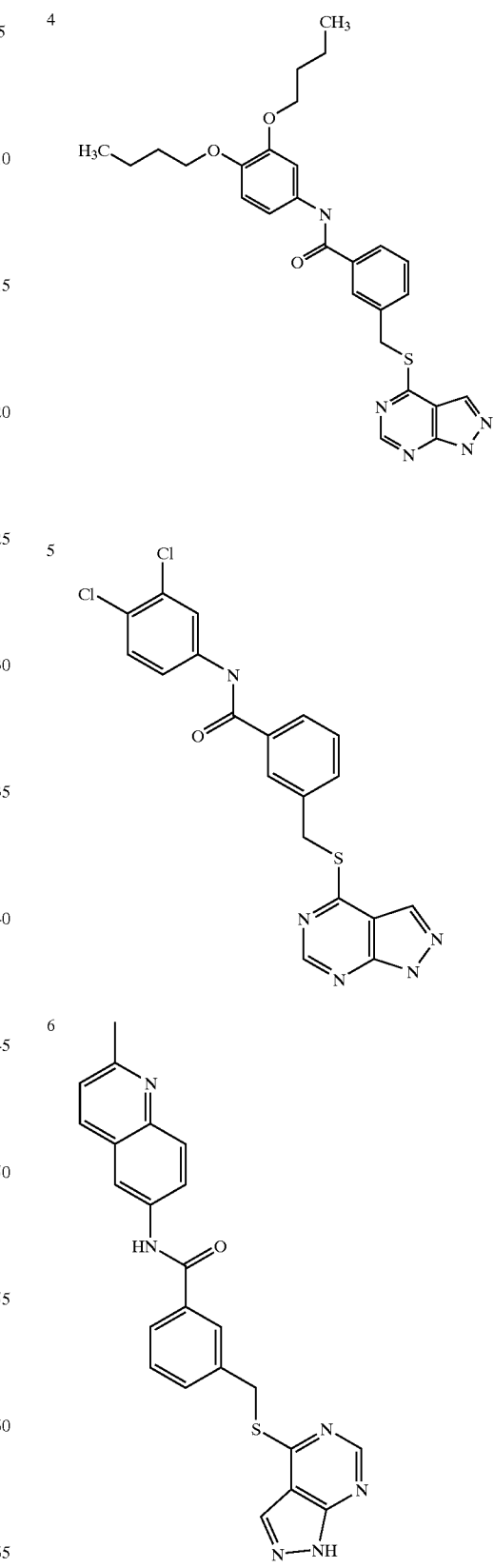

-continued
7
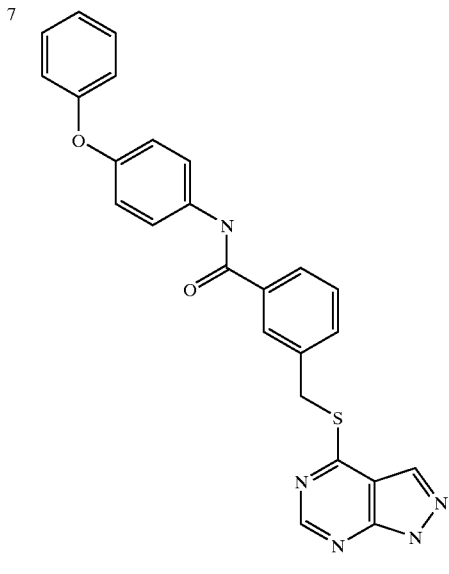
8
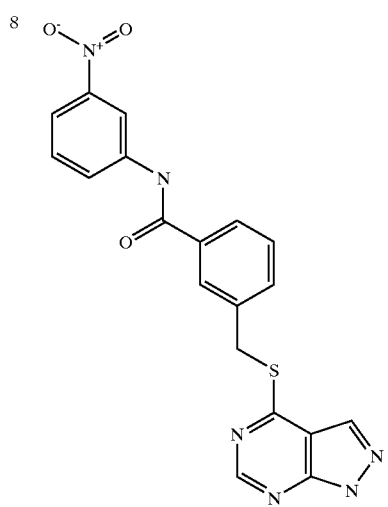
9
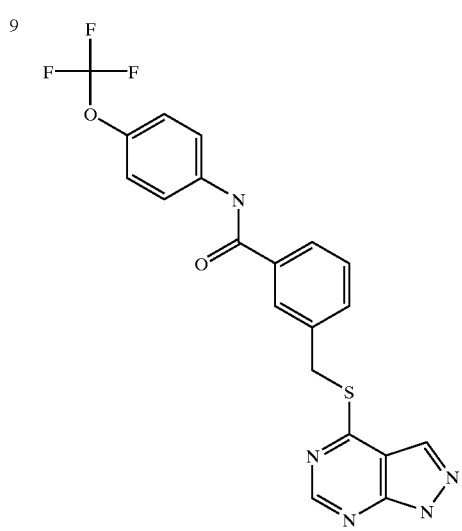
-continued
10
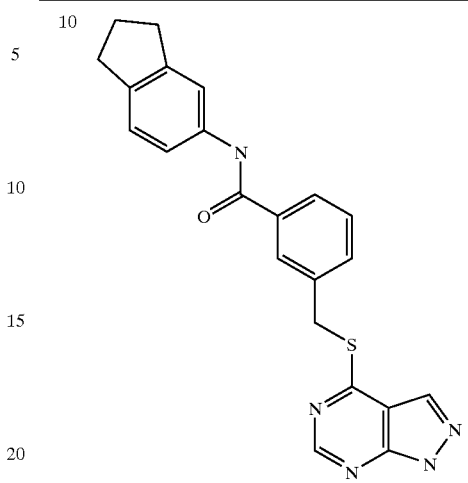
11
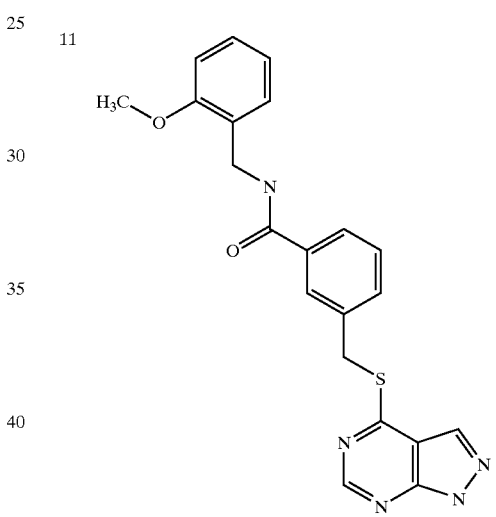
12
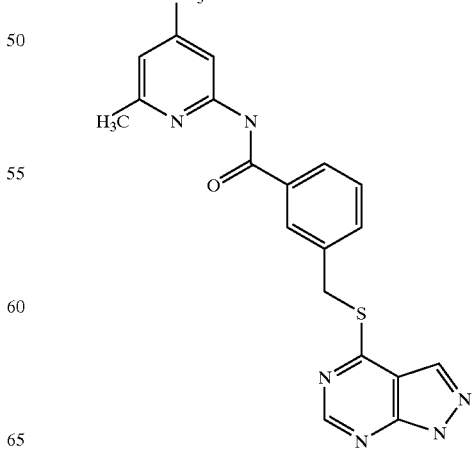

-continued
13 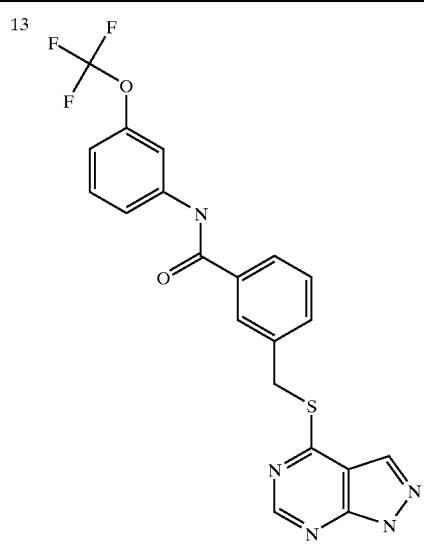
14 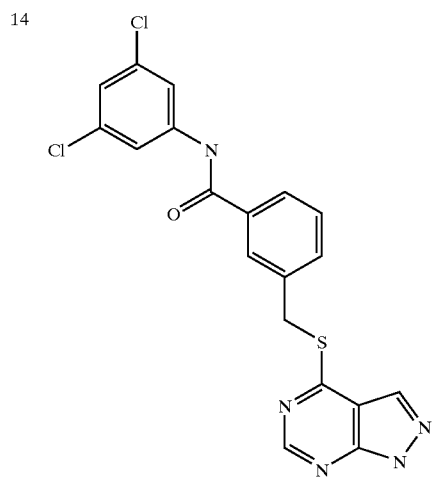
15 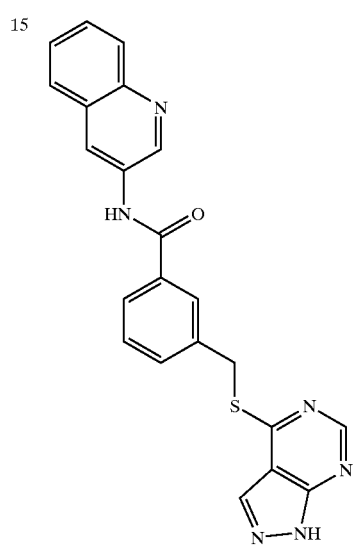
-continued
16 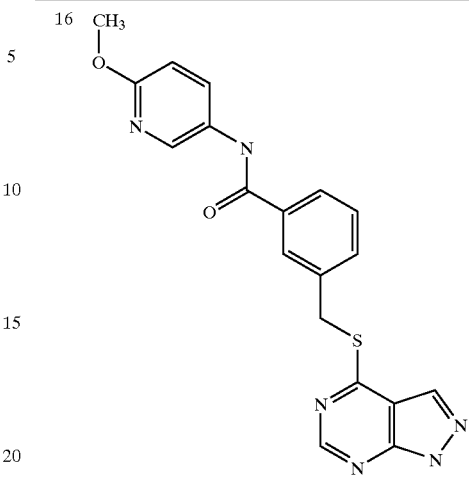
17 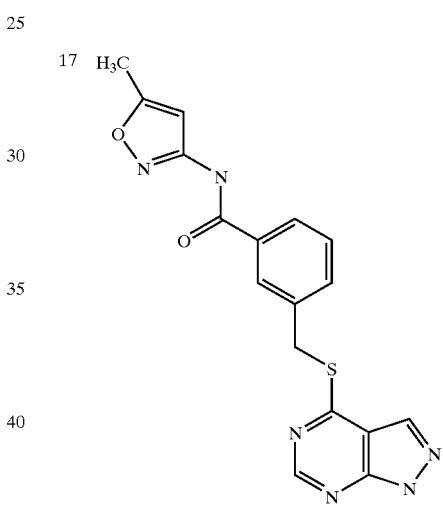
18 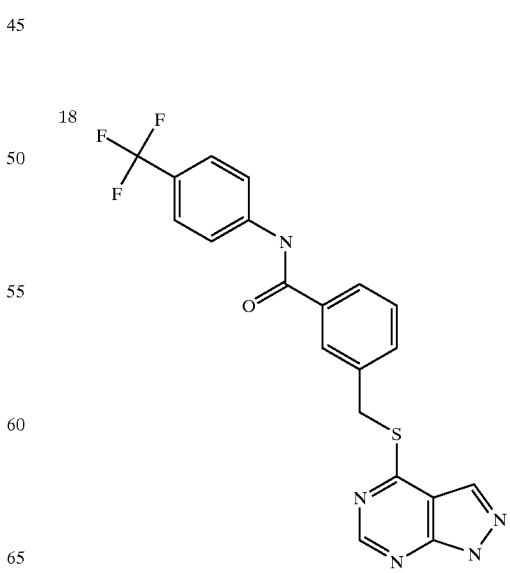

-continued
19 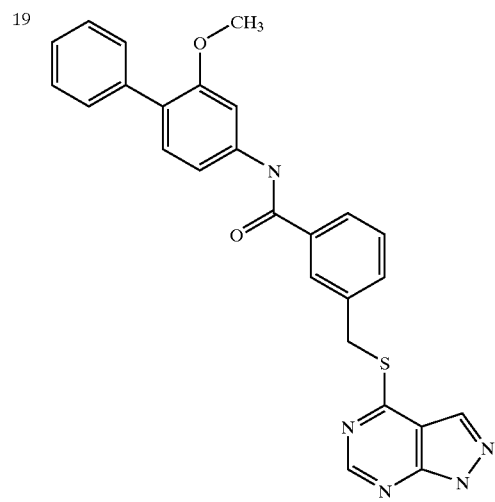
20 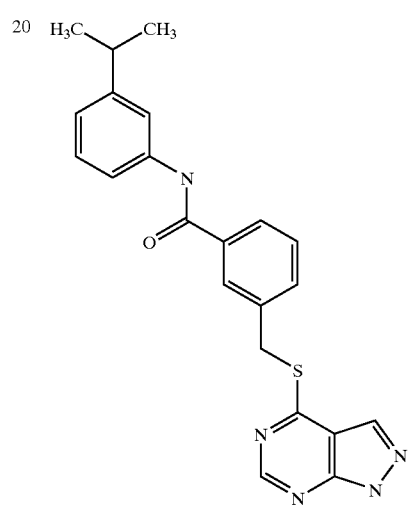
21 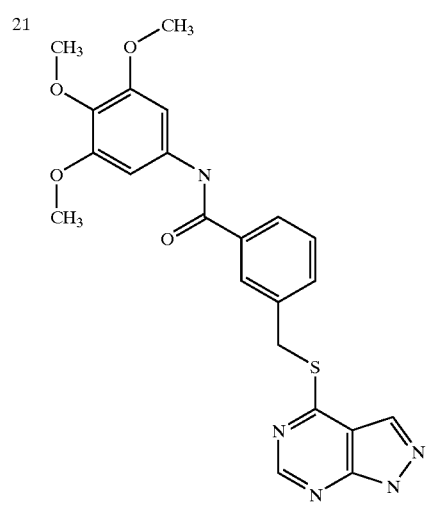
-continued
22 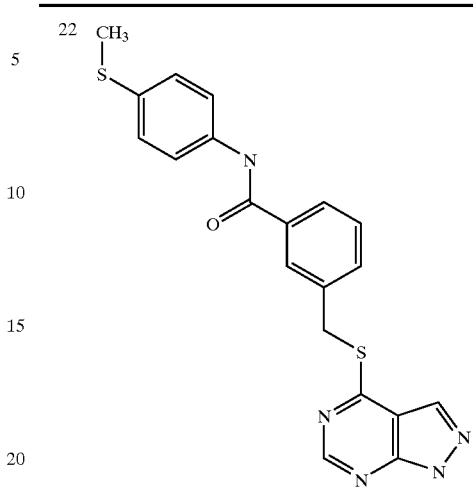
23 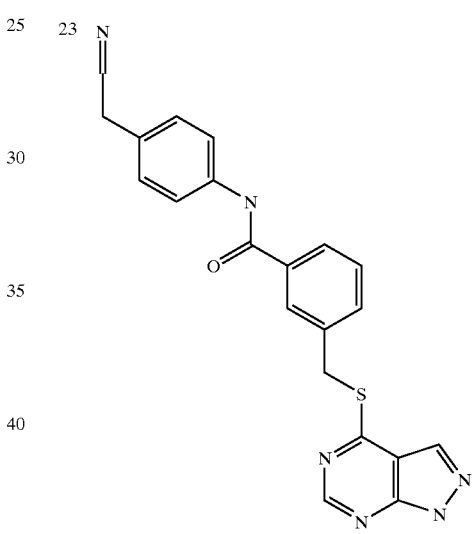
24 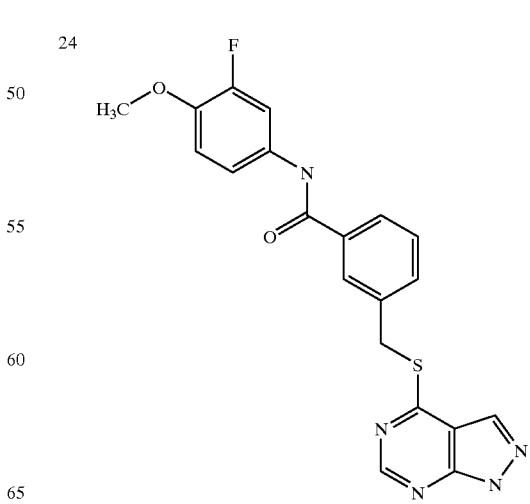

-continued
25
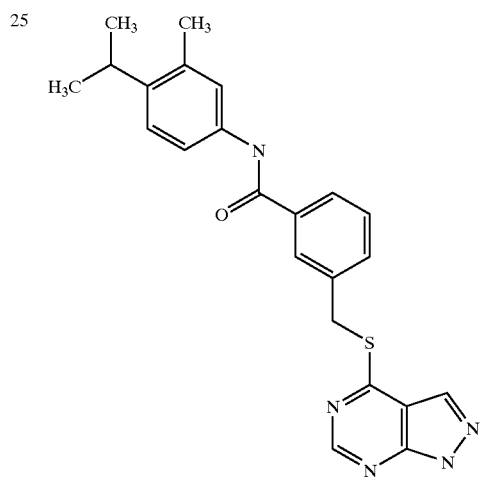
26
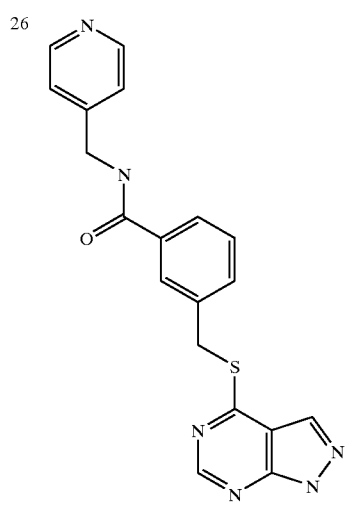
27
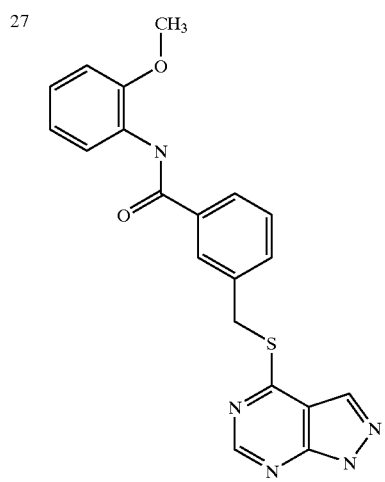
-continued
28
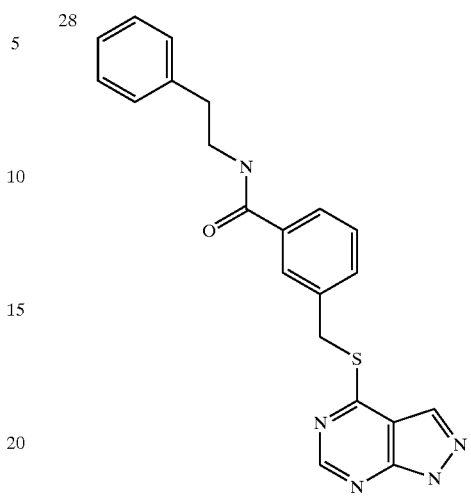
29
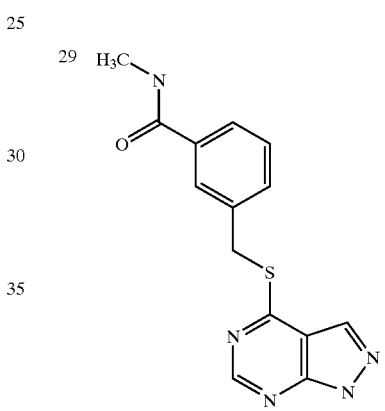
30
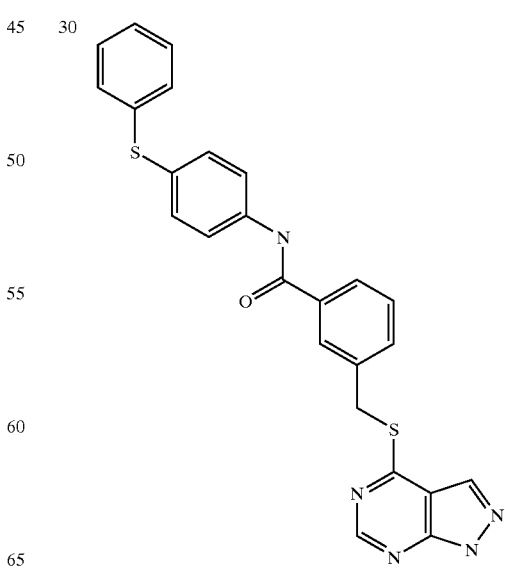

-continued
31 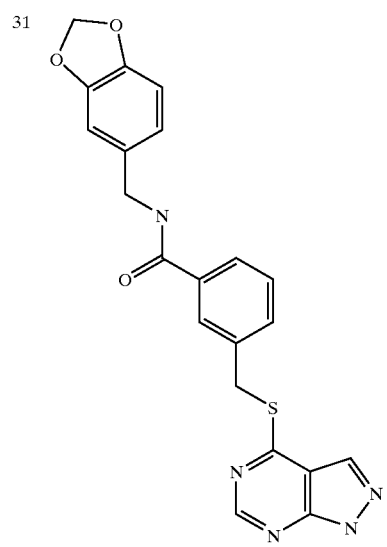
32 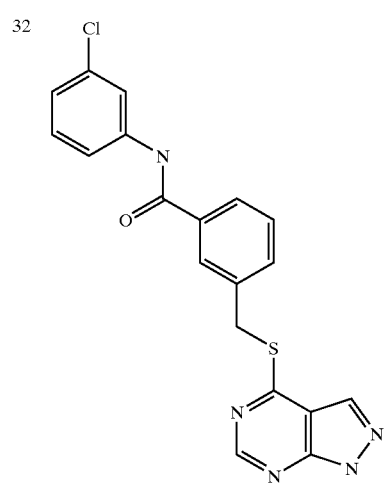
33 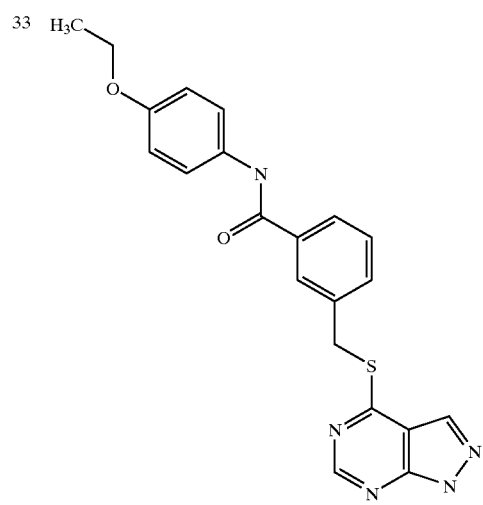
-continued
34 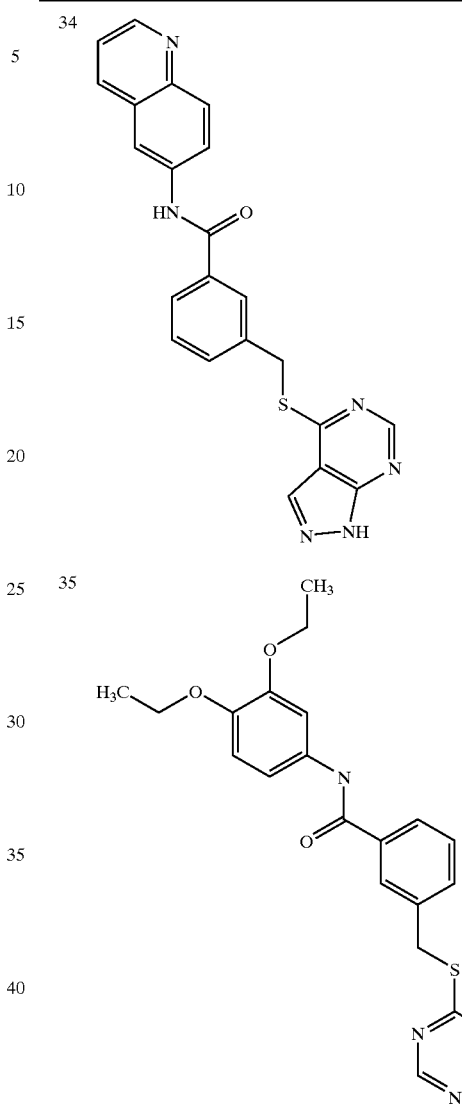
35
36

-continued
37 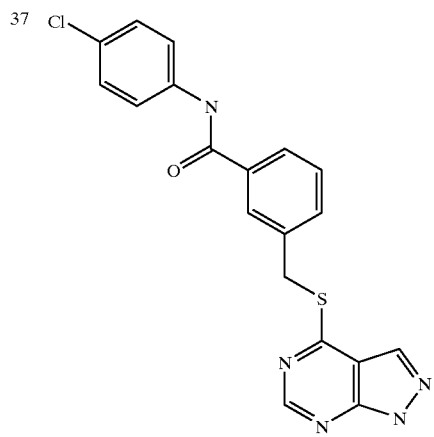
38 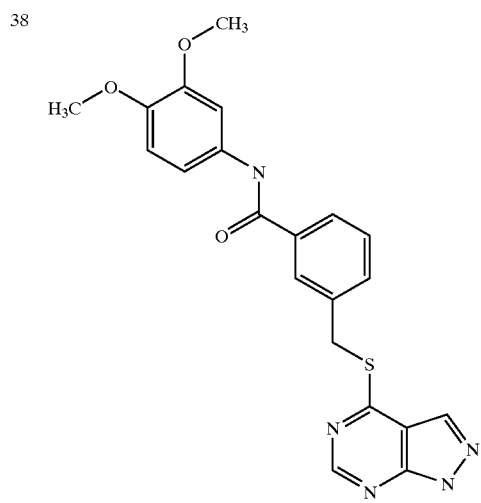
39 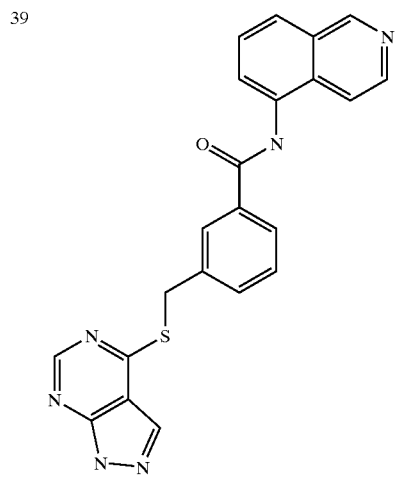
-continued
40 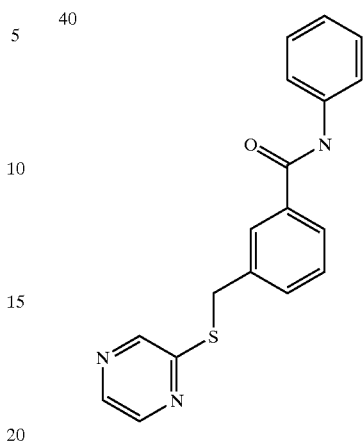
41 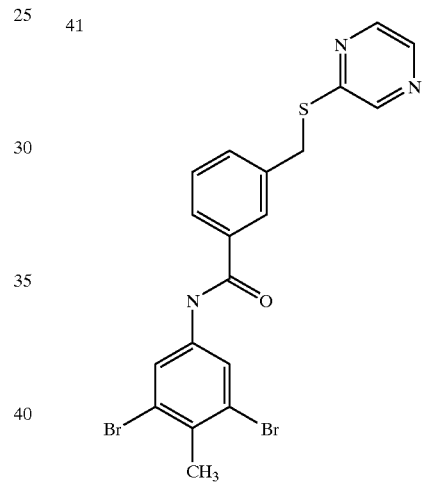
42 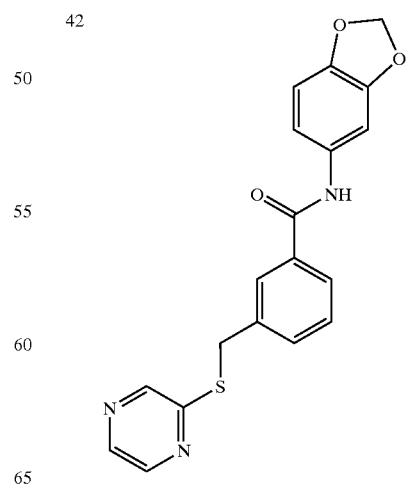

-continued
43
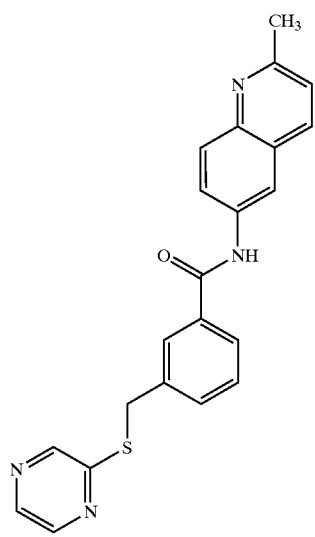
44
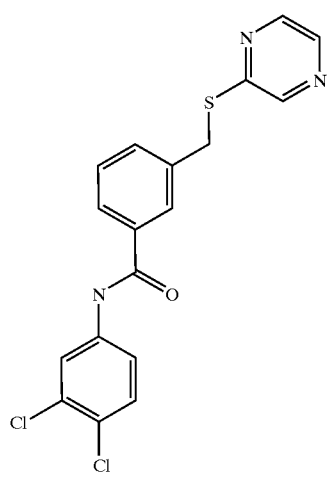
45
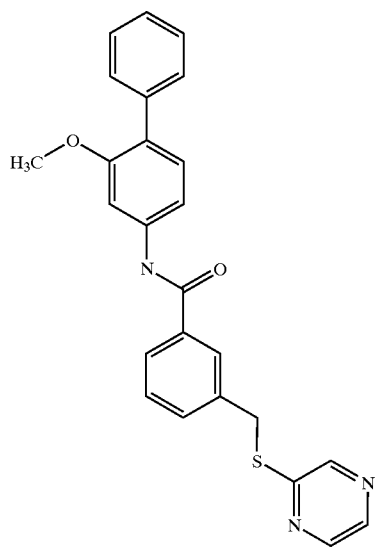
-continued
46
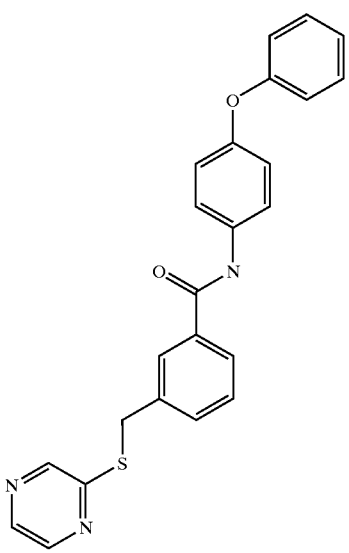
47
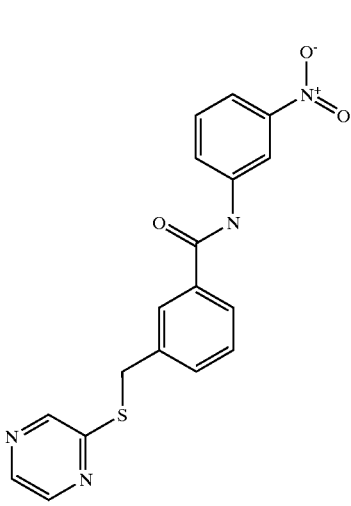
48
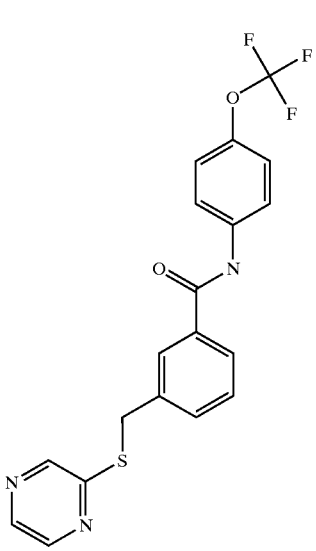

-continued
49
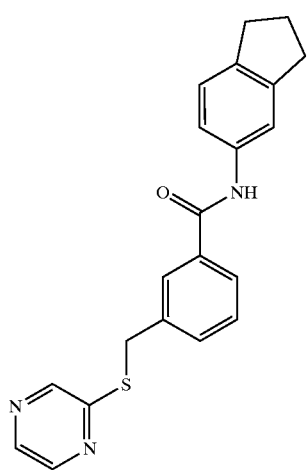
52
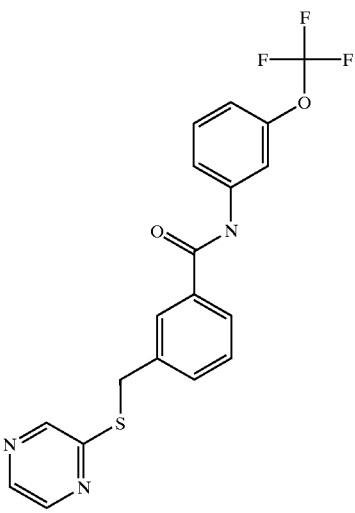
50
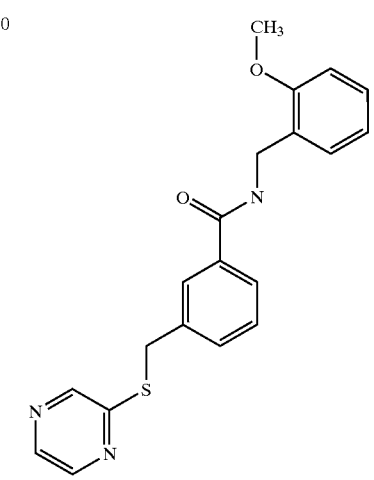
53
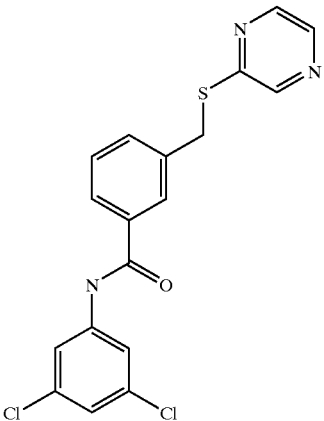
51
54
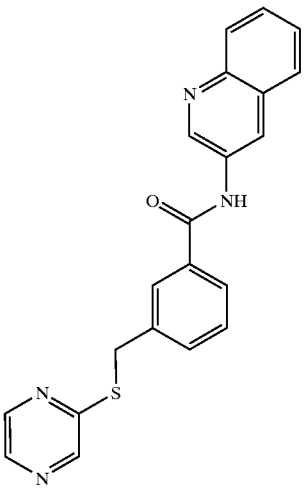

-continued
55 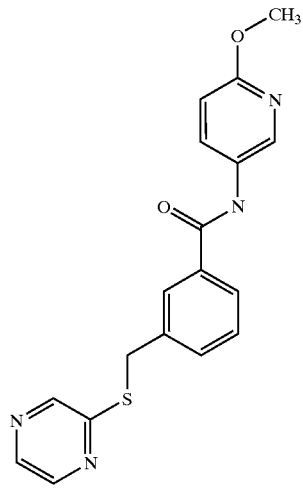
56 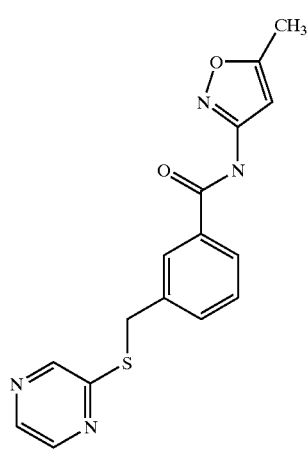
57 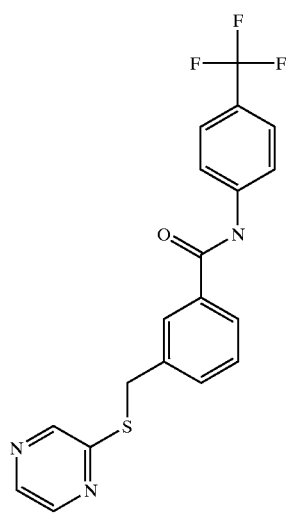
-continued
58 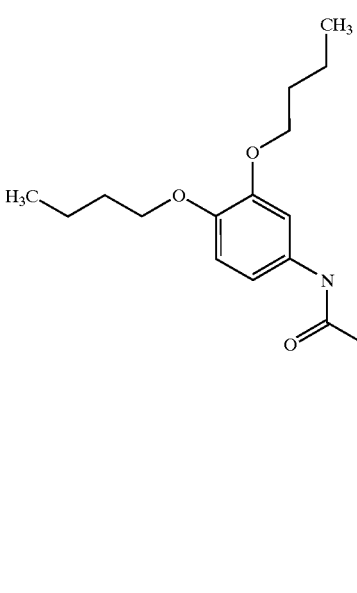
59 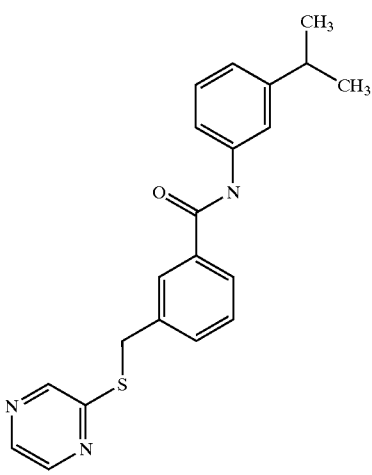
60 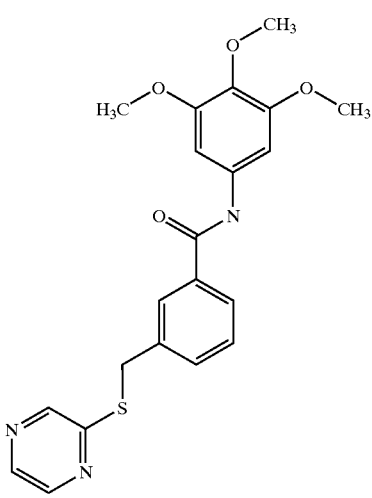

-continued
61
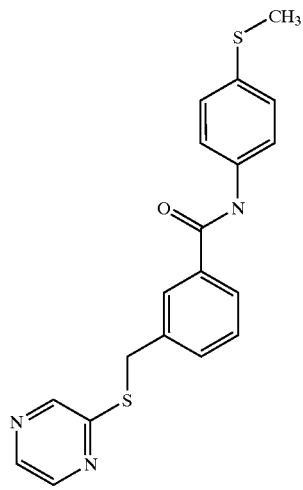
62
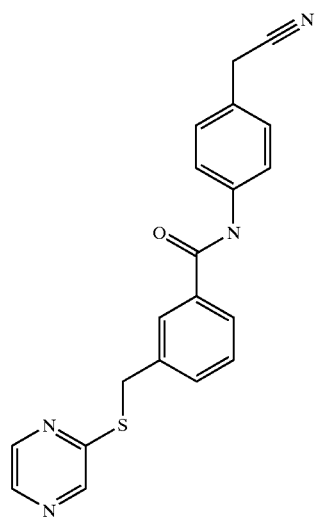
63
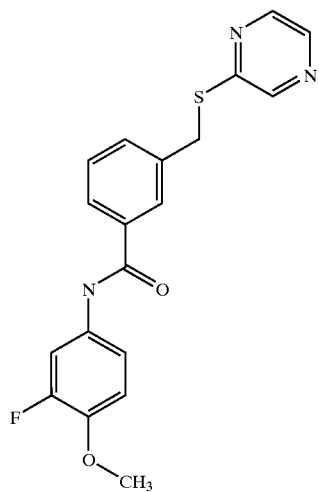
-continued
64
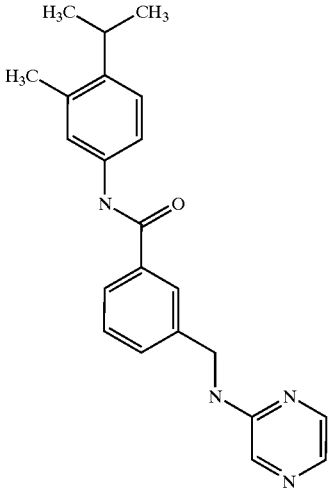
65
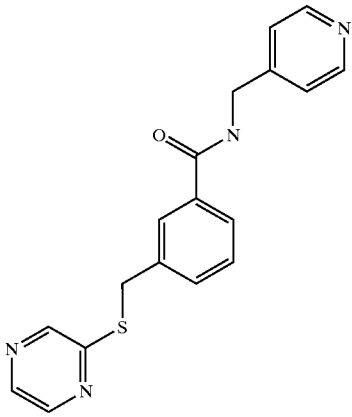
66

-continued
67
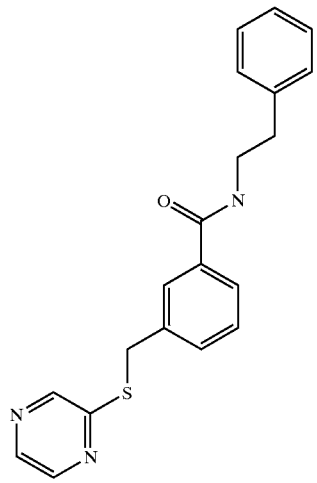
68
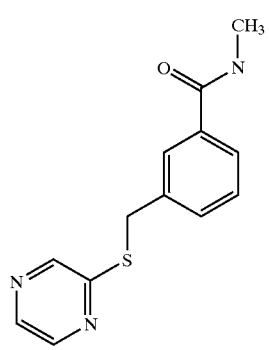
69
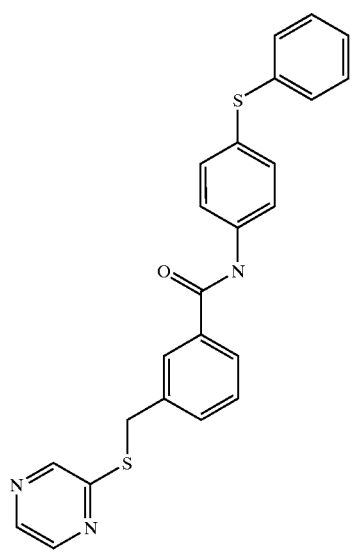
-continued
70
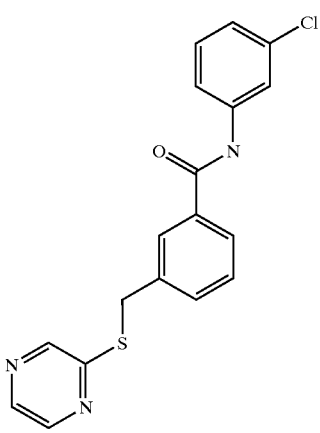
71
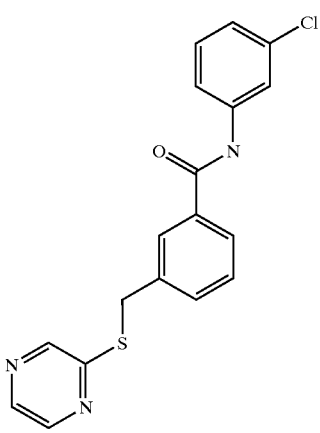
72
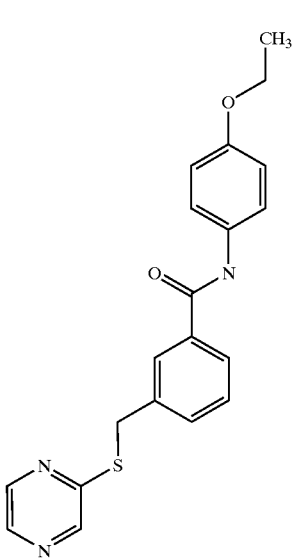

-continued
73
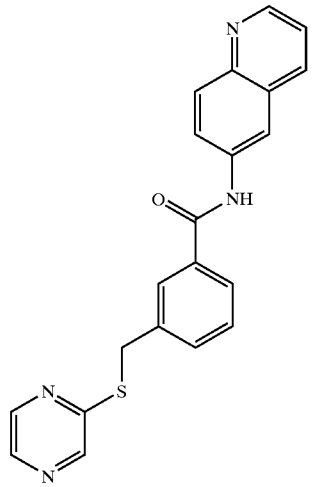
74
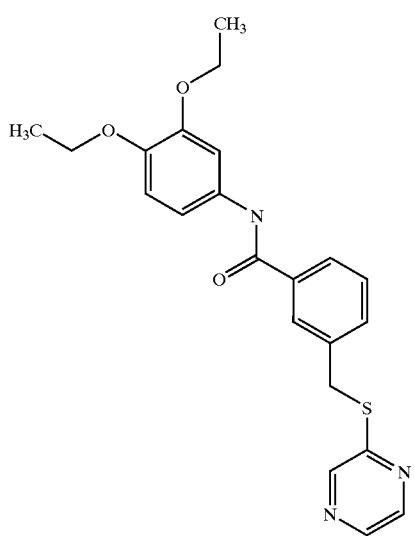
75
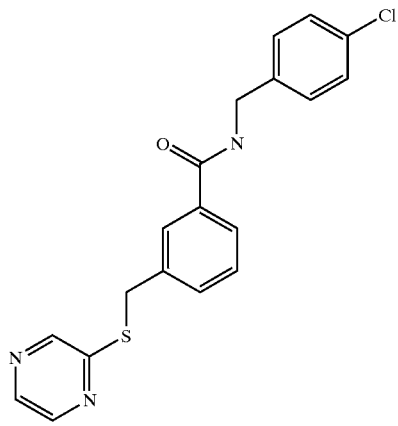
-continued
76
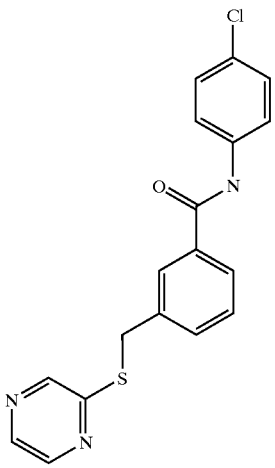
77
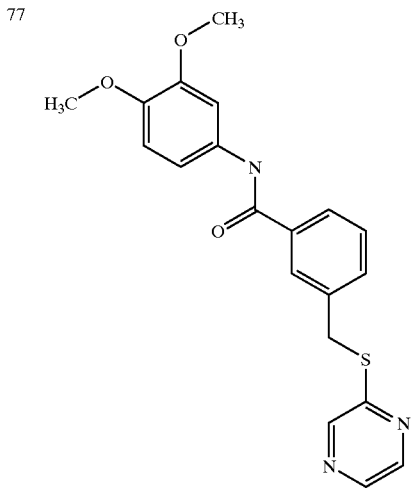
78
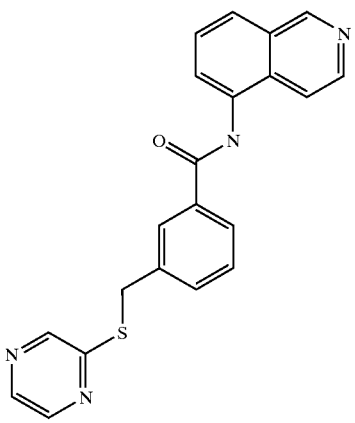

-continued
79
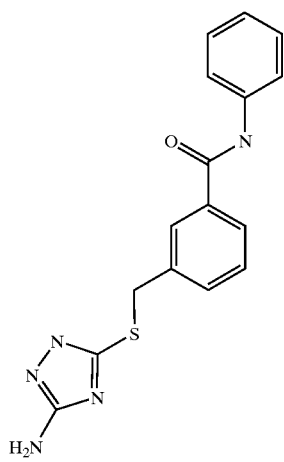
80
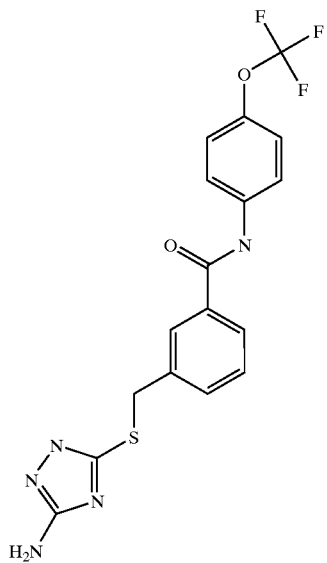
81
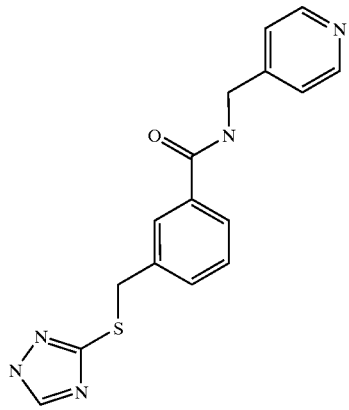
-continued
82
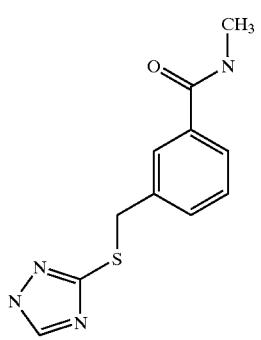
83
84
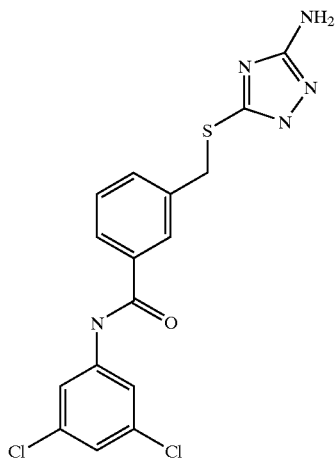

-continued
85
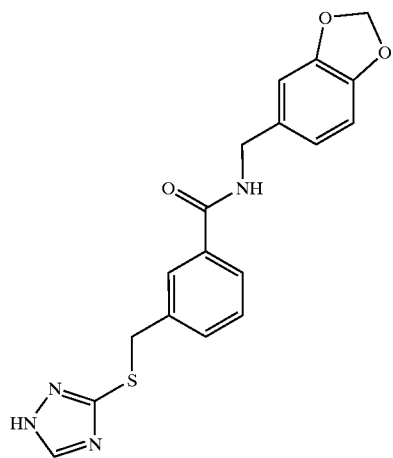
86
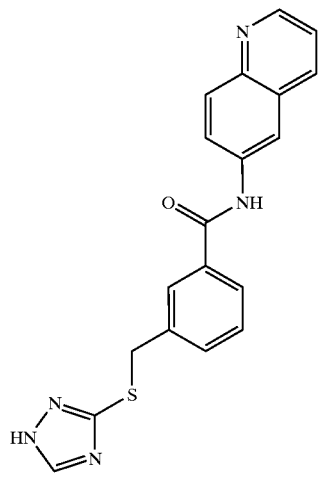
87
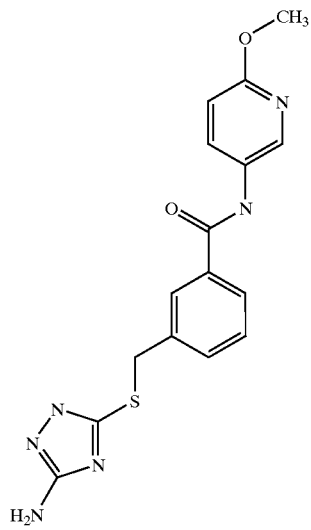
-continued
88
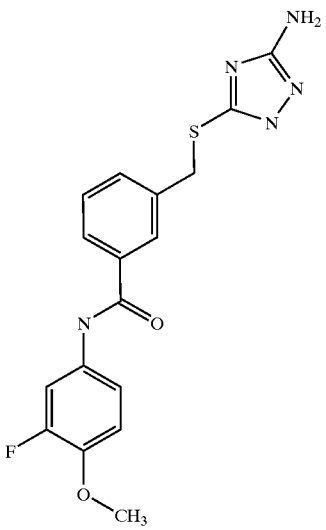
89
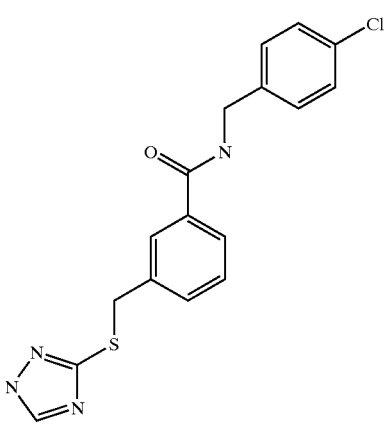
90
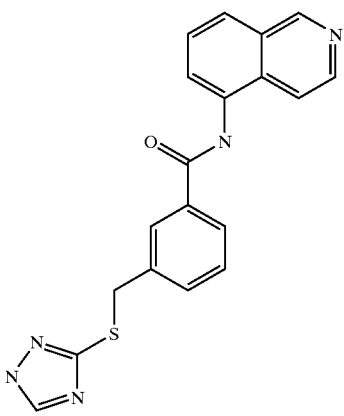

91 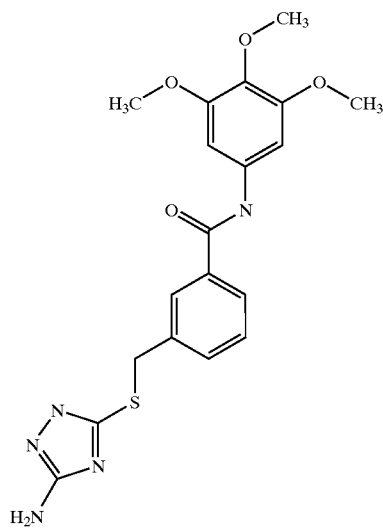
92 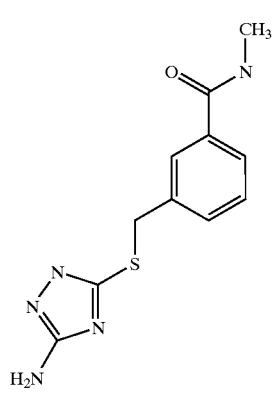
93 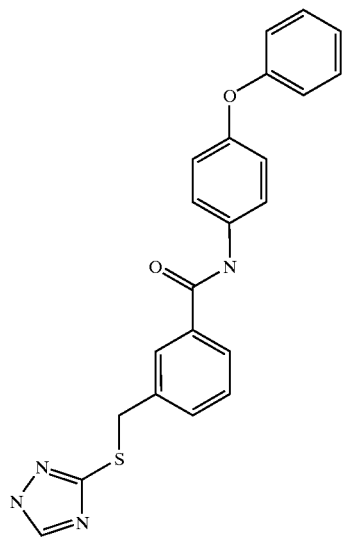
94 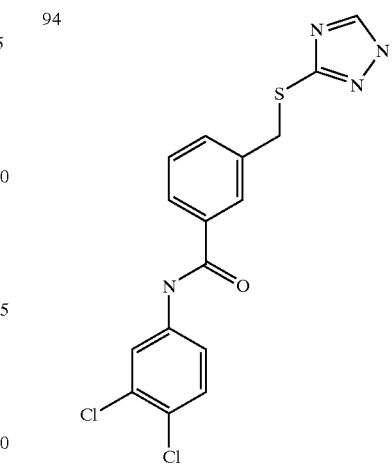
95 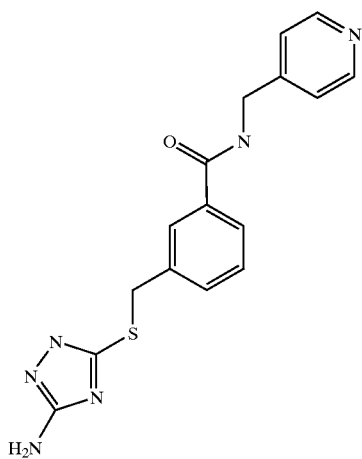
96 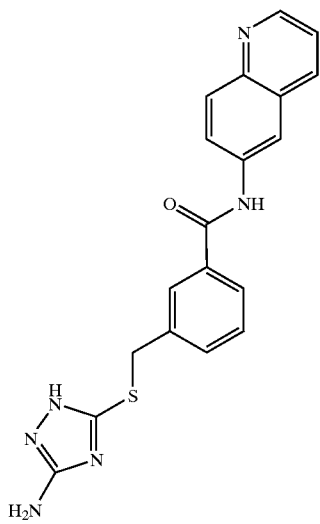

| 97 | 100 |
|---|---|
| 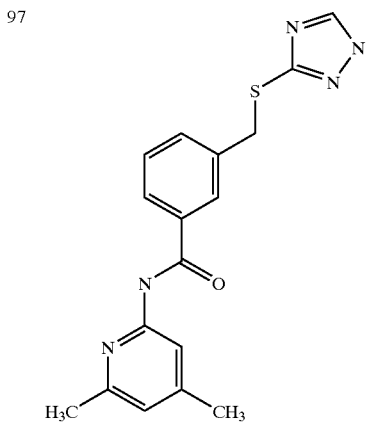 | 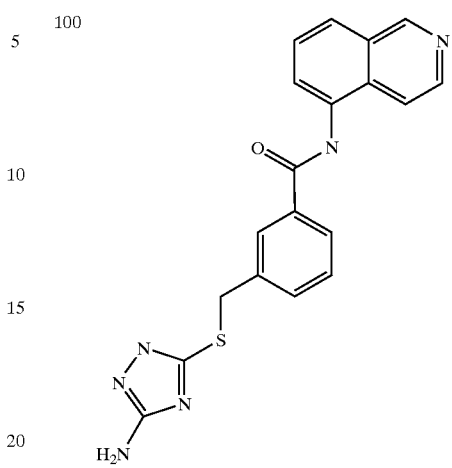 |
| 98 | 101 |
| 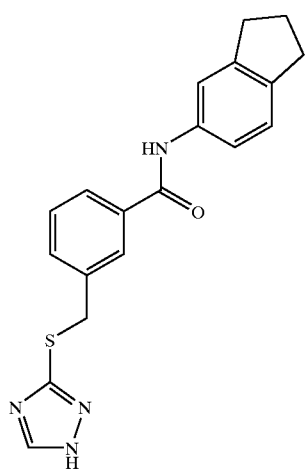 | 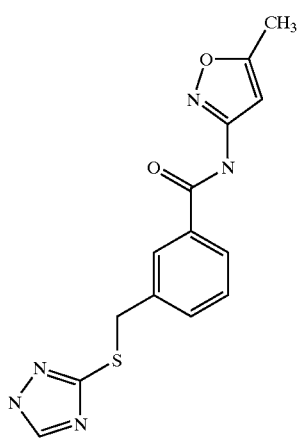 |
| 99 | 102 |
| 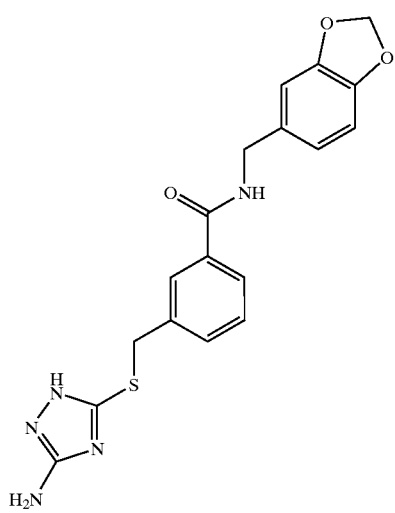 | 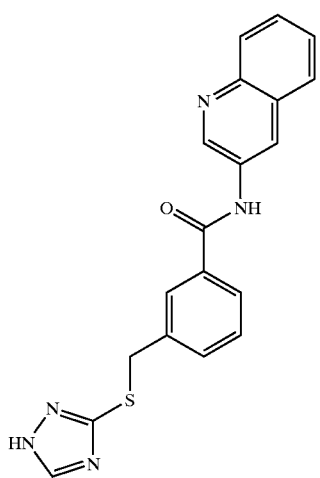 |

103 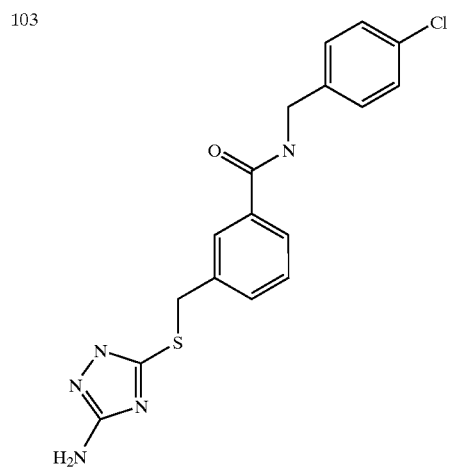
104 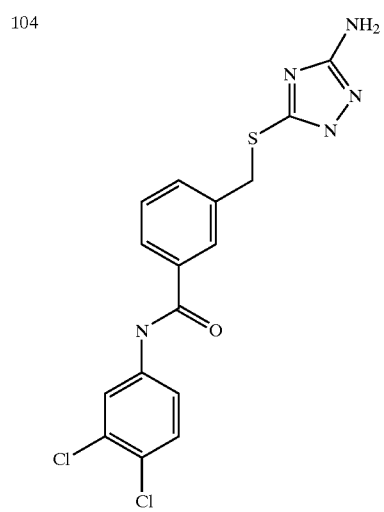
105 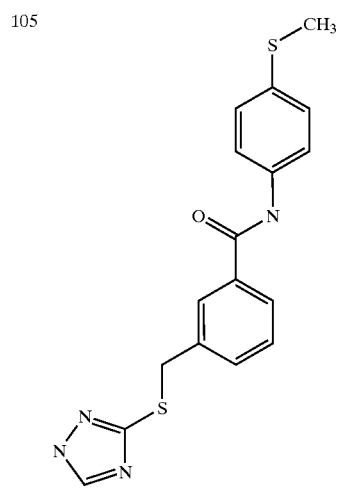
106 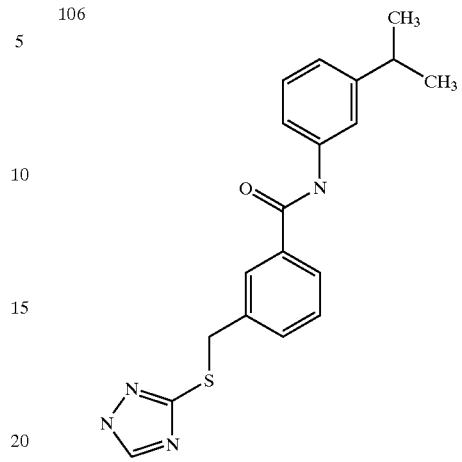
107 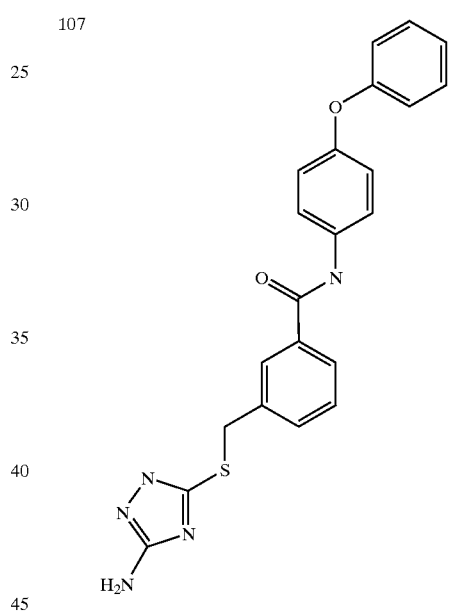
108 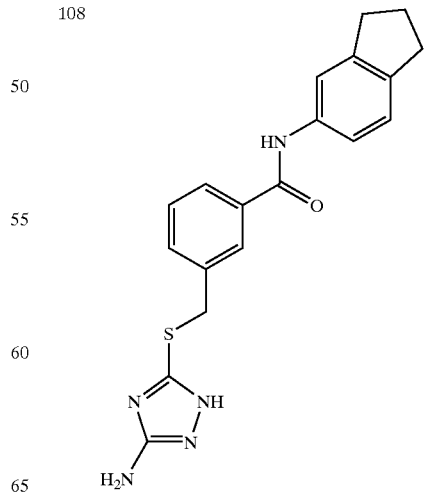

-continued
109
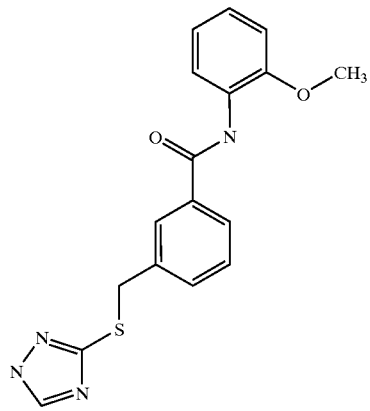
110
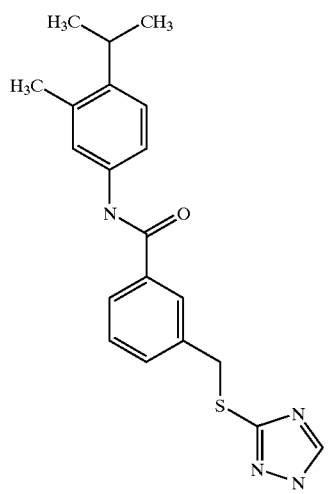
111
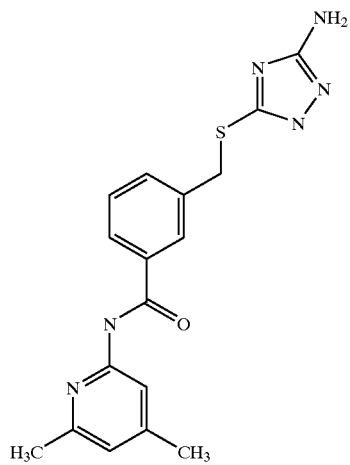
-continued
112
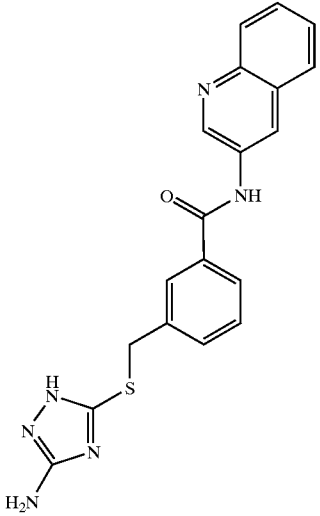
113
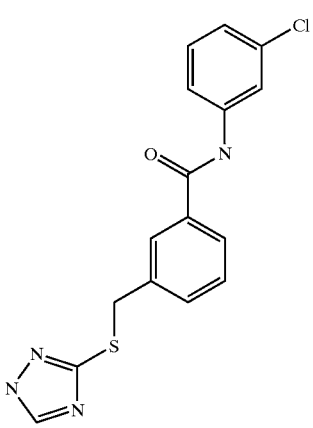
114
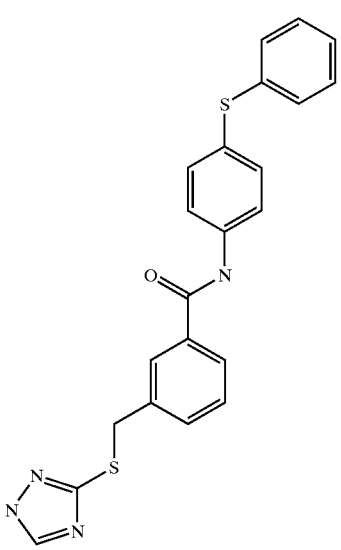

-continued
115 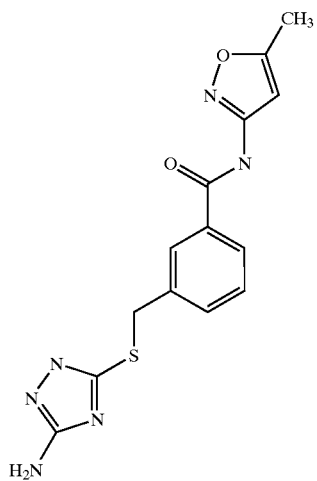
116 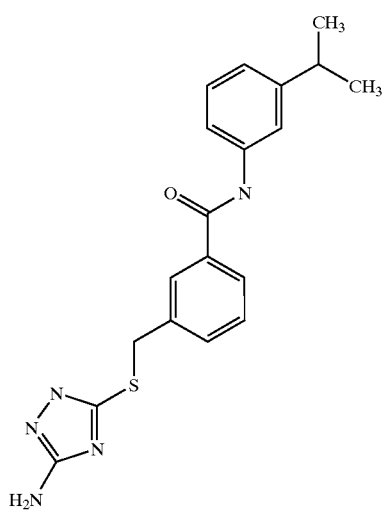
117 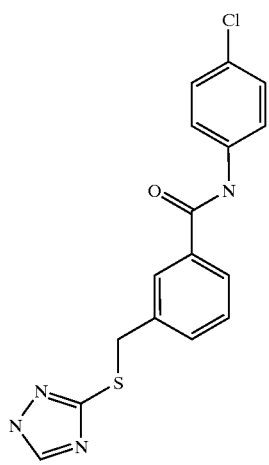
-continued
118 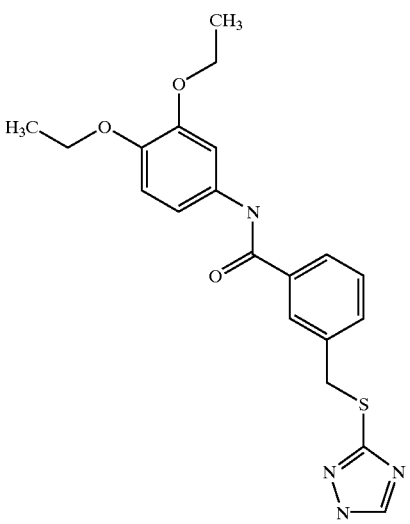
119 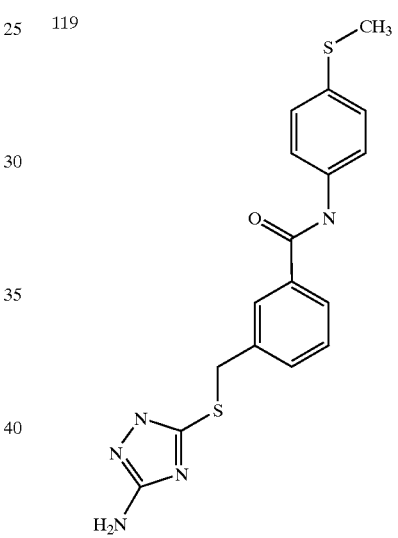
120 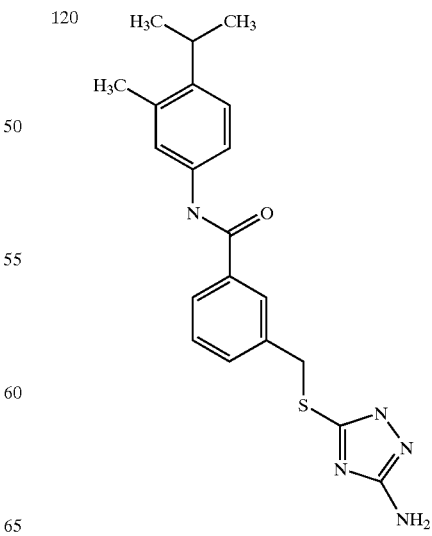

121 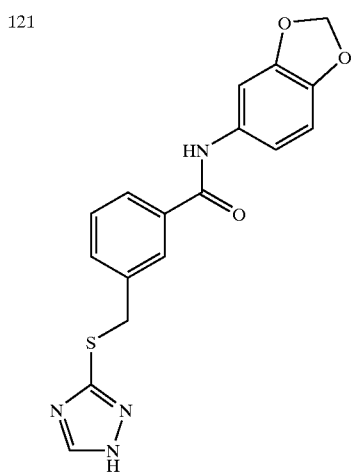
122 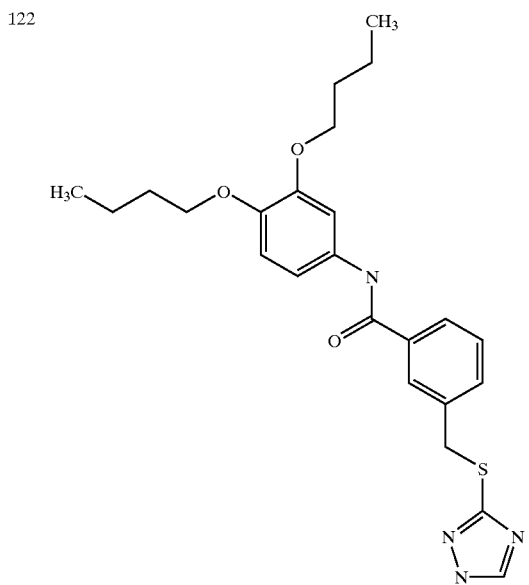
123 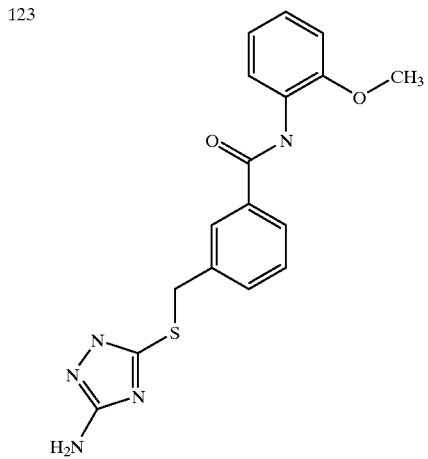
124 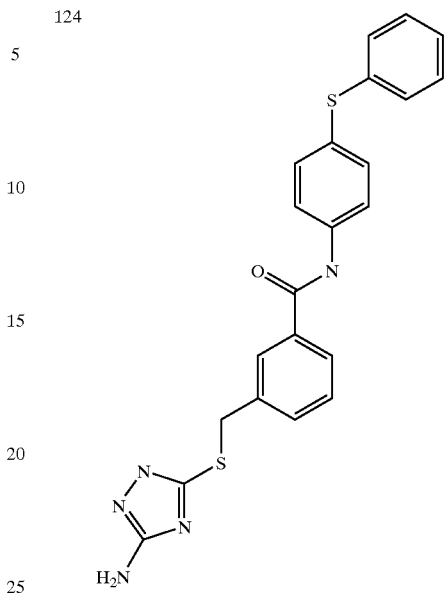
125 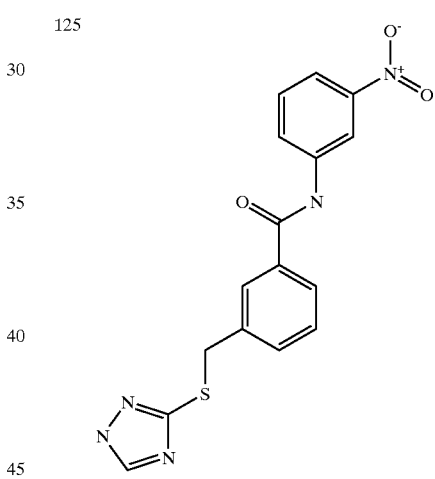
126 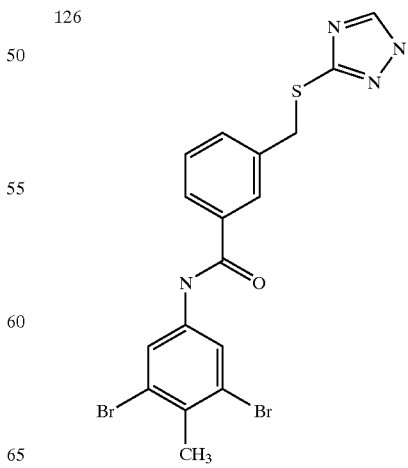

-continued
127
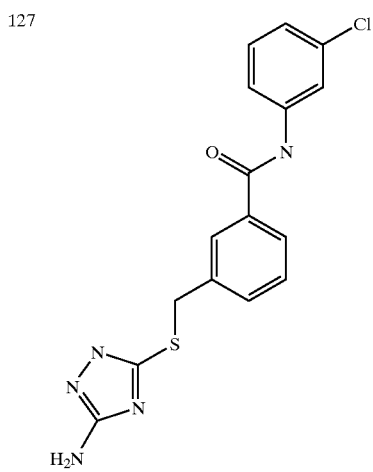
128
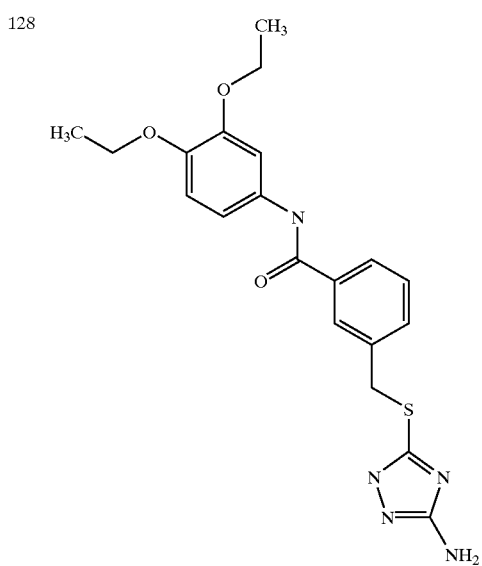
129
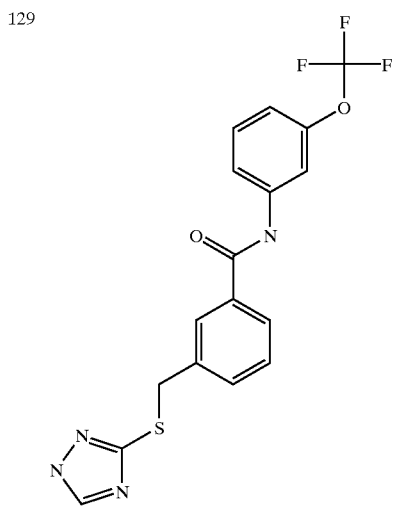
-continued
130
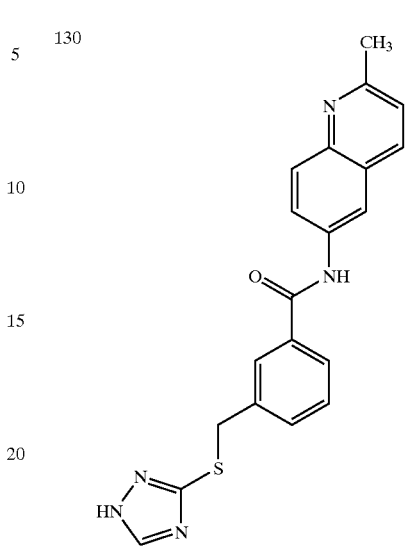
131
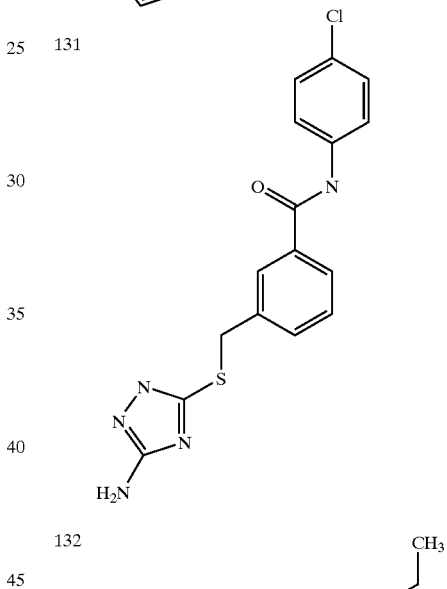
132
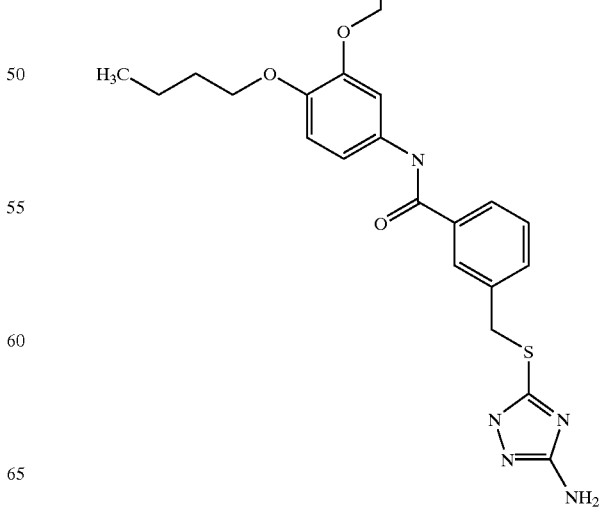

133
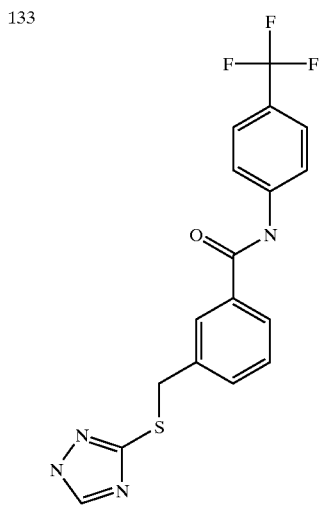
134
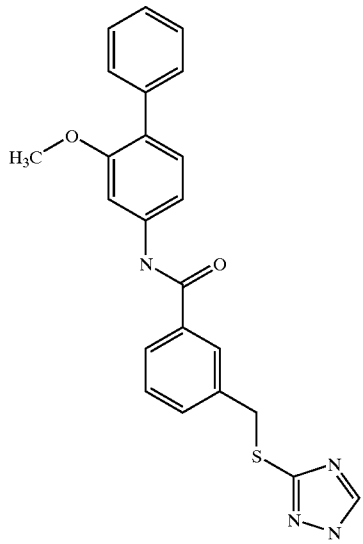
135
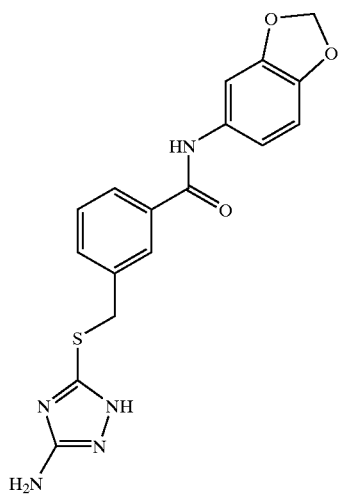
136
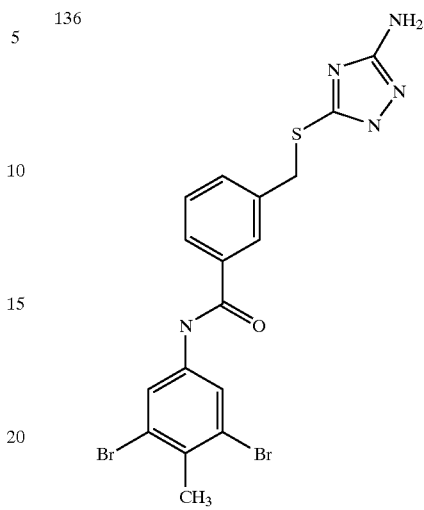
137
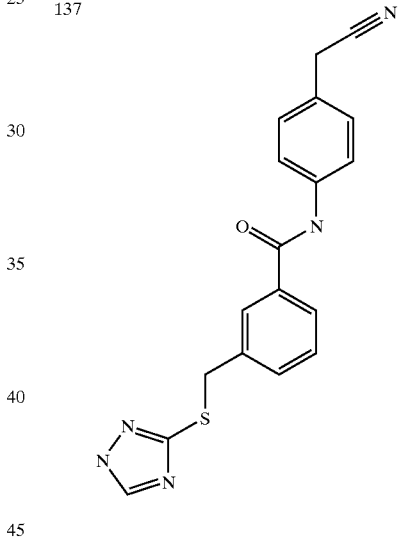
138
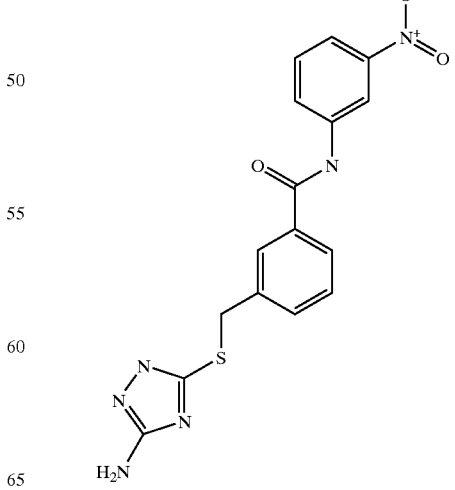

139 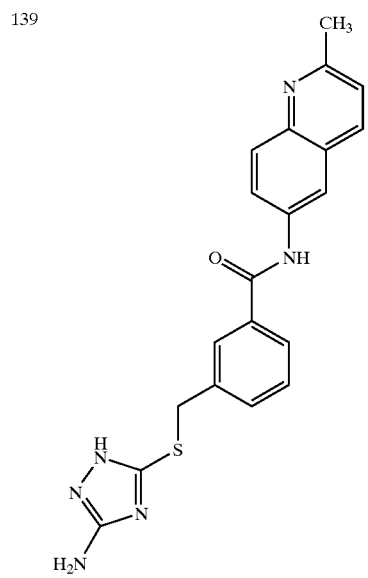
140 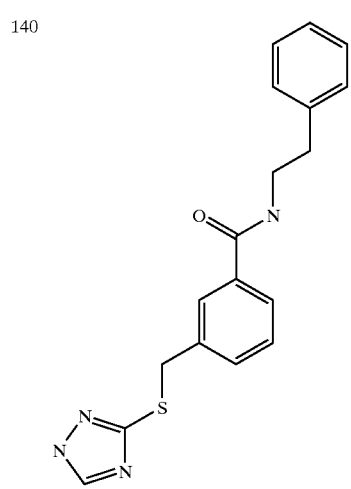
141 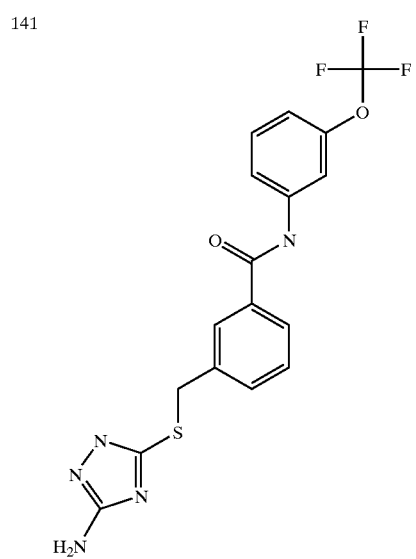
142 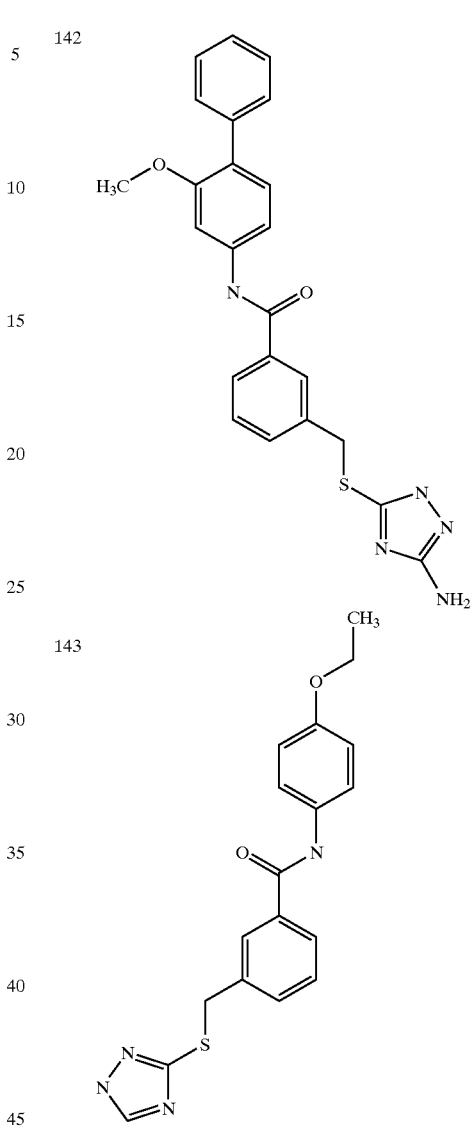
143
144 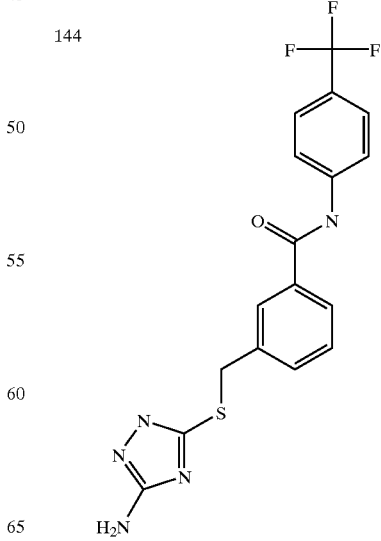

| 145 | 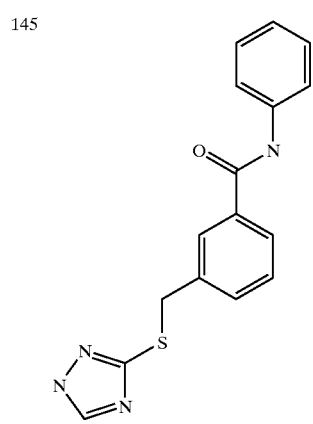 |
| --- | --- |
| 146 | 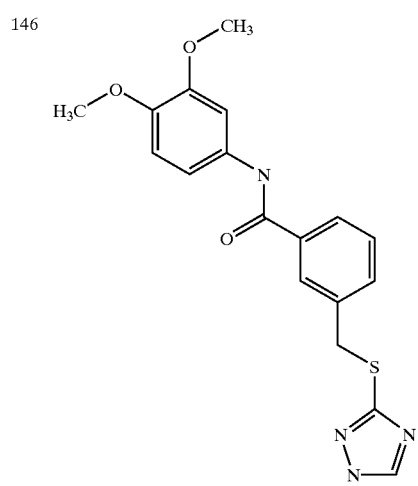 |
| 147 | 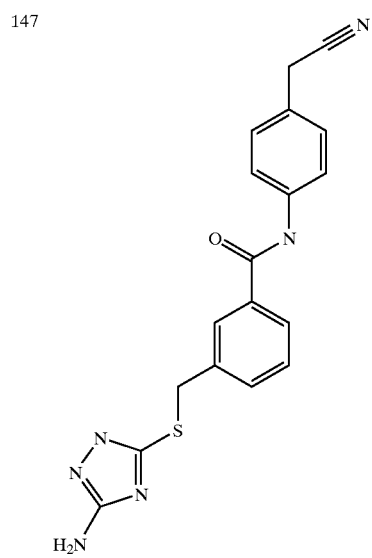 |
| 148 | 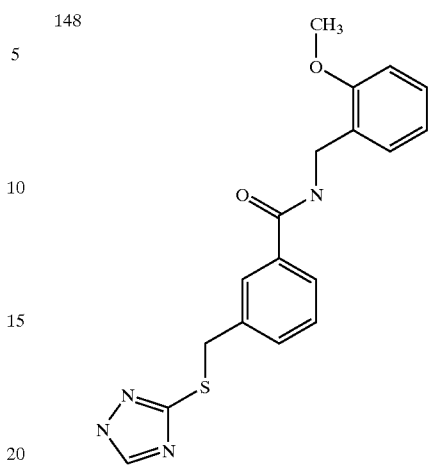 |
| 149 | 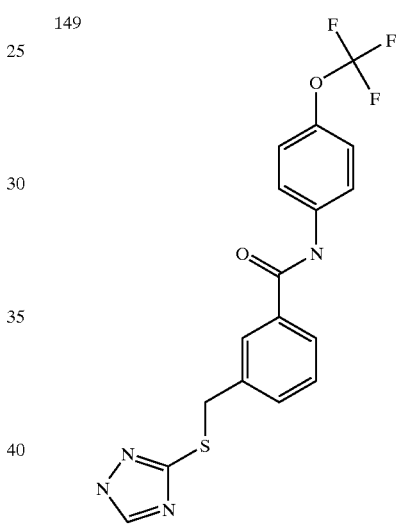 |
| 150 | 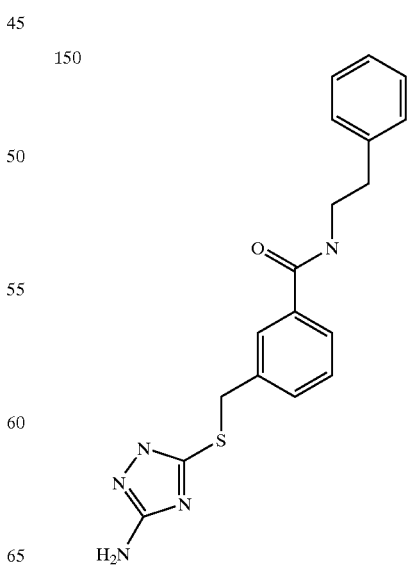 |

151 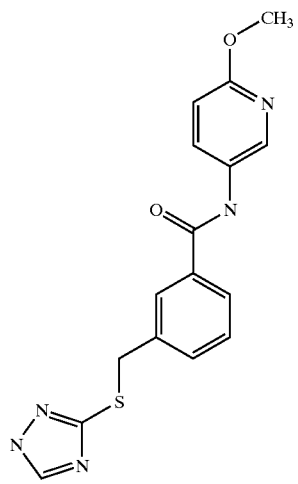
152 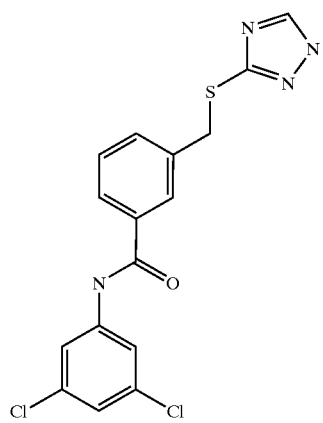
153 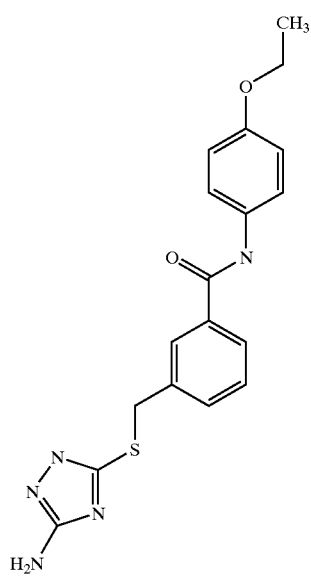
154 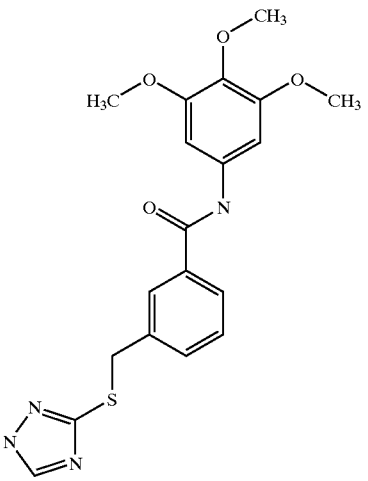
155 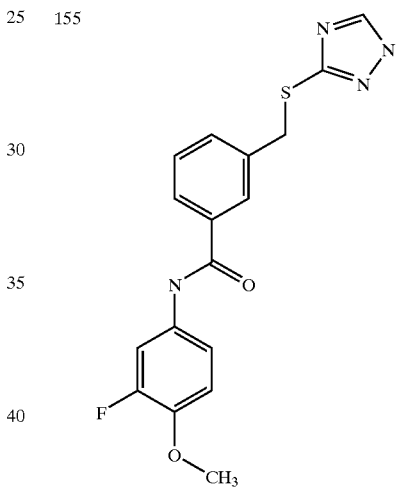
156 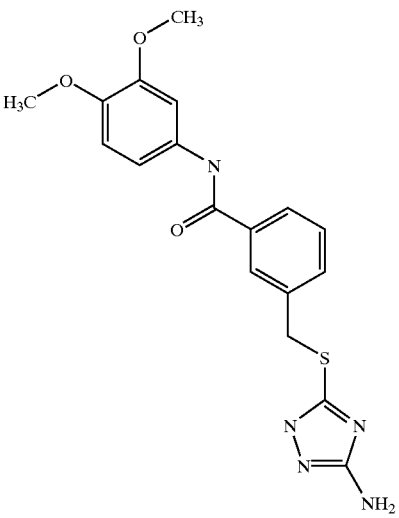

-continued
157 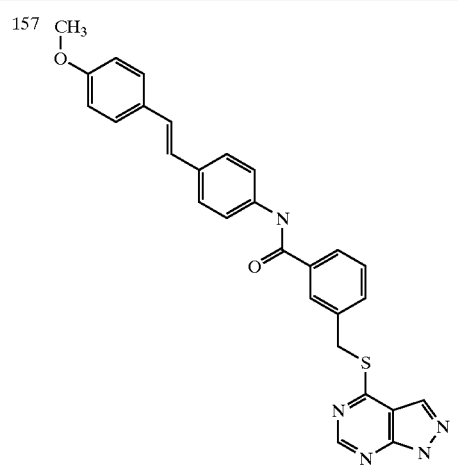
158 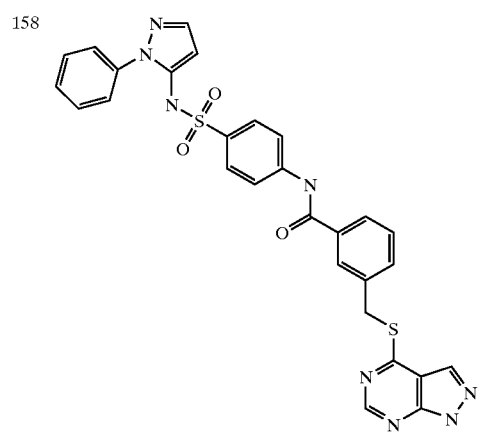
159 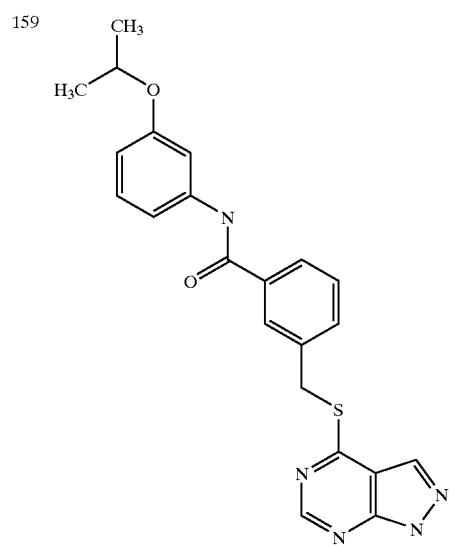
-continued
160 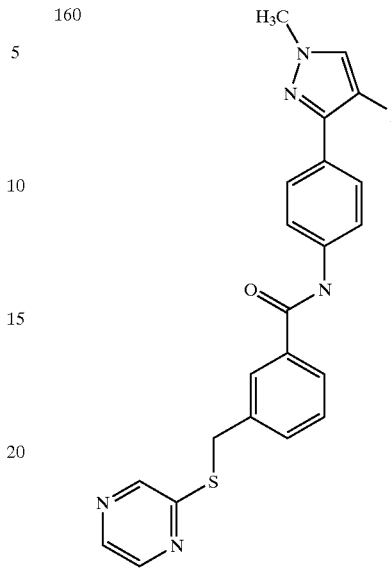
161 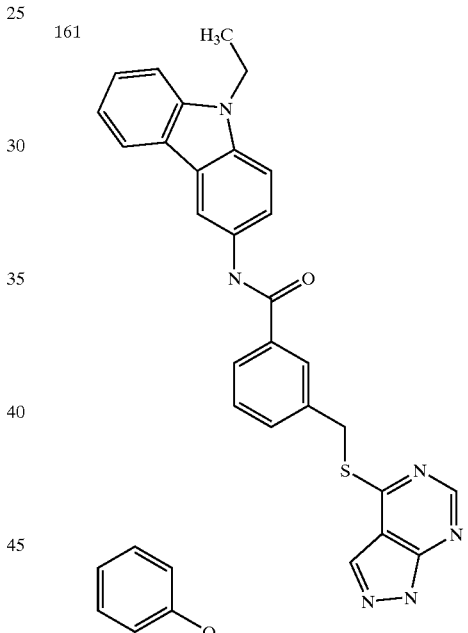
162 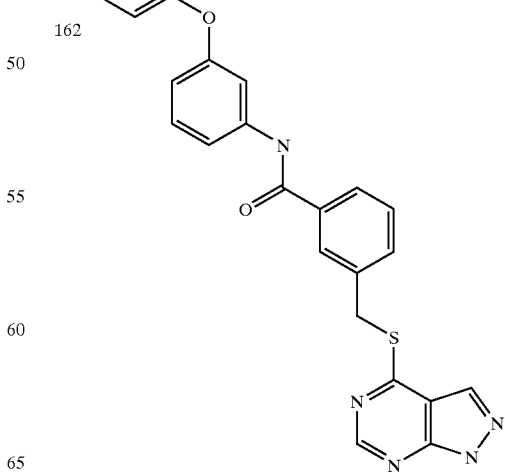

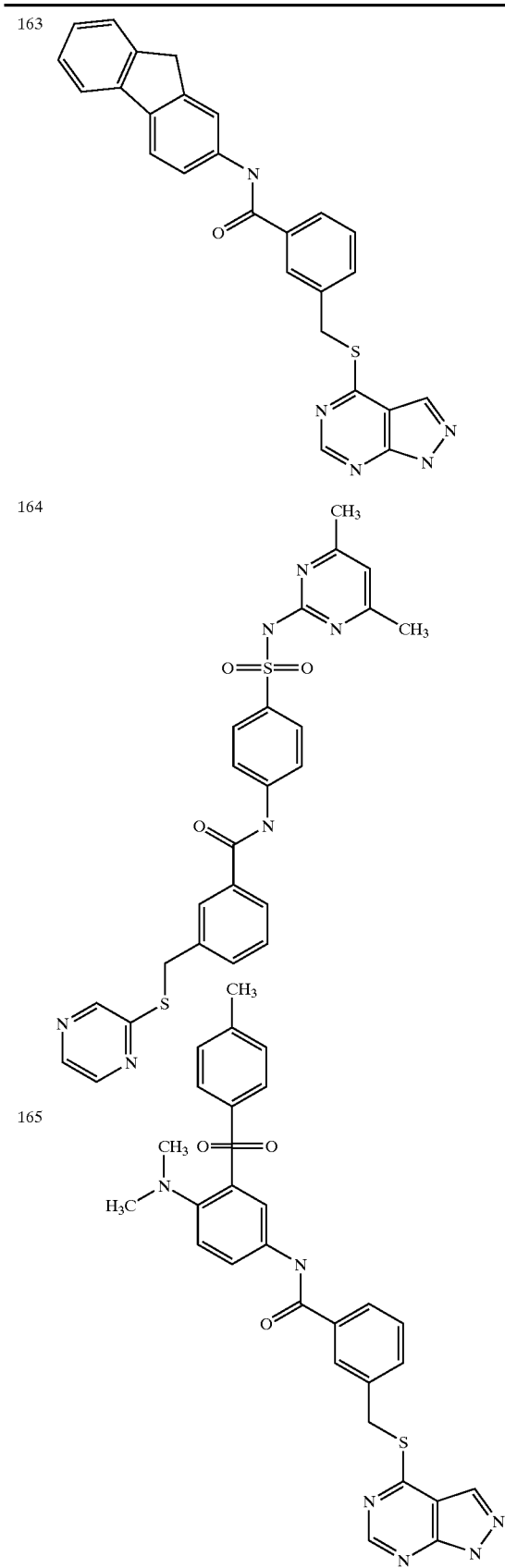
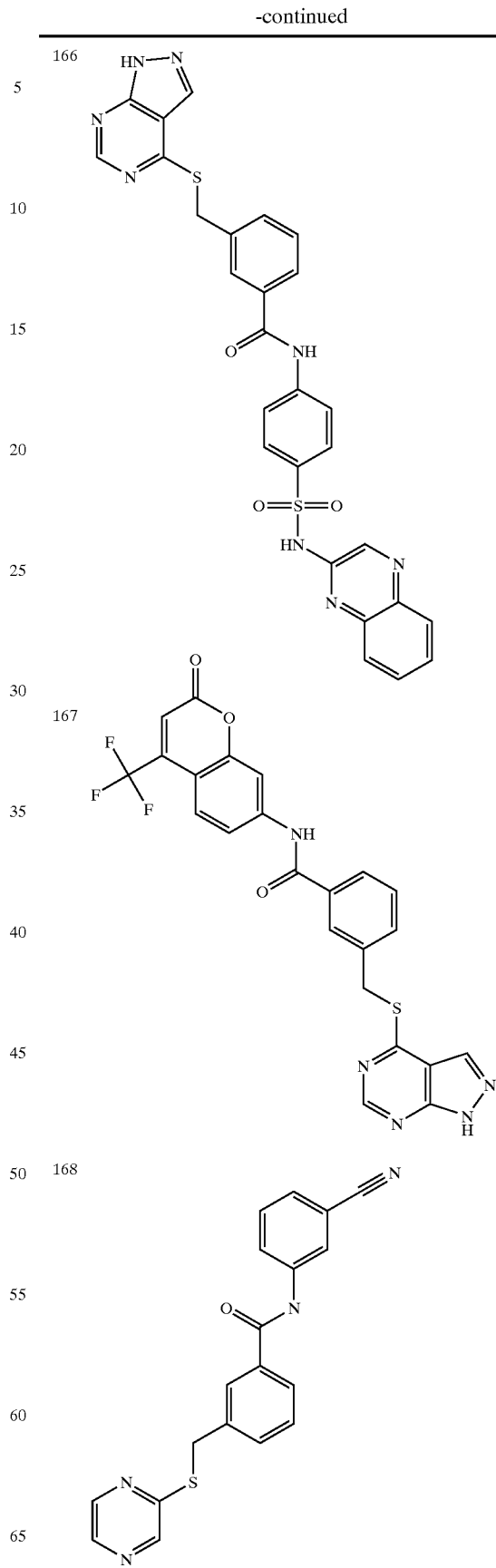

169 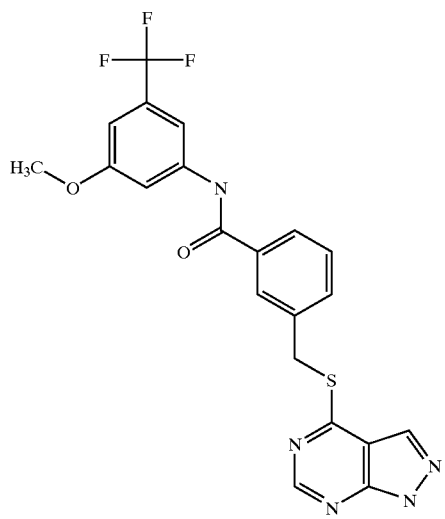
170 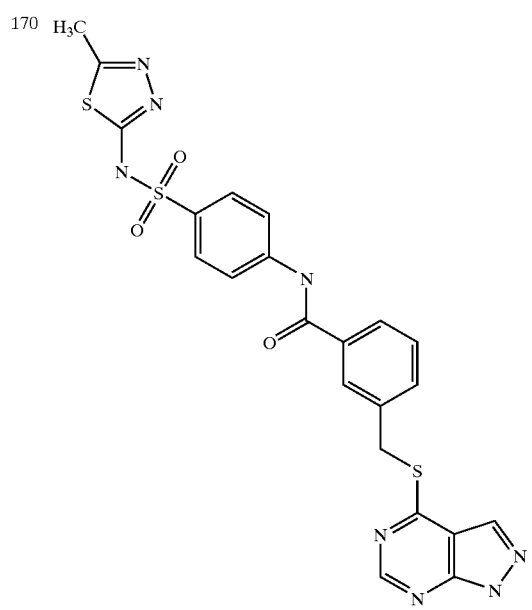
171 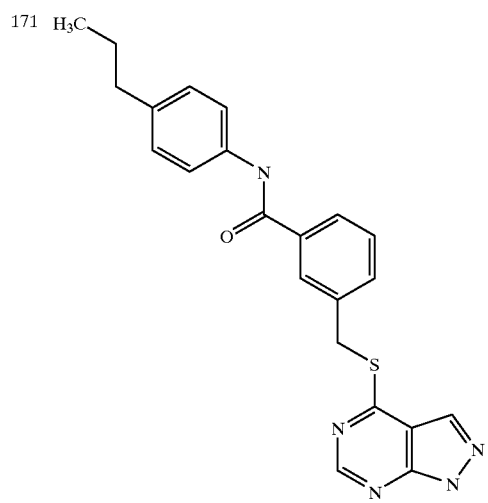
172 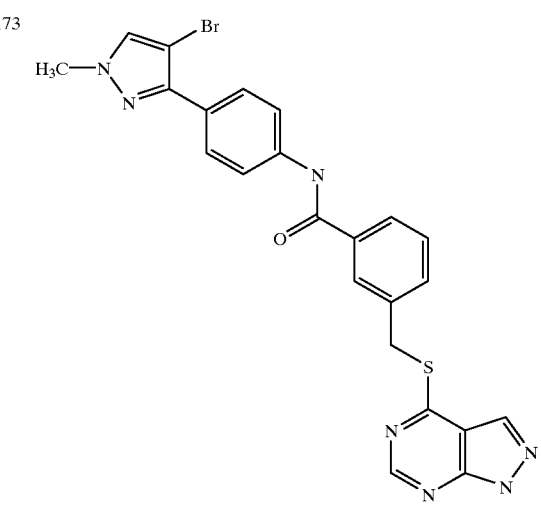
173 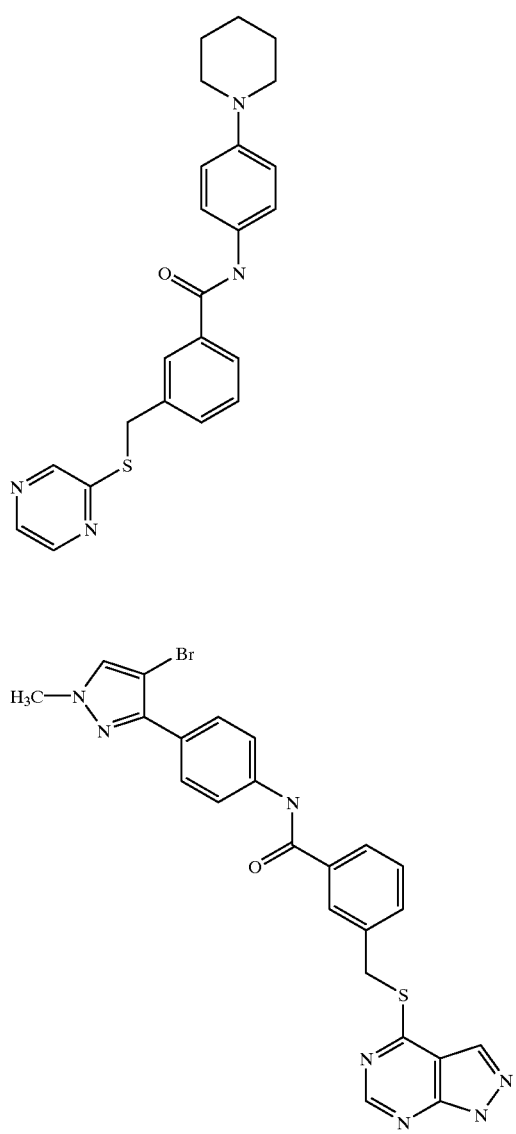
174 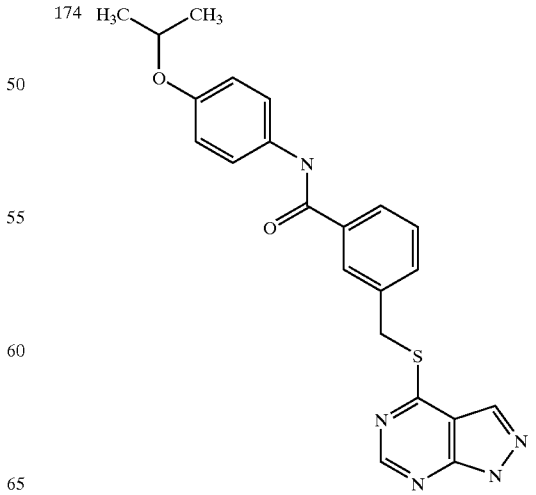

-continued
175 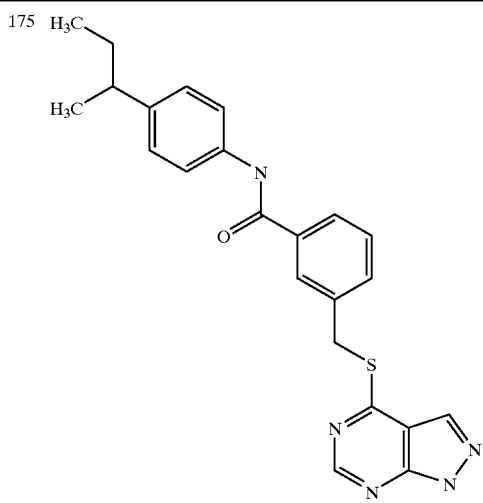
176 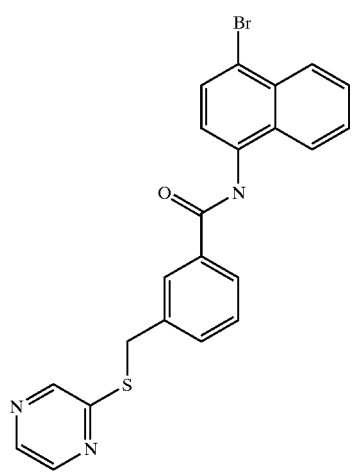
177 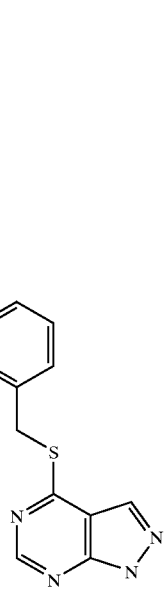
-continued
178 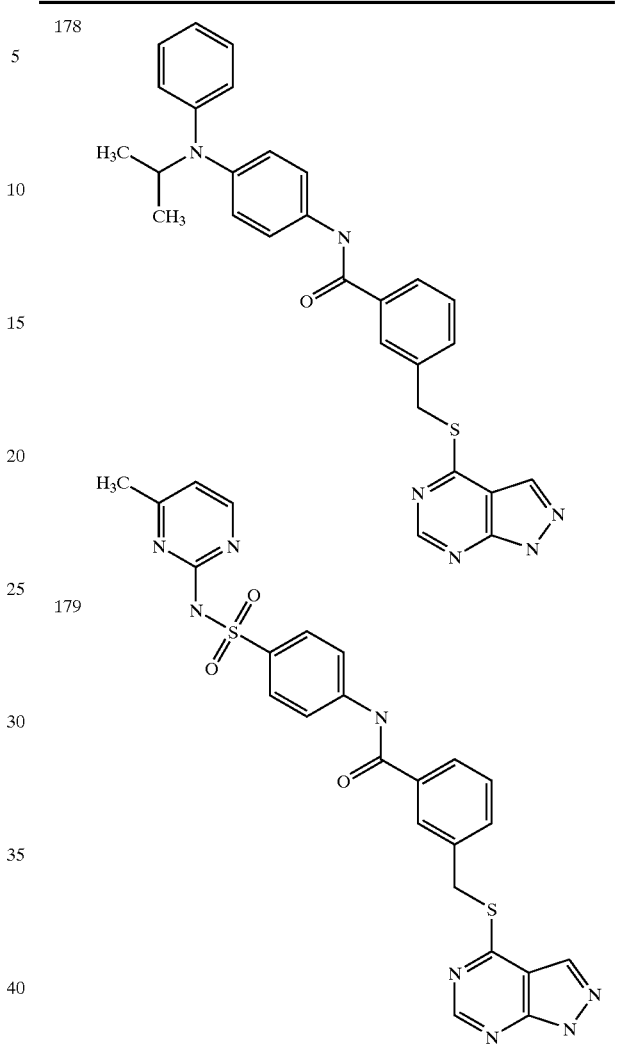
179
180 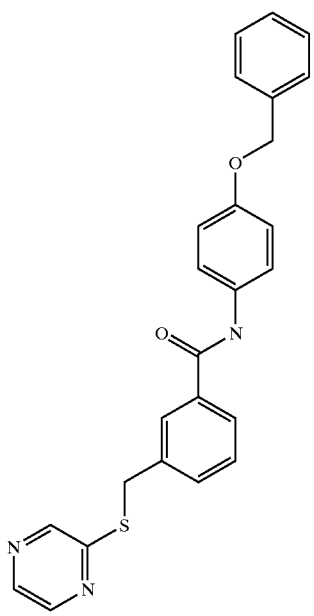

-continued
181 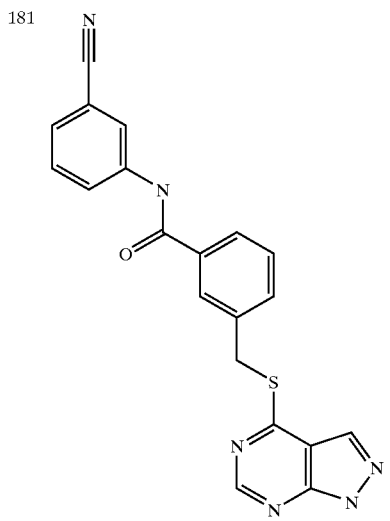
182 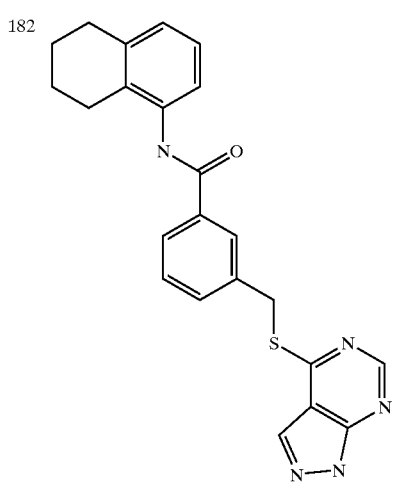
183 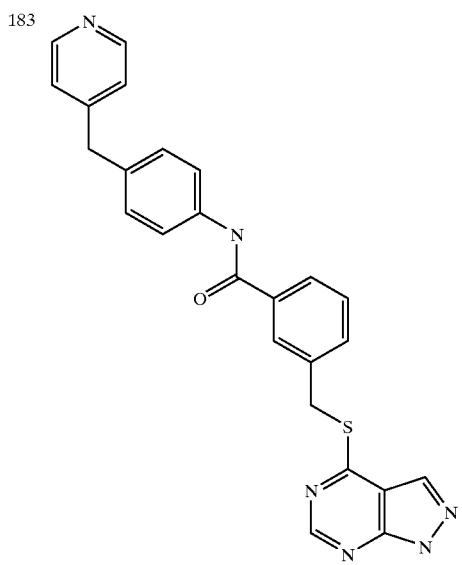
-continued
184 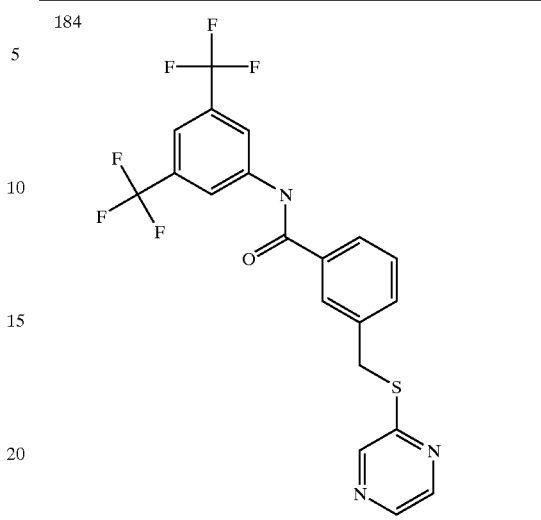
185 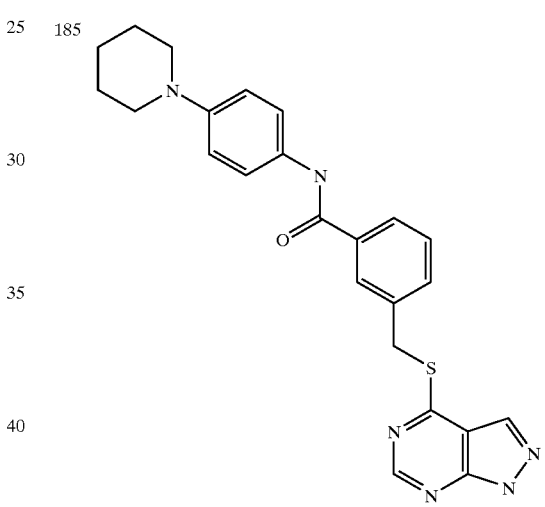
186 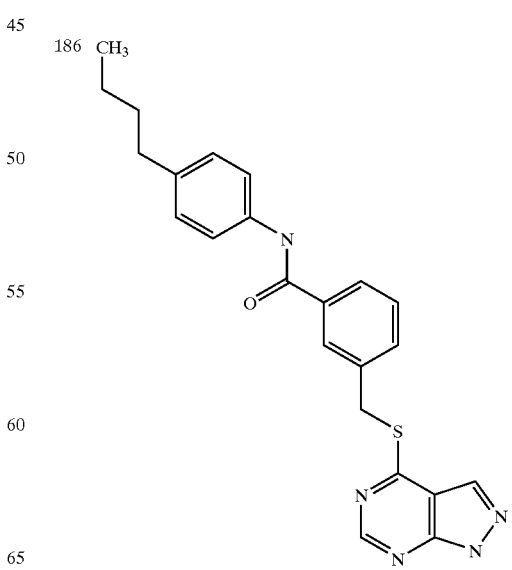

| 187 | 190 |
|---|---|
| 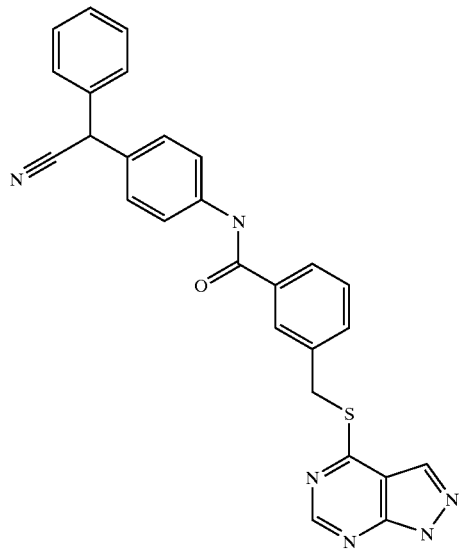 | 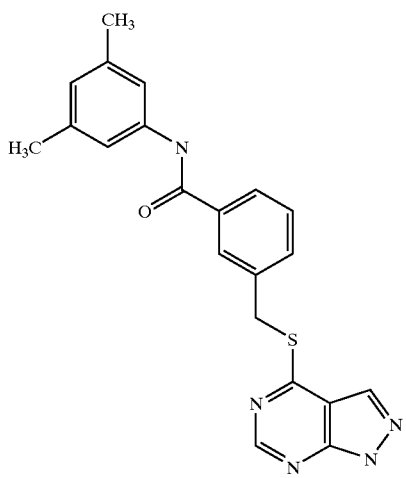 |
| 188 | 191 |
| 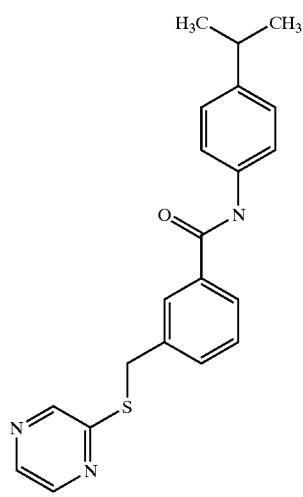 | 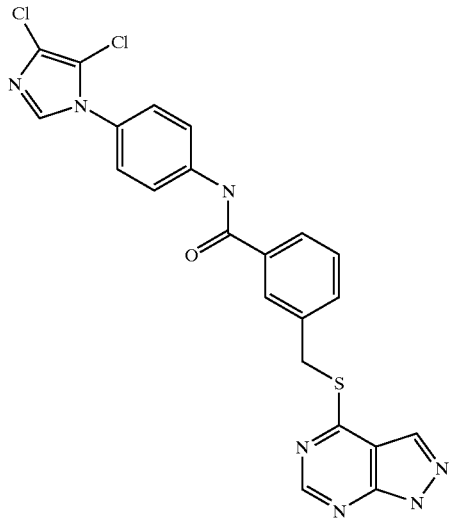 |
| 189 | 192 |
| 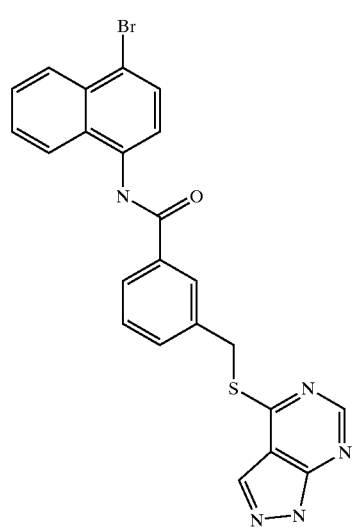 | 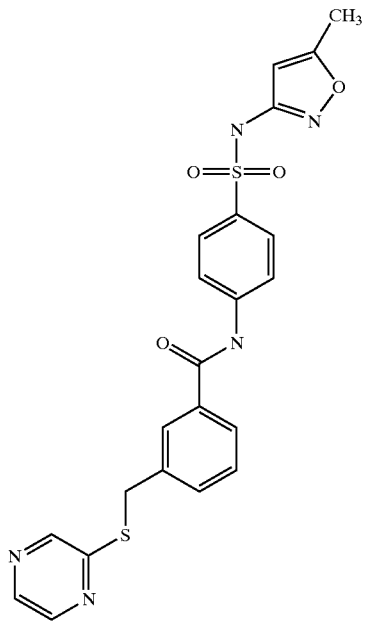 |

193 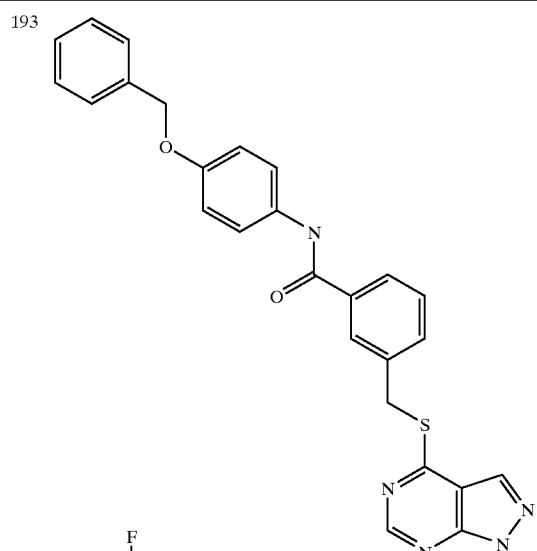
194 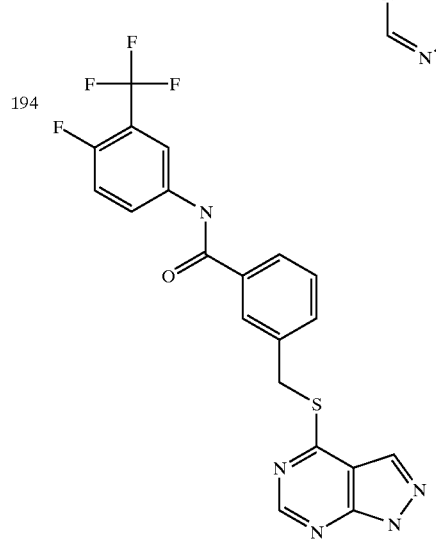
195 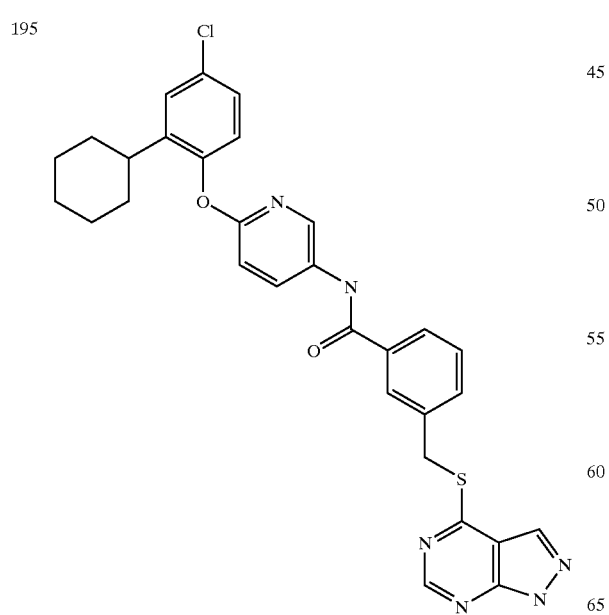
196 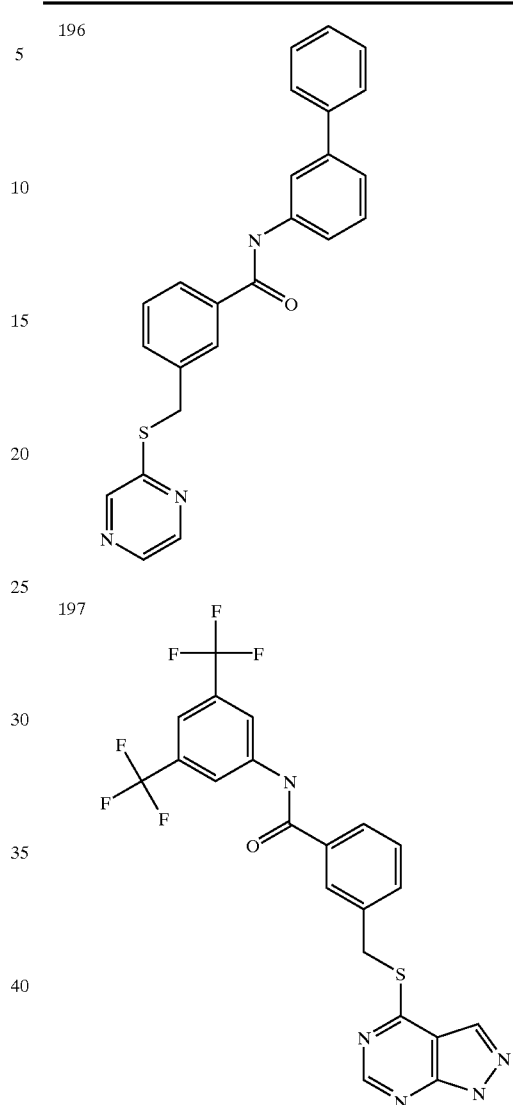
197 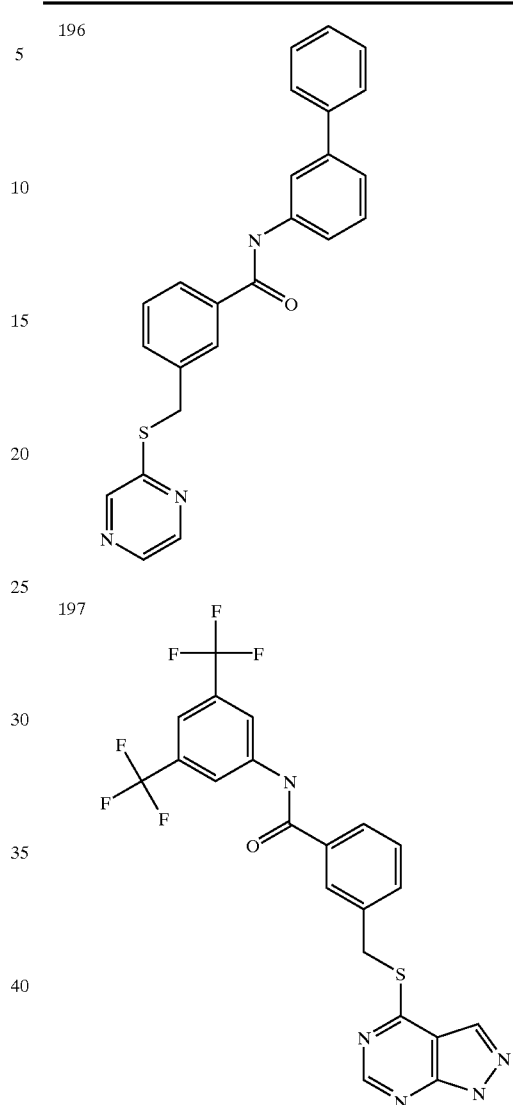
198 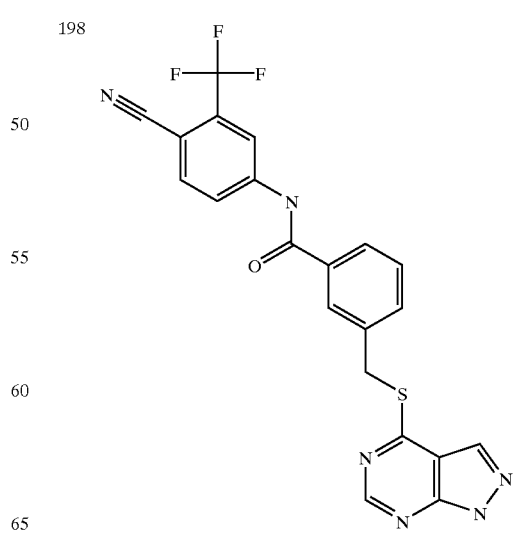

199 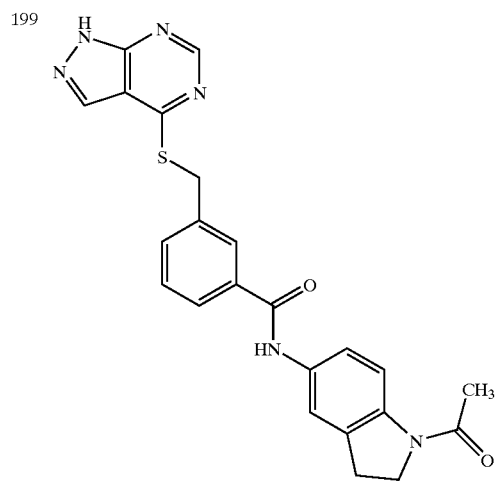
200 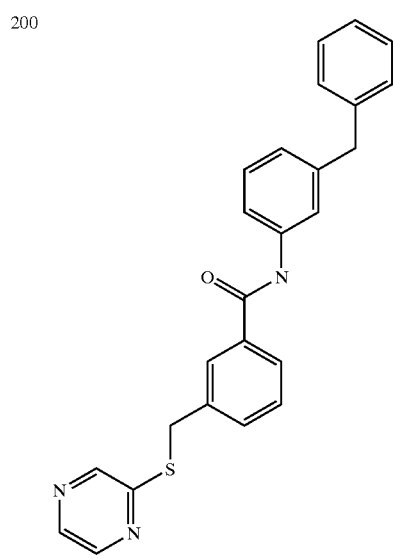
201 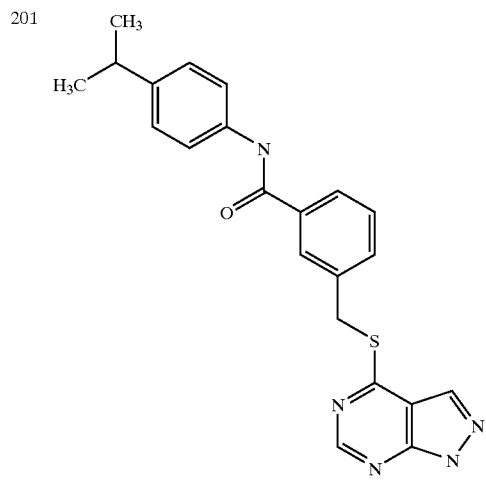
202 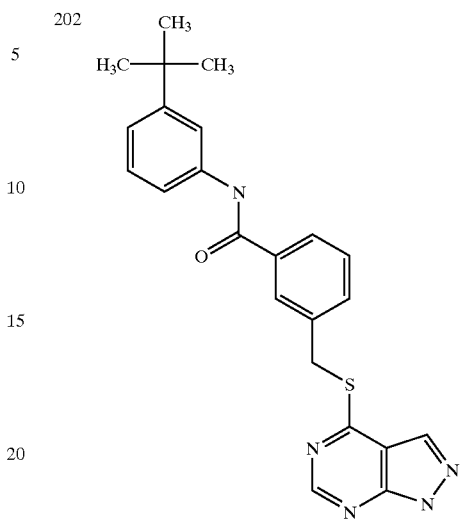
203 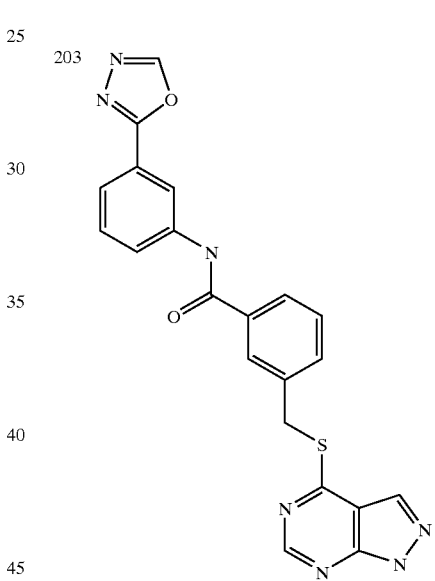
204 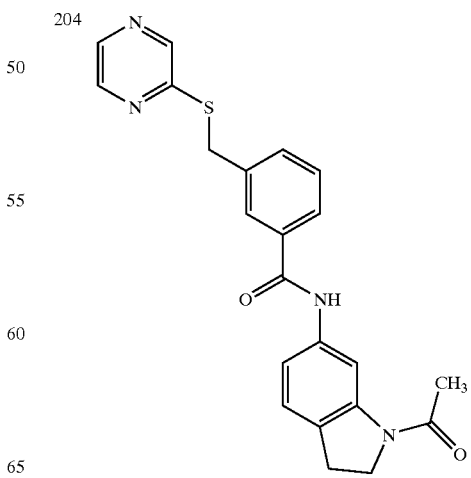

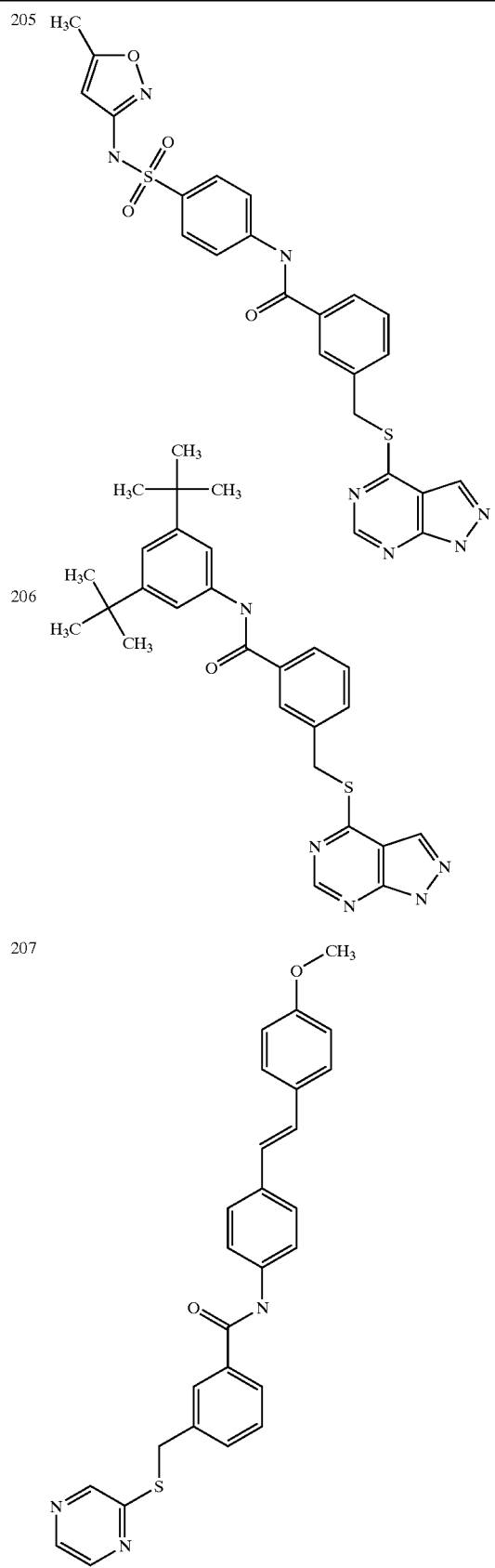
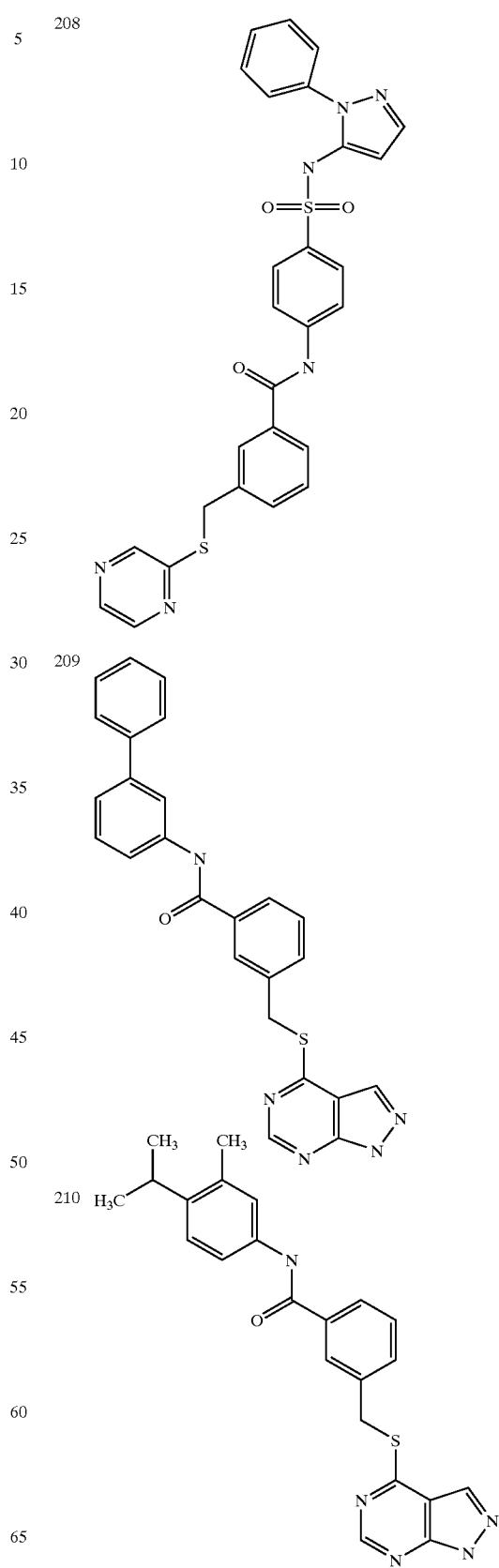

211 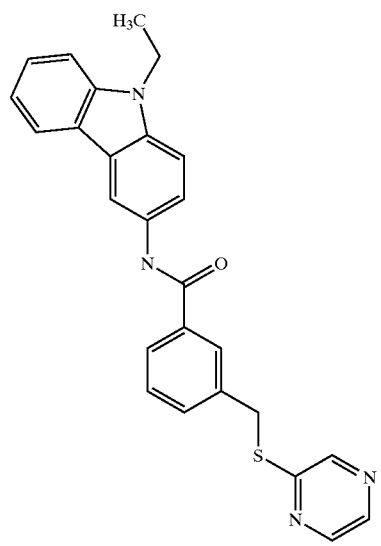
212 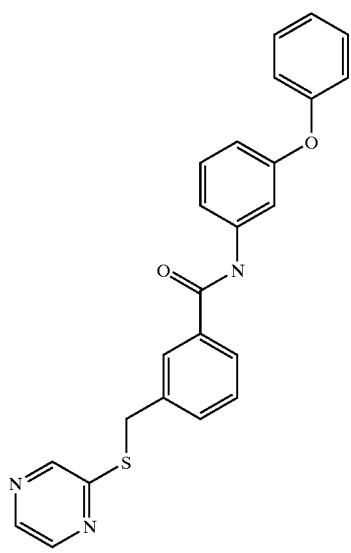
213 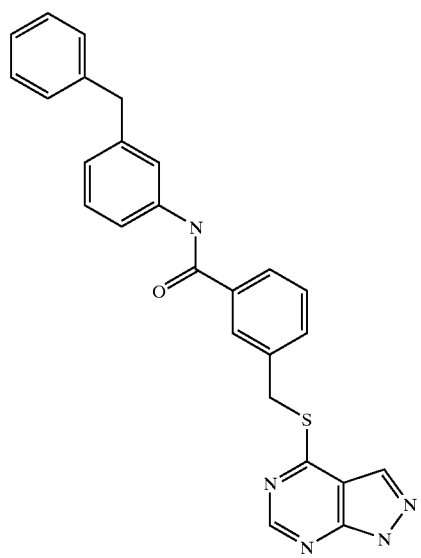
214 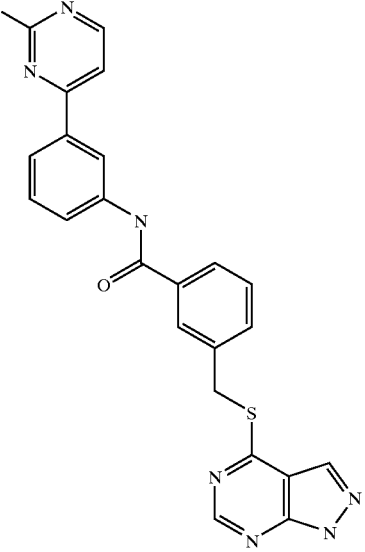
215 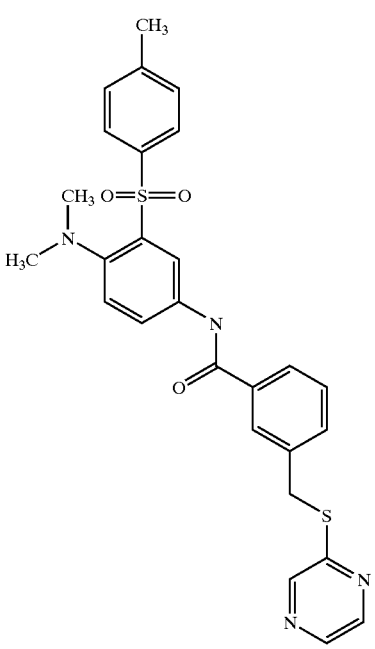
216 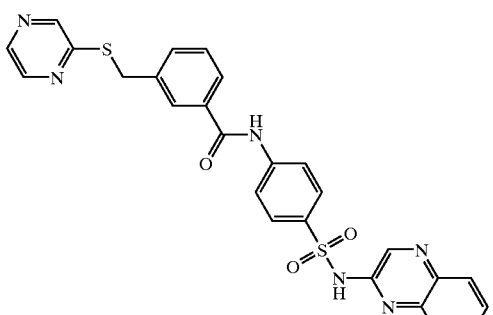

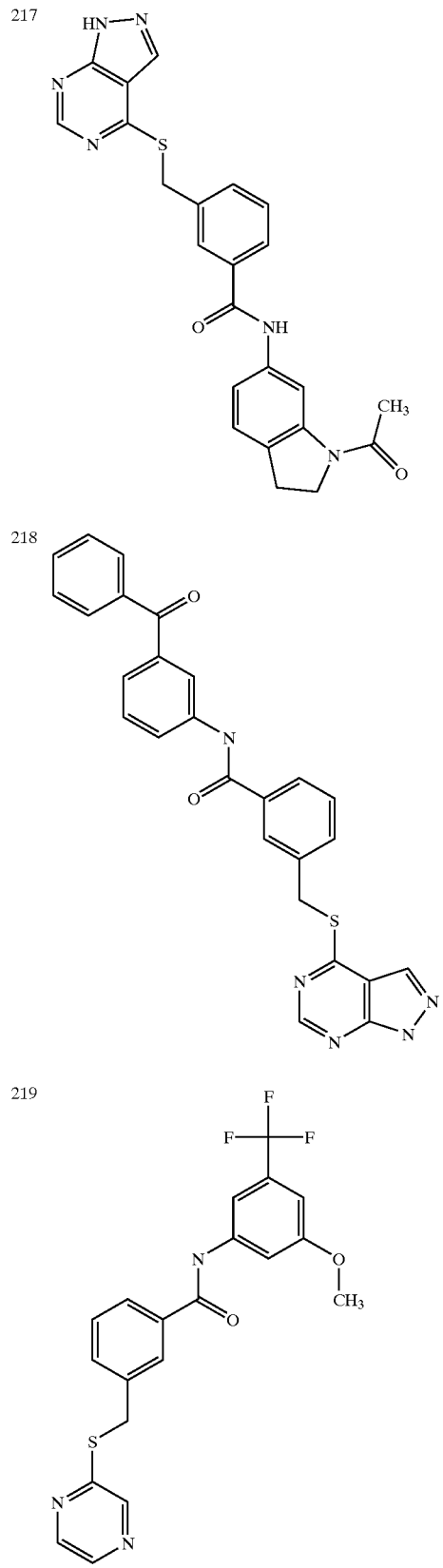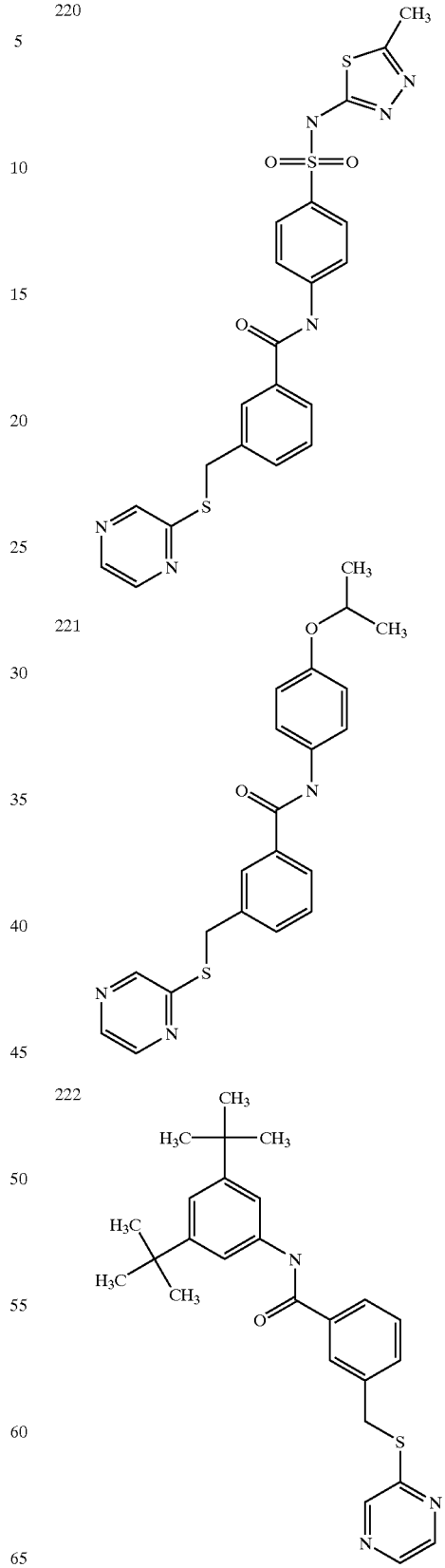

-continued
223
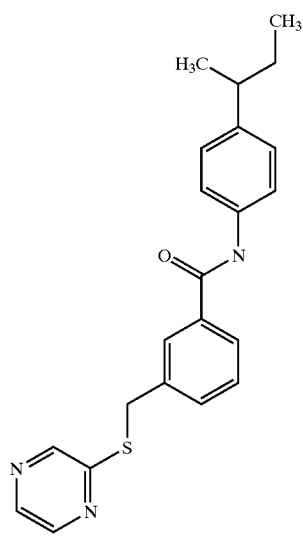
224
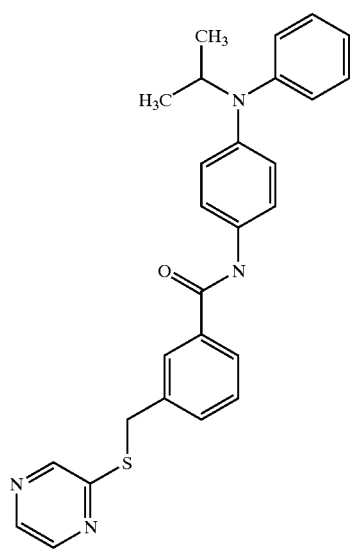
225
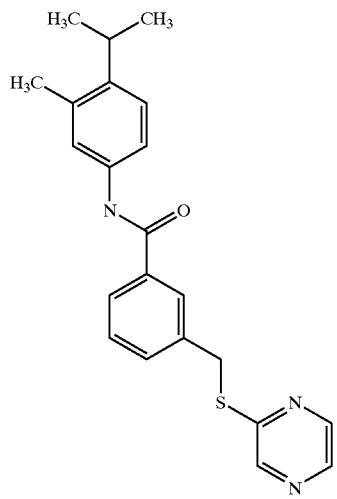
-continued
226
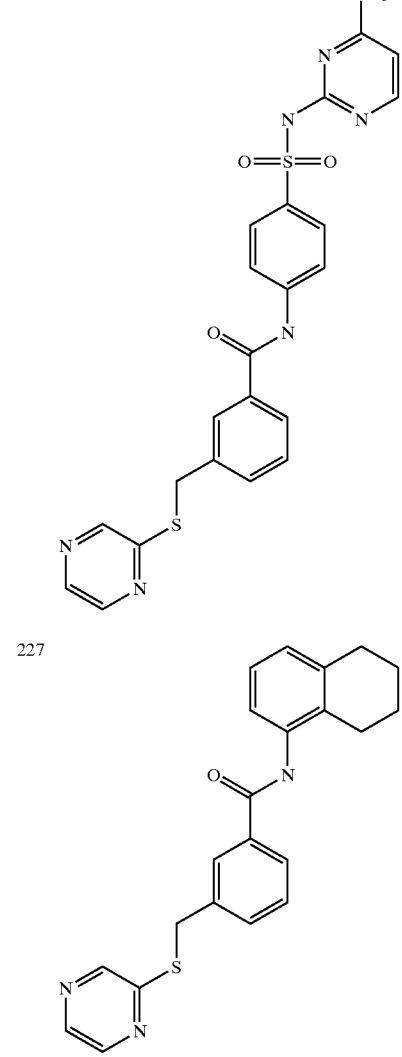
227
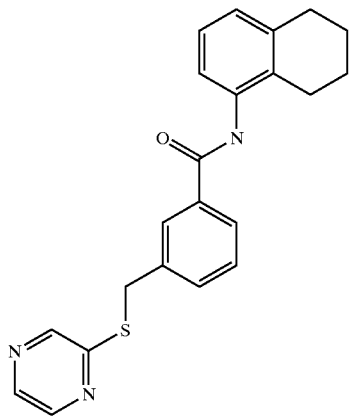
228
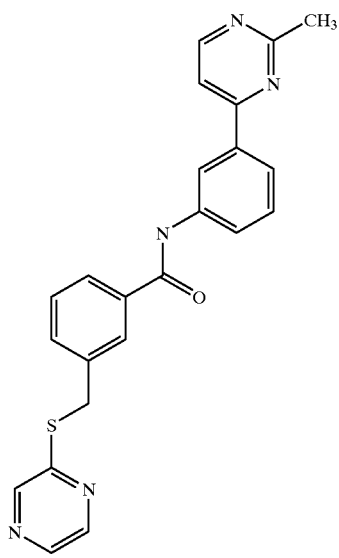

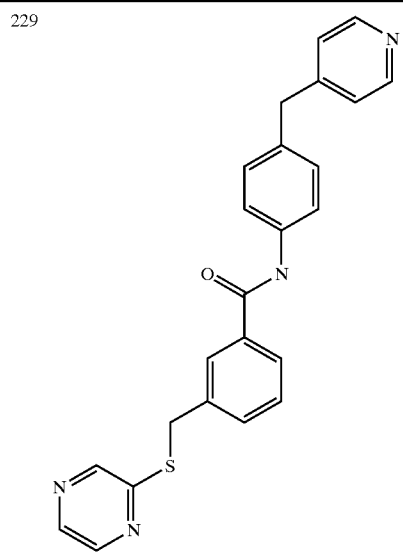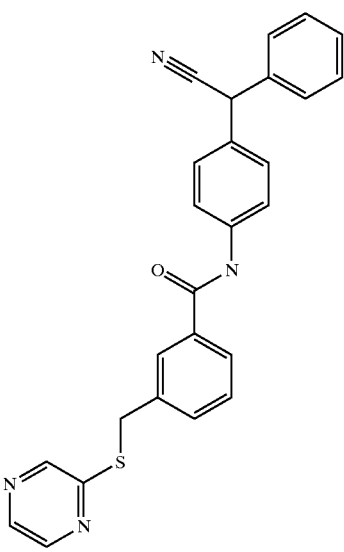

235 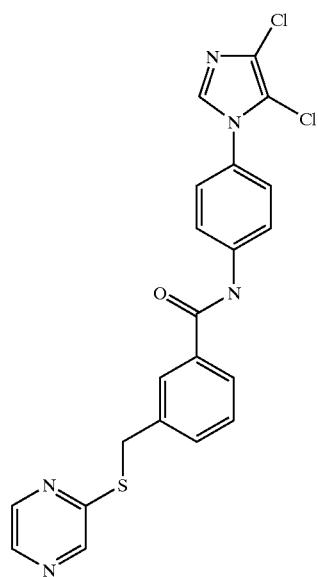
236 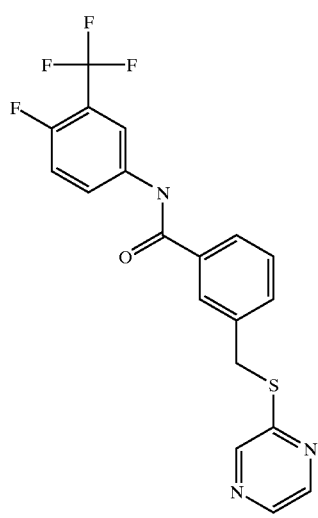
237 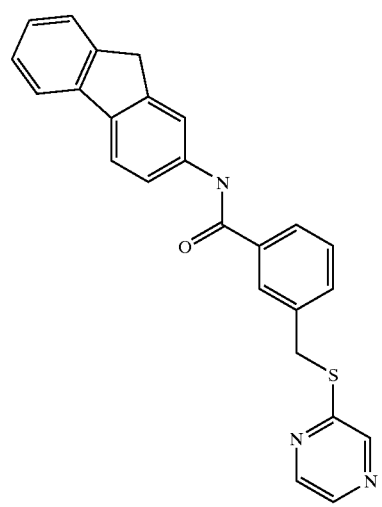
238 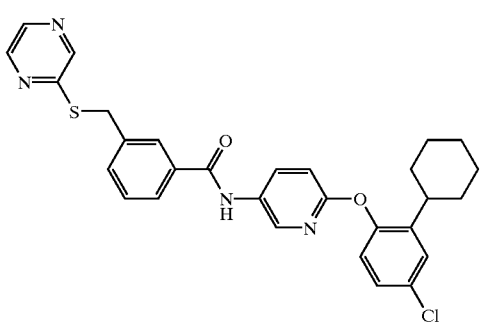
239 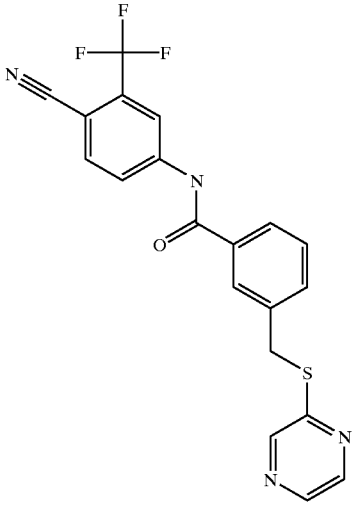
240 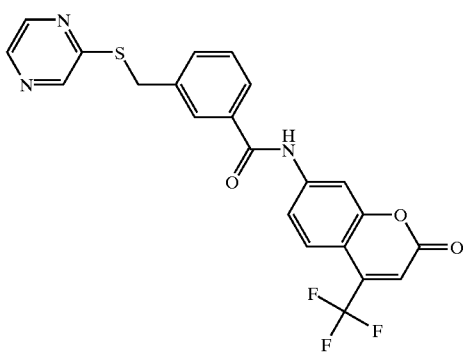
241 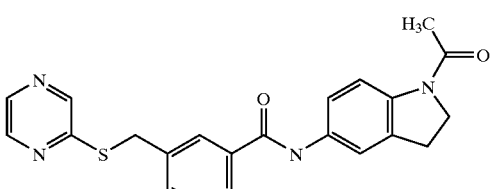

| 242 | 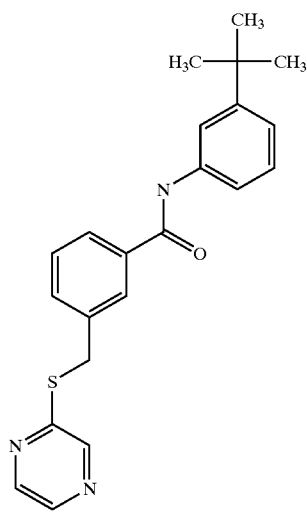 |
|---|---|
| 243 | 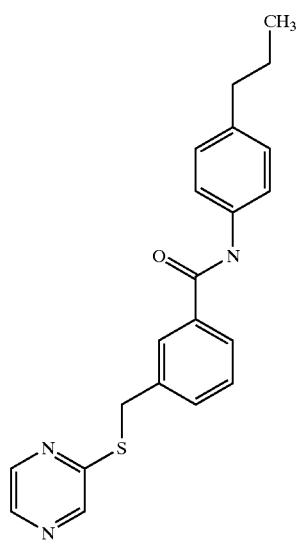 |
| 244 | 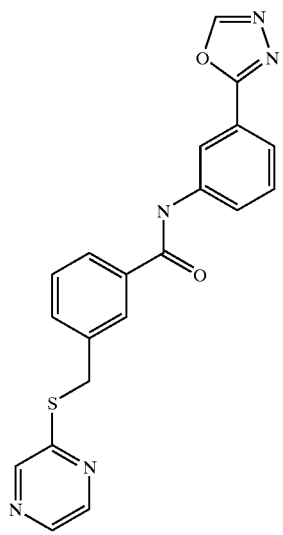 |

Example C-1

3-[(5-Cyanoamino-2H-[1,2,4]triazol-3-yl) sulfanylmethyl]-N-(3,4,5-trimethoxyphenyl) benzamide

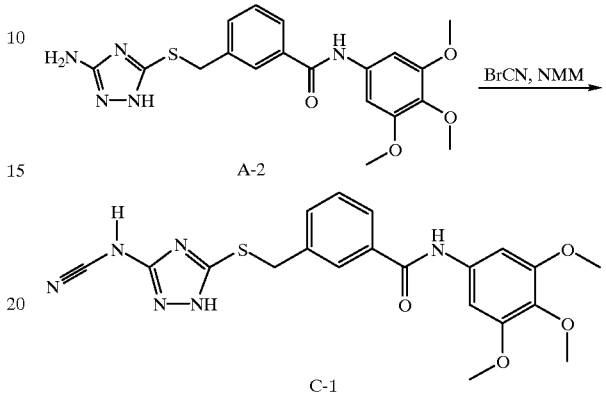

To a suspension of 0.300 g (0.73 mmol) of N-(3,4,5-trimethoxyphenyl)-3-[(5-amino-2H-[1,2,4]triazol-3-yl) sulfanylmethyl]benzamide, A-2, in 10 mL THF was added ethanol until the mixture became homogeneous. The mixture was cooled to 0° C. and 4-methylmorpholine (0.095 mL, 0.86 mmol) was added followed by cyanogen bromide (0.115 g, 1.08 mmol) in one portion. After stirring at 0 to 20° C. over 2 h, the mixture was partitioned between ethyl acetate (50 mL) and brine (50 mL). The aqueous layer was extracted twice with ethyl acetate (50 mL) and the combined organics were washed with brine (25 mL), dried over $NA_2SO_4$, and concentrated to dryness. The crude residue was triturated with a mixture of MTBE, ethyl acetate, and hexanes to yield the desired product as a pale yellow solid (0.27 g, 85%) that was collected by filtration: mp>165° C. (dec); $^1$H NMR (DMSO-$d_6$) δ10.14 (s, 1H), 8.19 (s, 1H), 7.96 (s, 1H), 7.84 (d, 1H, J=7.8 Hz), 7.62 (d, 1H, J=7.7 Hz), 7.49 (t, 1H, J=7.7 Hz), 7.18 (s, 2H), 4.39 (s, 2H), 3.77 (s, 6H), 3.69 (s, 3H). Anal. calc'd for $C_{20}H_{20}N_6O_4S.0.3$ EtOAc: C, 54.53; H, 4.84; N, 18.00; S, 6.87. Found: C, 54.86; H, 4.83; N, 17.91; S, 6.64.

Example C-2

3-[(5-(Methoxycarbonylamino)-2H-[1,2,4]triazol-3-yl)sulfanylmethyl]-N-(3,4,5-Trimethoxyphenyl) benzamide

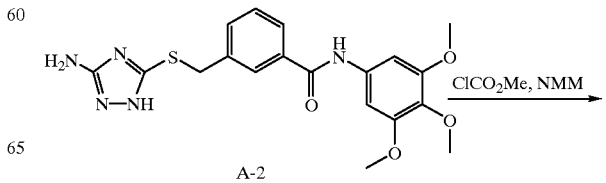

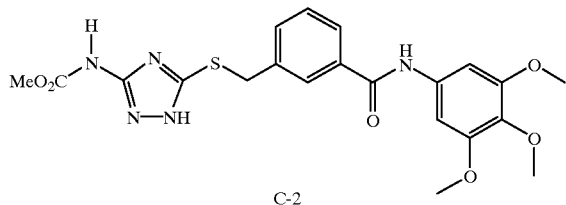

C-2

To a suspension of 0.154 g (0.37 mmol) of N-(3,4,5-trimethoxyphenyl)-3-[(5-amino-2H-[1,2,4]triazol-3-yl)sulfanylmethyl]benzamide, A-2, in dichloromethane (5 mL) at room temperature was added DMF until the mixture became homogeneous. To the mixture was added N-methylmorpholine (0.075 mL, 0.7 mmol) followed by methyl chloroformate (0.050 mL, 0.65 mmol). After stirring room temperature for 2 h, the mixture was partitioned between MTBE (50 mL) and brine (50 mL). The aqueous layer was extracted with 1:1 MTBE/ethyl acetate (2×50 mL) and the combined organics were washed with brine (25 mL), dried over $NA_2SO_4$, and concentrated to dryness. The crude residue was triturated with MTBE and filtered. The solid was triturated a second time with MTBE/ethyl acetate to yield N-(3,4,5-trimethoxyphenyl)-3-[(5-methylcarbamoyl-2H-[1,2,4]triazol-3-yl)sulfanylmethyl]benzamide, C-2, as a white solid (0.13 g, 74%): mp>150° C. (dec); $^1$H NMR (DMSO-$d_6$) δ10.10 (s, 1H), 7.97 (s, 1H), 7.84 (d, 1H, J=7.7 Hz), 7.61 (d, 1H, J=7.7 Hz), 7.48–7.45 (m, 2H), 7.21 (s, 2H), 4.38 (s, 2H), 3.90 (s, 3H), 3.77 (s, 6H), 3.64 (s, 3H). Anal. calc'd for $C_{21}H_{23}N_5O_6S \cdot 0.75\ H_2O$: C, 51.79; H, 5.07; N, 14.38; S, 6.58. Found: C, 52.13; H, 5.29; N, 14.11; S, 6.17.

Example C-3

N-(3,4,5-Trimethoxyphenyl)-3-[(5-acetylamino-2H-[1,2,4]triazol-3-yl)sulfanylmethyl]benzamide

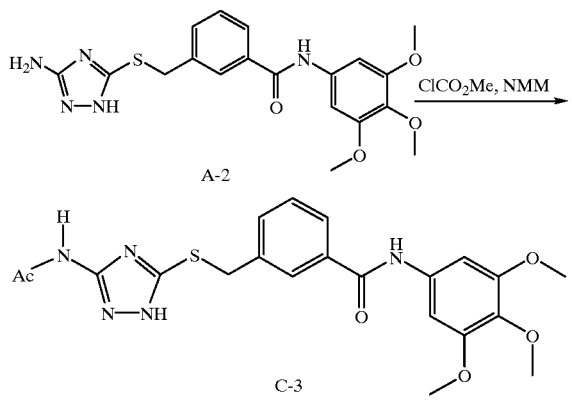

To a solution of 0.15 g (0.37 mmol) of N-(3,4,5-trimethoxyphenyl)-3-[(5-amino-2H-[1,2,4]triazol-3-yl)sulfanylmethyl]benzamide, A-2, in acetic acid (5 mL) at room temperature was added acetic anhydride (0.200 mL, 2.1 mmol). After stirring at room temperature for 1.5 hr, the mixture was added dropwise to a cold solution of phosphate buffer (1M, pH 7, 60 mL). The resulting precipitate was collected by filtration, washed with water, and dried under vacuum. The dried solid was triturated with MTBE/ethyl acetate and filtered to yield N-(3,4,5-trimethoxyphenyl)-3-[(5-acetylamino-2H-[1,2,4]triazol-3-yl)sulfanylmethyl] benzamide, C-3, as a white solid (0.12 g, 71%): mp 196–201° C.; $^1$H NMR (DMSO-$d_6$) δ10.14 (s, 1H), 8.02 (s, 1H), 7.85 (d, 1H, J=7.8 Hz), 7.65 (d, 1H, J=7.8 Hz), 7.49 (t, 1H, J=7.7 Hz), 7.22 (s, 2H), 4.40 (s, 2H), 3.78 (s, 6H), 3.65 (s, 3H), 2.50 (s, 3H, obscured by DMSO). Anal. calc'd for $C_{21}H_{23}N_5O_5S \cdot 0.9\ H_2O$: C, 53.24; H, 5.28; N, 14.78; S, 6.77. Found: C, 53.28; H, 4.98; N, 14.48; S, 6.68.

Example D-1

N-(4-Isopropyl-3-methylphenyl)-3-[(pyrazin-2-yl)methylsulfanyl]benzamide

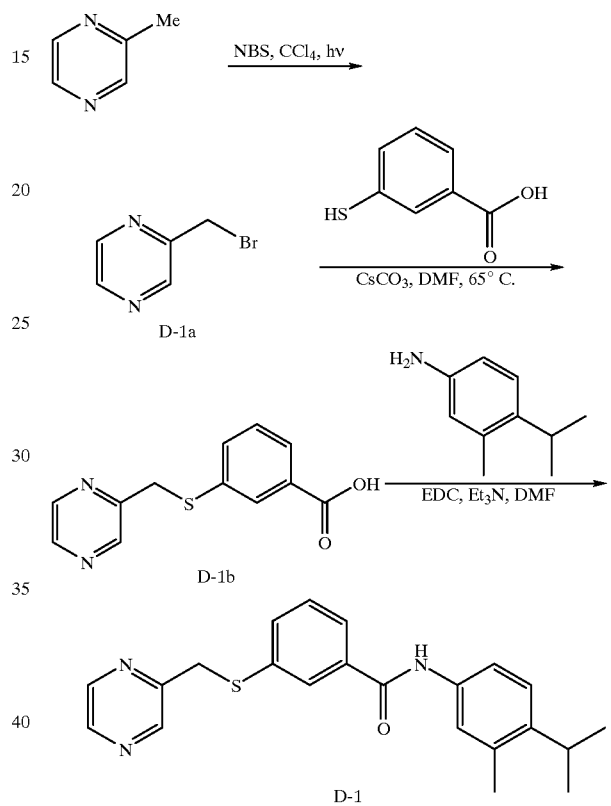

(a) A suspension of methyl pyrazine (5 g, 53 mmol) and N-bromosuccinimide (9.45 g, 53 mmol) in carbon tetrachloride (200 mL) was heated at reflux while exposed to a 100 watt light source. After 4 hr, the dark mixture was allowed to cool to room temperature and was decanted. The supernatant was filtered and the filtrate reduced to ~25 mL volume then passed through silica gel using a gradient of 0% to 5% ethyl acetate in $CHCl_3$. Decomposition was evident upon concentration of chromatographed product. The residue was taken up in $CH_2Cl_2$, washed with water, dried over sodium sulfate, and concentrated cold. Unstable oily 2-(bromomethyl)pyrazine, D-1a, (2 g, 22%) was used quickly in next reaction: $^1$H NMR (CDCl$_3$) δ8.72 (s, 1H), 8.55 (d, 1H, J=1.8 Hz), 8.51 (d, 1H, J=2.5 Hz), 4.56 (s, 2H).

(b) 3-[(Pyrazin-2-yl)methylsulfanyl]benzoic acid, D-1b, was prepared in a manner similar to that described in example A-1, step (b): mp 131–135° C.

(c) To a solution of 3-[(pyrazin-2-yl)methylsulfanyl]benzoic acid, D-1b, (0.15 g, 0.61 mmol), 4-isopropyl-3-methylaniline hydrochloride (0.113 g, 0.61 mmol), and triethylamine (0.09 mL, 0.65 mmol) in 2 mL DMF at room temperature was added EDC (0.116 g, 0.61 mmol). After stirring at room temperature for 24 hr, the mixture was partitioned between ethyl acetate (30 mL) and brine (30 mL). The aqueous layer was extracted twice with ethyl acetate (30 mL) and the combined organics were washed twice with water (20 mL), once with brine (25 mL), dried over sodium sulfate, and concentrated to dryness. The residue was filtered through silica gel using 10% methanol in chloroform and then purified by radial chromatography with a 2 mm rotor using a gradient of 0% to 50% ethyl acetate in hexanes as eluent to yield N-(4-isopropyl-3-methylphenyl)-3-[(pyrazin-2-yl)methylsulfanyl]benzamide, D-1, as a pale amber oil (0.09 g, 35%): $^1$H NMR (DMSO-$d_6$) $\delta$10.10 (s, 1H), 8.68 (s, 1H), 8.57 (d, 1H, J=1.6 Hz), 8.51 (d, 1H, J=2.4 Hz), 7.92 (s, 1H), 7.76 (d, 1H, J=7.7 Hz), 7.59 (d, 1H, J=7.9 Hz), 7.55 (d, 1H, J=8.3 Hz), 7.52 (d, 1H, J=1.9 Hz), 7.46 (t, 1H, J=7.8 Hz), 7.21 (d, 1H, J=8.4 Hz), 4.50 (s, 2H), 3.11–3.05 (m, 1H), 2.30 (s, 3H), 1.18 (d, 6H, J=6.8 Hz). Anal. calc'd for $C_{22}H_{23}N_3OS \cdot 0.4 H_2O$: C, 68.68; H, 6.24; N, 10.92; S, 8.33. Found: C, 68.86; H, 6.11; N, 10.70; S, 8.23

Example D-2

N-(2-Methylquinolin-6-yl)-3-[(pyrazin-2-yl)methylsulfanyl]benzamide

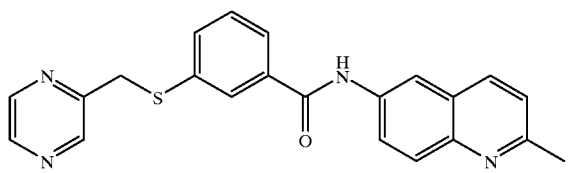

D-2

Example D-2 was prepared in a similar manner to that described for D-1, except that 6-amino-2-methylquinoline was used in place of 4-isopropyl-3-methylaniline in step (c): mp 102–105° C.; $^1$H NMR (DMSO-$d_6$) $\delta$10.53 (s, 1H), 8.69 (s, 1H), 8.57 (d, 1H, J=1.3 Hz), 8.52 (d, 1H, J=2.4 Hz), 8.46 (s, 1H), 8.22 (d, 1H, J=8.4 Hz), 7.80–7.97 (m, 2H), 7.91 (d, 1H, J=9.1 Hz), 7.82 (d, 1H, J=7.8 Hz), 7.63 (d, 1H, J=7.8 Hz), 7.51 (d, 1H, J=7.8 Hz), 7.40 (d, 1H, J=8.5 Hz), 4.52 (s, 2H), 2.65 (s, 3H). Anal. calc'd for $C_{22}H_{18}N_4OS \cdot 0.3 H_2O \cdot 0.2$ EtOAc: C, 66.87; H, 4.97; N, 13.68; S, 7.83. Found: C, 66.77; H, 5.18; N, 13.40; S, 7.61.

Example D-3

N-(2-Methyl-quinolin-6-yl)-3-(pyridin-3-ylmethylsulfanyl)-benzamide dihydrochloride

D-3

Example D-3 was prepared in a similar manner to that described for D-1, except that 3-picolyl chloride was used in place of 2-(bromomethyl)pyrazine in step (b), and 6-amino-2-methylquinoline was used in place of 4-isopropyl-3-methylaniline in step (c): HPLC $R_t$=12.2 min.; TLC $R_f$=0.4 (5% methanol/chloroform); $^1$H NMR (500 MHz, DMSO-$d_6$ w/$D_2O$) $\delta$8.95 (d, 1H, J=8.6 Hz), 8.77–8.73 (m, 2H), 8.66 (dd, 1H, J=1.1, 5.5 Hz), 8.41–8.33 (m, 2H), 8.20 (d, 1H, J=9.2 Hz), 7.97–7.83 (m, 4H), 7.66–7.53 (m, 2H), 4.51 (s, 2H), 2.94 (s, 3H); $^{13}$C NMR (75 MHz, DMSO-$d_6$ w/$D_2O$) $\delta$167.8, 158.4, 146.8, 146.4, 144.5, 143.8, 140.5, 139.5, 136.7, 136.6, 136.4, 134.9, 131.7, 130.5, 130.4, 129.2, 128.4, 128.2, 126.0, 122.7, 119.0, 35.2, 22.3; MS (ESI) m/z 386 [M+H]$^+$. Anal. calc'd for $C_{23}H_{19}N_3O_2S \cdot 2 HCl \cdot 0.3 H_2O$: C, 59.56; H, 4.69; N, 9.06; S, 6.91. Found: C, 59.56; H, 4.66; N, 9.00; S, 6.82.

Example E-1

N-(2-methyl-quinolin-6-yl)-3-[{5-(phenylamino)-2-H-pyrazol-3-yl}methylsulfanyl]benzamide

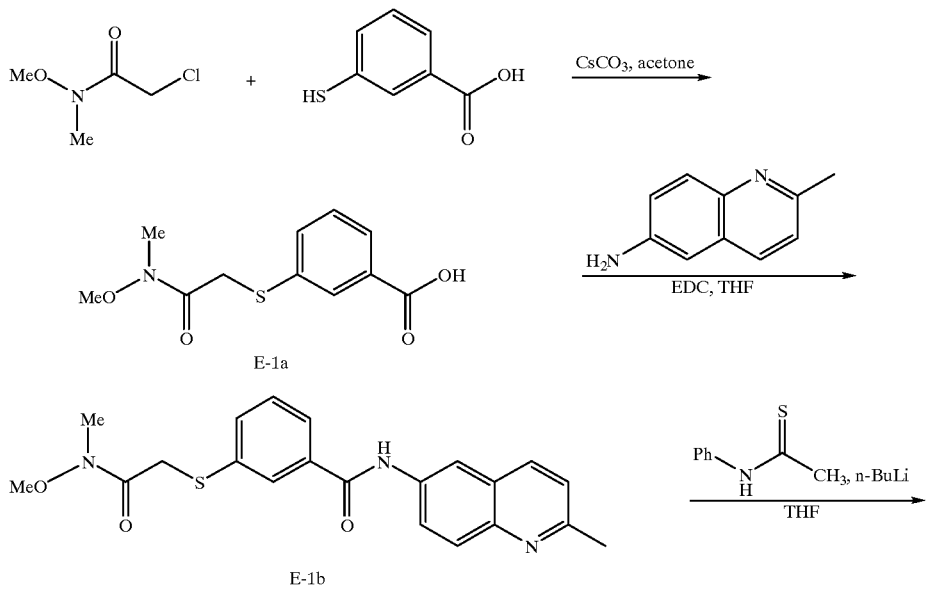

-continued

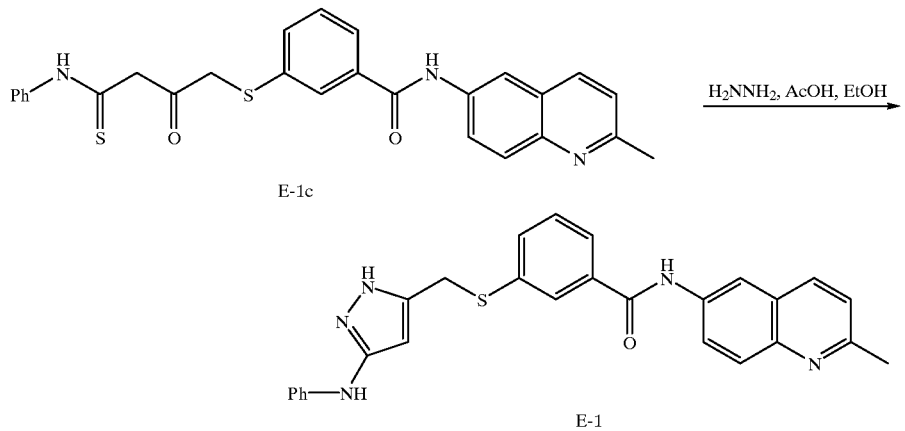

(a) To a solution of 3-thiobenzoic acid (5.0 g, 32.4 mmol) in 150 mL of acetone was added cesium carbonate (22.2 g, 68.1 mmol) and 2-chloro-N-methoxy-N-methylacetamide (4.9 g, 35.7 mmol). After stirring for 1 h, the reaction was quenched with dropwise addition of 1N HCl. The reaction mixture was partitioned between 100 mL of ethyl acetate and 50 mL of 1N HCl, dried over sodium sulfate, and evaporated. The residue was chromatographed on silica gel using 33% hexane/66% ethyl acetate/1% acetic acid to afford 2-[(3-carboxyphenyl)sulfanyl]-N-methoxy-N-methylacetamide, E-1a, as a white solid 8.5 g (96%). $^1$H NMR (500 MHz, CDCl$_3$) δ8.15 (t, 1H, J=1.5 Hz), 8.06 (br s, 1H), 7.92 (dt, 1H, J=7.8, 1.2 Hz), 7.68 (dq, 1H, J=6.0, 1.2 Hz), 3.88 (s, 2H), 3.74 (s, 3H), 3.22 (s, 3H).

(b) To a solution of 2-[(3-carboxyphenyl)sulfanyl]-N-methoxy-N-methylacetamide, E-1a, (0.84 g, 3.1 mmol) and EDC (0.66 g, 3.4 mmol) in 10 mL of THF was added 6-amino-2-methylquinoline (0.54 g, 3.4 mmol). After 3 h, the solution was concentrated and the residue was purified by column chromatography with 1:2 hexane/ethyl acetate to afford 3-[(N-methoxy-N-methylcarbamoyl)methylsulfanyl]-N-(2-methylquinolin-6-yl)benzamide, E-1b, as a white crystalline solid 0.89 g (72%): $^1$H NMR (500 MHz, CDCl$_3$) δ8.50 (br s, 1H), 8.45 (d, 1H, J=1.2 Hz), 8.05–7.97 (m, 3H), 7.73 (dd, 1H, J=7.8, 1.5 Hz), 7.57 (dt, 1H, J=13.4, 4.8 Hz), 7.56 (d, 1H, J=4.5 Hz), 7.39 (t, 1H, J=4.5 Hz), 7.27 (d, 1H, J=4.8 Hz), 3.88 (s, 2H), 3.80 (s, 3H), 3.24 (s, 3H), 2.71 (s, 3H); MS (ESI): Calculated for C$_{21}$H$_{21}$N$_3$O$_3$S (M+H$^+$): 395. Found: 395. Anal. calc'd for C$_{20}$H$_{24}$N$_2$O$_6$S.0.2 H$_2$O: C, 63.20; H, 5.41; N, 10.53; S, 8.03. Found: C, 63.03; H, 5.32; N, 10.35; S, 7.92.

(c) To a solution of thioacetanilide (0.30 g, 1.95 mmol) in 10 mL of anhydrous THF at –78° C. was added n-BuLi (1.56 mL, 3.89 mmol, 2.5 M in hexane) over a 5 min period. The mixture was warmed to 0° C. for 1 h, then recooled to –78° C. To this solution was added a solution of 3-[(N-methoxy-N-methylcarbamoyl)methylsulfanyl]-N-(2-methylquinolin-6-yl)benzamide, E-1b, (0.35 g, 0.89 mmol) in 5 mL in THF, and the resulting solution was warmed to 0° C. After 1 h, a solution of 1:1 methanol:acetic acid (1.0 mL) was added dropwise over 1 min. The reaction solution was partitioned between 30 mL of MTBE and extracted with 1N hydrochloric acid (2×20 mL) and saturated brine (1×30 mL), and the organic layer was dried over sodium sulfate and concentrated to give a yellow oil. Purification using column chromatography with 3:1 hexane/ethyl acetate afforded N-(2-methyl-quinolin-6-yl)-[2-oxo-3-phenylthiocarbamoyl-propylsulfanyl]benzamide, E-1c, as a pale yellow foam 0.25 g (56%): $^1$H NMR (500 MHz, CDCl$_3$) δ8.66 (br s, 1H), 8.26 (br s, 1H), 7.94–7.85 (3H, m), 7.81 (br s, 1H), 7.71–7.66 (m, 2H), 7.51 (br s, 1H), 7.45–7.41 (m, 1H), 7.26–7.21 (m 4H), 7.13–7.10 (m, 1H), 3.50 (br s, 2H), 2.67 (s, 3H), 2.03 (s, 2H); MS (ESI): Calculated for C$_{27}$H$_{23}$N$_3$O$_2$S$_2$ (M+H$^+$): 486 Found: 486.

(d) To a solution containing N-(2-methyl-quinolin-6-yl)-[2-oxo-3-phenylthiocarbamoyl-propylsulfanyl]benzamide, E-1c, in 4 mL of ethanol was added acetic acid (0.038 mL, 0.67 mmol) followed by hydrazine monohydrate (0.032 mL, 0.63 mmol). The solution was stirred for 2 h, then concentrated to give the crude product as an amber oil. Purification by radial chromatography (1 mm silica plate) with 90% ethyl acetate/10% methanol as eluant afforded a tan solid. Precipitation of product from dichloromethane by dropwise addition of hexane gave 0.12 g (58%) of N-(2-methyl-quinolin-6-yl)-3-[{5-(phenylamino)-2-H-pyrazol-3-yl}methylsulfanyl]benzamide, E-1, as a white solid: mp 172–174° C. HPLC Rt=13.51 min.; $^1$H NMR (500 MHz, Acetone-d$_6$) δ8.40–8.38 (m, 1H), 8.01 (d, 1H, J=8.5 Hz), 7.91 (s, 1H), 7.86 (dd, 1H, J=8.0, 1.2 Hz), 7.76 (t, 2H, J=9.5 Hz), 7.47 (d, 1H, J=8.0 Hz), 7.35 (t, 1H, J=7.5 Hz), 7.24 (d, 1H, J=8.5 Hz), 7.16 (br s, 2H), 7.02 (t, 2H, J=7.0 Hz), 6.59 (t, 1H, J=7.0 Hz), 5.73 (s, 1H), 4.18 (s, 2H), 2.52 (s, 3H); HRMS (FAB): Calculated for C$_{27}$H$_{23}$N$_5$OS (M+H$^+$): 466.1702. Found: 466.1715. Anal. calc'd for C$_{27}$H$_{23}$N$_5$OS.0.5 CH$_2$Cl$_2$: C, 65.05; H, 4.76; N, 13.79; S, 6.31. Found C, 64.94; H, 4.72; N, 13.47; S, 6.51.

Example E-2

N-(3,4,5-trimethoxyphenyl)-3-[2-(5-phenylamino-2H-pyrazol-3-yl)ethyl]benzamide

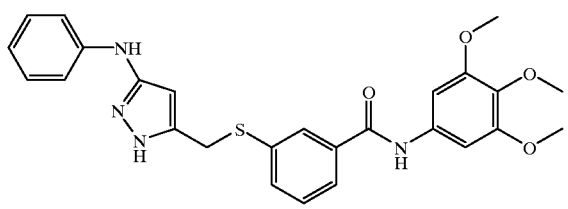

Example E-2 was prepared in a similar manner to that described for E-1, except that 3,4,5-trimethoxyaniline was used in place of 6-amino-2-methylquinoline in step (b): mp 67–69° C. $^1$H NMR (500 MHz, CDCl$_3$) δ8.20 (br s, 1H), 7.75 (br s, 1H), 7.64 (d, 1H, J=7.8 Hz), 7.42 (d, 1H, J=7.2 Hz), 7.29 (t, 1H, J=7.5 Hz), 6.96–6.91 (m, 3H), 6.83 (t, 1H, J=7.2 Hz), 5.89 (s, 1H), 4.05 (s, 2H), 3.80 (s, 3H), 3.75 (s, 6H); HRMS (FAB): Calculated for C$_{26}$H$_{26}$N$_4$O$_4$S (M+H$^+$): 491.1753 Found: 491.1737. Anal. calc'd for C$_{26}$H$_{26}$N$_4$O$_4$S.0.4 Et$_2$O: C, 63.72; H, 5.81; N, 10.77; S, 6.16. Found: C, 63.47; H, 5.88; N, 10.52; S, 6.34.

Example F-1

3-[{5-((E)-2-(4-Hydroxy-3-methoxyphenyl)ethenyl)-2H-pyrazol-3-yl}methylsulfanyl]-N-(2-methylquinolin-6-yl)benzamide 4 Å molecular sieves, acetic acid (0.16 mL, 2.60 mmol), and hydrazine carboxylic acidt-butyl ester (0.34 g, 2.60 mmol). After stirring for 18 h, the mixture was filtered and the filtrate was concentrated to give a crude product as a tan solid, which was chromatographed on silica with 2:1 hexane/ethyl acetate to furnish N-[3-(4-hydroxy-3-methoxy-phenyl)-1-methyl-(E)-2-propenylidene]hydrazinecarboxylic acid t-butyl ester, F-1a, 0.68 g (86%) as a white solid. TLC Rf=0.45 (40% hexane/60% ethyl acetate). $^1$H NMR (500 MHz, CDCl$_3$) δ7.87 (br s, 1H), 7.11–7.08 (m, 2H), 6.98–6.52 (m, 2H), 6.89 (d, 1H, J=8.0 Hz), 5.82 (br s, 1H), 3.93 (s, 3H), 2.13 (s, 3H), 1.53 (s, 9H); LRFAB: Calculated for C$_{16}$H$_{22}$N$_2$O$_4$ (M+H$^+$): 307. Found: 307.

(b) To a solution of N-[3-(4-hydroxy-3-methoxy-phenyl)-1-methyl-(E)-2-propenylidene]hydrazinecarboxylic acid

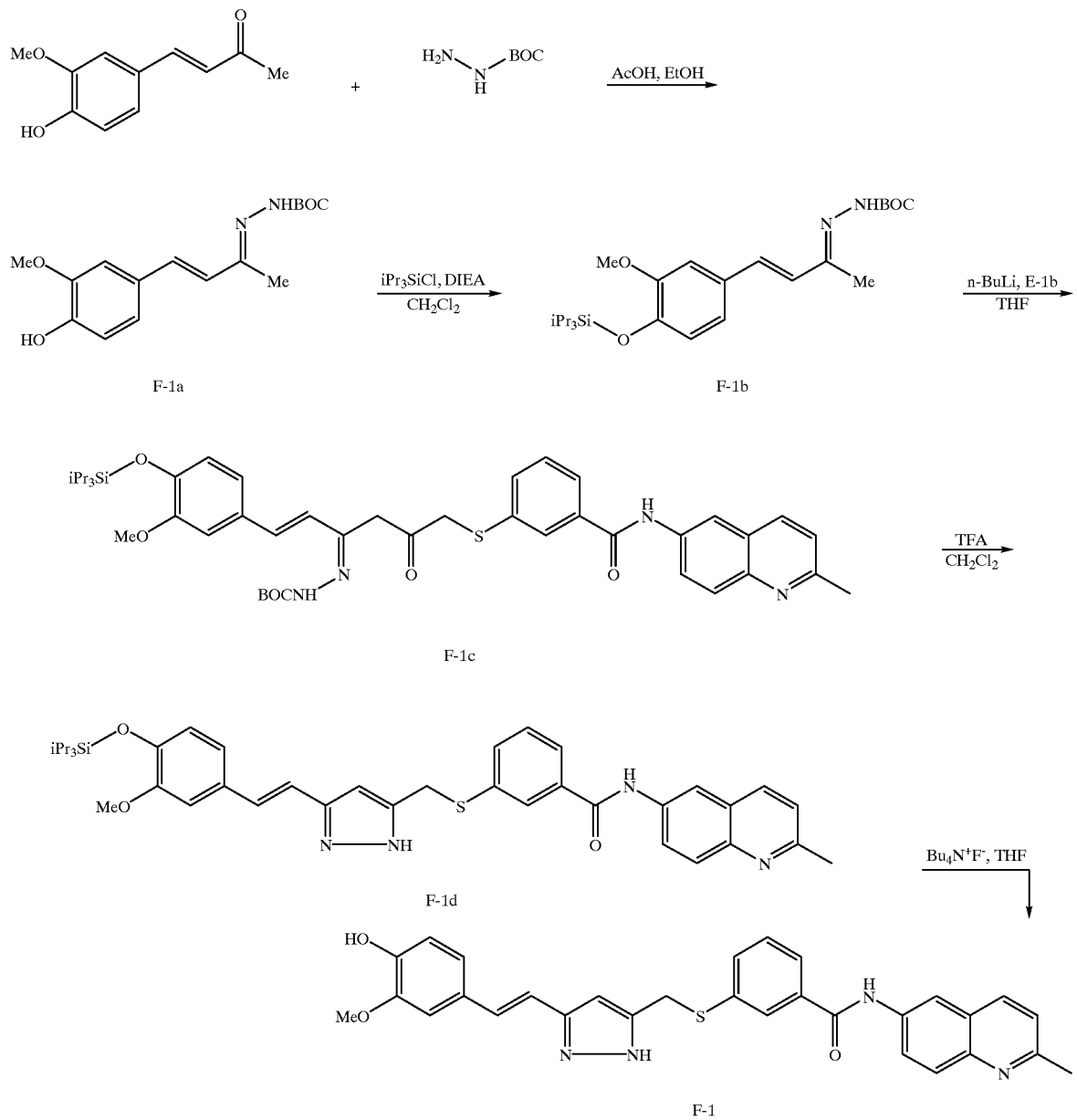

(a) To 5 mL of ethanol was added (E)-4-(4-hydroxy-3-methoxy-phenyl)-but-3-en-2-one (0.50 g, 2.60 mmol), 1 g of t-butyl ester, F-1a, (0.50 g, 1.63) in 5 mL of dichloromethane was added diisopropylethylamine (64 mL, 3.92 mmol) and chlorotriisopropylsilane (0.77 mL, 3.59 mmol). After 20 h, the mixture was concentrated and the residue was partitioned between 30 mL of MTBE and saturated sodium bicarbonate (2×30 mL). The organic layer was filter through 10 g of silica and concentrated to afford a yellow oil. Purification was accomplished using chromatotron with a 2 mm rotor eluting with 80% hexane/20% ethyl acetate to give 0.48 g (65%) of N-{3-[4-methoxy-3-(triisopropylsilanyloxy)-phenyl]-1-methyl)-(E)-2-propenylidene] hydrazinecarboxylic acid t-butyl ester, F-1b, as a white solid: TLC Rf=0.82 (60% hexane/40% ethyl acetate); $^1$H NMR (500 MHz, CDCl$_3$) δ7.47 (br s, 1H),7.02 (d, 1H, J=1.5 Hz), 6.94 (d, 1H, J=16.5 Hz), 6.87 (dd, 1H, J=8.3 Hz, 1.5 Hz), 6.82 (d, 1H, J=8.0 Hz), 6.77 (d, 1H, J=16.5 Hz), 3.81 (s, 3H), 2.02 (s, 3H), 1.50 (s, 9H), 1.29–1.23 (m, 3H), 1.09 (d, 18H, J=7.0 Hz); LRFAB: Calculated for C$_{25}$H$_{42}$N$_2$O$_4$Si (M+H$^+$): 463; Found: 463.

(c) To a −78° C. solution of N-{3-[4-methoxy-3-(triisopropylsilanyloxy)-phenyl]-1-methyl-(E)-2-propenylidene]hydrazinecarboxylic acid t-butyl ester, F-1b, (0.33 g, 0.72 mmol) in 10 mL of anhydrous THF was added n-BuLi (0.61 mL, 3.89 mmol, 2.5 M in hexane) over 5 minutes. After the addition was complete, the mixture was warmed to 0° C. for 1 h and then recooled to −78° C. To the resulting mixture was added a solution of 3-[(N-methoxy-N-methylcarbamoyl)methylsulfanyl]-N-(2-methylquinolin-6-yl)benzamide, E-1b, (0.14 g, 0.36 mmol) in 5 mL in THF, and the resulting mixture was warmed to 0° C. After 1 h, the reaction was cooled to −78° C. and quenched by adding 1:1 acetic acid:methanol (1 mL). The reaction mixture was then partitioned between 30 mL of MTBE and 1 N aq. HCl (2×20 mL). The organic layer was dried over sodium sulfate and concentrated to give a yellow oil. Purification by silica gel chromatography, with 2:1 hexane/ethyl acetate as eluant, afforded 0.12 g (43%) of N$^2$-[1-{4-methoxy-3-(triisopropylsilanyloxy)-phenyl}-6-{3-(2-methylquinolin-6-ylcarbamoyl)phenylsulfanyl}-5-oxo-(E)-hex-1-en-3-ylidene}-hydrazainecarboxylic quinolin-6-ylcarbamoyl)phenylsulfanyl}-5-oxo-(E)-hex-1-en-3-ylidene]-hydrazinecarboxylic acid t-butyl ester, F-1c, as a pale yellow foam: TLC R$_f$=0.50 (60% ethyl acetate/hexane); $^1$H NMR (500 MHz, CDCl$_3$) δ8.64 (s, 1H), 8.12–8.10 (m, 2H), 8.03 (br s, 1H), 7.90 (d, 1H, J=8.0 Hz), 7.77 (d, 2H, J=7.0 Hz), 7.46 (t, 1H, J=8.0 Hz), 7.31 (d, 1H, J=5.0 Hz), 6.91–6.78 (m, 5H), 3.92–3.60 (m, 4H), 2.73 (s, 3H), 1.54–1.43 (m, 3H), 1.20 (s, 9H), 1.07 (d, 18H, J=9.5 Hz).

(d) To a solution of 0.10 g (0.14 mmol) of N$^2$-[1-{4-methoxy-3-(triisopropylsilanyloxy)-phenyl}-6-{3-(2-methyl-quinolin-6-ylcarbamoyl)phenylsulfanyl}-5-oxo-(E)-hex-1-en-3-ylidene]-hydrazinecarboxylic acid t-butyl ester, F-1c, in 5 mL of dichloromethane was added 5 mL of trifluoroacetic acid. After 1 h, the reaction mixture was concentrated, 5 mL of toluene added, and the solvent removed again to give an amber oil. The residue was purified by silica gel chromatography with 1:1:1 hexane/dichloromethane/ethyl acetate as eluant to give 0.089 g (92%) of 3-[{5-{(E)-2-(3-methoxy-4-triisopropylsilanyloxyphenyl)ethenyl}-2H-pyrazol-3-yl}methylsulfanyl]-N-(2-methylquinolin-6-yl)benzamide, F-1d, as tan solid: TLC Rf=0.18 (50% ethyl acetate/hexane); $^1$H NMR (300 MHz, Acetone-d$_6$) δ10.21 (br s, 1H), 8.95 (d, 1H, J=1.5 Hz), 8.71 (d, 1H, J=8.4 Hz), 8.43–8.31 (m, 3H), 8.10 (d, 1H, J=7.5 Hz), 7.88–7.82 (m, 2H), 7.85 (t, 1H, J=7.8 Hz), 7.41–7.19 (m, 4H), 7.11 (d, 1H, J=8.1 Hz), 6.69 (s, 1H), 4.57 (s, 2H), 4.10 (s, 3H), 3.05 (s, 3H), 1.57–1.47 (m, 3H), 1.34 (d, 18H, J=8.5 Hz); MS (ESI): Calculated for C$_{39}$H$_{46}$N$_3$OSi (M+H$^+$): 678; Found: 678.

(e) To a solution of 3-[{5-{(E)-2-(3-methoxy-4-triisopropylsilanyloxyphenyl)ethenyl}-2H-pyrazol-3-yl}methylsulfanyl]-N-(2-methylquinolin-6-yl)benzamide, F-1d, (0.057 g, 0.084 mmol) in 5 mL THF was added tetrabutylammonium fluoride (1M) in tetrahydrofuran (0.093 mL, 0.092 mmol). After 3 h, the solution was concentrated and the residue was partitioned between 20 mL of ethyl acetate and 20 mL of 1M phosphate buffer at 7.0 pH. The organic layer was filtered through 10 g of silica with 50 mL dichloromethane and concentrated to give the crude product as an amber oil. The residue was further purified by radial chromatography on a 1 mm plate with 3:1 hexane/ethyl acetate as eluant. The purified product was dissolved in 1 mL of dichloromethane and hexane was added dropwise to precipitate 0.34 g (77%) of 3-[{5-((E)-2-(4-hydroxy-3-methoxyphenyl)ethenyl)-2H-pyrazol-3-yl}methylsulfanyl]-N-(2-methylquinolin-6-yl)benzamide, F-1, as a white solid: HPLC Rt=13.12 min.; TLC Rf=0.30 (50% ethyl acetate/hexane); $^1$H NMR (500 MHz, CDCl$_3$) δ9.67 (br s, 1H), 8.41 (br s, 1H), 8.03 (d, 1H, J=8.5 Hz), 7.89–7.87 (m, 2H), 8.79 (d, 1H, J=9.0 Hz), 7.71 (d, 1H, J=7.5 Hz), 7.33 (t, 1H, J=8.0 Hz), 7.25 (d, 1H, J=8.5 Hz), 7.01 (s, 1H), 6.78 (d, 1H, J=16.5 Hz), 6.83–6.78 (m, 2H), 6.67 (d, 1H, J=8 Hz), 6.29 (s, 1H), 4.19 (s, 2H), 3.74 (s, 3H), 2.53 (s, 3H). HRMS (FAB): Calculated for C$_{30}$H$_{26}$N$_4$O$_3$S (M+H$^+$): 655.0780 Found: 655.0804. Anal. calc'd for C$_{30}$H$_{26}$N$_4$O$_3$S.0.8 EtOAc: C, 67.23; H, 5.51; N, 9.45; S, 5.41. Found: C, 67.08; H, 5.60; N, 9.73; S, 5.45.

Example F-2

3-[5-(2-(3,4-Dimethoxyphenyl)ethenyl)-2H-pyrazol-3-yl)methylsulfanyl]-N-(2-methylquinolin-6-yl) benzamide

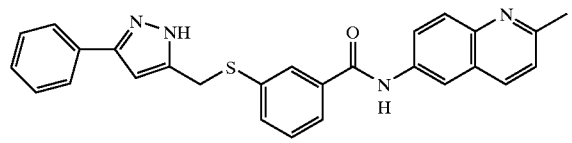

F-2

Example F-2 was prepared in a similar manner to that described for F-1, except that acetophenone was used in place of 4-(4-hydroxy-3-methoxy-phenyl)-but-3-en-2-one in step (a), and the protection/deprotection steps (b) and (e) were not needed: mp 99–101° C.; TLC Rf=0.50 (75% dichloromethane/25% ethyl acetate); HPLC Rt=14.04 min.; $^1$H NMR (500 MHz, CDCl$_3$) δ8.33 (br s, 1H), 8.21 (d, 1H, J=2.0 Hz) 7.95 (br s, 1H), 7.80 (d, 1H, J=8.5 Hz), 7.75 (d, 1H, J=9.1 Hz), 7.70 (d, 1H, J=7.5 Hz), 7.61 (d, 2H, J=7.5 Hz), 7.51 (dd, 1H, J=9.3, 2.5 Hz), 7.43 (d, 1H , J=8.0 Hz), 7.32–7.25 (m, 5H), 7.15 (d, 8.5 Hz), 6.57 (s, 1H), 4.26 (s, 2H), 2.61 (s, 3H). HRMS (FAB): Calculated for C$_{27}$H$_{22}$N$_4$OS (M+H$^+$): 451.1593. Found: 451.1580. Anal. calc'd for C$_{27}$H$_{22}$N$_4$OS.0.8 EtOAc: C, 70.42; H, 5.30; N, 11.33; S, 6.48. EtOAc Found: C, 70.39; H, 5.34; N, 11.29; S, 6.48.

Example F-3

3-(2-{5-[(E)-2-(3,4-Dimethoxyphenyl)ethenyl]-2H-pyrazol-3-yl}-ethyl)-N-(3-methyl-4-isopropylphenyl)-benzamide

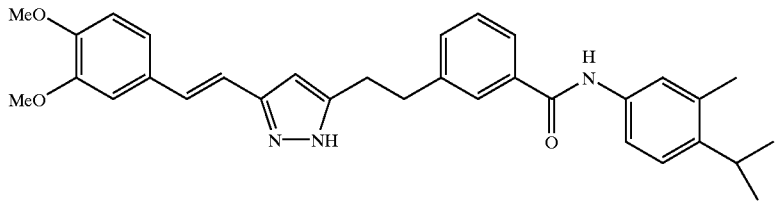

Example F-3 was prepared in a similar manner to that described for F-1, except that (E)-4-(3,4-dimethoxyphenyl)-but-3-en-2-one was used in place of (E)-4-(4-hydroxy-3-methoxyphenyl)-but-3-en-2-one in step (a), N-(4-isopropyl-3-methyl-phenyl)-3-[2-(N-methoxy-N-methylcarbamoyl)-ethyl]benzamide, G-1f, (from Example G-1, step (f)) was used in place of 3-[(N-methoxy-N-methylcarbamoyl)methylsulfanyl]-N-(2-methylquinolin-6-yl)benzamide, E-1b, in step (c) and the protection/deprotection steps (b) and (e) were not needed: HPLC Rt=16.37 min.; $^1$H NMR (300 MHz, CDCl$_3$) δ7.71 (br s, 1H), 7.69–7.66 (m, 2H), 7.44–7.17 (m, 5H), 7.01–6.81 (m, 5H), 6.25 (s, 1H), 3.89 (d, 6H, J=1.5 Hz), 3.12–3.01 (m, 5H), 2.32 (s, 3H), 1.20 (d, 6H, J=5.1 Hz); HRMS (FAB): Calculated for m/z C$_{32}$H$_{35}$N$_3$O$_3$ (M+Cs$^+$): 642.1733, Found: 642.1712. Anal. calc'd for C$_{32}$H$_{35}$N$_3$O$_3$: C, 75.42; H, 6.92; N, 8.24. Found C, 75.45; H, 7.08; N, 8.16.

Example F-4

4-Fluoro-3-[{5-((E)-1-propenyl)-2H-pyrazol-3-yl}methoxy]-N-[4-(pyrrolidin-1-yl)-3-trifluoromethylphenyl]benzamide

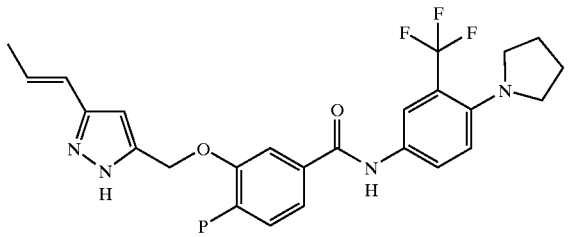

Example F-4 was prepared in a similar manner to that described for F-1, except that (E)-3-penten-2-one was used in place of (E)-4-(4-hydroxy-3-methoxyphenyl)-but-3-en-2-one in step (a), 4-fluoro-N-[4-(pyrrolidin-1-yl)-3-trifluoromethylphenyl]-3-[2-(N-methoxy-N-methylcarbamoyl)methoxy]benzamide, (prepared in a similar manner as described for 4-fluoro-N-[4-(imidazol-1-yl)-3-trifluoromethyl-phenyl]-3-[(N-methoxy-N-methylcarbamoyl)methoxy]benzamide, J-1d, in Example F-3

J-1) was used in place of 3-[(N-methoxy-N-methylcarbamoyl)methylsulfanyl]-N-(2-methylquinolin-6-yl)benzamide, E-1b, in step (c) and the protection/deprotection steps (b) and (e) were not needed: HPLC Rt=16.27 min. $^1$H NMR (300 MHz, CDCl$_3$) δ7.75 (m, 4H), 7.45 (d, 1H, J=8.7 Hz), 7.42–7.37 (m, 1H), 7.35–7.28 (m, 2H), 7.15 (t, 1H, J=8.4 Hz), 7.00 (d, 1H, J=8.7 Hz), 6.56 (d, 1H, J=8.9 Hz), 6.37 (s, 1H), 6.27–6.15 (m, 2H), 5.60 (s, 1H), 5.23 (s, 1H), 3.30–3.29 (m, 4H), 1.98 –1.95 (m, 4H), 1.92 (d, 3H, J=6.3 Hz); MS (ESI): m/z Calculated for C$_{25}$H$_{24}$F$_4$N$_4$O$_2$ (M+H$^+$): 489, Found: 489. Anal. calc'd for C$_{25}$H$_{24}$F$_4$N$_4$O$_2$: C, 61.47; H, 4.95; N, 11.47. Found C, 61.32; H, 5.06; N 11.33.

Example F-5

3-(2-{5-[(E)-2-(3,4-Dimethoxyphenyl)ethenyl]-2H-pyrazol-3-yl}-ethyl)-N-(3-methyl-4-isopropylphenyl)-benzamide

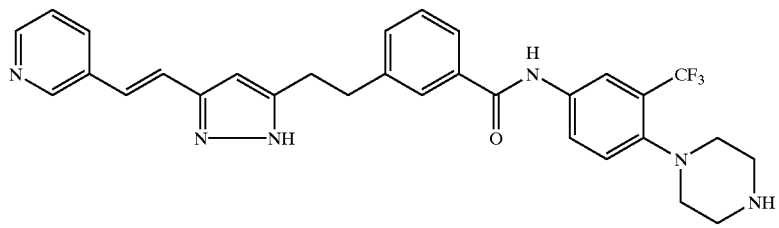

Example F-5 was prepared in a similar manner to that described for F-3, except that (E)-4-(pyridin-3-yl)-3-buten-2-one was used in place of (E)-4-(3,4-dimethoxyphenyl)-but-3-en-2-one in step (a), and 4-[4-(t-butoxycarbonyl)piperazin-1-yl]-3-trifluoromethylaniline, prepared according to the procedure described in WO 99/21845 (p. 58) for the preparation of 1-methyl-4-(4-nitrophenyl)piperazine, was used in place of 4-isopropyl-3-methylaniline in step (d) of Example G-1, and the final deprotection step (e) was carried out in a manner similar to that described in Example G-10: HPLC Rt=13.53 min.; $^1$H NMR (300 MHz, DSMO-d$_6$) δ8.69 (s, 1H), 8.44 (d, 1H, J=3.3 Hz), 8.14 (s, 1H), 8.07–7.82 (m, 2H), 7.86 (s, 1H), 7.81–7.79 (m, 1H), 7.54–7.43 (m, 3H), 7.39–7.37 (m, 1H), 7.25–7.04 (m, 2H), 310–2.98 (m, 4H), 2.83–2.78 (m, 8H); HRMS (FAB): Calculated for C$_{30}$H$_{29}$F$_3$N$_6$O (M+H$^+$): 547.2433 Found: 547.2445. Anal. calc'd for C$_{28}$H$_{30}$N$_4$O.0.5 H$_2$O.0.2 CH$_2$Cl$_2$: C, 63.35; H 5.35; N, 14.68. Found C, 63.26; H, 5.38; N 14.25.

Example G-1
N-(4-Isopropyl-3-methyl-phenyl)-3-{2-[5-(4-(methylsulfamoyl)phenylamino)-2H-pyrazol-3-yl]-ethyl}-benzamide
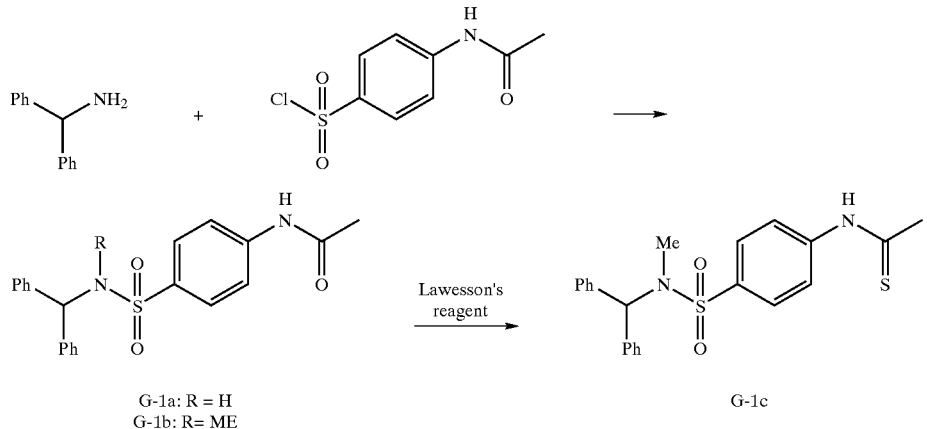
G-1a: R = H
G-1b: R = ME
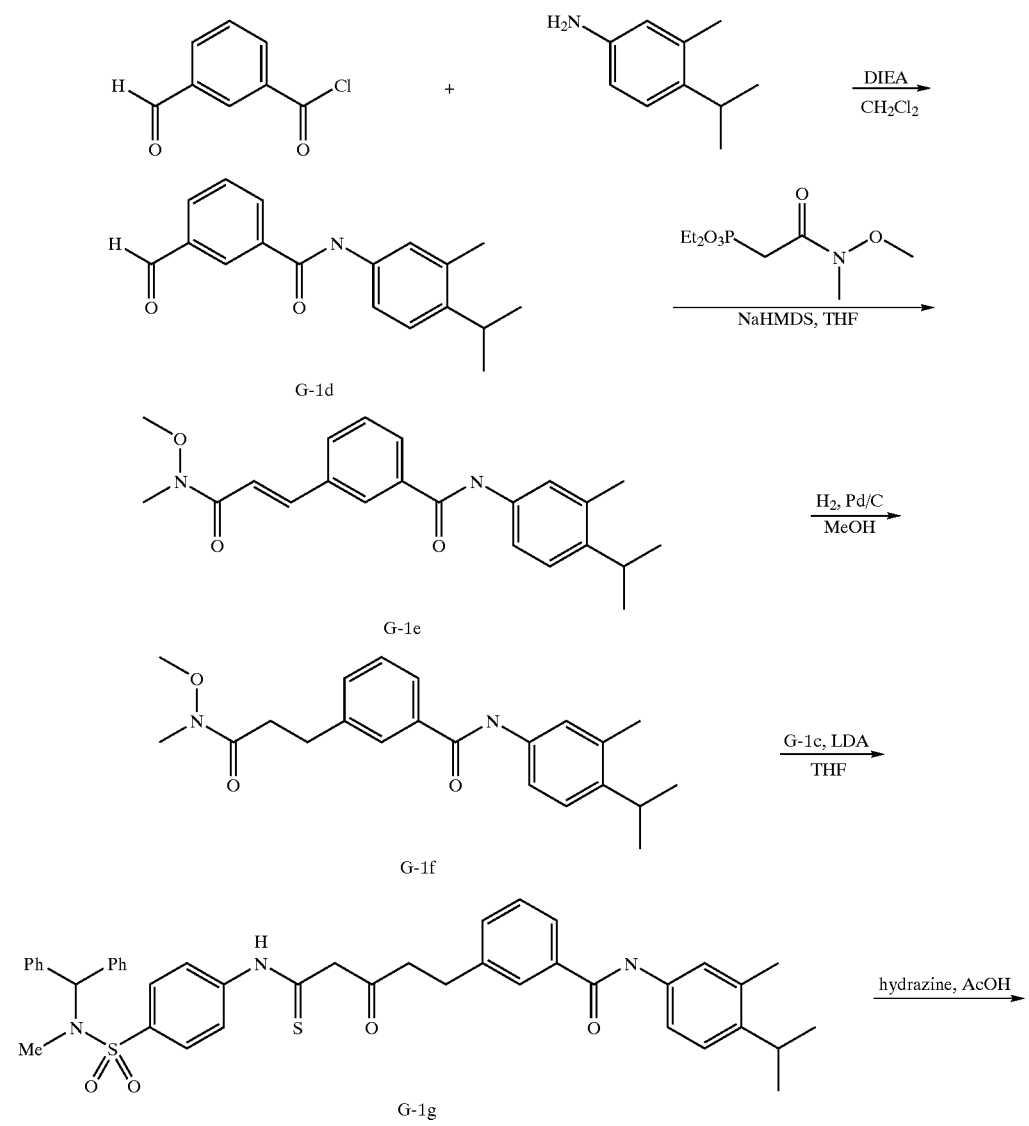

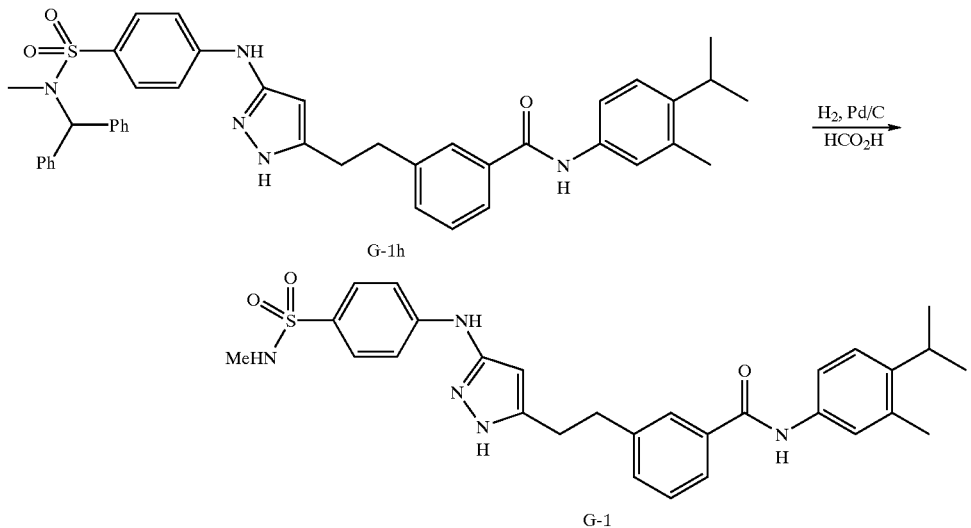

(a) To a solution of 4-acetylamino-benzenesulfonyl chloride (2.00 g, 8.56 mmol) in 25 mL of DMF was added 4-dimethylaminopyridine (0.11 g, 0.86 mmol) and diphenylaminomethane (1.79 mL, 10.27 mmol). After 4 h, the reaction mixture was added to 125 mL of water, and the precipitate was collected by filtration, washed with diethyl ether (2×20 mL), then dried under high vacuum for 4 h to afford 1.98 g (61%) of N-(diphenylmethyl)-4-(acetylamino) benzenesulfonamide, G-1a: HPLC Rt=12.90 min.; $^1$H NMR (500 MHz, CDCl$_3$) δ10.20 (br s, 1H), (8.82 (d, 1H, J=2.0 Hz), 7.57 (s, 4H), 7.24–7.20 (m, 8H), 7.18–7.13 (m, 2H), 5.58–7.52 (m, 1H), 3.38 (s, 3H); LRFAB: Calculated for $C_{21}H_{20}N_2O_3S$ (M+H$^+$): 381 Found:381.

(b) To DMF (15 mL) was added N-(diphenylmethyl)-4-(acetylamino)benzenesulfonamide, G-1a, (1.50 g, 3.94 mmol), potassium carbonate (1.37 g, 9.86 mmol), and iodomethane (0.37 mL, 5.93 mmol). The reaction mixture was stirred for 3 h at 60° C., cooled to 25° C., and partitioned between 50 mL of MTBE and 1N HCl (2×50 mL). The organic layer was dried over sodium sulfate and concentrated to give an amber oil, which was purified by chromatography on silica gel (3:1 hexane:ethyl acetate) to give 1.50 g (98%) of N-(diephenylmethyl)-N-methyl-4-(acetylamino) benzenesulfonamide, G-1b: TLC Rf=0.62 40% hexane/ethyl acetate; $^1$H NMR (300 MHz, CDCl$_3$) δ7.67–7.64 (m, 1H), 7.58–7.52 (m, 2H), 7.28–7.23 (m, 8H), 7.21–7.08 (m, 3H), 6.47 (s, 1H), 2.68 (s, 3H), 2.20 (s, 3H).

(c) To a solution of 2.00 g, (5.30 mmol) of N-(diphenylmethyl)-N-methyl-4-(acetylamino) benzenesulfonamide, G-1b, in toluene (30 mL) was added 2,4-bis(4-methoxyphenyl)-1,3-dithia-2,4-diphosphetane-2,4-disulfide (1.07 g, 2.64 mmol). The solution was warmed to 100° C. for 2 h then cooled to 25° C. The reaction mixture was filtered through a silica gel plug using 50 mL of MBTE and concentrated. The residue was purified by chromatography on silica gel (5:1 hexane/ethyl acetate) to afforded 1.62 g (77%) of 4-[N-(diphenylmethyl)-N-methylsulfamoyl]-thioacetanilide, G-1c, as a yellow oil: HPLC Rt=18.67 min.; $^1$H NMR (300 MHz, CDCl$_3$) δ7.84 (d, 1H, J=8.7 Hz), 7.72 (d, 1H, J=8.5 Hz), 7.28–7.25 (m, 8H), 7.09–7.07 (m, 2H), 6.46 (s, 1H), 2.77 (s, 3H), 2.56 (s, 3H).

(d) To a solution of 5.00 g (33.26 mmol) 3-formylbenzoic acid in dichloromethane at 0° C. was added oxalyl chloride (3.48 mL, 39.92 mmol) and DMF (0.01 mL). The reaction was stirred for 3 h at 25° C., and then concentrated to dryness. The residue (2.1 g, 12.45 mmol) was dissolved in dichloromethane (30 mL) and 4-isopropyl-3-methylaniline.HCl (2.55 g, 13.70 g) added, followed by diisopropylethylamine (4.48 mL). After stirring for 2 h, the solution was washed with sat. sodium bicarbonate (2×20 mL) and 1N HCl (2×20 mL) and the organic layer dried over sodium sulfate and concentrated to dryness. The residue was purified on silica gel (3:1 hexane:ethyl acetate) to provide 2.99 g (90%) of 3-formyl-N-(4-isopropyl-3-methylphenyl) benzamide, G-1d, as a off-white solid: $^1$H NMR (300 MHz, CDCl$_3$) δ10.12 (s, 1H), 8.60–8.58 (m, 1H), 8.38–8.36 (m, 1H), 8.21–8.15 (m, 2H), 8.07–8.04 (m, 1H), 7.93 (br s, 1H), 7.71–7.67 (m, 1H), 7.44 (br s, 1H), 7.27–7.24 (s, 1H), 3.15–3.10 (m, 1H), 2.35 (s, 3H), ), 1.23 (d, 6H, J=6.7 Hz).

(e) To a solution of 2-diethyl(N-methoxy-N methylcarbamoylmethyl)phosphonate (1.70 mL, 7.82 mmol) in 15 ml of THF at –78° C. was added sodium bis(trimethylsilyl) amide (9.24 mL, 1M in THF) dropwise over 2 min. After the addition was complete, the reaction was warmed to 0° C. for 1 h. To this solution was added a solution of 2.00 g (7.11 mmol) of 3-formyl-N-(4-isopropyl-3-methyl-phenyl)-benzamide, G-1d, in 20 mL of THF. The solution was stirred for 1 h, then quenched with 1:1 MeOH/AcOH (1 mL). The mixture was partitioned between 50 mL of ethyl acetate and 1N HCl (2×20 mL), and the organic layer was dried over sodium sulfate and concentrated. The residue was purified on silica gel (2:1 hexane:ethyl acetate) and to afford 1.33 g (51%) of N-(4-isopropyl-3-methylphenyl)-3-[(E)-2-(N-methoxy-N-methylcarbamoyl)ethenyl]-benzamide, G-1e, as a white solid foam: $^1$H NMR (300 MHz, CDCl$_3$) δ8.10 (br s, 1H), 7.83–7.79 (m, 2H), 7.73–7.68 (m, 2H), 7.52–7.45 (m, 3H), 7.28–7.24 (m, 1H), 7.12 (d, 1H, J=15.9 Hz), 3.78 (s, 3H), 3.31 (s, 3H), 3.15–3.10 (m, 1H), 2.36 (s, 3H), 1.23 (d, 6H, J=6.0 Hz).

(f) A mixture of 0.90 g (2.46 mmol) N-(4-isopropyl-3-methylphenyl)-3-[(E)-2-(N-methoxy-N-methylcarbamoyl) ethenyl]-benzamide, G-1e, and 0.1 g of 10% palladium on carbon in 20 ml of 1:1 MeOH:EtOAc was stirred under 1 atm H$_2$ for 18 h. The reaction was filtered though a 0.5 uM teflon filter and concentrated to give 0.90 g (100%) of N-(4-isopropyl-3-methylphenyl)-3-[2-(N-methoxy-N-methylcarbamoyl)ethyl]-benzamide, G-1f: $^1$H NMR (300

MHz, CDCl₃) δ7.74 (s, 2H), 7.68 (d, 1H, J=4.2 Hz), 7.44–7.40 (m, 4H), 7.25–7.23 (m, 1H), 3.63 (s, 3H), 3.18 (s, 3H), 3.14–3.11 (m, 1H), 3.06–3.03 (m, 2H), 2.79 (t, 2H, J=4.5 Hz), 2.36 (s, 3H), 1.22 (d, 6H, J=4.2 Hz).

(g) To a solution of 0.45 g (1.34 mmol) of 4-[N-(diphenylmethyl)-N-methylsulfamoyl]thioacetanilide, G-1c, and 0.16 mL (1.34 mmol) of N,N'-dimethylpropyleneurea (DMPU) in 15 mL of THF at –78° C. was added 1.07 mL (2.68 mmol) 2.5 M n-BuLi in hexane. After 0.25 h, the reaction was warmed to 0° C. for 0.5 h, then recooled to –78° C. To the reaction mixture was added a solution of 0.23 g (0.62 mmol) of N-(4-isopropyl-3-methylphenyl)-3-[2-(N-methoxy-N-methylcarbamoyl)ethyl]-benzamide, G-1f, in 5 mL of THF. The reaction was warmed to 0° C. for 1 hour and then quenched by dropwise addition of 0.5 mL of 1:1 MeOH/AcOH. The mixture was partitioned between 30 mL of ethyl acetate and sat. sodium bicarbonate (2×10 mL). The organic layer was dried over sodium sulfate and concentrated. The residue was purified by chromatography on silica gel (1:2 ethyl acetate:hexane) to afford 0.24 g (54%) of 3-[4-{4-(N-(diphenylmethyl)-N-methylsulfamoyl)phenylthiocarbamoyl}-3-oxo-butyl]-N-(4-isopropyl-3-methyl-phenyl)benzamide, G-1g, as an amber oil: ¹H NMR (500 MHz, CDCl₃) δ7.91–7.83 (m, 2H), 7.74–7.64 (m, 3H), 7.59–7.47 (m, 3H), 7.41–7.23 (m, 8H) 7.12–7.04 m, 6H), 6.43 (s, 1H), 7.25–7.23 (m, 1H), 3.63 (s, 3H), 3.18 (s, 3H), 3.18–3.13 (m, 1H), 3.11–3.01 (m, 2H), 2.83 (s, 2H), 2.78 (s, 3H), 2.37–2.32(m, 2H), 1.21 (d, 6H, 1.5 Hz).

(h) To a solution of 0.36 g (0.51 mmol) of 3-[4-{4-(N-(diphenylmethyl)-N-methylsulfamoyl)phenylthiocarbamoyl}-3-oxo-butyl]-N-(4-isopropyl-3-methylphenyl)benzamide, G-1g, in 5 ml of ethanol were added acetic acid (0.20 mL, 0.34 mmol) and hydrazine monohydrate (0.016 mL, 0.34 mmol). After 1 h, the solution was partitioned between ethyl acetate (30 mL) and 1N HCL (2×20 mL). The organic layer was washed with sat. sodium bicarbonate (2×20 mL), dried over sodium sulfate, and concentrated to give a yellow oil. Purification by chromatography on silica gel (25% ethyl acteate:hexane) afforded 0.28 g (79%) of 3-{2-[5-{4-(N-(diphenylmethyl)-N-methylsulfamoyl)phenylamino}-2H-pyrazol-3-yl]ethyl}-N-(4-isopropyl-3-methyl-phenyl)-benzamide, G-1h, as yellow solid: ¹H NMR (300 MHz, CDCl₃) δ8.09 (s, 1H), 7.67 (br s, 1H), 7.63 (d, 1H, J=7.5 Hz), 7.48–7.42 (m, 3H), 7.60–7.22 (m, 10H), 7.01–7.04 (m, 3H), 7.01 (d, 2H, J=8.4 Hz), 6.43 (s, 1H), 5.78 (s, 1h), 3.13–3.04 (m, 1H), 2.93–2.84 (m, 4H), 2.61 (s, 3H), 2.28 (s, 3H), 1.19 (d, 6H, J=6.6 Hz); MS (ESI): m/z Calculated for C₄₂H₄₃N₅O₃S (M–H⁻): 696 Found 696.

(i) To a solution of 3-{2-[5-{4-(N-(diphenylmethyl)-N-methylsulfamoyl)phenylamino}-2H-2H-pyrazol-3-yl]ethyl}-N-(4-isopropyl-3-methyl-phenyl)-benzamide, G-1h, in 0.025 mL of formic acid and 1.2 mL of acetic acid was added 0.08 g of 10% palladium on carbon. The mixture was stirred at 80° C. for 96 h, then cooled to room temperature and filtered though a 0.5 μM Teflon filter. The filtrate was concentrated and the residue was purified by chromatography on silica gel (2:1 ethyl acetate:hexane) to afford N-(4-isopropyl-3-methylphenyl)-3-{2-[5-(4-(N-methylsulfamoyl)phenylamino)-2H-pyrazol-3-yl]ethyl}benzamide, G-1, (0.053 g, 87%): HPLC Rt=14.65 min; ¹H NMR (Acetone-d₆) δ7 91 (br s, 1H),. 7.59 (br s, 1H),. 7.69 (d, 1H, J=6.0 Hz), 7.52–7.25 (m, 7H), 7.08 (d, 1H, J=8.1 Hz), 3.51–2.89 (m, 5H), 2.40 (s, 3H), 2.19 (s, 3H), 1.08 (d, 6H, J=6.9 Hz); HRMS (FAB): Calculated for C₂₉H₃₃N₅O₃S (M+H⁺): 532.2382, Found: 532.2891

Example G-2

N-(2-Methylquinolin-6-yl)-3-[2-(5-phenylamino-2H-pyrazol-3-yl)ethyl]benzamide

G-2

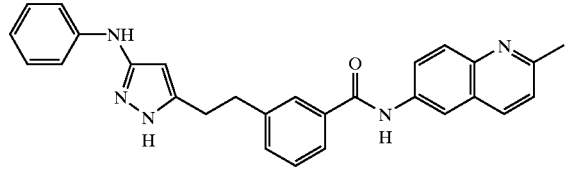

Example G-2 was made in a similar manner to that described for G-1, except that 6-amino-2-methylquinoline was used in place of 4-isopropyl-3-methylaniline in step (d), and thioacetanilide was used instead of 4-[N-(diphenylmethyl)-N-methylsulfamoyl]thioacetanilide, G-1c, in step (g), and the final deprotection step (i) was not needed: mp 98–102° C. ¹H NMR (500 MHz, CDCl₃) δ8.79 (d, 1H, J=2 Hz), 8.32 (br s, 1H), 7.95 (d, 1H, J=8.5 Hz), 7.92 (d, 1H, J=9.0 Hz), 7.22 (d, 1H, J=7.5 Hz), 6.74 (dd, 1H, J=9.0, 2.0 Hz), 7.37 (t, 1H, J=7.5 Hz), 7.31–7.20 (m, 6H), 7.06 (d, 2H, J=8.0 Hz), 6.85 (t, 1H, J=7.5 Hz), 5.81 (s, 1H), 2.96 (t, 2H, J=6.0 Hz), 2.91 (t, 2H, J=6.0 Hz) 2.65 (s, 3H); HRMS (FAB): Calculated for C₂₈H₂₅N₅O (M+H⁺): 448.2137 Found: 448.2129. Anal. calc'd for C₂₈H₂₅N₅O.0.3 EtOAc: C, 73.99; H, 5.83; N, 14.78. Found C, 73.72; H, 5.88; N, 14.78

Example G-3

N-(4-isopropyl-3-methylphenyl)-3-[2-(5-phenylamino-2H-pyrazol-3-yl)ethyl]benzamide

G-3

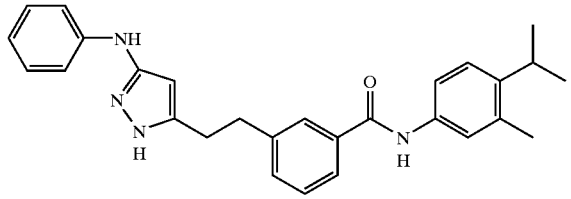

Example G-3 was made in a similar manner to that described for G-1, except thioacetanilide was used instead of 4-[N-(diphenylmethyl)-N-methylsulfamoyl]thioacetanilide, G-1c, in step (g), and the final deprotection step (i) was not needed: mp 150–151 °C.; ¹H NMR (500 MHz, CDCl₃) δ7.84 (s, 1H), 7.65 (d, 1H, J=7.5 Hz), 7.62 (s, 1H), 7.42–7.35 (m, 3H), 7.36 (t, 1H, J=7.5 Hz), 7.28–7.17 (m, 4H), 7.05 (d, 2H, J=8.5 Hz), 5.80 (s, 1H), 3.12–3.07 (m, 1H), 2.97 (t, 2H, J=7.5 Hz), 2.90 (t, 2H, J=7.0 Hz), 2.30 (s, 3H); HRMS (FAB): Calculated for C₂₈H₃₀N₄O (M+H⁺): 439.2498 Found: 439.2488. Anal. calc'd for C₂₈H₃₀N₄O.0.1CH₂Cl₂ Found: C, 75.49; H 6.81; N, 12.53. Found C, 75.44; H, 6.81; N 12.53.

Example G-4

N-(4-Isopropyl-3-methyl-phenyl)-3-{2-[5-(6-methoxypyridin-3-yl)amino-2H-pyrazol-3-yl]-ethyl}-benzamide

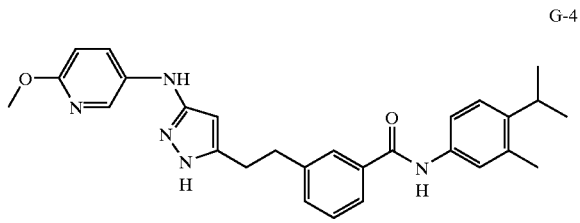

G-4

Example G-4 was made in a similar manner to that described for G-1, except that N-(6-methoxy-pyridin-3-yl)acetamide was used instead of N-(diphenylmethyl)-N-methyl-4-(acetylamino)-benzenesulfonamide, G-1b, in step (c). $^1$H NMR (300 MHz, CDCl$_3$) δ7.97 (d, 1H, J=2.7 Hz), 7.84 (br s, 1H), 7.67–7.62 (m, 2H), 7.49 (dd, 1H, J=8.9, 3.0 Hz), 7.42–7.42–7.40 (m, 3H), 7.30–7.61 (m, 2H), 7.19 (d, 1H, J=9.0 Hz), 5.66 (s, 1H), 3.88 (s, 3H), 3.10 (q, 1H, J=6.6 Hz), 2.97–2.90 (m, 4H), 2.17 (s, 3H), 1.23 (d, 6H, J=4.2 Hz); HRMS (FAB): Calculated for C$_{28}$H$_{31}$N$_5$O$_2$ (M+H$^+$): 470.2556, Found: 470.2563. Anal. calc'd for C$_{28}$H$_{33}$N$_5$O$_2$Cl$_2$: C, 61.99; H, 6.13; N, 12.91. Found C, 61.83; H, 6.39; N 12.83.

Example G-5

N-(4-Dimethylamino-3-trifluoromethylphenyl)-3-{2-[5-(6-methoxypyridin-3-yl)amino-2H-pyrazol-3-yl]ethyl}-benzamide

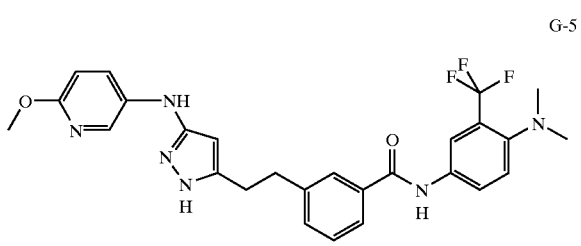

G-5

Example G-5 was made in a similar manner to that described for G-1, except that 4-dimethylamino-3-trifluoromethylaniline, prepared according to the procedure described in WO 99/21845 (p. 58) for the preparation of 1-methyl-4-(4-nitrophenyl)piperazine, was used in place of 4-isopropyl-3-methylaniline in step (d), and N-(6-methoxy-pyridin-3-yl)acetamide was used instead of N-(diphenylmethyl)-N-methyl-4-(acetylamino)-benzenesulfonamide, G-1b, in step (c): $^1$H NMR (300 MHz, CDCl$_3$) δ8.27 (br s, 1H), 7.93 (d, 1H, J=1.5 Hz), 7.84 (dd, 1H, J=4.5, 1.5 Hz), 7.88 (d, 1H, J=2.7 Hz), 7.64 (d, 1H, J=5.7 Hz), 7.60 (s, 1H), 7.37 (dd, 1H, J=8.7, 3.0 Hz), 7.66 (d, 1H, 4.5 Hz), 7.58 (s, 1H), 7.43 (dd, 1H, J=5.40, 1.5 Hz), 7.33 (t, 1H, J=4.8 Hz), 7.29–7.26 (m, 2H), 6.63 (d, 1H, J=5.4 Hz), 5.62 (s, 1H) 3.86 (s, 3H), 2.94–2.86 (m, 4H), 2.69 (s, 6H); HRMS (FAB): Calculated for C$_{27}$H$_{27}$F$_3$N$_6$O$_2$ (M+H$^+$): 525.2226, Found: 525.2208. Anal. calc'd for C$_{27}$H$_{27}$F$_3$N$_6$O.0.5H$_2$O: C, 60.78; H, 5.29; N, 15.75. Found C, 61.15; H, 5.25; N 15.7

Example G-6

N-(6-Dimethylamino-5-trifluoromethylpyridin-3-yl)-3-{2-[5-(6-methoxypyridin-3-yl)amino-2H-pyrazol-3-yl]ethyl}-benzamide

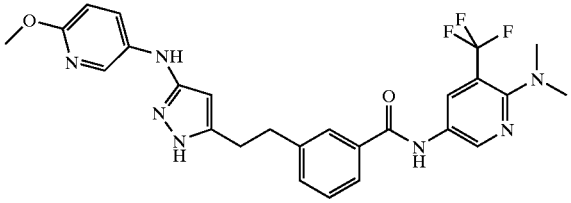

G-6

Example G-6 was made in a similar manner to that described for G-1, except that 5-amino-2-(dimethylamino)-3-trifluoromethylpyridine, prepared according to the procedure described in WO 99/21845 (p. 58) for the preparation of 1-methyl-4-(4-nitrophenyl)piperazine, was used in place of 4-isopropyl-3-methylaniline in step (d), and N-(6-methoxy-pyridin-3-yl)acetamide was used instead of N-(diphenylmethyl)-N-methyl-4-(acetylamino)-benzenesulfonamide, G-1b, in step (c): HPLC Rt=14.04 min; $^1$H NMR (300 MHz, CDCl$_3$) δ8.73 (br s, 1H), 8.47 (d, 1H, J=2.4 Hz), 8.18 (d, 1H, J=2.0 Hz), 7.88 (d, 1H, J=2.7 Hz), 7.64 (d, 1H, J=5.7 Hz), 7.60 (s, 1H), 7.37 (dd, 1H, J=8.7, 3.0 Hz), 7.29–7.21 (m, 2H), 6.58 (d, 1H, J=8.7 Hz), 5.78 (s, 1H), 3.83 (s, 3H), 2.94 (s, 6H), 2.86–2.76 (m, 4H); HRMS (FAB): Calculated for C$_{26}$H$_{26}$F$_3$N$_7$O$_3$ (M+H$^+$): 526.2178, Found: 526.2194. Anal. calc'd for C$_{26}$H$_{26}$F$_3$N$_7$O$_3$.0.4 Et$_2$O: C, 59.71; H, 5.45; N, 17.66. Found C, 59.58; H, 5.44; N 17.53.

Example G-7

N-(3,5-Dichloro-4-dimethylaminophenyl)-3-{2-[5-(6-methoxy-pyridin-3-yl)amino-2H-pyrazol-3-yl]ethyl}benzamide

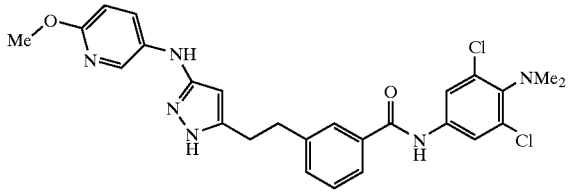

G-7

Example G-7 was made in a similar manner to that described for G-1, except that 3,5-dichloro-4-(pyrrolidino)aniline, prepared according to the procedure described in WO 99/21845 (p. 58) for the preparation of 1-methyl-4-(4-nitrophenyl)piperazine, was used in place of 4-isopropyl-3-methylaniline in step (d), and N-(6-methoxy-pyridin-3-yl)acetamide was used instead of N-(diphenylmethyl)-N-methyl-4-(acetylamino)-benzenesulfonamide, G-1b, in step (c): HPLC Rt=16.07 min; $^1$H NMR (300 MHz, Acetone-d$_6$) δ8.25 (d, 1H, J=2.7 Hz), 7.91 (br s, 2H), 7.87 (s, 1H), 7.82–7.78 (m, 2H), 7.45–7.38 (m, 3H), 6.61 (d, 1H, J=9.3 H), 5.62 9s, 1H), 3.78 (s, 3H), 3.31–2.97 (m, 4H), 2.84 (m, 6H); HRMS (FAB): Calculated for C$_{26}$H$_{26}$N$_6$O$_2$ (M+H$^+$): 525.1573, Found: 525.1559. Anal. calc'd for C$_{26}$H$_{26}$N$_6$O$_{23}$.0.3 Et$_2$O: C, 59.65; H, 5.34; N, 15.35. Found C, 59.35; H, 5.25; N 17.35.

Example G-8

3-{2-[5-(6-Methoxypyridin-3-yl)amino-2H-pyrazol-3-yl]-ethyl}-N-(4-pyrrolidin-1-yl-3-trifluoromethylphenyl)benzamide

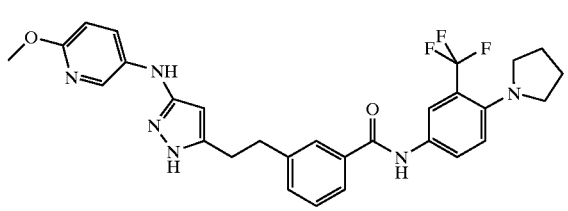

G-8

Example G-8 was made in a similar manner to that described for G-1, except that 4-(pyrrolidin-1-yl)-3-trifluoromethylaniline, prepared according to the procedure described in WO 99/21845 (p. 58) for the preparation of 1-methyl-4-(4-nitrophenyl)piperazine, was used in place of 4-isopropyl-3-methylaniline in step (d), and N-(6-methoxy-pyridin-3-yl)acetamide was used instead of N-(diphenylmethyl)-N-methyl-4-(acetylamino)-benzenesulfonamide, G-1b, in step (c): HPLC Rt=15.66 min; $^1$H NMR (300 MHz, CDCl$_3$) δ8.35 (br s, 1H), 7.91 (d, 1H, J=1.5 Hz), 7.70 (d, 1H, J=1.2 Hz), 7.64 (dd, 2H, J=12.5, 4.5 Hz), 7.57 (s, 1H), 7.38 (dd, 1H, J=5.3, 1.5 Hz), 7.27–7.20 (m, 1H), 6.90 (d. 1H, J=5.4 Hz), 6.59 (d, 1H, J=5.1 Hz), 5.60 (s, 1H), 3.84 (s, 3H), 3.25 (t, 4H, 3.6 Hz), 2.88–2.76 (m, 4H), 1.94–1.90 (m, 4H); HRMS (FAB): Calculated for C$_{29}$H$_{29}$F$_3$N$_6$O$_2$ (M+H$^+$): 551.2382, Found: 551.2389. Anal. calc'd for C$_{29}$H$_{29}$F$_3$N$_6$O$_2$.0.2CH$_2$Cl$_2$: C, 61.09; H; 5.18; N, 14.59. Found C, 61.36; H, 5.18; N 14.59.

Example G-9

3-{2-[5-(6-Methoxypyridin-3-yl)amino-2H-pyrazol-3-yl]-ethyl}-N-[4-(4-t-butoxycarbonylpiperazin-1-yl)-3-trifluoromethylphenyl]benzamide Example G-9 was made in a similar manner to that described for G-1, except that 4-[4-(t-butoxycarbonyl)piperazin-1-yl]-3-trifluoromethylaniline, prepared according to the procedure described in WO 99/21845 (p. 58) for the preparation of 1-methyl-4-(4-nitrophenyl)piperazine, was used in place of 4-isopropyl-3-methylaniline in step (d), and N-(6-methoxy-pyridin-3-yl)acetamide was used instead of N-(diphenylmethyl)-N-methyl-4-(acetylamino)-benzenesulfonamide, G-1b, in step (c): $^1$H NMR (300 MHz, CDCl$_3$) δ8.27 (br s, 1H), 7.95–7.87 (m, 3H), 7.70 (d, 1H, J=7.5 Hz), 7.59 (br s, 1H), 7.57 (s, 1H), 7.47 (dd, 1H, J=8.7, 3.0 Hz), 7.43–7.32 (m, 2H), 7.29–7.21 (m, 2H), 7.28–7.26 (m, 2H), 6.66 (d, 1H, J=8.7 Hz), 5.60 (s, 1H), 3.88 (s, 3H), 3.56–3.51 (m, 4H), 3.26–3.24 (m, 4H), 3.00–2.93 (m, 4H), 2.83–2.82 (m, 4H), 1.49 (s, 9H); HRMS (FAB): Calculated for C$_{34}$H$_{38}$F$_3$N$_7$O$_4$ (M+Na$^+$): 688.2835, Found: 688.2856. Anal. calc'd for C$_{34}$H$_{38}$F$_3$N$_7$O.0.4H$_2$O: C, 60.68; H, 5.81; N, 14.57. Found C, 60.90; H, 5.88; N 14.57.

Example G-10

3-{2-[5-(6-Methoxypyridin-3-yl)amino)-2H-pyrazol-3-yl]ethyl}-N-(4-piperazin-1-yl-3-trifluoromethylphenyl)benzamide

G-10

To a solution of 0.075 g (0.113 mmol) of 3-{2-[5-(6-Methoxypyridin-3-yl)amino-2H-pyrazol-3-yl]-ethyl}-N-[4-(4-t-butoxycarbonyl)piperazin-1-yl-3-trifluoromethylphenyl]benzamide, G-9, in 5 mL of dichloromethane was added 5 mL of trifluoroacetic acid. After 2 h, the reaction mixture was concentrated. The residue was dissolved in 20 mL chloroform/isopropanol (10:1) and washed with sat. aq. sodium bicarbonate (2×10 mL). The organic layer was filtered though a silica plug using ethanol to elute product and concentrated to afford 3-{2-[5-(6-methoxypyridin-3-yl)amino)-2H-pyrazol-3-yl]ethyl}-N-(4-piperazin-1-yl-3-trifluoromethylphenyl)benzamide, G-10,

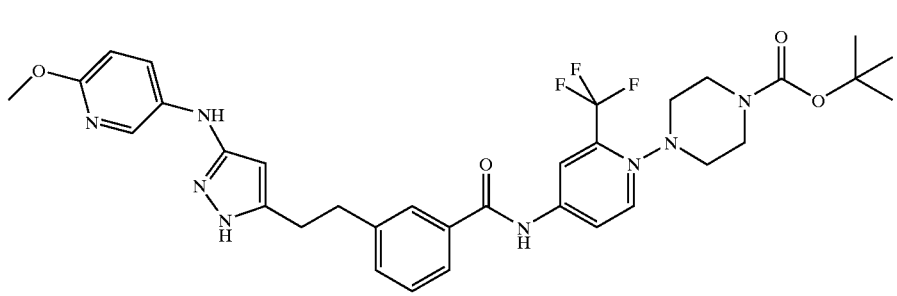

G-9 as off-white solid (0.056 g, 88%): HPLC Rt=12.95 min.; $^1$H NMR (300 MHz, CDCl$_3$) δ11.38 (br s, 1H), 8.51 (br s, 1H), 7.95 (d, 1H, J=2.1 Hz), 8.20–8.10 (m, 1H), 8.01 (d, 1H, J=8.7), 7.87 (s, 1H), 7.75 (d, 1H, J=6.6 Hz), 7.64 (dd, 1H, J=6.5, 2.7 Hz), 7.45 (d, 1H, J=8.7 Hz), 7.35–7.28 (m, 2H), 6.56 (d, 1H, J=8.9 Hz), 5.60 (s, 1H), 3.85 (s, 3H), 2.99–2.80 (m, 12H); HRMS (FAB): Calculated for C$_{29}$H$_{30}$F$_3$N$_7$O$_2$ (M+H$^+$): :566.2491, Found: 566.2511.

Example G-11

4-Fluoro-3-[{5-(pyridin-3-yl)amino-2H-pyrazol-3-yl}methoxy]-N-[((4-pyrrolidin-1-yl)-3-trifluoromethylphenyl)benzamide

G-11

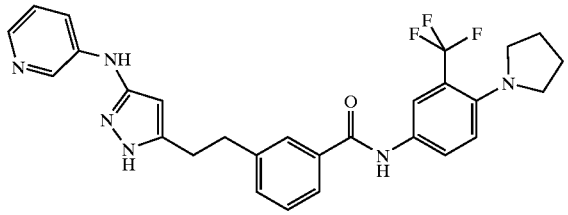

Example G-11 was made in a similar manner to that described for G-1, except that 4-(pyrrolidin-1-yl)-3-trifluoromethylaniline, prepared according to the procedure described in WO 99/21845 (p. 58) for the preparation of 1-methyl-4-(4-nitrophenyl)piperazine, was used in place of 4-isopropyl-3-methylaniline in step (d), and N-(pyridin-3-yl)acetamide was used instead of N-(diphenylmethyl)-N-methyl-4-(acetylamino)-benzenesulfonamide, G-1b, in step (c): HPLC Rt=14.78 min; $^1$H NMR (300 MHz, Acetone-d$_6$) δ9.53 (br s, 1H), 8.55 (d, 1H, J=2.1 H), 8.10 (d, 1H, J=2.7 Hz), 7.93–7.76 (m, 6H), 7.45–7.37 (m, 2H), 7.20 (d, 1H, J=9.0 Hz), 7.14–7.10 (m, 1H), 3.28–3.21 (m, 4H), 3.09–2.96 (m, 4H), 1.96–1.92 (m, 4H); HRMS (FAB): Calculated for $C_{28}H_{27}F_3N_6O$ (M+H$^+$): 521.2277, Found: 521.266. Anal. calc'd for $C_{28}H_{27}F_3N_6O\cdot0.9H_2O$: C, 62.65; H, 5.41; N, 15.66. Found C, 62.84; H, 5.33; N 15.66.

Example H-1

N-(4-Isopropyl-3-methyl-phenyl)-3-[2-(5-phenyl-amino-2-H-pyrazol-3-yl)cyclopropyl]-benzamide

H-1

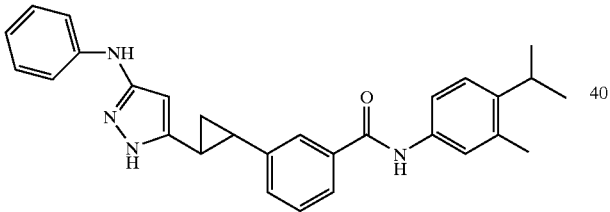

Example H-1 was made in a similar manner to that described for E-1, except that N-(4-isopropyl-3-methylphenyl)-3-[2-(N-methoxy-N-methylcarbamoyl)cyclopropyl]benzamide, prepared as described below, was used instead of in step (c): HPLC R$_t$=16.47 min.; $^1$H NMR (300 MHz, CDCl$_3$) δ8.13 (br s, 1H), 7.59–7.50 (m, 1H), 7.44–7.40 (m, 2H), 7.31–7.25 (m, 3H), 7.22–7.17 (m, 3H), 7.02 (d, 2H, J=7.8 Hz), 6.83 (t, 1H, J=7.5 Hz), 5.71 (s, 1H), 3.14–3.53 (m, 1H), 2.18–2.16 (m, 1H), 2.08–2.04 (m, 1H), 1.38–1.35 (m, 2H), 1.23 (d, 6H, J=6.9 Hz); HRMS (FAB): Calculated for $C_{29}H_{30}N_4O$ (M+H$^+$): 451.2498, Found: 451.2510. Calculated for $C_{29}H_{30}N_4O\cdot0.5H_2O$: C, 75.79; H, 6.80; N, 12.19. Found C, 75.83; H, 6.81; N 12.19.

N-(4-Isopropyl-3-methyl-phenyl)-3-[2-(N-methoxy-N-methyl-carbamoyl)-cyclopropyl]-benzamide was prepared as follows: To a solution of trimethylsulfoxonium iodide (0.46 g, 2.01 mmol) in 10 mL of DMSO was added sodium hydride (0.08 g, 2.01 mmol, 60% oil dispersion) at −10° C. After 30 min, to the reaction solution was added dropwise a solution of 0.35 g (0.96 mmol) of N-(4-isopropyl-3-methylphenyl)-3-[2-(N-methoxy-N-methylcarbamoyl)ethenyl]-benzamide, G-1e, in 5 ml of DMSO. The reaction was allowed to warm to 25° C. After 2 h, the reaction was quenched with dropwise addition of 1N HCl. The reaction mixture was partitioned between 30 mL dichloromethane and 30 mL of saturated NaHCO$_3$ and the organic layer was dried over sodium sulfate and evaporated to a give a crude yellow oil. The oil was purified by silica gel chromatography using 75% hexane/25% ethyl acetate to afford 0.11 g (29%) of N-(4-isopropyl-3-methylphenyl)-3-[2-(N-methoxy-N-methylcarbamoyl)cyclopropyl]benzamide as a clear oil: $^1$H NMR (300 MHz, CDCl$_3$) δ8.18 (br s, 1H), 7.67–7.62 (m, 2H), 7.46–7.44 (m, 2h), 7.36–7.26 (m, 3H), 7.20 (d, 1H, J=9.0 Hz), 3.67 (s, 3H), 3.21 (S, 3H), 2.55–2.45 (m, 2H), 2.31 (s, 3H), 1.65–1.59 (m, 1H), 1.37–1.31 (m, 1H), 1.21 (d, 6H, J=6.9 Hz); MS (ESI): Calculated for $C_{23}H_{28}N_2O_3$ (M−H): 379, Found: 379.

Example I-1

3-[({3-[(E)-2-(4-hydroxy-3-methoxyphenyl)ethenyl]-1H-pyrazol-5-yl}methyl)amino]-N-(3-methyl-4-isopropylphenyl)benzamide

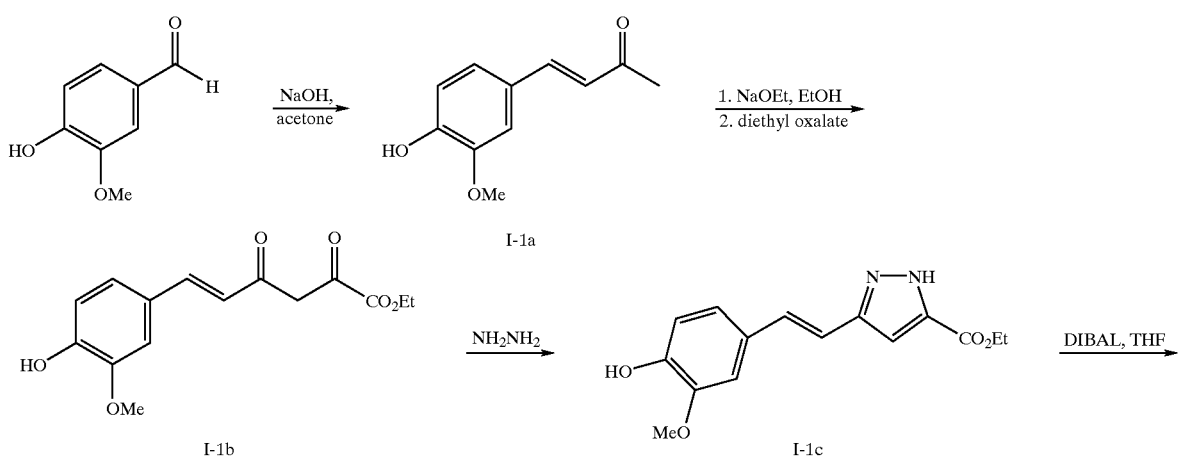

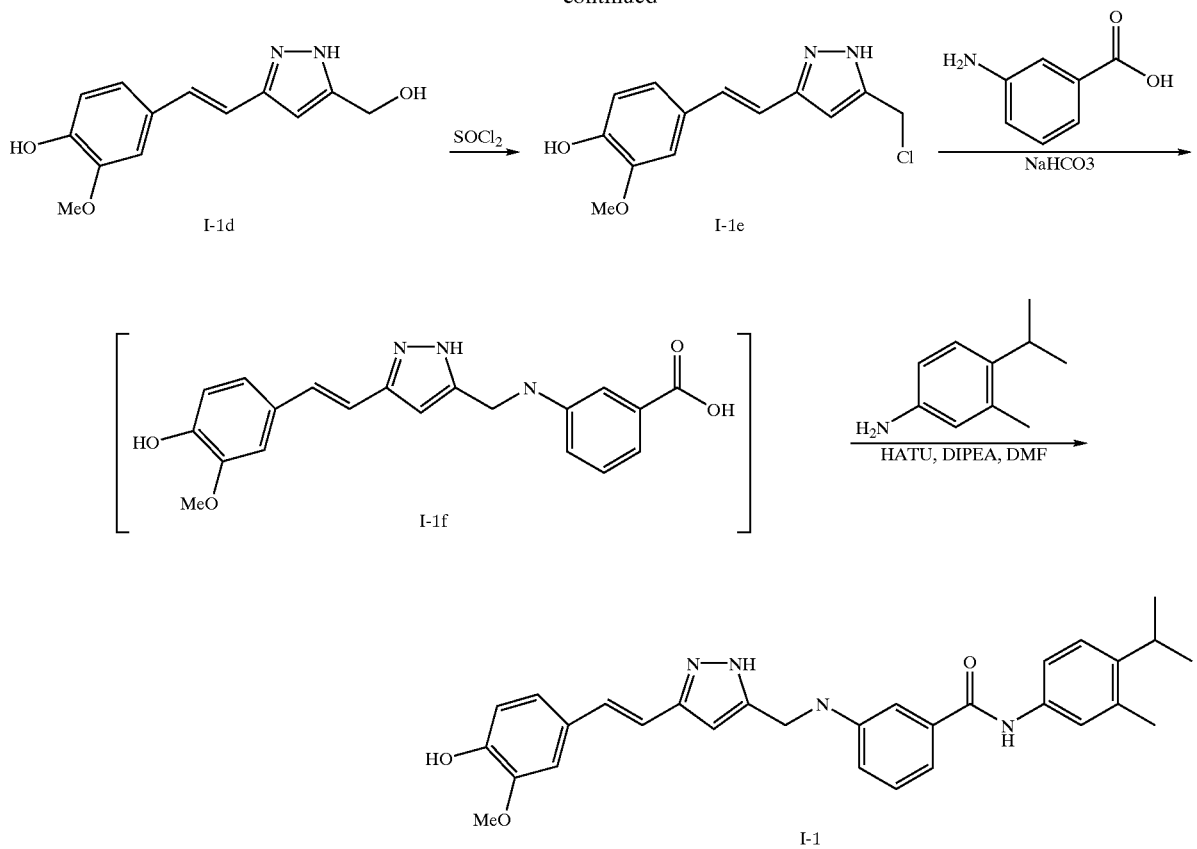

(a) Vanillin (9.12 g, 0.06 mole) was dissolved in 36 mL of acetone and 12.5 mL of 50% aq. NaOH solution was added dropwise with vigorous stirring. To the resulting solid was added 25 mL of water and the dark red solution was refluxed for 5 min. This reaction mixture was kept at room temperature for 24 h and acidified with acetic acid. The reaction mixture was concentrated to provide a yellow solid, which was filtered, washed with water and dried to yield 10.2 g (88%) of (E)-1-(3-methoxy-4-hydroxyphenyl)-1-butene-3-one, I-1a: $^1$H NMR (300 MHz, CDCl$_3$) δ7.43 (d, 1H, J=16.3 Hz), 7.04–7.09 (m, 2H), 6.91 (d, 1H, J=7.9 Hz), 6.57 (d, 1H, J=16.3 Hz), 6.02 (s, 1H), 3.92 (s, 3H), 2.35 (s, 3H).

(b) Sodium metal (3.7 g, 0.16 mole) was dissolved in 100 mL of absolute ethanol under an inert atmosphere. An solution of 16.2 g (953 mmol) of E-1-(3-methoxy-4-hydroxyphenyl)-1-butene-3-one, I-1a, of ethanol was then added slowly over 30 min to the sodium ethoxide solution. After the addition the reaction mixture was stirred at for 15 min followed by the addition of diethyl oxalate (7.7 g, 0.53 mole) and the dark red solution was stirred at room temperature for 5 h. Concentrated HCl was added to the reaction mixture until acidic. A dark yellow solid separated out which was stirred in an ice bath for 1 h. The solid was filtered, washed and dried to afford 8.4 g (55%) of the desired ethyl (E)-6-(4-hydroxy-3-methoxyphenyl)-2,4-dioxo-5-hexenoate, I-1b: $^1$H NMR (300 MHz, CDCl$_3$) δ14.86 (br s, 1H), 7.54 (d, 1H, J=15.9 Hz), 7.00 (d, 1H, J=8.3 Hz), 6.93 (s, 1H), 6.81 (d, 1H, J=8.3 Hz), 6.36–6.41 (m, 2H), 5.84 (s, 1H), 4.23 (q, 2H, J=7.2 Hz), 3.81 (s, 3H), 1.25 (t, 3H, J=7.2 Hz).

(c) To a solution of 8.1 g (27.7 mmol) of ethyl 6-(3'-methoxy-4'-hydroxyphenyl)-2,4-dioxo-5-hexenoate, I-1b, in 125 mL of acetic acid was added 1 mL of hydrazine (30.5 mmol) and the reaction was stirred at 65° C. or 90 min. The reaction was cooled to room temperature and added slowly to 500 mL of ice cold water upon which a white solid separated out. The solid was filtered, washed and dried to afford 7.25 g (91%) of ethyl (E)-3-[(2)-(4-hydroxy-3-methoxyphenyl)ethenyl]-1H-pyrazole-5-carboxylate, I-1c: $^1$H NMR (300 MHz, DMSO-d$_6$) δ13.61 (s, 1H), 9.34 (s, 1H), 7.23 (d, 1H, J=16.6 Hz), 7.19 (s, 1 H), 6.92–7.01 (m, 2H), 6.84 (d, 1H, J=7.9 Hz), 4.32 (q, 2H, J=7.2Hz) (s, 1H), 3.88 (s, 3H), 1.36 (t, 3H, J=7.2 Hz); APCIMS m/z 289 [M+H]$^+$.

(d) To 40 ml of 1 M diisobutylauminum hydride in THF was added dropwise 2.5 g (9.8 mmol) of ethyl (E)-3-[2-(3-methoxy-4-hydroxyphenyl)ethenyl]-1H-pyrazole-5-carboxylate, I-1c, in 25 mL of THF and the reaction was stirred at room temperature. The reaction was monitored by TLC and quenched after 6 h with water and extracted with 3×150 mL of ethyl actate. The combined organic layers were concentrated and the residue was purified using silica gel column chromatography to afford 1.2 g (53%) of 4-{(E)-2-[5-(hydroxymethyl)-1H-pyrazol-3-yl]ethenyl}-2-methoxyphenol, I-1d: $^1$H NMR (300 MHz, DMSO-d$_6$) δ12.58 (br s, 1H), 9.13 (s, 1H), 7.12 (s, 1H), 6.98 (d, 1H, J=16.6 Hz), 6.88–6.92 (m, 2H), 6.74 (d, 1H, J=8.4 Hz), 6.34 (s, 1H), 5.10 (brs, 1H), 4.42 (d, 2H, J=5.6 Hz), 3.81 (s, 3H); APCIMS m/z 247 [M+H]$^+$.

(e) To 72 mg (0.3 mmol) of 4-{(E)-2-[5-(hydroxymethyl)-1H-pyrazol-3-yl]ethenyl}-2-methoxyphenol, I-1d, was added 1 mL of thionyl chloride. After 10 min, the reaction was quenched by adding 10 mL of ice cold water slowly and the mixture was extracted with 2×10 mL of ethyl acetate.

The extracts were combined, concentrated, and filtered through a silica gel plug. All the washings were collected, the solvent removed under vacuo to obtain 32 mg (76%) of 4-{(E)-2-[5-(chloromethyl)-1H-pyrazol-3-yl]ethenyl}-2-methoxyphenol, I-1e: $^1$H NMR (300 MHz, DMSO-$d_6$) δ12.89 (brs, 1H), 9.20 (s, 1H), 7.11 (s, 1 H), 7.04 (d, 1H, J=16.7 Hz), 6.74–6.90 (m, 2H), 6.75 (d, 1H, J=8.0 Hz), 6.45 (s, 1H), 4.69 (s, 2H), 3.81 (s, 3H); APCIMS m/z 265 [M+H]$^+$.

(f) To 132 mg (0.5 mmol) of 4-{(E)-2-[5-(chloromethyl)-1H-pyrazol-3-yl]ethenyl}-2-methoxyphenol, I-1e, in 2 mL of DMF was added 3-aminobenzoic acid (75 mg, 0.55 mmol) and an excess of NaHCO$_3$ and the reaction mixture stirred at room temperature for 16 h. The crude reaction mixture was filtered through a plug of silica gel to remove NaHCO$_3$ and washed with ethyl acetate. The filtrates were collected and the solvents removed in vacuo to yield 60 mg of crude 3-[({3-[(E)-2-(4-hydroxy-3-methoxyphenyl)ethenyl]-1H-pyrazol-5-yl}methyl)amino]benzoic acid, I-1f, which was redissolved in 2 mL of DMF. To the resulting solution were added HATU (95 mg, 0.25 mmol) and diisopropylethylamine (0.04 mL, 0.23 mmol) followed by 3-methyl-4-isopropylaniline (90 mg, 0.6 mmol) and the reaction mixture stirred at room temperature for 16 h. After conventional aqueous work-up, 16 mg of 3-[({3-[(E)-2-(4-hydroxy-3-methoxyphenyl)ethenyl]-1H-pyrazol-5-yl}methyl)amino]-N-(3-methyl-4-isopropylphenyl)benzamide, I-1, was isolated using HPLC; $^1$H NMR (300 MHz, DMSO-$d_6$) δ9.91 (s, 1H), 7.51–7.54 (m, 2H), 7.03–7.20 (m, 7H), 6.98 (d, 1H, J=15.5 Hz), 6.82–6.90 (m, 4H), 6.74 (d, 1H, J=9.0 Hz), 6.35 (s, 1H), 4.28 (s, 2H), 3.80 (s, 3H), 3.01–3.08 (m, 1H), 2.27 (s, 3H), 1.16 (d, 6H, J=6.0 Hz); APCIMS m/z 497 [M+H]$^+$.

Example I-2

3-[({5-[(E)-2-(4-hydroxy-3-methoxyphenyl)ethenyl]-1H-pyrazol-3-yl}methyl)amino]-N-phenylbenzamide

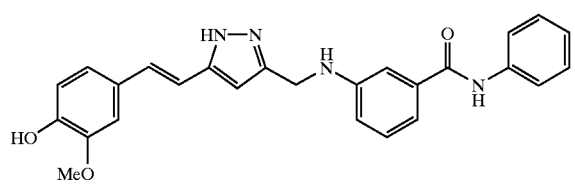

Example I-2 was prepared in a similar manner to that described for I-1, except that aniline was used in place of 3-methyl-4-isopropylaniline in step (f): HPLC R$_t$=6.38 min.; $^1$H NMR (300 MHz, CD$_3$OD) δ7.55 (d, 2H, J=9.0 Hz), 7.21–7.26 (m, 2H), 7.11–7.16 (m, 2H), 7.02–7.08 (m, 2H), 6.97–6.98 (m, 1H), 6.90 (d, 1H, J=15.0 Hz), 6.78–6.86 (m, 2H), 6.74 (d, 1H, J=15.0 Hz), 6.65–6.67 (m, 1H), 6.33 (s, 1H), 4.27 (s, 2H), 3.77 (s, 3H); APCIMS m/z 441 [M+H]$^+$.

Example J-1

4-Fluoro-N-[4-(imidazol-1-yl)-3-trifluoromethylphenyl]-3-[5-(6-methoxypyridin-3-yl)amino-2H-pyrazol-3-ylmethoxy]-benzamide

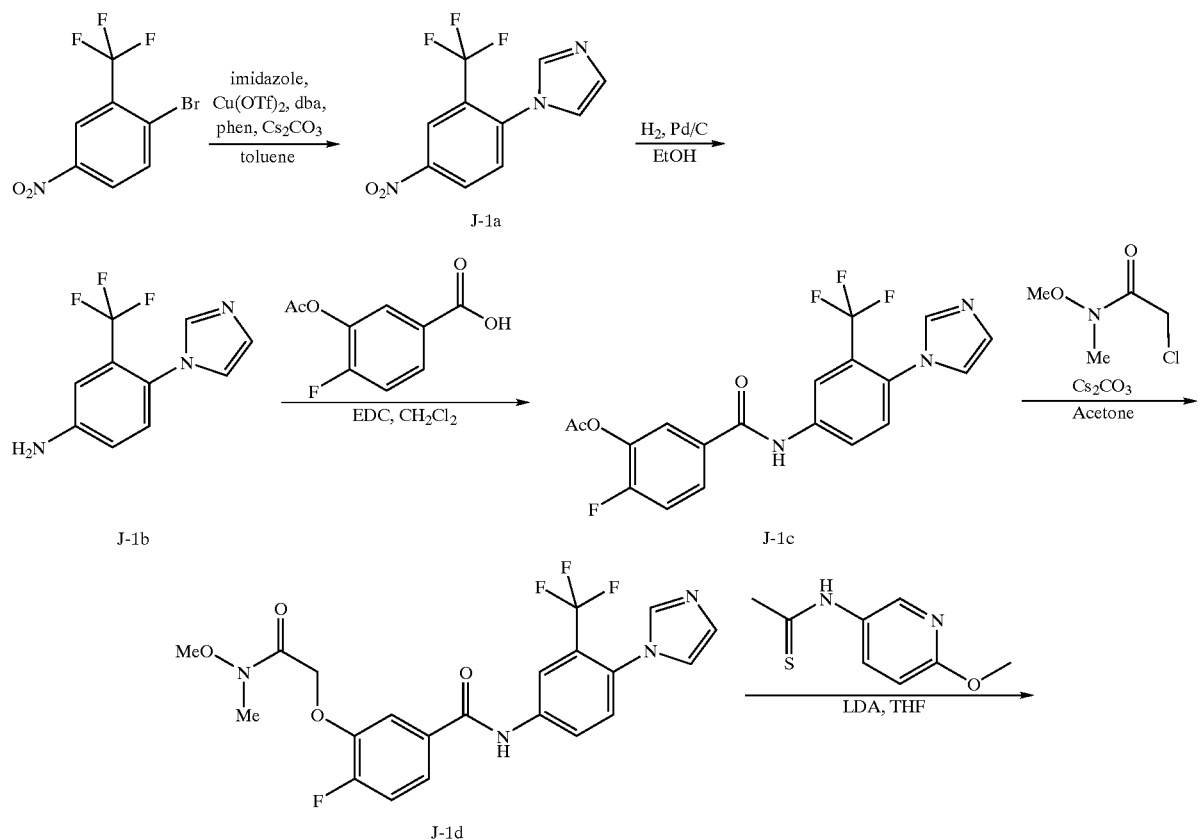

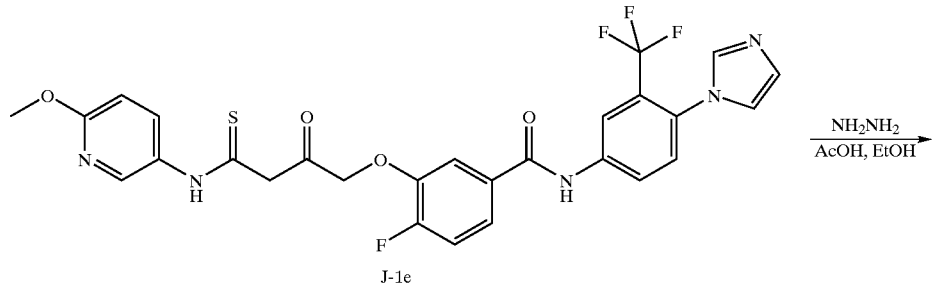

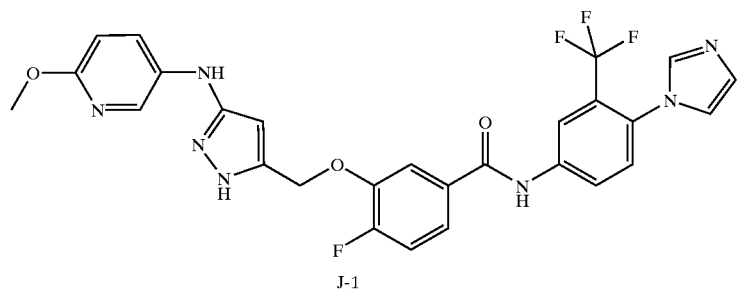

(a) To a solution of 2-bromo-5-nitrobenzotrifluoride (1.50 g, 5.54 mmol) in toluene (11 mL) under argon purge was added imidazole (0.57 g, 8.31 mmol), trans,trans-dibenzylidene acetone (0.13 g, 0.56 mmol), 1,10-phenanthroline (1.00 g, 5.54 mmol), cesium carbonate (1.99 g, 6.10 mmol) and copper(II)triflate.benzene (0.015 g, 0.028 mmol). The slurry was heated at 90° C. for 18 h, and then cooled to 25° C. The mixture was filtered through a silica gel plug with 30 mL of ethyl acetate and the filtrate was concentrated. The residue was purified by chromatography on silica gel (hexane/ethyl acetate) to afford 0.83 g (58.2%) of 1-(4-Nitro-2-trifluoromethylphenyl)-1H-imidazole, J-1a, as an amber solid: HPLC Rt=10.45 min.; $^1$H NMR (300 MHz, CDCl$_3$) δ8.72 (d, 1H, J=2.1 Hz), 8.58 (dd, 1H, J=8.7, 2.7 Hz), 7.70–7.67 (m, 2H), 7.26 (s, 1H), 7.21 (s, 1H); MS (ESI): Calculated for C$_{10}$H$_6$F$_3$N$_3$O$_2$ (M+H$^+$): 257, Found: 257.

(b) To a solution of 0.60 g (2.33 mmol) of 1-(4-nitro-2-trifluoromethylphenyl)-1H-imidazole, J-1a, in 10 mL of methanol was added 0.10 g of 10% Pd/C. The mixture was stirred under a hydrogen atmosphere (1 atm) for 18 h, and then filtered through a 0.22 μM teflon filter membrane. The filtrate was concentrated to afford 0.51 g (100%) of 1-(4-amino-2-trifluomethylphenyl)imidazole, J-1b, as a yellow solid: HPLC Rt=8.89 min.; $^1$H NMR (300 MHz, CDCl$_3$) δ7.62 (s, 1H), 7.13–7.02 (m, 4H), 6.86 (d, 1H, J=8.4, 2.4 Hz). MS (ESI): Calculated for C$_{10}$H$_8$F$_3$N$_3$ (M+H$^+$): 228, Found: 228.

(c) To a solution of 3-acetoxy-4-fluorobenzoic acid (0.49 g, 2.48 mmol) in dichloromethane (5 mL) was added oxayl chloride (0.26 ml, 2.97 mmol) and DMF (0.1 mL). After 1 h, the mixture was concentrated and then re-dissolved in 5 mL of dichloromethane. To this solution was added 0.56 g (2.47 mmol) of 1-(4-amino-2-trifluomethylphenyl) imidazole, J-1b, and diisopropylethylamine (0.39 mL, 2.48 mmol). After 1 h the solution was partitioned between 30 mL of ethyl acetate and sat. aq. sodium bicarbonate (2×20 mL). The organic layer was dried over sodium sulfate and concentrated. The residue was purified by chromatography on silica gel (1:1 hexane:ethyl acetate) to provide 0.49 g (57%) of 3-acetoxy-4-fluoro-N-[4-(imidazol-1-yl)-3-trifluoromethylphenyl]-benzamide, J-1c, as clear oil: $^1$H NMR (300 MHz, CDCl$_3$) δ8.12–8.02 (m, 3H), 7.92–7.89 (m, 1H), 7.63 (s, 1H), 7.37–7.12 (m, 5H), 2.36 (s, 1H); MS (ESI): Calculated for C$_{19}$H$_{13}$F$_4$N$_3$O$_3$ (M+H$^+$): 408, Found: 408.

(d) To a solution of 0.33 g (0.83 mmol) 3-acetoxy-4-fluoro-N-[4-(imidazol-1-yl)-3-trifluoromethylphenyl]-benzamide, J-1c, in 5 mL acetone and 0.5 mL of methanol was added cesium carbonate (0.54 g, 1.65 mmol) and 2-chloro-N-methoxy-N-methyl-acetamide (0.15 g, 1.07 mmol) and the resulting mixture was stirred for 6 h at 45° C. After cooling to room temperature, the mixture was partitioned between ethyl acetate and sat. brine (2×20 mL). The organic layer was filtered though a silica gel plug and concentrated. The residue was purified by titurated with diethyl ether (2×20 mL) to give 0.35 g (92%) of 4-fluoro-N-[4-(imidazol-1-yl)-3-trifluoromethylphenyl]-3-[(N-methoxy-N-methylcarbamoyl)methoxy]benzamide, J-1d, as a white solid: Rt=11.95 min.; $^1$H NMR (300 MHz, CDCl$_3$) δ8.34 (d, 1H, J=2.4 Hz), 8.11 (dd, 1h, J=8.7 Hz), 7.64–7.54 (m, 3H), 7.42 (d, 1H, J=8.7 Hz), 7.22–7.15 (m, 2H), 6.97 (s, 1H), 502 (s, 2H), 3.72 (s, 3H), 3.06 (s, 3H); MS (ESI): Calculated for C$_{21}$H$_{18}$F$_4$N$_4$O$_4$ (M+H$^+$): 467, Found: 467.

(e) To a –78° C. solution of 0.13 g (0.71 mmol) N-(6-methoxy-pyridin-3-yl)-thioacetamide in 5 mL of dry THF was added dropwise 0.71 mL (1.42 mmol) of LDA (2.0 M in THF). The solution was stirred for 15 min at –78° C., warmed to 0° C. for 1 h, and then cooled to –78° C. To the resulting solution was added, over a 5 min period, a solution of 0.15 g (0.32 mmol) 4-fluoro-N-[4-(imidazol-1-yl)-3-trifluoromethyl-phenyl]-3-[(N-methoxy-N-methylcarbamoyl)methoxy]benzamide, J-1d, in 5 mL of THF. After stirring for 1 h at 0° C., the reaction was quenched with 1 mL of 1:1 methanol:acetic acid. The mixture was partitioned between ethyl acetate and sat. sodium carbonate (2×20 mL) and the organic layer was dried over sodium sulfate and concentrated. The residual yellow oil was purified by radial chromatography (2 mm plate eluting with 1:2:1 hexane:ethyl acetate:dichloromethane) to give 0.091 g (49%) of 4-fluoro-N-[4-(imidazol-1-yl)-3-trifluoromethylphenyl]-3-[3-(6-methoxypyridin-3-yl)thiocarbamoyl-2-oxo-propoxy]-benzamide, J-1e, as a yellow solid: $^1$H NMR (300 MHz, CDCl$_3$) δ8.74 (br s, 1H), 8.19 (d, 2H, J=2.7 Hz), 8.05 (d, 1H, J=2.7 Hz), 7.96 (dd, 2H, J=10.2, 3.0 Hz), 7.41 (dd, 1H, J=8.4, 2.7 Hz), 7.28 (s, 1H), 6.82–6.77 (m, 4H), 2.74 (s, 2H); MS (ESI): Calculated for C$_{27}$H$_{21}$F$_4$N$_5$O$_4$S (M+H$^+$): 588, Found: 588.

(e) To a solution of 0.061 g (0.10 mmol) of 4-fluoro-N-[4-(imidazol-1-yl)-3-trifluoromethyl-phenyl]-3-[3-(6-methoxypyridin-3-yl)thiocarbamoyl-2-oxo-propoxy]-benzamide, J-1e, in ethanol (2 mL) was added hydrazine monohydrate (0.080 mL, 0.16 mmol) and acetic acid (0.09 mL, 0.16 mmol). After 2 h the solution was concentrated and the residue was purified by chromatography on silica gel (1:2 hexane:ethyl acetate) to afford 0.031 g (54%) of 4-fluoro-N-(4-(imidazol-1-yl)-3-trifluoromethyl-phenyl)-3-[5-(6-methoxy-pyridin-3-yl)amino-2H-pyrazol-3-ylmethoxy]benzamide, J-1, as a off white solid: $^1$H NMR (300 MHz, CDCl$_3$) δ8.34 (s, 1H), 8.12–8.10 (m, 2H), 7.85 (t, 1H, 3.0 Hz), 7.69–7.57 (m, 2H), 7.41 (d, 1H, J=8.7 Hz), 7.22–7.13 (m, 2H), 6.97 (d, 1H, J=6.0 Hz), 6.52 (d, 1H, J=9.0 Hz), 5.88 (s, 1H), 5.19 (s, 2H), 3.68 (s, 3H); LCESI: Calculated for C$_{27}$H$_{21}$F$_4$N$_7$O$_3$ (M+H$^+$): 568, Found: 568. Anal. calc'd for C$_{27}$H$_{21}$F$_4$N$_7$O$_3$·1.2CH$_2$Cl$_2$ Found: C, 50.59; H 3.52; N, 14.65. Found C, 50.69; H, 3.78; N 14.79.

Example J-2

4-Fluoro-3-[5-(6-methoxy-pyridin-3-yl)amino-2H-pyrazol-3-yl]methoxy-N-(4-pyrrolidin-1-yl-3-trifluoromethyl-phenyl)-benzamide

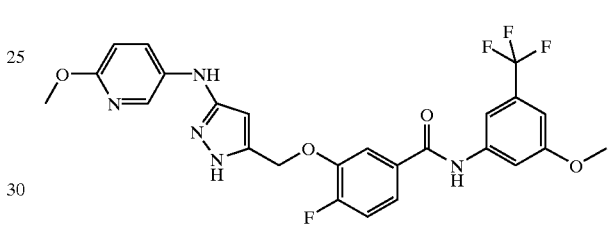

Example J-2, was prepared in a similar manner to that described for J-1, except that 4-(pyrrolidino)-3-trifluoromethylaniline (see example G-8) was used in place of 1-(4-amino-2-trifluomethylphenyl)imidazole, J-1b, in step (c): HPLC Rt=15.55 min.; $^1$H NMR (300 MHz, CDCl$_3$) δ7.98 (d, 1H, J=2.7 Hz), 7.85 (br s, 1H), 7.68–7.63 (m, 3H), 7.49 (dd, 1H, J=8.7, 3.0 Hz), 7.18–7.11 (m, 1H), 6.95 (d, 1H, J=8.7 Hz), 6.67 (d, 1H, J=8.7 Hz), 5.93 (s, 1H), 5.87 (s, 1H), 5.17 (s, 2H), 3.88 (s, 3H), 3.31–3.27 (m, 4H), 2.05–1.96 (m, 4H); HRMS (MALDI):: Anal. Calculated for C$_{28}$H$_{26}$F$_4$N$_6$O$_3$ (M+Na$^+$): 593.1900, Found: 593.1873. Anal. calc'd for C$_{28}$H$_{26}$F$_4$N$_6$O$_3$: C, 58.95; H, 4.95; N, 14.73. Found C, 58.87; H, 4.91; N 14.87.

Example J-3

4-Fluoro-3-[5-(6-methoxypyridin-3-yl)amino-2H-pyrazol-3-yl]methoxy-N-(3-methoxy-5-trifluoromethyl-phenyl)-benzamide

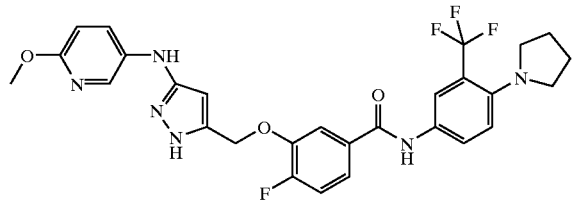

Example J-3, was prepared in a similar manner to that described for J-1, except that 5-methoxy-3-trifluoromethylaniline (Aldrich) was used in place of 1-(4-amino-2-trifluomethylphenyl)imidazole, J-1b, in step (c): Rt=14.50 min.; $^1$H NMR (300 MHz, CDCl$_3$) δ8.05 (d, 1H, J=3.0 Hz), 7.88 (s, 1H), 7.68 (dd, 1H, J=9.5, 2.1 Hz), 7.56–7.53 (m, 2H), 7.42–7.39 (m, 1H), 7.34 (s, 1H), 7.26–7.17 (m, 1H), 6.94 (s, 1H), 7.70 (d, 1H, J=9.0 Hz), 5.95 (s, 1H), 5.76 (br s, 1H), 5.21 (s, 2H), 3.90 (s, 3H), 3.87 (s, 3H); HRMS (FAB): Calculated for C$_{25}$H$_{21}$F$_4$N$_5$O$_4$ (M+Na$^+$): 554.1427, Found: 554.1423. Anal. calc'd for C$_{25}$H$_{21}$F$_4$N$_5$O$_4$·0.2 hexane: C, 57.35; H, 4.37; N, 12.76. Found C, 57.00; H, 4.60; N 13.00.

Example K-1

N-(4-Isopropyl-3-methyl-phenyl)-3-(Isoquinolin-4-yl)methoxy-benzamide

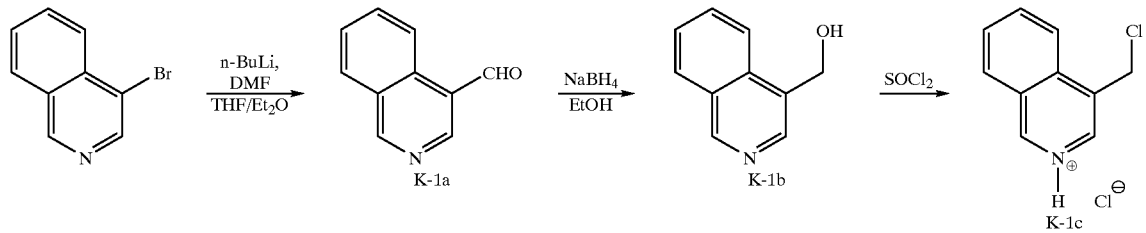

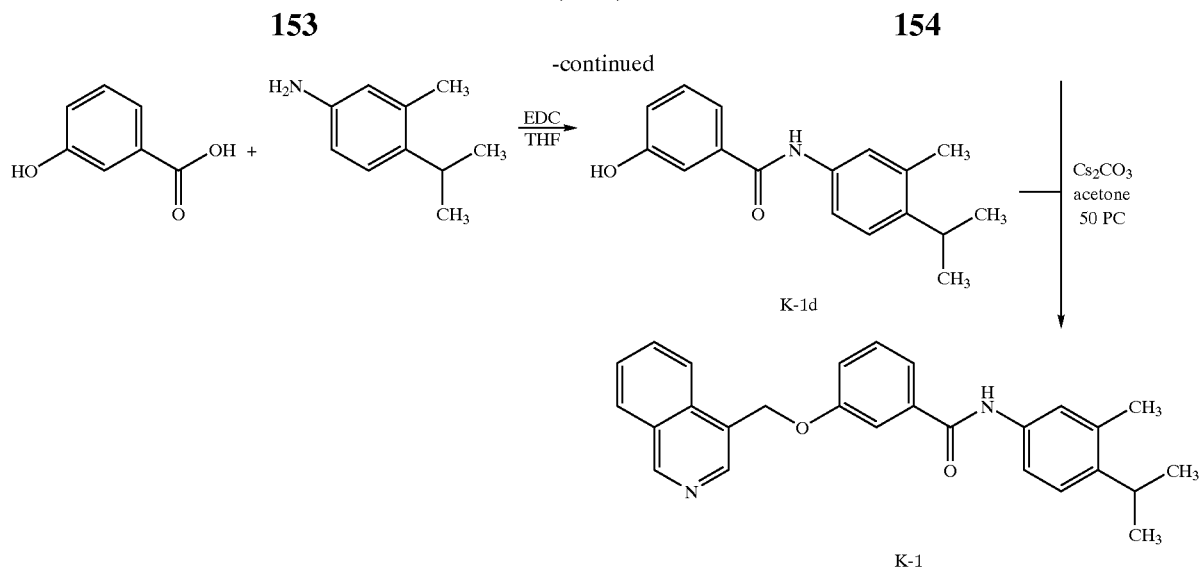

(a) A 2.6 M solution of n-BuLi in hexanes (7.4 mL, 19.2 mmol, 2.0 eq) was added to a solution of THF (40 mL) and ether (40 mL) and cooled to −78° C. 4-Bromoisoquinoline (Aldrich, 2.0 g, 9.6 mmol, 1.0 eq) was added to the anion in one portion and the dark orange solution was aged at −78° C. for 30 minutes to give a brown slurry. The mixture was treated with DMF (1.7 mL, 24.0 mmol, 2.5 eq) to give a brown solution. After 15 min, the reaction was quenched with ethanol (40 mL). The resultant pale yellow solution was treated with a saturated solution of ammonium chloride (200 mL) and extracted with MTBE (3×200 mL). The combined organic extracts were washed with brine (200 mL), dried over magnesium sulfate, filtered and concentrated under reduced pressure to give an orange solid (1.8 g). The crude product was purified by flash chromatography over silica gel using 50% ethyl acetate/cyclohexane ($R_f$ 0.5) to give isoquinoline-4-carbaldehyde, K-1a, as a yellow solid (1.3 g, 84%): HPLC $R_t$=8.8 min.; TLC $R_f$=0.2 (5% ethyl acetate/35% cyclohexane/dichloromethane); $^1$H NMR (300 MHz, CDCl$_3$) δ10.41 (s, 1H), 9.46 (s, 1H), 9.23 (d, 1H, J=8.5 Hz), 8.95 (s, 1H), 8.12 (d, 1H, J=8.1 Hz), 7.97 (t, 1H, J=7.6 Hz), 7.78 (t, 1H, J=7.3 Hz); MS (ESI) m/z 158 [M+H]$^+$.

(b) To a solution of 1.4 g (8.9 mmol) of isoquinoline-4-carbaldehyde, K-1a, in ethanol (50 mL) at 0° C. was added with sodium borohydride (372 mg, 9.8 mmol, 1.1 eq). The mixture was stirred at 0° C. for 1.5 hours and at room temperature for 1.0 h. The reaction was quenched with 25% ammonium acetate (500 mL). The ethanol was removed under reduced pressure and the resultant mixture was extracted with ethyl acetate (3×500 mL). The combined organic extracts were washed with brine (200 mL), dried over magnesium sulfate, filtered and concentrated under reduced pressure to give a yellow oil (1.5 g). The crude product was purified by radial chromatography over silica gel using 5–10% methanol/dichloromethane to give, after concentration from 50% ethyl acetate/cyclohexane, 4-(hydroxymethyl)isoquinoline, K-1b, as a tan solid (0.95 g, 68%): HPLC $R_t$=6.7 min.; TLC $R_f$=0.2 (50% ethyl acetate/cyclohexane); $^1$H NMR (300 MHz, DMSO-d$_6$) δ9.24 (s, 1H), 8.49 (s, 1H), 8.14 (d, 1H, J=8.4 Hz), 7.82 (t, 1H, J=7.6 Hz), 7.70 (t, 1H, J=7.6 Hz), 5.36 (t, 1H, J=5.4 Hz), 4.95 (d, 2H, J=5.2 Hz); MS (FAB) m/z 160 [M+H]$^+$.

(c) A solution of 4-(hydroxymethyl)isoquinoline, K-1b, (900 mg, 5.7 mmol, 1.0 eq) in ethanol (10 mL) was treated with concentrated hydrochloric acid (1.0 mL, 12.6 mmol, 2.1 eq). The mixture was stirred for 30 min and then the solvent was removed under reduced pressure. The tan residue was repeatedly evaporated from toluene (3×10 mL) to give a tan solid (1.1 g, 100%). The resulting unpurified 4-(hydroxymethyl)isoquinoline hydrochloride was then treated with thionyl chloride (10 mL) and the resultant mixture was heated to 70° C. After 1.5 hours, the solvent was removed under reduced pressure to give 4-(chloromethyl)isoquinoline hydrochloride, K-1c, as a tan solid (1.1 g, 95%): HPLC $R_t$=11.2 min.; $^1$H NMR (300 MHz, DMSO-d$_6$) δ9.81 (s, 1H), 8.83 (s, 1H), 8.52 (d, 1H, J=8.1 Hz), 8.42 (d, 1H, J=8.6 Hz), 8.23 (t, 1H, J=7.8 Hz), 8.01 (t, 1H, J=7.8 Hz), 5.41 (s, 2H); $^{13}$C NMR (75 MHz, DMSO-d$_6$) δ149.6, 136.2, 135.9, 134.1, 131.9, 131.4, 130.6, 127.8, 124.2; MS (FAB) m/z 177/179 [M]. Anal. calc'd for C$_{10}$H$_8$ClN.HCl: C, 56.10; H, 4.24; Cl, 33.12; N, 6.54. Found: C, 56.15; H, 4.32; Cl, 33.23; N, 6.37.

(d) A suspension of 3-methyl-4-isopropyl aniline hydrochloride (6.7 g, 36.2 mmol, 1.0 eq) in THF (240 mL) was treated with triethylamine (5.0 mL, 36.2 mmol, 1.0 eq). The gray mixture was then treated with 3-hydroxybenzoic acid (Aldrich, 5.0 g, 36.2 mmol, 1.0 eq), followed by 1-(3-dimethylaminopropyl)-3-ethylcarbodiimide hydrochloride (7.6 g, 39.8 mmol, 1.1 eq). The resultant slurry was stirred at room temperature for 18 h. The solvent was removed under reduced pressure and the residue was extracted with water (200 mL) and ethyl acetate (3×200 mL). The combined organic extracts were washed with 5% KHSO$_4$ (2×200 mL); water, (200 mL), brine (200 mL), dried over magnesium sulfate, filtered and concentrated under reduced pressure to give a brown solid (8.0 g). The crude product was purified by flash chromatography on silica gel using 3–5% methanol/dichloromethane to give 3-hydroxy-N-(4-isopropyl-3-methyl-phenyl)-benzamide, K-1d, as an off-white solid (1.1 g, 11%): HPLC $R_t$=13.9 min.; TLC $R_f$=0.4 (3% methanol/dichloromethane); $^1$H NMR (500 MHz, DMSO-d$_6$) δ9.99 (s, 1H), 9.71 (s, 1H), 7.55–7.29 (m, 5H), 7.19 (d, 1H, J=8.1 Hz), 7.97–7.95 (m, 1H), 3.09–3.06 (m, 1H), 2.29 (s, 3H), 1.18 (d, 6H, J=6.9 Hz); $^{13}$C NMR (75 MHz, DMSO-d$_6$) δ165.6, 157.7, 142.0, 136.9, 134.9, 129.7, 125.0, 122.4, 118.8, 118.7, 118.4, 114.8, 28.7, 23.5, 19.5; MS (ESI) m/z 268 [M−H]$^-$. Anal. calc'd for C$_7$H$_{19}$NO$_2$: C, 75.81; H, 7.11; N, 5.20. Found: C, 75.35; H, 7.23; N, 5.12.

(e) To a clear solution of 3-hydroxy-N-(4-isopropyl-3-methyl-phenyl)-benzamide, K-1d, (0.538 g, 2.0 mmol, 1.0 eq) in acetone (40 mL) was added cesium carbonate (5.2 g, 16.0 mmol, 8.0 eq). The resultant mixture was stirred at room temperature for 30 minutes, treated with 4-chloromethyl-isoquinoline hydrochloride, K-1c, (0.469 g, 2.2 mmol, 1.1 eq) and warmed to 50° C. After 18 hours, the reaction was diluted with water (200 mL) and extracted with ethyl acetate (3×200 mL). The combined organic extracts were washed with brine (300 mL), dried over magnesium sulfate, filtered and concentrated under reduced pressure to give a yellow oil (1.7 g). The oil was purified by radial chromatography over silica gel eluting with 50% ethyl acetate/cyclohexane ($R_f$ 0.3) to give, after concentration from MTBE, N-(4-isopropyl)-3-methyl-phenyl)-3-(Isoquinolin-4-yl)methoxy-benzamide, K-1, (0.69 g, 83%) as a light yellow foam: HPLC $R_t$=16.9 min.; TLC $R_f$=0.6 (3% methanol/chloroform); $^1$H NMR (500 MHz, DMSO-$d_6$) δ10.06 (s, 1H), 9.37 (s, 1H), 8.69 (s, 1H), 8.22 (d, 1H, J=8.1 Hz), 8.17 (d, 1H, J=8.5 Hz), 7.90 (t, 1H J=7.7 Hz), 7.77 (t, 1H, J=7.5 Hz), 7.69 (s, 1H), 7.60–7.34 (m, 5H), 7.21 (d, 1H, J=8.4 Hz), 5.66 (s, 2H), 3.09–3.07 (m, 1H), 2.30 (s, 3H), 1.18 (d, 6H, J=6.8 Hz); $^{13}$C NMR (75 MHz, DMSO-$d_6$) δ165.1, 158.6, 153.9, 143.5, 142.2, 136.8, 136.7, 135.0, 134.1, 131.5, 130.0, 128.6, 128.3, 128.0, 126.0, 125.0, 123.6, 122.5, 120.7, 118.8, 118.3, 114.3, 66.2, 28.7, 23.5, 19.4; MS (ESI) m/z 411 [M+H]$^+$. Anal. calc'd for $C_{27}H_{26}N_2O_2 \cdot 0.3 H_2O$: C, 77.97; H, 6.45; N, 6.74. Found: C, 77.76; H, 6.64; N, 6.48.

Example K-2

3-(Isoquinolin-4-yl)methoxy-N-(3,4,5-trimethoxyphenyl)benzamide hydrochloride

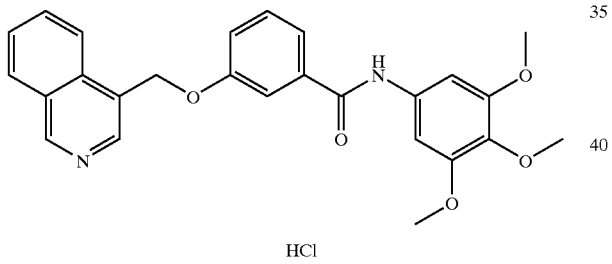

K-2

HCl

Example K-2 was prepared in a similar manner to that described for K-1, except that 3,4,5-trimethoxyaniline (Aldrich) was used in place of 3-methyl-4-isopropylaniline in step (d). The product was isolated as the hydrochloride salt as follows. A solution of 3-(isoquinolin-4-yl)methoxy-N-(3,4,5-trimethoxyphenyl)benzamide (116 mg, 0.26 mmol) in ethanol was treated with concentrated hydrochloric acid (0.1 mL, 1.2 mmol). After several minutes, the solvent was removed under reduced pressure to give 3-(isoquinolin-4-yl)methoxy-N-(3,4,5-trimethoxyphenyl) benzamide hydrochloride as a white solid (126 mg, 100%): HPLC $R_t$=13.4 min.; TLC $R_f$=0.5 (5% methanol/chloroform); $^1$H NMR (300 MHz, DMSO-$d_6$) δ10.10 (s, 1H), 9.70 (s, 1H), 8.72 (s, 1H), 8.41 (d, 1H, J=8.1 Hz), 8.30 (d, 1H, J=8.5 Hz), 8.10 (t, 1H, J=7.8 Hz), 7.90 (t, 1H, J=7.6 Hz), 7.67 (s, 1H), 7.53 (d, 1H, J=7.7 Hz), 7.41 (t, 1H, J=7.9 Hz), 7.29 (dd, 1H, J=8.2, 1.6 Hz), 7.16 (s, 2H), 5.70 (s, 2H), 3.66 (s, 6H), 3.53 (s, 3H); $^{13}$C NMR (75 MHz, DMSO-$d_6$) δ165.1, 158.2, 152.9, 149.5, 136.7, 136.1, 135.8, 135.6, 134.2, 133.5, 131.0, 130.9, 130.3, 130.0, 127.6, 124.4, 121.0, 118.6, 114.5, 98.6, 65.4, 60.5, 56.1; MS (ESI) m/z 445 [M+H]$^+$. Anal. calc'd for $C_{25}H_{22}N_4O_3 \cdot HCl \cdot 0.5 H_2O$: C, 63.73; H, 5.35; N, 5.72. Found: C, 63.52; H, 5.51; N, 5.50.

Example K-3

3-(Isoquinolin-4-yl)methoxy-N-(2-methyl-quinolin-6-yl)-benzamide hydrochloride

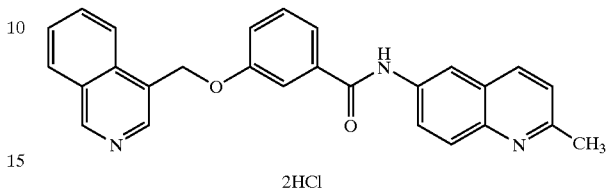

K-3

2HCl

Example K-3, which was isolated as a dihydrochloride salt as described in Example K-2, was prepared in a similar manner to that described for K-1, except that 6-amino-2-methylquinoline (Maybridge) was used in place of 3-methyl-4-isopropylaniline in step (d): HPLC $R_t$=13.2 min.; TLC $R_f$=0.5 (5% methanol/chloroform); $^1$H NMR (300 MHz, DMSO-$d_6$ w/$D_2O$) δ9.78 (s, 1 H), 9.0 (d, 1H, J=8.7 Hz), 8.84 (d, 2H, J=1.9 Hz), 8.55 (d, 1H, J=8.2 Hz), 8.45–8.40 (m, 2H) 8.27–8.22 (m, 2H), 8.05 (t, 1H, J=7.5 Hz), 7.92 (d, 1H, J=8.7 Hz), 7.83 (t, 1H, J=1.8 Hz), 7.72 (d, 1H, J=7.7 Hz), 7.60 (t, 1H, J=8.0 Hz), 7.48 (dd, 1H, J=8.2, 1.8 Hz), 5.84 (s, 2H), 2.95 (s, 3H); $^{13}$C NMR (75 MHz, DMSO-$d_6$ w/$D_2O$) δ167.9 159.8, 158.2, 151.2, 146.7, 140.7, 137.6, 137.4, 136.3, 135.4, 132.6, 132.2, 132.1, 132.0, 130.3, 129.2, 129.1, 125.9, 125.7, 122.9, 122.7, 120.8, 118.7, 116.1, 66.9, 22.0; MS (FAB) m/z 420 [M+H]$^+$. Anal. calc'd for $C_{27}H_{21}N_3O_2 \cdot 2HCl \cdot 0.3 H_2O$: C, 65.14; H, 4.78; N, 8.44. Found: C, 65.18; H, 4.84; N, 8.38.

Example K-4

3-(Isoquinolin-4-yl)methoxy-N-(2-methyl-4-methylsulfanyl-quinolin-6-yl)-benzamide hydrochloride

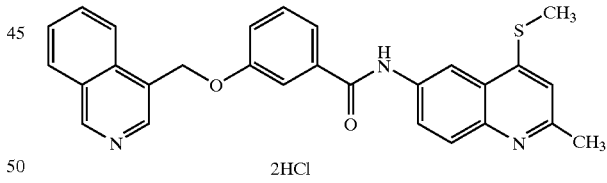

K-4

2HCl

Example K-4, which was isolated as a dihydrochloride salt as described in Example K-2, was prepared in a similar manner to that described for K-1, except that 2-methyl-4-methylsulfanyl-quinolin-6-ylamine, K-4d (vide infra), was used in place of 3-methyl-4-isopropylaniline in step (d): HPLC $R_t$=14.4 min.; TLC $R_f$=0.5 (5% methanol/chloroform); $^1$H NMR (500 MHz, DMSO-$d_6$) δ11.10 (s, 1H), 9.80 (s, 1H), 9.07 (s, 1H), 8.89 (s, 1H), 8.54 (t, 2H, J=7.6 Hz), 8.46 (d, 1H, J=8.5 Hz), 8.33 (d, 1H, J=9.2 Hz), 8.22 (t, 1H, J=7.5 Hz), 8.04 (t, 2H, J=7.6 Hz), 7.95 (s, 1H), 7.79–7.78 (m, 2H), 7.63 (t, 1H, J=7.9 Hz), 7.52 (d, 1H, J=6.6 Hz), 5.88 (s, 2H), 2.94 (s, 3H), 2.92 (s, 3H); HRMS (FAB) calcd for $C_{28}H_{23}N_3O_2S$ [M+H]$^+$ 466.1589, found 466.1577.

The intermediate 2-methyl-4-methylsulfanyl-quinolin-6-ylamine, K-4d, was prepared as follows:

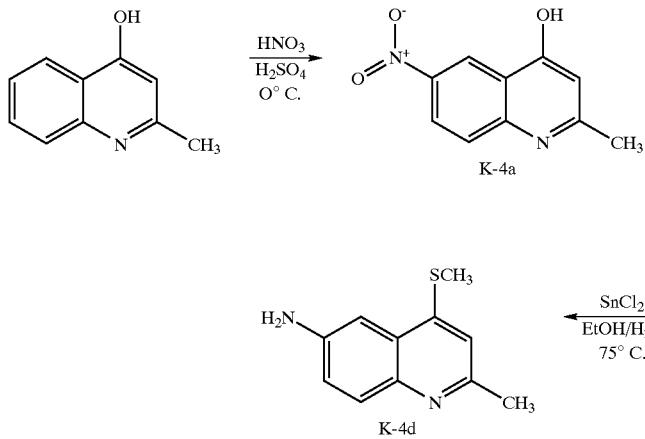
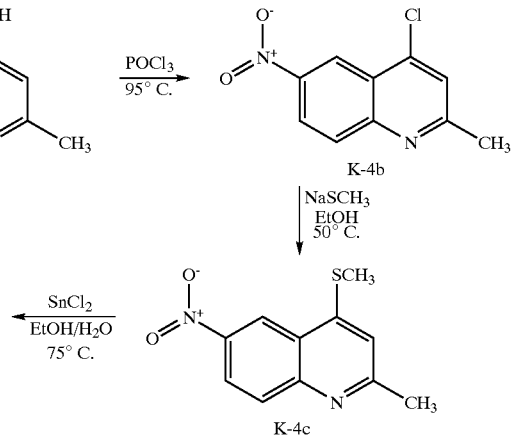

(a) A solution of 2-methyl-quinolin-4-ol (Aldrich, 9.2 g, 57.9 mmol. 1.0 eq) in concentrated sulfuric acid (60 mL) was cooled to 0° C. and treated with fuming nitric acid (3.9 mL, 57.9 mmol, 1.0 eq). The dark orange solution was stirred at 0° C. for 15 minutes and then poured into ice water (1000 mL) to give a yellow precipitate. After standing for 18 hours, the mixture was filtered and the yellow precipitate was washed with ice water to give 2-methyl-6-nitro-quinolin-4-ol, K-4a, as a yellow solid (6.9 g, 58%): HPLC $R_t$=6.8 min.; $^1$H NMR (500 MHz, DMSO-$d_6$) δ8.10 (s, 1H), 8.42 (dd, 1H, J=9.2, 2.6 Hz), 7.70 (d, 1H, J=9.1 Hz), 6.15 (s, 1H), 2.42 (s, 3H); MS (ESI) m/z 203 [M−H]$^−$.

(b) A solution of 2-methyl-6-nitro-quinolin-4-ol, K-4a, (6.9 g, 33.8 mmol) in phosphorus oxychloride (70 mL) was heated to 95° C. After 1 hour, the reaction mixture gives no starting material by HPLC analysis. The black solution was cooled to room temperature and poured into ice water (500 mL). The aqueous layer was made basic by the addition of concentrated ammonium hydroxide, and extracted with chloroform (3×500 mL). The combined organic extracts were washed with 5.0 N ammonium hydroxide (500 mL), water (500 mL), brine (500 mL), dried over magnesium sulfate, filtered and concentrated under reduced pressure. The crude product was passed through a silica gel plug, eluting with 20% ethyl acetate/chloroform, to give a brown solid (6.4 g). The product was crystallized from hot ethanol to give 4-chloro-2-methyl-6-nitro-quinoline, K-4b, as tan needles (3.6 g, 48%): mp 142–144° C.; HPLC $R_t$=13.5 min.; TLC $R_f$=0.3 (20% ethyl acetate/cyclohexane); $^1$H NMR (500 MHz, DMSO-$d_6$) δ8.92, (d, 1H, J=2.5 Hz), 8.52 (dd, 1H, J=9.2, 2.6 Hz), 8.20 (d, 1H, J=9.2 Hz), 7.94 (s, 1H), 2.73 (s, 3H); MS (ESI) m/z 223 [M+H]$^+$.

(c) A solution of 4-chloro-2-methyl-6-nitro-quinoline, K-4b, (372 mg, 1.7 mmol, 1.0 eq) in anhydrous ethanol (70 mL) was treated with sodium thiomethoxide (619 mg, 8.8 mmol, 5.2 eq), and the resultant green slurry was heated at 50° C. After 2.5 hours, the solvent was removed under reduced pressure and the residue was partitioned between water (100 mL) and chloroform (3×100 mL). The combined organic extracts were washed with brine (100 mL), dried over magnesium sulfate, filtered and concentrated under reduced pressure to give a yellow solid (430 mg). The crude product was purified by radial chromatography over silica gel using 5% ethyl acetate/chloroform, followed by crystallization from hot ethanol, to give 2-methyl-4-methylsulfanyl-6-nitro-quinoline, K-4c, as yellow needles (250 mg, 46%): HPLC $R_t$=13.1 min.; TLC $R_f$=0.5 (10% ethyl acetate/chloroform); $^1$H NMR (500 MHz, DMSO-$d_6$) δ8.70 (d, 1H, J=2.4 Hz), 8.32 (dd, 1H, J=9.2, 2.5 Hz), 7.97 (d, 1H, J=9.2 Hz), 7.35 (s, 1H), 2.61 (s, 3H), 2.58 (s, 3H); MS (ESI) m/z 235 [M+H]$^+$.

(d) A mixture of 2-methyl-4-methylsulfanyl-6-nitro-quinoline, K-4c, (200 mg, 0.85 mmol, 1.0 eq), and tin(II) chloride dihydrate (965 mg, 4.27 mmol, 5.0 eq) in anhydrous ethanol (50 mL) was heated to 75° C. to give an orange solution. After 30 minutes, the reaction mixture was concentrated under reduced pressure to about 10 mL. The resultant mixture was poured into ice water (100 mL), and the aqueous layer was adjusted to pH 10 using concentrated ammonium hydroxide. The aqueous layer was extracted with ethyl acetate (3×100 mL), the combined organic layers were washed with brine (100 mL), dried over magnesium sulfate, filtered and concentrated under reduced pressure to give a yellow solid (250 mg). The crude product was purified by radial chromatography over silica gel using 30% ethyl acetate/dichloromethane w/0.5% methanol to give 2-methyl-4-methylsulfanyl-quinolin-6-ylamine, K-4d, as a yellow solid (70 mg, 40%): HPLC $R_t$=9.0 min.; TLC $R_f$=0.6 (5% methanol/chloroform); $^1$H NMR (500 MHz, DMSO-$d_6$) δ7.58 (d, 1H, J=8.9 Hz), 7.08 (dd, 1H, J=8.9, 2.4 Hz), 7.02 (s, 1H), 6.90 (d, 1H, J=2.4 Hz), 5.58 (s, 2H), 2.58 (s, 3H), 2.51 (s, 3H); MS (ESI) m/z 205 [M+H]$^+$.

Example K-5

3-(Pyridin-3-yl)methoxy-N-(3,4,5-trimethoxyphenyl)benzamide

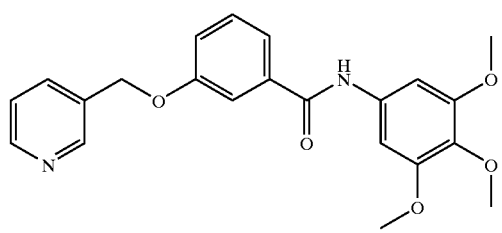

Example K-5, which was obtained as a white solid in a 62% yield, was prepared in a similar manner to that described for K-1, except that 3,4,5-trimethoxyaniline was used in place of 3-methyl-4-isopropylaniline in step (d), and 3-picolyl chloride hydrochloride was used in place of 4-(chloromethyl)isoquinoline hydrochloride, K-1c, in step (e): HPLC $R_t$=18.1 min.; TLC $R_f$=0.5 (5% methanol/chloroform); $^1$H NMR (500 MHz, CDCl$_3$) δ8.73 (s, 1H), 8.60 (d, 1H, J=2.9 Hz), 8.22 (s, 1H), 7.91 (d, 1H, J=7.4 Hz), 7.61 (s, 1H), 7.52–7.41 (m, 3H), 7.16 (d, 1H, J=7.6 Hz), 7.04 (s, 2H), 5.19 (s, 2H), 3.87 (s, 6H), 3.85 (s, 3H); $^{13}$C NMR (125 MHz, CDCl$_3$) δ165.2, 158.5, 153.3, 147.9, 147.4, 136.6, 136.4, 134.9, 134.0, 133.0, 130.0, 124.0, 119.7, 118.8, 113.3, 98.0, 67.4, 61.0, 56.1; MS (FAB) m/z 395 [M+H]$^+$. Anal. calc'd for C$_{22}$H$_{22}$N$_2$O$_5$: C, 66.99; H, 5.62; N, 7.10. Found: C, 67.00; H, 5.65; N, 7.09.

Example K-6

N-(Naphthalen-2-yl)-3-(pyridin-3-yl)methoxybenzamide

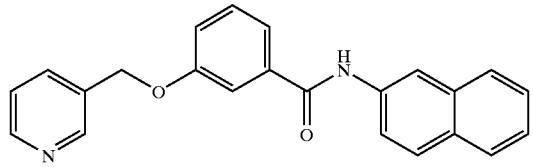

K-6

Example K-6, which was obtained as a white solid in a 19% yield, was prepared in a similar manner to that described for K-1, except 2-aminonaphthalene (Aldrich) was used in place of 3-methyl-4-isopropylaniline in step (d), and 3-picolyl chloride hydrochloride was used in place of 4-(chloromethyl)isoquinoline hydrochloride, K-1c, in step (e): HPLC $R_t$=22.5 min.; TLC $R_f$=0.4 (5% methanol/chloroform); $^1$H NMR (300 MHz, CDCl$_3$) δ10.41 (s, 1H), 8.72 (d, 1H, J=1.8 Hz), 8.58 (dd, 1H, J=4.8, 1.6 Hz), 8.44 (d, 1H, J=1.5 Hz), 7.94–7.81 (m, 5H), 7.68–7.62 (m, 2H), 7.53–5.28 (m, 5H), 5.27 (s, 2H); $^{13}$C NMR (125 MHz, DMSO-d$_6$) δ165.6, 158.5, 149.6, 149.5, 137.0, 136.7, 136.1, 133.7, 132.8, 130.4, 130.0, 128.5, 127.8, 127.7, 126.7, 125.2, 124.0, 121.3, 120.7, 118.4, 117.0, 114.4, 67.6; MS (FAB) m/z 355 [M+H]$^+$. Anal. calcd for C$_{23}$H$_{18}$N$_2$O$_2$: C, 77.95; H, 5.12; N, 7.70. Found: C, 77.41; H, 5.22; N, 7.79.

Example K-7

N-(1-Allyl-1H-indol-5-yl)-3-(pyridin-3-yl)methoxybenzamide

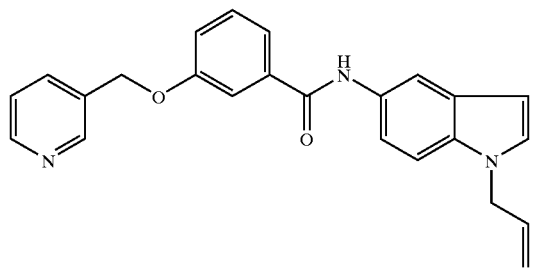

K-7

Example K-7, which was obtained as a light yellow solid in a 25% yield, was prepared in a similar manner to that described for K-1, except 1-allyl-1H-indol-5-ylamine, K-7b (vide infra), was used in place of 3-methyl-4-isopropylaniline in step (d), and 3-picolyl chloride hydrochloride was used in place of 4-(chloromethyl)isoquinoline hydrochloride, K-1c, in step (e): HPLC $R_t$=21.6 min.; TLC $R_f$=0.7 (5% methanol/chloroform); $^1$H NMR (300 MHz, DMSO-d$_6$) δ10.14 (s, 1H), 8.77 (d, 1H, J=1.5 Hz), 8.62 (d, 1H, J=5.1 Hz), 8.05 (s, 1H), 7.98 (d, 1H, J=8.1 Hz), 7.68–7.66 (m, 2H), 7.53–7.28 (m, 7H), 6.49 (d, 1H, J=2.9 Hz), 6.10–6.01 (m, 1H), 5.30 (s, 2H), 5.20 (d, 1H, J=10.3 Hz), 5.05 (d, 1H, J=17.3 Hz), 4.86 (d, 2H, J=5.2 Hz); HRMS (FAB) calcd for C$_{24}$H$_{21}$N$_3$O$_2$ [M+H]$^+$384.1712, found 384.1708.

The intermediate 1-allyl-1H-indol-5-ylamine, K-7b, was prepared as follows:

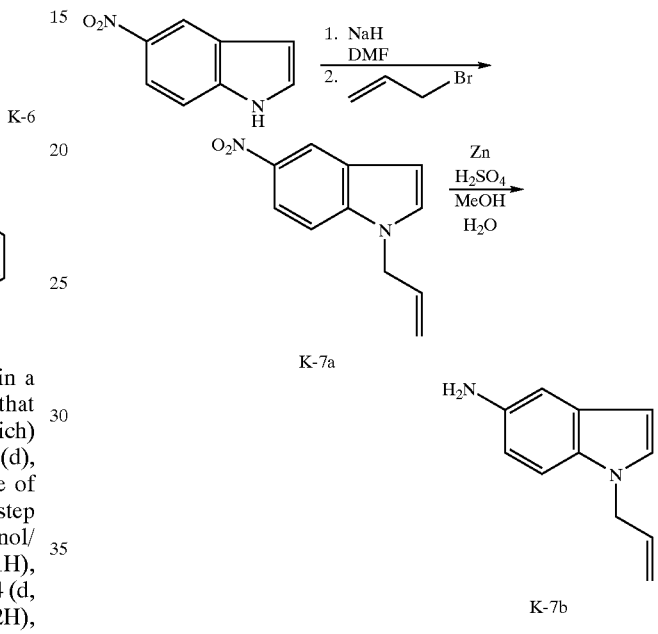

(a) A solution of 5-nitro-1H-indole (Acros, 2.0 g, 13.5 mmol, 1.0 eq) in DMF (125 mL) was cooled to 0° C., treated with sodium hydride (60% in mineral oil, 600 mg, 14.9 mmol, 1.1 eq) and stirred for 2.0 hours. The resulting red solution was treated with allyl bromide (1.3 mL, 14.9 mmol, 1.1 eq) and stirred for 1.0 hour at room temperature. The reaction was diluted with water (1.0 L) and extracted with MTBE (3×500 mL). The combined organic extracts were washed with water (500 mL), brine (200 mL), dried over magnesium sulfate, filtered and concentrated under reduced pressure to give a brown oil (2.7 g). The crude product was purified by radial chromatography over silica gel using 5–30% ethyl acetate/cyclohexane to give 1-allyl-5-nitro-1H-indole, K-7a, as a light yellow oil (2.5 g, 90%): TLC $R_f$=0.3 (5% ethyl acetate/cyclohexane); $^1$H NMR (300 MHz, CDCl$_3$) δ6.60 (d, J=2.2 Hz, 1H), 8.11 (dd, 1H, J=9.2, 2.2 Hz), 7.34 (d, 1H, J=9.2 Hz), 7.26–7.24 (m, 1H), 6.70 (d, 1H, J=3.3 Hz), 6.06–5.94 (m, 1H), 5.26 (dd, 2H, J=10.3, 0.7 Hz), 5.08 (dd, 1H, J=17.3, 0.7 Hz), 4.79 (d, 2H, J=5.5 Hz); MS (FAB) m/z 203 [M+H]$^+$.

(b) A mixture of water (20 mL), methanol (20 mL), zinc (4.2 g, 64.2 mmol, 5.6 eq) and 1-allyl-5-nitro-1H-indole, K-7a, (2.3 g, 11.4 mmol, 1.0 eq) was treated with concentrated sulfuric acid (6 mL, 333 mmol, 29 eq) at 0° C. The mixture was gradually warmed to room temperature. After 18 hours, the mixture was filtered, and the pH of the resulting brown solution was adjusted to 9 with a saturated sodium bicarbonate solution. The resulting slurry was filtered and extracted with chloroform (3×500 mL). The combined organic extracts were washed with brine (200 mL), dried over magnesium sulfate, filtered and concentrated under reduced pressure to give a black oil (0.94 g). The crude product was purified by radial chromatography over silica gel using 40% ethyl acetate/cyclohexane with 0.5% methanol to give 1-allyl-1H-indol-5-ylamine, K-7b, as a dark brown oil (233 mg, 5%): TLC $R_f$=0.3 (30% ethyl acetate/cyclohexane); $^1$H NMR (300 MHz, CDCl$_3$) δ7.16 (d, 1H, J=8.4 Hz), 7.07–7.03 (m, 2H), 6.77 (dd, 1H, J=8.6, 2.0 Hz), 6.36 (d, 1H, J=2.9 Hz), 6.04–5.91 (m, 1H), 5.18 (dd, 1H, J=10.3, 1.1 Hz), 5.05 (dd, 1H, J=16.9, 1.1 Hz), 4.67 (d, 2H, J=5.5 Hz), 3.8 (br s, 2H); MS (FAB) m/z 171 [M−H]$^−$.

Example K-8

3-(Pyridin-3-yl)methoxy-N-quinolin-6-yl-benzamide

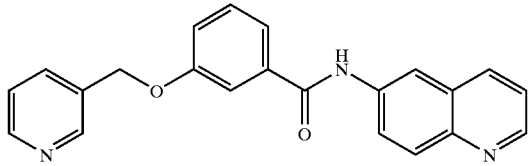

K-8

Example K-8, which was obtained as a white solid in a 20% yield, was prepared in a similar manner to that described for K-1, except 6-aminoquinoline (Fluka) was used in place of 3-methyl-4-isopropylaniline in step (d), and 3-picolyl chloride hydrochloride was used in place of 4-(chloromethyl)isoquinoline hydrochloride, K-1c, in step (e): HPLC $R_t$=17.0 min.; TLC $R_f$=0.6 (5% methanol/chloroform); $^1$H NMR (300 MHz, DMSO-d$_6$) δ10.60 (s, 1H), 8.86 (d, 1H, J=3.3 Hz), 8.78 (s, 1H), 8.63–8.60 (m, 2H), 8.39 (d, 1H, J=8.5 Hz), 8.12–8.04 (m, 2H), 7.98 (d, 1H, J=8.1 Hz), 7.74–7.70 (m, 2H), 7.67–7.49 (m, 3H), 7.37–7.34 (m, 1H), 5.32 (s, 2H); HRMS (FAB) calcd for C$_{22}$H$_{17}$N$_3$O$_2$ [M+H]$^+$356.1399, found 384.1406.

Example K-9

N-(2-Methyl-quinolin-6-yl)-3-(pyridin-3-yl)methoxy-benzamide

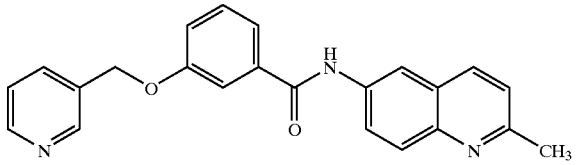

K-9

Example K-9, which was obtained as a white solid in a 16% yield, was prepared in a similar manner to that described for K-1, except 6-amino-2-methylquinoline (Maybridge) was used in place of 3-methyl-4-isopropylaniline in step (d), and 3-picolyl chloride hydrochloride was used in place of 4-(chloromethyl)isoquinoline hydrochloride, K-1c, in step (e): HPLC $R_t$=19.9 min.; TLC $R_f$=0.2 (3% methanol/chloroform); $^1$H NMR (300 MHz, DMSO-d$_6$) δ10.54 (s, 1H), 8.77 (d, 1H, J=0.7 Hz), 8.62 (dd, 1H, J=4.8, 1.4 Hz), 8.52 (d, 1H, J=1.9 Hz), 8.26 (d, 1H, J=8.8 Hz), 8.05–7.93 (m, 3H), 7.71–7.69 (m, 2H), 7.66–7.43 (m, 3H), 7.36–7.33 (m, 1H), 5.32 (s, 2H), 2.69 (s, 3H); $^{13}$C NMR (125 MHz, DMSO-d$_6$) δ165.4, 158.1, 157.4, 149.3, 149.2, 144.5, 136.3, 135.8, 132.4, 129.7, 128.5, 126.3, 124.1, 123.6, 122.4, 120.4, 118.1, 116.4, 114.1, 67.3, 24.7; HRMS (FAB) calcd for C$_{23}$H$_{19}$N$_3$O$_2$ [M+H]$^+$370.1556, found 370.1549.

Example K-10

N-(4-Isopropyl-3-methyl-phenyl)-4-fluoro-3-(Isoquinolin-4-yl)methoxy-benzamide

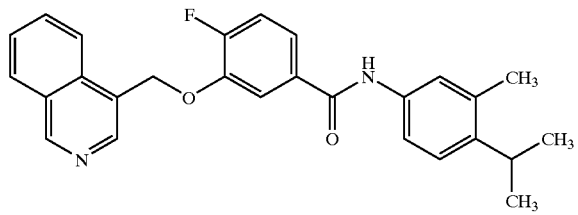

K-10

Example K-10 was prepared in a similar manner to that described for K-1, except 4-fluoro-3-hydroxybenzoic acid was used in place of 3-hydroxybenzoic acid in step (d): $^1$H NMR (300 MHz, CDCl$_3$) δ9.28 (s, 1H), 8.63 (s, 1H),), 8.11(d, 1H, J=8.23 Hz) 8.05 (d, 1H, J=8.11 Hz), 7.79 (m, 2H), 7.68 (m, 2H), 7.40 (m, 3H), 7.22 (m, 2H), 5.60 (s, 2H), 3.12 (br, 1H), 2.35 (s, 3H), 1.22 (d, 6H, J=6.9 Hz). MS (FAB) m/z 429 [M+H]$^+$. Anal. calcd for C$_{27}$H$_{25}$FN$_2$O$_2$·0.8H$_2$O: C, 73.22; H, 6.05; N, 6.33. Found: C, 73.21; H, 5.73; N, 6.19.

Example K-11

N-(4-Isopropyl-3-methyl-phenyl)-4-methyl-3-(Isoquinolin-4-yl)methoxy-benzamide

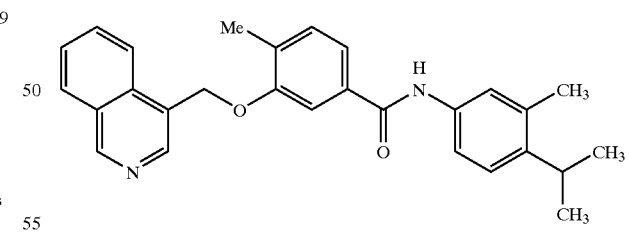

K-11

Example K-11 was prepared in a similar manner to that described for K-1, except 4-methyl-3-hydroxybenzoic acid was used in place of 3-hydroxybenzoic acid in step (d): $^1$H NMR (300 MHz, CDCl$_3$) δ9.29 (s, 1H), 8.67 (s, 1H),), 8.07 (s, 1H), 8.04 (s, 1H), 7.80–7.64 (m, 4H), 7.46–7.30 (m, 4H), 7.23 (m, 1H), 5.54 (s, 2H), 3.19–3.06 (m, 1H), 2.36 (s, 3H), 2.25 (s, 3H), 1.23 (d, 6H, J=6.84 Hz). MS (ESI) m/z 425 [M+H]$^+$. Anal. calc'd for C$_{28}$H$_{28}$N$_2$O$_2$: C, 79.22; H, 6.65; N, 6.60. Found: C, 79.27; H, 6.74; N, 6.60.

Example K-12

N-(4-Isopropyl-3-methyl-phenyl)-4-chloro-3-(Isoquinolin-4-yl)methoxy-benzamide

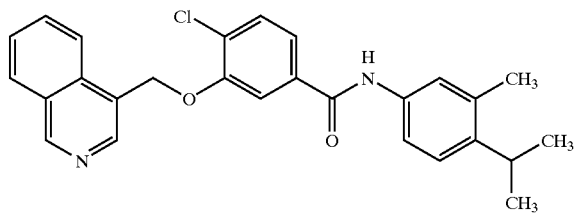

K-12

Example K-12 was prepared in a similar manner to that described for K-1, except 4-chloro-3-hydroxybenzoic acid was used in place of 3-hydroxybenzoic acid in step (d): $^1$H NMR (300 MHz, CDCl$_3$) δ9.30 (br, s,1H), 8.70 (br, s, 1H),), 8.14–8.04 (m, 2H), 7.82–7.65 (m, 4H), 7.50–7.32 (m, 4H), 7.23 (m, 1H), 5.61 (s, 2H), 3.13 (m, 1H), 2.36 (s, 3H), 1.23(d, 6H, J=6.89 Hz). EIMS m/z 444 [M$^+$]. Anal. calc'd for C$_{27}$H$_{25}$ClN$_2$O$_2$: C, 72.88; H, 5.66; N, 6.30. Found: C, 72.86; H, 5.71; N, 6.24.

Example L-1

3-(6-Aminopyridin-3-yl)methoxy-N-(4-Isopropyl-3-methyl-phenyl)-benzamide

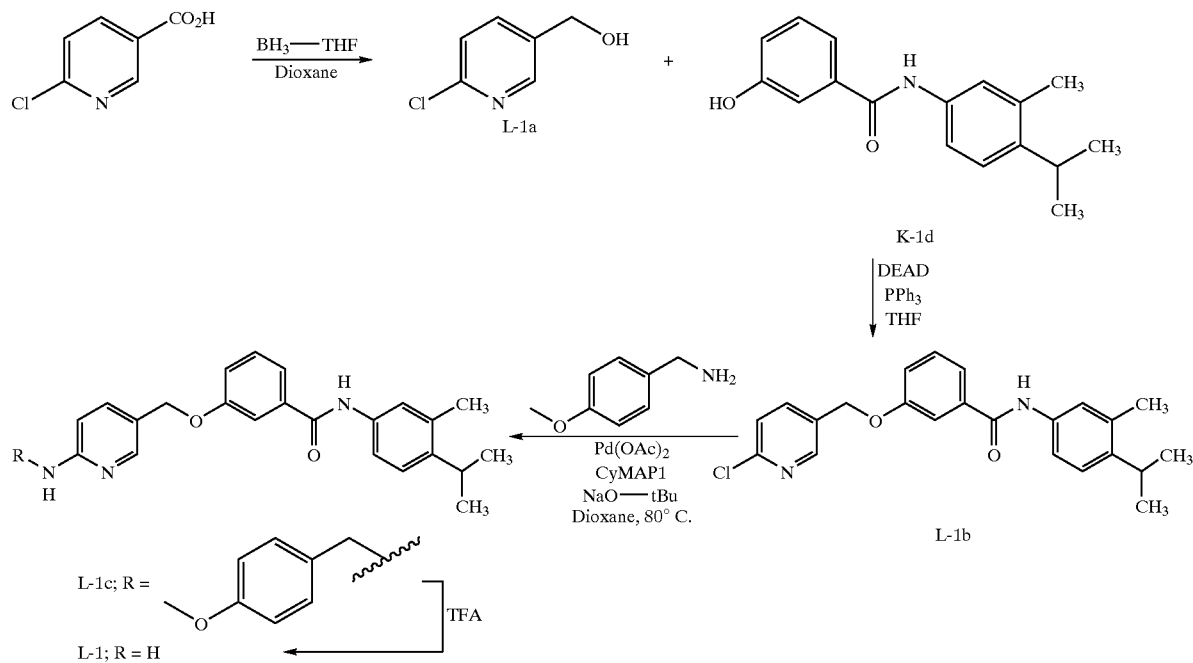

(a) A solution of 6-chloronicotinic acid (Aldrich, 10.0 g, 63.7 mmol, 1.0 eq) in dioxane (300 mL) was treated with a 1.0 M solution of borane in THF (320 mL, 329 mmol, 5.0 eq) at room temperature. The resultant orange solution was stirred for one hour and then heated to 75° C. After 2.5 h, the reaction was quenched with ethanol (100 mL), and the solvent was removed under reduced pressure. The crude product was stirred in 1.2 M HCl (350 mL) and the pH was subsequently adjusted to 9 with solid NaOH. The aqueous layer was extracted with ethyl acetate (3×200 mL) and the combined organic extracts were washed with water (200 mL), brine (200 mL), dried over magnesium sulfate, filtered and concentrated under reduced pressure to give a yellow oil (23.4 g). The crude product was purified by flash chromatography over silica gel using 30–60% ethyl acetate/cyclohexane to give (6-chloropyridin-3-yl)methanol, L-1a, as a white crystalline solid (5.0 g, 54%): HPLC R$_t$=2.9 min.; TLC R$_f$=0.5 (5% methanol/dichloromethane); $^1$H NMR (300 MHz, DMSO-d$_6$) δ8.35 (d, 1H, J=1.9 Hz), 7.79 (dd, 1H, J=8.2, 2.4 Hz), 7.48 (d, 1H, J=8.2 Hz), 5.42 (t, 1H, J=5.6 Hz), 4.53 (d, 2H, J=5.7 Hz); $^{13}$C NMR (75 MHz, DMSO-d$_6$) δ148.9, 148.4, 138.5, 137.6, 124.2, 60.2; MS (ESI) m/z 144 [M+H]$^+$.

(b) A solution of the (6-chloropyridin-3-yl)-methanol, L-1a, (186 mg, 1.3 mmol, 1.0 eq), 3-hydroxy-N-(4-isopropyl-3-methyl-phenyl)-benzamide, K-1d, (350 mg, 1.3 mmol, 1.0 eq) and triphenylphosphine (10 g, 3.9 mmol, 3.0 eq) in THF (15 mL) was protected from light and treated with diethyl azodicarboxylate (0.62 mL, 3.9 mmol, 3.0 eq). After 18 h, the resultant light yellow solution was poured into 50% brine (200 mL) and extracted with ethyl acetate (3×100 mL). The combined organic extracts were washed with brine (200 mL), dried over magnesium sulfate, filtered through a silica gel plug, and concentrated under reduced pressure to give a yellow oil (2.6 g). The crude product was purified by radial chromatography over silica gel using 5–10% ethyl acetate/45% cyclohexane/dichloromethane to give 3-(6-chloropyridin-3-yl)methoxy-N-(4-isopropyl-3-methyl-phenyl)-benzamide, L-1b, as a white solid (380 mg, 74%): HPLC R$_t$=16.2 min.; TLC R$_f$=0.4 (30% ethyl acetate/cyclohexane); $^1$H NMR (300 MHz, DMSO-d$_6$) δ10.07 (s, 1H), 8.56 (d, 1H, J=2.3 Hz), 7.99 (dd, 1H, J=8.2, 2.4 Hz), 7.60–7.44 (m, 6H), 7.27–7.19 (m, 2H), 5.25 (s, 2H), 3.31–3.03 (m, 1H), 2.29 (s, 3H), 1.18 (d, 6H, J=6.9 Hz); $^{13}$C NMR (75 MHz, DMSO-d$_6$) δ165.1, 158.2, 150.2, 149.6, 142.2, 139.8, 136.8, 136.7, 135.0, 132.4, 130.0, 125.0, 124.6, 122.5, 120.7, 118.8, 118.2, 114.2, 66.6, 28.7, 23.5, 19.5; MS (ESI) m/z 393 [M−H]$^-$.

(c) A solution of 3-(6-chloropyridin-3-yl)methoxy-N-(4-isopropyl-3-methyl-phenyl)-benzamide, L-1b, (300 mg, 0.76 mmol, 1.0 eq), 4-methoxybenzylamine (Aldrich, 0.12 mL, 0.91 mmol, 1.2 eq), palladium acetate (Strem, 6.8 mg, 0.03 mmol, 4 mol %), and CyMAP1 (J. Am. Chem. Soc. 1998, 120, 9722–23, 11.8 mg, 0.03 mmol, 4 mol %) in dioxane (10 mL) was treated with sodium-tert-butoxide (169 mg, 1.82 mmol, 1.4 eq). The resultant orange solution was warmed to 80° C. for 18 hours. The reaction mixture was poured into 50% brine (100 mL) and extracted with ethyl acetate (3×75 mL). The combined organic extracts were washed with brine (200 mL), dried over magnesium sulfate, filtered through a silica gel plug, and concentrated under reduced pressure to give a yellow oil (330 mg). The crude product was purified by radial chromatography over silica gel using 45% ethyl acetate/cyclohexane to give, from MTBE, N-(4-isopropyl-3-methyl-phenyl)-3-[6-{(4-methoxybenzyl)amino}pyridin-3-ylmethoxy]-benzamide, L-1c, as a white solid (189 mg, 50%): HPLC $R_t$=14.7 min.; TLC $R_f$=0.4 (4% methanol/dichloromethane); $^1$H NMR (300 MHz, DMSO-d$_6$) δ9.43 (s, 1H), 7.74 (s, 1H), 7.27–7.18 (m, 3H), 7.02–6.82 (m, 6H), 6.70–6.62 (m, 4H), 6.41 (d, 1H, J=8.5 Hz), 4.79 (s, 2H), 4.32 (d, 2H, J=5.5 Hz), 3.69 (s, 3H), 2.97–2.90 (m, 1H), 2.13 (s, 3H), 1.05 (d, 6H, J=6.7 Hz); $^{13}$C NMR (75 MHz, DMSO-d$_6$) δ169.9, 158.4, 158.3, 157.0, 147.4, 144.8, 140.4, 138.0, 137.2, 135.7, 132.7, 129.0, 128.8, 125.8, 125.3, 120.8, 119.2, 116.7, 115.5, 113.9, 108.2, 55.4, 50.7, 44.0, 28.7, 23.3, 19.2; MS (ESI) m/z 494 [M–H]$^-$.

(d) A solution of N-(4-isopropyl-3-methyl-phenyl)-3-[6-{(4-methoxybenzyl)amino}pyridin-3-ylmethoxy]-benzamide, L-1c, (120 mg, 0.24 mmol) in trifluoroacetic acid (6 mL) was stirred at room temperature. After 18 hours, the resultant cherry red solution was concentrated under reduced pressure and extracted with 50% sodium bicarbonate (25 mL) and ethyl acetate (3×25 mL). The combined organic extracts were washed with 5% sodium bicarbonate (50 mL), brine (50 mL), dried over magnesium sulfate, and concentrated under reduced pressure to give a clear oil (132 mg). The crude product was purified by radial chromatography over silica gel using 5% methanol/chloroform with 0.1% ammonium hydroxide to give, 3-(6-amino-pyridin-3-yl)methoxy-N-(4-isopropyl-3-methyl-phenyl)-benzamide, L-1, as a white solid (75 mg, 82%): mp 78–81° C.; HPLC $R_t$=12.1 min.; TLC $R_f$=0.4 (8% methanol/chloroform); $^1$H NMR (300 MHz, DMSO-d$_6$) δ9.32 (s, 1H), 7.54 (d, 1H, J=2.0 Hz), 7.13 (dd, 1H, J=8.4, 2.4 Hz), 6.90–6.71 (m, 2H), 6.58 (d, 1H, J=1.5 Hz), 6.54–6.47 (m, 4H), 6.23 (d, 1H, J=8.5 Hz), 5.70 (s, 2H), 4.66 (s, 2H), 2.94–2.78 (m, 1H), 2.02 (s, 3H), 0.94 (d, 6H, J=6.8 Hz); MS (ESI) m/z 494 [M–H]$^-$. Anal. calcd for $C_{23}H_{25}N_3O_2$.0.4 hexane: C, 74.42; H, 7.52; N, 10.25. Found: C, 74.09; H, 7.49; N, 10.00.

Example M-1

3-(6-Aminopyridin-3-yl)methoxy-N-(2-methyl-quinolin-6-yl)-benzamide

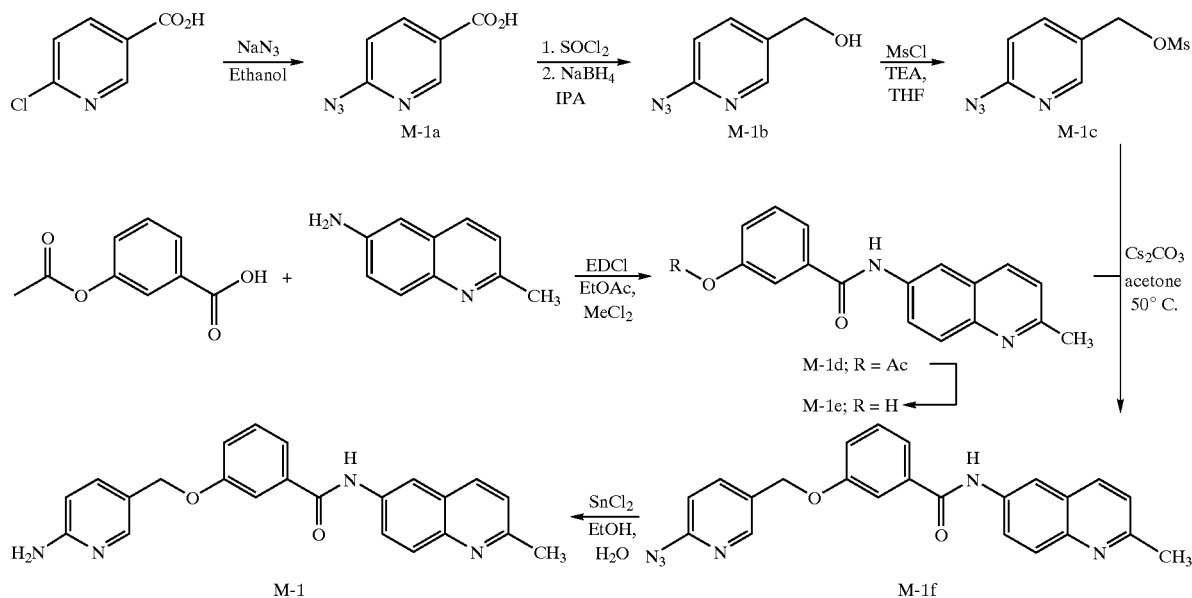

(a) A mixture of 6-chloronicotinic acid (Aldrich, 5.0 g, 31.6 mmol, 1.0 eq), water (10 mL) and ethanol (35 mL) was treated with sodium azide (2.15 g, 33.8 mmol, 1.1 eq). The resulting orange solution was heated to 75° C. After 18 h, the solvent was removed under reduced pressure and the resultant white slurry was repeatedly evaporated with toluene to give the crude 6-azido-nicotinic acid/NaCl mixture, M-1a, as a white solid (6.9 g, 98%): TLC $R_f$=0.2 (6% methanol/dichloromethane w/0.1% Acetic acid); $^1$H NMR (500 MHz, DMSO-d$_6$) δ9.41 (s, 1H), 7.98 (s, 1H), 7.97 (s, 1H).

(b) A mixture of 6-azidonicotinic acid/NaCl, M-1a, (6.9 g, 31.1 mmol), and thionyl chloride (100 mL) was heated to 75° C. After 2 hours, the crude acid chloride hydrochloride salt was obtained by removing the thionyl chloride under pressure. The resultant slurry was evaporated from toluene and then added to a slurry of isopropanol (100 mL) and sodium borohydride at −10° C. The resultant yellow slurry was warmed to room temperature over several hours and stirred at room temperature for 12 h. The reaction mixture was poured into water (500 mL) and extracted with ethyl acetate (3×500 mL). The combined organic extracts were washed with brine (200 mL), dried over magnesium sulfate, filtered and concentrated under reduced pressure to give a yellow solid (2.3 g). The crude product was purified by radial chromatography over silica gel using 1–3% methanol/dichloromethane to give (6-azidopyridin-3-yl)-methanol, M-1b, as a white solid (850 mg, 18%): TLC $R_f$=0.4 (5% methanol/chloroform); $^1$H NMR (500 MHz, DMSO-$d_6$) δ9.14 (s, 1H), 8.19 (d, 1H, J=9.0 Hz), 7.84 (dd, 1H, J=9.4, 1.0 Hz), 5.67 (t, 1H, J=5.6 Hz), 4.66 (d, 2H, J=5.6 Hz).

(c) A solution of (6-azidopyridin-3-yl)-methanol, M-1b, (350 mg, 2.3 mmol, 1.0 eq) in THF (25 mL) was cooled to −78° C. and treated with mesyl chloride (265 μL, 3.4 mmol, 1.5 eq). After 60 minutes at −78° C., the clear solution was treated with triethylamine (0.70 mL, 5.1 mmol, 2.2 eq), and the reaction mixture was warmed to −20° C. over 2.5 hours. The resultant cloudy reaction mixture was monitored by TLC (3% methanol/dichloromethane), which gave only product ($R_f$0.4) and no starting material ($R_f$0.2). To obtain an analytical sample, an aliquot of the reaction mixture was diluted in 25% ammonium acetate and extracted with ethyl acetate. The organic extract was washed with water, brine, dried over magnesium sulfate, filtered and concentrated under reduced pressure to give (6-azidopyridin-3-yl)methyl methanesulfonate, M-1c, as a tan solid: TLC $R_f$=0.6 (5% methanol/chloroform); $^1$H NMR (500 MHz, DMSO-$d_6$) δ9.5 (s, 1H), 8.30 (d, 1H, J=9.4 Hz), 7.94 (d, 1H, J=9.6 Hz), 5.46 (s, 2H), 3.35 (s, 3H).

(d) A solution of 3-acetoxybenzoic acid (Aldrich, 1.8 g, 9.9 mmol, 1.0 eq) and 6-amino-2-methylquinoline (Avocado, 1.6 g, 9.9 mmol, 1.0 eq) in ethyl acetate (50 mL) was treated with a solution of 1-(3-dimethylaminopropyl)-3-ethylcarbodiimide hydrochloride (2.3 g, 11.8 mmol, 1.2 eq) in dichloromethane (50 mL). After 18 h, the resultant tan slurry was poured into 5% sodium bicarbonate (200 mL) and extracted with 10% isopropyl alcohol/chloroform (3×150 mL). The combined organic extracts were washed with brine (200 mL), dried over magnesium sulfate, filtered through a silica gel plug and concentrated under reduced pressure to give a yellow solid (2.8 g). The crude product was purified by radial chromatography over silica gel using 1–2% methanol/dichloromethane to give an unpure product as a yellow solid (2.6 g). The unpure product was washed with MTBE and the solids were collected to give 3-acetoxy-N-(2-methyl-quinolin-6-yl)benzamide, M-1d, as a light yellow solid (2.3 g, 84%): HPLC $R_t$=11.2 min.; TLC $R_f$=0.3 (3% methanol/dichloromethane); $^1$H NMR (300 MHz, DMSO-$d_6$) δ10.40 (s, 1H), 8.29 (d, 1H, J=2.2 Hz), 8.04 (d, 1H, J=8.5 Hz), 7.83–7.72 (m, 3H), 7.59 (t, 1H, J=1.8 Hz), 7.45 (t, 1H, J=7.9 Hz), 7.24 (d, 1H, J=8.4 Hz), 2.48 (s, 3H), 2.16 (s, 3H); MS (ESI) m/z 321 [M+H]$^+$.

(e) A solution of 3-acetoxy-N-(2-methyl-quinolin-6-yl)benzamide, M-1d, (2.2 g, 6.9 mmol, 1.0 eq) in methanol (65 mL) and THF (60 mL) was treated with a solution of potassium carbonate (4.8 g, 34.5 mmol, 5.0 eq) in water (45 mL). After 3.0 h, the cloudy reaction mixture was concentrated under reduced pressure and extracted with water (100 mL) and ethyl acetate (3×100 mL). The combined organic extracts were washed with brine (200 mL), dried over magnesium sulfate and concentrated under reduced pressure to give a light yellow solid (2.0 g). The crude product was washed with dichloromethane and the solids were collected to give 3-hydroxy-N-(2-methyl-quinolin-6-yl)-benzamide, M-1e, as a light yellow solid (1.6 g, 83%): HPLC $R_t$=9.5 min.; TLC $R_f$=0.3 (5% methanol/dichloromethane); $^1$H NMR (300 MHz, DMSO-$d_6$) δ10.43 (s, 1H), 9.78 (s, 1H), 8.47 (d, 1H, J=2.2 Hz), 8.20 (d, 1H, J=8.4 Hz), 8.00–7.87 (m, 2H), 7.44–7.32 (m, 4H), 7.01–6.98 (m, 1H), 2.64 (s, 3H); $^{13}$C NMR (75 MHz, DMSO-$d_6$) δ166.2, 157.7, 157.6, 144.8, 136.8, 136.6, 136.1, 129.8, 128.8, 126.7, 124.4, 122.8, 119.0, 118.6, 116.6, 114.9, 25.0; MS (ESI) m/z 279 [M+H]$^+$.

(f) A mixture of 3-hydroxy-N-(2-methyl-quinolin-6-yl)-benzamide, M-1e, (0.64 g, 2.3 mmol, 1.0 eq) and cesium carbonate (3.0 g, 9.2 mmol, 4.0 eq) in acetone (45 mL) was treated with unpurified (6-azidopyridin-3-yl)methyl methanesulfonate, M-1c, (524 mg, 2.3 mmol, 1.0 eq). After 18 h at 50° C., the resultant pink slurry was poured into 5% sodium bicarbonate (400 mL) and extracted with 5% isopropyl alcohol/chloroform (3×300 mL). The combined organic extracts were washed with brine (300 mL), dried over magnesium sulfate and concentrated under reduced pressure to give a light yellow solid (0.99 g). The crude product was washed with diethyl ether and the solids were collected to give 3-(6-azidopyridin-3-yl)methoxy-N-(2-methyl-quinolin-6-yl)-benzamide, M-1f, as a light yellow solid (0.87 g, 92%): HPLC $R_t$=11.7 min.; TLC $R_f$=0.5 (5% methanol/dichloromethane); $^1$H NMR (500 MHz, DMSO-$d_6$) δ10.51 (s, 1H), 9.53 (s, 1H), 8.46 (d, 1H, J=2.0 Hz), 8.30 (d, 1H, J=9.2 Hz), 8.21 (d, 1H, J=9.0 Hz), 8.02–7.98 (m, 2H), 7.91 (d, 1H, J=9.1 Hz), 7.72 (s, 1H), 7.66 (d, 1H, J=7.8 Hz), 7.54 (t, 1H, J=8.0 Hz), 7.40 (d, 1H, J=8.4 Hz), 7.36 (dd, 1H, J=8.2, 2.0 Hz), 5.40 (s, 2H), 2.51 (s, 3H); MS (ESI) m/z 411 [M+H]$^+$.

(g) A solution of 3-(6-azidopyridin-3-yl)methoxy-N-(2-methyl-quinolin-6-yl)-benzamide, M-1f, (58 mg, 0.14 mmol, 1.0 eq) in anhydrous ethanol (20 mL) was treated with tin(II) chloride dihydrate (158 mg, 0.70 mmol, 5.0 eq) and warmed to 70° C. After 18 h, the light yellow solution was concentrated under reduced pressure and treated with a saturated sodium bicarbonate solution (100 mL). The aqueous layer was extracted with ethyl acetate (3×100 mL) and the combined organic extracts were washed with brine (200 mL), dried over magnesium sulfate, filtered and concentrated under reduced pressure to give a white foam (60 mg). The crude product was purified by radial chromatography over silica gel using 5% methanol/chloroform to give 3-(6-aminopyridin-3-yl)methoxy-N-(2-methyl-quinolin-6-yl)-benzamide, M-1, as a white solid (23 mg, 42%): mp 189–192° C.; HPLC $R_t$=11.4 min.; TLC $R_f$=0.3 (5% methanol/chloroform); $^1$H NMR (500 MHz, DMSO-$d_6$) δ10.48 (s, 1H), 8.49 (d, 1H, J=2.0 Hz), 8.22 (d, 1H, J=8.5 Hz), 8.05 (d, 1H, J=1.8 Hz), 8.00 (dd, 1H, J=9.1, 2.2 Hz), 7.92 (d, 1H, J=9.1 Hz), 7.64–7.41 (m, 4H), 7.41 (d, 1H, J=8.4 Hz), 7.26 (dd, 1H, J=8.2, 1.9 Hz), 6.49 (d, 1H, J=8.4 Hz), 6.05 (s, 2H), 5.01 (s, 2H), 2.66 (s, 3H); MS (ESI) m/z 385 [M+H]$^+$. Anal. calcd for $C_{23}H_{20}N_4O_2 \cdot 0.5\ H_2O$: C, 70.21; H, 5.38; N, 14.24. Found: C, 70.42; H, 5.34; N, 13.85.

Example N-1

3-(6-Acetylaminopyridin-3-yl)methoxy-N-(2-methyl-quinolin-6-yl)-benzamide

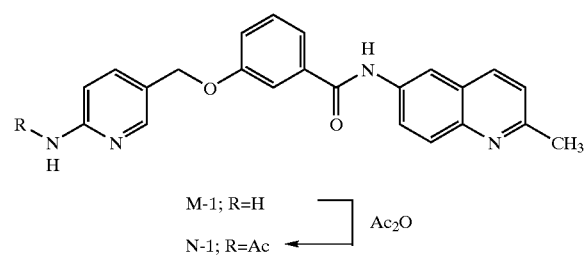

A cloudy suspension of 3-(6-amino-pyridin-3-yl)methoxy-N-(2-methyl-quinolin-6-yl)-benzamide, M-1, (40 mg, 0.10 mmol) in acetic anhydride (5 mL), THF (5 mL) and dichloromethane (3 mL) was stirred at room temperature.

After 18 h, the resultant yellow solution was concentrated under reduced pressure and chased with toluene to give a yellow solid (56 mg). The crude product was purified by radial chromatography over silica gel using 3–10% methanol/dichloromethane to give 3-[6-(acetylaninopyridin-3-yl)methoxy-N-(2-methyl-quinolin-6-yl)-benzamide, N-1, as a white solid (40 mg, 91%): HPLC $R_t$=11.5 min.; TLC $R_f$=0.5 (8% methanol/chloroform); $^1$H NMR (300 MHz, DMSO-$d_6$) δ10.63 (s, 1H), 10.56 (s, 1H), 8.54 (s, 1H), 8.50 (s, 1H), 8.29 (d, 1H, J=8.4 Hz), 8.18 (d, 1H, J=8.6 Hz), 8.07–7.95 (m, 3H), 7.71–7.67 (m, 2H), 7.56 (t, 1H, J=8.0 Hz), 7.47 (d, 1H, J=8.1 Hz), 7.35 (d, 1H, J=7.2 Hz), 5.25 (s, 2H), 2.71 (s, 3H), 2.71 (s, 3H); MS (ESI) m/z 427 [M+H]$^+$. Anal. calc'd for $C_{25}H_{22}N_4O_3 \cdot 0.1\ H_2O$: C, 70.11; H, 5.23; N, 13.08. Found: C, 69.71; H, 5.33; N, 12.82.

Example N-2

3-(6-Acetylaminopyridin-3-yl)methoxy-N-(4-Isopropyl-3-methyl-phenyl)-benzamide

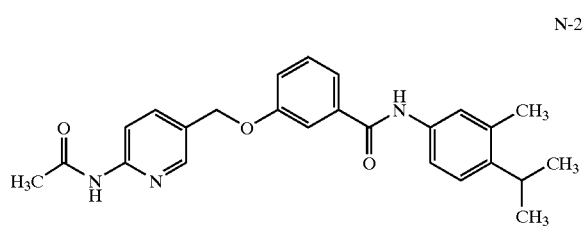

N-2

A clear solution of 3-(6-amino-pyridin-3-yl)methoxy-N-(4-isopropyl-3-methyl-phenyl)-benzamide, L-1, (30 mg, 0.08 mmol) in acetic anhydride (1.0 mL) was stirred at room temperature for 18 h. The resultant clear solution was concentrated under reduced pressure and chased with toluene to give a clear oil. The crude product was extracted with 5% sodium bicarbonate (25 mL) and ethyl acetate (3×25 mL). The combined ethyl acetate extracts were dried using brine (25 mL) and magnesium sulfate to give a clear oil (30 mg), which was identified as 3-(6-diacetylamino-pyridin-3-yl)methoxy-N-(4-isopropyl-3-methyl-phenyl)-benzamide by MS (ESI) (m/z 460). After purification by radial chromatography over silica gel, the diacetylated compound (24 mg, 0.05 mmol, 1.0 eq) was dissolved in methanol (0.5 mL) and treated with calcium carbonate (10 mg, 0.1 mmol, 2.1 eq) and water (0.5 mL). The resultant white slurry was heated at 60° C. for 18 hours. The reaction mixture was poured into water (25 mL) and extracted with ethyl acetate (3×25 mL). The combined organic extracts were washed with brine (50 mL), dried over magnesium sulfate, and concentrated under reduced pressure to give a clear oil (40 mg). The crude product was purified by radial chromatography over silica gel using 2–5% methanol/dichloromethane to give 3-(6-acetylaminopyridin-3-yl)methoxy-N-(4-isopropyl-3-methyl-phenyl)-benzamide, N-2, as a white solid (20 mg, 61%): mp 98–101° C.; HPLC $R_t$=12.4 min.; $^1$H NMR (300 MHz, DMSO-$d_6$) δ10.51 (s, 1H), 9.54 (s, 1H), 8.19 (s, 1H), 8.06 (d, 1H, J=8.2 Hz), 7.72 (d, 1H, J=8.3 Hz), 7.11–6.97 (m, 3H), 6.82–6.71 (m, 4H), 5.04 (s, 2H), 3.08–3.01 (m, 1H), 2.22 (s, 3H), 2.13 (s, 3H), 1.13 (d, 6H, J=6.7 Hz); MS (ESI) m/z 418 [M+H]$^+$. Anal. calc'd for $C_{25}H_{27}N_3O_3 \cdot 0.4$ hexane $\cdot .05\ H_2O$: C, 71.39; H, 7.35; N, 9.12. Found: C, 71.11; H, 7.48; N, 8.70.

Example O-1

4-Fluoro-N-(1,2,3,4-tetrahydroquinolin-6-yl)-3-(isoquinolin-4-ylmethoxy)-benzamide bistrifluoroacetic acid salt

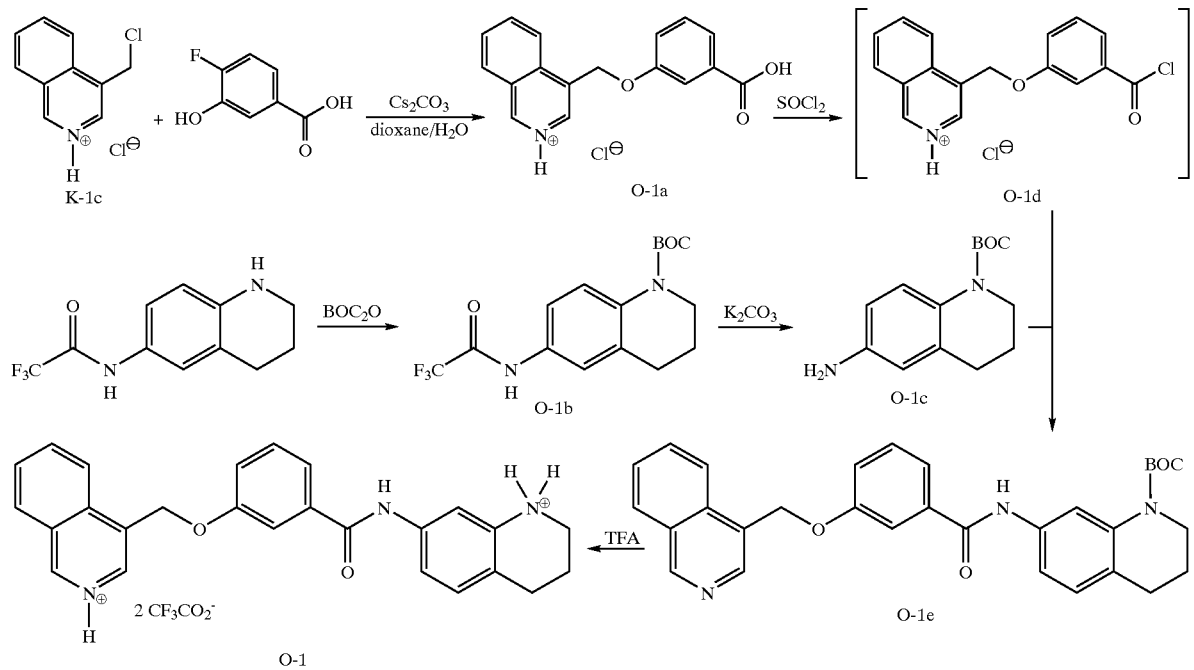

(a) To a stirred mixture of 4-fluoro-3-hydroxy-benzoic acid (0.73 g, 4.7 mmol) and $Cs_2CO_3$ (4.58 g, 14.1 mmol) in dioxane/$H_2O$ (1:1, 20 ml) was added 1.0 g (4.7 mmol) of 4-chloromethyl-isoquinoline.HCl, K-1c. After heating at 65° C. for 24 hrs, the solvent was removed, water was added, the pH was adjusted to 6, and the solution was extracted with ethyl acetate (30 ml×3). The combined extracts were washed with 1N HCl. A precipitate formed and was filtered and dried to provide 0.41 g (29%) of 4-fluoro-3-(isoquinolin-4-yl)methoxy-benzoic acid hydrochloride, O-1a, as a solid. $^1$H NMR (300 MHz, DMSO-d$_6$) δ9.84 (s, 1H), 8.79 (s, 1H), 8.54 (d, J=8.1 Hz, 1H), 8.44 (d, J—8.36 Hz, 1H), 8.21 (m, 1H), 8.02 (m, 2H), 7.65 (m, 1H), 7.40 (dd, J=11.00, 8.46 Hz, 1H), 5.865 (s, 2H).

(b) To an ice cooled solution of 0.45 g (1.85 mmol) of 6-(2,2,2-trifluoroacetylamino)-1,2,3,4-tetrahydroquinoline (Forbes, et al., *J. Med. Chem.*, 38, 2524 (1995)) in THF (20 ml) was added di-t-butyl-dicarbonate (0.89 g, 4.08 mmol). After refluxing for 24 h, the solvent was removed and the residue was purified on silica gel using a gradient of 0% to 2% ethyl acetate in dichloromethane as eluant to obtain 0.42 g (66%) of 1-(tert-butoxycarbonyl)-6-(2,2,2-trifluoroacetylamino)-1,2,3,4-tetrahydroquinoline, O-1b, as a solid: $^1$H NMR (300 MHz, CDCl$_3$) δ7.78 (br s, 1H), 7.71 (d, J=8.9 Hz, 1H), 7.43 (d, J=2.6 Hz, 1H), 7.19 (dd, J=8.9, 2.6 Hz, 1H), 3.70 (m, 2H), 2.77 (t, J=6.5 Hz, 2H), 1.90 (t, J=6.4 Hz, 2H); 1.52 (s, 9H).

c) To stirred solution of 0.41 g (1.19 mmol) of 1-(tert-butoxycarbonyl)-6-(2,2,2-trifluoroacetylamino)-1,2,3,4-tetrahydroquinoline, O-1b, in methanol (20 ml) was added K$_2$CO$_3$ (0.25 g, 1.79 mmol). After refluxing for 24 h, the methanol was removed, followed by addition of water and ethyl acetate. The layers were separated, and the aqueous layer was extracted with ethyl acetate. The combined extracts were washed with brine, dried over MgSO$_4$, and concentrated to leave 0.228 g (77%) of 6-amino-1-(tert-butoxycarbonyl)-1,2,3,4-tetrahydroquinoline, O-1c, as an oil: $^1$H NMR (300 MHz, CDCl$_3$) δ7.38 (d, J=8.5 Hz, 1H), 6.47 (dd, J=8.7, 2.7 Hz, 1H), 6.39 (m, 1H), 3.64 (m, 2H), 3.40 (brs, 1H), 2.65 (t, J=6.6 Hz, 2H), 1.86 (t, J=6.2 Hz, 2H), 1.50, (s, 9H).

(d) A solution of 0.35 g (1.17 mmol) of 4-fluoro-3-(isoquinolin4-yl)methoxy-benzoic acid hydrochloride, O-1a, in SOCl$_2$ (5 ml) was stirred and heated at 60° C. for 3 h. The thionyl chloride was removed under reduced pressure to provide crude acid chloride O-1d, which was dissolved in dichloromethane (15 ml) under argon. The solution was cooled to 0° C. followed by addition of 0.260 g (1.07 mmol) of 6-amino-1-(tert-butoxycarbonyl)-1,2,3,4-tetrahydroquinoline, O-1c, and diisopropylethylamine (0.3 g, 2.34 mmol). After stirring for 24 hrs, dichloromethane (15 ml) was added, and the solution was washed with sat. NaHCO$_3$, and dried over sodium sulfate and concentrated. The residue was purified on silica gel using a gradient of 0% to 5% ethyl acetate in dichloromethane as eluant to obtain 0.190 g (30%) of 4-fluoro-N-{1-(tert-butoxycarbonyl)-1,2,3,4-tetrahydroquinolin-6-yl}-3-(isoquinolin-4-ylmethoxy)-benzamide, O-1e.

(e) A solution of O-1e (0.185 g, 0.35 mmol) in 4N HCl in dioxane (5 ml) was stirred for 6 hrs at 0° C. The solvent was removed under reduced pressure to give 0.123 g (82%) of 4-Fluoro-N-(1,2,3,4-tetrahydroquinolin-6-yl)-3-(isoquinolin-4-yl-methoxy)-benzamide hydrochloride as a solid. This product was further purified on semi-preparative C18-reverse phase HPLC eluting with 5 to 95% acetonitrile/water containing 0.1% trifluoroacetic acid to provide 4-fluoro-N-(1,2,3,4-tetrahydroquinolin-6-yl)-3-(isoquinolin-4-yl-methoxy)-benzamide bistrifluoroacetic acid salt, O-1: $^1$H NMR (300 MHz, DMSO-d$_6$) δ10.59 (s, 1H), 9.81 (s, 1H), 8.83 (s, 1H), 8.52 (d, 1H, J=8.37 Hz) 8.45 (d, 1H, J=8.59 Hz), 8.24–8.17 (m, 2H), 8.01 (dd, 1H, J=7.35 Hz, J=7.6 Hz), 7.79–7.70 (m, 3H), 7.43 (dd, 1H, J=10.87 Hz, J=10.7 Hz), 7.25 (d, 1H, J=8.46 Hz), 5.93 (s, 2H), 3.73–3.64 (m, 1H), 3.52–3.45 (m, 1H), 3.37–3.35 (m, 1H), 2.87–2.83 (m, 2H), 2.02–1.94 (m, 2H). MS (ESI) m/z 428 [M]$^+$. Anal. calc'd for C$_{26}$H$_{22}$FN$_3$O$_2$.2 CF$_3$CO$_2$H.0.8 H$_2$O: C, 53.78; H, 3.85; N, 6.27. Found: C, 53.58; H, 4.00; N, 6.20.

Example O-2

N-(2,2-Difluoro-benzo[1,3]dioxol-4-yl)-3-(2-isoquinolin-4-yl-ethyl)-benzamide trifluoro-acetic acid salt

O-2

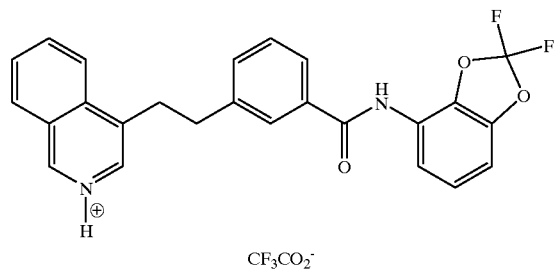

CF$_3$CO$_2$$^-$

Example O-2 was prepared in a similar manner to that described for O-1, except that 4-amino-(2,2-difluoro-benzo[1,3]dioxole was used in place of 6-amino-1-(tert-butoxycarbonyl)-1,2,3,4-tetrahydroquinoline, O-1c, and 3-{2-(isoquinolin-4-yl)ethyl}benzoic acid, S-1e (from example S-1 below), was used in place of 4-fluoro-3-(isoquinolin-4-yl)methoxy-benzoic acid, O-1a, in step (d), and the final deprotection step was not needed: $^1$H NMR (300 MHz, DMSO-d$_6$) δ10.70 (s, 1H), 9.88 (s, 1H), 8.63–8.51 (m, 3H), 8.26 (dd, 1H, J=8.3 Hz, J=8.5 Hz), 8.05 (m, 2H), 7.87 (m, 1H), 7.62–7.43 (m, 2H), 7.31–7.25 (m, 3H), 3.62–3.51 (m, 2H), 3.17–3.09 (m, 2H). MS (ESI) m/z 433 [M]$^+$. Anal. calc'd for C$_{25}$H$_{18}$ F$_2$N$_2$O$_3$.C$_2$F$_3$OOH: C, 59.35; H, 3.50; N, 5.31. Found: C, 59.35; H, 3.60; N, 5.12.

Example O-3

4-Fluoro-N-(2-methyl-1,2,3,4-tetrahydroquinolin-6-yl)-3-(isoquinolin-4-yl-methoxy)-benzamide bistrifluoroacetic acid salt

O-3

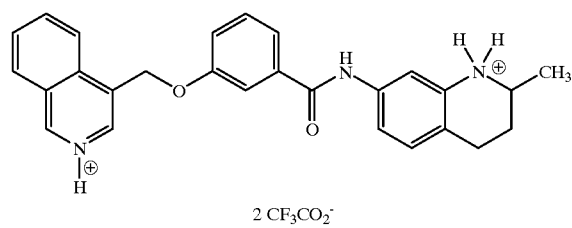

2 CF$_3$CO$_2$$^-$

Example O-3 was prepared in a similar manner to that described for O-1, except that 6-amino-1-(tert-butoxycarbonyl)-2-methyl-1,2,3,4-tetrahydroquinoline was used in place of 6-amino-1-(tert-butoxycarbonyl)-1,2,3,4-tetrahydroquinoline in step (d): $^1$H NMR (300 MHz, DMSO-d$_6$) δ10.15 (s, 1H), 9.54 (s, 1H), 8.73 (s, 1H),), 8.35–8.26 (m, 2H), 8.04–7.98 (m, 2H), 7.86 (dd, 1H, J=7.12

Hz, J=7.08 Hz), 7.67–7.62 (m, 1H), 7.52–7.49 (m, 2H), 7.41 (dd, 1H, J=10.96 Hz, J=10.99 Hz), 6.90 (d, 1H, J=8.37 Hz), 5.78 (s, 2H), 3.46 (m, 1H), 2.87–2.68 (m, 2H), 2.01–1.97 (m, 1H), 1.69–1.63 (m, 1H), 1.27 (d, 3H, J=6.41 Hz). MS (ESI) m/z 442 [M]$^+$. Anal. calc'd for $C_{27}H_{24}FN_3O_2 \cdot 2$ $CF_3CO_2H$: C, 55.61; H, 3.91; N, 6.28. Found: C, 55.51; H, 3.88; N, 6.22.

Example P-1

N'-{4-[3-(4-Isopropyl-3-methyl-phenylcarbamoyl)-phenoxy

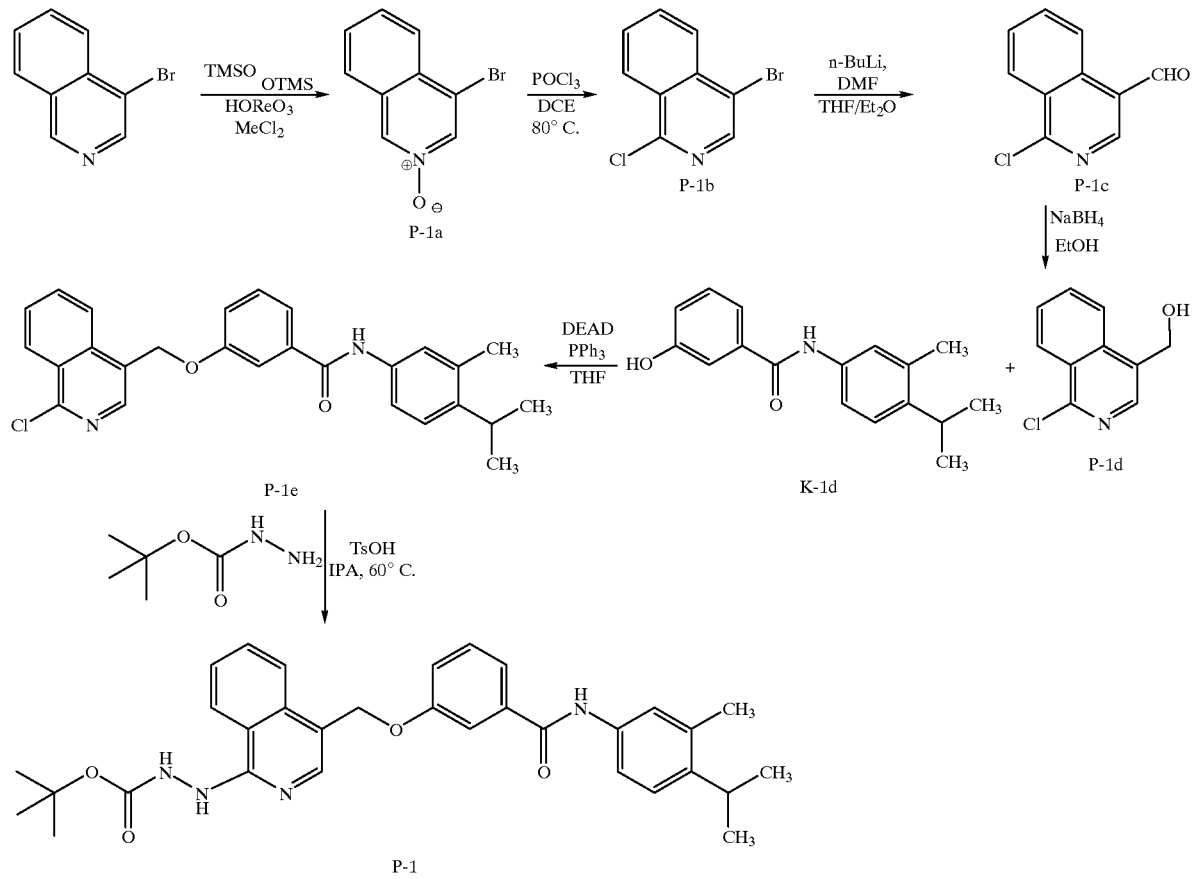

(a) A solution of 4-bromoisoquinoline (Aldrich, 7.7 g, 37.0 mmol, 1.0 eq) and perrhenic acid (70% in $H_2O$, 33 μL, 0.2 mmol, 0.5 mol %) in dichloromethane (20 mL) was treated with bis(trimethylsilyl)peroxide (Gelest, 9.9 g, 55.5 mmol, 1.5 eq). After 18 hours, the resultant yellow suspension was cooled to 0° C. and diluted with cyclohexane (30 mL). The solids were collected and washed with cold cyclohexane to give 4-bromoisoquinoline N-oxide, P-1a, as a yellow solid (7.1 g, 86%): HPLC $R_t$=7.7 min.; TLC $R_f$=0.5 (5% methanol/dichloromethane); $^1$H NMR (300 MHz, DMSO-d$_6$) δ8.97 (s, 1H), 8.58 (d, 1H, J=1.7 Hz), 7.97–7.87 (m, 2H), 7.74–7.67 (m, 2H); $^{13}$C NMR (75 MHz, DMSO-d$_6$) δ138.6, 135.5, 130.6, 130.2, 129.6, 127.4, 126.0, 125.7, 120.1; MS (ESI) m/z 224/226 [M+H]$^+$.

(b) A yellow suspension of 4-bromoisoquinoline N-oxide, P-1a, (6.9 g, 30.8 mmol. 1.0 eq) in 1,2-dichloroethane (60 mL) was treated with phosphorus oxychloride (Aldrich, 9.0 mL, 96.4 mmol, 1.8 eq) and warmed to 80° C. After 1.5 hours, the resultant green suspension was carefully poured into a cold solution of 50% saturated sodium bicarbonate (500 mL) and the aqueous layer was extracted with diethyl ether (3×300 mL). The combined organic extracts were washed with water (200 mL), brine (200 mL), dried over magnesium sulfate, and concentrated under reduced pressure to give a tan solid (6.8 g). The crude product was dissolved in a minimal amount of dichloromethane and purified by flash chromatography over silica gel using 5% ether/cyclohexane to give 4-bromo-1-chloro-isoquinoline, P-1b, as a white solid (5.7 g, 77%): HPLC $R_t$=15.4 min.; TLC $R_f$=0.4 (5% ether/cyclohexane); $^1$H NMR (300 MHz, DMSO-d$_6$) δ8.68 (s, 1H), 8.42 (d, 1H, J=8.4 Hz), 8.26 (d, 1H, J=8.3 Hz), 8.15 (t, 1H, J=7.6 Hz), 8.02 (t, 1H, J=7.6 Hz); $^{13}$C NMR (75 MHz, DMSO-d$_6$) δ150.4, 143.0, 135.8, 133.8, 130.8, 127.3, 126.8, 126.5, 119.0; MS (ESI) m/z 242/244 [M+H]$^+$.

(c) 1-Chloro-isoquinoline-4-carbaldehyde, P-1c, which was obtained as a white solid in a 95% yield, was prepared in a similar manner to that described for isoquinoline-4-carbaldehyde, K-1a, in example K-1, except that 4-bromo-1-chloro-isoquinoline, -1b, was used in place of 4-bromoisoquinoline: HPLC $R_t$=11.9 min.; TLC $R_f$=0.6 (20% ethyl acetate/cyclohexane); $^1$H NMR (300 MHz, DMSO-d$_6$) δ10.40 (s, 1H), 9.15 (d, 1H, J=8.5 Hz), 8.93 (s, 1H), 8.46 (d, 1H, J=8.5 Hz), 8.12 (t, 1H, J=7.1 Hz), 8.00 (t, 1H, J=7.8 Hz); $^{13}$C NMR (75 MHz, DMSO-d$_6$) δ193.6, 156.5, 151.4, 134.8, 133.9, 130.4, 126.9, 126.0, 124.9, 124.6; MS (ESI) m/z 192 [M+H]$^+$.

(d) (1-Chloro-isoquinolin-4-yl)-methanol, P-1d, which was obtained as a white solid in a 96% yield, was prepared in a similar manner to that described for isoquinolin-4-yl-methanol, K-1b, except that 1-chloro-isoquinoline-4-carbaldehyde, P-1c, was used in place isoquinoline-4-carbaldehyde, K-1a: HPLC $R_t$=9.0 min.; TLC $R_f$=0.2 (2% methanol/dichloromethane); $^1$H NMR (300 MHz, DMSO-$d_6$) δ8.52 (d, 1H, J=8.5 Hz), 8.50 (s, 1H), 8.42 (d, 1H, J=8.3 Hz), 8.15 (t, 1H, J=7.6 Hz), 8.05 (t, 1H, J=7.6 Hz), 5.71 (br s, 1H), 5.15 (s, 2H); $^{13}$C NMR (75 MHz, DMSO-$d_6$) δ150.1, 140.0, 136.0, 131.9, 131.8, 129.3, 126.3, 125.8, 124.6, 59.0; MS (ESI) m/z 194 [M+H]$^+$.

(e) 3-(1-Chloro-isoquinolin-4-ylmethoxy)-N-(4-isopropyl-3-methyl-phenyl)-benzamide, P-1e, which was obtained as a white solid in a 64% yield, was prepared in a similar manner to that described for 3-(6-chloropyridin-3-yl)methoxy-N-(4-isopropyl-3-methyl-phenyl)-benzamide, L-1b, except that (1-chloro-isoquinolin-4-yl)-methanol, P-1d, was used in place of (6-chloropyridin-3-yl)-methanol, L-1a: HPLC $R_t$=18.0 min.; TLC $R_f$=0.5 (5% ethyl acetate/45% dichloromethane/cyclohexane); $^1$H NMR (300 MHz, DMSO-$d_6$) δ10.06 (s, 1H), 8.52 (s, 1H), 8.38 (d, 1H, J=8.5 Hz), 8.25 (d, 1H, J=8.3 Hz), 8.01 (t, 1H, J=7.6 Hz), 7.90 (t, 1H, J=8.2 Hz), 7.68 (s, 1H), 7.61–7.46 (m, 4H), 7.35 (d, 1H, J=7.9 Hz), 7.20 (d, 1H, J=8.4 Hz), 5.65 (s, 2H), 3.12–3.05 (m, 1H), 2.29 (s, 3H), 1.17 (d, 6H, J=6.9 Hz); $^{13}$C NMR (75 MHz, DMSO-$d_6$) δ165.1, 158.4, 151.5, 142.2, 141.9, 136.8, 136.7, 136.3, 135.0, 132.6, 130.0, 129.8, 127.1, 126.6, 126.1, 125.0, 124.7, 122.5, 120.8, 118.9, 118.3, 114.3, 65.6, 28.7, 27.2, 23.5, 19.4; MS (ESI) m/z 443 [M–H]$^-$.

(f) A mixture of 3-(1-chloro-isoquinolin-4-ylmethoxy)-N-(4-isopropyl-3-methyl-phenyl)-benzamide, P-1e, (50 mg, 0.11 mmol, 1.0 eq), tert-butyl carbazate (75 mg, 0.56 mmol, 5.0 eq) and para-toluenesulfonic acid monohydrate (31 mg, 0.16 mmol, 1.5 eq) in isopropyl alcohol (1.5 mL) was warmed to 60° C. After 4.5 h the resultant white suspension was poured into 5% sodium bicarbonate (25 mL) and extracted with ethyl acetate (3×25 mL). The combined organic extracts were washed sequentially with water (25 mL), sodium citrate (0.5 M, pH 4.5, 25 mL), water (25 mL) and brine (25 mL). The organic extracts were dried over magnesium sulfate, filtered, and concentrated under reduced pressure to give a clear oil (90 mg). The crude product was purified by radial chromatography over silica gel using 2–3% methanol/dichloromethane to give, from methyl tert-butyl ether, N'-{4-[3-(4-isopropyl-3-methyl-phenylcarbamoyl)-phenoxymethyl]-isoquinolin-1-yl}-hydrazinecarboxylic acid tert-butyl ester, P-1, as a white solid (55 mg, 93%): mp 125–129° C.; HPLC $R_t$=16.5 min.; TLC $R_f$=0.5 (4% methanol/dichloromethane); $^1$H NMR (300 MHz, DMSO-$d_6$) δ10.04 (s, 1H), 9.35 (s, 1H), 8.78 (s, 1H), 8.33 (d, 1H, J=8.3 Hz), 8.10 (s, 1H), 7.96 (d, 1H, J=8.3 Hz), 7.76 (t, 1H, J=7.6 Hz), 7.64–7.27 (m, 7H), 7.20 (d, 1H, J=8.4 Hz), 5.41 (s, 2H), 3.09–3.05 (m, 1H), 2.29 (s, 3H), 1.40 (s, 9H), 1.17 (d, 6H, J=6.8 Hz); $^{13}$C NMR (75 MHz, DMSO-$d_6$) δ165.8, 159.4, 157.2, 155.6, 143.8, 141.5, 137.1, 136.3, 136.1, 135.6, 131.2, 130.2, 127.1, 125.7, 124.2, 122.4, 122.3, 119.7, 119.0, 118.6, 118.5, 117.8, 113.9, 81.9, 67.3, 29.3, 28.6, 27.3, 23.6, 19.8; MS (ESI) m/z 541 [M+H]$^+$. Anal. calc'd for $C_{32}H_{36}N_4O_4 \cdot 0.25$ hexane: C, 71.57; H, 7.08; N, 9.97. Found: C, 71.38; H, 7.18; N, 9.66.

Example Q-1

N-(4-Isopropyl-3-methyl-phenyl)-3-{1-[N'-(3-methoxy-benzylidene)-hydrazino]-isoquinolin-4-ylmethoxy}-benzamide

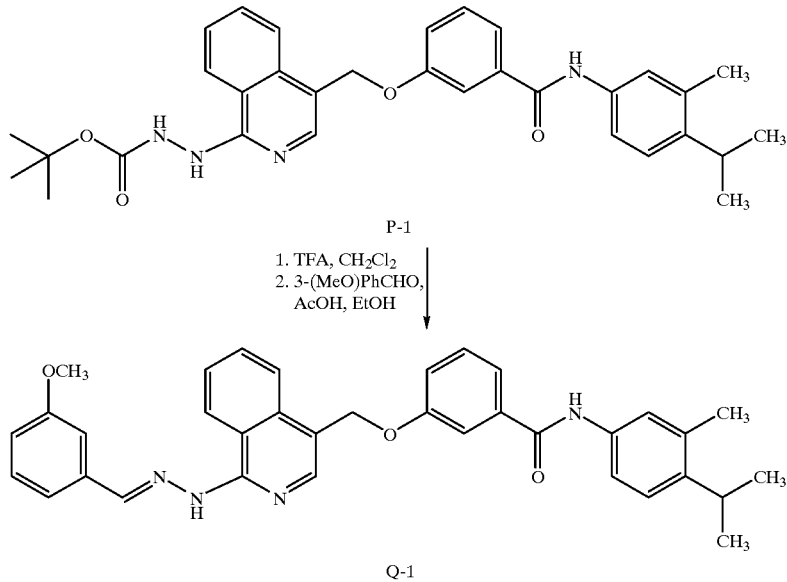

A solution of N'-{4-[3-(4-isopropyl-3-methyl-phenylcarbamoyl)-phenoxymethyl]-isoquinolin-1-yl}-hydrazinecarboxylic acid tert-butyl ester, P-1, (94 mg, 0.21 mmol, 1.0 eq) in dichloromethane (2.0 mL) was treated with trifluoroacetic acid (0.5 mL). After 1.5 hours, the resultant yellow solution was carefully poured into 5% sodium bicarbonate (50 mL) and extracted with ethyl acetate (3×25 mL). The combined organic extracts were washed with brine (25 mL), dried over magnesium sulfate, and concentrated under reduced pressure to give a yellow solid (97 mg). The crude product was dissolved in ethyl alcohol (4 mL) and treated with acetic acid (3 drops), and 3-methoxybenzaldehyde (Aldrich, 40 μL, 0.32 mmol, 1.5 eq). After 18 hours, the resultant yellow suspension was poured into 5% sodium bicarbonate (25 mL). The aqueous layer was diluted with brine (15 mL) and extracted with ethyl acetate (3×25 mL). The combined organic extracts were washed with brine (50 mL), dried over magnesium sulfate, and concentrated under reduced pressure to give a yellow residue (128 mg). The crude product was purified by radial chromatography over silica gel using 1–2% methanol/dichloromethane to give N-(4-isopropyl-3-methylphenyl)-3-{1-[N'-(3-methoxybenzylidene)hydrazino]isoquinolin-4-yl}methoxy-benzamide, Q-1, as a yellow solid (25 mg, 21%): mp 125–129° C.; HPLC $R_t$=18.3 min.; TLC $R_f$=0.5 (4% methanol/dichloromethane); $^1$H NMR (300 MHz, DMSO-$d_6$) δ10.94 (s, 1H), 8.43 (br s, 2H), 7.65–7.22 (m, 13H), 7.20 (d, 1H, J=8.4 Hz), 6.99 (d, 1H, J=8.2 Hz), 5.24 (s, 2H), 3.84 (s, 3H), 3.10–3.05 (m, 1H), 2.29 (s, 3H), 1.17 (d, 6H, J=6.8 Hz); MS (ESI) m/z 559 [M+H]$^+$. Anal. calc'd for $C_{35}H_{34}N_4O_3$.0.5 hexane: C, 75.84; H, 6.87; N, 9.31. Found: C, 75.81; H, 6.89; N, 9.09.

Example R-1

N-(3,5-Diallyl-4-methyl-phenyl)-3-(isoquinolin-4-ylmethoxy)-benzamide

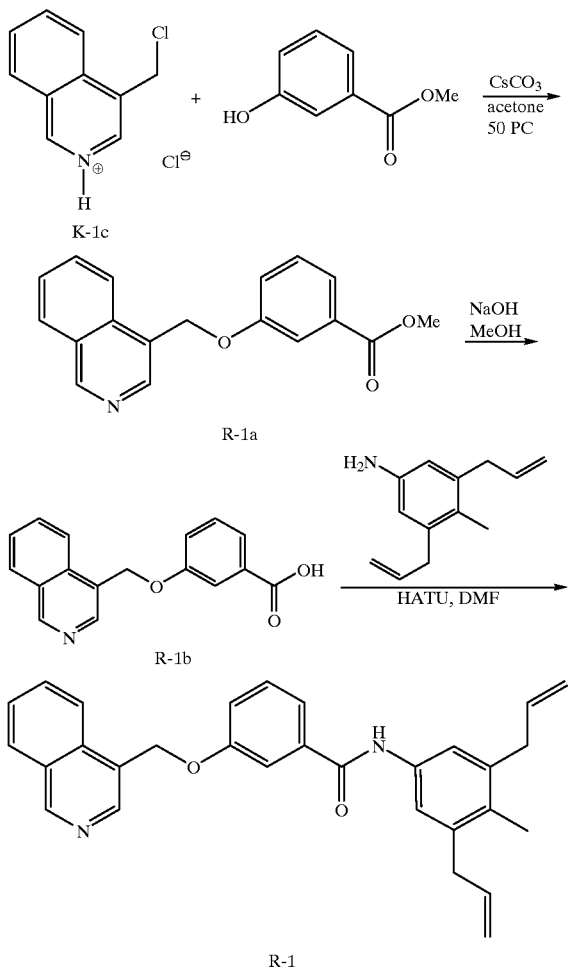

(a) To a solution of 1.0 g (4.7 mmol) of 4-(chloromethyl)isoquinoline hydrochloride, K-1c, in DMF (10 mL) and acetone (25 mL) was added methyl 3-hydroxybenzoate (800 mg, 5.3 mmol) and cesium carbonate (3.8 g, 11.7 mmol). After refluxing for 20 h the solution was cooled, concentrated and diluted with dichloromethane. The solution was washed with sodium bicarbonate and brine. After drying over the sodium sulfate the product was precipitated from diethyl ether/hexanes yielding 1.15 grams (84% yield) of methyl 3-(isoquinolin-4-yl)methoxy-benzoate, R-1a, as a white solid: $^1$H NMR (300 MHz, DMSO-$d_6$) δ9.35 (s, 1H), 8.67 (s, 1H), 8.20 (d, J=8.0 Hz, 1H), 8.15 (d, J=8.6 Hz, 1H), 7.88 (ddd, J=7.0, 7.0, 1.3 Hz, 1H), 7.75 (ddd, J=7.5, 7.5, 1.0 Hz, 1H), 7.65 (m, 1H), 7.60 (m, 1H), 7.49 (dd, J=8.1 Hz, 1H), 7.41 (m, 1H), 5.64 (s, 2H), 3.86 (s, 3H).

(b) To methyl 3-(isoquinolin-4-yl)methoxy-benzoate, R-1a, (2.24 g, 7.64 mmol) in 95% EtOH (50 mL) was added 1 N NaOH (8 ml). After stirring for two hours at 70° C. the solution was cooled and concentrated to about 10 mL. With ice cooling the solution was acidified with 1N HCl. The resulting white precipitate was filtered yielding 1.3 g of 3-(isoquinolin-4-yl)methoxy-benzoic acid hydrochloride, R-1b, as a white solid. Extraction of the mother liquors with dichloromethane three times resulted in 480 mg more product. (74% overall yield). $^1$H NMR (300 MHz, DMSO-$d_6$) δ9.77 (s, 1H), 8.81 (s, 1H), 8.50 (d, J=8.2 Hz, 1H), 8.39 (d, J=8.5 Hz, 1H), 8.18 (dd, J=8.4, 8.4 Hz, 1H), 7.99 (dd, J=7.5, 7.5 Hz, 1H), 7.69 (m, 1H), 7.61 (m, 1H), 7.48 (dd, J=8.1, 8.1 Hz, 1H), 7.41 (m, 1H), 5.76 (s, 2H).

(c) To a solution of 72 mg (0.38 mmol) 3,5-diallyl-4-methylaniline, prepared as described in steps (d) through (f) below, in DMF (6 mL) was added 120 mg (0.380 mmol) of 3-(isoquinolin-4-ylmethoxy)-benzoic acid hydrochloride, R-1b, 160 μL (0.92 mmol) of diisopropylethylamine and PyBop (240 mg, 0.46 mmol). After stirring for 2.5 h, DMAP (3 mg) was added. At five hours all but 3 mL of solvent was removed, and the remaining solution was diluted with dichloromethane (40 ml) and washed with water, and brine. After drying over sodium sulfate, the solution was concentrated and chromatographed with silica gel eluting with 20 to 40% ethyl acetate/dichloromethane yielding 130 mg (75% yield) of N-(3,5-diallyl-4-methyl-phenyl)-3-(isoquinolin-4-yl)methoxy-benzamide, R-1, as a white foam. $^1$H NMR (300 MHz, CDCl$_3$) δ9.29 (s, 1H), 8.63 (s, 1H),), 8.06 (m, 2H), 7.79 (m, 1H), 7.62–7.82 (m, 3H), 7.44 (m, 2H), 7.35 (s, 2H), 7.23 (m, 1H), 5.97 (m, 2H), 5.53 (s, 2H), 5.03 (m, 4H), 3.41 (d, 4H, J=6.2 Hz), 2.18 (s, 3H). MS (FAB) m/z 449 [M+H]$^+$. Anal. calcd for $C_{30}H_{28}N_2O_2$.0.35 $H_2O$: C, 79.22; H, 6.36; N, 6.16. Found: C, 79.14; H, 6.24; N, 6.43.

(d) To 3,5-dibromoaniline (2.0 g, 6.5 mmol) in CH$_2$Cl$_2$ (40 mL) was added diisopropylethylamine (2.27 mL, 13 mmol). The solution was cooled to 0° C. followed by addition of trifluoroacetic anhydride (1.37 mL, 9.8 mmol) in CH$_2$Cl$_2$ (5 mL) over three minutes. After addition the cooling bath was removed, and DMAP (approximately 3 mgs) was added. At one hour the solution was diluted with CH$_2$Cl$_2$ (40 mL) and washed with water and brine and dried over sodium sulfate. The solution was concentrated and chromatographed though a short plug of silica gel eluting with 30% ethyl acetate/hexanes which resulted in 2.68 g, (quantitative yield), of N-(3,5-dibromo-4-methyl-phenyl)-2,2,2-trifluoro-acetamide an off-white solid. $^1$H NMR (300 MHz, CDCl$_3$) δ7.80 (s, 3 H, including NH), 2.56 (s, 3H).

(e) To dry, degassed toluene (25 mL) was added N-(3,5-dibromo-4-methyl-phenyl)-2,2,2-trifluoroacetamide (1.0 g, 2.78 mmol), allyltributyltin (2.6 mL, 8.4 mmol) and Pd(PPh$_3$)$_4$ (200 mgs, 0.160 mmol). After refluxing for 14 hours, most of the solvent was removed and the solution was diluted with diethyl ether. Approximately 100 mL of water was added followed by DBU (1.4 mL, 0.92 mmol) which resulted in a gummy precipitate. This heterogeneous solution was filtered through a short plug of silica gel eluting with diethyl ether. After concentration the residue was chromotographed twice with 10 to 20% ethyl acetate/hexanes resulting in 315 mg (40% yield) of N-(3,5-diallyl-4-methyl-phenyl)-2,2,2-trifluoroacetamide as a white solid. $^1$H NMR (300 MHz, CDCl$_3$) δ7.72 (br s, 1H), 7.25 (s, 2H), 5.94 (m, 2H), 5.09 (dd, J=10.2, 1.5 Hz, 2H), 4.98 (dd, J=15.4, 1.8 Hz), 3.40 (d, J=6.2 Hz), 2.18 (s, 3H).

(f) To N-(3,5-diallyl-4-methyl-phenyl)-2,2,2-trifluoroacetamide (255 mg, 0.90 mmol) in 95% ethanol (10 mL) was added 1N NaOH$_{(aq)}$ (2 mL). After heating to 80° C. for 16 h, the solution was cooled to room temperature. After concentration the residue was diluted with ethyl acetate (30 mL) and washed with water and brine and dried over sodium sulfate. Removal of the solvent led to 160 mg (95% yield) of 3,5-diallyl-4-methylaniline as an orange oil. $^1$H NMR (300 MHz, CDCl$_3$) δ6.42 (s, 2H), 5.91 (m, 2H), 5.04 (dd, J=10.6, 1.7 Hz, 2H), 4.98 (dd, J=17.2. 1.8 Hz), 3.31 (d, J=6.3 Hz), 2.08 (s, 3H).

Example R-2

N-(3,5-Dibromo-4-methyl-phenyl)-3-(isoquinolin-4-ylmethoxy)-benzamide

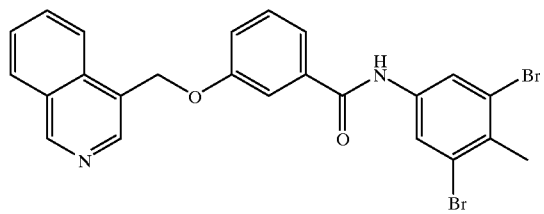

R-2

Example R-2 was prepared in a similar manner to that described for R-1, except that 3,5-dibromo-4-methylaniline was used in place of 3,5-diallyl-4-bromoaniline in step (c): $^1$H NMR (300 MHz, DMSO-d$_6$) δ10.36 (s, 1H), 9.36 (s, 1H), 8.69 (s, 1H), 8.20 (m, 1H), 8.14 (s, 2H), 7.89 (m, 1H), 7.76 (m, 1H), 7.68 (m, 1H), 7.58 (m, 1H), 7.51 (m, 1H), 7.38 (m, 1H), 5.65 (s, 2H), 2.48 (s, 3H). Anal. calc'd for C$_{24}$H$_{18}$N$_2$O$_2$Br$_2$.0.4 H$_2$O: C, 54.04; H, 3.55: N, 5.25. Found: C, 53.96; H, 3.50; N, 5.08.

Example R-3

3-(Isoquinolin-4-ylmethoxy)-N-(5,5,8,8-tetramethyl-5,6,7,8-tetrahydronaphthalen-2-yl)-benzamide

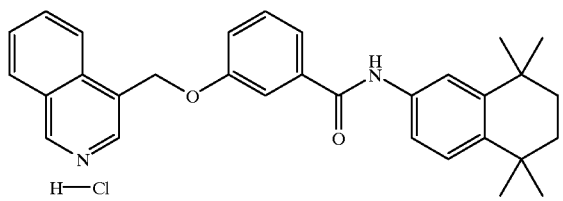

R-3

Example R-3 was prepared in a similar manner to that described for R-1, except that 2-amino-5,5,8,8-tetramethyl-5,6,7,8-tetrahydro-naphthalene was used in place of 3,5-diallyl-4-bromoaniline in step (c): $^1$H NMR (300 MHz, DMSO-d$_6$) δ10.12 (s, 1H), 9.77 (s, 1H), 8.23 (s, 1H), 8.49 (d, 1H, J=8.2 Hz), 8.39 (d, 1H, J=8.4 Hz), 8.18 (dd, 1H, J=7.8 Hz, J=7.7 Hz), 7.99 (dd, 1H, J=7.4 Hz, J=7.4 Hz), 7.76 (s, 1H), 7.70 (d, 1H, J=2.2 Hz), 7.63 (d, 1H, J=7.7 Hz), 7.58 (dd, 1H, J=8.6 Hz, J=2.2 Hz), 7.51 (dd, 1H, J=7.7 Hz, J=7.7 Hz), 7.38 (dd, 1H, J=8.2 Hz, J=1.9 Hz), 7.28, (d, 1H, 8.6 Hz), 5.79 (s, 2H), 1.64 (s, 4H), 1.25 (s, 6H), 1.24 (s, 6H). MS (ESI) m/z 465 [M+H]$^+$. Anal. calc'd for C$_{31}$H$_{32}$N$_2$O$_2$.1.0 HCl.0.8 H$_2$O: C, 72.23; H, 6.77; N, 5.43. Found: C, 72.07; H, 6.63; N, 5.43. The intermediate 2-amino-5,5,8,8-tetramethyl-5,6,7,8-tetrahydro-naphthalene was prepared by reduction of 2-nitro-5,5,8,8-tetramethyl-5,6,7,8-tetrahydro-naphthalene (Kagechika, H. et al., J. Med. Chem., 31, 2182–2192 (1998)) in a similar manner to that described in step (b) of Example J-1.

Example R-4

3-(Isoquinolin-4-ylmethoxy)-N-(3-trifluoromethoxy-phenyl)-benzamide

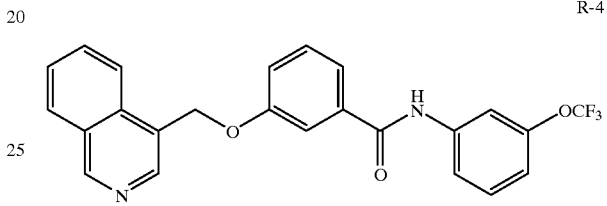

R-4

Example R-4 was prepared in a similar manner to that described for R-1, except that 3-(trifluoromethoxy)aniline was used in place of 3,5-diallyl-4-bromoaniline in step (c): $^1$H NMR (300 MHz, CDCl$_3$) δ9.22 (s, 1H), 8.55 (s, 1H),) 7.99 (m, 2H), 7.73 (m, 2H), 7.65 (m, 1H), 7.60 (m, 1H), 7.54 (m, 1H), 7.47 (m, 1H), 7.27–7.40 (m, 2H), 7.18 (m, 1H), 6.99 (m, 1H), 5.41 (s, 2H). MS (ESI) m/z 439 [M+H]$^+$. Anal. calc'd for C$_{24}$H$_{17}$F$_3$N$_2$O$_3$: C, 65.75; H, 3.91; N, 6.39. Found: C, 65.58; H, 4.02; N, 6.37.

Example R-5

N-(2,4-Dimethylquinolin-6-yl)-3-(isoquinolin-4-ylmethoxy)-benzamide

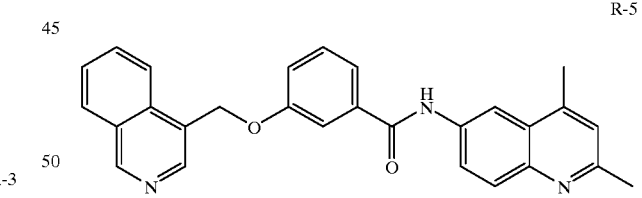

R-5

Example R-5 was prepared in a similar manner to that described for R-1, except that 6-amino-2,4-dimethylquinoline was used in place of 3,5-diallyl-4-bromoaniline in step (c): $^1$H NMR (300 MHz, CDCl$_3$) δ10.50 (s, 1H), 9.36 (s, 1H), 8.70 (s, 1H), 8.56 (d, 1H, J=2.2 Hz), 8.20 (m, 2H), 8.06 (m, 1H), 7.9 (m, 2H), 7.76 (m, 2H), 7.66 (m, 1H), 7.53 (dd, 1H, J=7.8, 7.8 Hz), 7.39 (m, 1H), 7.27 (s, 1H), 5.67 (s, 2H), 2.61 (s, 3H), 2.58 (s, 3H). MS (FAB) m/z 435 [M+H]$^+$. Anal. calcd for C$_{27}$H$_{22}$N$_4$O$_2$.0.1 H$_2$O: C, 74.33; H, 5.13; N, 12.84. Found: C, 79.13; H, 4.97; N, 12.74. The intermediate 6-amino-2,4-dimethylquinoline was prepared by reduction of 6-nitro-2,4-dimethylquinoline (Price, C. et al., J. Org. Chem., 12, 203 (1947)) in a similar manner to that described in step (b) of Example J-1.

Example R-6

3-(Isoquinolin-4-ylmethoxy)-benzoic acid N'-(4-trifluoromethyl-phenyl)hydrazide

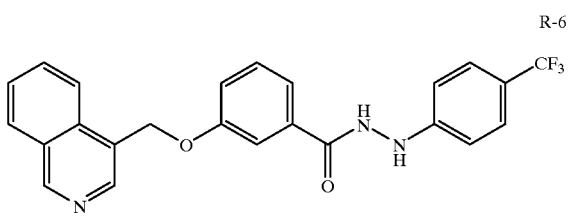

R-6

Example R-6 was prepared in a similar manner to that described for R-1, except that 4-trifluoromethylphenyl-hydrazine was used in place of 3,5-diallyl-4-bromoaniline in step (c): $^1$H NMR (300 MHz, CDCl$_3$) δ9.28 (s, 1H), 8.62 (s, 1H),), 8.05 (m, 3H), 7.79(dd, 1H, J=8.36 Hz, J=8.27 Hz), 7.67 (dd, 1H, J=7.98 Hz, J=8.14 Hz), 7.59 (m, 1H), 7.51–7.42 (m, 4H), 7.27 (m, 1H), 6.98 (s, 1H), 6.95 (s, 1H), 6.47 (br, 1H), 5.51 (s, 2H). MS (ESI) m/z 438 [M+H]$^+$. Anal. calc'd for C$_{24}$H$_{18}$F$_3$N$_3$O$_2$: C, 65.90; H, 4.15; N, 9.61. Found: C, 65.75; H, 4.20; N, 9.51.

Example R-7

N-Benzyloxy-3-(isoquinolin-4-ylmethoxy)-benzamide

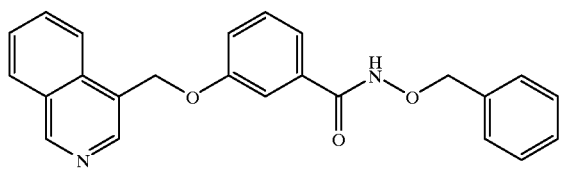

R-7

Example R-2 was prepared in a similar manner to that described for R-1, except that O-benzylhydroxylamine was used in place of 3,5-diallyl-4-bromoaniline in step (c): $^1$H NMR (300 MHz, CDCl$_3$) δ9.26 (s, 1H), 8.59 (s, 1H),), 8.57 (s, 1H), 8.05 (m, 2H), 7.78 (dd, 1H, J=8.23 Hz, J=8.44 Hz), 7.67 (dd, 1H, J=7.89 Hz, J=8.16 Hz), 7.47–7.43 (m, 3H), 7.42–7.32 (m, 3H), 7.24–7.16 (m, 3H), 5.47 (s, 2H), 5.05 (s, 2H). MS (ESI) m/z 385 [M+H]$^+$. Anal. calc'd for C$_{24}$H$_{20}$N$_2$O$_3$: C, 74.98; H, 5.24; N, 7.29. Found: C, 74.85; H, 5.31; N, 7.18.

Example R-8

3-(Isoquinolin-4-ylmethoxy)-benzoic acid N'-phenyl-hydrazide

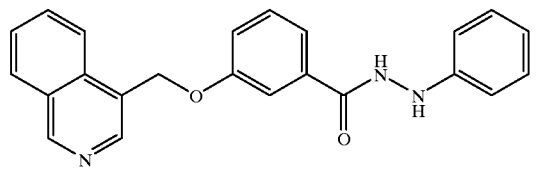

R-8

Example R-2 was prepared in a similar manner to that described for R-1, except that phenyl-hydrazine was used in place of 3,5-diallyl-4-bromoaniline in step (c): $^1$H NMR (300 MHz, CDCl$_3$) δ9.28 (s, 1H), 8.62 (s, 1H),), 8.06 (s, 1H), 8.04 (s, 1H), 7.94 (m, 1H), 7.78 (m, 1H), 7.67 (m, 1H), 7.59 (m, 1H), 7.44 (m, 2H), 7.25 (m, 3H), 6.93 (m, 3H), 6.38 (m, 1H), 5.50 (s, 2H). MS (ESI) m/z 370 [M+H]$^+$. Anal. calcd for C$_{23}$H$_{19}$N$_3$O$_2$.0.35 H$_2$O: C, 73.52; H, 5.29; N, 11.18. Found: C, 73.72; H, 5.36; N, 10.90.

Example R-9

N-(5,7-dimethyl[1,8]naphthydrin-2-yl)-3-(isoquinolin-4-ylmethoxy)-benzamide

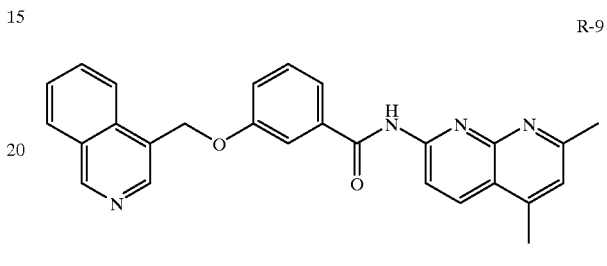

R-9

Example R-9 was prepared in a similar manner to that described for R-1, except that 2-amino-5,7-dimethyl[1,8]naphthydrine was used in place of 3,5-diallyl-4-bromoaniline in step (c): $^1$H NMR (300 MHz, CDCl$_3$) δ9.30 (s, 1H), 8.96 (s, 1H), 8.64 (s, 2H), 8.40 (d, 1H, J=9.0 Hz), 8.08 (m, 2H), 7.81 (m, 1H), 7.73 (m, 1H), 7.69 (m, 1H), 7.62 (m, 1H), 7.48 (dd, 1H, J=7.8, 7.8 Hz), 7.29 (m, 1H), 7.15 (d, J=0.7 Hz), 5.55 (s, 2H), 2.72 (s, 3H), 2.69 (d, 3H, J=0.7 Hz). MS (FAB) m/z 435 [M+H]$^+$. Anal. calc'd for C$_{27}$H$_{22}$N$_4$O$_2$.0.1 H$_2$O: C, 74.33; H, 5.13; N, 12.84. Found: C, 79.13; H, 4.97; N, 12.74

Example R-10

3-(Isoquinolin-4-ylmethoxy)-N-(1,1,3,3-tetramethyl-1,3-dihydroisobenzofuran-5-yl)-benzamide

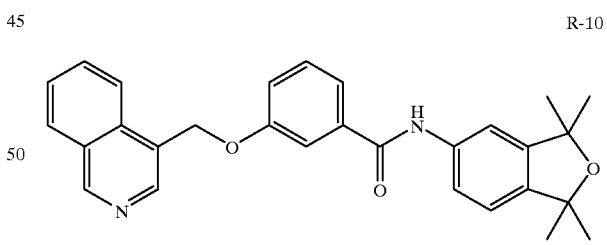

R-10

Example R-10 was prepared in a similar manner to that described for R-1, except that 5-amino-1,1,3,3-tetramethyl-1,3-dihydroisobenzofuran was used in place of 3,5-diallyl-4-bromoaniline in step (c): δ$^1$H NMR (300 MHz, CDCl$_3$ 9.29 (s, 1H), 8.63 (s, 1H), 8.06 (m, 2H), 7.90 (m, 1H), 7.79 (dd, 1H, J=8.38 Hz, J=7.72 Hz ), 7.68 (dd, 1H, J=8.05 Hz, J=8.08 Hz), 7.62 (m, 1H), 7.55 (d, 1H, J=1.8 Hz), 7.45 (m, 2H), 7.40 (m, 1H), 7.22 (m, 1H), 7.08 (d, 1H, J=8.12 Hz), 5.52 (s, 2H), 1.54 (s, 6H), 1.51 (s, 6H). MS (ESI) m/z 453 [M+H]$^+$. Anal. calcd for C$_{29}$H$_{28}$N$_2$O$_3$×0.4 H$_2$O: C, 75.76; H, 6.31; N, 6.09. Found: C, 75.72; H, 6.31; N, 5.94.

Example R-11

N-(3,5-Dichloro-4-pyrrolidin-1-yl-phenyl)-4-fluoro-3-(pyridin-3-ylmethoxy)-benzamide

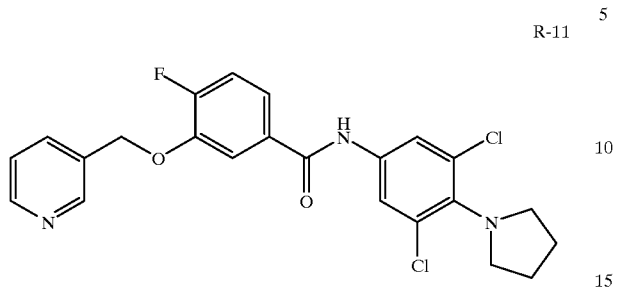

R-11

Example R-11 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-picolyl chloride hydrochloride was used in place of 4-(chloromethyl)isoquinoline hydrochloride, K-1c, in step (a), and 1-(4-amino-2,6-dichlorophenyl)pyrrolidine was used in place of 3,5-diallyl-4-bromoaniline in step (c): mp 163–167° C.; HPLC $R_t$=17.7 min.; TLC $R_f$=0.3 (40% ethyl acetate/cyclohexane); $^1$H NMR (300 MHz, DMSO-$d_6$) δ10.40 (s, 1H), 8.72 (s, 1H), 8.60 (d, 1H, J=3.9 Hz), 7.94–7.84 (m, 4H), 7.66–7.62 (m, 1H), 7.49–7.42 (m, 2H), 5.33 (s, 2H), 3.24–3.20 (m, 4H), 1.98–1.96 (m, 4H); MS (ESI) m/z 460 [M+H]$^+$. Anal. calc'd for $C_{23}H_{20}Cl_2FN_3O_2$: C, 60.01; H, 4.38; N, 9.13. Found: C, 60.08; H, 4.49; N, 9.02.

Example R-12

4-Fluoro-N-(4-morpholin-4-yl-3-trifluoromethylphenyl)-3-(pyridin-3-ylmethoxy)-benzamide

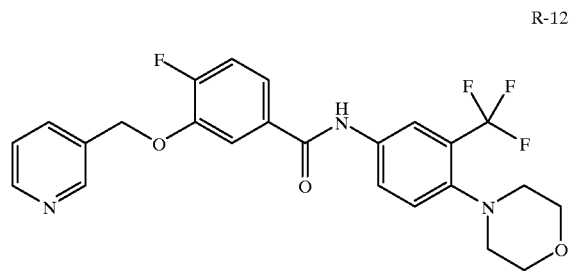

R-12

Example R-12 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-picolyl chloride hydrochloride was used in place of 4-(chloromethyl)isoquinoline hydrochloride, K-1c, in step (a), and 1-(4-amino-2-trifluoromethylphenyl)morpholine was used in place of 3,5-diallyl-4-bromoaniline in step (c): mp 160–161° C.; HPLC $R_t$=14.4 min.; TLC $R_f$=0.2 (50% ethyl acetate/cyclohexane); $^1$H NMR (300 MHz, DMSO-$d_6$) δ10.46 (s, 1H), 8.72 (s, 1H), 8.60 (d, 1H, J=4.1 Hz), 8.14 (d, 1H, J=2.4 Hz), 8.06 (dd, 1H, J=8.8, 2.4 Hz), 7.94–7.86 (m, 2H), 7.69–7.61 (m, 2H), 7.50–7.41 (m, 2H), 5.34 (s, 2H), 3.71 (t, 4H, J=4.4 Hz), 2.85 (t, 4H, J=4.4 Hz); MS (ESI) m/z 476 [M+H]$^+$. Anal. calc'd for $C_{24}H_{21}F_4N_3O_3$: C, 60.63; H, 4.45; N, 8.84. Found: C, 60.84; H, 4.57; N, 8.81.

Example R-13

4-Fluoro-N-[4-(piperazin-1-yl)-3-trifluoromethylphenyl]-3-(pyridin-3-yl)methoxybenzamide

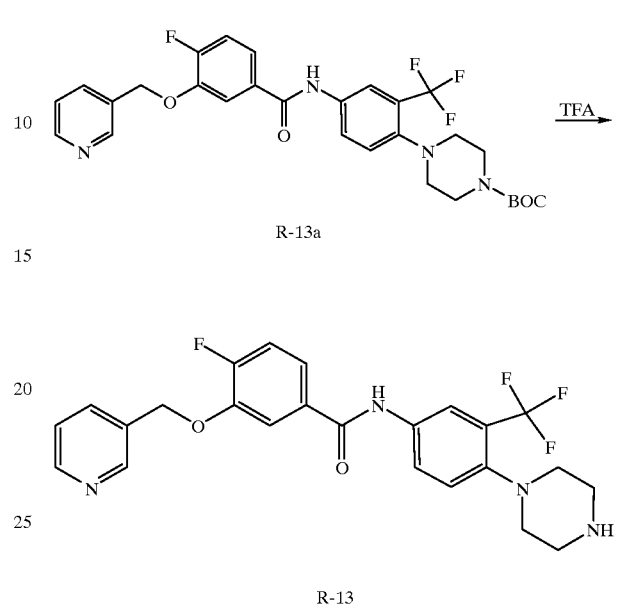

R-13a

R-13

(a) 4-Fluoro-N-[4-{4-(t-butoxycarbonyl)piperazin-1-yl}-3-trifluoromethylphenyl]-3-(pyridin-3-yl)methoxybenzamide, R-13a, was prepared in a similar manner to that described for Example R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-picolyl chloride hydrochloride was used in place of 4-(chloromethyl)isoquinoline hydrochloride, K-1c, in step (a), and 1-(4-amino-2-trifluoromethylphenyl)-4-(t-butoxycarbonyl)piperazine was used in place of 3,5-diallyl-4-bromoaniline in step (c).

(b) A solution of 4-fluoro-N-[4-{4-(t-butoxycarbonyl)piperazin-1-yl}-3-trifluoromethylphenyl]-3-(pyridin-3-yl)methoxybenzamide, R-13a, (65 mg, 0.11 mmol) in methylene chloride (4 mL) was treated with trifluoroacetic acid (1 mL). After 18 hours, the solution was concentrated under reduced pressure. The resultant residue was treated with 5% sodium bicarbonate (25 mL) and extracted with ethyl acetate (3×25 mL). The combined organic extracts were washed with water (50 mL), brine (50 mL), dried over magnesium sulfate, filtered, and concentrated under reduced pressure to give a tan solid (48 mg). The crude product was purified by radial chromatography over silica gel using 5–15% methanol/chloroform with 0.1% ammonium hydroxide to give 4-fluoro-N-[4-(piperazin-1-yl)-3-trifluoromethylphenyl]-3-(pyridin-3-yl)methoxybenzamide, R-13, as a white solid (34 mg, 63%): mp 123–131° C.; HPLC $R_t$=13.2 min.; TLC $R_f$=0.3 (6% methanol/chloroform w/0.1% NH$_4$OH); $^1$H NMR (300 MHz, DMSO-$d_6$) δ10.43 (s, 1H), 8.72 (d, 1H, J=1.6 Hz), 8.60 (dd, 1H, J=4.8, 1.5 Hz), 8.12 (d, 1H, J=2.3,Hz), 8.05–8.02 (m, 1H), 7.94–7.86 (m, 2H), 7.69–7.64 (m, 1H), 7.54 (d, 1H, J=8.8 Hz), 7.49–7.41 (m, 2H), 5.33 (s, 2H), 2.82–2.79 (m, 4H), 2.78–2.75 (m, 4H); MS (ESI) m/z 475 [M+H]$^+$. Anal. calc'd for $C_{24}H_{22}F_4N_4O_2$: C, 60.76; H, 4.67; N, 11.81. Found: C, 60.66; H, 4.98; N, 11.38.

Example R-14

4-Fluoro-N-(4-morpholin-4-yl-3-trifluoromethyl-phenyl)-3-(isoquinolin-4-ylmethoxy)-benzamide

R-14

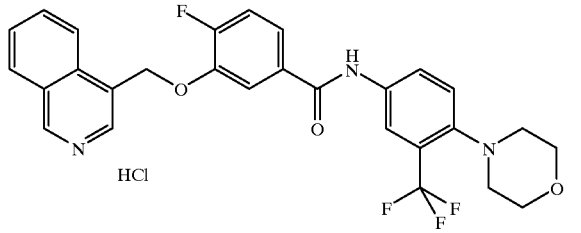

Example R-14 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate in step (a), and 1-(4-amino-2-trifluoromethylphenyl)morpholine was used in place of 3,5-diallyl-4-bromoaniline in step (c): mp 175–180° C.; HPLC $R_t$=15.3 min.; TLC $R_f$=0.3 (1% methanol/methylene chloride); $^1$H NMR (300 MHz, DMSO-$d_6$) δ10.67 (s, 1H), 9.80 (s, 1H), 8.83 (s, 1H), 8.52 (d, 1H, J=8.2 Hz), 8.44 (d, 1H, J=8.5 Hz), 8.23–8.17 (m, 3H), 8.12 (dd, 1H, J=8.8, 2.3 Hz), 8.00 (t, 1H, J=7.4 Hz), 7.74–7.70 (m, 1H), 7.62 (d, 1H, J=8.7 Hz), 7.46 (dd, 1H, J=11.0, 8.4 Hz), 5.91 (s, 2H), 3.71 (t, 4H, J=4.2 Hz), 2.84 (t, 4H, J=4.2 Hz); MS (ESI) m/z 526 [M+H]$^+$. Anal. calcd for $C_{28}H_{23}F_4N_3O_3$·1.3 HCl: C, 58.70; H, 4.28; N, 7.33; Cl, 8.05. Found: C, 59.05; H, 4.59; N, 7.28; Cl, 8.01.

Example R-15

4-Fluoro-N-(4-piperazin-1-yl-3-trifluoromethyl-phenyl)-3-(isoquinolin-4-ylmethoxy)-benzamide

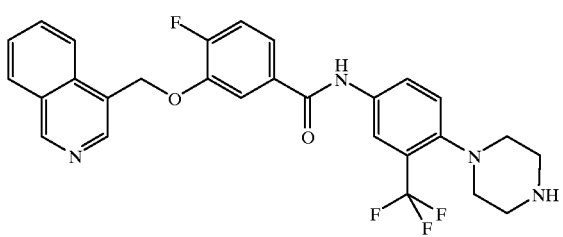

Example R-15 was prepared in a similar manner to that described for R-13, except that 4-(chloromethyl) isoquinoline hydrochloride, K-1c, was used in place of 3-picolyl chloride hydrochloride in step (a): mp 103–107° C.; HPLC $R_t$=14.7 min.; TLC $R_f$=0.3 (5% methanol/chloroform with 0.1% NH$_4$OH); $^1$H NMR (300 MHz, DMSO-$d_6$) δ10.45 (s, 1H), 9.37 (s, 1H), 8.68 (s, 1H), 8.23–8.17 (m, 2H), 8.14–8.13 (m, 1H), 8.06–8.02 (m, 2H), 7.92–7.87 (m, 1H), 7.79–7.74 (M, 1H), 7.69–7.65 (m, 1H), 7.55 (d, 1H, J=8.5 Hz), 7.42 (dd, 1H, J=11.0, 8.6 Hz), 5.72 (s, 2H), 2.80 (br. s, 4H), 2.77 (br. s, 4H); MS (ESI) m/z 525 [M+H]$^+$. Anal. calcd for $C_{28}H_{24}F_4N_4O_2$·0.1 hexanes (MW 533.1 g/mol): C, 64.43; H, 4.80; N, 10.51. Found: C, 64.68; H, 5.07; N, 10.16.

Example R-16

4-Fluoro-N-(4-morpholin-4-yl-3-trifluoromethyl-phenyl)-3-(quinolin-3-ylmethoxy)-benzamide

R-16

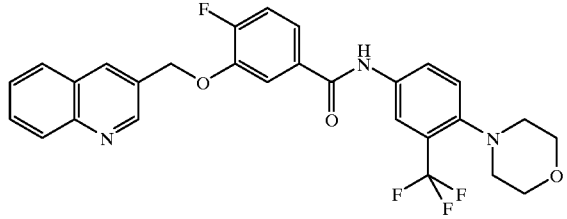

Example R-16 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-chloromethylquinoline hydrochloride was used in place of 4-(chloromethyl)isoquinoline hydrochloride, K-1c, in step (a), and 1-(4-amino-2-trifluoromethylphenyl)morpholine was used in place of 3,5-diallyl-4-bromoaniline in step (c): mp 81–84° C.; HPLC $R_t$=15.4 min.; TLC $R_f$=0.5 (1% methanol/methylene chloride); $^1$H NMR (300 MHz, DMSO-$d_6$) δ10.46 (s, 1H), 9.04 (d, 1H, J=2.2 Hz), 8.49 (s, 1H), 8.14 (d, 1H, J=2.4 Hz), 8.08–8.04 (m, 3H), 7.93 (dd, 1H, J=8.2, 1.8 Hz), 7.83–7.78 (m, 1H), 7.70–7.60 (m, 3H), 7.46 (dd, 1H, J=11.0, 8.5 Hz), 5.52 (s, 2H), 3.70 (t, 4H, J=4.3 Hz), 2.84 (t, 4H, J=4.3 Hz); MS (ESI) m/z 526 [M+H]$^+$. Anal. calc'd for $C_{28}H_{23}F_4N_3O_3$: C, 64.00; H, 4.41; N, 8.00. Found: C, 64.15; H, 4.53; N, 7.97.

Example R-17

4-Fluoro-N-(4-piperazin-1-yl-3-trifluoromethyl-phenyl)-3-(quinolin-3-ylmethoxy)-benzamide

R-17

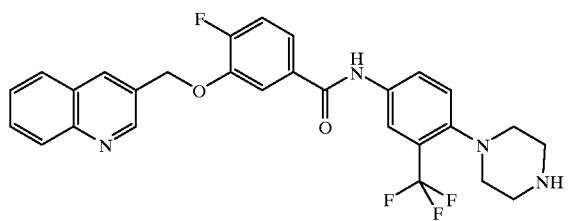

Example R-17 was prepared in a similar manner to that described for R-13, except that 3-(chloromethyl)quinoline hydrochloride was used in place of 3-picolyl chloride hydrochloride in step (a): mp 76–78° C.; HPLC $R_t$=14.7 min.; TLC $R_f$=0.3 (3% methanol/chloroform w/0.1% NH$_4$OH); $^1$H NMR (300 MHz, DMSO-$d_6$) δ10.44 (s, 1H), 9.04 (d, 1H, J=2.0 Hz), 8.48 (s, 1H), 8.12 (d, 1H, J=2.1 Hz), 8.08–8.02 (m, 3H), 7.93–7.91 (m, 1H), 7.83–7.78 (m, 1H), 7.68–7.63 (m, 2H), 7.54 (d, 1H, J=8.9 Hz), 7.46 (dd, 1H, J=11.0, 8.5 Hz), 5.52 (s, 2H), 2.81 (br. s, 4H), 2.78 (br. s, 4H); MS (ESI) m/z 525 [M+H]$^+$. Anal. calc'd for $C_{28}H_{24}F_4N_4O_2$: C, 64.12; H, 4.61; N, 10.68. Found: C, 64.53; H, 4.99; N, 10.25.

Example R-18

N-(3,5-Dichloro-4-morpholin-4-yl-phenyl)-4-fluoro-3-(pyridin-3-ylmethoxy)-benzamide

R-18

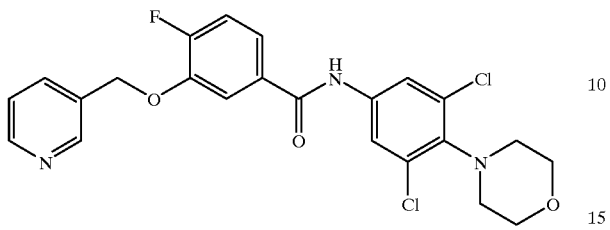

Example R-18 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-picolyl chloride hydrochloride was used in place of 4-(chloromethyl) isoquinoline hydrochloride, K-1c, in step (a), and 1-(4-amino-2,6-dichlorophenyl)morpholine was used in place of 3,5-diallyl-4-bromoaniline in step (c): mp 209–211° C.; HPLC $R_t$=15.0 min.; TLC $R_f$=0.3 (40% ethyl acetate/cyclohexane); $^1$H NMR (300 MHz, DMSO-$d_6$) δ10.41 (s, 1H), 8.71 (s, 1H), 8.58 (d, 1H, J=4.7 Hz), 7.93–7.82 (m, 4H), 7.63–7.60 (m, 1H), 7.49–7.41 (m, 2H), 5.32 (s, 2H), 3.70 (br. s, 4H), 3.12 (br. s, 4H); $^{13}$C NMR (75 MHz, DMSO-$d_6$) δ164.4, 154.0 (d, $J_{CF}$=250 Hz), 149.4, 149.2, 146.0 (d, $J_{CF}$=11 Hz), 139.5, 137.4, 136.0, 134.2, 131.8, 130.9 (d, $J_{CF}$=3 Hz), 123.8, 121.6 (d, $J_{CF}$=8 Hz), 120.4, 116.1 (d, $J_{CF}$=19 Hz), 115.0 (d, $J_{CF}$=2 Hz), 68.3, 67.0, 49.4; MS (ESI) m/z 476 [M+H]$^+$. Anal. calc'd for $C_{23}H_{20}Cl_2FN_3O_3$: C, 58.00; H, 4.23; Cl, 8.82; N, 14.89. Found: C, 57.89; H, 4.24; Cl, 14.88; N, 8.69.

Example R-19

N-(3,5-Dichloro-4-piperazin-1-yl-phenyl)-4-fluoro-3-(pyridin-3-ylmethoxy)-benzamide

R-19

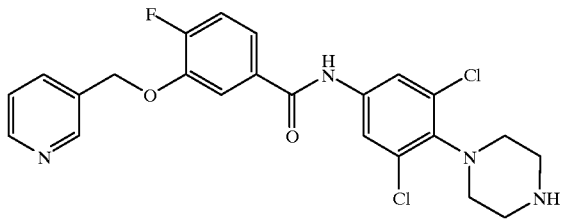

Example R-19 was prepared in a similar manner to that described for R-13, except that 1-(4-amino-2,6-dichlorophenyl)-4-(t-butoxycarbonyl)piperazine was used in place of 1-(4-amino-2-trifluoromethylphenyl)-4-(t-butoxycarbonyl)piperazine in step (a) mp 81–85° C.; HPLC $R_t$=11.7 min.; TLC $R_f$=0.4 (5% methanol/chloroform w/0.1% NH$_4$OH); $^1$H NMR (300 MHz, DMSO-$d_6$) δ10.38 (s, 1H), 8.71 (d, 1H, J=1.8 Hz), 8.58 (dd, 1H, J=4.7, 1.3 Hz), 7.93–7.82 (m, 4H), 7.65–7.60 (m, 1H), 7.49–7.41 (m, 2H), 5.32 (s, 2H), 3.05–3.02 (m, 4H), 2.88–2.79 (m, 4H); $^{13}$C NMR (75 MHz, DMSO-$d_6$) δ164.7, 152.2 (d, $J_{CF}$=250 Hz), 149.8, 149.5, 146.2 (d, $J_{CF}$=11 Hz), 140.7, 137.3, 136.2, 134.4, 132.1, 131.2 (d, $J_{CF}$=3 Hz), 124.0, 121.8 (d, $J_{CF}$=8 Hz), 120.7, 116.4 (d, $J_{CF}$=19 Hz), 115.3, 68.6, 50.8, 46.6; MS (ESI) m/z 475 [M+H]$^+$. Anal. calc'd for $C_{23}H_{21}Cl_2FN_4O_2$: C, 58.12; H, 4.45; Cl, 14.92; N, 11.79. Found: C, 57.99; H, 4.60; Cl, 14.59; N, 11.38.

Example R-20

4-Fluoro-N-[4-(piperazin-1-yl)-3-trifluoromethylphenyl]-3-(pyridin-3-yl)methoxybenzamide

R-20

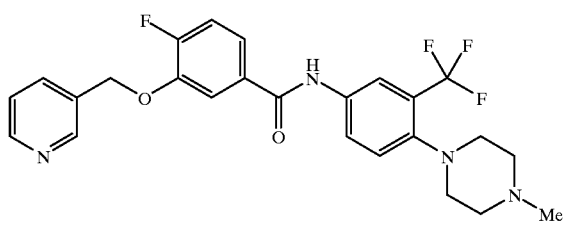

Example R-20 was prepared in a similar manner to that described for R-1, except that ethyl 4-fluoro-3-hydroxybenzoate, prepared by conventional Fischer esterification of 4-fluoro-3-hydroxybenzoic acid, was used in place of methyl 3-hydroxybenzoate and 3-picolyl chloride hydrochloride was used in place of 4-(chloromethyl) isoquinoline hydrochloride, K-1c, in step (a), and 1-(4-amino-2-trifluoromethylphenyl)-4-methylpiperazine was used in place of 3,5-diallyl-4-bromoaniline in step (c): mp 61–66° C.; HPLC $R_t$=13.0 min.; TLC $R_f$=0.5 (5% methanol/chloroform w/0.1% NH$_4$OH); $^1$H NMR (300 MHz, DMSO-$d_6$) δ10.46 (s, 1H), 8.72 (s, 1H), 8.59 (d, 1H, J=4.4 Hz), 8.14 (d, 1H, J=2.0 Hz), 8.05 (dd, 1H, J=8.6, 1.6 Hz), 7.94–7.86 (m, 2H), 7.69–7.65 (m, 1H), 7.60 (d, 1H, J=8.8 Hz), 7.49–7.41 (m, 2H), 5.33 (s, 2H), 2.92 (s, 4H), 2.88 (br. s, 4H), 2.42 (s, 3H); MS (ESI) m/z 489 [M+H]$^+$. Anal. calc'd for $C_{25}H_{24}F_4N_4O_2$×1.3 H$_2$O: C, 58.66; H, 5.24; N, 10.95. Found: C, 58.17; H, 4.80; N, 10.52.

Example R-21

4-Fluoro-N-(4-imidazol-1-yl-3-trifluoromethyl-phenyl)-3-(pyridin-3-ylmethoxy)-benzamide

R-21

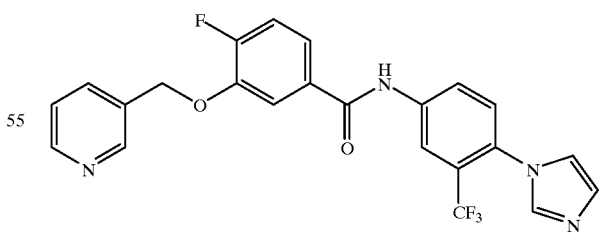

Example R-21 was prepared in a similar manner to that described for R-1, except that imidazol-1-yl-trifluoromethyl-phenylamine, J-1b, was used in place of 3,5-diallyl-4-bromoaniline and 4-fluoro-3-(pyridin-3-ylmethoxy)-benzoic acid, which was prepared as described in R-11, was used in place of 3-(isoquinolin-4-ylmethoxy)- benzoic acid, R-1b: HPLC R$_t$ 12.8 min.; TLC R$_f$ 0.3 (5% methanol-chloroform w/0.1% ammonium hydroxide); $^1$H NMR (DMSO-d$_6$, 300 MHz) δ10.73 (s, 1H), 8.73 (s, 1H), 8.59 (s, 1H), 8.39 (d, 1H, J=2.2 Hz), 8.21 (dd, 1H, J=8.6, 2.1 Hz), 7.94–7.83 (m, 3H), 7.73–7.68 (m, 1H), 7.60 (d, 1H, J=8.7 Hz), 7.51–7.40 (m, 3H), 7.10 (s, 1H), 5.35 (s, 2H); MS (ESI) m/z 457 (M+H)$^+$. Anal. calcd for C$_{23}$H$_{16}$F$_4$N$_4$O$_2$: C, 60.53; H, 3.53; N, 12.28. Found: C, 60.37; H, 3.62; N, 12.21.

Example R-22

4-Fluoro-N-(4-pyrazol-1-yl-3-trifluoromethyl-phenyl)-3-(pyridin-3-ylmethoxy)-benzamide

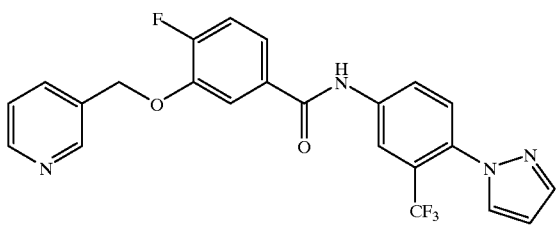

R-22

Example R-22 was prepared in a similar manner to that described for R-1, except that pyrazol-1-yl-trifluoromethyl-phenylamine was used in place of 3,5-diallyl-4-bromoaniline and 4-fluoro-3-(pyridin-3-ylmethoxy)-benzoic acid, which was prepared as described in R-11, was used in place of 3-(isoquinolin-4-ylmethoxy)-benzoic acid, R-1b: HPLC R$_t$ 13.9 min.; TLC R$_f$ 0.2 (2% methanol-chloroform w/0.1% ammonium hydroxide); $^1$H NMR (DMSO-d$_6$, 300 MHz) δ10.72 (s, 1H), 8.72 (d, 1H, J=1.8 Hz), 8.60 (dd, 1H, J=4.6, 1.2 Hz), 8.38 (d, 1H, J=2.3 Hz), 8.21 (dd, 1H, J=8.7, 2.3 Hz), 8.02 (d, 1H, J=2.2 Hz), 7.95–7.89 (m, 2H), 7.74–7.69 (m, 2H), 7.68 (d, 1H, J=8.7 Hz), 7.51–7.44 (m, 2H), 6.52–6.51 (m, 1H), 5.35 (s, 2H); MS (ESI) m/z 457 (M+H)$^+$. Anal. calcd for C$_{23}$H$_{16}$F$_4$N$_4$O$_2$: C, 60.53; H, 3.53; N, 12.28. Found: C, 60.39; H, 3.64; N, 12.19.

Example R-23

4-Fluoro-3-(pyridin-3-ylmethoxy)-N-(4-[1,2,4]triazol-1-yl-3-trifluoromethyl-phenyl)-benzamide

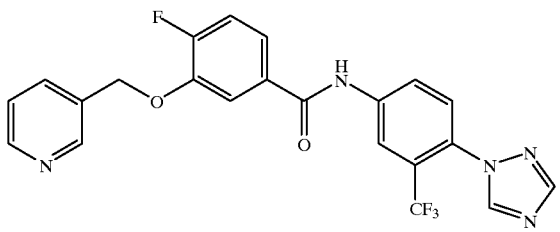

R-23

Example R-23 was prepared in a similar manner to that described for R-1, except that [1,2,4]triazol-1-yl-trifluoromethyl-phenylamine was used in place of 3,5-diallyl-4-bromoaniline and 4-fluoro-3-(pyridin-3-ylmethoxy)-benzoic acid, which was prepared as described in R-11, was used in place of 3-(isoquinolin-4-ylmethoxy)-benzoic acid, R-1b: HPLC R$_t$ 12.4 min.; TLC R$_f$ 0.3 (5% methanol-chloroform w/0.1% ammonium hydroxide); $^1$H NMR (DMSO-d$_6$, 300 MHz) δ10.79 (s, 1H), 8.89 (s, 1H), 8.73 (d, 1H, J=1.7 Hz), 8.60 (dd, 1H, J=4.8, 1.8 Hz), 8.44 (d, 1H, J=2.3 Hz), 8.28–8.24 (m, 2H), 7.96–7.90 (m, 2H), 7.74–7.69 (m, 2H), 7.52–7.45 (m, 2H), 5.35 (s, 2H); MS (ESI) m/z 458 (M+H)$^+$. Anal. calcd for C$_{22}$H$_{15}$F$_4$N$_5$O$_2$: C, 56.65; H, 3.46; N, 15.02. Found: C, 56.53; H, 3.44; N, 14.96.

Example R-24

N-(3,5-Dichloro-4-imidazol-1-yl-phenyl)-4-fluoro-3-(pyridin-3-ylmethoxy)-benzamide

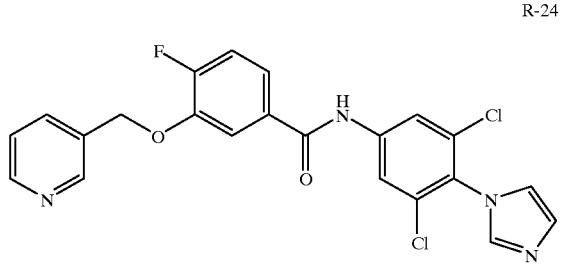

R-24

Example R-24 was prepared in a similar manner to that described for R-1, except that 3,5-dichloro-4-imidazol-1-yl-phenylamine was used in place of 3,5-diallyl-4-bromoaniline and 4-fluoro-3-(pyridin-3-ylmethoxy)-benzoic acid, which was prepared as described in R-11, was used in place of 3-(isoquinolin-4-ylmethoxy)-benzoic acid, R-1b: HPLC R$_t$ 13.0 min.; TLC R$_f$ 0.7 (5% methanol-dichloromethane); $^1$H NMR (DMSO-d$_6$, 300 MHz) δ10.65 (s, 1H), 8.89 (s, 1H), 8.72 (d, 1H, J=1.9 Hz), 8.60 (dd, 1H, J=4.8, 1.6 Hz), 8.11 (s, 2H), 7.95–7.91 (m, 1H), 7.88 (dd, 1H, J=8.2, 2.0 Hz), 7.81 (s, 1H), 7.71–7.66 (m, 1H), 7.51–7.44 (m, 2H), 7.33 (s, 1H), 7.13 (s, 1H), 5.34 (s, 2H); $^{13}$C NMR (DMSO-d$_6$, 75 MHz) δ165.2, 154.6 (d, J$_{CF}$=251.1 Hz), 149.9, 149.6, 146.4 (d, J$_{CF}$=11.1 Hz), 141.2, 138.4, 136.3, 133.1, 132.2, 130.9 (d, J$_{CF}$=3.5 Hz), 129.2, 128.3, 124.1, 122.0 (d, J$_{CF}$=7.6 Hz), 121.3, 119.9, 116.6 (d, J$_{CF}$=18.7 Hz), 115.6 (d, J$_{CF}$=1.7 Hz), 68.8; MS (ESI) m/z 457 (M+H)$^+$. Anal. calcd for C$_{22}$H$_{15}$Cl$_2$FN$_4$O$_2$: C, 57.78; H, 3.31; N, 12.25; Cl, 15.51. Found: C, 57.38; H, 3.52; N, 11.90; Cl, 16.40.

Example R-25

3-(5-Bromo-pyridin-3-ylmethoxy)-4-fluoro-N-(4-piperazin-1-yl-3-trifluoromethyl-phenyl)-benzamide

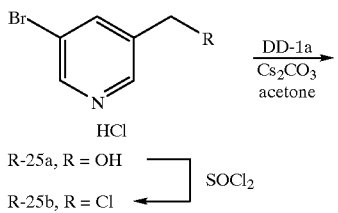

R-25a, R = OH
R-25b, R = Cl

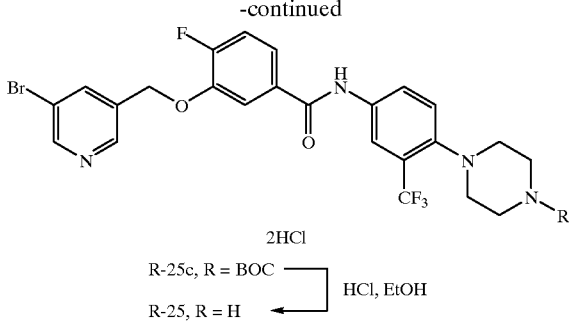

2HCl

R-25c, R = BOC
R-25, R = H

HCl, EtOH (a) (5-Bromo-pyridin-3-yl)-methanol hydrochloride, R-25a, was prepared according to the procedure described in *J. Med. Chem.*, 1997, 40, 2866–2875: HPLC R$_t$ 3.9 min.; TLC R$_f$ 0.2 (free base; 40% ethyl acetate-cyclohexane); $^1$H NMR (DMSO-d$_6$, 300 MHz) δ8.70 (d, 1H, J=2.2 Hz), 8.58–8.57 (m, 1H), 8.11 (t, 1H, J=2.0 Hz), 4.57 (s, 2H); $^{13}$C NMR (DMSO-d$_6$, 75 MHz) δ144.1, 141.9, 140.2, 120.8, 59.9; MS (ESI) m/z 188/190 (M+H)$^+$.

(b) To a solution of (5-bromo-pyridin-3-yl)-methanol hydrochloride, R-25a, (1.9 g, 8.5 mmol, 1.0 eq) was added thionyl chloride (6 mL, 85 mmol, 10 eq). The amber solution was warmed to 70° C. for 2 h. The crude product was cooled to room temperature, diluted with toluene (50 mL) and concentrated under reduced pressure to give 3-bromo-5-chloromethyl-pyridine hydrochloride, R-25b, as a tan solid: HPLC R$_t$ 10.1 min.; $^1$H NMR (DMSO-d$_6$, 300 MHz) δ8.72 (d, 1H, J=2.2 Hz), 8.68 (d, 1H, J=1.7 Hz), 8.21 (t, 1H, J=2.0 Hz), 4.43(s, 2H); $^{13}$C NMR (DMSO-d$_6$, 75 MHz) δ149.8, 148.0, 140.2, 136.4, 120.5, 42.3; MS (ESI) m/z 206/208 (M+H)$^+$.

(c) 4-[({1-[3-(5-Bromo-pyridin-3-ylmethoxy)-4-fluorophenyl]-methanoyl}-amino)-trifluoromethyl-phenyl]-piperazine-1-carboxylic acid tert-butyl ester, R-25c, was prepared in a similar manner to that described for R-1a, except that 3-bromo-5-chloromethyl-pyridine hydrochloride, R-25b, was used in place of 4-(chloromethyl) isoquinoline hydrochloride, K-1c, and 4-({[1-(4-fluoro-3-hydroxy-phenyl)-methanoyl]-amino}-trifluoromethyl-phenyl)-piperazine-1-carboxylic acid tert-butyl ester, DD-1a, was used in place of 3-hydroxybenzoate: HPLC R$_t$ 19.2 min.; TLC R$_f$ 0.3 (2% methanol-dichloromethane); $^1$H NMR (DMSO-d$_6$, 300 MHz) δ10.44 (s, 1H), 8.74 (d, 1H, J=2.2 Hz), 8.72 (d, 1H, J=1.7 Hz), 8.21 (t, 1H, J=2.0 Hz), 8.14 (d, 1H, J=2.4 Hz), 8.04 (dd, 1H, J=8.6, 2.4 Hz), 7.86 (dd, 1H, J=8.2, 2.0 Hz), 7.71–7.66 (m, 1H), 7.60 (d, 1H, J=8.8 Hz), 7.46 (dd, 1H, J=11.0, 8.5 Hz), 5.34 (s, 2H), 3.44 (br. s, 4H), 2.80 (t, 4H, J=4.7 Hz), 1.44 (s, 9H); MS (ESI) m/z 653/655 (M+H)$^+$.

(d) 3-(5-Bromo-pyridin-3-ylmethoxy)-4-fluoro-N-(4-piperazin-1-yl-3-trifluoromethyl-phenyl)-benzamide dihydrochloride, R-25, was prepared in the manner similar to that described in example AA-1, step (i), except 4-[({1-[3-(5-bromo-pyridin-3-ylmethoxy)-4-fluoro-phenyl]-methanoyl}-amino)-trifluoromethyl-phenyl]-piperazine-1-carboxylic acid tert-butyl ester, R-25c, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC R$_t$ 13.1 min.; $^1$H NMR (DMSO-d$_6$, 300 MHz) δ10.59 (s, 1H), 9.05 (br. s, 2H), 8.74–8.72 (m, 2H), 8.20 (d, 2H, J=1.9 Hz), 8.12 (d, 1H, J=8.7 Hz), 7.92 (d, 1H, J=7.9 Hz), 7.71–7.68 (m, 1H), 7.56 (d, 1H, J=8.7 Hz), 7.44 (dd, 1H, J=11.0, 8.6 Hz), 5.36 (s, 2H), 3.17 (br. s, 4H), 3.07 (br. s, 4H); MS (ESI) m/z 553/555 (M+H)$^+$. Anal. calcd for C$_{24}$H$_{21}$BrF$_4$N$_4$O$_2$×2.0 HCl×0.6 H$_2$O: C, 45.24; H, 3.83; N, 8.79; Br, 12.54; Cl, 11.13. Found: C, 45.20; H, 3.94; N, 8.50; Br, 12.18; Cl, 10.81.

Example S-1

3-(2-Isoquinolin-4-yl-ethyl)-N-phenyl-benzamide

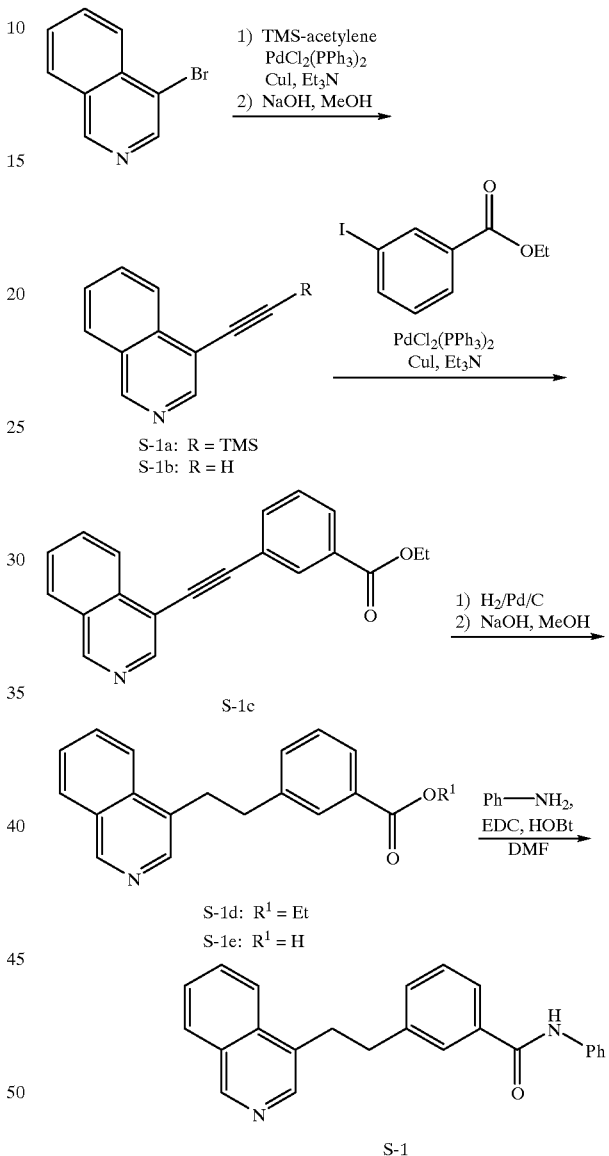

(a) 4-Bromoisoquinoline (1.0 g, 4.8 mmol), dichlorobis (triphenylphosphine)palladium (20.4 mg, 0.029 mmol), copper iodide (1.5 mg, 0.008 mmol), trimethylsilylacetylene (707 mg, 7.2 mmol) and triethylamine (20 ml) were heated in a sealed tube at 65° C. for 16 h. After concentration the residue was diluted with ethyl acetate, washed with brine, dried over sodium sulfate, filtered and concentrated to dryness. The crude residue was purified on silica gel using a gradient of 10% to 20% ethyl acetate in hexanes as eluant to obtain 1.01 g (93%) of 4-(trimethyl-silanylethynyl)-isoquinoline, S-1a, as a yellow liquid: $^1$H NMR (300 MHz, CDCl$_3$) δ9.18 (s, 1H), 8.70 (s, 1H), 8.34 (m, 1H), 8.14 (m, 1H), 7.78 (m, 1H), 7.65 (m, 1H), 0.35 (s, 9H).

(b) To a solution of NaOH (0.23 g, 5.78 mmol) in methanol was added 1.0 g (4.44 mmol) 4-(trimethyl-silanylethynyl)-isoquinoline, S-1a. After stirring for 2 h at room temperature the methanol was removed followed by addition of ethyl acetate. The organic solution was washed with water, brine and dried over sodium sulfate. Removal of solvent led to 0.65 g (96%) of 4-ethynyl-isoquinoline, S-1b: $^1$H NMR (300 MHz, CDCl$_3$) δ9.22 (s, 1H), 8.74 (s, 1H), 8.27 (m, 1H), 7.99 (m, 1H), 7.80 (m, 1H), 7.67 (m, 1H), 3.55 (s, 1H).

(c) 4-Ethynyl-isoquinoline, S-1b, (0.64 g, 4.18 mmol), ethyl 3-iodobenzoate (1.15 g, 4.18 mmol), dichlorobis (triphenylphosphine)palladium (7.02 mg, 0.010 mmol) and copper iodide (0.4 mg, 0.002 mmol) in triethylamine (20 ml) were stirred at room temperature for 14 h. The mixture was filtered through celite, and the filtrate was concentrated to remove triethylamine. To this residue was added ethyl acetate, and this solution was washed with brine, dried over sodium sulfate, and concentrated to dryness. The crude residue was purified on silica gel using a gradient 0% to 5% ethyl acetate in dichloromethane as eluant to obtain 1.1 g (87%) of ethyl 3-(isoquinolin-4-ylethynyl)benzoate, S-1c, as a semisolid: $^1$H NMR (300 MHz, CDCl$_3$) δ9.23 (brs, 1H), 8.80 (br s, 1H), 8.32 (m, 2H), 8.07 (m, 1H), 8.03 (m, 1H), 7.84 (m, 2H), 7.69 (m, 2H), 7.50 (dd, 1H, J=7.4 Hz), 4.43 (q, 2H, J=7.1 Hz), 1.44 (t, 3H, J=7.1 Hz).

(d) Ethyl 3-(isoquinolin-4-ylethynyl)benzoate, S-1c, (1.1 g, 3.64 mmol) and 10% Pd/C (0.5 g) in ethanol (20 ml) were stirred under one atm of hydrogen at room temperature for 16 h. The solution was filtered through celite, and the filtrate was concentrated leaving 1.02 g (91.6%) of ethyl 3-(isoquinolin-4-ylethyl)benzoate, S-1d, as a liquid: $^1$H NMR (300 MHz, CDCl$_3$) δ9.14 (s, 1H), 8.32 (s, 1H), 8.01 (m, 2H), 7.91 (m, 2H), 7.75 (m, 1H), 7.62 (m, 1H), 7.34 (m, 2H), 4.39 (q, 2H J=7.1 Hz), 3.35 (m, 2H), 3.10 (m, 2H), 1.40 (t, 3H, J=7.1 Hz).

(e) To a stirred solution of ethyl 3-(isoquinolin-4-ylethyl)benzoate, S-1d, (1.02 g, 3.3 mmol) in methanol (20 ml) was added 1N NaOH (3.63 ml, 3.63 mmol). After refluxing for 4 h, the methanol was removed. The solution was diluted with water and upon acidification to pH 3 a white precipitate formed which was subsequently filtered and dried under high vacuum to obtain 0.92 g (100%) of 3-(2-isoquinolin-4-yl-ethyl)-benzoic acid, S-1e: $^1$H NMR (300 MHz, CDCl$_3$) δ9.75 (s, 1H), 8.54 (m, 3H), 8.21 (m, 1H), 8.02 (m, 1H), 7.89 (br s, 1H), 7.80 (m, 1H), 7.57 (m, 1H), 7.43 (dd, 1H, J=7.7 Hz), 3.52 (m, 2H), 3.11 (m, 2H).

(f) To a stirred solution of 3-(2-isoquinolin-4-yl-ethyl)-benzoic acid, S-1e, (0.2 g, 0.64 mmol), N-hydroxybenzotriazole (0.11 g, 0.70 mmol), and aniline (0.06 g, 0.65 mmol) in DMF (10 ml) was added 1-ethyl-3-(3'-dimethylaminopropyl)carbodiimide HCl (0.148 g, 0.77 mmol) at 0° C. After stirring for 16 hrs. the DMF was removed, and ethyl acetate was added. This solution was washed with sat. NaHCO$_3$, brine and dried over sodium sulfate. The crude residue was purified on silica gel using a gradient of 0% to 30% ethyl acetate in dichloromethane as eluant to obtain 0.18 g (80%) of 3-(2-isoquinolin-4-yl-ethyl)-N-phenyl-benzamide, S-1, as a solid: $^1$H NMR (300 MHz, CDCl$_3$) δ9.16 (s, 1H), 8.30 (s, 1H), 8.04–7.99 (m, 2H), 7.76 (dd, 1H, J=8.34 Hz, J=8.37 Hz), 7.71–7.69 (m, 1H), 7.67–7.60 (m, 5H), 7.44–7.35 (m, 4H), 7.19–7.12 (m, 1H), 3.39–3.34 (m, 2H), 3.16–3.11 (m, 2H). MS (ESI) m/z 353 [M+H]$^+$. Anal. calc'd for C$_{24}$H$_{20}$N$_2$O.0.2 H$_2$O: C, 80.96; H, 5.78; N, 7.87. Found: C, 80.88; H, 5.85; N, 8.03.

Example S-2

3-(2-Isoquinolin-4-yl-ethyl)-N-(3,3,5-trimethyl-cyclohexyl)-benzamide

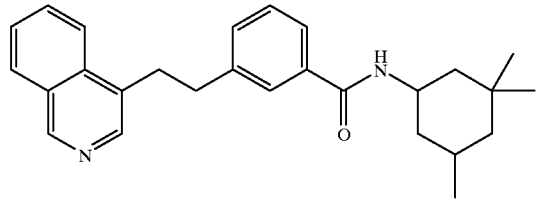

S-2

Example S-2 was prepared in a similar manner to that described for S-1, except that (±)-cis/trans-3,3,5-trimethylcyclohexylamine was used in place of aniline in step (f): $^1$H NMR (300 MHz, CDCl$_3$) δ9.14 (s, 1H), 8.31 (s, 1H), 8.01 (m, 2H), 7.75 (dd, 1H, J=8.4 Hz, J=8.4 Hz ), 7.63 (dd, 1H, J=8.0 Hz, J=8.0 Hz), 7.56 (m, 1H), 7.52 (m, 1H), 7.36–7.28 (m, 2H), 5.72 (d, 1H, J=7.9 Hz), 4.16 (m, 1H), 3.37 (m, 2H), 3.10 (m, 2H), 2.90 (m, 1H), 1.78 (m, 2H), 1.38 (m, 1H), 1.03 (s, 3H), 0.97(s, 3H), 0.92 (d, 3H, J=6.5 Hz), 0.84–0.64 (m, 3H). MS (ESI) mt/z 401 [M+H]$^+$. Anal. calc'd for C$_{27}$H$_{32}$N$_2$O.0.1 H$_2$O: C, 80.60; H, 8.07; N, 6.96. Found: C, 80.40; H, 8.20; N,6.85.

Example S-3

N-(4-Isopropyl-3-methyl-phenyl)-3-(2-isoquinolin-4-yl-ethyl)-benzamide

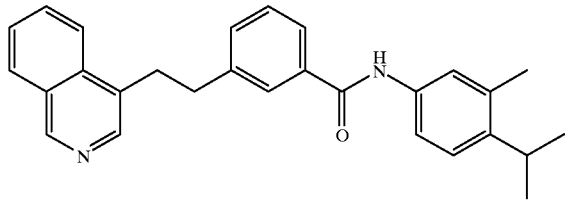

S-3

Example S-3 was prepared in a similar manner to that described for S-1, except that 4-isopropyl-3-methylaniline was used in place of aniline in step (f): $^1$H NMR (300 MHz, CDCl$_3$) δ9.16 (s, 1H), 8.31 (s, 1H), 8.04–7.99 (m, 2H), 7.76 (dd, 1H, J=8.4 Hz), 7.68–7.61 (m, 4H), 7.45–7.34 (m, 4H), 7.23 (m, 1H ), 3.39–3.34 (m, 2H), 3.15–3.10 (m, 3H), 2.36 (s, 3H), 1.23 (d, 6H, J=6.9 Hz). MS (ESI) m/z 409 [M+H]$^+$. Anal. calc'd for C$_{28}$H$_{28}$N$_2$O.0.2 H$_2$O: C, 81.60; H, 6.95; N, 6.80. Found: C, 81.51; H, 6.99; N, 6.85.

Example S-4

3-(2-Isoquinolin-4-yl-ethyl)-N-(2-methyl-quinolin-6-yl)-benzamide

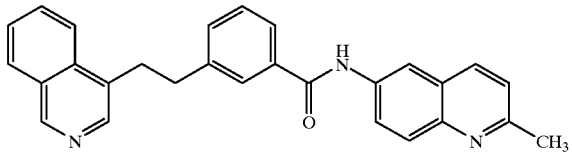

S-4

Example S-4 was prepared in a similar manner to that described for S-1, except that 6-amino-2-methylquinoline was used in place of aniline in step (f): $^1$H NMR (300 MHz, CDCl$_3$) δ9.16 (s, 1H), 8.44 (d, 1H, J=2.4 Hz), 8.29 (s, 1H), 8.07–7.97 (m, 5H), 7.79–7.71 (m,2H), 7.68–7.61 (m, 3H), 7.46–7.38 (m, 2H), 7.29 (d, 1H, J=8.4 Hz), 3.40–3.35 (m, 2H), 3.17–3.10 (m, 2H), 2.74 (s, 3H). MS (ESI) m/z 418 [M+H]$^+$. Anal. calc'd for C$_{28}$H$_{23}$N$_3$O.0.4 H$_2$O: C, 79.18; H, 5.65; N, 9.89. Found: C, 79.01; H, 5.86; N, 9.67.

Example S-5

N-(3,5-Dibromo-4-methyl-phenyl)-3-(2-isoquinolin-4-yl-ethyl)-benzamide

S-5

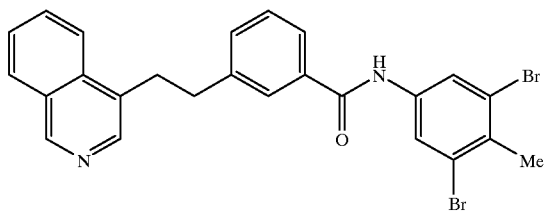

Example S-5 was prepared in a similar manner to that described for S-1, except that 3,5-dibromo-4-methylaniline was used in place of aniline in step (f): 1H NMR (300 MHz, CDCl$_3$) δ9.16 (s, 1H), 8.25 (s, 1H), 8.01 (m, 2H), 7.88 (s, 2H), 7.76 (dd, 1H, J=8.16 Hz, J=8.51 Hz), 7.68–7.61 (m, 3H), 7.52 (m, 1H), 7.43–7.35 (m, 2H), 3.41–3.32 (m, 2H), 3.15–3.09 (m, 2H), 2.54 (s, 3H). MS (ESI) m/z 525 [M+H]$^+$. Anal. calcd for C$_{25}$H$_{20}$N$_2$OBr$_2$.C$_2$F$_3$OOH: C, 50.80; H, 3.32; N, 4.39. Found: C, 50.84; H, 3.40; N, 4.51.

Example S-6

N-(4,6-Dimethyl-pyridin-2-yl)-3-(2-isoquinolin-4-yl-ethyl)-benzamide

S-6

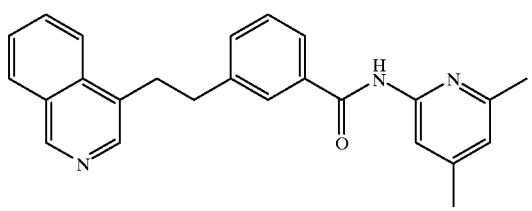

Example S-6 was prepared in a similar manner to that described for S-1, except that 2-amino-4,6-dimethylpyridine was used in place of aniline in step (f): $^1$H NMR (300 MHz, CDCl$_3$) δ9.16 (s, 1H), 8.40 (m,1H), 8.35 (s, 1H), 8.03 (m, 3H), 7.80–7.73 (m, 3H), 7.63 (dd, 1H, J=8.04 Hz, J=7.9 Hz), 7.44–7.36 (m, 2H), 6.79 (s, 1H), 3.39–3.34 (m, 2H), 3.16–3.10 (m, 2H), 2.45 (s, 3H), 2.37 (s, 3H). MS (ESI) m/z 382 [M+H]$^+$. Anal. calcd for C$_{25}$H$_{23}$N$_3$O.2C$_2$F$_3$OOH.0.5 H$_2$O: C, 56.31; H, 4.24; N, 6.79. Found: C, 56.16; H, 4.17; N, 6.75.

Example S-7

2-Chloro-4-fluoro-N-(4-isopropyl-3-methyl-phenyl)-5-(2-isoquinolin-4-yl-ethyl)-benzamide

S-7

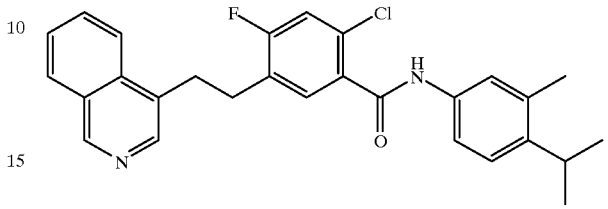

Example S-7 was prepared in a similar manner to that described for S-1, except that ethyl 2-chloro-4-fluoro-5-bromobenzoate was used in place of ethyl 3-iodobenzoate in step (c), and 4-isopropyl-3-methylaniline was used in place of aniline in step (f): $^1$H NMR (300 MHz, CDCl$_3$) δ9.15 (s, 1H), 8.27 (s, 1H),), 8.03(m, 2H), 7.81–7.76 (m, 2H), 7.64 (dd, 1H, J 7.17 Hz, J=7.11 Hz), 7.33 (d, 1H, J=7.91 Hz), 7.44–7.41 (m, 2H), 7.21–7.16 (m, 2H), 3.34–3.32 (m, 2H), 3.19–3.05 (m, 3H), 2.36 (s, 3H), 1.23(d, 6H, J=6.85 Hz). MS (ESI) m/z 461 [M]$^+$. Anal. calcd for C$_{28}$H$_{26}$ClFN$_2$O: C, 72.95; H, 5.69; N, 6.08. Found: C, 72.70; H, 5.76; N, 6.03.

Example S-8

2,4-Difluoro-N-(4-isopropyl-3-methyl-phenyl)-5-(2-isoquinolin-4-yl-ethyl)-benzamide

S-8

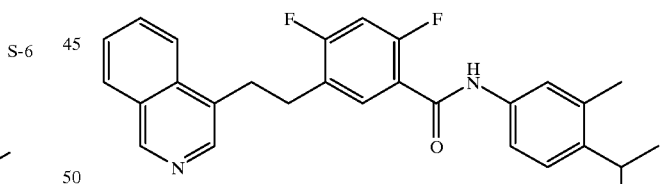

Example S-8 was prepared in a similar manner to that described for S-1, except that methyl 2,4-difluoro-5-bromobenzoate was used in place of ethyl 3-iodobenzoate in step (c), and 4-isopropyl-3-methylaniline was used in place of aniline in step (f): $^1$H NMR (300 MHz, CDCl$_3$) δ9.15 (s, 1H), 8.32 (s, 1H), 8.25 (m, 1H), 8.10–7.99 (m, 3H), 7.78 (dd, 1H, J=7.3 Hz, J=8.4 Hz), 7.64 (dd, 1H, J=8.4 Hz, J=8.0 Hz), 7.47–7.40 (m, 2H), 7.24 (m, 1H), 6.92 (dd, 1H, J=11.8 Hz, J=11.8 Hz), 3.35–3.30 (m, 2H), 3.17–3.07 (m, 3H), 2.36 (s, 3H), 1.24 (d, 6H, J=6.9 Hz). MS (ESI) m/z 445 [M]$^+$. Anal. calc'd for C$_{28}$H$_{26}$F$_3$N$_2$O: C, 75.66; H, 5.90; N, 6.30. Found: C, 75.42; H, 5.92; N, 6.22.

Example T-1

2-Fluoro-N-(4-isopropyl-3-methyl-phenyl)-5-(2-isoquinolin-4-yl-ethyl)-benzamide

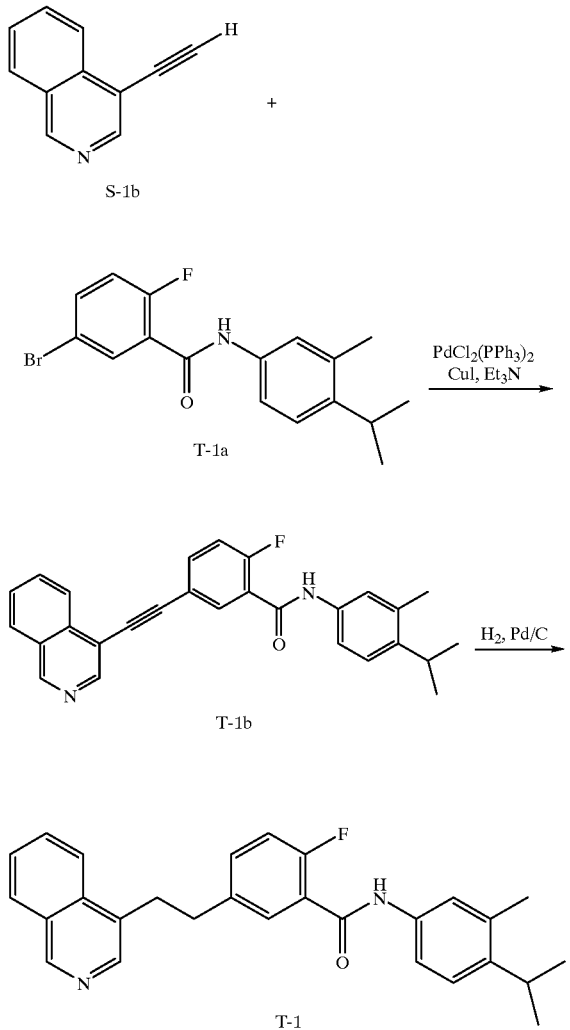

(a) 5-Bromo-2-fluoro-N-(4-isopropyl-3-methyl-phenyl)-benzamide, T-1a, was prepared from 4-isopropyl-3-methyl aniline and 4-bromo-2-fluorobenzoic acid in a manner similar to that described for 3-(2-isoquinolin-4-yl-ethyl)-N-phenyl-benzamide in Example S-1, step (f), except that benzotriazole-1-yl-oxy-tris-pyrrolidino-phosphonium hexafluorophosphate was used in place of 1-ethyl-3-(3'-dimethylaminopropyl)carbodiimide HCl and N-hydroxybenzotriazole: $^1$H NMR (300 MHz, CDCl$_3$) δ8.29 (dd, J=10.5, 7.9 Hz, 1H), 8.24 (br s, 1H), 7.60 (m, 1H), 7.42 (m, 2H), 7.24 (d, J=8.4 Hz, 1H), 7.08 (dd, J=11.4, 8.7 Hz, 1H), 3.12 (septet, J=6.8 Hz, 1H), 2.36 (s, 3H), 1.27 (d, J=6.8 Hz, 6H).

(b) 2-Fluoro-N-(4-isopropyl-3-methyl-phenyl)-5-isoquinolin-4-ylethynyl-benzamide, T-1b, was prepared in the manner similar to that described in Example S-1, step (c) for ethyl 3-isoquinolin-4-ylethynyl-benzoate, S-1c, except that 5-bromo-2-fluoro-N-(4-isopropyl-3-methyl-phenyl) benzamide, T-1a, was used in place of ethyl 3-iodobenzoate. $^1$H NMR (300 MHz, CDCl$_3$) δ9.23 (s, 1H), 9.08 (s, 1H), 8.47 (dd, J=7.5, 2.2 Hz, 1H), 8.34 (m, 2H), 8.02 (d, J=8.1 Hz, 1H), 7.84 (m, 1H), 7.78 (m, 1H), 7.69 (m, 1H), 7.48 (m, 2H), 7.25 (m, 2H), 3.14 (septet, J=6.8 Hz, 1H), 2.38 (s, 3H), 1.24 (d, J=6.8 Hz, 6H).

(c) 2-Fluoro-N-(4-isopropyl-3-methyl-phenyl)-5-(2-isoquinolin-4-yl-ethyl)-benzamide, T-1, was prepared in a manner similar to that described in Example S-1, step (d) for 3-(2-isoquinolin-4-yl-ethyl)-benzoic acid ethyl ester, S-1d: $^1$H NMR (300 MHz, CDCl$_3$) δ9.14 (s, 1H), 8.37 (m, 1H), ), 8.29 (s, 1H) 8.05–7.99 (m, 3H), 7.77 (dd, 1H, J=8.3 Hz), 7.63 (dd, 1H, J=8.1 Hz), 7.49–7.45 (m, 2H), 7.23 (m, 2H), 7.07 (dd, 1H, J=12 Hz), 3.37–3.2 (m, 2H), 3.18–3.07 (m, 3H), 2.37 (s, 3H), 1.23 (d, 6H, J=6.9 Hz). MS (ESI) m/z 427 [M+H]$^+$. Anal. calc'd for C$_{28}$H$_{27}$FN$_2$O: C, 78.85; H, 6.38; N, 6.57. Found: C, 78.91; H, 6.35; N, 6.39.

Example U-1

N-(2-Methyl-quinolin-6-yl)-3-(2-pyridin-3-yl-ethyl)-benzamide hydrochloride

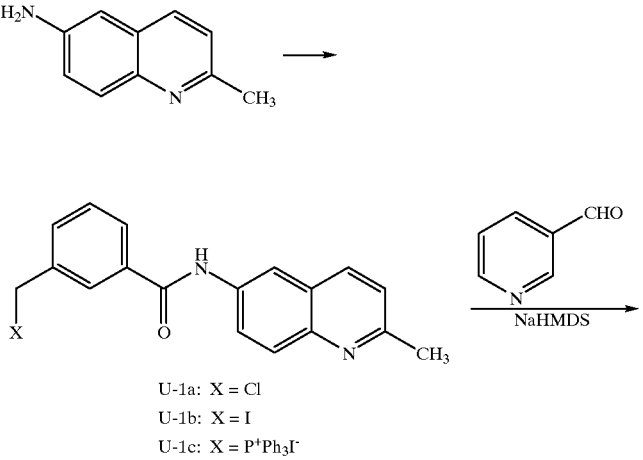

U-1a: X = Cl
U-1b: X = I
U-1c: X = P$^+$Ph$_3$I$^-$

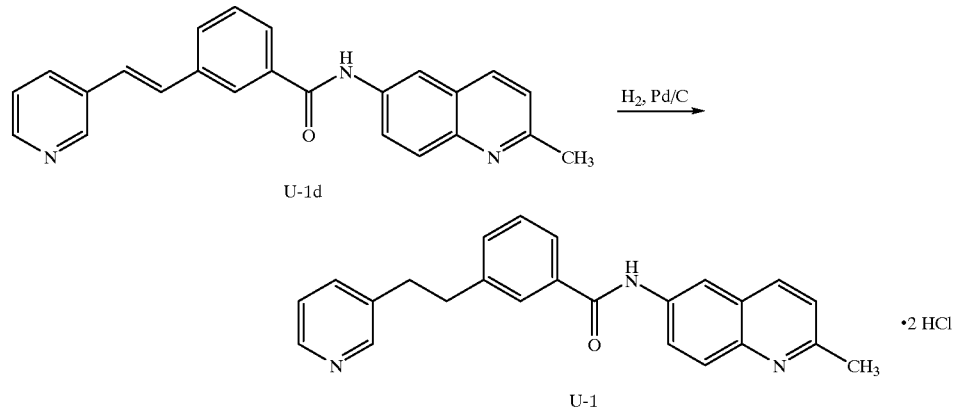

(a) A solution of 2-methyl-quinolin-6-ylamine (Maybridge, 836 mg, 5.29 mmol, 1.0 eq) and triethylamine (0.74 mL, 5.29 mmol, 1.0 eq) in dichloromethane (100 mL) was cooled to 0° C. and treated with 3-chloromethyl-benzoyl chloride (Aldrich, 0.75 mL, 5.29 mmol, 1.0 eq). A tan slurry forms within 30 minutes. After 1.0 hour, TLC (4% methanol/chloroform) gave no 2-methyl-quinolin-6-ylamine ($R_f$ 0.4), and a new spot with $R_f$ 0.6. A 5% sodium bicarbonate solution (100 mL) was added to the reaction mixture, and the aqueous layer was extracted with 10% isopropanol/chloroform (3×100 mL) to give a yellow solid (1.31 g). The product was washed with diethyl ether to give 3-chloromethyl-N-(2-methyl-quinolin-6-yl)-benzamide, U-1a, as a yellow solid (1.28 g, 78%): HPLC $R_t$=12.8 min.; TLC $R_f$=0.6 (4% methanol/chloroform); $^1$H NMR (300 MHz, DMSO-d$_6$) δ10.56 (s, 1H), 8.46 (d, 1H, J=2.2 Hz), 8.22 (d, 1H, J=8.4 Hz), 8.07–7.90 (m, 4H), 7.70–7.69 (m, 1H), 7.58 (t, 1H, J=7.6 Hz), 7.40 (d, 1H, J=8.4 Hz), 4.88 (s, 2H), 2.65 (s, 3H); $^{13}$C NMR (75 MHz, DMSO-d$_6$) □ 165.8, 158.0, 144.2, 138.4, 136.6, 136.5, 135.4, 132.5, 129.3, 128.4, 127.9, 126.7, 124.6, 123.0, 117.0, 116.8, 46.0, 24.7; MS (ESI) m/z 311 [M+H]$^+$.

(b) A solution of 3-chloromethyl-N-(2-methyl-quinolin-6-yl)-benzamide, U-1a, (500 mg, 1.6 mmol, 1.0 eq) in acetone (250 mL) was heated to 55° C. and treated with sodium iodide (3.2 g, 150 mmol, 13 eq). After 2.0 h, no starting material was detected by HPLC, and the resulting yellow solution was concentrated under reduced pressure. The resulting residue was treated with water (100 mL) and the aqueous layer was extracted with chloroform (3×100 mL). The combined organic extracts were washed with Na$_2$S$_2$O$_3$ (100 mL), brine (100 mL), dried over magnesium sulfate, filtered and concentrated under reduced pressure to give 3-iodomethyl-N-(2-methyl-quinolin-6-yl)-benzamide, U-1b, as a yellow solid (615 mg, 96%): HPLC $R_t$=13.6 min.; TLC $R_f$=0.5 (5% methanol/chloroform); $^1$H NMR (300 MHz, DMSO-d$_6$) δ10.52 (s, 1H), 8.44 (d, 1H, J=2.1 Hz), 8.22 (d, 1H, J=8.5 Hz), 8.12–7.88 (m, 4H), 7.68–7.66 (m, 1H), 7.51 (t, 1H, J=7.7 Hz), 7.40 (d, 1H, J=8.5 Hz), 4.72 (s, 2H), 2.65 (s, 3H); MS (ESI) m/z 403 [M+H]$^+$.

(c) A solution of 3-iodomethyl-N-(2-methyl-quinolin-6-yl)-benzamide, U-1b, (565 mg, 1.4 mmol, 1.0 eq) in acetone (140 mL) was treated with triphenylphosphine (1.80 g, 7.0 mmol, 5.0 eq) and heated to 55° C. to give a yellow solution. After 18 hours, the resulting slurry gave no starting material ($R_f$ 0.5) by TLC (5% methanol/chloroform), only product with $R_f$ 0.0–0.3. The solvent was removed under reduced pressure and the resulting solid was washed with methyl-tert-butyl ether (4×25 mL) to give N-(2-methyl-quinolin-6-yl)-3-[(triphenylphosphanyl)-methyl]-benzamide iodide, U-1c, as a yellow solid (809 mg, 87%): HPLC $R_t$=14.4 min.; TLC $R_f$=0.0–0.3 (5% methanol/chloroform); $^1$H NMR (500 MHz, DMSO-d$_6$) δ10.24 (s, 1H), 8.18 (d, 1H, J=1.1 Hz), 8.02 (d, 1H, J=8.5 Hz), 7.80 (d, 1H, J=7.8 Hz), 7.75–7.71 (m, 5H), 7.60–7.45 (m, 13H), 7.27–7.21 (m, 2H), 7.00 (d, 1H, J=7.7 Hz), 5.10 (d, 2H, J=15.7 Hz), 2.46 (s, 3H); MS (ESI) m/z 537 [M+H]$^+$.

(d) A solution of N-(2-methyl-quinolin-6-yl)-3-[(triphenylphosphanyl)-methyl]-benzamide iodide, U-1c, (600 mg, 0.90 mmol, 1.0 eq) in THF (20 mL) was cooled to −78° C. and treated with a 1.0 M solution of sodium bis(trimethylsilyl)amide in THF (1.9 mL, 1.9 mmol, 2.1 eq) to give a dark orange solution. The solution was aged for 30 min at −78° C., then treated with pyridine-3-carbaldehyde (93 μL, 0.99 mmol, 1.1 eq). The orange mixture was allowed to gradually warm to −30° C. over 2 h, removed from the cold bath and stirred at room temperature for 1.0 hour. The reaction was quenched with water (100 mL) and the aqueous layer was extracted with chloroform (3×100 mL). The combined organic extracts were washed with brine (100 mL), dried over magnesium sulfate, filtered and concentrated under reduced pressure to give a black oil (700 mg). The crude product was purified by radial chromatography over silica gel using 3–4% methanol/chloroform to give trans-N-(2-methyl-quinolin-6-yl)-3-(2-pyridin-3-yl-vinyl)-benzamide, U-1d, as a white solid (59 mg, 18%): HPLC $R_t$=12.3 min.; TLC $R_f$=0.4 (5% methanol/chloroform); $^1$H NMR (500 MHz, DMSO-d$_6$) δ10.50 (s, 1H), 8.45–8.41 (m, 3H), 8.20 (d, 1H, J=8.4 Hz), 7.96 (dd, 1H, J=2.3, 9.1 Hz), 7.91–7.88 (m, 3H), 7.63–7.60 (m, 1H), 7.47 (t, 1H, J=7.5 Hz), 7.41–7.39 (m, 2H), 7.31 (dd, 1H, J=4.8, 8.0 Hz), 6.92 (d, 1H, J=12.3 Hz), 6.78 (d, 1H, J=12.3 Hz), 2.64 (s, 3H); MS (ESI) m/z 366 [M+H]$^+$. Anal. calc'd for C$_{24}$H$_{19}$N$_3$O.0.2 H$_2$O: C, 78.11; H, 5.30; N, 11.39. Found: C, 78.08; H, 5.38; N, 11.25.

(d) A solution of trans-N-(2-methyl-quinolin-6-yl)-3-(2-pyridin-3-yl-vinyl)-benzamide, U-1d, (44 mg, 0.12 mmol) in methanol (3 mL) was shaken vigorously under hydrogen (40 psi) with 5% palladium on carbon for 24 h. The catalyst was filtered off, and the filtrate was concentrated under reduced pressure to give a clear oil (50 mg). The crude product was purified by radial chromatography over silica gel using 2–4% methanol/dichloromethane to give a clear oil. The oil was dissolved in ethanol and treated with 0.1 mL concentrated hydrochloric acid. The solvent was removed under reduced pressure to give N-(2-methyl-quinolin-6-yl)-

3-(2-pyridin-3-yl-ethyl)-benzamide hydrochloride, U-1, as a white solid (35 mg, 66%): HPLC R$_t$ 12.4 min.; $^1$H NMR (500 MHz, DMSO-d$_6$ w/D$_2$O) δ(s, 1H), 8.96 (d, 1H, J=8.7 Hz), 8.82–8.81 (m, 2H), 8.74 (d, 1H, J=5.4 Hz), 8.46 (d, 1H, J=8.0 Hz), 8.38 (dd, 1H, J=1.8, 9.2 Hz), 8.23 (d, 1H, J=9.2 Hz), 7.98–7.89 (m, 4H), 7.53–7.52 (m, 2H), 3.21 (t, 2H, J=7.8 Hz), 3.11 (t, 2H, J=7.7 Hz), 2.93 (s, 3H); $^{13}$C NMR (75 MHz, DMSO-d$_6$ w/D$_2$O) δ166.9, 156.6, 146.1, 144.8, 141.8, 141.3, 141.1, 140.2, 139.1, 135.0, 144.4, 132.8, 129.1, 128.5, 128.2, 127.6, 127.0, 126.1, 124.3, 121.4, 117, 35.7, 33.5, 20.9; MS (ESI) m/z 368 [M+H]$^+$. Anal. calc'd for C$_{24}$H$_{21}$N$_3$O.2HCl.0.3 H$_2$O: C, 64.66; H, 5.34; N, 9.43; Cl, 15.91. Found: C, 64.63; H, 5.40; N, 9.10; Cl, 15.62.

Example U-2

N-(4-Isopropyl-3-methyl-phenyl)-3-(2-pyridin-3-yl-ethyl)-benzamide

U-2

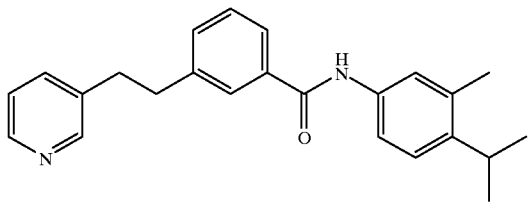

Example U-2 was prepared in a similar manner to that described for U-1, except that 3-methyl-4-isopropylaniline was used in place of 6-amino-2-methylquinoline in step (a): mp 143–144° C.; HPLC R$_t$=15.7 min.; TLC R$_f$=0.4 (2% methanol/dichloromethane); $^1$H NMR (300 MHz, DMSO-d$_6$) δ10.04 (s, 1H), 8.45 (s, 1H), 8.40 (d, 1H, J=4.5 Hz), 7.82–7.76 (m, 2H), 7.67 (d, 1H, J=7.5 Hz), 7.55–7.41 (m, 4H), 7.32–7.28 (m, 1H), 7.20 (d, 1H, J=8.3 Hz), 3.12–3.03 (m, 1H), 2.98 (s, 4H), 2.29 (s, 3H), 1.18 (d, 6H, J=6.8 Hz); HRMS (FAB) calcd for C$_{24}$H$_{26}$N$_2$O [M+H]$^+$359.2123, found 359.2117.

Example V-1

N-{3-[(1H-pyrazolo[3,4-d]-pyrimidin-4-ylsulfanylmethyl]phenyl}-(3-bromo-4-methyl)benzamide

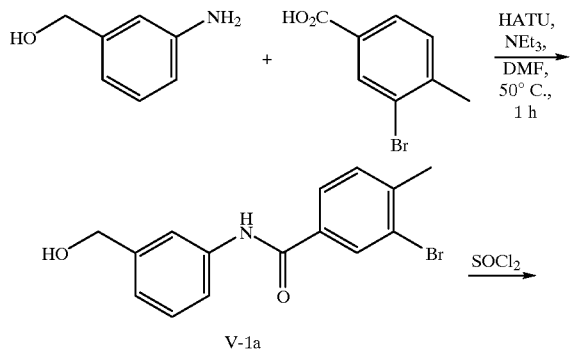

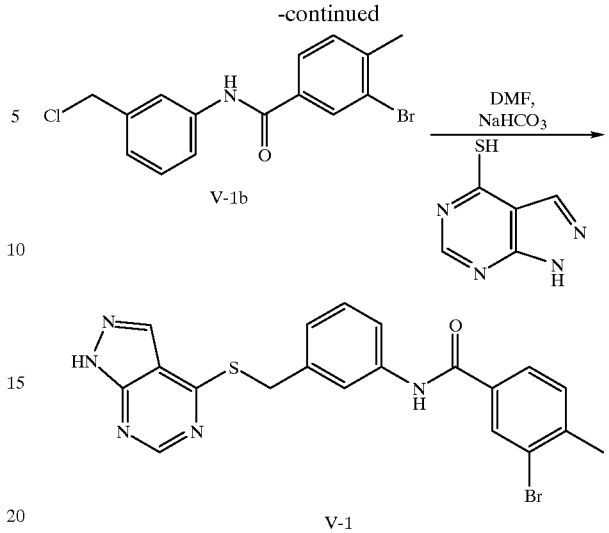

(a) To a solution of 3-amino benzyl alcohol (123 mg, 1 mmol), 3-bromo-4-methylbenzoic acid (215 mg, 1 mmol) and O-(7-azabenzotriazol-1-yl)-N,N,N',N'-tetramethyluronium hexafluorophosphate (HATU, 380 mg, 1 mmol) in 5 mL DMF was added 0.14 mL of triethylamine (1 mmol) and the reaction mixture stirred at 50° C. for 1 h. The solvent was removed in vacuo and the residue was purified by chromatography to obtain 3-bromo-N-[3-hydroxymethyl)phenyl]-4-methylbenzamide, V-1a, (310 mg, 96%): $^1$H NMR (300 MHz, DMSO-d$_6$) δ10.03 (s, 1H), 7.97 (s, 1H), 7.67 (d, 1H, J=7.5 Hz), 7.52 (s, 1H), 7.43 (d, 1H, J=7.6 Hz), 7.28 (d, 1H, J=6.9 Hz), 7.06 (m, 1H), 6.81–6.84 (d, 1H, J=7.1 Hz), 5.01 (br s, 1H), 4.27 (d, 2H, J=4.5 Hz), 2.20 (s, 3H); APCIMS m/z 338 [M+H]$^+$.

(b) To 3-bromo-N-[3-hydroxymethyl)phenyl]-4-methylbenzamide, V-1a, (310 mg, 0.96 mmol) was added 5 mL of thionyl chloride and the reaction mixture stirred for 15 min. Thionyl chloride was removed in vacuo and the crude dissolved in ethyl acetate and filtered through a plug of silica gel. The filtrate and washings were combined and the solvent removed to obtain 3-bromo-N-[3-chloromethyl)phenyl]-4-methylbenzamide, V-1b (217 mg, 66%): $^1$H NMR (300 MHz, DMSO-d$_6$) δ10.45 (s, 1H), 8.30 (s, 1H), 7.97–8.01 (m, 2H), 7.83 (d, 1H, J=8.3 Hz), 7.62 (d, 1H, J=8.3 Hz), 7.42–7.49 (m, 1H), 7.27 (d, 1H, J=7.5 Hz), 4.87 (s, 2H), 2.52 (s, 3H).

(c) To a solution of 97 mg (0.64 mmol) of 4-mercapto-1H-pyrazolo-[3,4-d]pyrimidine in 2 mL of DMF was added NaHCO$_3$ (80 mg) and 217 mg (0.64 mmol) of 3-bromo-N-[3-chloromethyl)phenyl]-4-methylbenzamide, V-1b. The reaction mixture stirred at 50° C. for 2 h. The solvent was removed and water was added to the residue. The resulting solid was filtered, washed with water and dried. The desired N-{3-[(1H-pyrazolo[3,4-d]-pyrimidin-4-ylsulfanylmethyl]phenyl}-(3-bromo-4-methy)benzamide, V-1, was obtained by silica gel column chromatography purification (85 mg, 30%): $^1$H NMR (300 MHz, DMSO-d$_6$) δ14.14 (s, 1H), 10.31 (s, 1H), 8.82 (s, 1H), 8.33 (s, 1H), 8.20 (s, 1H), 7.9–7.93 (m, 2H), 7.71 (d, 1H,J=6.8 Hz), 7.54 (d, 1H,J=7.9 Hz), 7.34 (dd, 1H, J=7.50, 7.9 Hz), 7.25 (d, 1H, J=6.8 Hz), 4.73 (s, 2H), 2.54 (s, 3H): APCIMS m/z 454 [M+H]$^+$.

Example V-2

N-{3-[(1H-pyrazolo[3,4-d]-pyrimidin-4-ylsulfanylmethyl]phenyl}-3,5-bis(trifluoromethyl)benzamide

V-2

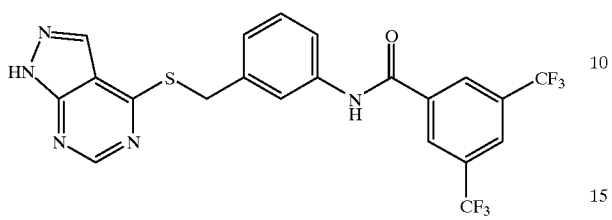

Example V-2 was prepared in a similar manner to that described for V-1, except that 3,5-bis(trifluoromethyl)benzoic acid was used in place of 3-bromo-4-methylbenzoic acid in step (a): $^1$H NMR (300 MHz, DMSO-$d_6$) δ14.05 (s, 1H), 10.60 (s, 1H), 8.73 (s, 1H), 8.52 (s, 2H), 8.31 (s, 1H), 8.23 (s, 1H), 7.82 (s, 1H), 7.63 (d, 1H, J=7.5 Hz), 7.20–7.32 (m, 2H), 4.66 (s, 2H); APCIMS m/z 498 [M+H]$^+$.

Example V-3

N-{3-[(1H-pyrazolo[3,4-d]-pyrimidin-4-yl)sulfanylmethyl]phenyl}-(4-hydroxy-3-methoxy)benzamide

V-3

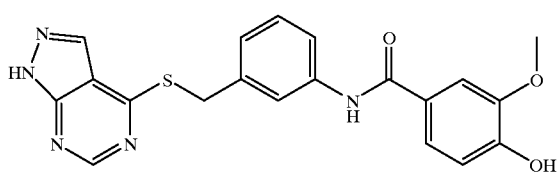

Example V-3 was prepared in a similar manner to that described for V-1, except that 4-hydroxy-3-methoxybenzoic acid was used in place of 3-bromo-4-methylbenzoic acid in step (a): $^1$H NMR (300 MHz, DMSO-$d_6$) δ14.05 (s, 1H), 9.93 (s, 1H), 9.63 (s, 1H), 8.72 (s, 1H), 8.23 (s, 1H), 7.81 (s, 1H), 7.58 (m, 1H), 7.43 (s, 2H), 7.13–7.25 (m, 2H), 6.78–6.80 (m, 1H), 4.66 (s, 2H), 3.27 (s, 3H); APCIMS m/z 408 [M+H]$^+$.

Example V-4

N-{3-[(1H-pyrazolo[3,4-d]-pyrimidin-4-yl)sulfanylmethyl]phenyl}-(4-hydroxy-3-t-butyl)benzamide

V-4

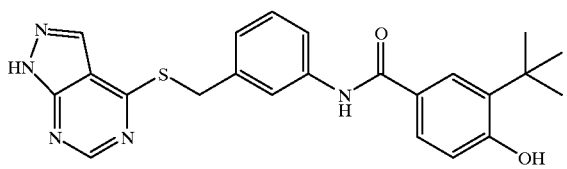

Example V-4 was prepared in a similar manner to that described for V-1, except that 3-t-butyl-4-hydroxybenzoic acid was used in place of 3-bromo-4-methylbenzoic acid in step (a): $^1$H NMR (300 MHz, DMSO-$d_6$) δ13.96 (s, 1H), 9.91 (s, 1H), 9.83 (s, 1H), 8.63 (s, 1H), 8.14 (s, 1H), 7.71 (s, 1H), 7.57 (s, 1H), 7.47–7.53 (m, 2H), 7.11 (dd, 1H, J=7.9, 8.0 Hz), 7.01 (d, 1H, J=7.2 Hz), 6.69 (d, 1H, J=8.3 Hz), 4.52 (s, 2H), 1.22 (s, 9H); APCIMS m/z 434 [M+H]$^+$.

Example V-5

N-{3-[(1H-pyrazolo[3,4-d]-pyrimidin-4-yl)sulfanylmethyl]phenyl}-4-t-butylbenzamide

V-5

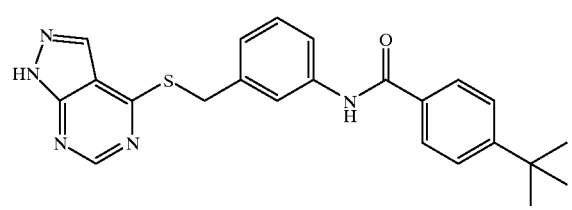

Example V-5 was prepared in a similar manner to that described for V-1, except that 4-t-butylbenzoic acid was used in place of 3-bromo-4-methylbenzoic acid in step (a): $^1$H NMR (300 MHz, DMSO-$d_6$) δ14.05 (s, 1H), 10.02 (s, 1H), 8.73 (s, 1H), 8.23 (s, 1H), 7.85 (s, 1H), 7.79 (d, 2H,J=8.3 Hz), 7.61 (d, 1H, J=7.6 Hz), 7.46(d, 2H,J=8.3 Hz), 7.23 (dd, 1H,J=7.50, 7.9 Hz), 7.13 (d, 1H,J=7.6 Hz), 4.68 (s, 2H), 1.25 (s, 9H); APCIMS m/z 418 [M+H]$^+$.

Example V-6

N-{3-[(1H-pyrazolo[3,4-d]-pyrimidin-4-yl)sulfanylmethyl]phenyl}-(4-phenoxy)benzamide

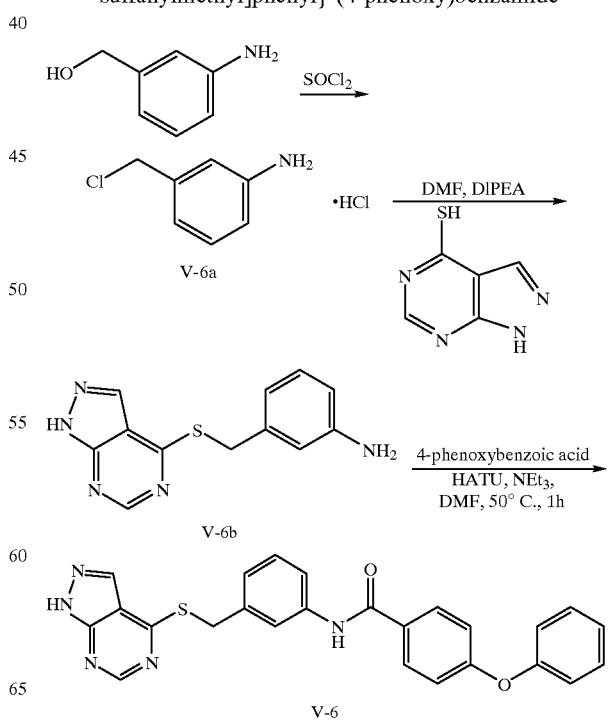

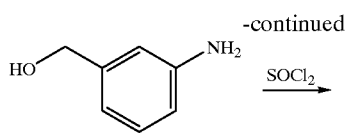
-continued

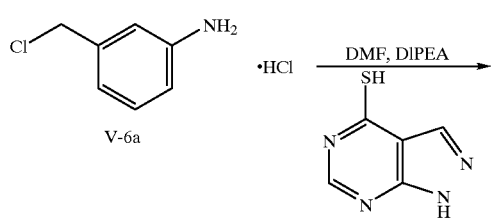

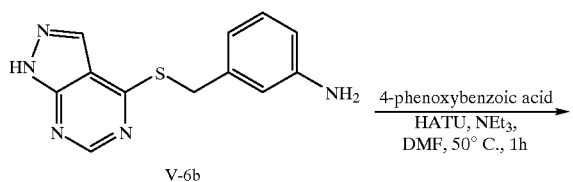

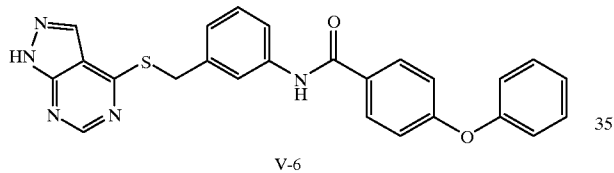

(a) To 3-aminobenzyl alcohol (1.23 g, 10 mmol) was added 20 mL of thionyl chloride and the reaction was stirred at room temperature when a yellow solid separated out within five min. The reaction was monitored by TLC for completion and excess thionyl chloride was removed in vacuo to obtain the hydrochloride salt of 3-aminobenzylchloride (V-6a). To 4-mercapto-1H-pyrazolo-[3,4-d]pyrimidine (1.5 g, 10 mmol) in 5 mL of DMF was added 4.6 mL of diisopropylethylamine (25 mmol) followed by the addition of the hydrochloride salt of 3-aminobenzylchloride (V-6a) and the reaction mixture stirred at 50° C. for 1 h. The solvent was removed in vacuo and the product 3-[(1H-pyrazolo[3,4-d]-pyrimidin-4-yl)sulfanylmethyl]aniline, V-6b, crystallized (1.1 g, 42%): $^1$H NMR (300 MHz, DMSO-$d_6$) δ14.13 (s, 1H), 8.79 (s, 1H), 8.31 (s, 1H), 7.18 (dd, 1H, J=8.0, 8.3 Hz), 6.80 (d, 1H, J=8.3 Hz), 4.64 (s, 2H); APCIMS m/z 258 [M+H]$^+$.

(b) To a solution of 64.5 mg (0.25 mmol) of 3-[(1H-pyrazolo[3,4-d]-pyrimidin-4-yl)sulfanyl-methyl]aniline, V-6b, and 53.5 mg (0.25 mmol) of 4-phenoxybenzoic acid in 2 mL DMF was added O-(7-azabenzotriazol-1-yl)-N,N,N',N'-tetramethyluronium hexafluorophosphate (HATU, 95 mg, 0.25 mmol) and triethylamine (0.03 mL, 0.25 mmol). The reaction was stirred at 50° C. for 1 h. After a conventional aqueous work-up, N-{3-[(1H-pyrazolo[3,4-d]-pyrimidin-4-yl)sulfanylmethyl]phenyl}-(4-phenoxy)benzamide, V-6, was obtained by chromatography on silica gel: $^1$H NMR (300 MHz, DMSO-$d_6$) δ14.10 (s, 1H), 10.19 (s, 1H), 8.79 (s, 1H), 8.30 (s, 1H), 7.97 (d, 2H,J=8.7 Hz), 7.90 (s, 1H), 7.67 (d, 1H, J=8.3 Hz), 7.46 (dd, 2H,J=7.60, 8.3 Hz), 7.31 (d, 1H,J=7.6 Hz), 7.267 (d, 1H,J=8.3 Hz), 7.19–7.22 (m, 2H), 7.07–7.12 (m, 3H), 4.70 (s, 2H); APCIMS m/z 454 [M+H]$^+$.

Example V-6c 0.1 M solutions of different acids, an amine template, HATU, and triethylamine were prepared in anhydrous DMF. To each tube in an array of 8×11 culture tubes (10×75 mm) was added 105 μL (0.0105) of a different acid. To this was added 100 μL (0.01 mmol) of the amine solution, 105 μL (0.0105 mmol) of the triethylamine solution followed by 105 μL (0.0105 mmol) of the o-(7-azabenzotriazol-1-yl)-N, N,N',N'-tetra-methyluronium hexafluorophosphate solution. The reactions were stirred in a heating block at 50° C. for 3 h. The reaction mixtures were transferred to a 1 mL 96-well plates using a liquid handler. The solvents were removed using the SpeedVac™ apparatus and the crude reaction mixtures were redissolved in DMSO to give a final theoretical concentration of 10 mM.

Example V-6d

Using the general procedure described in Example V-6c above, the following compounds were made:

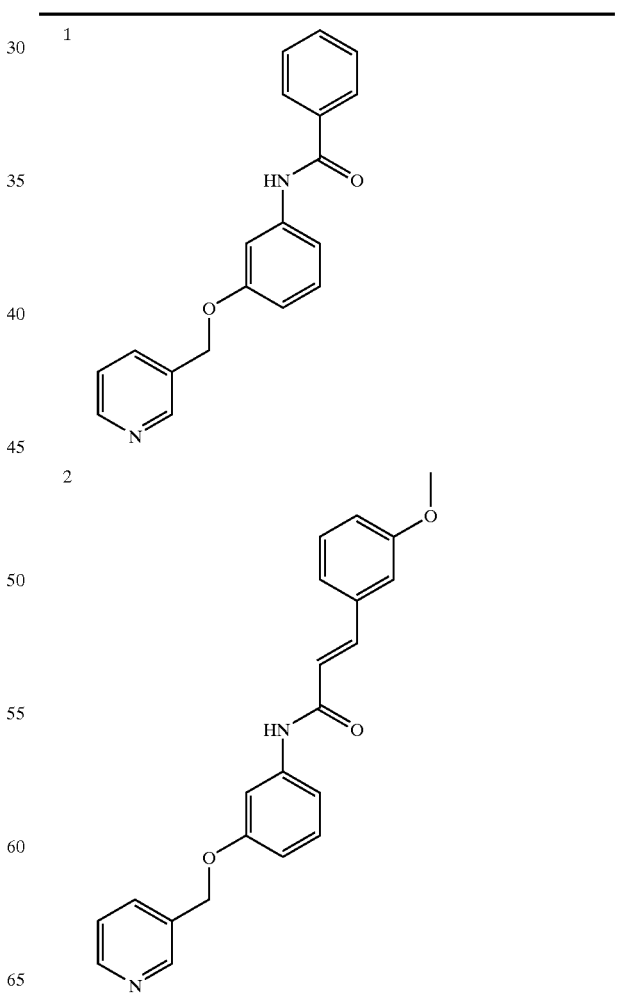

-continued
3
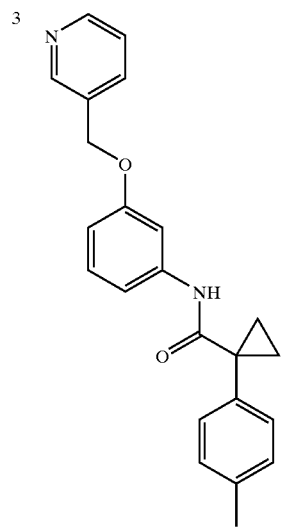
4
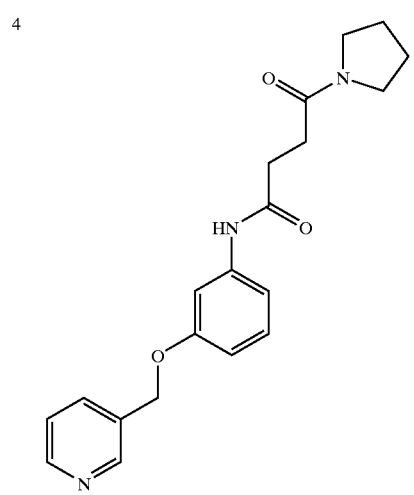
5
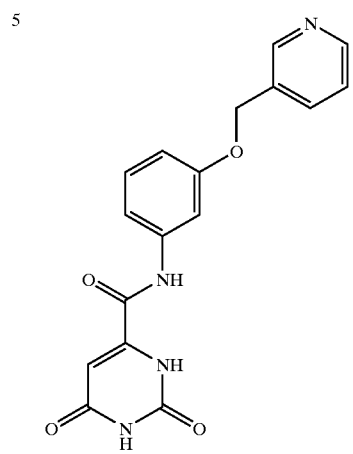
-continued
6
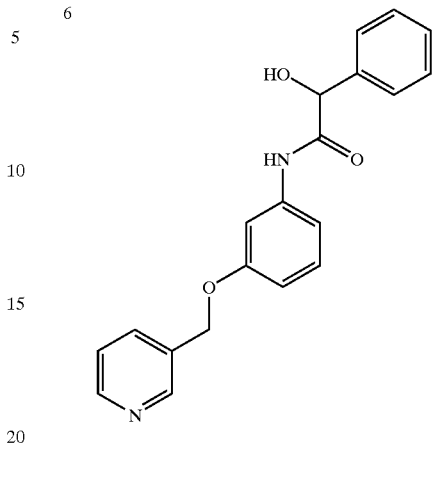
7
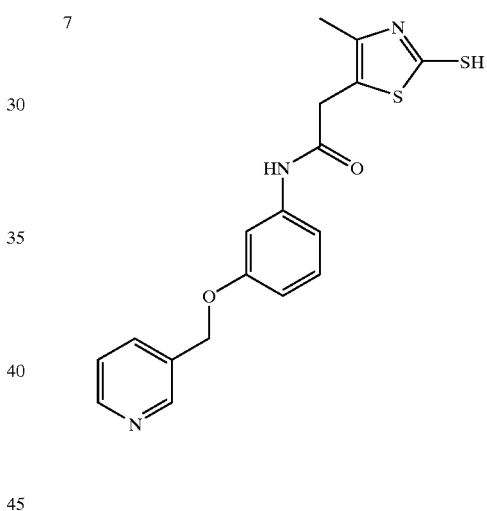
8
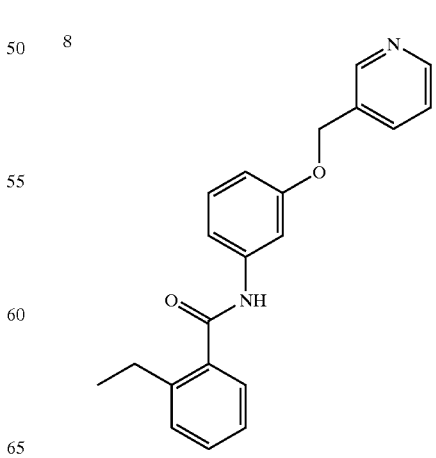

9
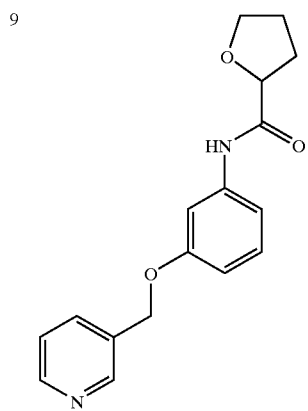
10
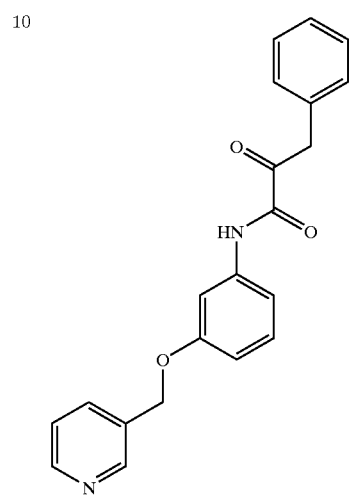
11
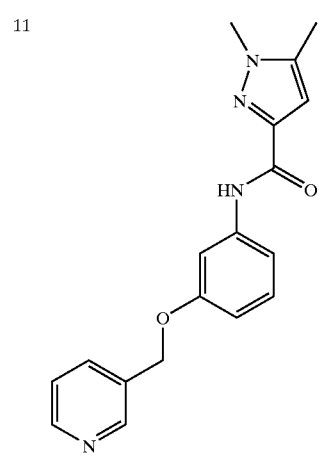
12
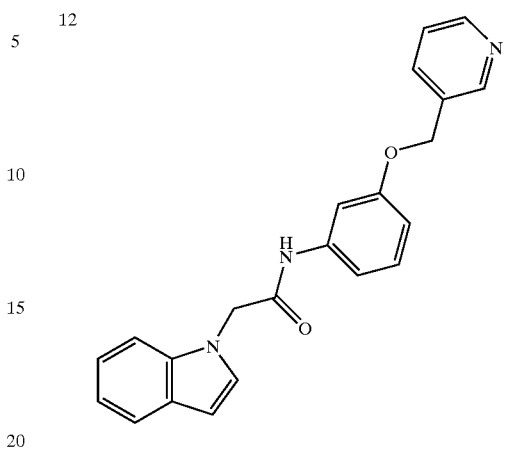
13
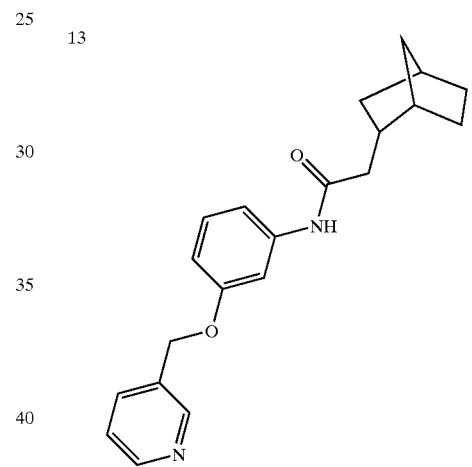
14
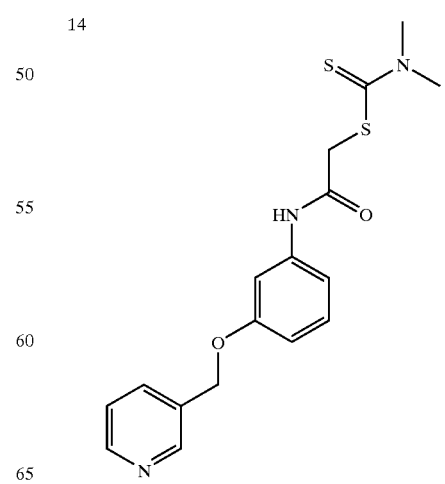

-continued
15
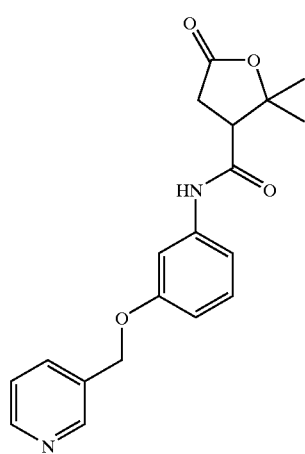
16
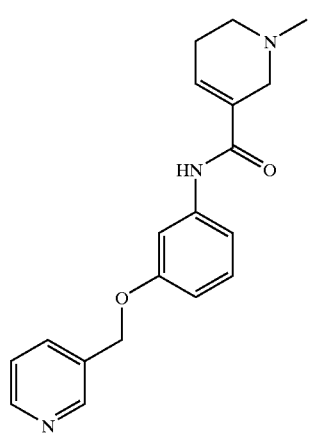
17
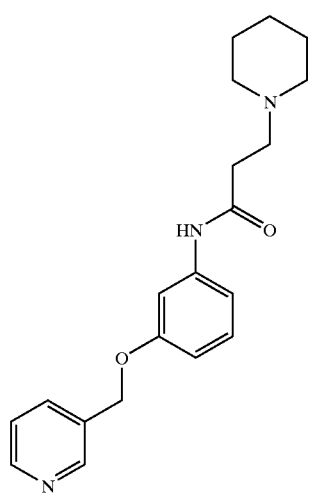
-continued
18
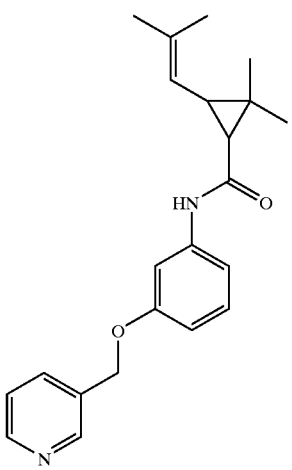
19
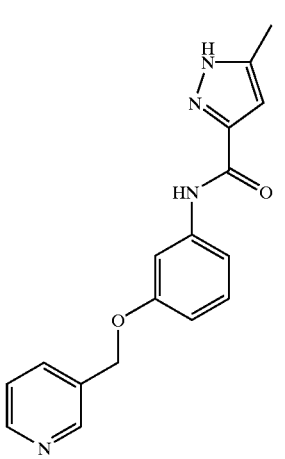
20
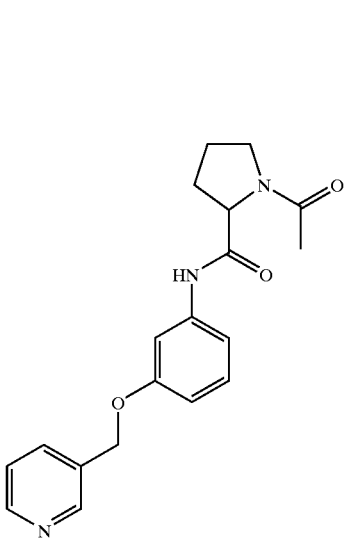

-continued
21
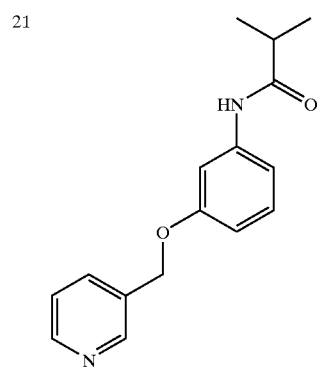
24
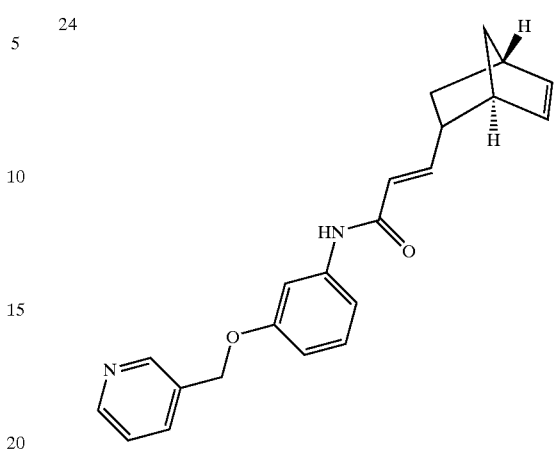
22
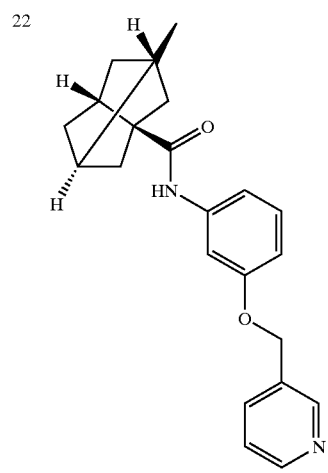
25
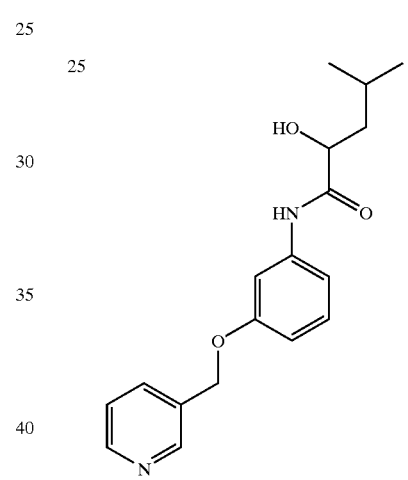
23
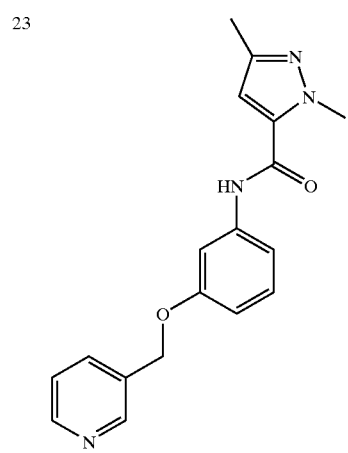
26
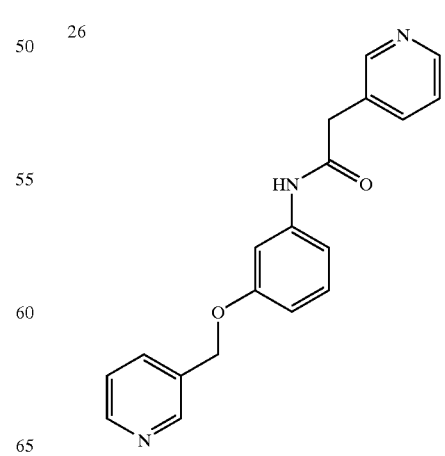

-continued
27
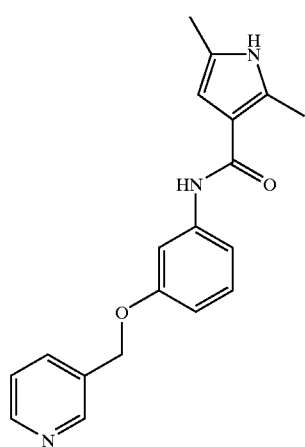
28
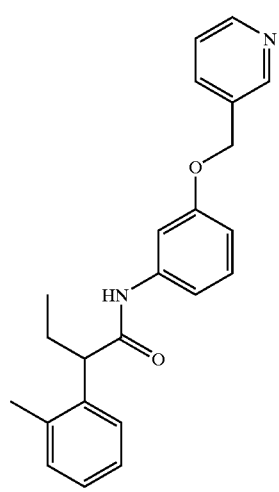
29
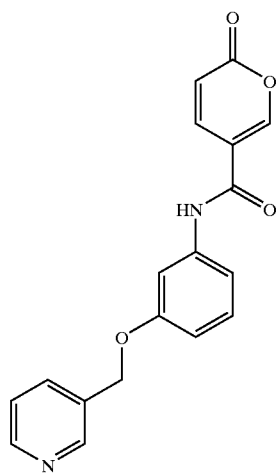
-continued
30
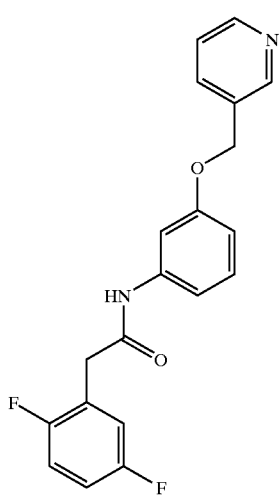
31
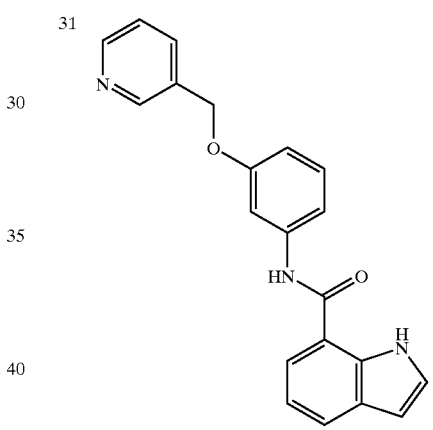
32
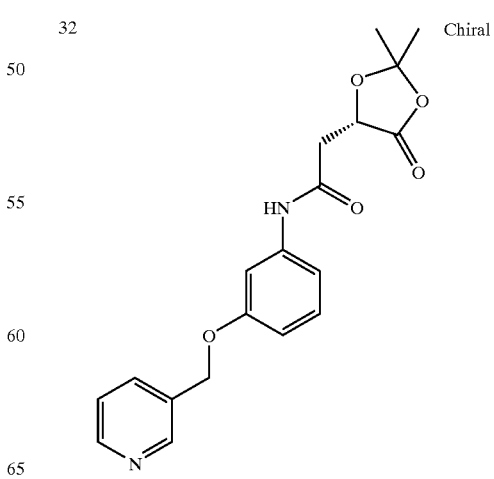

33 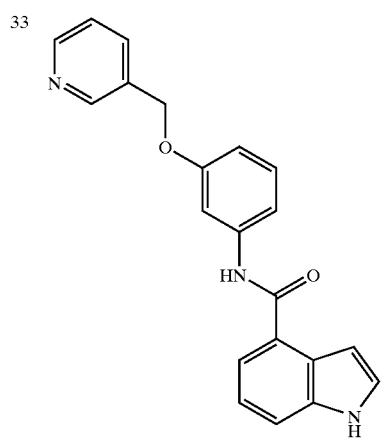
36 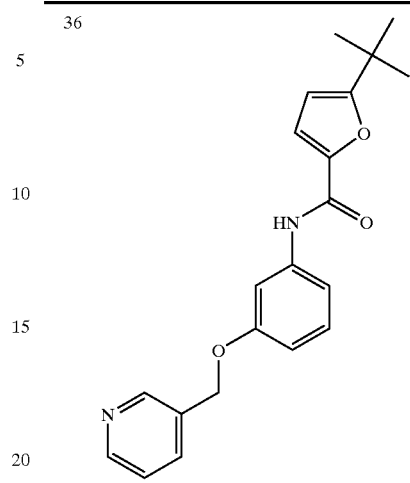
34 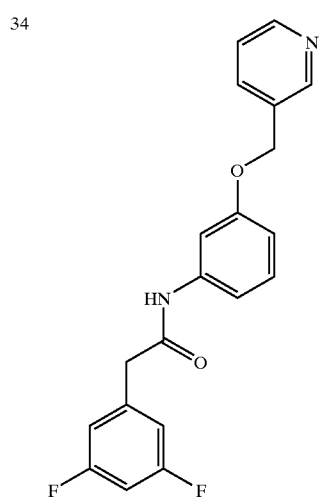
37 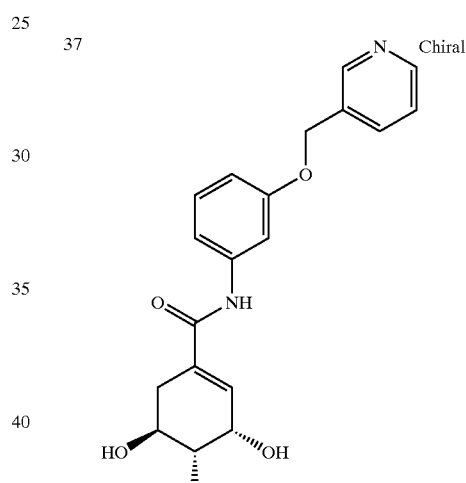
35 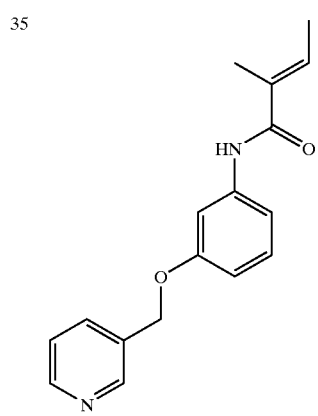
38 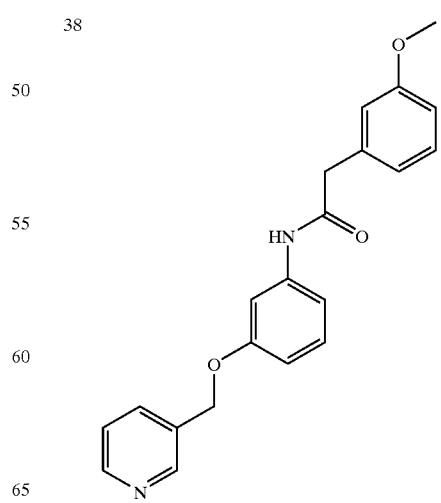

-continued
39
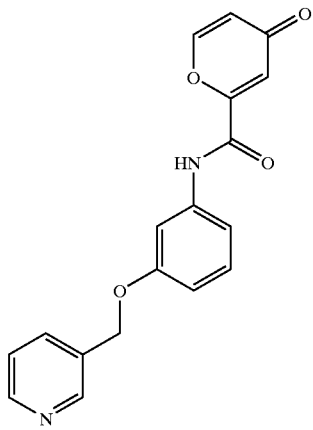
40
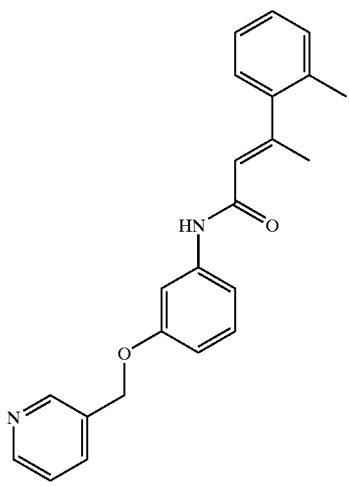
41
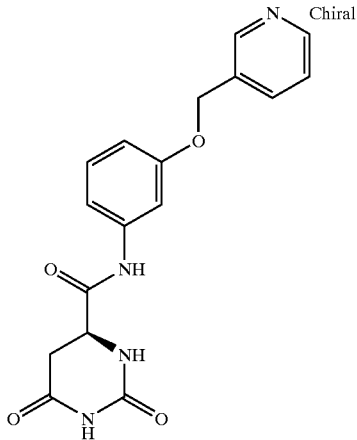
-continued
42
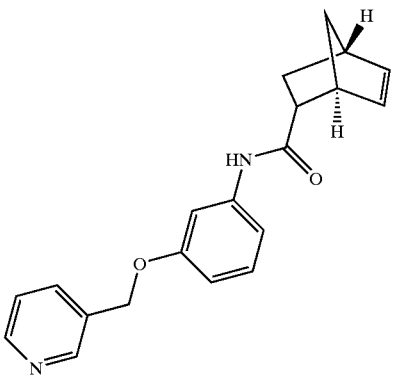
43
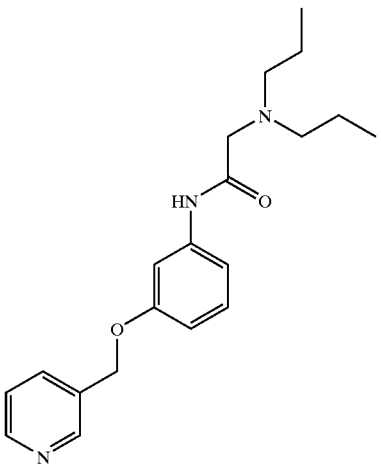
44
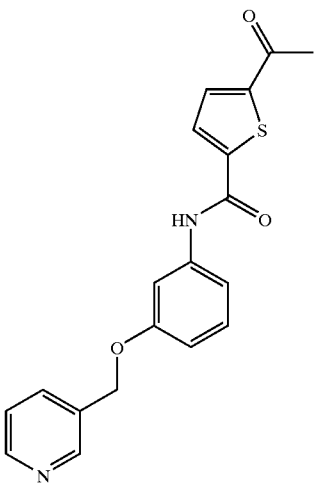

-continued
45
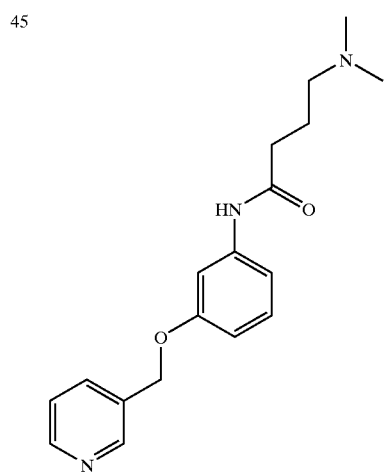
46
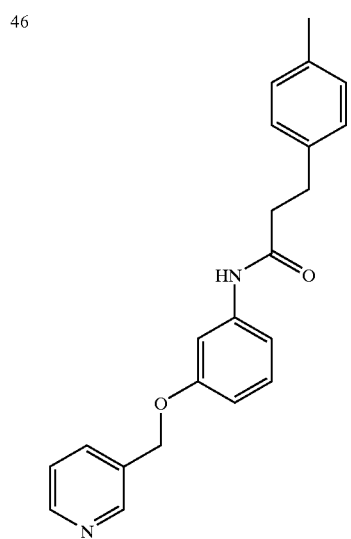
47
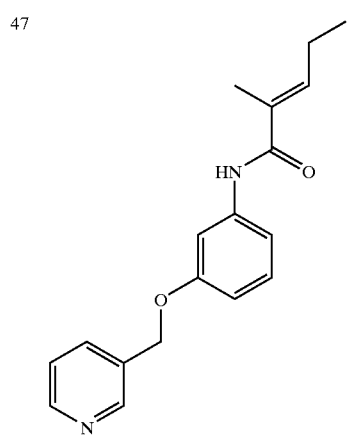
-continued
48
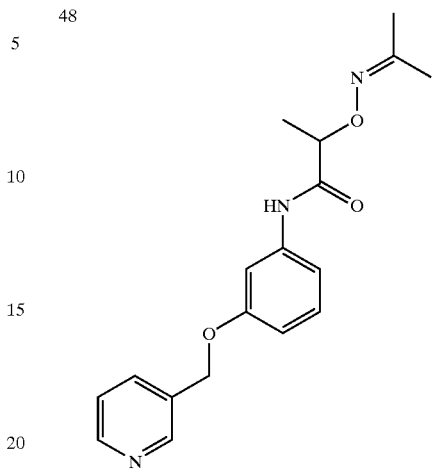
49
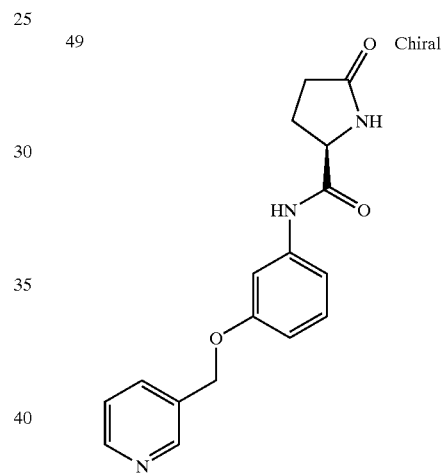
50
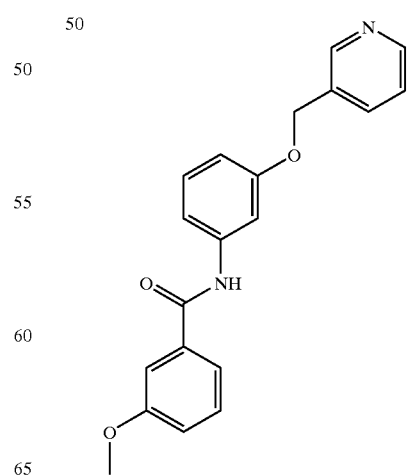

-continued
51
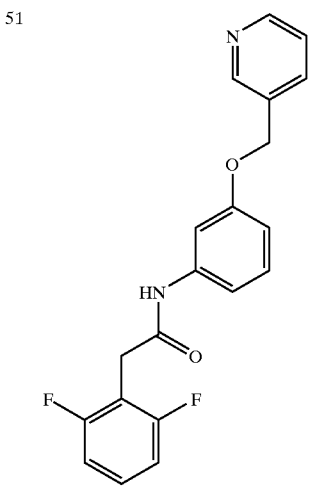
54
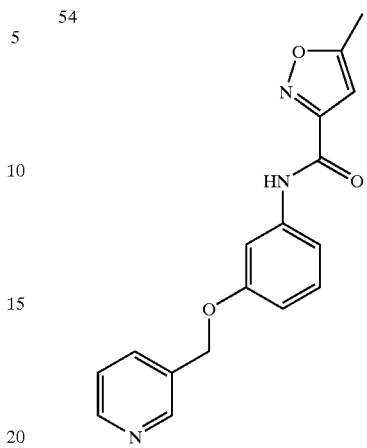
52
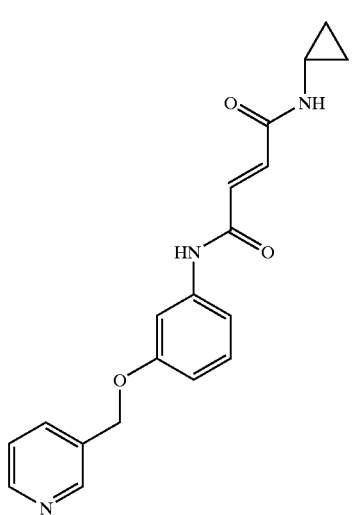
55
56
53
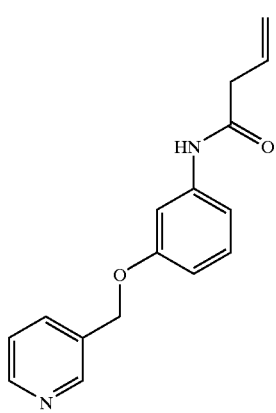

-continued
57
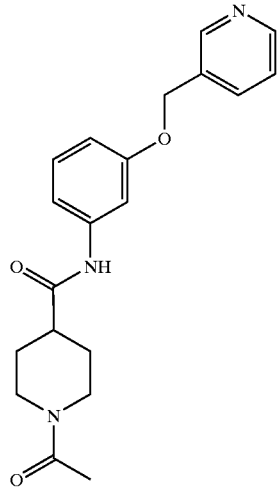
58
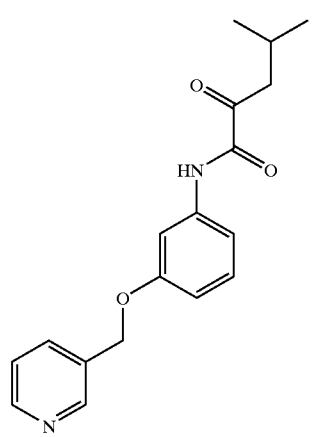
59
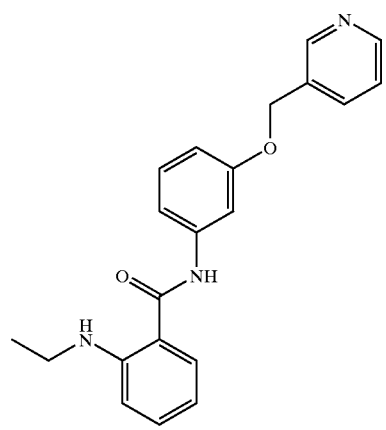
-continued
60
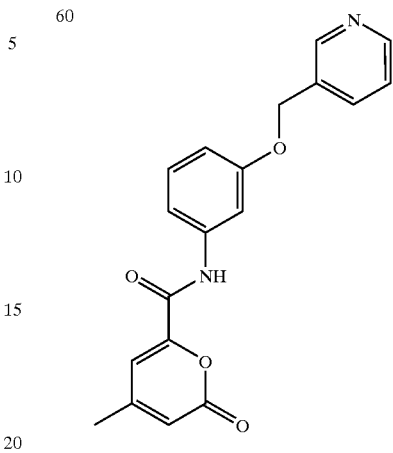
61
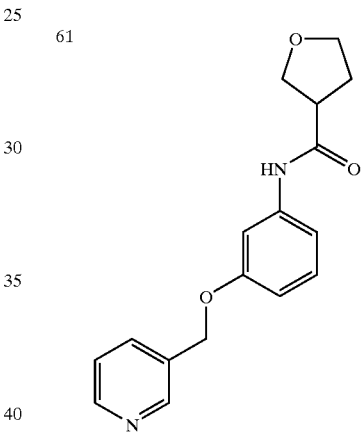
62
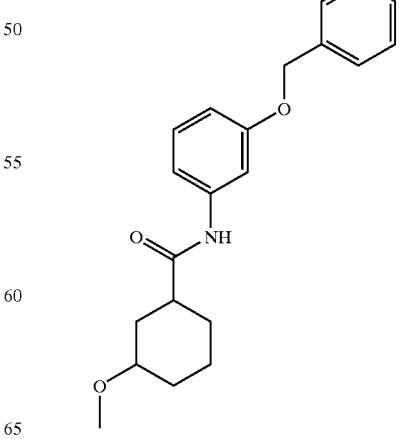

-continued
63
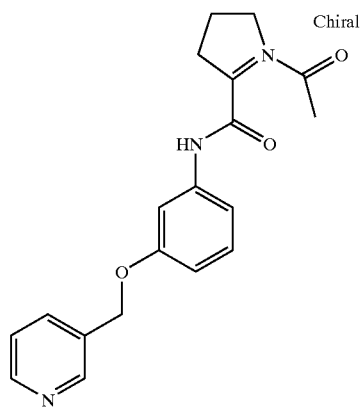
64
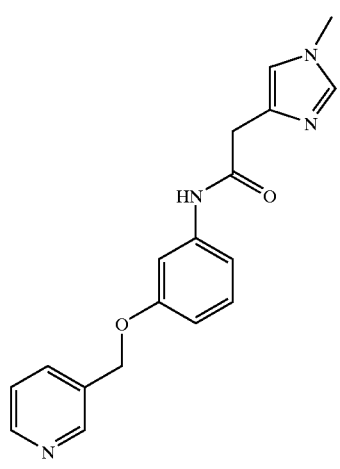
65
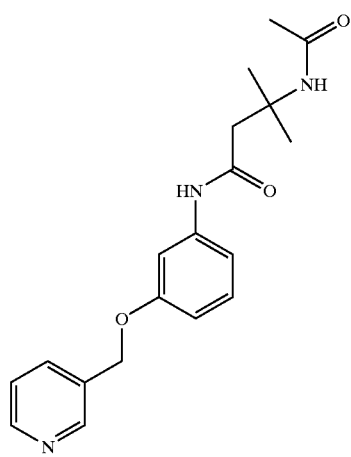
-continued
66
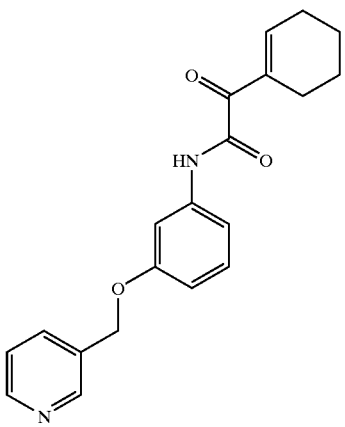
67
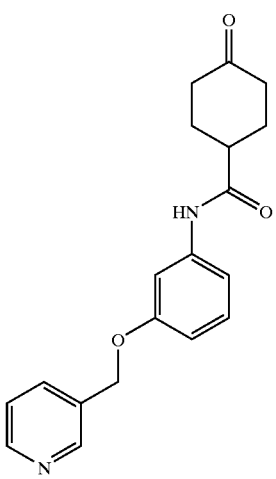
68
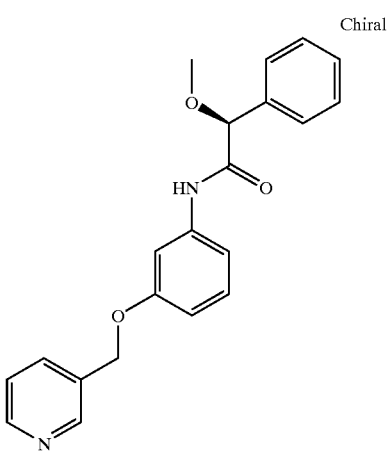

| 69 | 72 |
|---|---|
| 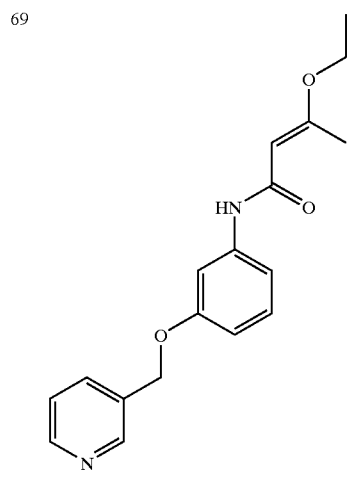 | 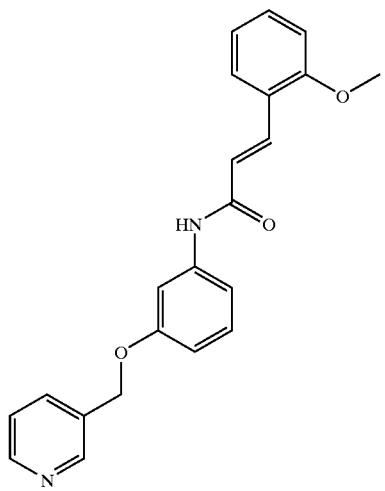 |
| 70 | 73 |
| 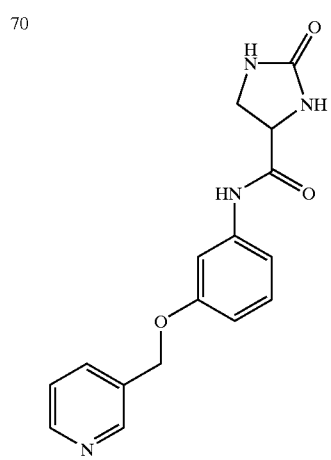 | 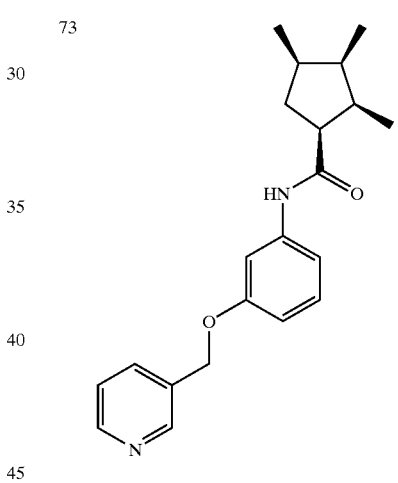 |
| 71 | 74 |
| 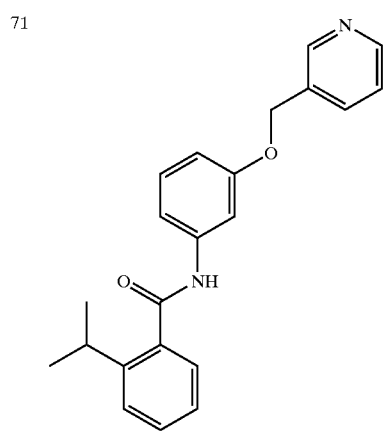 | 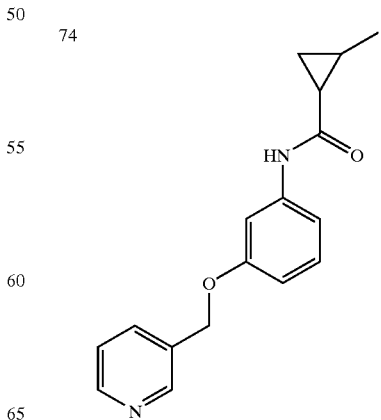 |

-continued
75 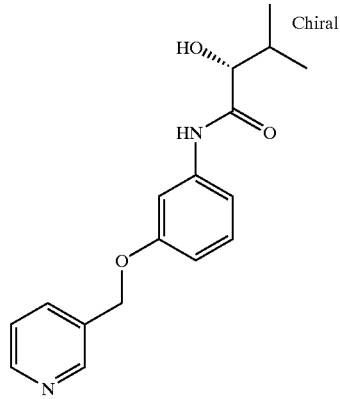
76 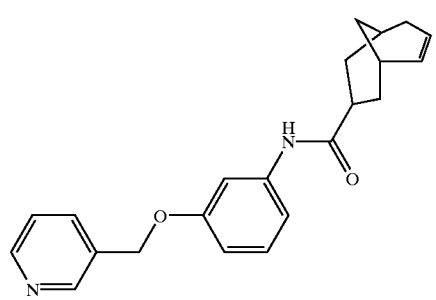
77 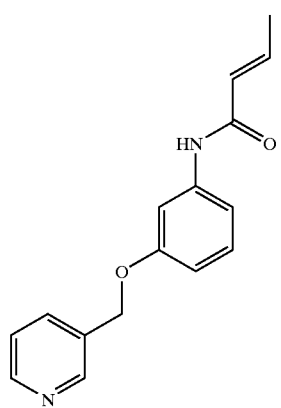
78 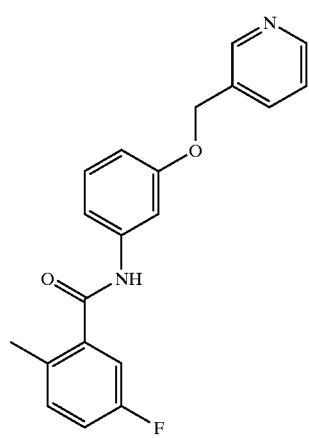
-continued
79 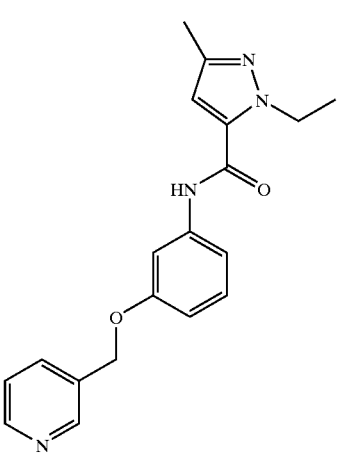
80 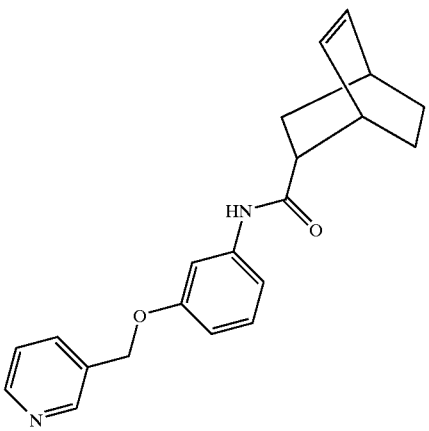
81 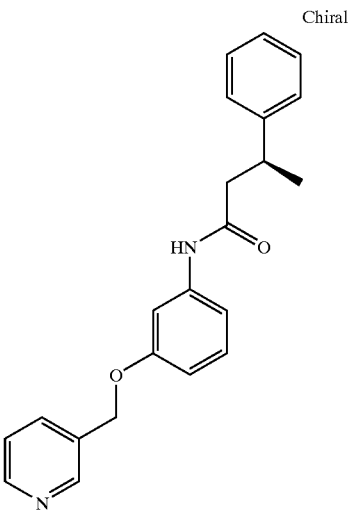

| 82 | 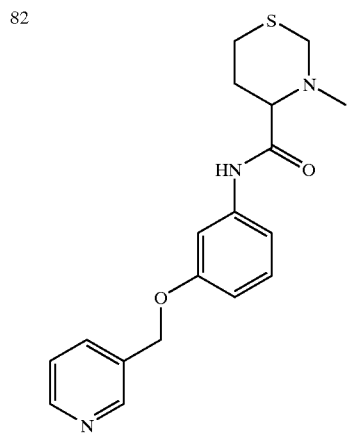 |
|---|---|
| 83 | 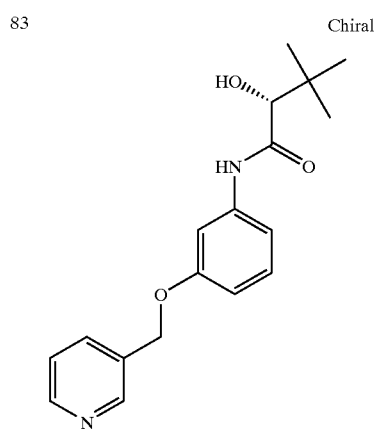 Chiral |
| 84 | 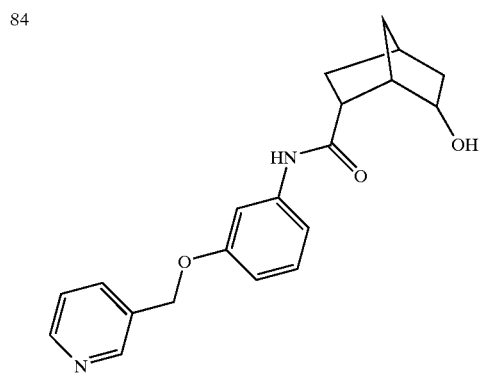 |
| 85 | 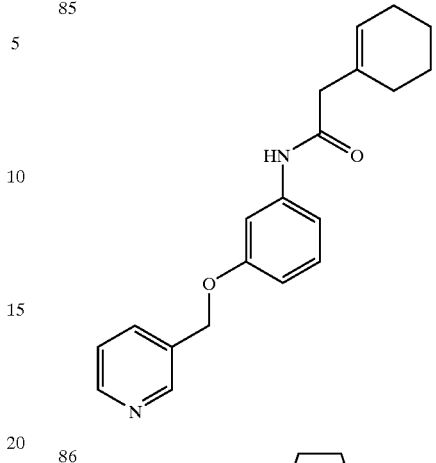 |
|---|---|
| 86 | 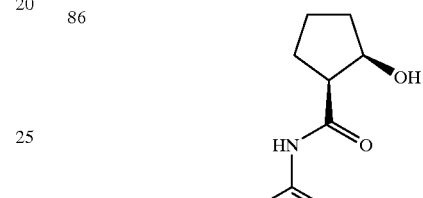 |
| 87 | 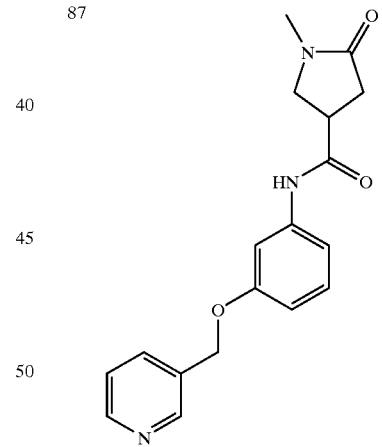 |
| 88 | 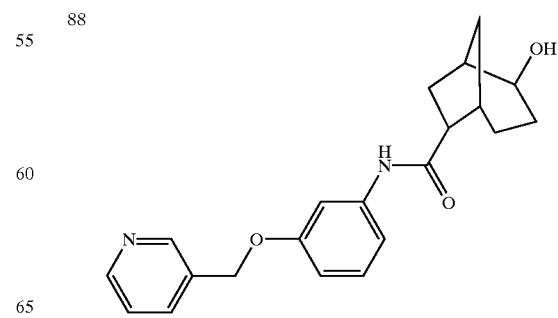 |

-continued

89

90

91

-continued

92

93  Chiral

94

-continued
95
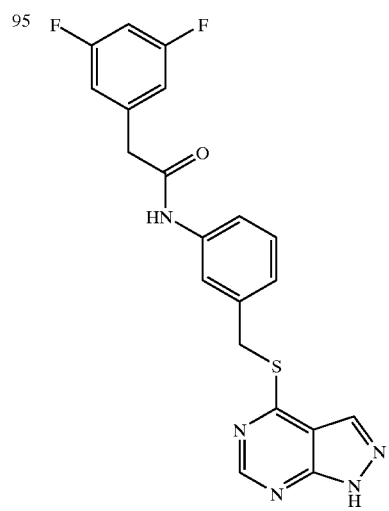
96
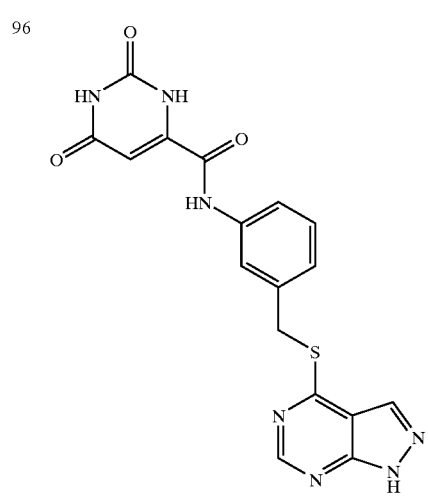
97
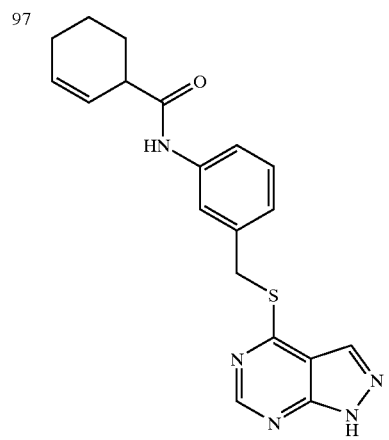
-continued
98
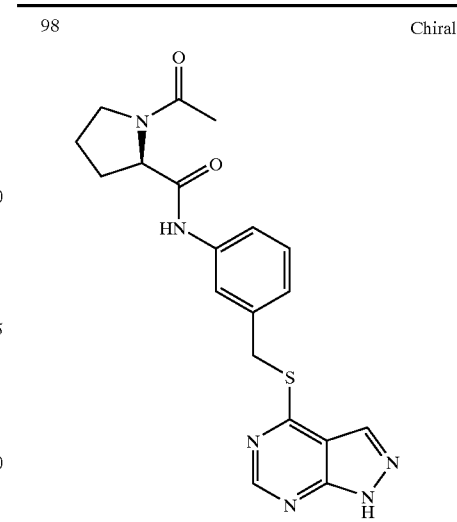
Chiral
99
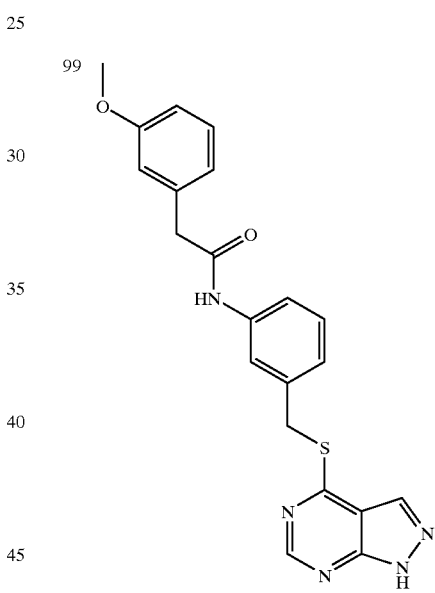
100
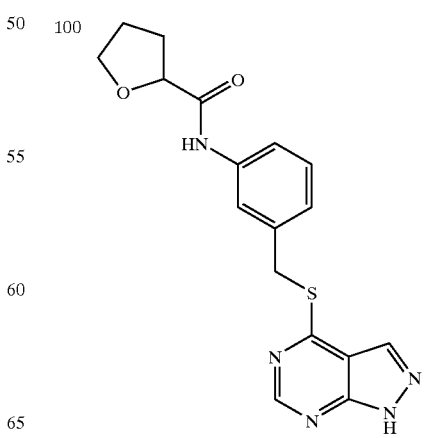

-continued
101
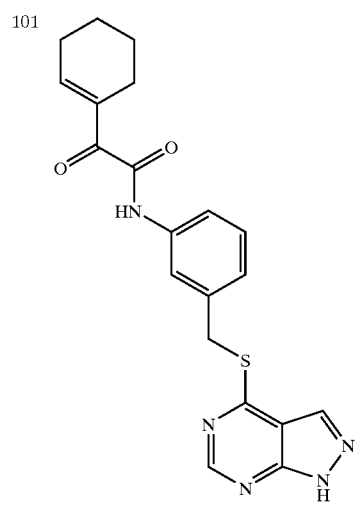
102
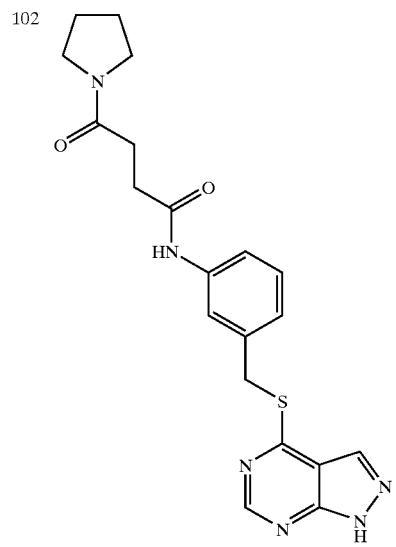
103
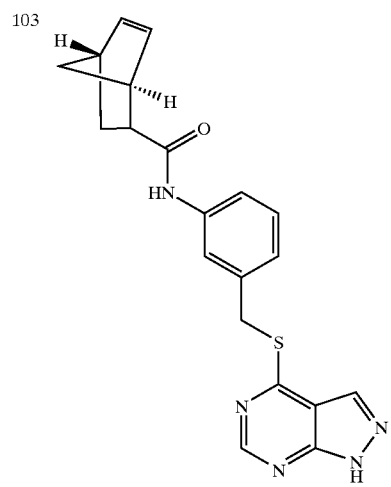
-continued
104
105
106
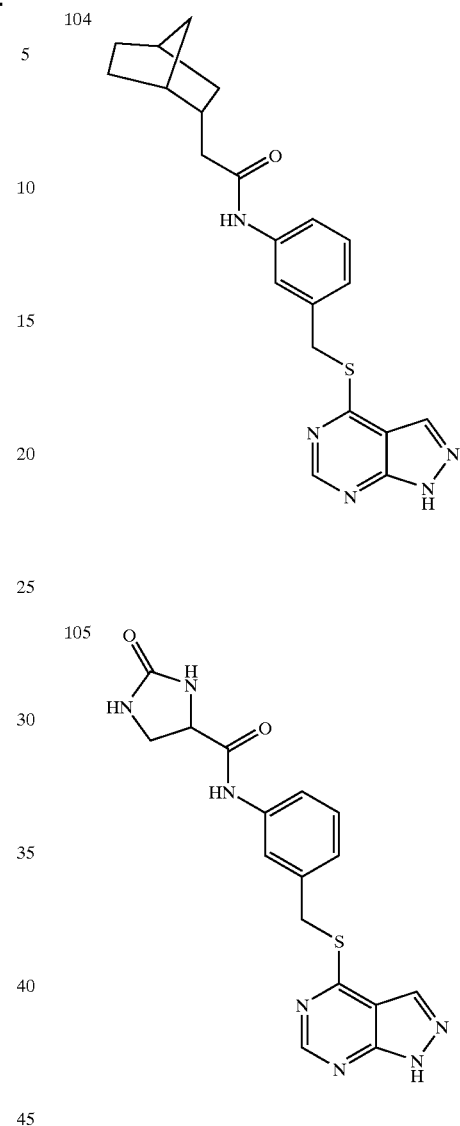
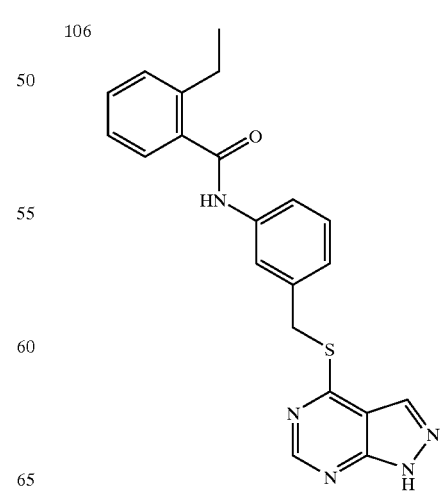

| 241 | 242 |
|---|---|
| -continued | -continued |
107
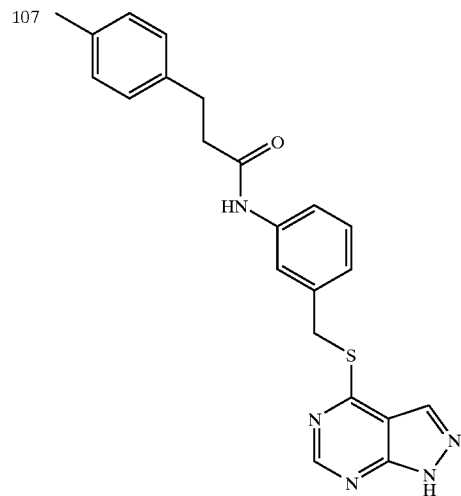
110
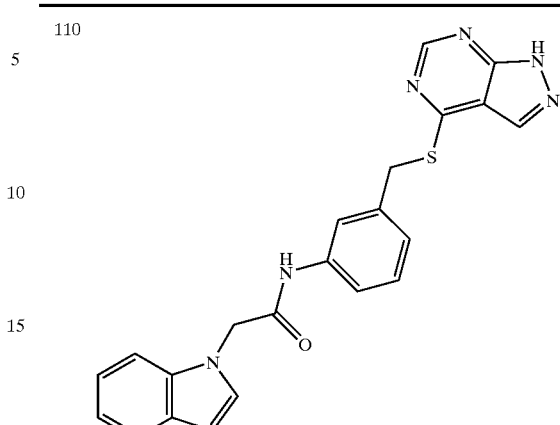
108
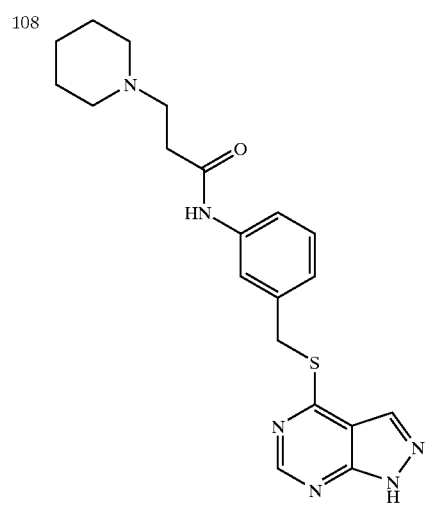
111
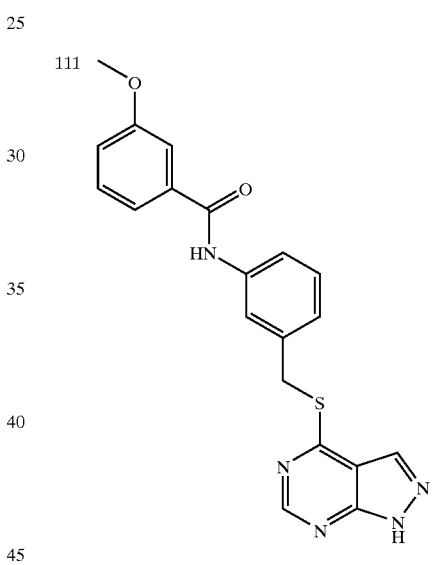
109
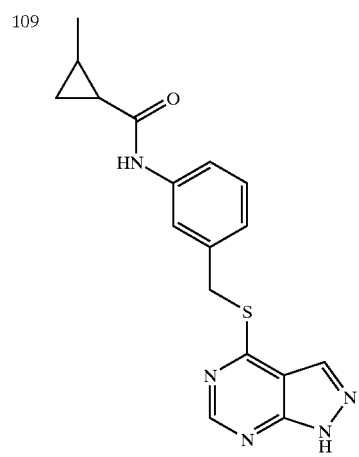
112
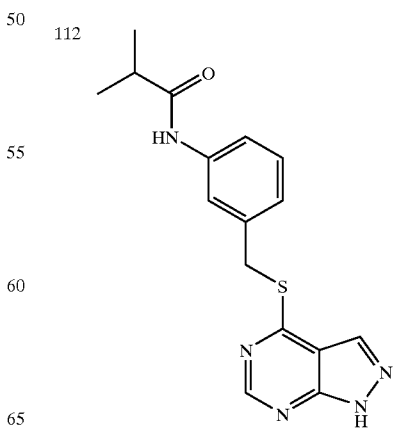

-continued
113
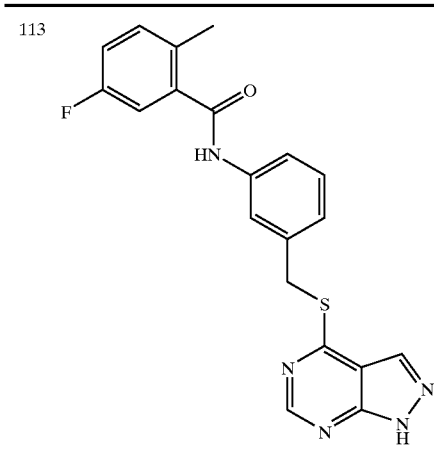
114
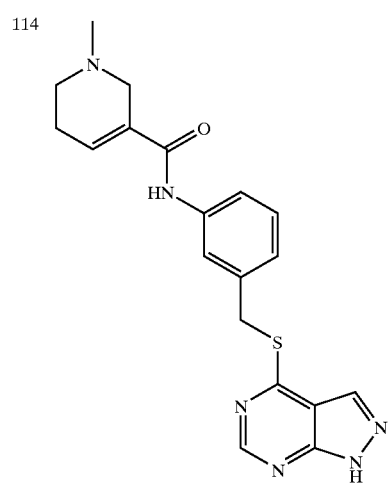
115
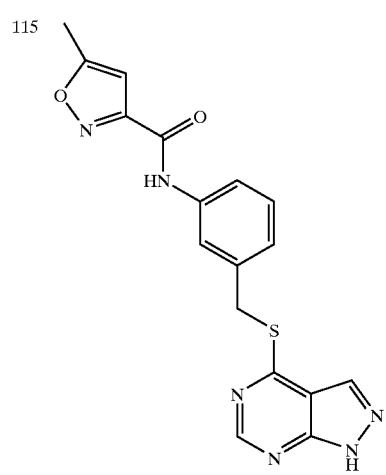
-continued
116
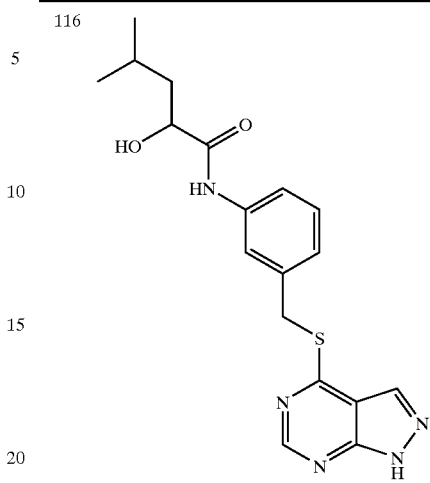
117
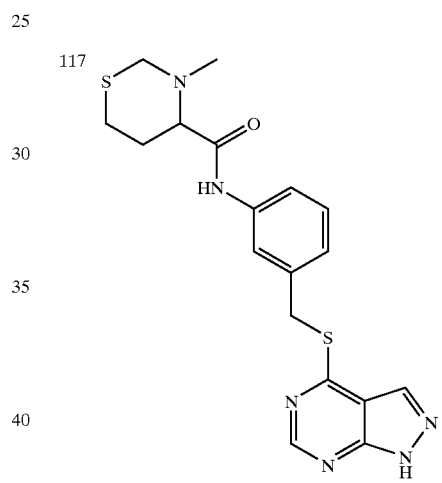
118
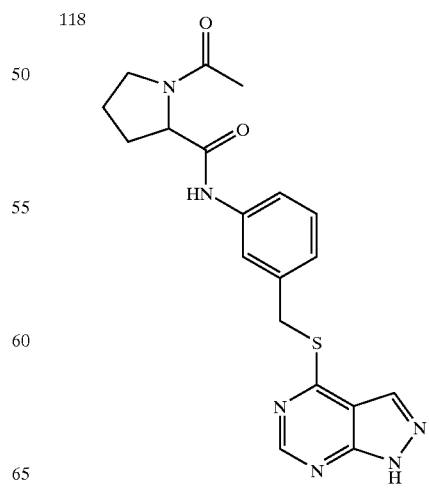

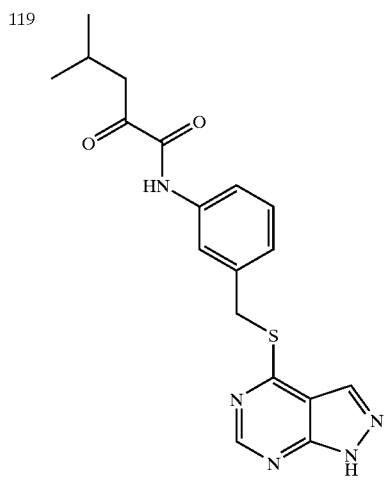
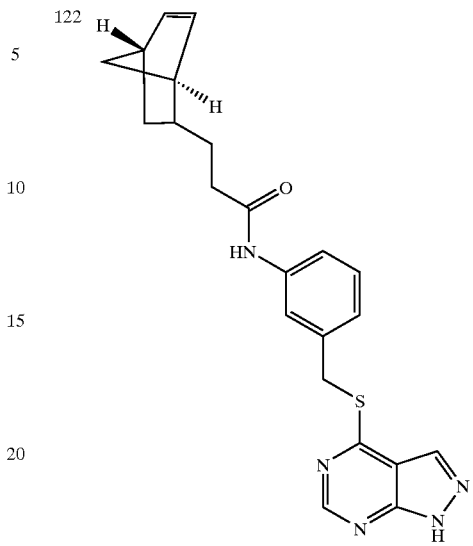

-continued
125
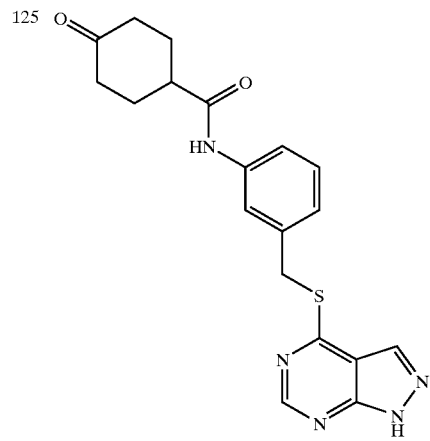
126
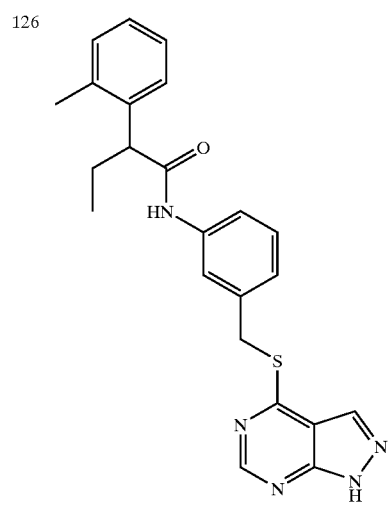
127
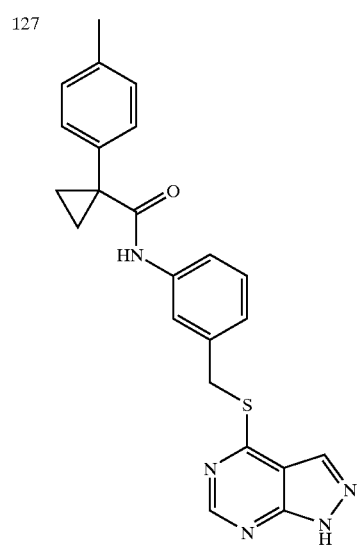
-continued
128  Chiral
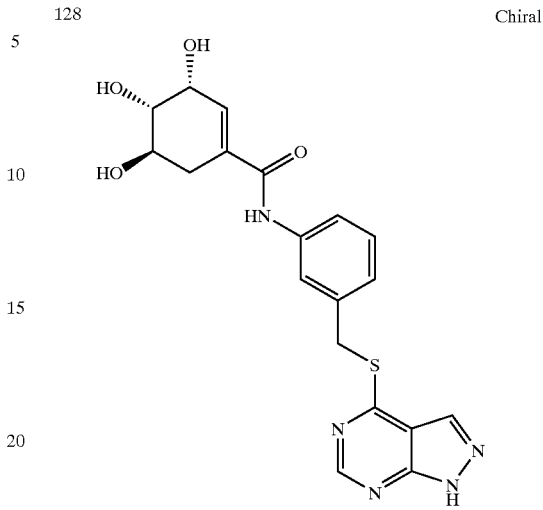
129
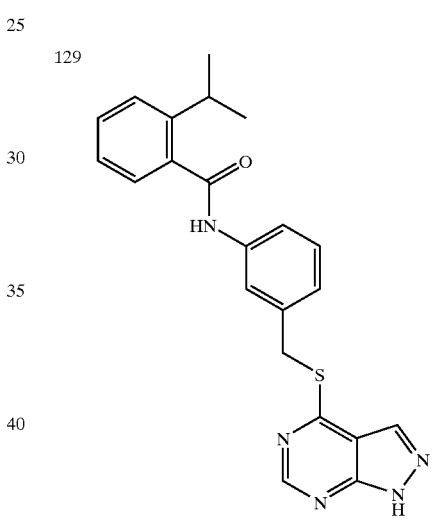
130  Chiral
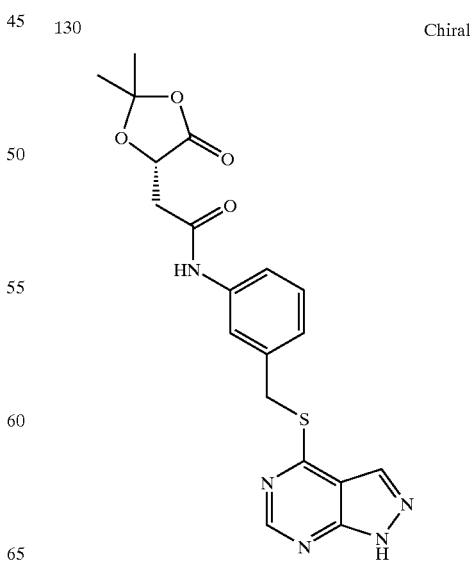

-continued
131
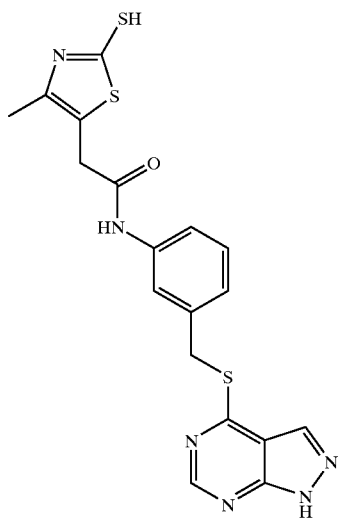
132  Chiral
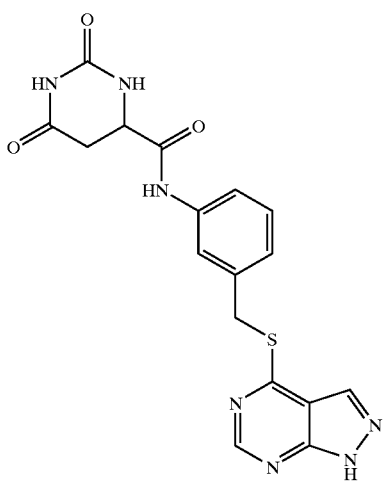
133  Chiral
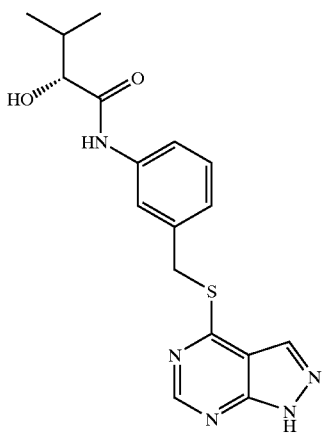
-continued
134
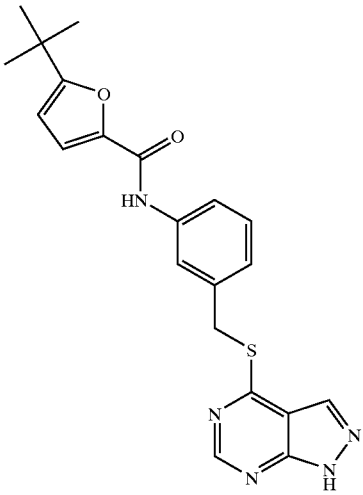
135
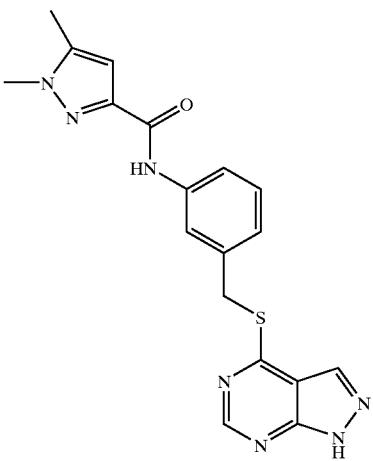
136
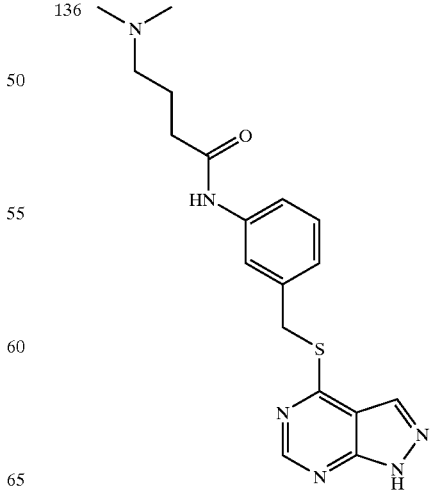

-continued
137
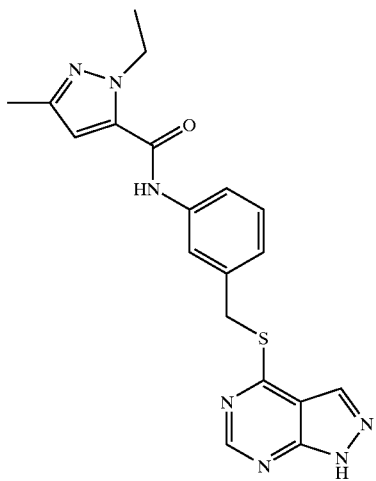
138
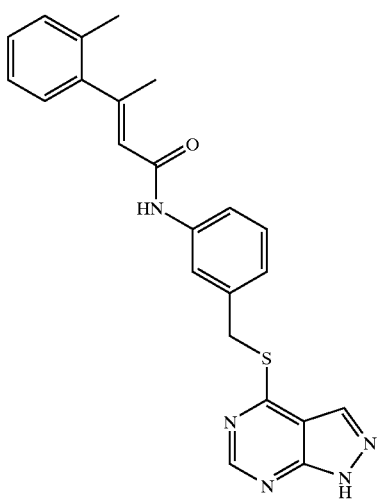
139
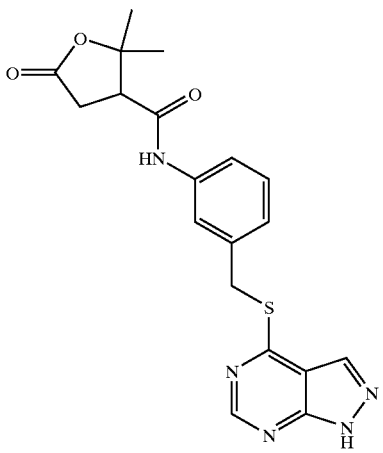
-continued
140 Chiral
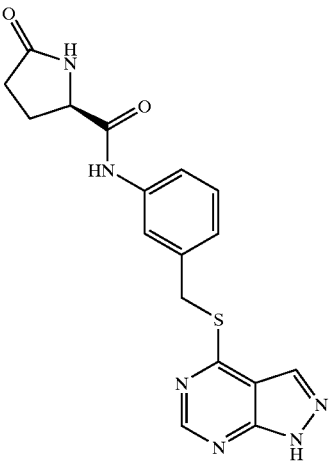
141 Chiral
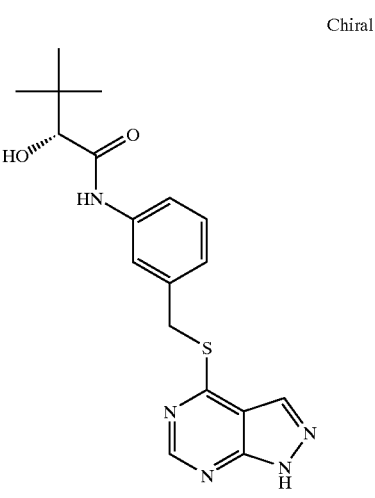
142
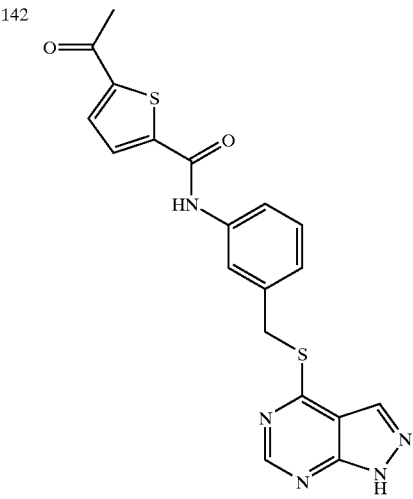

-continued
143
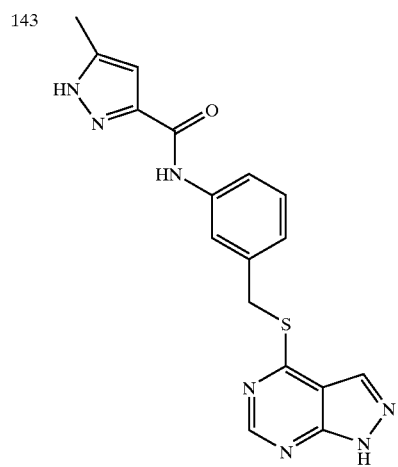
144
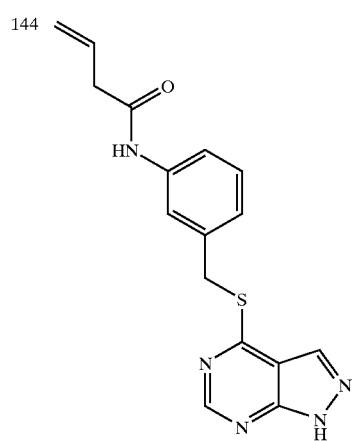
145
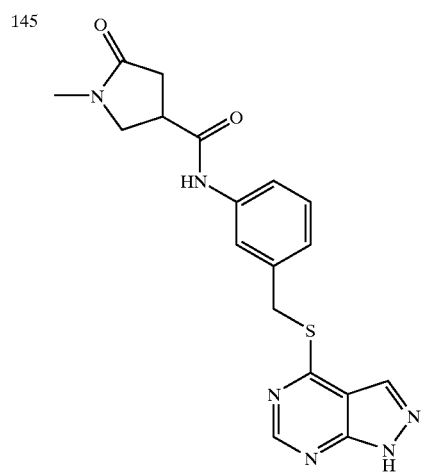
-continued
146
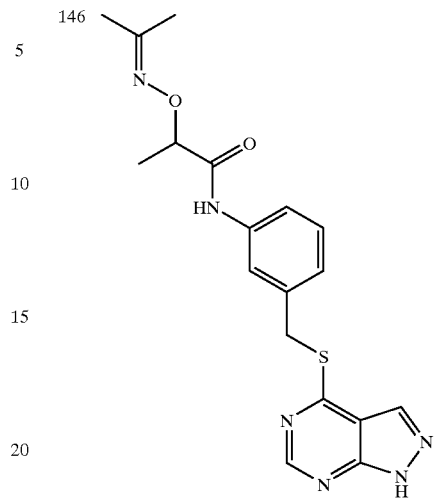
147
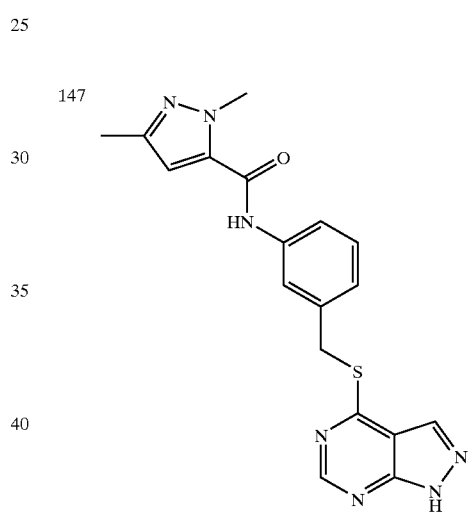
148
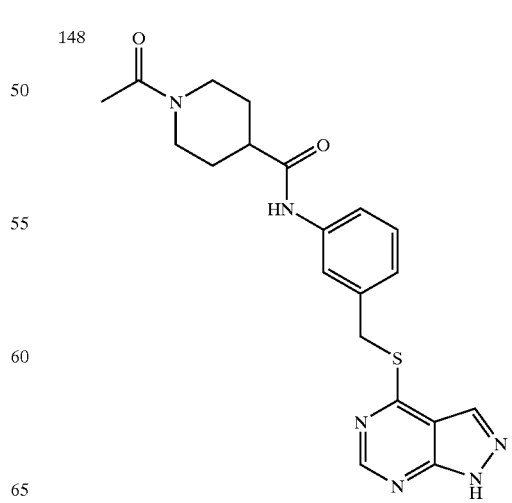

-continued
149 Chiral
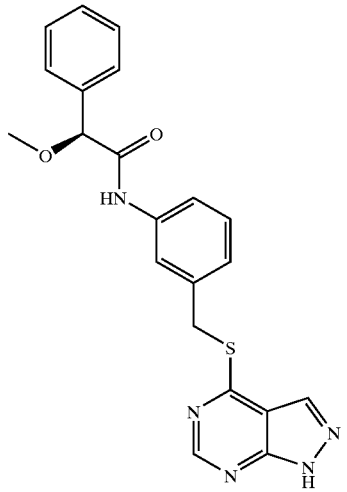
150
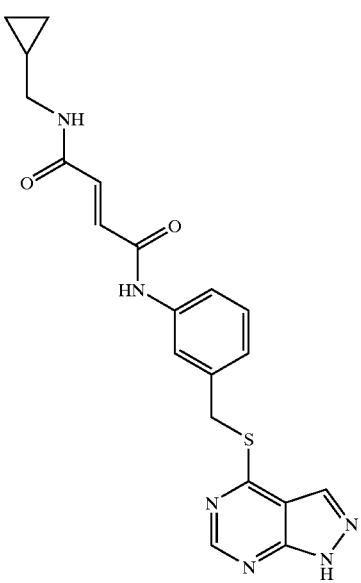
151
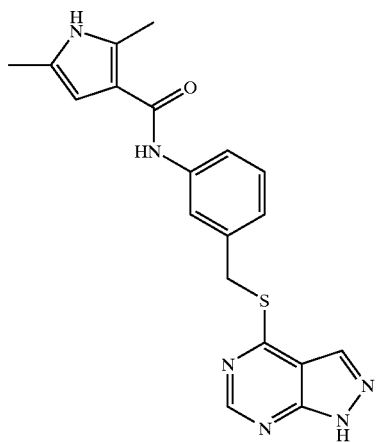
-continued
152
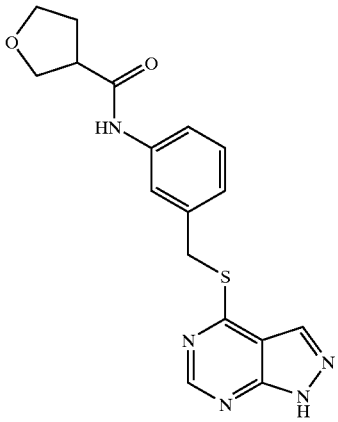
153
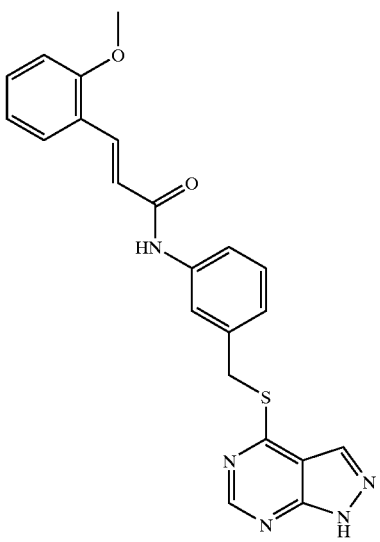
154
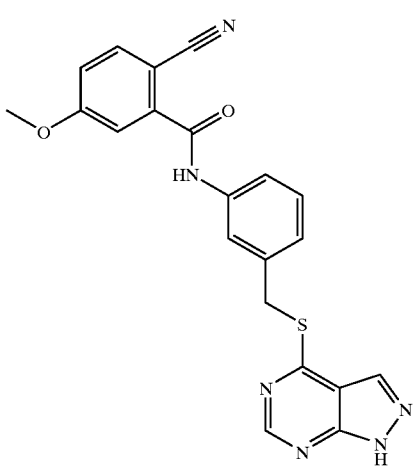

155 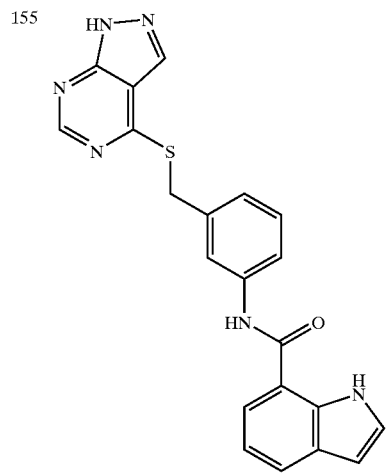
156 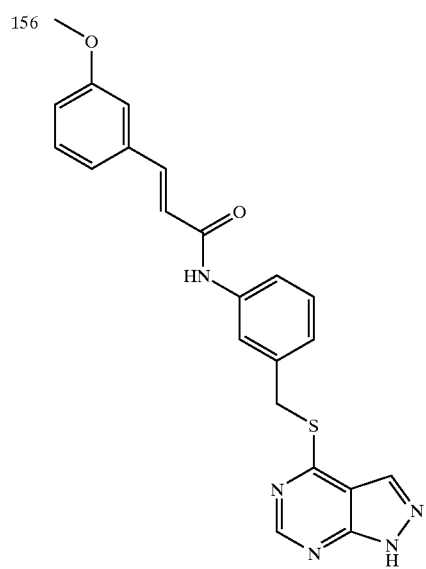
157 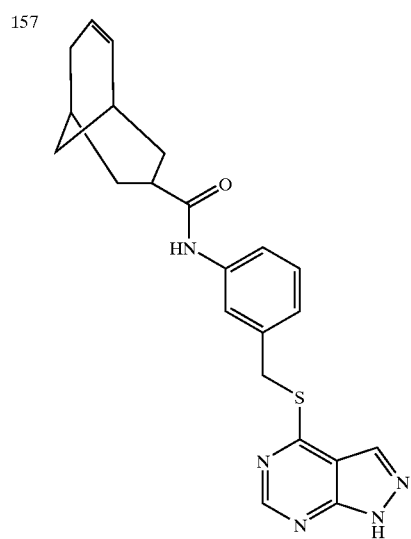
158 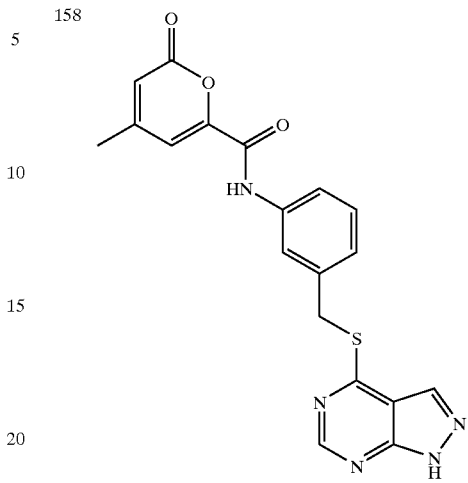
159 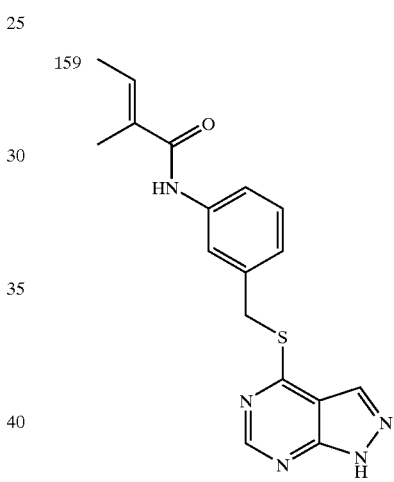
160 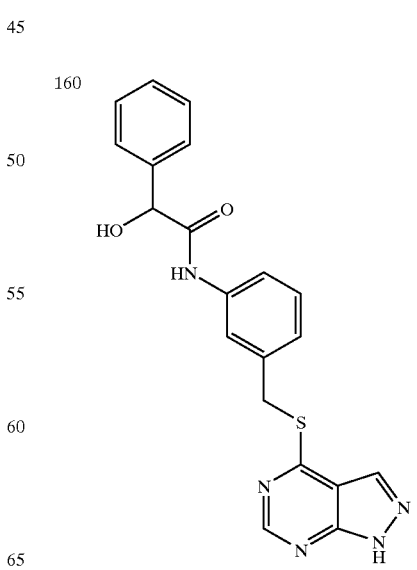

161 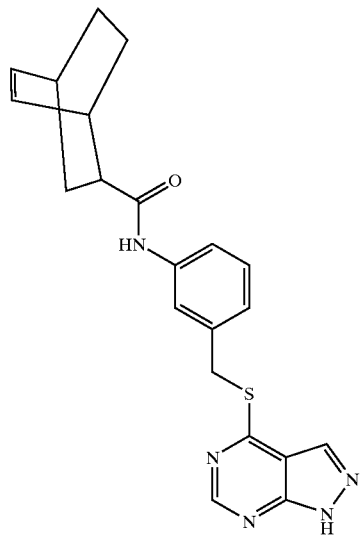
162 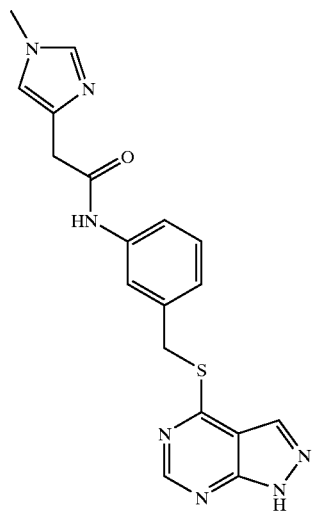
163 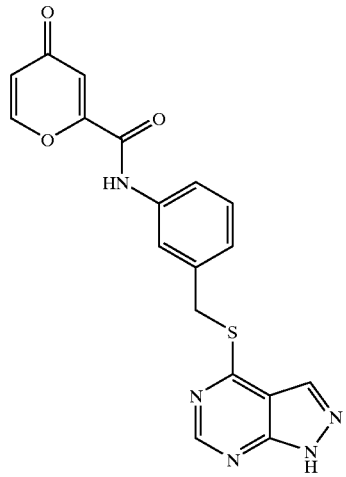
164 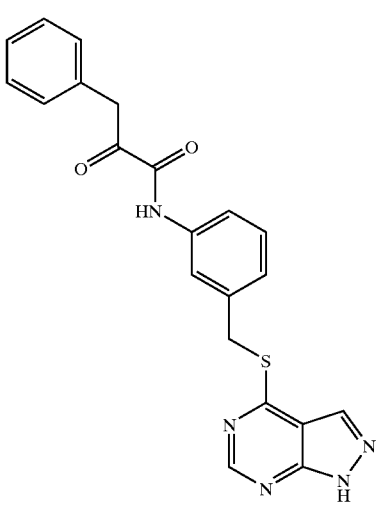
165 
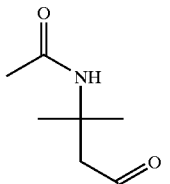
166 

| 261 | 262 |
|---|---|
| -continued | -continued |
| 167 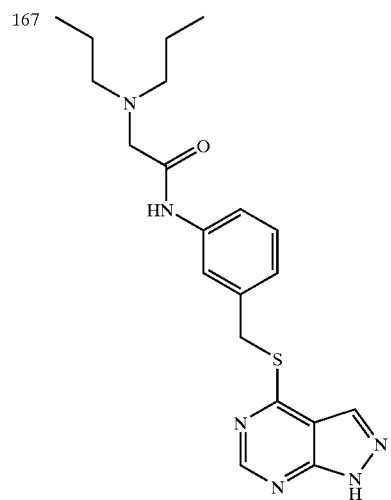 | 170 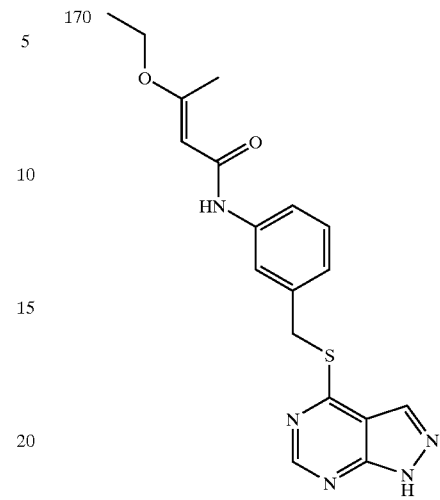 |
| 168 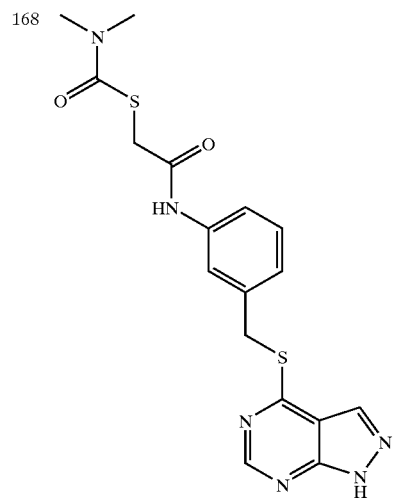 | 171 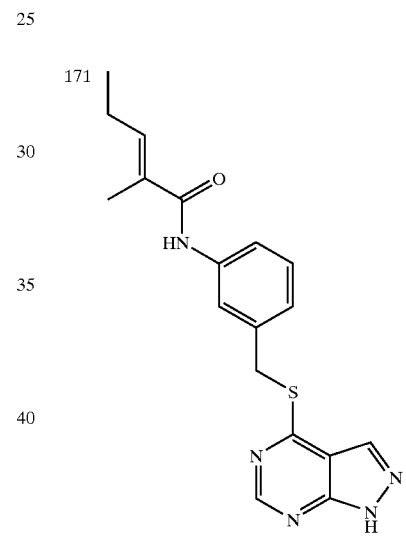 |
| 169 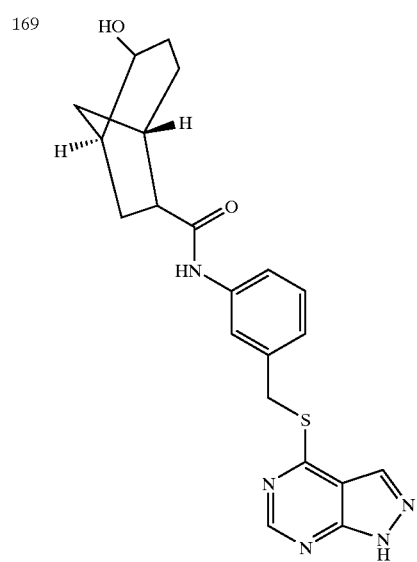 | 172 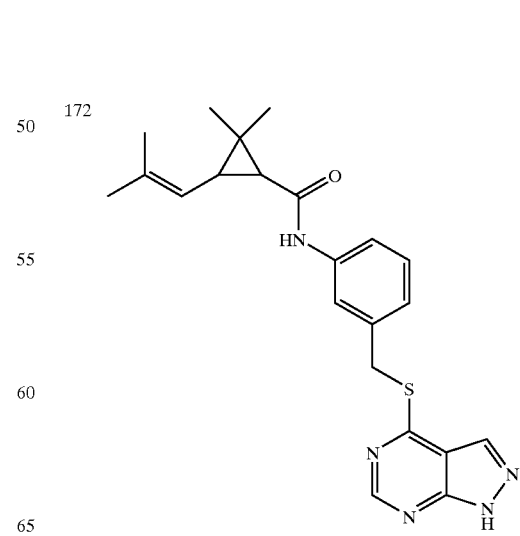 |

-continued

173
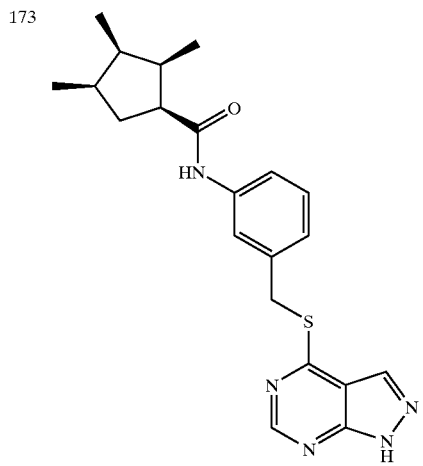

174
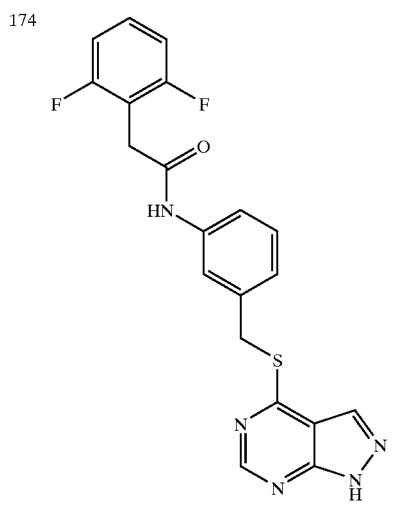

175
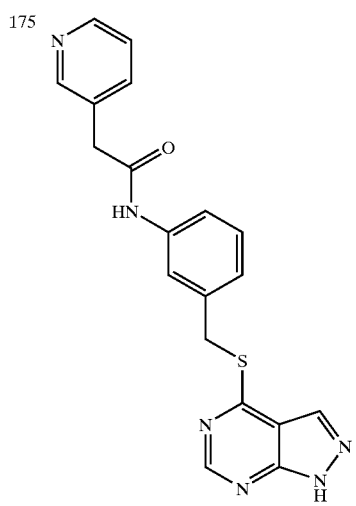

-continued

176
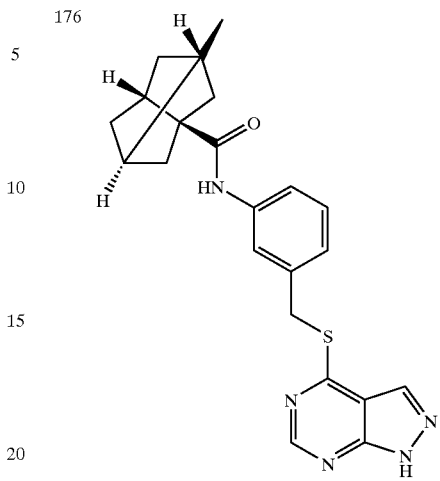

Example V-7

N-{3-[(1H-pyrazolo[3,4-d]pyrimidin-4-ylsulfanyl)methyl]phenyl}-N'-[3,5-bis-(trifluoromethyl)phenyl]urea

V-7

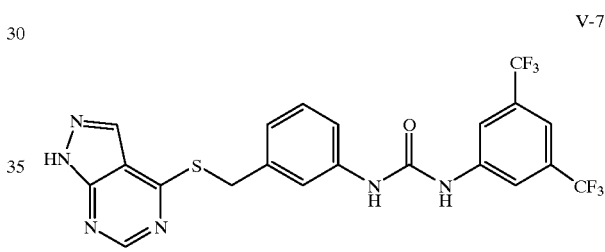

To a solution of 64.5 mg (0.25 mmol) of 3-[(1H-pyrazolo[3,4-d]-pyrimidin-4-yl)sulfanyl-methyl]aniline, V-6b, and 3,5-bis(trifluoromethyl)phenyl isocyanate (61.2 mg, 0.25 mmol) in 2 mL DMF was added 20 mg of NaHCO$_3$ and the reaction stirred at 50° C. for 1 h. After conventional aqueous work-up, purification by silica gel chromatography provided N-{3-[(1H-pyrazolo[3,4-d]pyrimidin-4-ylsulfanyl)methyl]phenyl}-N-[3,5-bis-trifluoromethyl)phenyl]urea, V-7: $^1$H NMR (300 MHz, DMSO-d$_6$) δ14.09 (s, 1H), 9.34 (s, 1H), 9.01 (s, 1H), 8.78 (s, 1H), 8.29 (s, 1H), 8.12 (s, 2H), 7.63 (s, 2H), 7.37 (d, 1H, J=7.5 Hz), 7.25 (dd, 1H, J=7.6, 8.3 Hz), 7.12 (d, 1H, J=7.6 Hz), 4.68 (s, 2H); APCIMS m/z 513 [M+H]$^+$.

Example V-7a 0.1 M solutions of the amine template, HATU, and isocyanate were prepared in anhydrous DMF. To each tube in an array of 8×11 culture tubes (10×75 mm) was added 100 μL (0.01 mmol) of the amine solution. To this was added 100 μL (0.01 mmol) of a different isocyanate solution followed by the addition of 10 mg of sodium bicarbonate. The reactions were stirred at 50° C. for 2 h. The reaction mixtures were transferred to a 1 mL 96-well plate using a liquid handler. The solvents were removed using the Speed-Vac™ apparatus and the crude reaction mixtures were redissolved in DMSO to give a final theoretical concentration of 10 mM.

Example V-7b
Using the general procedure described in Example V-7a above, the following compounds were made:
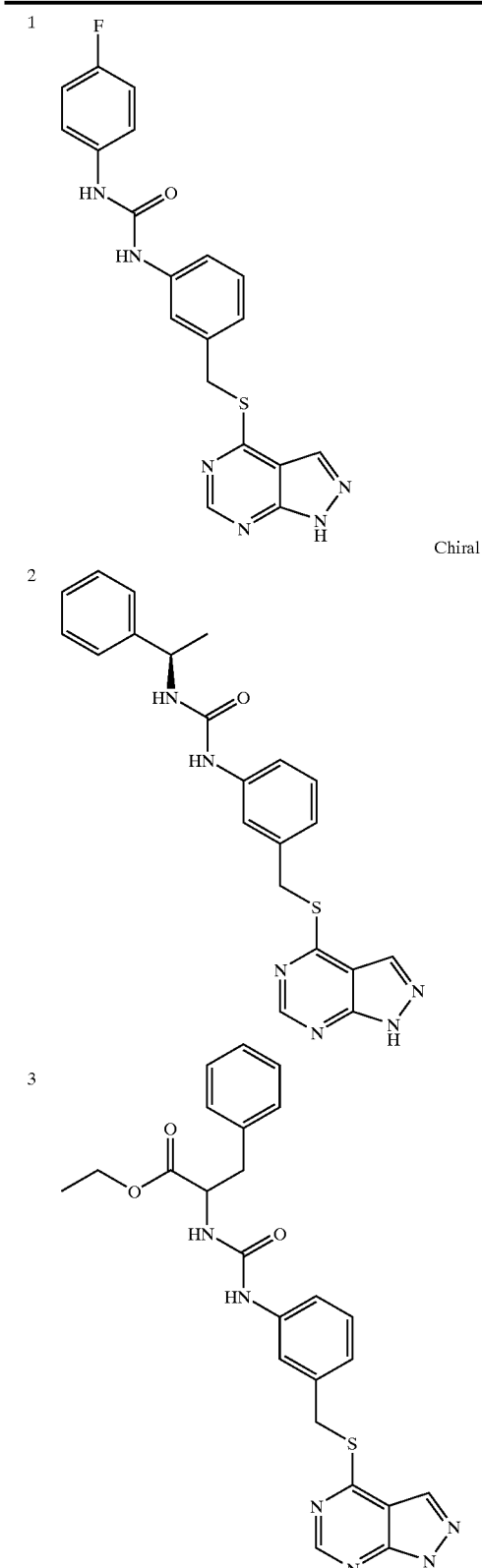
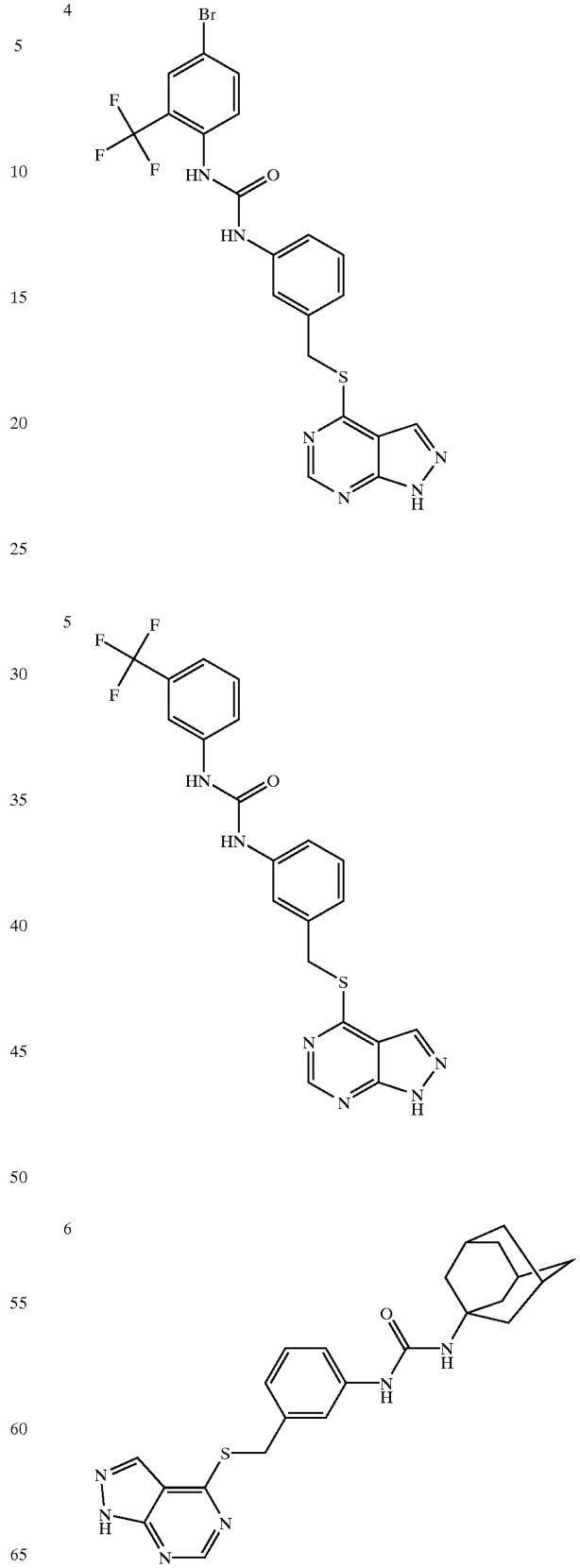

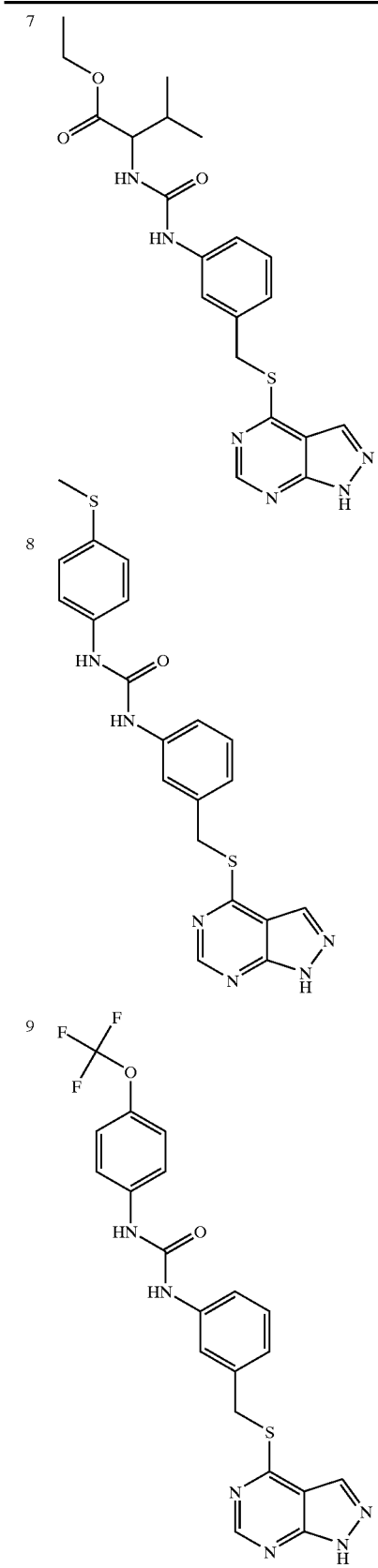
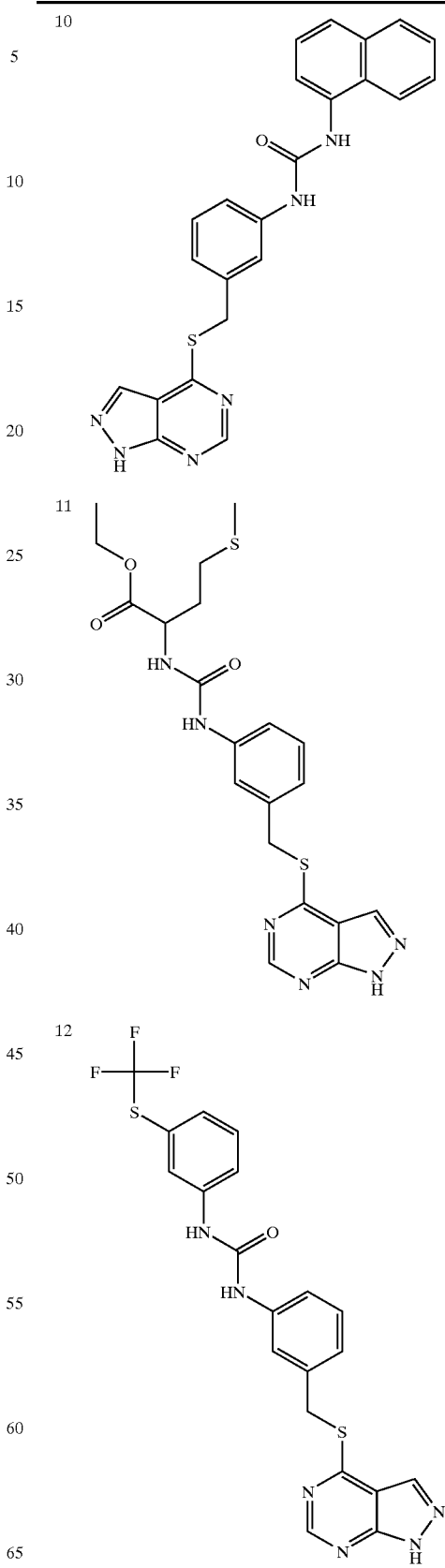

-continued
13
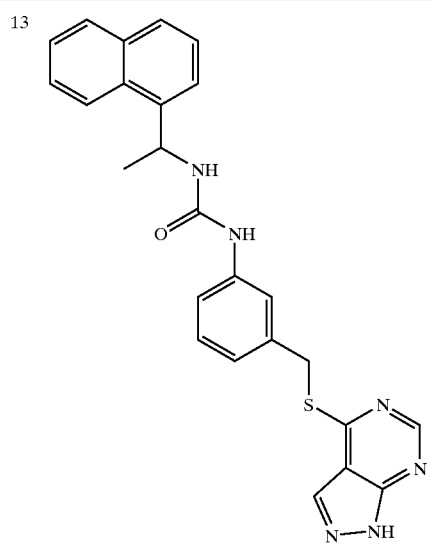
14
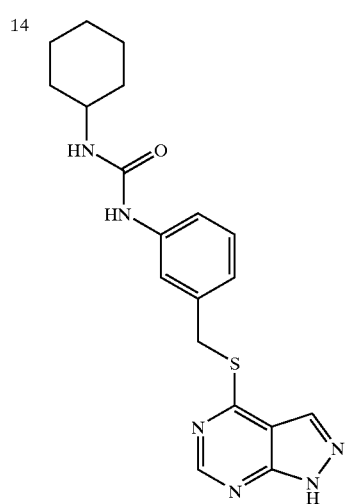
15
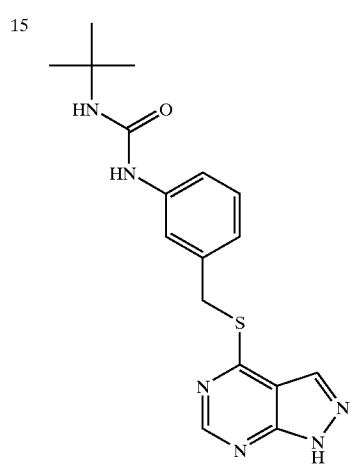
-continued
16 Chiral
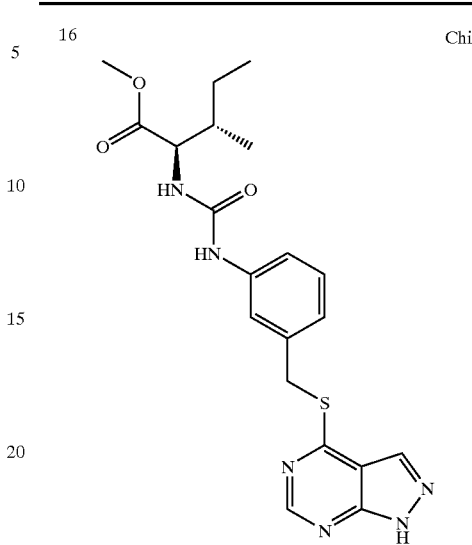
17
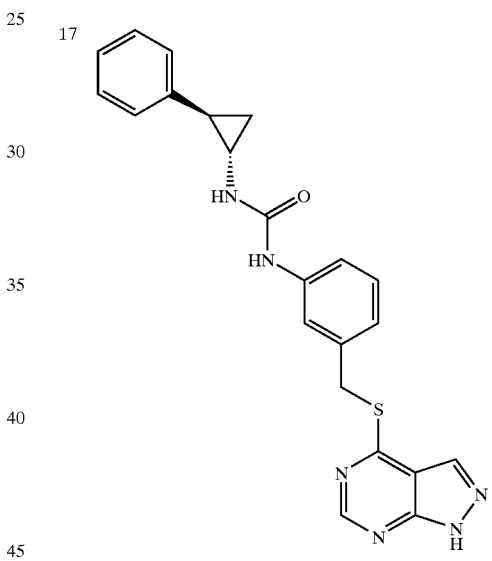
18
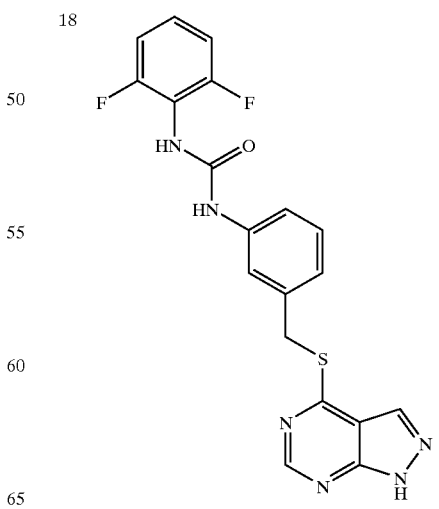

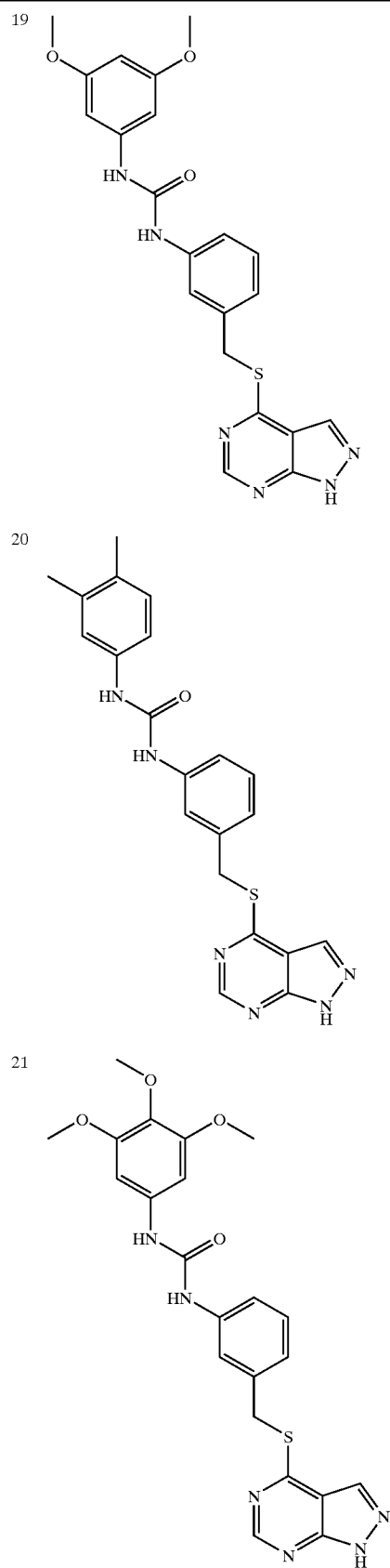
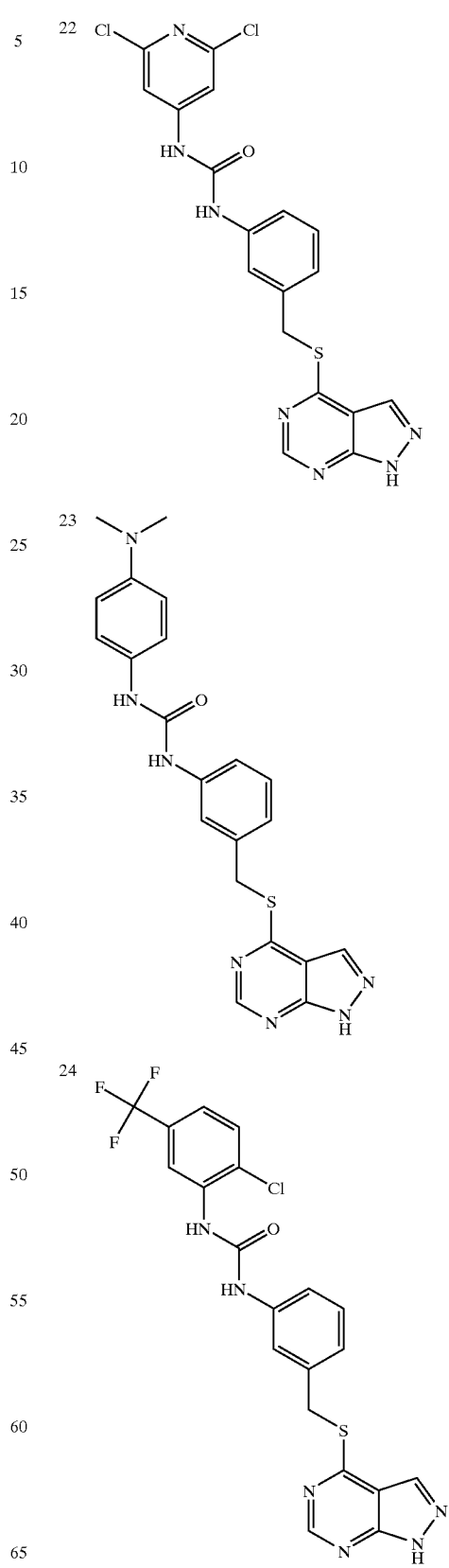

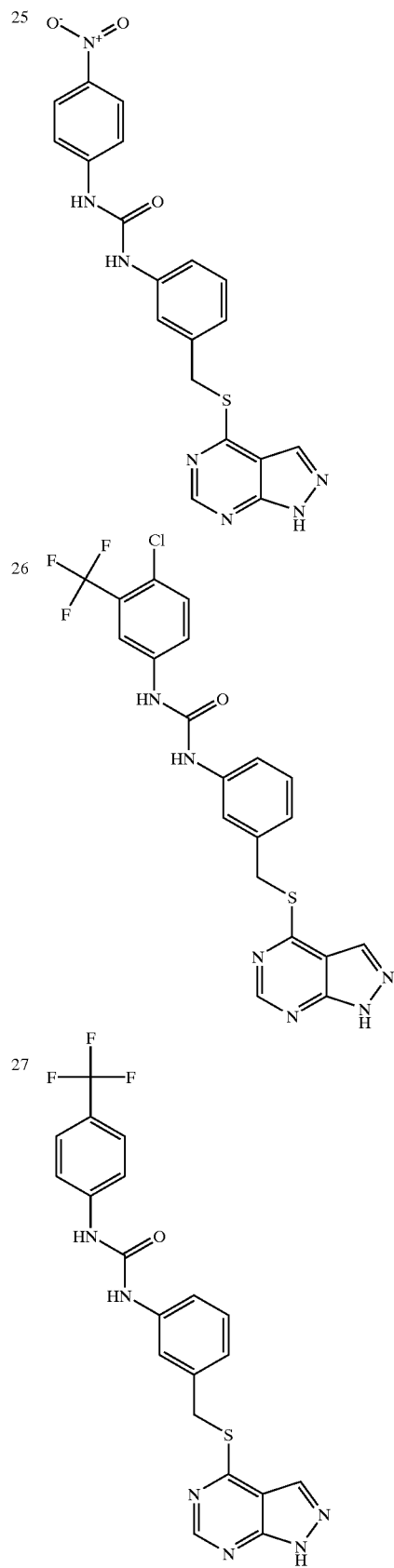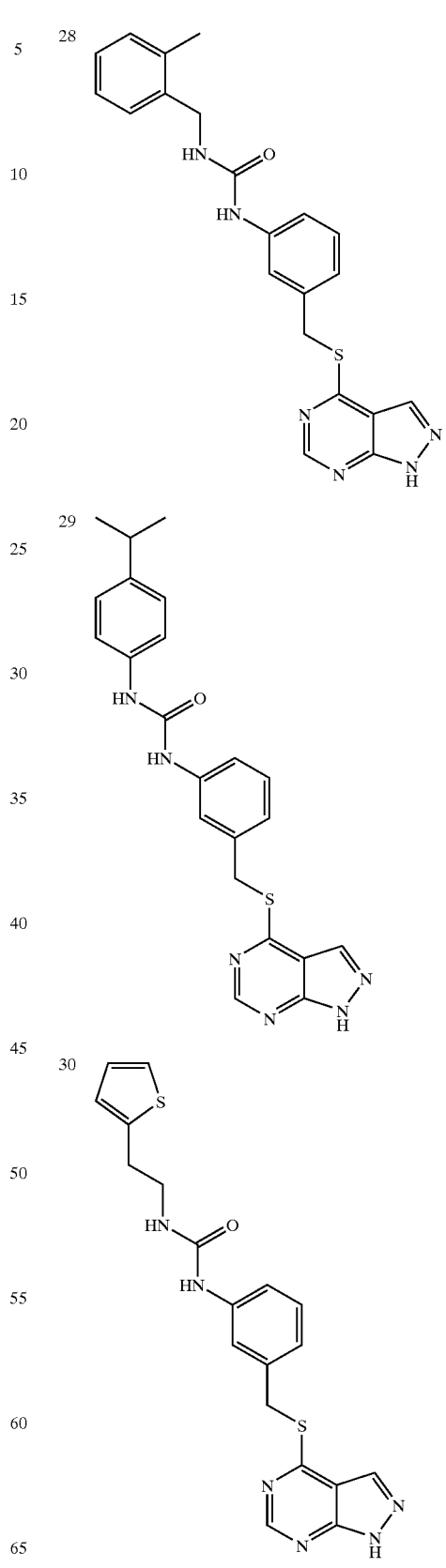

| 31 | 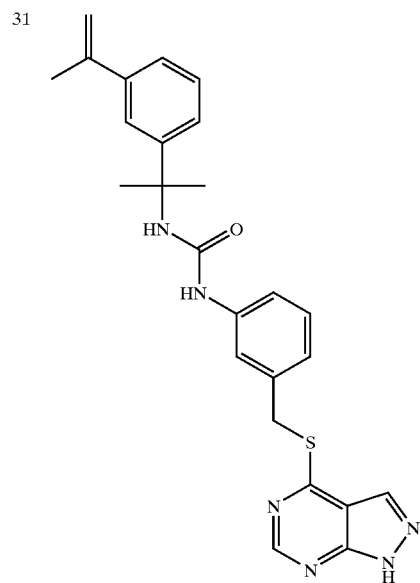 | 34 | 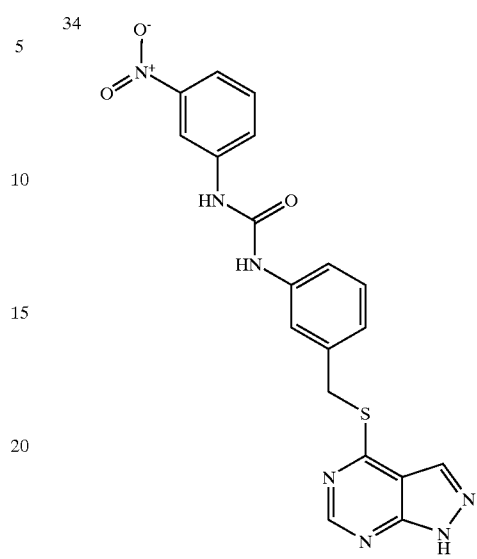 |
| 32 | 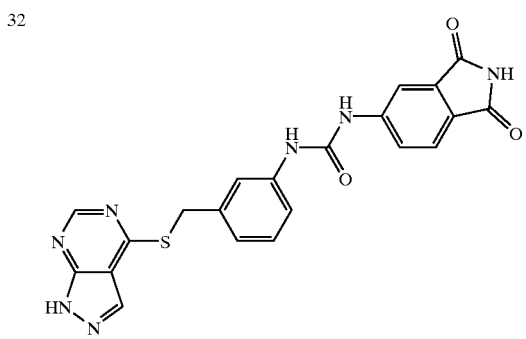 | 35 | 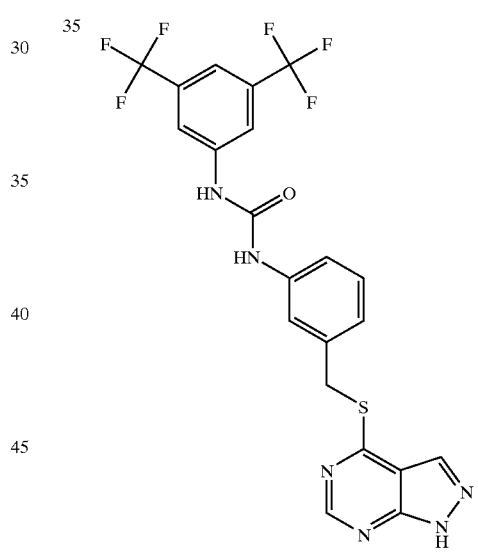 |
| 33 | 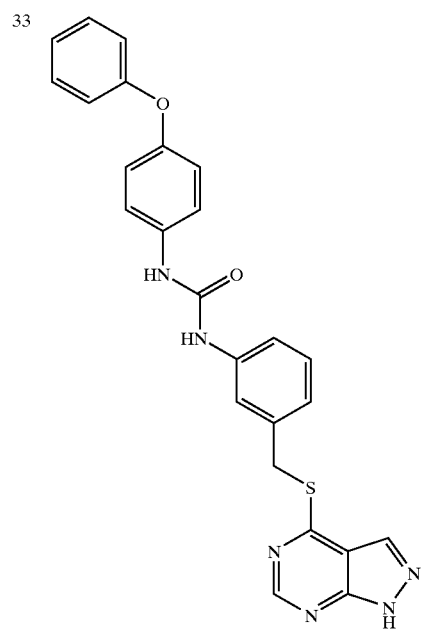 | 36 | 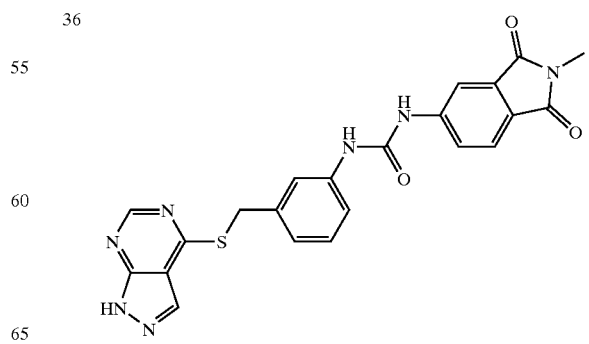 |

-continued
37
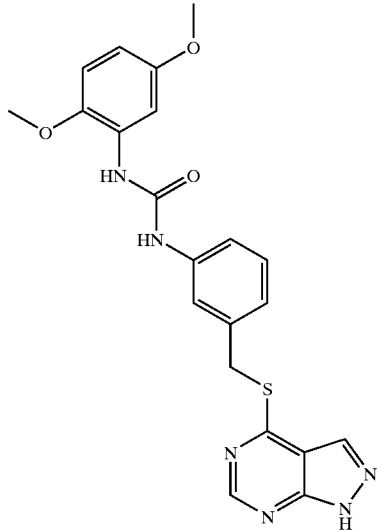
38
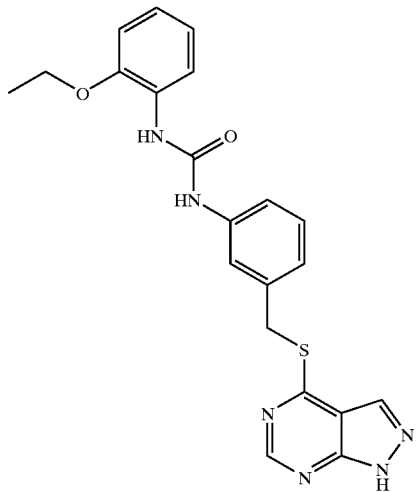
39
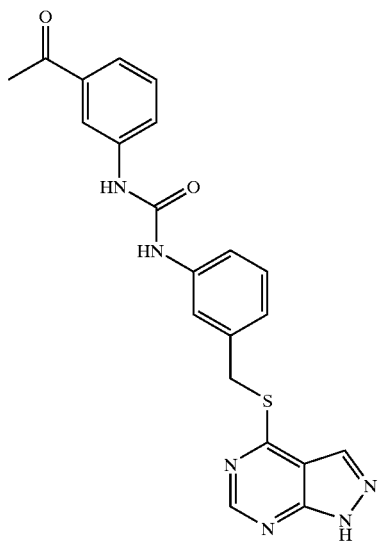
-continued
40
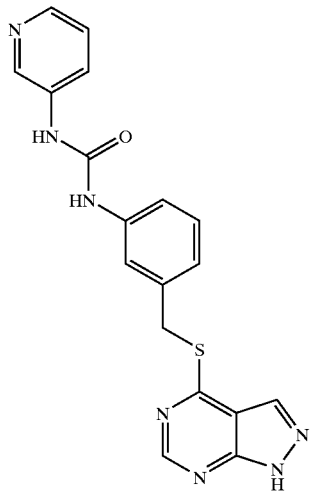
41
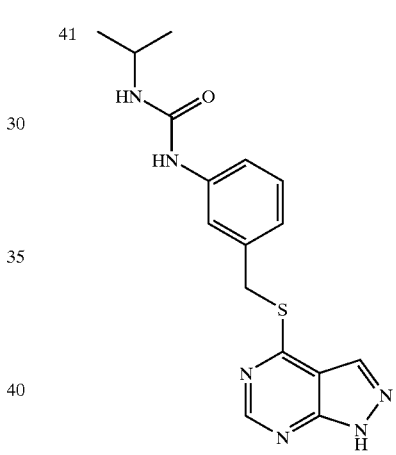
42
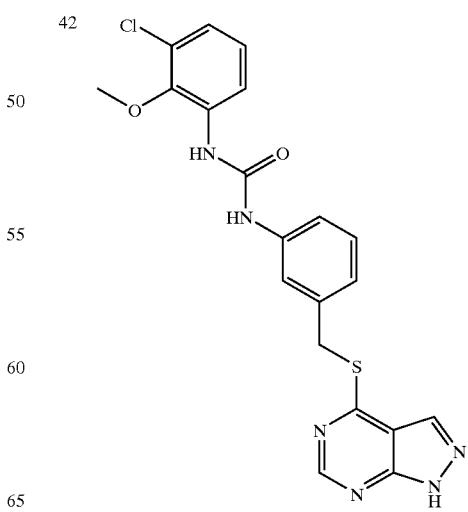

-continued

43

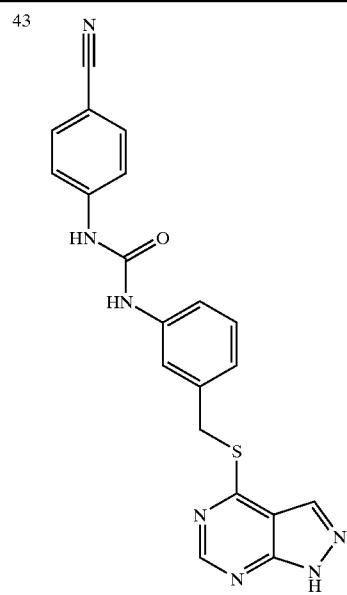

Example V-8

N-{3-[(1H-pyrazolo[3,4-d]pyrimidin-4-ylsulfanyl)methyl]phenyl}-N'-(pyridin-3-yl)urea

V-8

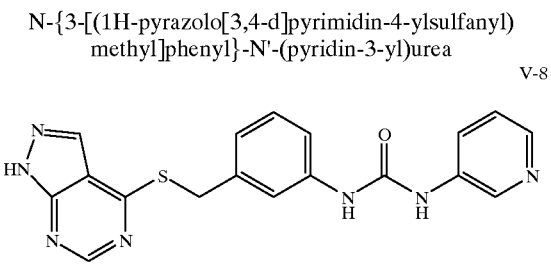

Example V-8 was prepared in a manner similar to that described in Example V-7, except that 3,5-bis(trifluoromethyl)phenyl isocyanate was replaced by 3-pyridyl isocyanate: HPLC R$_t$=7.12 min.; $^1$H NMR (300 MHz, DMSO-d$_6$) δ14.12 (s, 1H), 8.79–8.84 (m, 3H), 8.59 (s, 1H), 8.30 (s, 1H), 8.17 (s, 1H), 7.92 (d, 1H, J=8.3 Hz), 7.59 (s, 1H) 7.21–7.38 (m, 3H), 7.09 (d, 1H, J=7.2 Hz), 4.67 (s, 2H); APCIMS m/z 377 [M+H]$^+$.

Example V-9

N-{3-[(1H-pyrazolo[3,4-d]-pyrimidin-4-yl)sulfanylmethyl]phenyl}-(3,5-di-t-butyl)benzamide

V-9

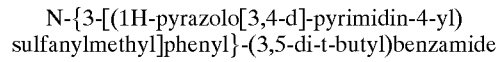
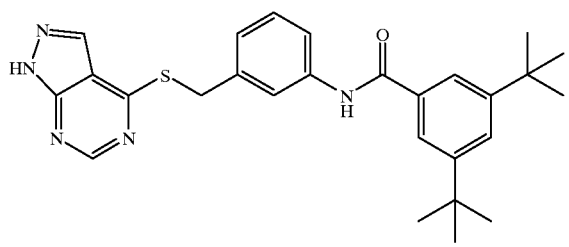

Example V-9 was prepared in a manner similar to that described in Example V-6, except that 3,5-di-(t-butyl) benzoic acid was used in place of 4-phenoxybenzoic acid in step (b): HPLC R$_t$=5.16 min.; $^1$H NMR (300 MHz, DMSO-d$_6$) δ14.12 (s, 1H), 10.19 (s, 1H), 8.80 (s, 1H), 8.30 (s, 1H), 7.87 (s, 1H), 7.72 (s, 2H), 7.66 (d, 2H,J=7.8 Hz), 7.60 (s, 1H), 7.31 (dd, 1H,J=7.60, 7.9 Hz), 7.22 (d, 1H,J=7.5 Hz), 4.70 (s, 2H), 1.33 (s, 18H); APCIMS m/z 474 [M+H]$^+$.

Example V-10

3-Bromo-4-hydroxy-N-{3-[(1H-pyrazolo[3,4-d]-pyrimidin-4-yl)sulfanylmethyl]phenyl}-benzamide

V-10

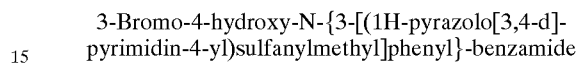
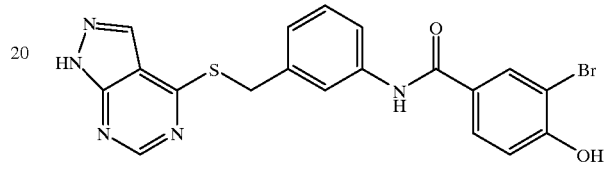

Example V-10 was prepared in a manner similar to that described in Example V-6, except that 3-bromo-4-hydroxybenzoic acid was used in place of 4-phenoxybenzoic acid in step (b): $^1$H NMR (300 MHz, DMSO-d$_6$) δ10.07 (s, 1H), 8.79 (s, 1H), 8.30 (s, 1H), 8.14 (d, 1H, J=2.1 Hz), 7.88 (s, 1H), 7.80 (dd, 1 H, J=2.1, 8.1 Hz), 7.66 (d, 1H, J=8.6 Hz), 7.29 (dd, 1H, J=7.7, 7.8 Hz), 7.18 (d, 1H, J=7.6 Hz), 7.01 (d, 1H, J=8.5 Hz), 4.69 (s, 2H); APCIMS m/z 456 [M+H]$^+$.

Example V-11

N-{3-[(1H-pyrazolo[3,4-d]-pyrimidin-4-yl)sulfanylmethyl]phenyl}-quinoline-6-carboxamide

V-11

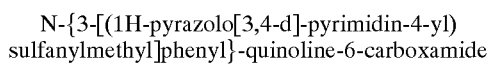
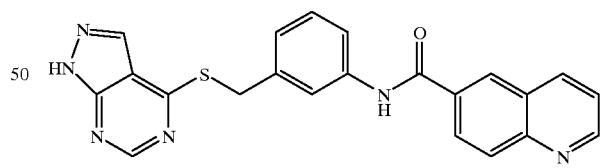

Example V-11 was prepared in a manner similar to that described in Example V-6, except that quinoline-6-carboxylic acid was used in place of 4-phenoxybenzoic acid in step (b): 1H NMR (300 MHz, DMSO-d$_6$) δ14.12 (s, 1H), 10.53 (s, 1H), 9.00 (dd, 1H, J=1.5, 4.2 Hz), 8.80 (s, 1H), 8.61 (d, 1H, J=1.9 Hz), 8.52 (d, 1H, J=8.0 Hz), 8.30 (s, 1H), 8.23 (dd, 1H, J=1.9, 8.7 Hz), 8.12 (d, 1H, J=8.7 Hz), 7.96 (s, 1H), 7.73 (d, 1H, J=7.9 Hz), 7.64 (dd, 1 H, J=4.5, 8.4 Hz), 7.34 (dd, 1H, J=7.9, 8.0 Hz), 7.24 (d, 1H, J=7.5 Hz), 7.05–7.12 (m, 1H), 4.72 (s, 2H); APCIMS m/z 413 [M+H]$^+$.

Example V-12

5-Fluoro-N-{3-[(1H-pyrazolo[3,4-d]-pyrimidin-4-yl)sulfanylmethyl]-phenyl}-indole-2-carboxamide

V-12

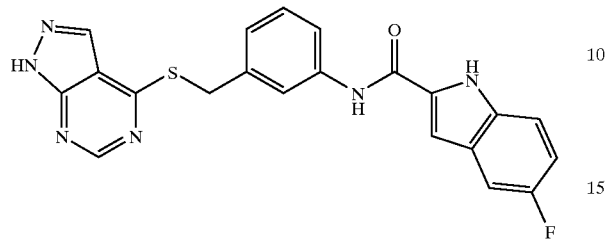

Example V-12 was prepared in a manner similar to that described in Example V-6, except that 5-fluoroindole-2-carboxylic acid was used in place of 4-phenoxybenzoic acid in step (b): $^1$H NMR (300 MHz, DMSO-d$_6$) δ14.12 (s, 1H), 11.83 (s, 1H), 10.27 (s, 1H), 8.80 (s, 1H), 8.30 (s, 1H), 7.91 (s, 1H), 7.73 (d, 1H, J=8.3 Hz), 7.47 (s, 1H), 7.44 (dd, 1H, J=4.1, 4.60 Hz), 7.40 (d, 1 H, J=1.9 Hz), 7.32 (dd, 1H, J=7.5, 8.0 Hz), 7.21 (d, 1H, J=7.1 Hz), 7.05–7.12 (m, 1H), 4.71 (s, 2H); APCIMS m/z 419 [M+H]$^+$.

Example V-13

N-{3-[(1H-pyrazolo[3,4-d]-pyrimidin-4-yl)sulfanylmethyl]phenyl}-indole-6-carboxamide

V-13

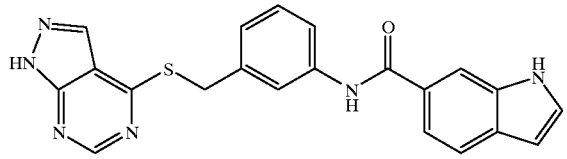

Example V-13 was prepared in a manner similar to that described in Example V-6, except that indole-6-carboxylic acid was used in place of 4-phenoxybenzoic acid in step (b): $^1$H NMR (300 MHz, DMSO-d$_6$) δ14.12 (s, 1H), 11.45 (s, 1H), 10.18 (s, 1H), 8.80 (s, 1H), 8.31 (s, 1H), 8.04 (s, 1H), 7.96 (s, 1H), 7.70 (d, 1H, J=7.9 Hz), 7.62 (s, 2H), 7.54 (s, 1H), 7.31 (dd, 1H, J=7.9, 8.0 Hz), 7.18 (d, 1 H, J=7.5 Hz), 7.30–6.52 (s, 1H), 4.70 (s, 2H); APCIMS m/z 401 [M+H]$^+$.

Example V-14

The following compounds were made using the general procedure described above in Example V-6c, except for the use of different acids and amines, which yielded the products indicated below (wherein for convenience, and as understood in the art, not all hydrogen atoms have been expressly indicated for each carbon and/or nitrogen atom).

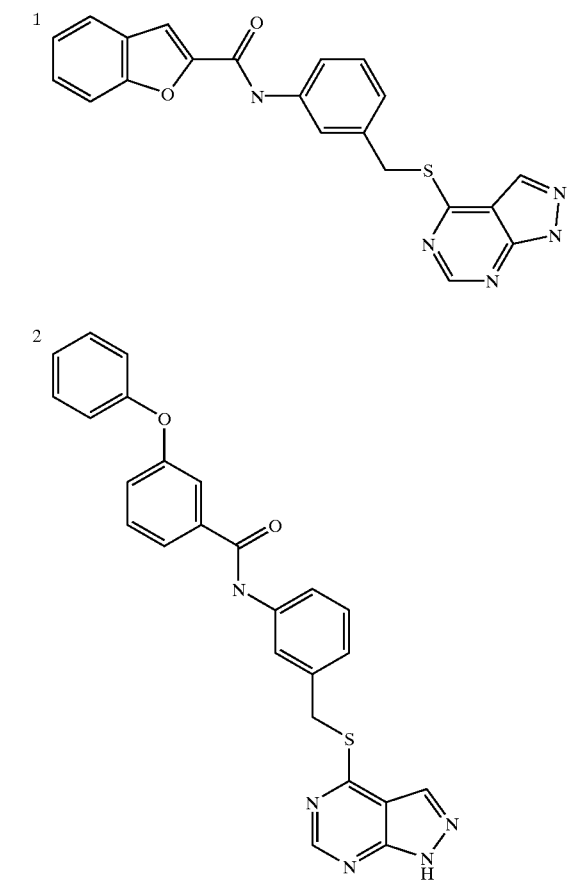

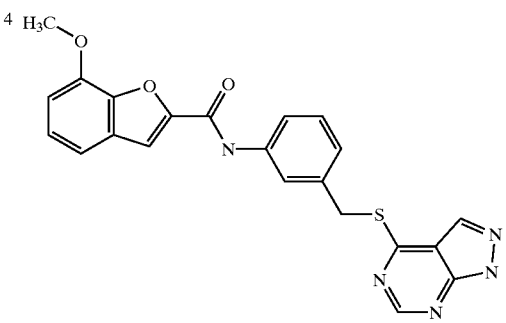

-continued
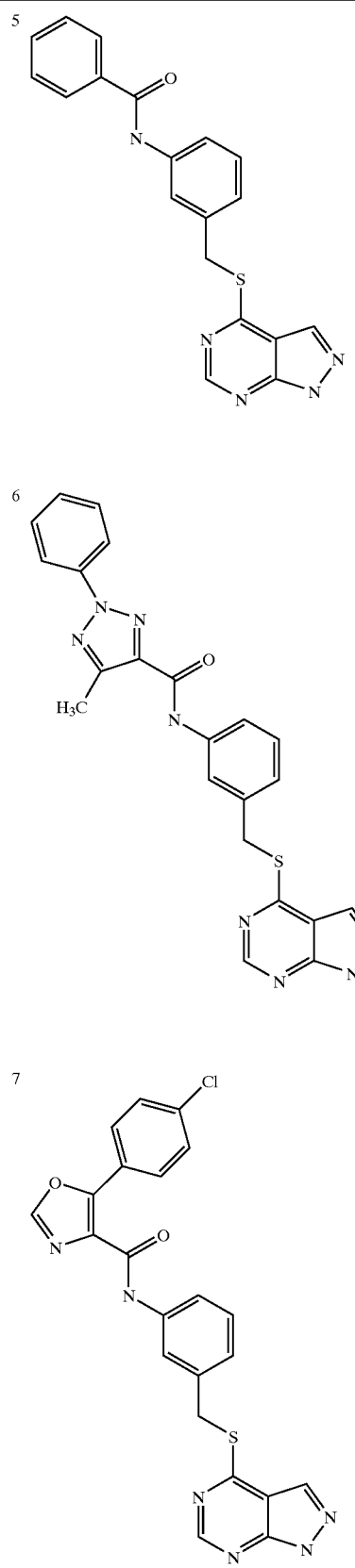
-continued
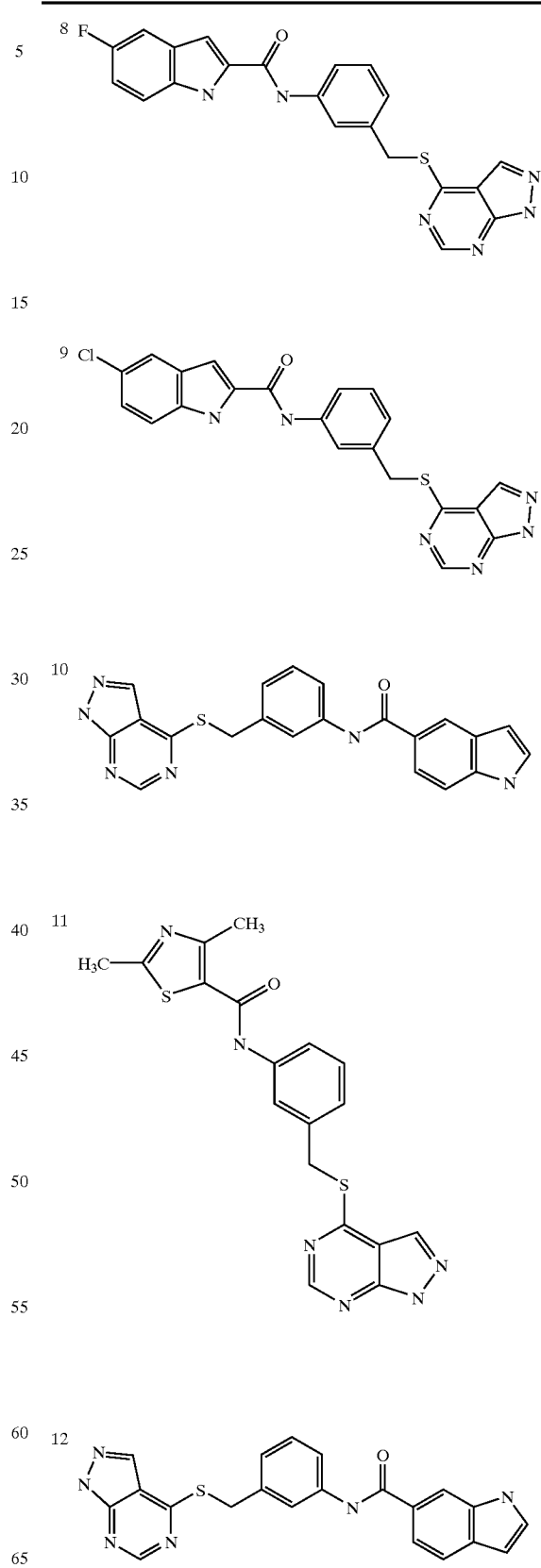

-continued
13
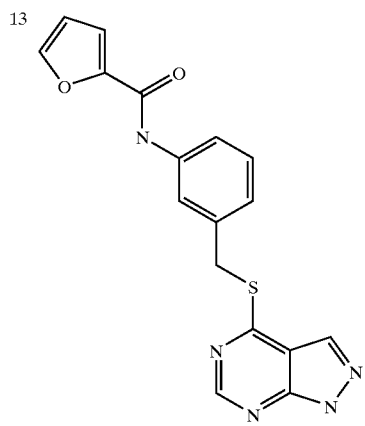
14
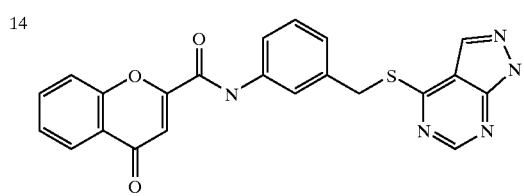
15
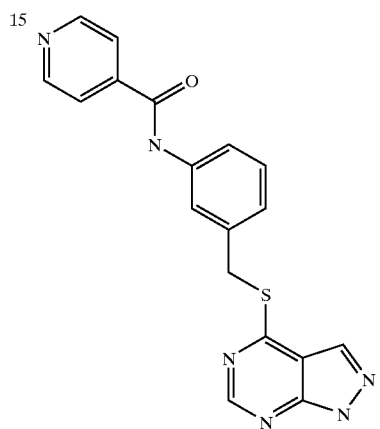
16
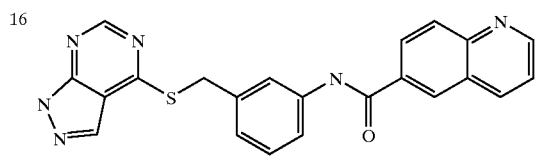
17
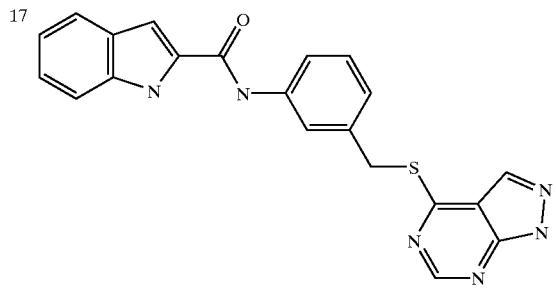
-continued
18
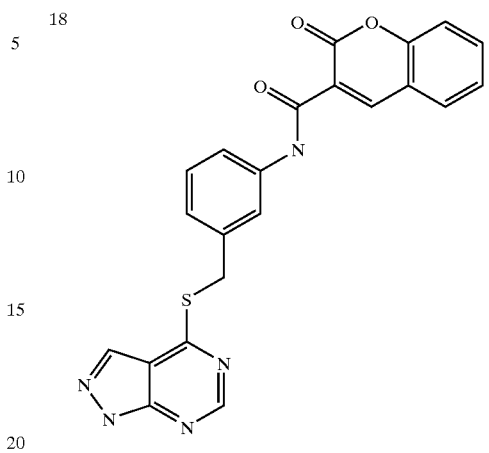
19
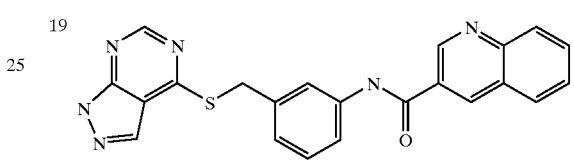
20
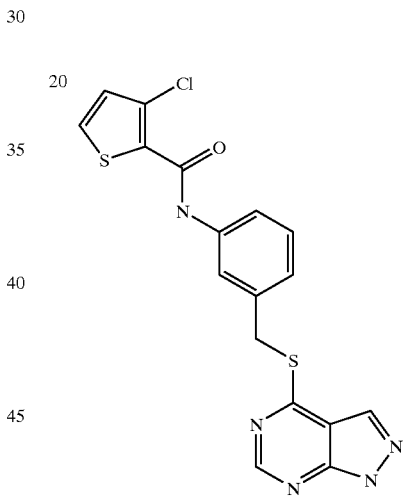
21
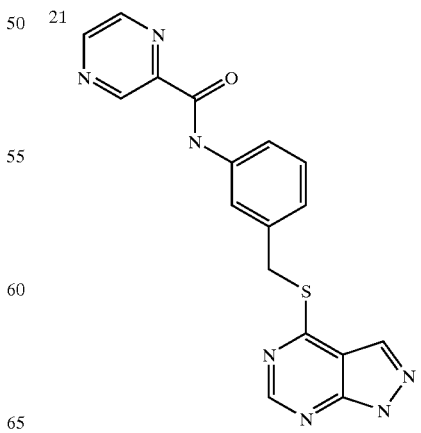

-continued
22
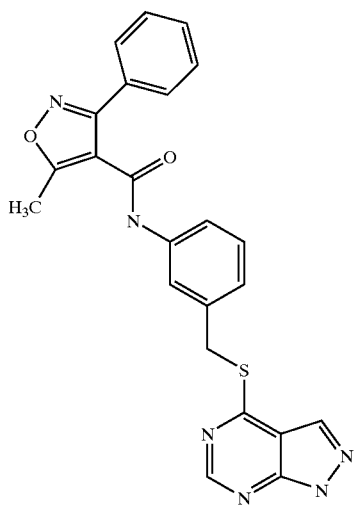
23
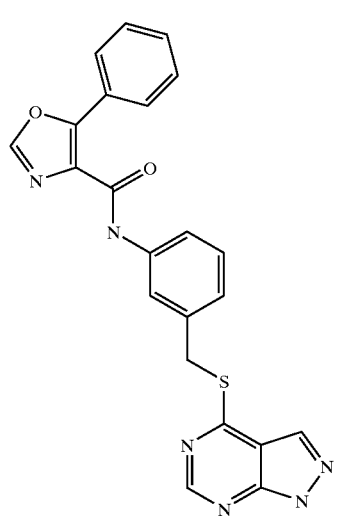
24
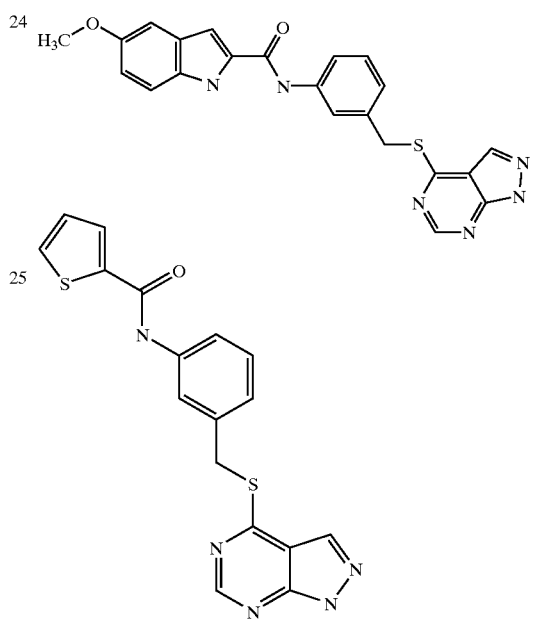
25
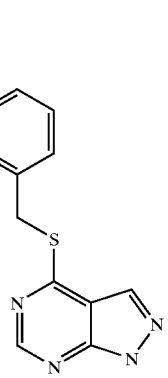
-continued
26
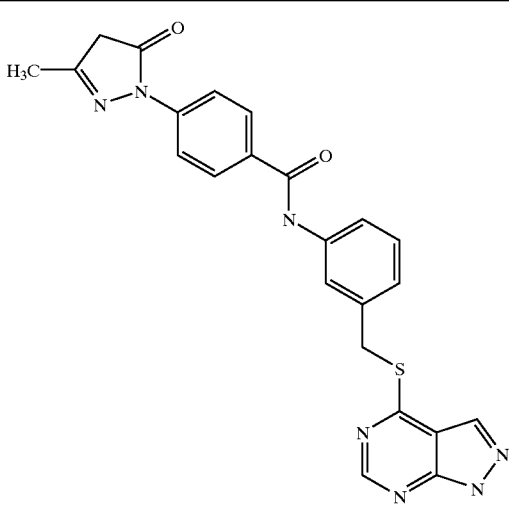
27
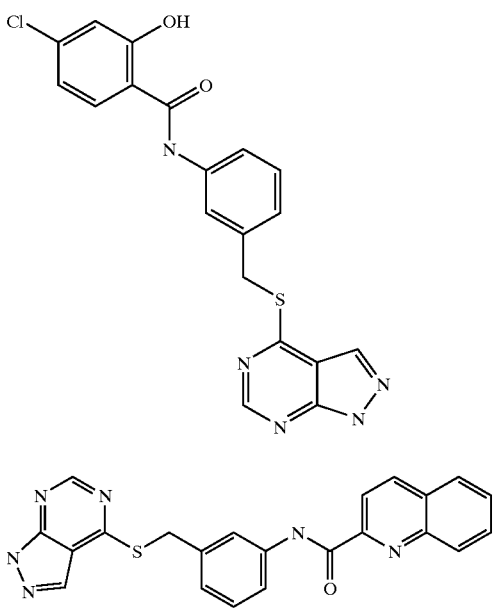
28
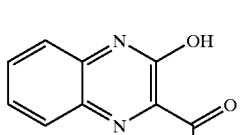
29
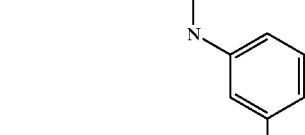

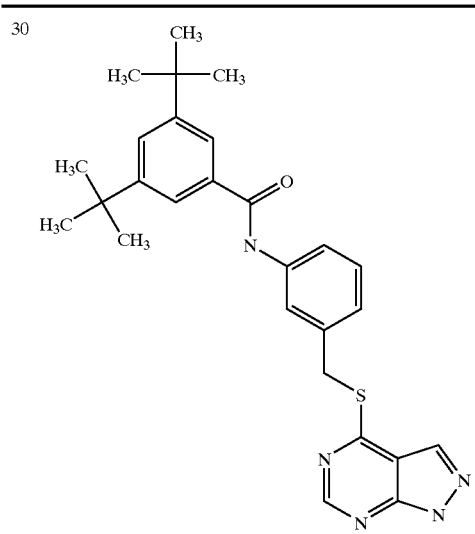
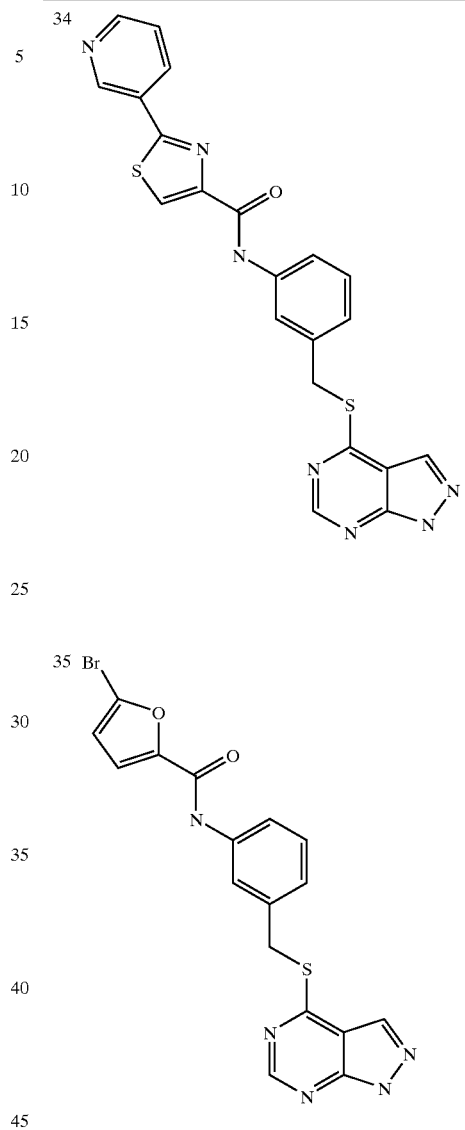

37
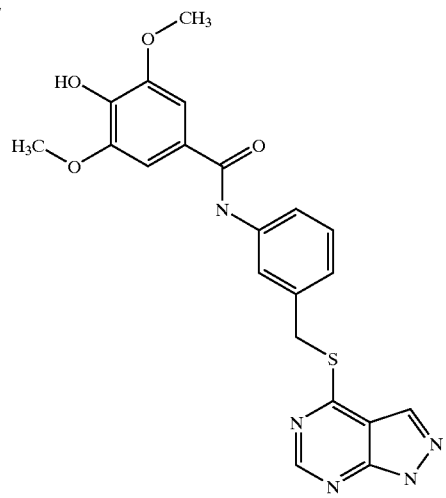
38
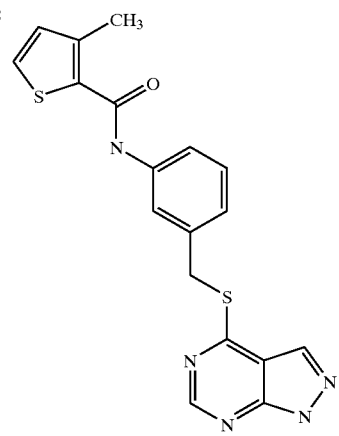
39
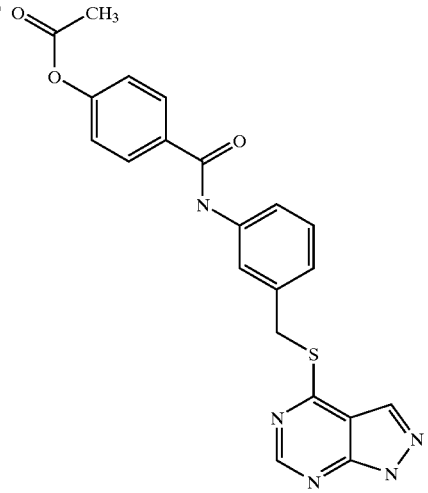
40
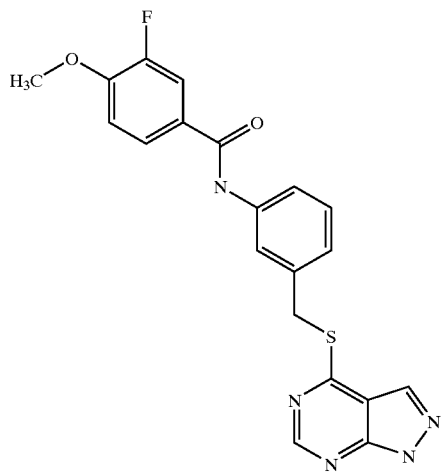
41
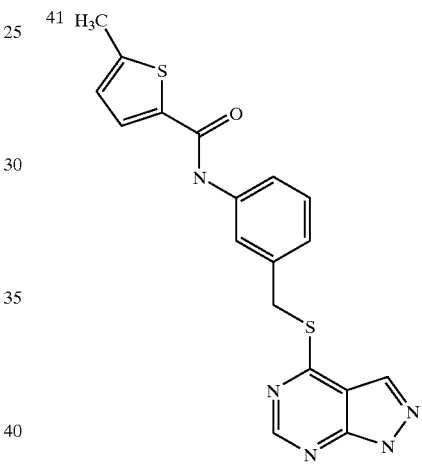
42
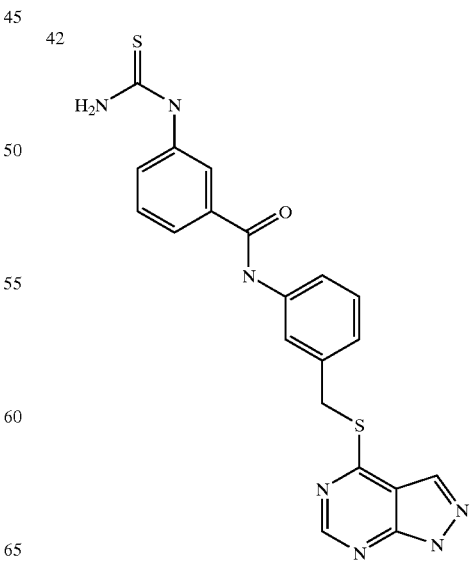

-continued
43
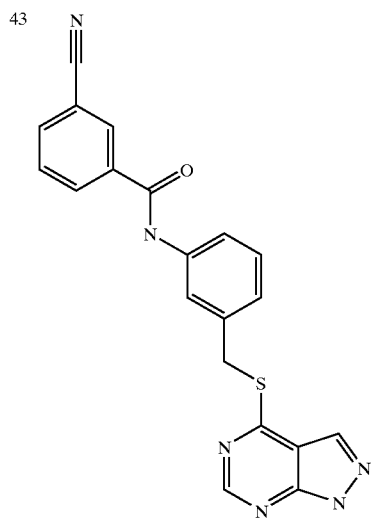
44
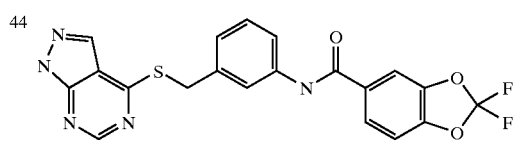
45
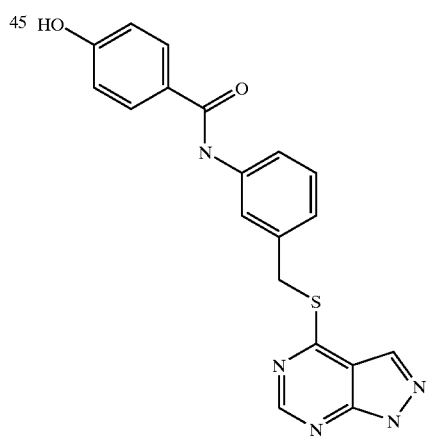
46
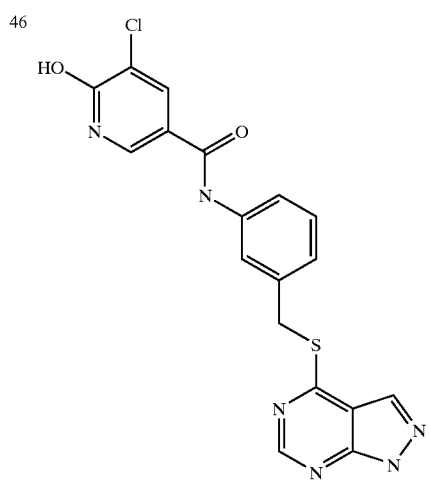
-continued
47
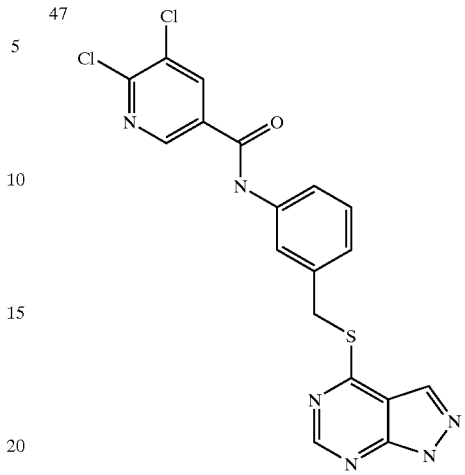
48
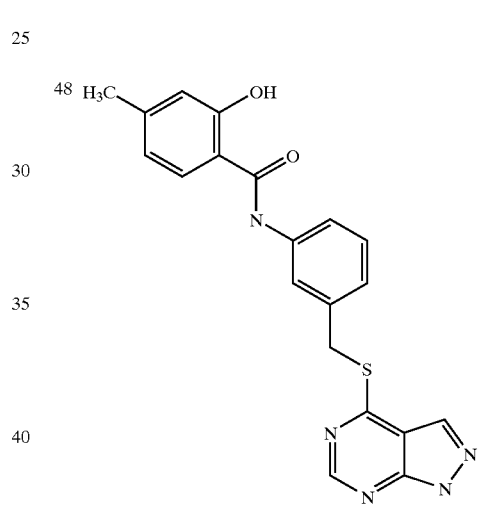
49
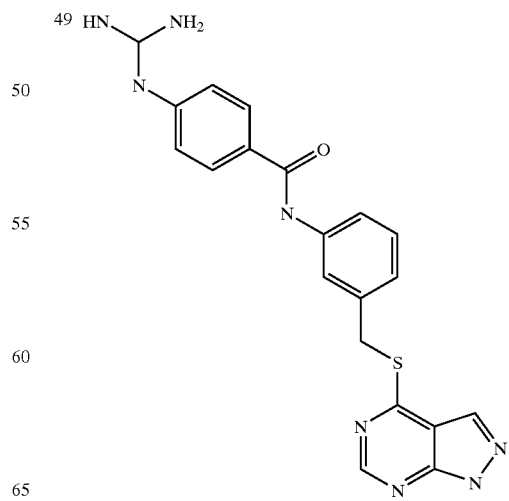

| 295 | 296 |
|---|---|
| -continued | -continued |
| 50 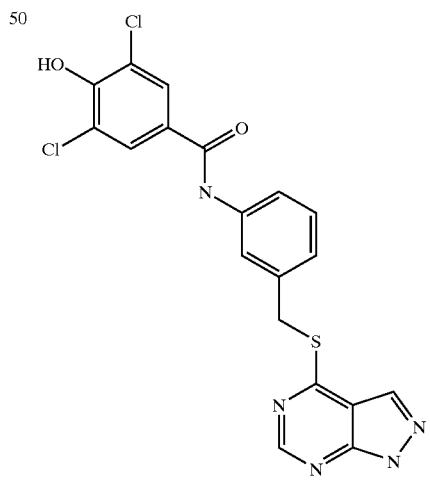 | 54 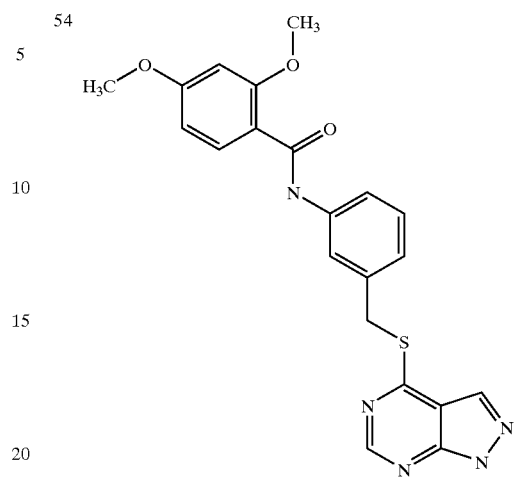 |
| 51 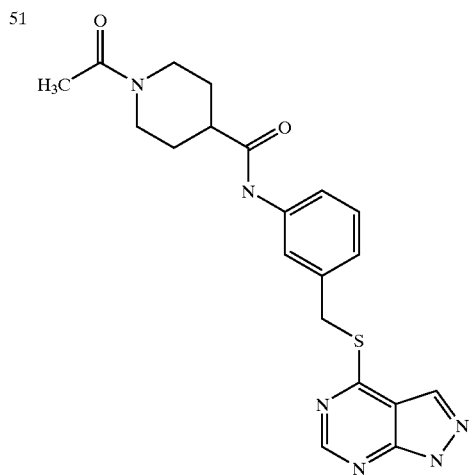 | 55 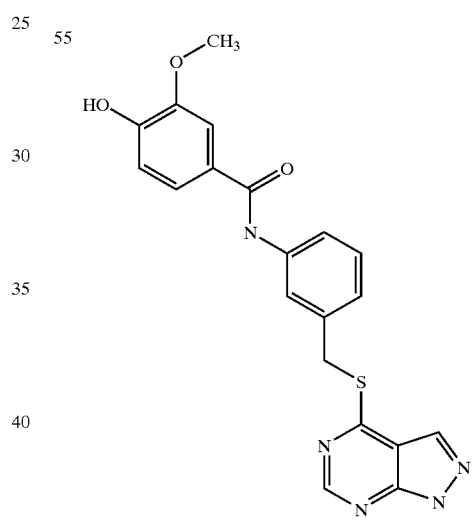 |
| 52 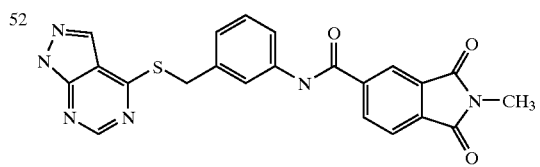 | |
| 53 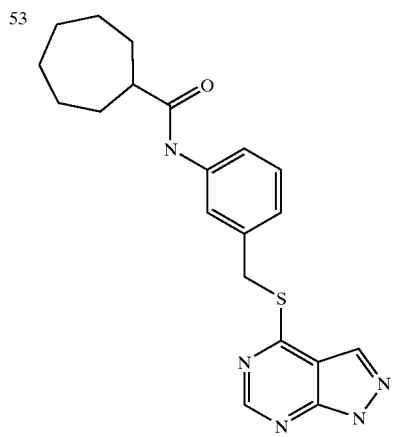 | 56 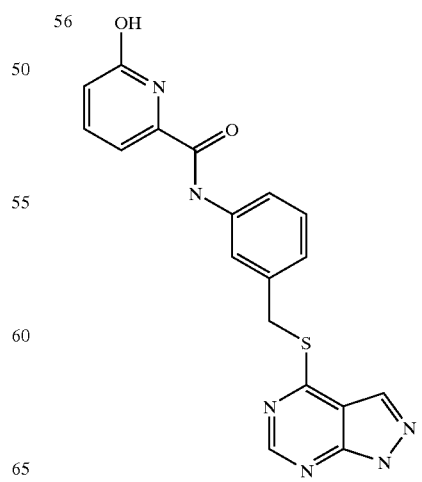 |

57 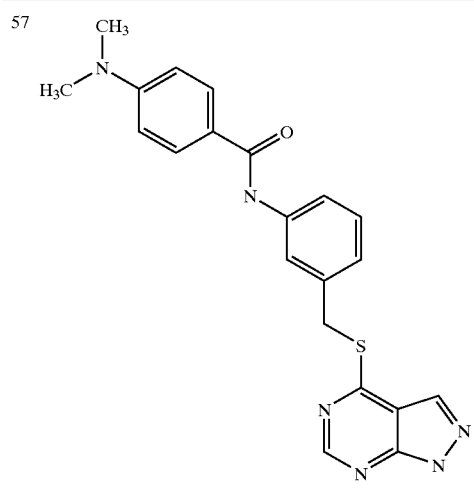
60 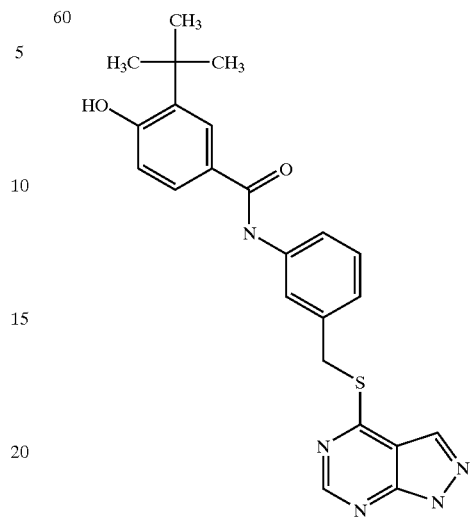
58 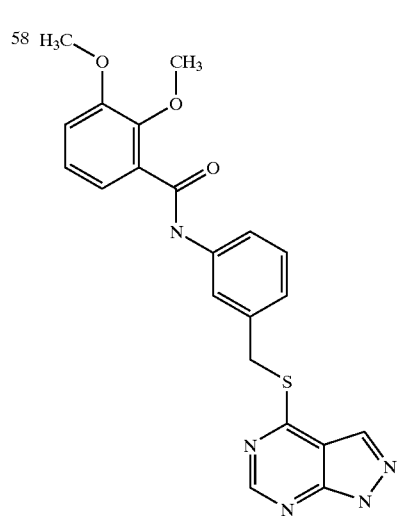
61 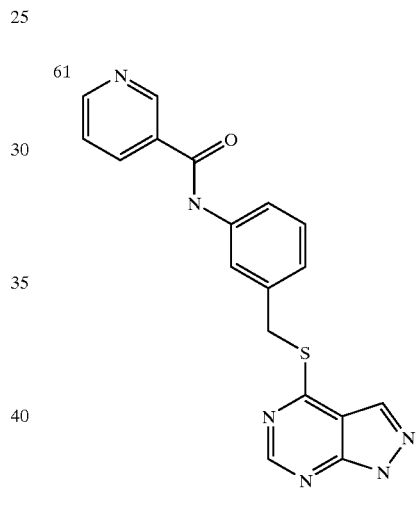
59 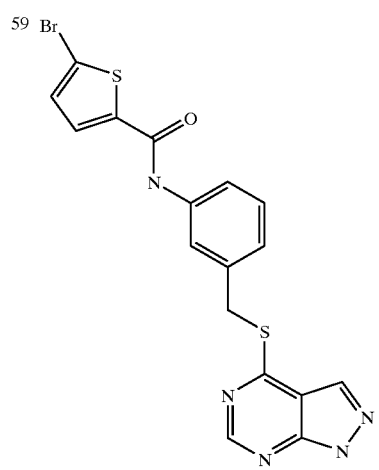
62 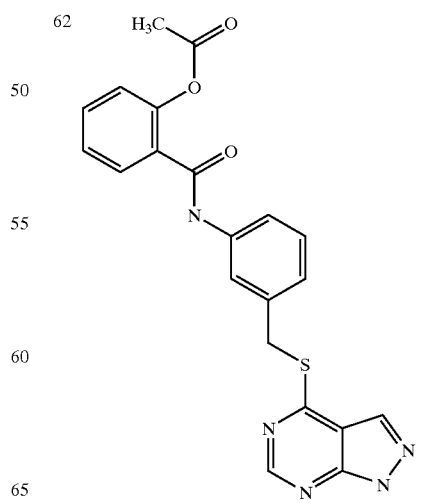

-continued
63
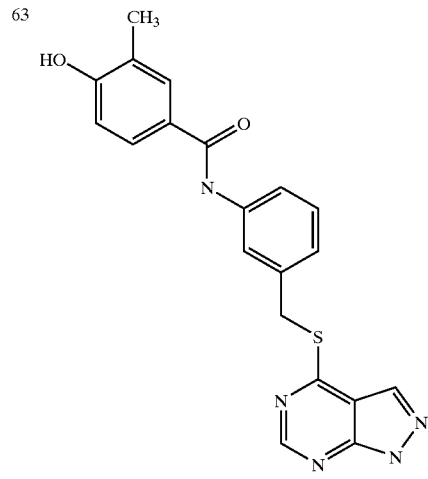
64
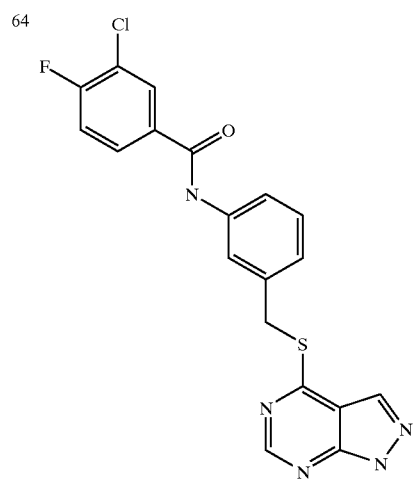
65
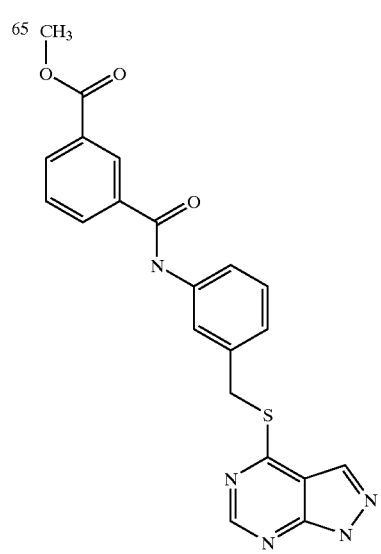
-continued
66
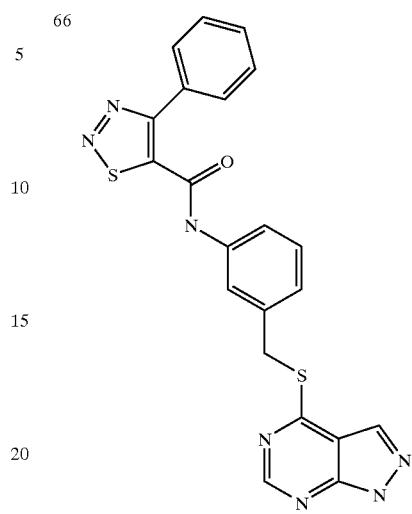
67
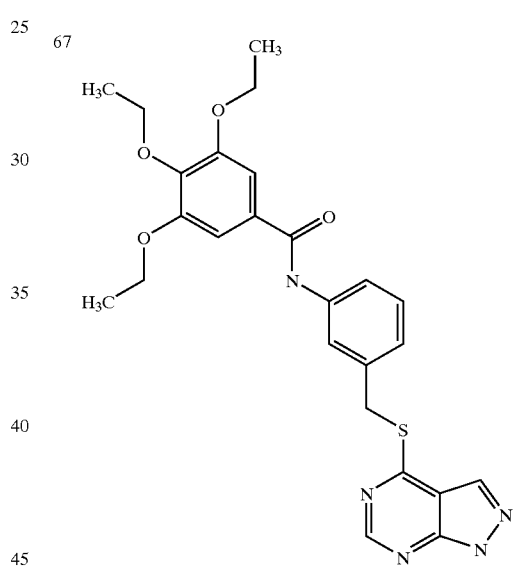
68
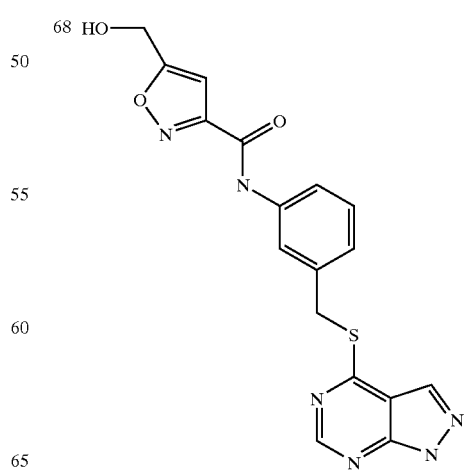

69
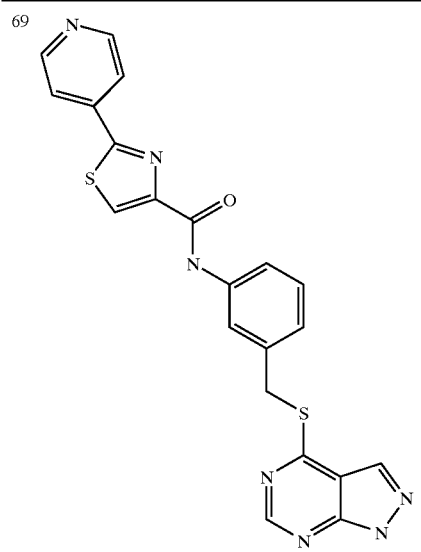
70
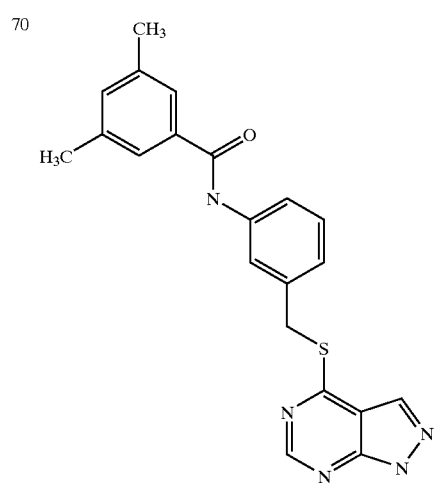
71
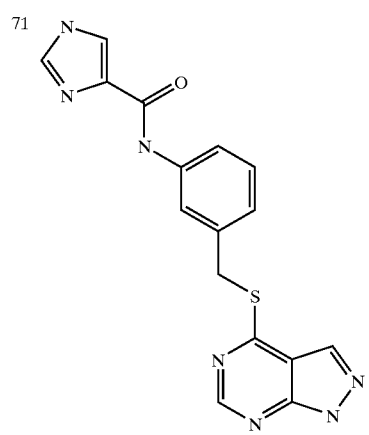
72
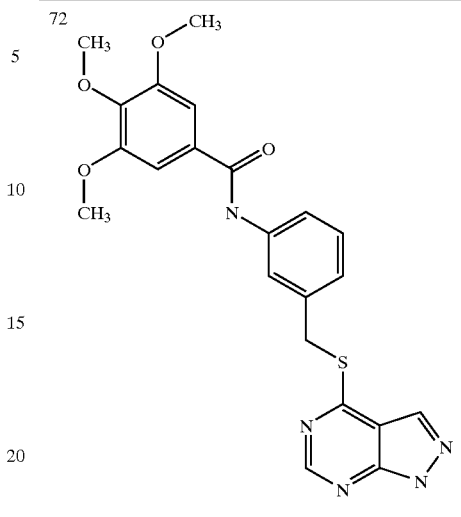
73
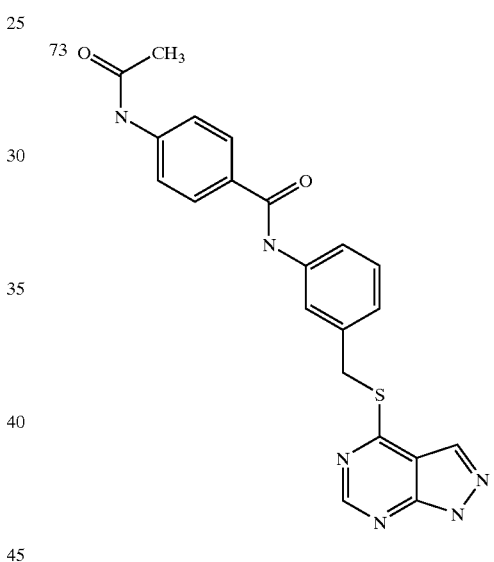
74
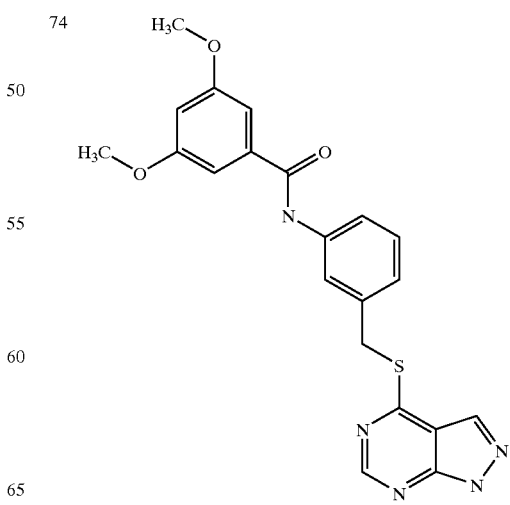

| 75 | 78 |
|---|---|
| 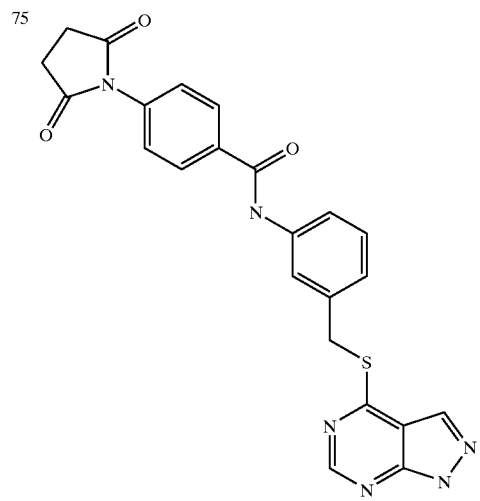 | 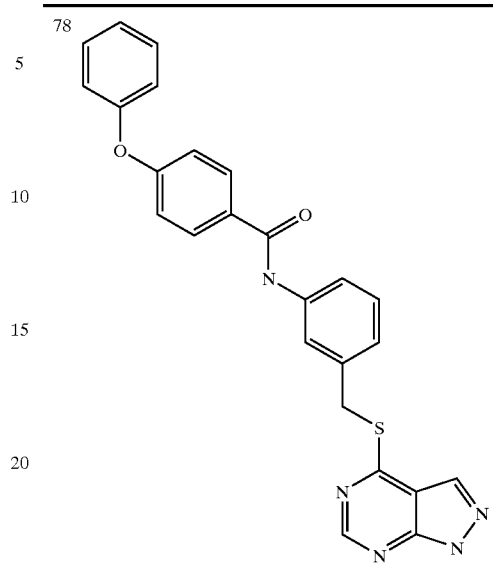 |
| 76 | 79 |
| 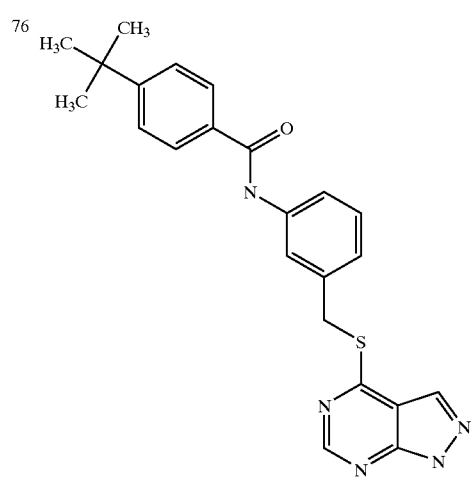 | 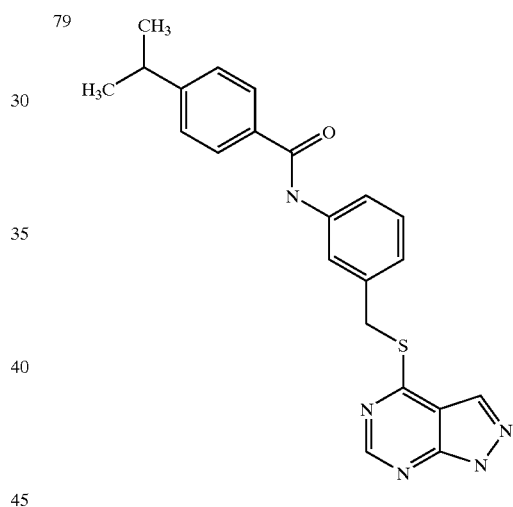 |
| 77 | 80 |
| 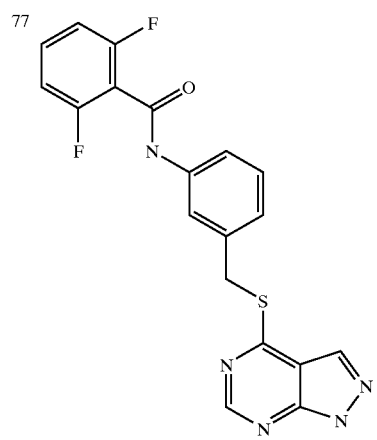 | 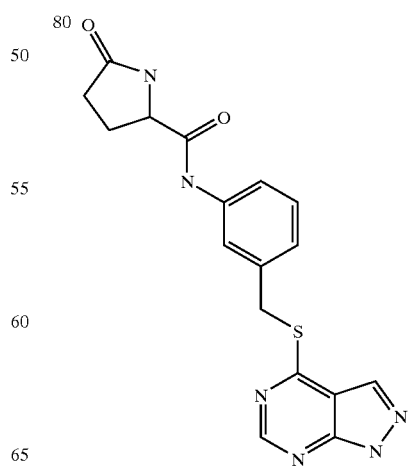 |

| 81 | 84 |
|---|---|
| 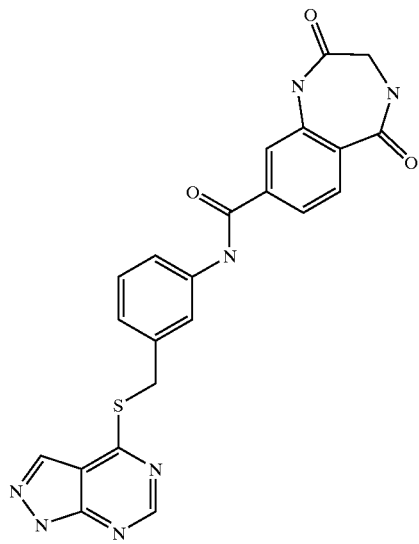 | 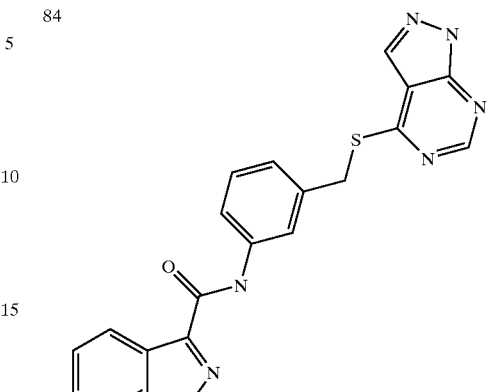 |
| 82 | 85 |
| 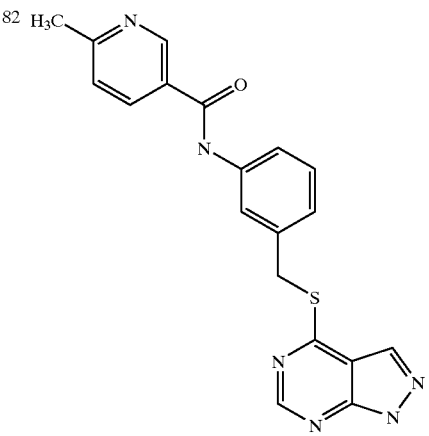 | 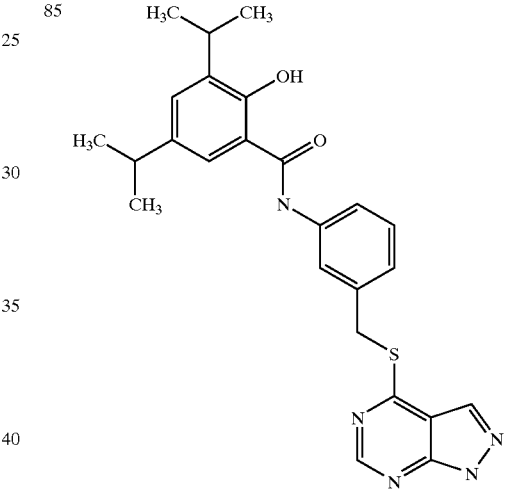 |
| 83 | 86 |
| 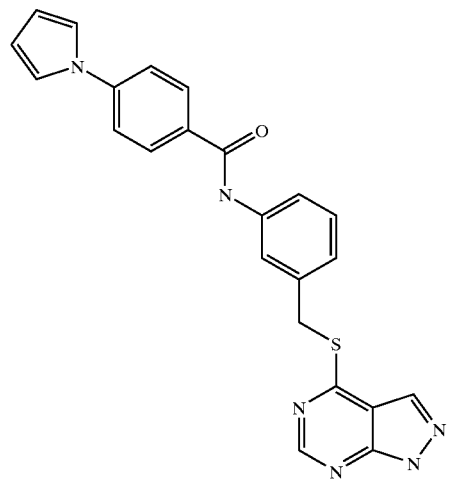 | 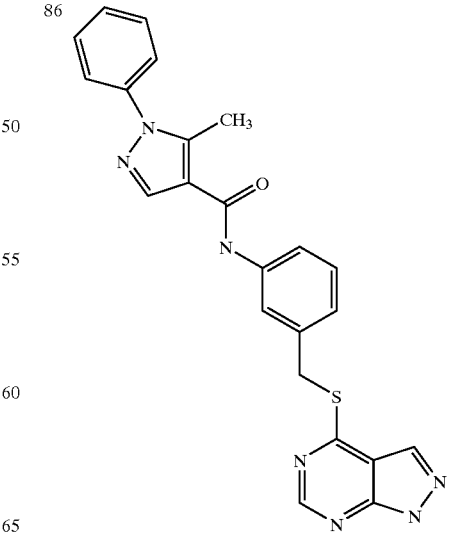 |

-continued

87 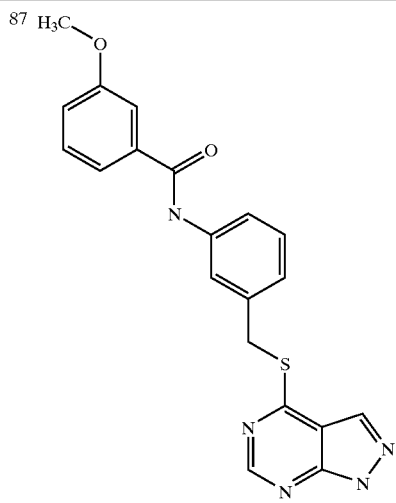

88 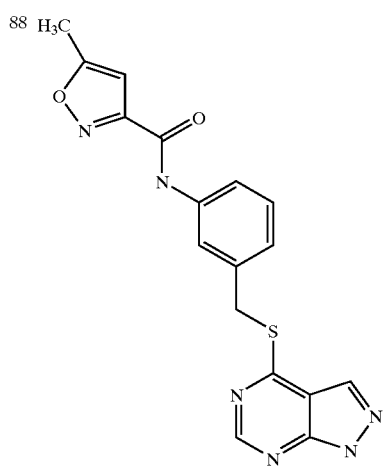

Example V-15

(R/S)-2-(2-methylphenyl)-N-{3-[(1H-pyrazolo[3,4-d]pyrimidin-4-ylsulfanyl)methyl)methyl}phenyl}butanamide

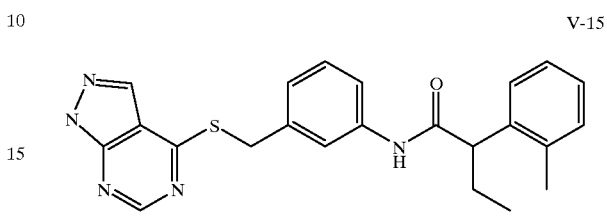

V-15

Example V-15 was prepared in a manner similar to that described in Example V-6, except that 3-(o-tolyl)-butyric acid was used in place of 4-phenoxybenzoic acid in step (b): $^1$H NMR (300 MHz, DMSO-d$_6$) δ14.08 (s, 1H), 9.95 (s, 1H), 8.76 (s, 1H), 8.26 (s, 1H), 7.71 (s,1H), 7.50–7.48 (d, 1H, J=8.31 Hz), 7.40–7.37 (dd, 1H, J=2.08, 8.31 Hz), 7.25–7.20 (d, 1H, J=7.74, 7.93 Hz), 7.16–7.09 (m, 4H), 4.64 (s, 2H), 3.76–3.72 (dd, 1H, J=5.48, 5.67 Hz), 2.38 (s, 3H), 1.99–1.92 (m, 1H), 1.63–1.60 (m, 1H), 0.90–0.80 (t, 3H, J=7.18, 7.37 Hz); APCIMS m/z 418 [M+H]$^+$.

Example W-1

3-t-Butyl-4-hydroxy-N-{3-[5-(6-methoxy-pyridin-3-ylamino)-2 H-pyrazol-3-ylmethylsulfanyl]-phenyl}-benzamide

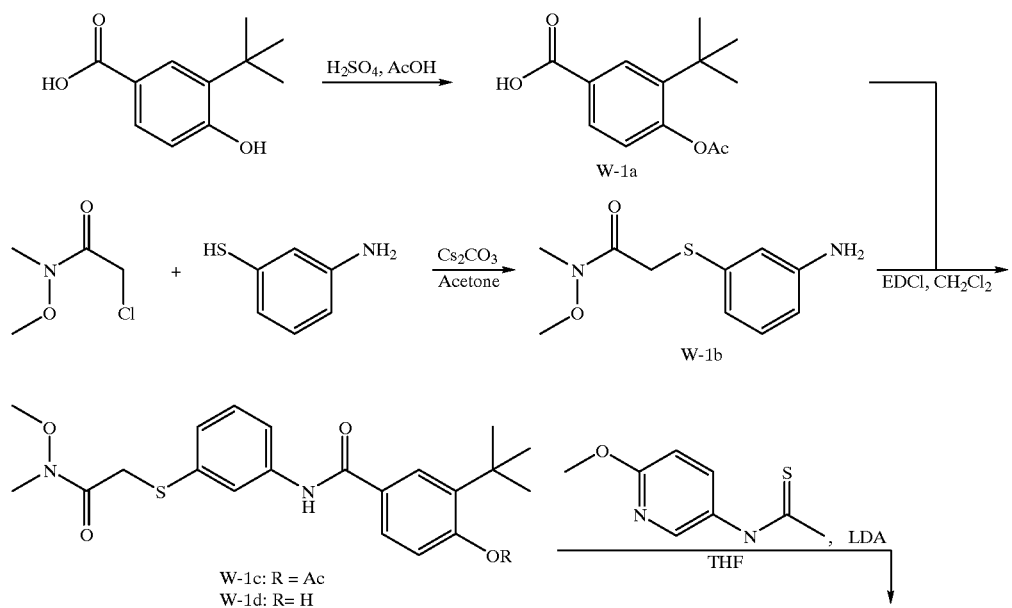

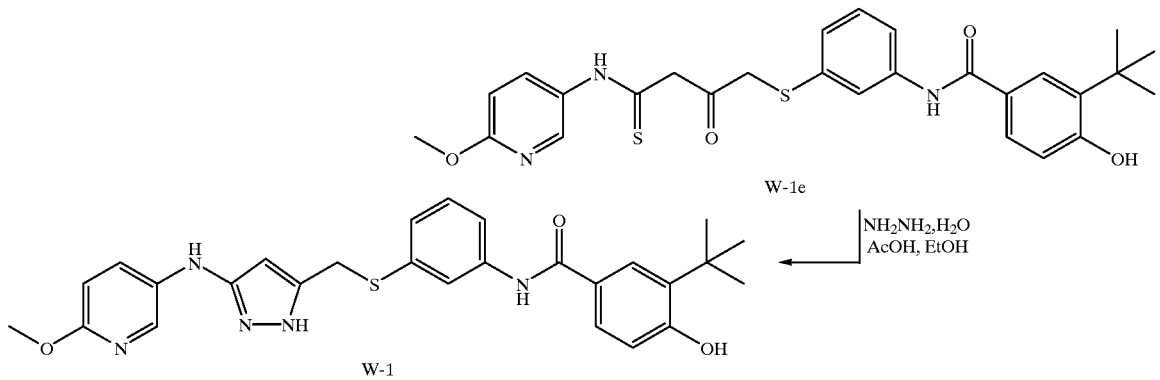

(a) A solution of 3-t-butyl4-hydroxy-benzoic acid (1.0 g, 5.2 mmol, 1.0 eq) in acetic anhydride (5.0 mL) was treated with concentrated sulfuric acid (0.03 mL, 0.5 mmol, 0.1 eq). The clear reaction mixture was warmed to 90° C. After 18 h, the resultant black solution was concentrated under reduced pressure and treated with 1.0 M hydrochloric acid (100 mL). The aqueous layer was extracted with ethyl acetate (3×50 mL) and the combined organic extracts were washed with water (50 mL), brine (50 mL), dried over magnesium sulfate, filtered, and concentrated under reduced pressure to give a brown solid (1.2 g). The crude product was purified by radial chromatography over silica gel using 10–20% ethyl acetate/cyclohexane with 0. 1% acetic acid to give 4-acetoxy-3-t-butyl-benzoic acid, W-1a, as a white solid (309 mg, 26%): mp 123–125° C.; TLC Rf=0.6 (20% ethyl acetate/cyclohexane with 0.1% acetic acid); IR (KBr) 3418 (br), 1789, 1766 cm-1; 1H NMR (300 MHz, DMSO-d6) δ8.12 (d, 1H, J=2.1 Hz), 8.06 (dd, 1H, J=8.4, 2.1 Hz), 7.36 (d, 1H, J=8.4 Hz), 2.39 (s, 3H), 1.36 (S, 9H).

(b) A slurry of 3-mercaptoaniline (1.00 mL, 9.42 mmol), 2-chloro-N-methoxy-N-methyl-acetamide and cesium carbonate (6.12 g, 18.84 mmol) in 5 mL of acetone was stirred for 18 h. The reaction mixture was partitioned between ethyl acetate (30 mL) and sat. sodium carbonate (2×50 mL) and the organic layer concentrated to dryness to give an amber oil. Purification by chromatography on silica gel using hexane/ethyl acetate (1:1) afforded 1.57 g (56%) of 2-(3-aminophenylsulfanyl)-N-methoxy-N-methyl-acetamide, W-1b, as a clear oil. HPLC $R_t$=5.85 min; 1H NMR (300 MHz, CDCl$_3$) δ7.26 (s, 1H), 7.08 (t, 1H, J=8.1 Hz), 6.84–6.82 (m, 2H), 6.54 (d, 1H, J=8.7 Hz), 3.82 (s, 2H), 3.75 (s, 3H), 3.22 (s, 3H).

(c) To a solution of 0.24 g (0.81 mmol) of 2-(3-amino-phenylsulfanyl)-N-methoxy-N-methyl-acetamide, W-1b, in dichloromethane (3 mL) was added 0.18 g (0.89 mmol) of 3-t-butyl-4-acetoxy-benzoic acid, W-1b, and EDC (0.18 g, 0.97 mmol). After 18 h, the reaction was partitioned between ethyl acetate (30 mL) and sat. sodium bicarbonate (2×20 mL) and washed with 1N HCl (2×20 mL). The organic layer was dried over sodium sulfate and concentrated to a give yellow oil, which was purified by chromatography on silica gel using hexane/ethyl acetate (1:1) as eluant to afford 4-acetoxy-3-t-butyl-N-{3-[(methoxy-methyl-carbamoyl)-methylsulfanyl]-phenyl}benzamide, W-1c, as a colorless oil, 0.31 g (86%). HPLC $R_t$=13.65 min.; 1H NMR (300 MHz, CDCl$_3$) δ8.41 (br s, 1H), 7.94 (d, 1H, J=2.1 Hz), 7.75 (t, 1H, J=1.8 Hz), 7.63 (dd, 1H, J=8.4, 2.1 Hz), 7.57–7.53 (m, 1H), 7.28–7.15 (m, 2H), 7.03 (d, 1H, J=8.4 Hz), 5.30 (s, 1H), 3.83 (s, 2H), 3.72 (s, 3H), 3.18 (s, 3H), 2.36 (s, 3h), 1.36 (s, 9H). LCESI: Calculated for C$_{23}$H$_{28}$N$_2$O$_5$S (M+H$^+$): 445, Found: 445.

(d) To a solution of 0.30 g (0.68 mmol) of 4-acetoxy-3-t-Butyl-N-{3-[(methoxy-methyl-carbamoyl)-methylsulfanyl]-phenyl}benzamide, W-1c, in 7 mL of methanol/acetone/water (1:5:1) was added was potassium carbonate (0.55 g, 1.35 mmol). The reaction mixture was stirred for 1 h at room temperature and then partitioned between 1N HCl (2×20 mL) and ethyl acetate (30 mL). The organic dried over sodium sulfate and concentrated to give a yellow oil. Trituration with diethyl ether (2×5 mL) gave 0.22 g (81%) of 3-t-butyl-4-hydroxy-N-{3-[(methoxy-methyl-carbamoyl)-methylsulfanyl]-phenyl}benzamide, W-1d, as a white solid: HPLC Rt=13.12 min.; 1H NMR (300 MHz, CDCl$_3$) δ8.04 (d, 1H, J=2.1 Hz), 8.00 (br s, 1H), 7.85 (dd, 1H, J=8.4, 2.4 Hz), 7.74 (d, 1H, 7.8 Hz), 7.49 (t, 1H, J=7.8 Hz), 7.39 (d, 1H, J=7.5 Hz), 7.02 (d, 1H, J=8.4 Hz), 4.13 (s, 2H), 3.95 (s, 3H), 3.41 (s, 3H), 1.64 (s, 9H). LCESI: Calculated for C$_{21}$H$_{26}$N$_2$O$_4$S (M+H$^+$): 403, Found: 403.

(e) To a solution of 0.24 g (1.31 mmol) of N-(6-methoxy-pyridin-3-yl)-thioacetamide in anhydrous THF (5 mL) at −78° C. was added dropwise 1.32 mL (2.64 mmol) of LDA (2.0 M in THF). The reaction mixture was stirred for 0.25 h at −78° C., warmed to 0° C. for 1 h, and then recooled to −78° C. To the resulting solution was added dropwise over a 5 min period a solution of 0.17 g (0.41 mmol) of 3-t-butyl-4-hydroxy-N-{3-[(methoxy-methyl-carbamoyl)-methylsulfanyl]-phenyl}benzamide, W-1d, in 5 mL of THF. After 1 h at 0° C., the reaction was quenched with methanol/acetic acid (0.5 mL:0.5 mL) and then partitioned between 30 mL of ethyl acetate and sat. sodium carbonate (2×20 mL). The organic layer was concentrated to give a yellow oil, which was purified by chromatography on silica gel (1:1 hexane/ethyl acetate) to afford 0.22 g (96%) of 3-t-Butyl-4-hydroxy-N-{3-[3-(6-methoxy-pyridin-3-ylthiocarbamoyl)-2-oxo-propylsulfanyl]-phenyl}benzamide, W-1e, as a pale yellow foam: HPLC Rt=13.12 min.; 1H NMR (300 MHz, CDCl$_3$) δ8.23–8.18 (m, 1H), 8.08–7.98 (m, 2H), 7.86–7.70 (m, 2H), 7.58–7.40 (m, 2H), 7.28–7.15 (m, 2H), 6.82–6.68 (m, 2H). 3.94 (s, 3H), 3.89 (s, 2H), 2.74 (s, 2H). 1.36 (s, 9H). LCESI: Calculated for C$_{27}$H$_{29}$N$_3$O$_4$S$_2$ (M+H$^+$): 524, Found: 524.

(f) To a solution of 0.18 g (0.33 mmol) of 3-t-butyl-4-hydroxy-N-{3-[3-(6-methoxy-pyridin-3-ylthiocarbamoyl)-2-oxo-propylsulfanyl]-phenyl}-benzamide, W-1e, in ethanol (2 mL) was added hydrazine mono-hydrate (0.25 mL, 0.50 mmol) and acetic acid 0.025 mL, 0.28 mL). After 2 h, the reaction solution was concentrated and the residue was purified by chromatography (4:1 hexane:ethyl acetate) to afford 0.11 g (62%) of 3-t-Butyl-4-hydroxy-N-{3-[5-(6-methoxy-pyridin-3-ylamino)-2H-pyrazol-3- ylmethylsulfanyl]-phenyl}-benzamide, W-1: HPLC Rt=13.65 min.; $^1$H NMR (300 MHz, CDCl$_3$) δ7.88 (br s, 1H), 7.73 (d, 1H, J=2.4 Hz), 7.71 (s, 1H), 7.53 (dd, 1H, J=8.4, 2.4 Hz), 7.44 (br s, 1H), 7.17 (t, 1H, J=7.8 Hz), 7.02 (d, 1H, J=7.8 Hz), 7.71 (d, 1H, J=8.4 Hz), 7.55 (d, 1H J=8.7 Hz), 5.64 (s, 1H), 5.39 (s, 1H), 4.03 (s, 2H), 3.71 (s, 3H), 1.33 (s, 9H); LCESI: Calculated for C$_{27}$H$_{29}$N$_5$O$_3$S (M+H$^+$): 504, Found: 504. Anal. calc'd for C$_{27}$H$_{29}$N$_5$O$_3$S.0.3 CH$_2$Cl$_2$: C, 61.97; H, 5.64; N, 13.24. Found C, 61.78; H, 5.67; N, 13.16.

Example W-2

3-t-Butyl-4-hydroxy-N-[3-(pyridin-3-ylmethylsulfanyl)-phenyl]-benzamide

W-2

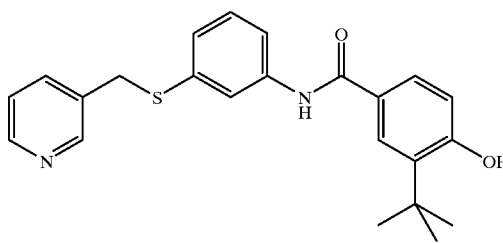

Example W-2 was prepared in a similar manner to that described for the preparation of the intermediate 3-t-butyl-4-hydroxy-N-{3-[(methoxy-methyl-carbamoyl)-methylsulfanyl]-phenyl}benzamide, W-1d, in example W-1, except that 3-picolyl chloride hydrochloride was used in place of 2-chloro-N-methoxy-N-methyl-acetamide in step (b): mp 95–100° C.; HPLC R$_t$=14.0 min.; TLC R$_f$=0.5 (5% methanol/dichloromethane); $^1$H NMR (300 MHz, DMSO-d$_6$) δ10.15 (s, 1H), 10.04 (s, 1H), 8.60 (s, 1H), 8.48 (d, 1H, J=3.6 Hz), 7.88 (s, 1H), 7.84–7.72 (m, 3H), 7.64 (d, 1H, J=8.1 Hz), 7.40–7.29 (m, 2H), 7.10 (d, 1H, J=8.0 Hz), 6.92 (d, 1H, J=8.4 Hz), 4.32 (s, 2H), 1.46 (s, 9H); MS (ESI) m/z 393 [M+H]$^+$. Anal. calc'd for C$_{23}$H$_{24}$N$_2$O$_2$S.0.5 MTBE: C, 72.63; H, 7.16; N, 6.22; S, 7.12. Found: C, 70.40; H, 6.86; N, 6.44; S, 7.17.

Example W-3

3-t-Butyl-4-hydroxy-N-[3-(isoquinolin-4-ylmethylsulfanyl)-phenyl]-benzamide

W-3

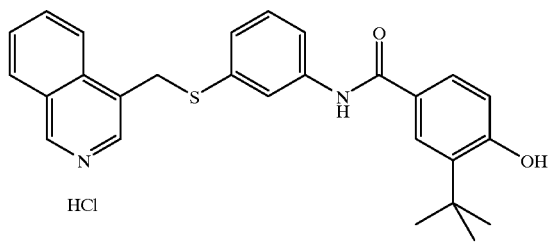

Example W-3, isolated as the hydrochloride salt as described in Example K-2, was prepared in a similar manner to that described for the preparation of the intermediate 3-t-butyl-4-hydroxy-N-{3-[(methoxy-methyl-carbamoyl)-methylsulfanyl]-phenyl}benzamide, W-1d, in example W-1, except that 4-chloromethylisoquinoline hydrochloride, K-1c, was used in place of 2-chloro-N-methoxy-N-methyl-acetamide in step (b): mp 205–210° C.; HPLC R$_t$=15.2 min.; TLC R$_f$=0.4 (5% methanol/dichloromethane); $^1$H NMR (300 MHz, DMSO-d$_6$) δ10.28 (s, 1H), 10.15 (s, 1H), 9.81 (s, 1H), 8.66–8.59 (m, 3H), 8.32 (t, 1H, J=7.8 Hz), 8.11 (t, 1H, J=7.6 Hz), 7.95 (s, 1H), 7.88 (d, 1H, J=2.0 Hz), 7.83 (dd, 1H, J=8.0, 2.0 Hz), 7.75 (d, 1H, J=9.0 Hz), 7.41 (t, 1H, J=8.0 Hz), 7.22 (d, 1H, J=7.7 Hz), 7.02 (d, 1H, J=8.4 Hz), 4.95 (s, 2H), 1.52 (s, 9H); MS (ESI) m/z 443 [M+H]$^+$. Anal. calc'd for C$_{27}$H$_{26}$N$_2$O$_2$S.HCl.0.2 H$_2$O: C, 66.45; H, 5.78; N, 5.743; S, 6.54. Found: C, 66.20; H, 6.23; N, 5.37; S, 6.13.

Example X-1

N-[3-(5-Bromo-pyridin-3-ylmethoxy)-phenyl]-3-t-butyl-4-hydroxy-benzamide

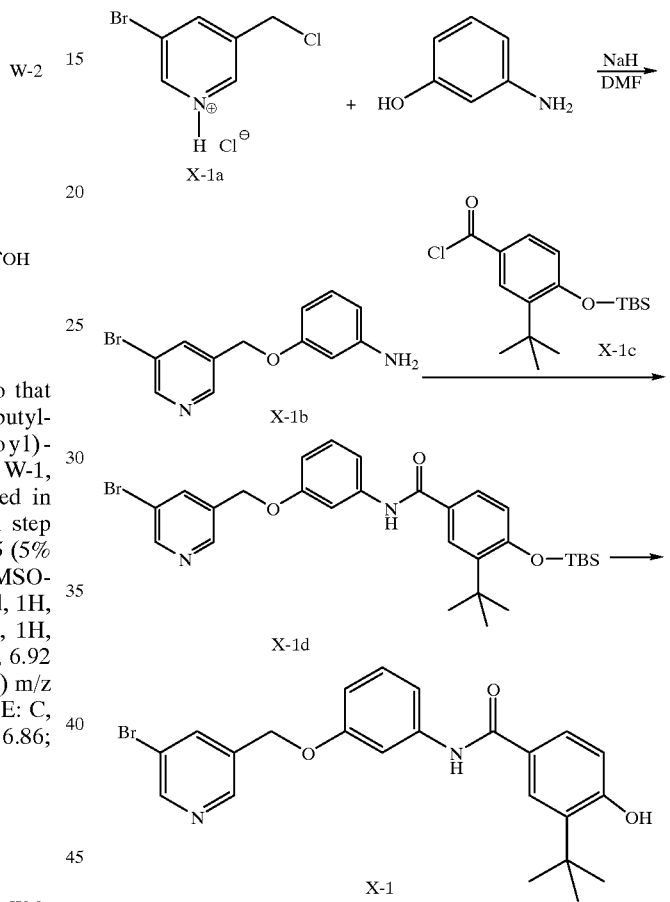

(a) To a solution of 156 mg (1.43 mmol) of 3-aminophenol in DMF at 0° C. was added 115 mg (2.86 mmol) of 60% sodium hydride dispersion in mineral oil. After 45 min, a slurry of 380 mg (1.57 mmol) of 5-bromo-3-chloromethylpyridine hydrochloride, X-1a, which was prepared from 5-bromo-3-(hydroxymethyl)pyridine (Hamel, P. et al., J. Med. Chem., 40, 2866–2875 (1997)) according to the procedure described in Example K-1, step (c), in DMF was added. The reaction was allowed to slowly warm to room temperature over 3 h and then partitioned between MTBE and sat. aq. ammonium chloride. The organic layer was washed with brine, dried over MgSO$_4$, and concentrated. The residue was purified by radial chromatography with a gradient of 0 to 1% methanol in 40% ethyl acetate/cyclohexane to give 318 mg of 3-(5-bromo-pyridin-3-ylmethoxy)aniline, X-1b, as a clear oil: $^1$H NMR (300 MHz, DMSO-d$_6$) δ8.68 (d, 1H, J=2.3 Hz), 8.64 (d, 1H, J=1.7 Hz), 8.10 (t, 1H, J=2.0 Hz), 6.91 (t, 1H, J=8.0 Hz), 6.17–6.22 (m, 3H), 5.10 (br s, 2H), 5.06 (s, 2H); MS (ESI) m/z 279/281 [M+H]$^+$.

(b) To a solution of 280 mg (1.0 mmol) 3-(5-bromo-pyridin-3-ylmethoxy)aniline, X-1b, in dichloromethane (10 mL) was sequentially added 326 mg (1.0 mmol) of 3-t-butyl-4-(t-butyl-dimethylsilanyloxy)-benzoyl chloride, X-1c, (Trova, M. P. et al., *J. Med. Chem.*, 36, 580–590 (1993)) and triethylamine (0.15 mL, 1.1 mmol). The resultant clear solution was stirred for 18 h at room temperature and then the solvent was removed under reduced pressure. The reaction mixture was treated with 5% sodium bicarbonate (100 mL) and extracted with 10% isopropanol/chloroform (3×50 mL). The combined organic extracts were washed with brine (50 mL), dried over magnesium sulfate, filtered, and concentrated under reduced pressure to give an off-white solid (569 mg). The crude product was purified by radial chromatography over silica gel using 1–2% methanol/dichloromethane to give N-[3-(5-bromo-pyridin-3-ylmethoxy)-phenyl]-3-t-butyl-4-(t-butyl-dimethyl-silanyloxy)-benzamide, X-1d, as a white solid (456 mg, 80%): HPLC $R_t$=20.6 min; TLC $R_f$=0.8 (4% methanol/dichloromethane); $^1$H NMR (300 MHz, DMSO-$d_6$) δ9.91 (s, 1H), 8.53–8.51 (m, 1H), 8.00 (t, 1H, J=2.0 Hz), 7.64 (d, 1H, J=2.3 Hz), 7.56 (dd, 1H, J=8.5, 2.2Hz), 7.41 (t, 1H, J=2.0Hz), 7.19–7.16(m, 1H), 7.09 (t, 1H, J=8.1 Hz), 6.78 (d, 1H, J=8.4 Hz), 6.60 (dd, 1H, J=8.0, 1.6 Hz), 5.00 (s, 2H), 1.23 (s, 9H), 0.86 (s, 9H), 0.20 (s, 6H); MS (ESI) m/z 569/571 [M+H]$^+$.

(c) To a solution of 100 mg (0.18 mmol) N-[3-(5-bromo-pyridin-3-ylmethoxy)-phenyl]-3-t-butyl-4-(t-butyl-dimethyl-silanyloxy)-benzamide, X-1d, in THF (7 mL) at 0° C. was added a 1.0 M solution of tetrabutylammonium fluoride in THF (0.27 mL, 0.27 mmol). The slightly yellow reaction mixture was warmed to room temperature over several hours and stirred an additional 15 h. The cloudy reaction mixture was concentrated under reduced pressure to give a clear oil. The crude product was purified by radial chromatography over silica gel using 2–4% methanol/dichloromethane to give N-[3-(5-bromo-pyridin-3-ylmethoxy)-phenyl]-3-t-butyl-4-hydroxy-benzamide, X-1, as a white solid (75 mg, 91%): mp 105–111° C.; HPLC $R_t$=14.7 min.; TLC $R_f$=0.4 (4% methanol/dichloromethane); $^1$H NMR (300 MHz, DMSO-$d_6$) δ10.11 (s, 1H), 10.01 (s, 1H), 8.74–8.72 (m, 2H), 8.21 (t, 1H, J=2.0 Hz), 7.78 (d, 1H, J=2.1 Hz), 7.72 (dd, 1H, J=8.3, 2.2 Hz), 7.61 (t, 1H, J=2.0 Hz), 7.40–7.37 (m, 1H), 7.29 (t, 1H, J=8.1 Hz), 6.91 (d, 1H, J=8.4 Hz), 6.79 (dd, 1H, J=7.8, 2.1 Hz), 5.20 (s, 2H), 1.43 (s, 9H); $^{13}$C NMR (75 MHz, DMSO-$d_6$) δ166.1, 159.5, 158.4, 150.1, 147.9, 141.2, 138.3, 135.4, 135.3, 129.7, 127.2, 127.1, 125.4, 120.5, 115.9, 113.5, 109.9, 107.2, 66.3, 34.8, 29.5; MS (ESI) m/z 455/457 [M+H]$^+$. Anal. calc'd for $C_{23}H_{23}BrN_2O_3$: C, 60.67; H, 5.09; Br, 17.55; N, 6.15. Found: C, 60.63; H, 5.24; Br, 17.69; N, 6.01.

Example X-2

4-Acetoxy-3-t-butyl-N-[3-(pyridin-3-ylmethoxy)phenyl]-benzamide

X-2

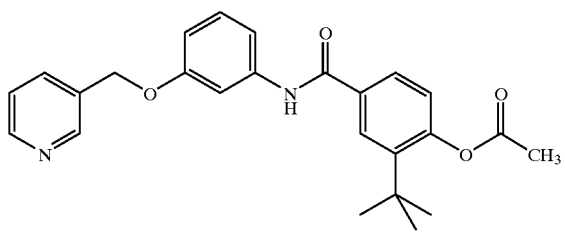

Example X-2 was prepared from 3-(pyridin-3-ylmethoxy)aniline, X-2a, prepared from 3-picolylchloride hydrochloride and 3-hydroxyaniline as described in Example X-1, step (a), and 4-acetoxy-3-t-butylbenzoic acid, W-1a, according to the procedure described in Example W-1, step (c): mp 58–62° C.; HPLC $R_t$=14.4 min.; TLC $R_f$=0.3 (4% methanol/dichloromethane); $^1$H NMR (300 MHz, DMSO-$d_6$) δ10.25 (s, 1H), 8.70 (s, 1H), 8.56 (d, 1H, J=4.3 Hz), 7.91–7.80 (m, 3H), 7.58–7.56 (m, 1H), 7.46–7.21 (m, 4H), 6.81–6.78 (m, 1H), 5.16 (s, 2H), 2.37 (s, 3H), 1.36 (s, 9H); MS (ESI) m/z 419 [M+H]$^+$. Anal. calc'd for $C_{25}H_{26}N_2O_4 \cdot 0.4 \, H_2O$: C, 70.53; H, 6.35; N, 6.58. Found: C, 70.87; H, 6.28; N, 6.59.

Example X-3

4-Acetoxy-3-t-butyl-N-[3-(isoquinolin-4-ylmethoxy)phenyl]-benzamide

X-3

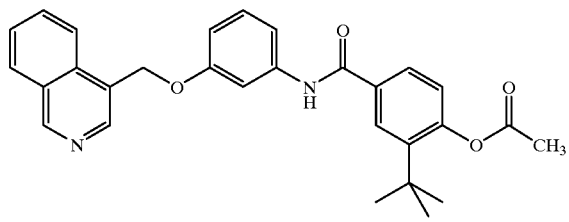

Example X-3 was prepared from 3-(isoquinolin-4-ylmethoxy)aniline, prepared from 4-chloromethylisoquinoline hydrochloride, K-1c, and 3-hydroxyaniline as described in Example X-1, step (a), and 4-acetoxy-3-t-butylbenzoic acid, W-1a, according to the procedure described in Example W-1, step (c): mp 83–86° C.; HPLC $R_t$=15.6 min.; TLC $R_f$=0.3 (1% methanol/dichloromethane); $^1$H NMR (300 MHz, DMSO-$d_6$) δ10.26 (s, 1H), 9.37 (s, 1H), 8.67 (s, 1H), 8.21 (d, 1H, J=7.9 Hz), 8.14 (d, 1H, J=8.8 Hz), 7.91–7.73 (m, 4H), 6.60 (t, 1H, J=2.2 Hz), 7.40–7.37 (m, 1H), 7.30 (t, 1H, J=8.1 Hz), 7.22 (d, 1H, J=8.3 Hz), 6.90 (dd, 1H, J=7.6, 2.2 Hz), 5.56 (s, 2H), 2.36 (s, 3H), 1.36 (s, 9H); MS (ESI) m/z 469 [M+H]$^+$. Anal. calc'd for $C_{29}H_{28}N_2O_4 \cdot 0.2 \, H_2O$: C, 73.77; H, 6.06; N, 5.93. Found: C, 73.46; H, 6.38; N, 5.82.

Example X-4

3-t-Butyl-4-hydroxy-N-[3-(pyridin-3-ylmethoxy)phenyl]-benzamide

X-4

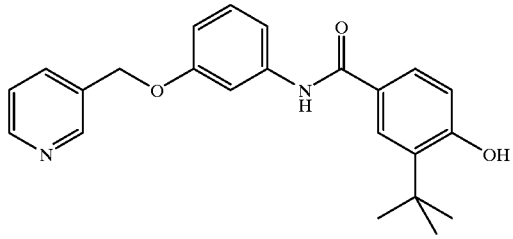

Example X-4 was prepared from 4-acetoxy-3-t-butyl-N-[3-(pyridin-3-ylmethoxy)phenyl]-benzamide, X-2, in a manner similar to that described in Example W-1, step (d): mp 104–107° C.; HPLC $R_t$=13.6 min; TLC $R_f$=0.5 (5% methanol/dichloromethane); $^1$H NMR (300 MHz, DMSO-$d_6$) δ10.07 (s, 1H), 9.96 (s, 1H), 8.69 (s, 1H), 8.56 (d, 1H, J=4.0 Hz), 7.90 (d, 1H, J=7.9 Hz), 7.74–7.67 (m, 2H), 7.57 (s, 1H), 7.47–7.42 (m, 1H), 7.35–7.33 (m, 1H), 7.24 (t, 1H, J=8.0 Hz), 6.87 (d, 1H, J=8.3 Hz), 6.77–6.74 (m, 1H), 5.15 (s, 2H), 1.40 (s, 9H); $^{13}$C NMR (75 MHz, DMSO-$d_6$) δ166.1, 159.5, 158.6, 149.5, 149.4, 141.2, 136.0, 135.4, 133.0, 130.0, 127.2, 127.1, 125.4, 124.0, 115.9, 113.3, 109.9, 107.2, 67.2, 34.5, 29.5; MS (ESI) m/z 375 [M–H]$^-$. Anal. calc'd for $C_{23}H_{24}N_2O_3$·0.5 MTBE: C, 72.83; H, 7.19; N, 6.66. Found: C, 72.61; H, 7.12; N, 6.66.

Example X-5

3-t-Butyl-4-hydroxy-N-[3-(isoquinolin-4-ylmethoxy)-phenyl]-benzamide

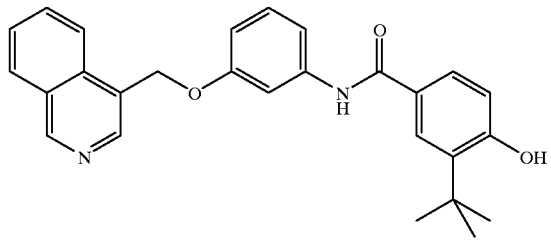

X-5

Example X-5 was prepared from 4-acetoxy-3-t-butyl-N-[3-(isoquinolin-4-ylmethoxy)phenyl]-benzamide, X-3, in a manner similar to that described in Example W-1, step (d): HPLC R$_t$=14.8 min; TLC R$_f$=0.4 (4% methanol/dichloromethane); $^1$H NMR (300 MHz, DMSO-$d_6$) δ10.09 (s, 1H), 9.97 (s, 1H), 9.34 (s, 1H), 8.65 (s, 1H), 8.20 (d, 1H, J=8.2 Hz), 8.13 (d, 1H, J=7.9 Hz), 7.90–8.86 (m, 1H), 7.78–7.59 (m, 4H), 7.38–7.35 (m, 1H), 7.26 (t, 1H, J=8.0 Hz), 6.85 (d, 2H, J=8.6 Hz), 5.54 (s, 2H), 1.38 (s, 9H); HRMS (FAB) calcd for $C_{27}H_{26}N_2O_3$ [M+ H]$^+$ 427.2022, found 427.2020.

Example Y-1

1-[3-(pyridin-3-ylmethoxy)phenylcarbamoyl] pyrrolidine

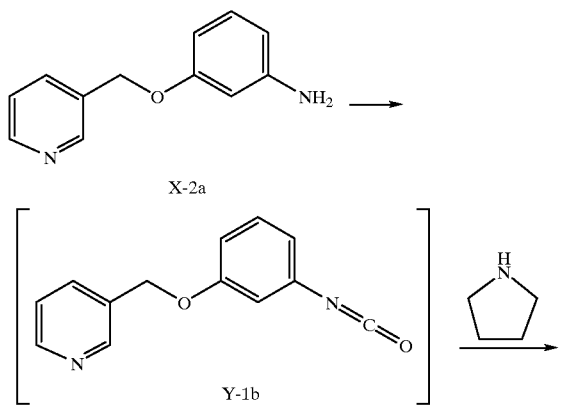

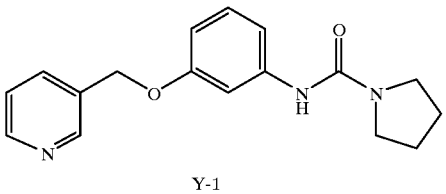

Y-1

A solution of 100 mg (0.50 mmol) of 3-(pyridin-3-ylmethoxy)aniline, X-2a, and 0.076 mL (0.55 mmol) of triethylamine in 2 mL of dichloromethane was added dropwise to a solution of triphosgene (54 mg, 0.18 mmol) in 2 mL of dichloromethane. After 20 min, a solution of pyrrolidine (0.042 mL) and triethylamine (0.076 mL) in 2 mL of dichloromethane was added to the reaction mixture. After 2 h, the reaction was partitioned between dichloromethane and 5% aq. sodium bicarbonate. The organic layer was washed with water and brine, dried over MgSO$_4$ and concentrated. The residue was purified by radial chromatography with a gradient of 0 to 2% methanol in 1:1 ethyl acetate:cyclohexane to give 81 mg (55%) of 1-[3-(pyridin-3-ylmethoxy) phenylcarbamoyl]pyrrolidine, Y-1, as a white solid: mp 138–140° C.; HPLC R$_t$=9.7 min.; TLC R$_f$=0.3 (5% methanol/dichloromethane); $^1$H NMR (300 MHz, DMSO-$d_6$) δ8.66 (d, 1H, J=1.7 Hz), 8.54 (dd, 1H, J=4.7, 1.5 Hz), 8.08 (s, 1H), 7.88–7.85 (m, 1H), 7.45–7.41 (m, 1H), 7.35–7.34 (m, 1H), 7.16–7.09 (m, 2H), 6.61–6.58 (m, 1H), 5.09 (s, 2H), 3.40–3.31 (m, 4H), 1.87–1.83 (m, 4H); $^{13}$C NMR (75 MHz, DMSO-$d_6$) δ158.5, 154.1, 149.4, 149.3, 142.3, 135.9, 133.1, 129.4, 123.9, 112.4, 108.0, 106.3, 67.1, 46.0, 25.4; MS (ESI) m/z 298 [M+H]$^+$. Anal. calc'd for $C_{17}H_{19}N_3O_2$: C, 68.67; H, 6.44; N, 14.13. Found: C, 68.41; H, 6.50; N, 13.89.

Example Y-2

4-[3-(pyridin-3-ylmethoxy)phenylcarbamoyl] morpholine

Y-2

Example Y-2 was prepared in a manner similar to that described in Example Y-1, except that morpholine was used in place of pyrrolidine: mp 58–62° C.; HPLC R$_t$=8.7 min.; TLC R$_f$=0.3 (5% methanol/methylene chloride); $^1$H NMR (300 MHz, DMSO-$d_6$) δ8.96 (s, 1H), 8.84 (d, 1H, J=5.3 Hz), 8.63 (s, 1H), 8.50 (d, 1H, J=7.8 Hz), 8.00–7.95 (m, 1H), 7.36 (s, 1H), 7.16 (t, 1H, J=8.1 Hz), 7.07 (d, 1H, J=7.9 Hz), 6.65–6.63 (m, 1H), 5.26 (s, 2H), 3.60 (t, 4H, J=4.5 Hz), 3.42 (t, 4H, J=4.5 Hz); $^{13}$C NMR (75 MHz, DMSO-$d_6$) δ157.7, 155.0, 143.8, 141.9, 141.1, 136.9, 129.2, 126.8, 112.6, 108.0, 106.2, 66.0, 65.4, 44.2; MS (ESI) m/z 314 [M+H]$^+$. Anal. calc'd for $C_{17}H_{19}N_3O_3$·HCl·0.3 H$_2$O: C, 57.48; H, 5.85; Cl, 9.98; N, 11.83. Found: C, 57.05; H, 5.83; Cl, 9.99; N, 11.50.

Example Z-1

3-[{6-Methoxy-7-(2-methoxyethoxy)cinnolin-4-yl}sulfanylmethyl]-N-phenyl-benzamide

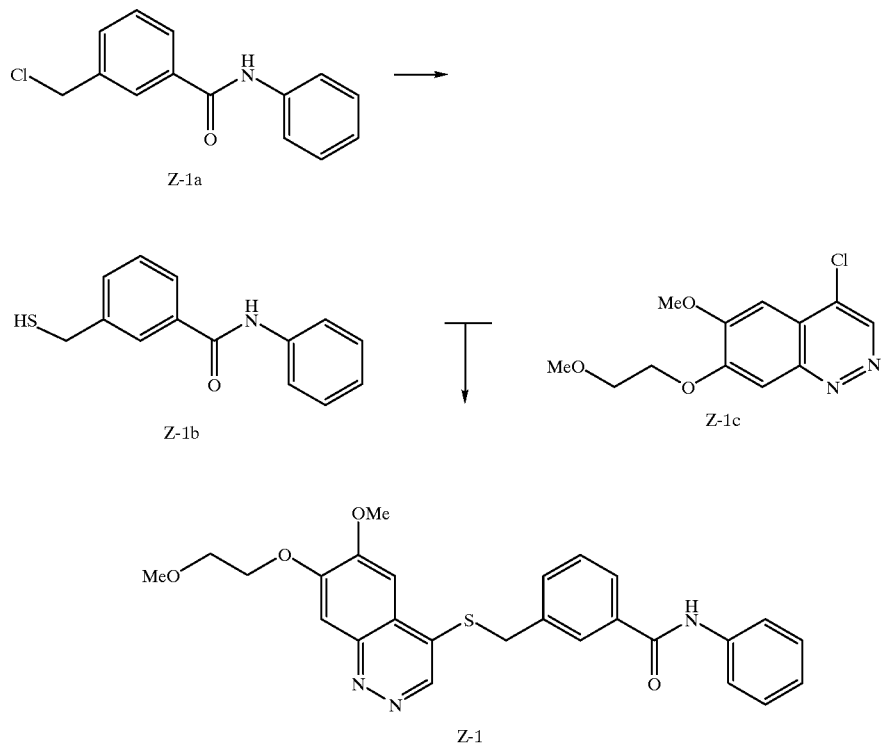

(a) To a solution of 0.30 g (1.33 mmol) of 3-(chloromethyl)-N-phenylbenzamide, Z-1a, which prepared in a manner similar to that described in Example A-1, step (a), in 6 mL of ethanol was added 0.20 g (2.65 mmol) of thiourea, and the mixture was heated to 80° C. After 3 h, 1.0 mL (3 mmol) of 2N aq. sodium hydroxide was added, and heating at 80° C. was continued. After an additional 2.5 h, the reaction was cooled to room temperature and 10 mL of water was added. The mixture was extracted with ethyl acetate, and the aqueous layer was neutralized with 1N aq. HCl and extracted again with ethyl acetate. The combined organic layers were washed with water and with brine, dried over sodium sulfate, and concentrated. The residue was purified by chromatography on silica gel, eluting with a gradient of 15% to 30% ethyl acetate in hexane, to provide 174 mg of 3-(mercaptomethyl)-N-phenylbenzamide, Z-1b: $^1$H NMR (300 MHz, CDCl$_3$) δ7.85 (s, 2H), 7.75 (m, 1H), 7.67 (m, 2H), 7.53 (m, 1H), 7.40, (m, 3H), 7.17 (m, 1H), 3.80 (d, 2H), 1.83 (t, 1H).

(b) To a solution of 50 mg (0.186 mmol) of 4-chloro-6-methoxy-7-(2-methoxyethoxy)cinnoline, Z-1c, (PCT application WO 97/34876, p.51) and 42.5 mg (0.189 mmol) of 3-(mercaptomethyl)-N-phenylbenzamide, Z-1b, in 1.2 mL of isopropanol was added 12.3 mg of potassium hydroxide in 1.2 mL of ethanol. The mixture was heated to 40° C. for 45 min, then cooled to room temperature. The precipitate was collected by filtration and air-dried to give 44.7 mg (47%) of 3-[{6-methoxy-7-(2-methoxyethoxy)cinnolin-4-yl}sulfanylmethyl]-N-phenyl-benzamide, Z-1: $^1$H NMR (300 MHz, DMSO-d$_6$) δ10.29 (s, 1H), 9.19 (s, 1H), 8.10 (s, 1H), 7.89 (m, 1H), 7.76 (m, 4H), 7.54 (m, 1H), 7.38 (m, 2H), 7.09 (m, 2H), 4.72 (s, 2H), 4.38 (m, 2H), 3.98 (s, 3H), 3.77 (m, 2H), 3.32 (s, 3H) MSESI$^{(+)}$: M+H$^+$ 476, M+Na$^+$ 498, M+K$^+$ 514.

Example AA-1

3-[2-(6-Acetylamino-pyridin-3-yl)-ethyl]-N-(4-piperazin-1-yl-3-trifluoromethylphenyl)-benzamide dihydrochloride

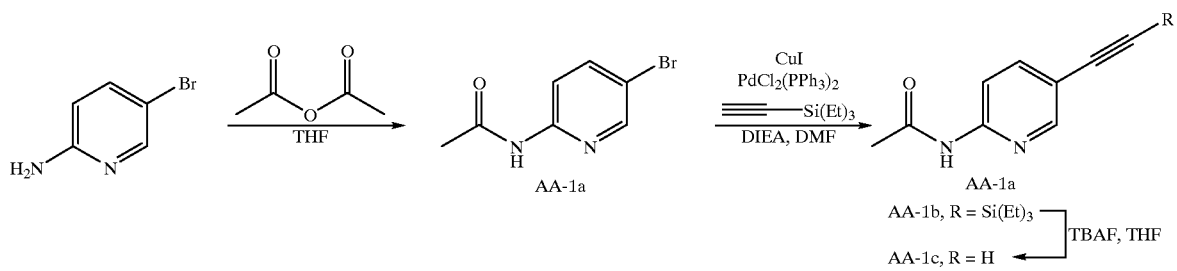

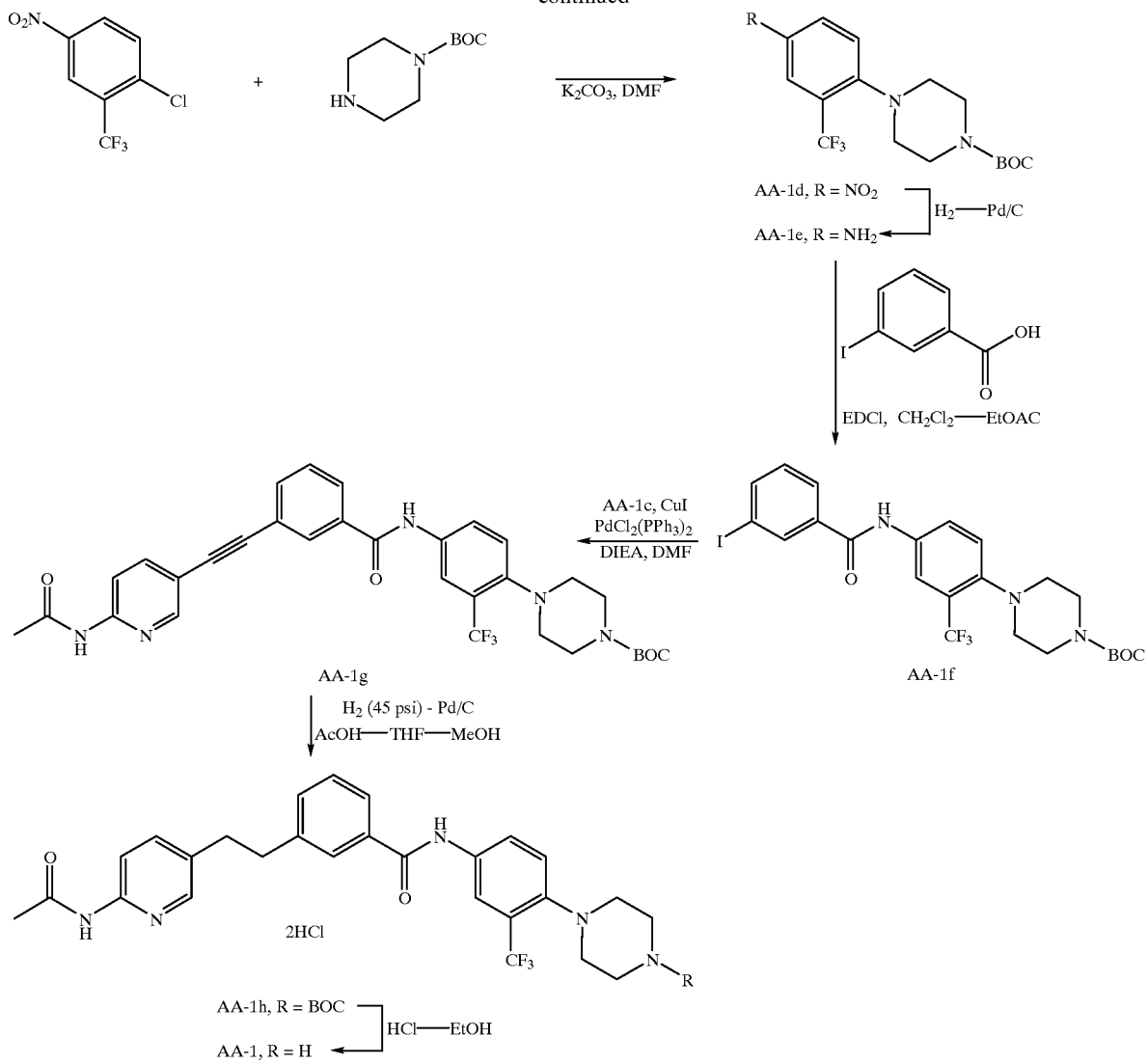

(a) To a solution of 5-bromo-pyridin-2-ylamine (Aldrich, 2.0 g, 11.6 mmol, 1.0 eq) in tetrahydrofuran (100 mL) was added acetic anhydride (3.0 mL, 31.8 mmol, 2.7 eq) and triethylamine (1.8 mL, 12.8 mmol, 1.1 eq). After 3 days, the solvent was removed and the crude reaction mixture was dissolved in ethyl acetate and sequentially washed with aqueous 5% sodium bicarbonate and brine. The crude product was dried over magnesium sulfate to give N-(5-bromo-pyridin-2-yl)-acetamide, AA-1a, as a white solid (2.5 g, 100%): HPLC $R_t$ 8.4 min.; TLC $R_f$ 0.7 (2% methanol-dichloromethane); $^1$H NMR (DMSO-$d_6$, 300 MHz) δ10.62 (s, 1H), 8.42 (dd, 1H, J=2.5, 0.7 Hz), 8.06 (d, 1H, J=9.0 Hz), 7.98 (dd, 1H, J=9.0, 2.4 Hz), 2.09 (s, 3H); $^{13}$C NMR (DMSO-$d_6$, 75 MHz) δ169.8, 151.4, 148.8, 140.8, 115.3, 113.5, 24.2; MS m/z 215/217 (M+H)$^+$.

(b) To a solution of N-(5-bromo-pyridin-2-yl)-acetamide, AA-1a, (2.2 g, 10.2 mmol, 1.0 eq) in degassed N,N-dimethylformamide (100 mL) was added diisopropylethylamine (3.6 mL, 20.4 mmol, 2.0 eq), copper(I) iodide (155 mg, 0.82 mmol, 0.08 eq), dichlorobis(triphenylphosphine)palladium(II) (286 mg, 0.41 mmol, 0.04 eq) and triethylethynyl-silane (Aldrich, 3.7 mL, 20.4 mmol, 2.0 eq). The resultant red solution was warmed to 115° C. for 2 days. The crude reaction mixture was poured into water and extracted with methyl-tert-butyl ether/ethyl acetate. The organic layer was washed with brine, dried over magnesium sulfate and purified over silica, which was eluted with 10% ethyl acetate-cyclohexane, to give N-(5-triethylsilanylethynyl-pyridin-2-yl)-acetamide, AA-1b, as a beige solid (1.2 g, 44%): HPLC $R_t$ 17.8 min.; TLC $R_f$ 0.5 (20% ethyl acetate-cyclohexane); $^1$H NMR (DMSO-$d_6$, 300 MHz) δ10.69 (s, 1H), 8.40 (d, 1H, J=1.7 Hz), 8.08 (d, 1H, J=8.6 Hz), 7.84 (dd, 1H, J=8.7, 2.3 Hz), 2.10 (s, 3H), 1.01 (t, 6H, J=7.8 Hz), 0.68 (q, 9H, J=7.8 Hz); MS (ESI) m/z 275 (M+H)$^+$.

(c) To a solution of N-(5-triethylsilanylethynyl-pyridin-2-yl)-acetamide, AA-1b, (1.0 g, 3.6 mmol, 1.0 eq) in tetrahydrofuran (40 mL) was added a solution of tetrabutylammonium fluoride (4.0 mL, 1.0 M, 4.0 mmol, 1.1 eq). The resultant amber solution was stirred at room temperature for 18 h. The solvent was removed under reduced pressure and the crude reaction mixture (1.1 g, tan solid) was dissolved in ethyl acetate and passed through a silica plug, which was eluted with ethyl acetate. The resultant yellow solid (1.0 g) was washed with 10% MTBE-cyclohexane to give N-(5-ethynyl-pyridin-2-yl)-acetamide, AA-1c, as a tan solid (491 mg, 84%): HPLC $R_t$ 7.1 min.; TLC $R_f$ 0.5 (30% ethyl acetate-cyclohexane); $^1$H NMR (DMSO-d$_6$, 300 MHz) δ10.65 (s, 1H), 8.41 (d, 1H, J=1.6 Hz), 8.08 (d, 1H, J=8.7 Hz), 7.86 (dd, 1H, J=8.6, 2.2 Hz), 4.29 (s, 1H), 2.10 (s, 3H); $^{13}$C NMR (DMSO-d$_6$, 75 MHz) δ169.5, 151.6, 150.8, 141.0, 113.6, 112.7, 82.6, 80.5, 23.9; MS (ESI) m/z 161 (M+H)$^+$.

(d) To a solution of 2-chloro-5-nitrobenzotrifluoride (Lancaster, 16.5 mL, 112 mmol, 1.0 eq) and piperazine-1-carboxylic acid tert-butyl ester (Aldrich, 2.5 g, 134 mmol, 1.2 eq) in N,N-dimethylformamide (225 mL) was added potassium carbonate (46.3 g, 336 mmol, 3.0 eq). The resultant red solution was warmed to 90° C. for 24 h. The crude product was poured into ice water (1.7 L) and extracted with ethyl acetate (3×300 mL). The combined organic extracts were diluted with methyl-tert-butyl ether (1.0 L) and sequentially washed with water and brine. The organic layer was dried over magnesium sulfate, filtered and concentrated under reduced pressure to give 4-(nitro-trifluoromethyl-phenyl)-piperazine-1-carboxylic acid tert-butyl ester, AA-1d, as an orange solid (43.6 g, 104%): HPLC R$_t$ 17.0 min.; TLC R$_f$ 0.5 (20% ethyl acetate-cyclohexane); $^1$H NMR (DMSO-d$_6$, 300 MHz) δ8.46–8.40 (m, 2H), 7.62 (d, 1H, J=8.9 Hz), 3.48 (t, 4H, J=4.8 Hz), 3.06 (t, 4H, J=5.0 Hz), 1.43 (s, 9H); MS (ESI) m/z 276 (M+H-BOC)$^+$.

(e) To a solution of 4-(nitro-trifluoromethyl-phenyl)-piperazine-1-carboxylic acid tert-butyl ester, AA-1d, (43.6 g, 116 mmol) and 10% palladium on carbon (4.3 g) in ethyl acetate (1.2 L) was added hydrogen (1 atm). The resultant slurry was stirred for 18 h, filtered through celite and concentrated under reduced pressure to give 4-[4-(t-butoxycarbonyl)piperazin-1yl]-3-trifluoromethylaniline, AA-1e, as a yellow solid (40 g, 92%): HPLC R$_t$ 14.8 min.; TLC R$_f$ 0.1 (10% ethyl acetate-cyclohexane); $^1$H NMR (DMSO-d$_6$, 300 MHz) δ7.22 (d, 1H, J=8.5 Hz), 6.82 (d, 1H, J=2.6 Hz), 6.75 (dd, 1H, J=8.5, 2.5 Hz), 5.37 (s, 2H), 3.37 (br. s, 4H), 2.66 (t, 4H, J=4.8 Hz), 1.41 (s, 9H); MS (ESI) m/z 346 (M+H)$^+$.

(f) To a solution of 4-[4-(t-butoxycarbonyl)piperazin-1yl]-3-trifluoromethylaniline, AA-1e, (10.0 g, 29.0 mmol, 1.0 eq) and 3-iodobenzoic acid (Aldrich, 8.6 g, 34.8 mmol, 1.2 eq) in ethyl acetate (300 mL) and dichloromethane (300 mL) was added 1-(3-dimethylaminopropyl)-3-ethylcarbodiimide hydrochloride (6.7 g, 34.8 mmol, 1.2 eq). The resultant brown solution was stirred for 18 h. The solvent was removed under reduced pressure and the crude product was purified over silica, which was eluted with 10–20% ethyl acetate-cyclohexane, to give 4-({[1-(3-iodo-phenyl)-methanoyl]-amino}-trifluoromethyl-phenyl)-piperazine-1-carboxylic acid tert-butyl ester, AA-1f, as a beige solid (10.3 g, 62%): HPLC R$_t$ 19.7 min.; TLC R$_f$ 0.5 (30% ethyl acetate-cyclohexane); $^1$H NMR (DMSO-d$_6$, 300 MHz) δ10.53 (s, 1H), 8.32 (s, 1H), 8.14 (d, 1H, J=2.3 Hz), 8.04 (dd, 1H, J=8.7, 2.3 Hz), 7.99–7.96 (m, 2H), 7.60 (d, 1H, J=8.8 Hz), 7.36 (t, 1H, J=7.8 Hz), 3.44 (br. s,4H), 2.51 (t, 4H, J=4.6 Hz), 1.43 (s, 9H); MS (ESI) m/z 576 (M+H)$^+$.

(g) 4-[({1-[3-(6-Acetylamino-pyridin-3-ylethynyl)-phenyl]-methanoyl}-amino)-trifluoromethyl-phenyl]-piperazine-1-carboxylic acid tert-butyl ester, AA-1g, was prepared in the manner similar to that described in example S-1, step (c) for ethyl 3-isoquinolin-4-ylethynyl-benzoate, S-1c, except that 4-({[1-(3-iodo-phenyl)-methanoyl]-amino}-trifluoromethyl-phenyl)-piperazine-1-carboxylic acid tert-butyl ester, AA-1f, was used in place of 3-iodobenzoate and N-(5-ethynyl-pyridin-2-yl)-acetamide, AA-1c, was used in place of 4-ethynyl-isoquinoline, S-1b: HPLC R$_t$ 18.1 min.; TLC R$_f$ 0.5 (2% methanol-dichloromethane); $^1$H NMR (DMSO-d$_6$, 300 MHz) δ10.71 (s, 1H), 10.55 (s, 1H), 8.17 (s, 2H), 8.14 (s, 1H), 8.07 (dd, 1H, J=8.6, 2.4 Hz), 8.01–7.96 (m, 2H), 7.80–7.78 (m, 1H), 7.65–7.58 (m, 2H), 3.44 (br. s, 4H), 2.80 (t, 4H, J=4.8 Hz), 2.13 (s, 3H), 1.44 (s, 9H); MS (ESI) m/z 608 (M+H)$^+$.

(h) 4-{[(1-{3-[2-(6-Acetylamino-pyridin-3-yl)-ethyl]-phenyl}-methanoyl)-amino]-trifluoro-methyl-phenyl}-piperazine-1-carboxylic acid tert-butyl ester, AA-1h, was prepared in a manner similar to that described in example S-1, step (d) for 3-(2-isoquinolin-4yl-ethyl)-benzoic acid ethyl ester, S-1d, except 4-[({1-[3-(6-acetylamino-pyridin-3-ylethynyl)-phenyl]-methanoyl}-amino)-trifluoromethyl-phenyl]-piperazine-1-carboxylic acid tert-butyl ester, AA-1g, was used instead of ethyl 3-(isoquinolin-4-ylethynyl)benzoate and the reduction was done at 45 psi of hydrogen in acetic acid-methanol-tetrahydrofuran: HPLC R$_t$ 17.1 min.; TLC R$_f$ 0.6 (4% methanol-dichloromethane); $^1$H NMR (DMSO-d$_6$, 300 MHz) δ10.40 (s, 1H), 10.35 (s, 1H), 8.16–8.14 (m, 2H), 8.05 (dd, 1H, J=8.8, 2.4 Hz), 7.98 (d, 1H, J=8.3 Hz), 7.84 (s, 1H), 7.81–7.77 (m, 1H), 7.64 (dd, 1H, J=8.6, 2.4 Hz), 7.58 (d, 1H, J=8.8 Hz), 7.44 (d, 1H, J=4.8 Hz), 3.44 (br. s, 4H), 2.98–2.91 (m, 4H), 2.80 (t, 4H, J=4.6 Hz), 2.06 (s, 3H), 1.43 (s, 9H); MS (ESI) m/z 612 (M+H)$^+$.

(i) 3-[2-(6-Acetylamino-pyridin-3-yl)-ethyl]-N-(4-piperazin-1-yl-3-trifluoromethyl-phenyl)-benzamide dihydrochloride, AA-1, was prepared in a manner similar to that described in example R-13, step (b) for 4-fluoro-N-[4-(piperazin-1-yl)-3-trifluoromethylphenyl]-3-(pyridin-3-yl) methoxybenzamide, R-13, except 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h, was used in place of 4-fluoro-N-[4-{t-butoxycarbonyl)piperazin-1-yl}]-3-trifluoromethylphenyl]-3-(pyridin-3-yl)methoxybenzamide, R-13a, and the deprotection was done with HCl in ethanol instead of trifluoroacetic acid in methylene chloride: HPLC R$_t$ 11.7 min.; TLC R$_f$ 0.4 (15% methanol-chloroform w/0.1% ammonium hydroxide); $^1$H NMR (DMSO-d$_6$, 300 MHz) δ10.97 (s, 1H), 10.52 (s, 1H), 9.23 (m, 2H), 8.22–8.12 (m, 3H), 7.91–7.82 (m, 4H), 7.56 (d, 1H, J=8.8 Hz), 7.44 (d, 2H, J=4.7 Hz), 3.17 (br. s, 4H), 3.07 (br. s, 4H), 2.97 (s, 4H), 2.12 (s, 3H); MS (ESI) m/z 512 (M+H)$^+$. Anal. calcd for $C_{27}H_{28}F_3N_5O_2 \times 2.0$ HCl×1.2 H$_2$O: C, 53.50; H, 5.39; N, 11.56; Cl, 11.70. Found: C, 53.44; H, 5.54; N, 11.19; Cl, 11.62.

Example AA-2

3-[2-(6-Amino-pyridin-3-yl)-ethyl]-N-(4-piperazin-1-yl-3-trifluoromethyl-phenyl)-benzamide dihydrochloride

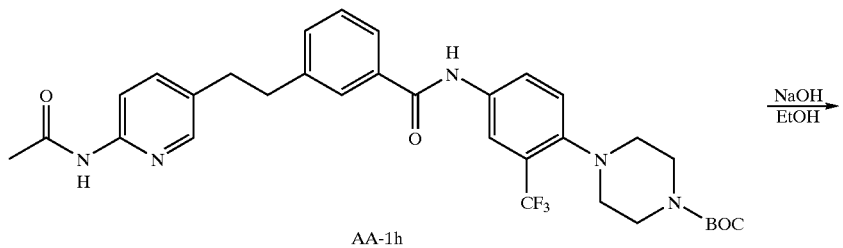

AA-1h

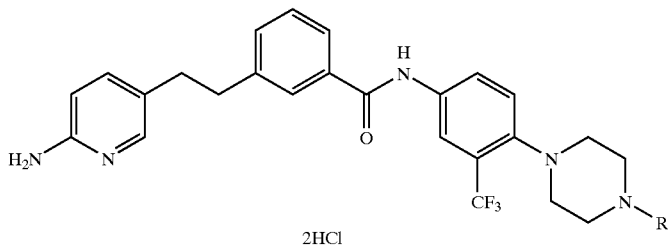

2HCl

(a) To a solution of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h, (100 mg, 0.16 mmol, 1.0 eq) in ethanol (3 mL) was added aqueous sodium hydroxide (2.8 mL, 1.0 M, 2.8 mmol, 1.8 eq). The clear solution was heated to 55° C. for 18 hours and poured into a mixture of aqueous 50% saturated sodium bicarbonate and ethyl acetate. The organic layer was washed with brine, dried over magnesium sulfate, filtered and purified by radial chromatography over silica, which was eluted with 3% methanol-chloroform with 0.1% ammonium hydroxide, to give 4-{[(1-{3-[2-(6-amino-pyridin-3-yl)-ethyl]-phenyl}-methanoyl)-amino]-trifluoromethyl-phenyl}-piperazine-1-carboxylic acid tert-butyl ester, AA-2a, as a white solid (54 mg, 59%): HPLC $R_t$ 17.0 min.; TLC $R_f$ 0.5 (5% methanol-chloroform w/0.1% ammonium hydroxide); $^1$H NMR (DMSO-$d_6$, 300 MHz) δ10.39 (s, 1H), 8.16 (d, 1H, J=2.4Hz), 8.05 (dd, 1H, J=8.6, 2.2Hz), 7.82–7.76 (m, 2H), 7.74 (dd, 1H, J=2.0 Hz), 7.57 (d, 1H, J=8.8 Hz), 7.44–7.42 (m, 2H), 7.27 (dd, 1H, J=8.4, 2.4 Hz), 6.38 (d, 1H, J=8.4 Hz), 5.63 (s, 2H), 3.44 (br. s, 4H), 2.92–2.72 (s, 8H), 1.43 (s, 9H); MS (ESI) m/z 570 (M+H)$^+$.

(b) 3-[2-(6-Amino-pyridin-3-yl)-ethyl]-N-(4-piperazin-1-yl-3-trifluoromethyl-phenyl)-benzamide dihydrochloride, AA-2, was prepared in a manner similar to that described in example AA-1, step (i), except 4-{[(1-{3-[2-(6-amino-pyridin-3-yl)-ethyl]-phenyl}-methanoyl)-amino]-trifluoromethyl-phenyl}-piperazine-1-carboxylic acid tert-butyl ester, AA-2a, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC $R_t$ 11.2 min.; $^1$H NMR (DMSO-$d_6$, 300 MHz) δ13.89 (s, 1H), 10.59 (s, 1H), 9.33 (s, 2H), 8.23 (d, 1H, J=2.2 Hz), 8.15–8.13 (m, 1H), 7.95–7.79 (m, 6H), 7.54 (d, 1H, J=8.7 Hz), 7.45–7.43 (m, 2H), 6.96 (d, 1H, J=9.0 Hz), 3.17 (s, 4H), 3.08 (s, 4H), 2.94–2.93 (m, 2H), 2.88–2.87 (m, 2H); MS (ESI) m/z 470 (M+H)$^+$. Anal. calcd for $C_{25}H_{26}F_3N_5O \times 2.0$ HCl: C, 55.36; H, 5.20; N, 12.91; Cl, 13.07. Found: C, 55.18; H, 5.16; N, 12.65; Cl, 13.28.

Example BB-1

3-[2-(3H-Imidazo[4,5-b]pyridin-6-yl)-ethyl]-N-(4-piperazin-1-yl-3-trifluoromethyl-phenyl)-benzamide dihydrochloride

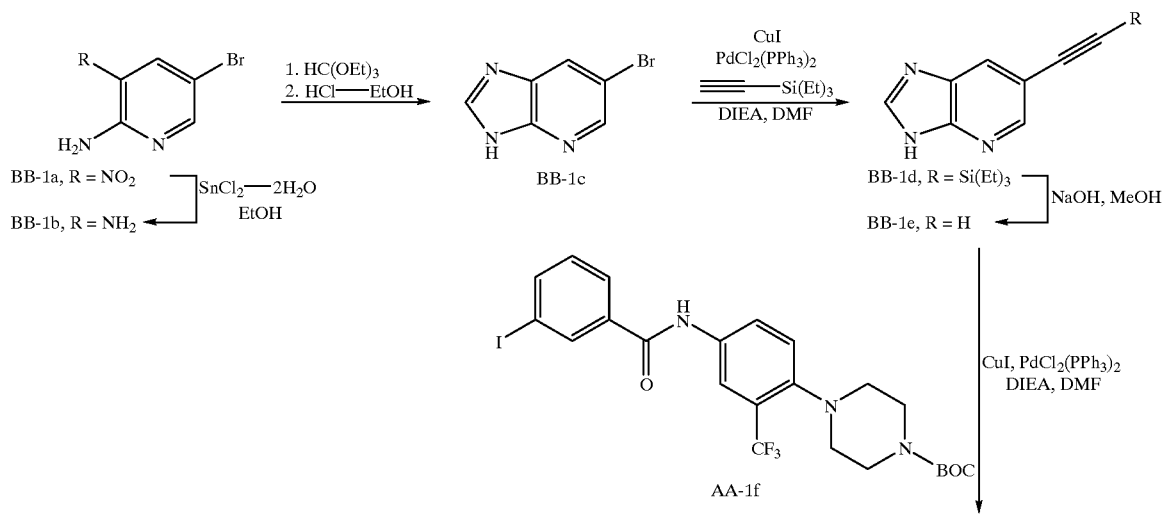

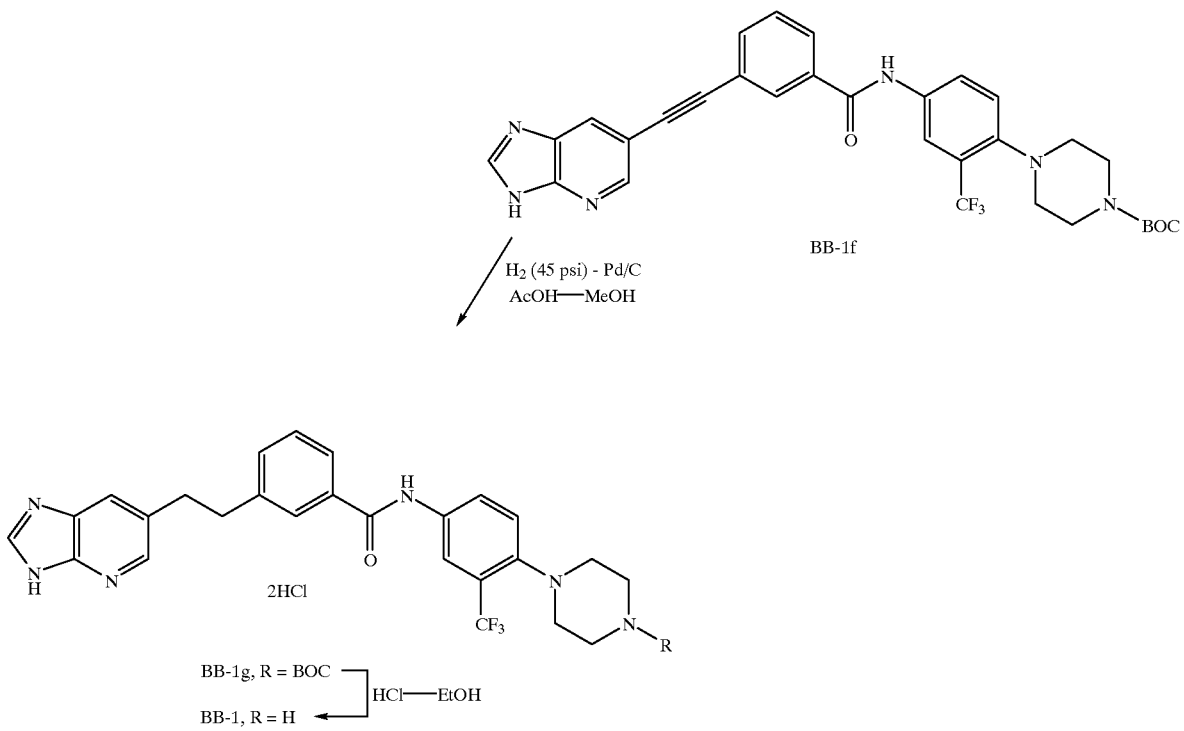

(a) To a solution of 5-bromo-3-nitro-pyridin-2-ylamine, BB-1a, (Lancaster, 8.9 g, 40.8 mmol, 1.0 eq) in ethanol (450 mL) was added tin(II) chloride dihydrate (32.3 g, 143 mmol, 3.5 eq). The resultant yellow slurry was warmed to 60° C. for 4 h. The solvent was removed under reduce pressure and the crude reaction mixture was treated with 10% ammonium hydroxide and extracted with ethyl acetate. The combined organic extracts were dried over magnesium sulfate, filtered, and concentrated under reduced pressure to give a black solid (7.5 g). The crude product was purified over silica (flash), which was eluted with 2–7% methanol-ethyl acetate, to give 5-bromo-pyridine-2,3-diamine, BB-1b, as a grey solid (7.0 g, 91%): HPLC $R_t$ 5.5 min.; TLC $R_f$ 0.5 (1% methanol-ethyl acetate); $^1$H NMR (DMSO-$d_6$, 300 MHz) δ7.28 (d, 1H, J=2.0 Hz), 6.80 (d, 1H, J=2.0 Hz), 5.60 (s, 2H), 4.99 (s, 2H); $^{13}$C NMR (DMSO-$d_6$, 75 MHz) δ147.4, 134.0, 131.9, 119.1, 106.4; MS m/z 188/190 (M+H)$^+$.

(b) A round bottom flask was charged with 5-bromo-pyridine-2,3-diamine, BB-1b, (4.6 g, 24.5 mmol) and triethylformate (50 mL). The resultant purple slurry was warmed to 130° C. for 18 h. The solvent was removed under reduced pressure at 85° C. and the resultant brown oil was dissolved in ethanol (70 mL) and treated with concentrated HCl (30 mL). The resultant brown slurry was warmed to 90° C. for 1 hour, concentrated under reduced pressure and treated with water (100 mL). The pH was adjusted to 9 with concentrated ammonium hydroxide and the aqueous layer was extracted with 10% isopropyl alcohol-ethyl acetate (5×100 mL). The combined organic layers were washed with aqueous 5% sodium bicarbonate, brine, dried over magnesium sulfate and filtered to give 6-bromo-3H-imidazo[4,5-b]pyridine, BB-1c, as a brown solid (4.5 g, 94%): HPLC $R_t$ 6.1 min.; $^1$H NMR (DMSO-$d_6$, 300 MHz) δ13.35, 12.93 (2 br. s, 1H), 8.56 (s, 1H), 8.50 (d, 1H, J=1.6 Hz), 8.37 (br. s, 1H); MS (ESI) m/z 196/198 (M−H)$^−$. Anal. calcd for $C_6H_4BrN_3$: C, 36.39; H, 2.04; N, 21.22; Br, 40.35. Found: C, 36.21; H, 2.09; N, 21.11; Br, 40.28.

(c) 6-Triethylsilanylethynyl-3H-imidazo[4,5-b]pyridine, BB-1d, was prepared in the manner similar to that described in example AA-1, step (b), except 6-bromo-3H-imidazo[4,5-b]pyridine, BB-1c, was used in place of N-(5-bromo-pyridin-2-yl)-acetamide, AA-1a: HPLC $R_t$ 14.8 min.; TLC $R_f$ 0.4 (5% methanol-methylene chloride); $^1$H NMR (DMSO-$d_6$, 300 MHz) δ13.34, 12.88 (2 br. s, 1H), 8.53 (s, 1H), 8.44 (s, 1H), 8.11 (br. s, 1H), 1.03 (t, 9H, J=7.8 Hz), 0.70 (q, 6H, J=7.8 Hz); MS (ESI) m/z 258 (M+H)$^+$.

(d) To a solution of 6-triethylsilanylethynyl-3H-imidazo [4,5-b]pyridine, BB-1d, (1.4 g, 5.4 mmol, 1.0 eq) in methanol (30 mL) was added aqueous sodium hydroxide (2.2 mL, 10 M, 22 mmol, 4.0 eq). The resultant brown solution was warmed to 40° C. for 24 h. The reaction mixture was poured into aqueous 5% sodium bicarbonate (200 mL) and the aqueous layer was extracted with 10% isopropyl alcohol-chloroform. The organic layer was washed with brine, dried over magnesium sulfate, filtered and concentrated under reduced pressure to give a yellow solid (1.3 g). The crude product was washed with methyl-tert-butyl ether/cyclohexane (2:1) to give 6-ethynyl-3H-imidazo[4,5-b]pyridine, BB-1e, as a yellow solid (750 mg, 97%): HPLC $R_t$ 5.1 min.; TLC $R_f$ 0.5 (5% methanol-chloroform w/0.1% ammonium hydroxide); $^1$H NMR (DMSO-$d_6$, 300 MHz) δ13.16 (br. s, 1H), 8.52 (s, 1H), 8.46 (d, 1H, J=1.7 Hz), 8.14 (s, 1H), 4.26 (s, 1H); MS (ESI) m/z 144 (M+H)$^+$.

(e) 4-[({1-[3-(3H-Imidazo[4,5-b]pyridin-6-ylethynyl)-phenyl]-methanoyl}-amino)-trifluoro-methyl-phenyl]-piperazine-1-carboxylic acid tert-butyl ester, BB-1f, was prepared in the manner similar to that described in example AA-1, step (g), except 6-ethynyl-3H-imidazo[4,5-b]

pyridine, BB-1e, was used instead of N-(5-ethynyl-pyridin-2-yl)-acetamide, AA-1c: HPLC R$_t$ 16.1 min.; TLC R$_f$ 0.5 (5% methanol-chloroform w/0.1% ammonium hydroxide); $^1$H NMR (DMSO-d$_6$, 300 MHz) δ13.20 (br. s, 1H), 10.57 (s, 1H), 8.60 (d, 1H, J=1.5 Hz), 8.56 (s, 1H), 8.26–8.18 (m, 3H), 8.08 (dd, 1H, J=8.8, 2.2 Hz), 7.83 (d, 1H, J=7.7 Hz), 7.80 (d, 1H, J=8.0 Hz), 7.66–7.59 (m, 2H), 3.44 (br. s, 4H), 2.81 (t, 4H, J=4.6 Hz), 1.44 (s, 9H); MS (ESI) m/z 591 (M+H)$^+$.

(f) 4-{[(1-{3-[2-(3H-Imidazo[4,5-b]pyridin-6-yl)-ethyl]-phenyl}-methanoyl)-amino]-trifluoromethyl-phenyl}-piperazine-1-carboxylic acid tert-butyl ester, BB-1g, was prepared in the manner similar to that described in example AA-1, step (h), except 4-[({1-[3-(3H-imidazo[4,5-b]pyridin-6-ylethynyl)-phenyl]-methanoyl}-amino)-trifluoromethyl-phenyl]-piperazine-1-carboxylic acid tert-butyl ester, BB-1f, was used instead of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1g: HPLC R$_t$ 15.4 min.; $^1$H NMR (DMSO-d$_6$, 300 MHz) δ12.93, 12.56 (2br. s, 1H), 10.40 (s, 1H), 8.35 (s, 1H), 8.31 (br. s, 1H), 8.16 (d, 1H, J=2.4 Hz), 8.05 (dd, 1H, J=8.8, 2.2 Hz), 7.87 (s, 1H), 7.80–7.78 (m, 2H), 7.58 (d, 1H, J=8.8 Hz), 7.46–7.41 (m, 2H), 3.44 (br. s, 4H), 3.11–3.03 (m, 4H), 2.80 (t, 4H, J=4.6 Hz), 1.43 (s, 9H); MS (ESI) m/z 595 (M+H)$^+$.

(g) 3-[2-(3H-Imidazo[4,5-b]pyridin-6-yl)-ethyl]-N-(4-piperazin-1-yl-3-trifluoromethyl-phenyl)-benzamide, BB-1, was prepared in the manner similar to that described in example AA-1, step (i), except 4-{[(1-{3-[2-(3H-imidazo[4,5-b]pyridin-6-yl)-ethyl]-phenyl}-methanoyl)-amino]-trifluoromethyl-phenyl}-piperazine-1-carboxylic acid tert-butyl ester, BB-1g, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC R$_t$ 10.0 min.; $^1$H NMR (DMSO-d$_6$, 300 MHz) δ10.57 (s, 1H), 9.28 (br. s, 3H), 8.54 (s, 1H), 8.28–8.22 (m, 2H), 8.14 (d, 1H, J=8.8 Hz), 7.95 (s, 1H), 7.83 (d, 1H, J=6.9 Hz), 7.54 (d, 1H, J=8.9 Hz), 7.47–7.44 (m, 2H), 3.18 (br. s, 6H), 3.07 (br. s, 6H); MS (ESI) m/z 495 (M+H)$^+$. Anal. calcd for C$_{26}$H$_{25}$F$_3$N$_6$O×2.0 HCl×1.0 H$_2$O×0.3 CH$_2$Cl$_2$: C, 51.70; H, 4.88; N, 13.76; Cl, 15.09. Found: C, 51.86; H, 4.95; N, 13.32; Cl, 14.98.

Example CC-1

5-{2-[3-(Piperazin-1-yl-trifluoromethyl-phenylcarbamoyl)-phenyl]-ethyl}-nicotinamide dihydrochloride

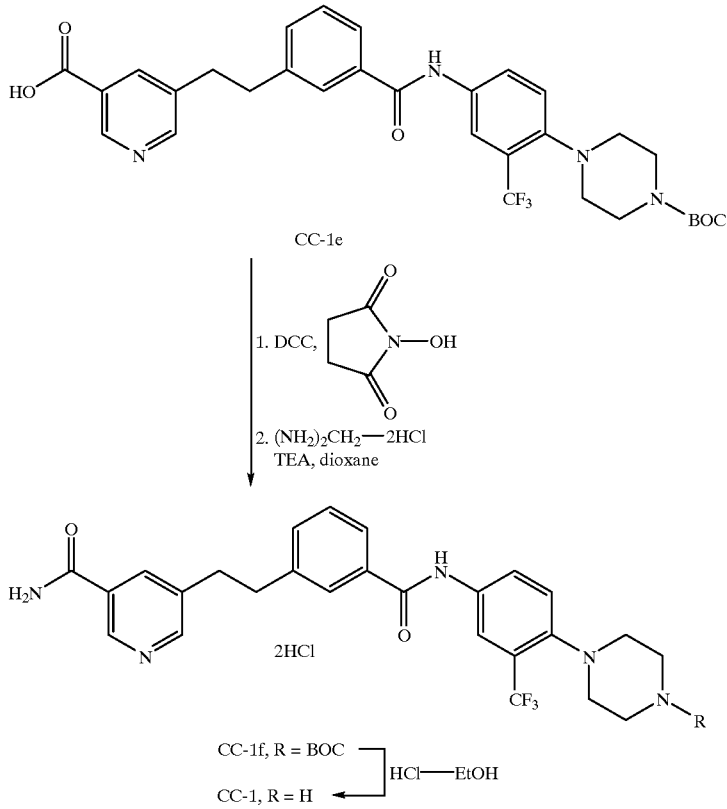

(a) 5-Triethylsilanylethynyl-nicotinic acid methyl ester, CC-1a, was prepared in the manner similar to that described in example AA-1, step (b), except 5-bromo-nicotinic acid methyl ester was used in place of N-(5-bromo-pyridin-2-yl)-acetamide, AA-1a: HPLC $R_t$ 20.1 min.; TLC $R_f$ 0.4 (20% ethyl acetate-cyclohexane); $^1$H NMR (DMSO-$d_6$, 300 MHz) δ9.04 (d, 1H, J=2.0 Hz), 8.88 (d, 1H, J=2.0 Hz), 8.25 (t, 1H, J=2.1 Hz), 3.90 (s, 3H), 1.02 (t, 9H, J=8.1 Hz), 0.70 (q, 6H, J=7.6 Hz).

(b) 5-Ethynyl-nicotinic acid methyl ester, CC-1b, was prepared in the manner similar to that described in example AA-1, step (c), except 5-triethylsilanylethynyl-nicotinic acid methyl ester, CC-1a, was used in place of N-(5-triethylsilanylethynyl-pyridin-2-yl)-acetamide, AA-1b: HPLC $R_t$ 9.3 min.; TLC $R_f$ 0.2 (20% ethyl acetate-cyclohexane); $^1$H NMR (DMSO-$d_6$, 300 MHz) δ9.06 (s, 1H), 8.91 (s, 1H), 8.30 (s, 1H), 4.58 (s, 1H), 3.90 (s, 3H).

(c) 4-({2-[3-(5-Methoxycarbonyl-pyridin-3-ylethynyl)-phenyl]-2-oxo-ethyl}-trifluoromethyl-phenyl)-piperazine-1-carboxylic acid tert-butyl ester, CC-1c, was prepared in the manner similar to that described in example AA-1, step (g), except 5-ethynyl-nicotinic acid methyl ester, CC-1b, was used instead of N-(5-ethynyl-pyridin-2-yl)-acetamide, AA-1c: HPLC $R_t$ 19.5 min.; TLC $R_f$ 0.3 (30% ethyl acetate-cyclohexane); $^1$H NMR (DMSO-$d_6$, 300 MHz) δ10.58 (s, 1H), 9.10 (d, 1H, J=2.0 Hz), 9.04 (d, 1H, J=2.0 Hz), 8.45 (t, 1H, J=2.1 Hz), 8.24 (s, 1H), 8.18 (d, 1H, J=2.3 Hz), 8.09–8.03 (m, 2H), 7.86 (d, 1H, J=7.8 Hz), 7.68–7.59 (m, 2H), 3.93 (s, 3H), 3.44 (br. s, 4H), 2.82–2.79 (m, 4H), 1.41 (s, 9H).

(d) To a solution of 4-({2-[3-(5-methoxycarbonyl-pyridin-3-ylethynyl)-phenyl]-2-oxo-ethyl}-trifluoromethyl-phenyl)-piperazine-1-carboxylic acid tert-butyl ester, CC-1c, (846 mg, 1.4 mmol, 1.0 eq) in isopropyl alcohol (90 mL) was added aqueous sodium hydroxide (4.2 mL, 1.0 M, 4.2 mmol, 3.0 eq). The resultant clear solution was warmed to 50° C. for 5 h. The solvent was removed under reduced pressure and the crude product was dissolved in ethyl acetate, which was sequentially washed with aqueous sodium citrate (0.5 M, pH 4.5) and brine. The organic layer was dried over magnesium sulfate, filtered and concentrated under reduced pressure to give 4-({2-[3-(5-carboxy-pyridin-3-ylethynyl)-phenyl]-2-oxo-ethyl}-trifluoromethyl-phenyl)-piperazine-1-carboxylic acid tert-butyl ester, CC-1d, as a white solid (800 mg, 96%): $^1$H NMR (DMSO-$d_6$, 300 MHz) δ10.59 (s, 1H), 9.08 (d, 1H, J=2.0 Hz), 9.00 (d, 1H, J=2.0 Hz), 8.42 (t, 1H, J=2.1 Hz), 8.24 (s, 1H), 8.18 (d, 1H, J=2.4 Hz), 8.09–8.02 (m, 2H), 7.88–7.85 (m, 1H), 7.68–7.59 (m, 2H), 3.44 (br. s, 4H), 2.81–2.78 (m, 4H), 1.43 (s, 9H).

(e) 4-[(2-{3-[2-(5-Carboxy-pyridin-3-yl)-ethyl]-phenyl}-2-oxo-ethyl)-trifluoromethyl-phenyl]-piperazine-1-carboxylic acid tert-butyl ester, CC-1e, was prepared in the manner similar to that described in example AA-1, step (h), except 4-({2-[3-(5-carboxy-pyridin-3-ylethynyl)-phenyl]-2-oxo-ethyl}-trifluoromethyl-phenyl)-piperazine-1-carboxylic acid tert-butyl ester, CC-1d, was used instead of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1g: HPLC (TFA buffered method) $R_t$ 16.4 min.; TLC $R_f$ 0.3 (3% methanol-dichloromethane w/0.1% acetic acid); $^1$H NMR (DMSO-$d_6$, 300 MHz) δ10.47 (s, 1H), 8.89 (s, 1H), 8.57 (s, 1H), 8.17–8.15 (m, 2H), 8.08–8.05 (m, 1H), 7.88 (s, 1H), 7.81–7.79 (m, 1H), 7.58 (d, 1H, J=8.8 Hz), 7.46–7.44 (m, 2H), 3.01 (s, 5H), 2.79 (m, 5H), 1.43 (s, 9H); MS (ESI) m/z 597 (M−H)$^−$.

(f) To a solution of 4-[(2-{3-[2-(5-carboxy-pyridin-3-yl)-ethyl]-phenyl}2-oxo-ethyl)-trifluoromethyl-phenyl]-piperazine-1-carboxylic acid tert-butyl ester, CC-1e, (250 mg, 0.42 mmol, 1.0 eq) in dioxane (9 mL) was added a solution of 1,3-dicyclohexylcarbodiimide (87 mg, 0.42 mmol, 1.0 eq) and N-hydroxysuccinimide (48 mg, 0.42 mmol, 1.0 eq) in dioxane (1 mL). The cloudy reaction mixture was sequentially stirred for 18 h, passed through a teflon filter (0.45 micron pore size), and the solvent removed under reduced pressure to give a white semi-solid (346 mg). To the crude product in dioxane (8 mL) was added triethylamine (0.23 mL, 1.68 mmol, 4.0 eq) and 1,2-diaminomethane dihydrochloride (50 mg, 0.42 mmol, 1.0 eq) in a minimal amount of water. The white slurry was stirred for 4 h at room temperature. The solvent was removed under reduced pressure and the crude product dissolved in ethyl acetate, which was sequentially washed with water and brine. The organic layer was dried over magnesium sulfate, filtered and concentrated under reduced pressure to give a yellow solid (360 mg). The crude product was purified by radial chromatography over silica gel, which was eluted with 3–9% methanol-dichloromethane, to give 4-[(2-{3-[2-(5-carbamoyl-pyridin-3-yl)-ethyl]-phenyl}-2-oxo-ethyl)-trifluoromethyl-phenyl]-piperazine-1-carboxylic acid tert-butyl ester, CC-1f, as a white solid (150 mg, 60%): HPLC $R_t$ 15.4 min.; TLC $R_f$ 0.5 (4% methanol-dichloromethane); $^1$H NMR (DMSO-$d_6$, 300 MHz) δ10.45 (s, 1H), 8.68 (d, 1H, J=1.8 Hz), 8.56 (d, 1H, J=1.8 Hz), 8.17–8.04 (m, 3H), 7.87–7.79 (m, 1H), 7.61–7.58 (m, 2H), 7.47–7.45 (m, 2H), 5.76 (s, 2H), 3.44 (s, 4H), 3.02 (m, 4H), 2.80 (s, 4H), 1.43 (s, 9H); MS (ESI) m/z 598 (M+H)$^+$.

(g) 5-(2-{3-[2-(Piperazin-1-yl-trifluoromethyl-phenyl)-ethanoyl]-phenyl}-ethyl)-nicotinamide dihydrochloride, CC-1, was prepared in the manner similar to that described in example AA-1, step (i), except 4-[(2-{3-[2-(5-carbamoyl-pyridin-3-yl)-ethyl]-phenyl}-2-oxo-ethyl)-trifluoromethyl-phenyl]-piperazine-1-carboxylic acid tert-butyl ester, CC-1f, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC $R_t$ 9.7 min.; $^1$H NMR (DMSO-$d_6$, 300 MHz) δ10.56 (s, 1H), 9.13 (br. s, 1H), 9.00 (d, 1H, J=2.0 Hz), 8.75 (d, 1H, J=1.9 Hz), 8.49 (s, 1H), 8.33 (s, 1H), 8.22 (d, 1H, J=2.5 Hz), 8.13 (dd, 1H, J=8.8, 2.2 Hz), 7.91 (s, 1H), 7.83–7.79 (m, 2H), 7.56 (d, 1H, J=8.7 Hz), 7.48–7.45 (m, 2H), 3.13 (s, 4H), 3.07 (m, 8H); MS (ESI) m/z 498 (M+H)$^+$. Anal. calcd for $C_{26}H_{26}F_3N_5O_2 \times 2.0$ HCl×0.5 $H_2O$: C, 53.89; H, 5.04; N, 12.09; Cl, 12.24. Found: C, 53.99; H, 5.19; N, 11.46; Cl, 11.79.

Example CC-2

5-{2-[3-(Piperazin-1-yl-trifluoromethyl-phenylcarbamoyl)-phenyl]-ethyl}nicotinic acid methyl ester dihydrochloride

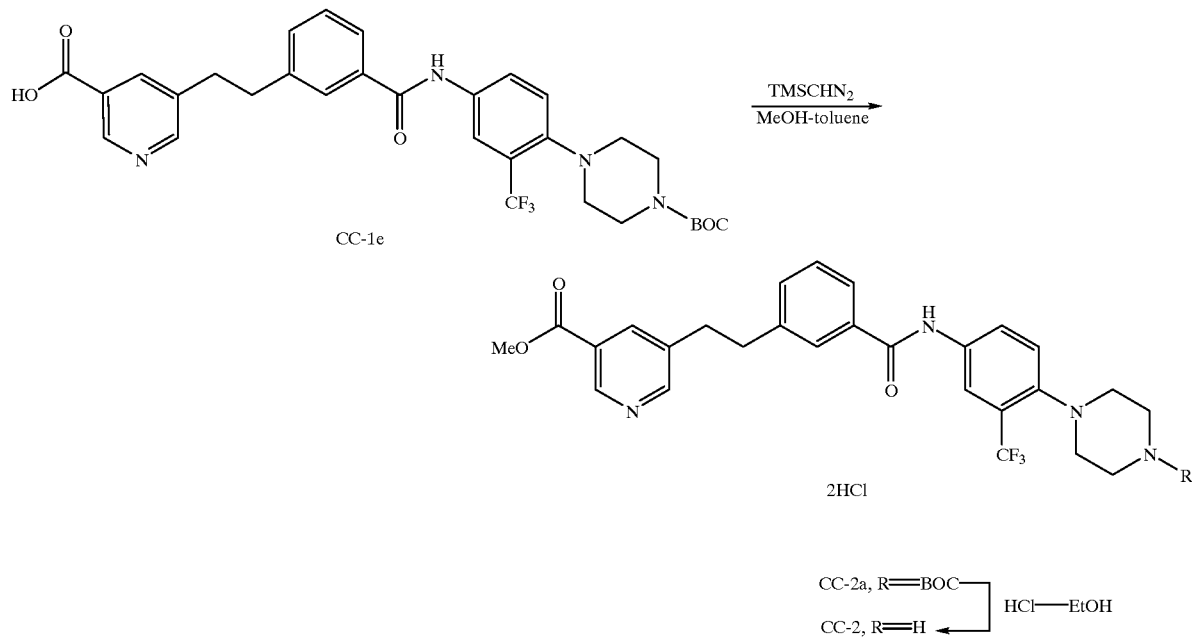

(a) To a solution of 4-[(2-{3-[2-(5-carboxy-pyridin-3-yl)-ethyl]-phenyl}-2-oxo-ethyl)-trifluoromethyl-phenyl]-piperazine-1-carboxylic acid tert-butyl ester, CC-1e, (100 mg, 0.17 mmol, 1.0 eq.) in methanol (4 mL) and toluene (4 mL) was added a solution of (trimethylsilyl)diazomethane (0.45 mL, 2.0 M, 0.90 mmol, 5.3 eq). The light yellow solution was stirred for 18 h. The solvent was removed under reduced pressure and the crude product was dissolved in ethyl acetate, which was sequentially washed with aqueous 5% sodium bicarbonate and brine. The organic layer was dried over magnesium sulfate, filtered and concentrated under reduced pressure to give a clear residue (105 mg). The crude product was purified by radial chromatography over silica gel, which was eluted with 2% methanol-dichloromethane, to give 4-{[(1-{3-[2-(5-methoxycarbonyl-pyridin-3-yl)-ethyl]-phenyl}-methanoyl)-amino]-trifluoromethyl-phenyl}-piperazine-1-carboxylic acid tert-butyl ester, CC-2a, as a white solid (74 mg, 71%): HPLC $R_t$ 18.1 min.; TLC $R_f$ 0.6 (3% methanol-dichloromethane w/0.1% acetic acid); $^1$H NMR (DMSO-$d_6$, 300 MHz) δ10.42 (s, 1H), 8.92 (d, 1H, J=1.8 Hz), 8.69 (d, 1H, J=2.0 Hz), 8.21 (s, 1H), 8.16 (d, 1H, J=2.2 Hz), 8.07–8.04 (m, 1H), 7.86 (s, 1H), 7.81–7.79 (m, 1H), 7.60 (d, 1H, J=8.2 Hz), 7.48–7.45

(m, 2H), 3.88 (s, 3H), 3.44 (br. s, 4H), 3.04 (s, 4H), 2.80 (t, 4H, J=4.3 Hz), 1.43 (s, 9H); MS (ESI) m/z 613 (M+H)+.

(b) 5-{2-[3-(Piperazin-1-yl-trifluoromethyl-phenylcarbamoyl)-phenyl]-ethyl}-nicotinic acid methyl ester dihydrochloride, CC-2, was prepared in the manner similar to that described in example AA-1, step (i), except, 4-{[(1-{3-[2-(5-methoxycarbonyl-pyridin-3-yl)-ethyl]-phenyl}-methanoyl)-amino]-trifluoromethyl-phenyl}-piperazine-1-carboxylic acid tert-butyl ester, CC-2a, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC R$_t$ 12.7 min.; $^1$H NMR (DMSO-d$_6$, 300 MHz) δ10.58 (s, 1H), 9.33 (br. s, 2H), 9.00 (s, 1H), 8.80 (s, 1H), 8.38 (s, 1H), 8.22 (s, 1H), 8.14 (d, 1H, J=8.4 Hz), 7.92 (s, 1H), 7.84–7.82 (m, 1H), 7.56 (d, 1H, J=8.6 Hz), 7.48–7.42 (m, 2H), 3.90 (s, 3H), 3.16 (s, 4H), 3.08 (s, 8H); MS (ESI) m/z 513 (M+H)+. Anal. calcd for C$_{27}$H$_{27}$F$_3$N$_4$O$_3$× 2.0 HCl×0.5 H$_2$O×0.5 ethyl acetate: C, 54.55; H, 5.37; N, 8.77. Found: C, 54.47; H, 5.45; N, 8.71.

Example DD-1

4-Fluoro-3-[2-(3H-imidazo[4,5-b]pyridin-6-yl)-ethyl]-N-(4-piperazin-1-yl-3-trifluoromethyl-phenyl)-benzamide dihydrochloride

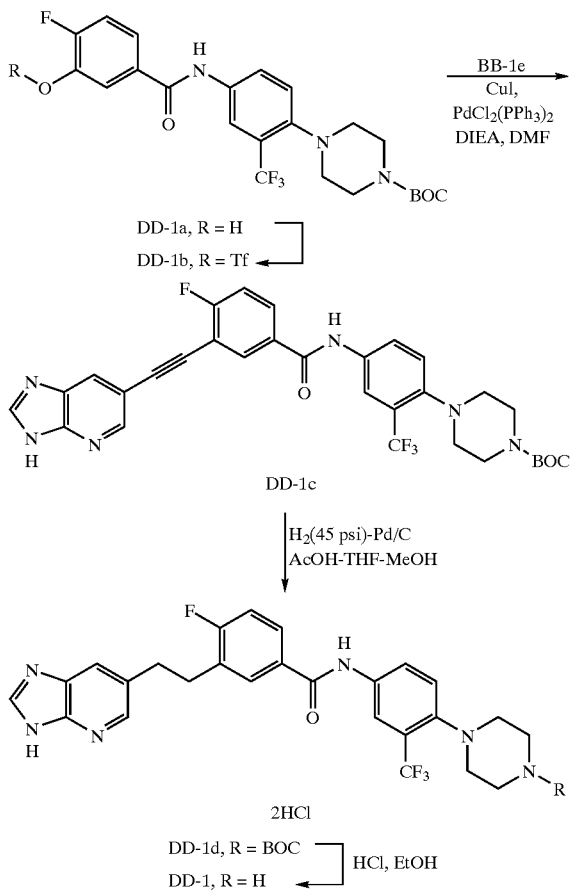

(a) 4-({[1-(4-Fluoro-3-hydroxy-phenyl)-methanoyl]-amino}-trifluoromethyl-phenyl)-piperazine-1-carboxylic acid tert-butyl ester, DD-1a, was prepared in a similar manner to that described in example M-1, step (e), except 4-({[1-(3-acetoxy-4-fluoro-phenyl)-methanoyl]-amino}-trifluoromethyl-phenyl)-piperazine-1-carboxylic acid tert-butyl ester was used instead of acetic acid 3-(2-methyl-quinolin-6-ylcarbamoyl)-phenyl ester, M-1d: HPLC R$_t$ 16.2 min.; TLC R$_f$ 0.3 (30% ethyl acetate-cyclohexane); $^1$H NMR (DMSO-d$_6$, 300 MHz) δ10.37 (s, 1H), 10.22 (s, 1H), 8.14 (d, 2H, J=2.4 Hz), 8.00 (dd, 1H, J=8.6, 2.0 Hz), 7.58–7.53 (m, 3H), 7.47–7.42 (m, 1H), 7.30 (dd, 1H, J=11.0, 8.6 Hz), 3.43 (br. s, 4H), 2.79 (t, 4H, J=4.8 Hz), 1.42 (s, 9H); MS (ESI) m/z 484 (M+H)+.

(b) To a solution of 4-({[1-(4-fluoro-3-hydroxy-phenyl)-methanoyl]-amino}-trifluoromethyl-phenyl)-piperazine-1-carboxylic acid tert-butyl ester, DD-1a, (900 mg, 1.86 mmol, 1.0 eq), in dioxane (40 mL) was added triethylamine (0.90 mL, 6.5 mmol, 3.0 eq) and 1,1,1-trifluoro-N-phenyl-N-[(trifluoromethyl)sulfonyl]methanesulfonamide (1.1 g, 3.0 mmol, 1.4 eq). The clear solution was stirred for 18 h. The solvent was removed under reduced pressure and the resultant oil was passed through a silica plug, which was eluted with ethyl acetate to give an amber oil (2.0 g). The crude product was purified by radial chromatography over silica gel, which was eluted with 15–25% ethyl acetate-cyclohexane, to give 4-({[1-(4-fluoro-3-trifluoromethanesulfonyloxy-phenyl)-methanoyl]-amino}-trifluoromethyl-phenyl)-piperazine-1-carboxylic acid tert-butyl ester, DD-1b, as a white solid (1.0 g, 91%): HPLC R$_t$ 19.9 min.; TLC R$_f$ 0.5 (30% ethyl acetate-cyclohexane); $^1$H NMR (DMSO-d$_6$, 300 MHz) δ10.61 (s, 1H), 8.25–8.22 (m, 1H), 8.12 (d, 1H, J=2.4 Hz), 8.02 (dd, 1H, J=8.8, 2.2 Hz), 7.86–7.80 (m, 1H), 7.60 (d, 1H, J=8.7 Hz), 7.30–7.25 (m, 1H), 3.44 (br. s, 4H), 2.80 (t, 4H, J=4.7 Hz), 1.43 (s, 9H); MS (ESI) m/z 638 (M+Na)+.

(c) 4-[({1-[4-Fluoro-3-(3H-imidazo[4,5-b]pyridin-6-ylethynyl)-phenyl]-methanoyl}-amino)-trifluoromethyl-phenyl]-piperazine-1-carboxylic acid tert-butyl ester, DD-1c, was prepared in the manner similar to that described in example AA-1, step (g), except 6-ethynyl-3H-imidazo[4,5-b]pyridine, BB-1e, was used instead of N-(5-ethynyl-pyridin-2-yl)-acetamide, AA-1c, and 4-({[1-(4-fluoro-3-trifluoromethanesulfonyloxy-phenyl)-methanoyl]-amino}-trifluoromethyl-phenyl)-piperazine-1-carboxylic acid tert-butyl ester, DD-1b, was used instead of 4-({[1-(3-iodo-phenyl)-methanoyl]-amino}-trifluoromethyl-phenyl)-piperazine-1-carboxylic acid tert-butyl ester, AA-1f: HPLC R$_t$ 16.3 min.; TLC R$_f$ 0.3 (4% methanol-chloroform w/0.1% ammonium hydroxide); $^1$H NMR (DMSO-d$_6$, 300 MHz) δ13.39, 12.93 (2 br. s, 1H), 10.56 (s, 1H), 8.58–8.55 (m, 3H), 8.33 (s, 1H), 8.16 (s, 1H), 8.07–8.05 (m, 2H), 7.61–7.52 (m, 2H), 3.44 (br. s, 4H), 2.80 (br. s, 4H), 1.43 (s, 9H); MS (ESI) m/z 609 (M+H)+.

(d) 4-{[(1-{4-Fluoro-3-[2-(3H-imidazo[4,5-b]pyridin-6-yl)-ethyl]-phenyl}-methanoyl)-amino]-trifluoromethyl-phenyl}-piperazine-1-carboxylic acid tert-butyl ester, DD-1d, was prepared in the manner similar to that described in example AA-1, step (h), except 4-[({1-[4-fluoro-3-(3H-imidazo[4,5-b]pyridin-6-ylethynyl)-phenyl]-methanoyl}-amino)-trifluoromethyl-phenyl]-piperazine-1-carboxylic acid tert-butyl ester, DD-1c, was used instead of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1g: HPLC R$_t$ 15.7 min.; TLC R$_f$ 0.4 (6% methanol-chloroform w/0.1% ammonium hydroxide); $^1$H NMR (DMSO-d$_6$, 300 MHz) δ10.43 (s, 1H), 8.37 (s, 1H), 8.21 (s, 1H), 8.13 (d, 1H, J=8.8 Hz), 8.05–7.97 (m, 2H), 7.91–7.86 (m, 2H), 7.60 (d, 1H, J=8.8 Hz), 7.34–7.28 (m, 1H), 3.44 (br. s, 4H), 3.08–3.06 (m, 4H), 2.80 (t, 4H, J=4.6 Hz), 1.43 (s, 9H); MS (ESI) m/z 613 (M+H)+.

(e) 4-Fluoro-3-[2-(3H-imidazo[4,5-b]pyridin-6-yl)-ethyl]-N-(4-piperazin-1-yl-3-trifluoromethyl-phenyl)- benzamide dihydrochloride, DD-1, was prepared in the manner similar to that described in example AA-1, step (i), except 4-{[(1-{4-fluoro-3-[2-(3H-imidazo[4,5-b]pyridin-6-yl)-ethyl]-phenyl}-methanoyl)-amino]-trifluoromethyl-phenyl}-piperazine-1-carboxylic acid tert-butyl ester, DD-1d, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC $R_t$ 10.5 min.; $^1$H NMR (DMSO-$d_6$, 300 MHz) δ10.68 (s, 1H), 9.36 (br. s, 3H), 8.55 (s, 1H), 8.26 (d, 2H, J=9.8 Hz), 8.12 (t, 2H, J=8.2 Hz), 7.93 (br. s, 1H), 7.56 (d, 1H, J=8.7 Hz), 7.30 (t, 1H, J=9.1 Hz), 3.16 (br. s, 6H), 3.08 (m, 6H); MS (ESI) m/z 513 (M+H)$^+$. Anal. calcd for $C_{26}H_{24}F_4N_6O \times 2.0$ HCl: C, 52.14; H, 4.63; N, 14.03; Cl, 11.84. Found: C, 52.54; H, 4.73; N, 13.41; Cl, 11.44.

Example EE-1

4-Fluoro-3-(5-furan-2-yl-pyridin-3-ylmethoxy)-N-(4-piperazin-1-yl-3-trifluoromethyl-phenyl)-benzamide dihydrochloride

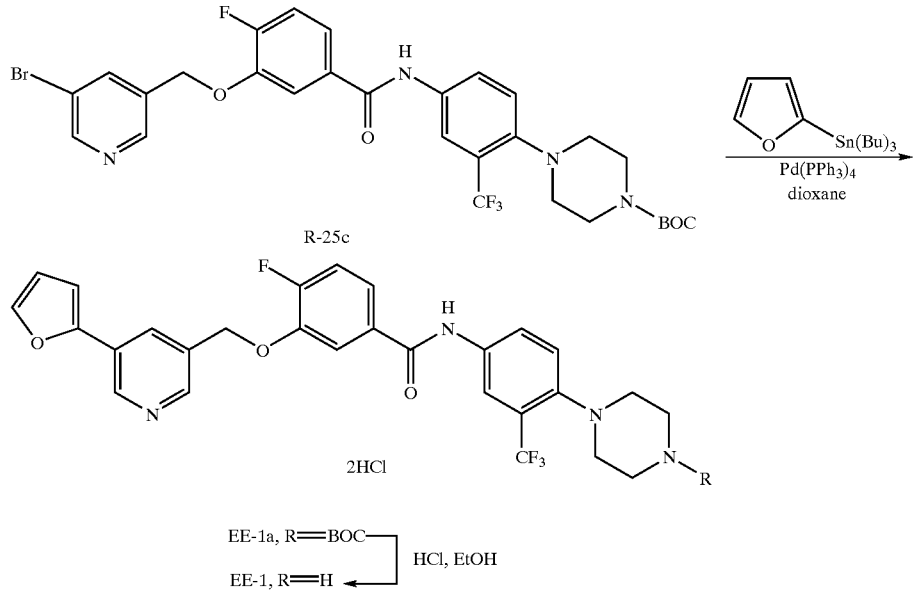

(a) To a solution of 4-[({1-[3-(5-bromo-pyridin-3-ylmethoxy)-4-fluoro-phenyl]-methanoyl}-amino)-trifluoromethyl-phenyl]-piperazine-1-carboxylic acid tert-butyl ester, R-25c, (80 mg, 0.12 mmol, 1.0 eq) in dioxane (3 mL) was added tributyl-furan-2-yl-stannane (0.05 mL, 0.14 mmol, 1.2 eq) and tetrakis(triphenylphosphine)palladium(0) (14 mg, 0.01 mmol, 10 mol %). The light yellow solution was warmed to 95° C. for 18 h. The solvent was removed under reduced pressure and the crude product was dissolved in ethyl acetate, which was sequentially washed with aqueous 10% potassium fluoride, water and brine. The organic layer was dried over magnesium sulfate, filtered and concentrated under reduced pressure to give a clear oil (127 mg). The crude product was purified by radial chromatography over silica gel, which was eluted with 1–3% methanol-dichloromethane, to give 4-[({1-[4-fluoro-3-(5-furan-2-yl-pyridin-3-ylmethoxy)-phenyl]-methanoyl}-amino)-trifluoromethyl-phenyl]-piperazine-1-carboxylic acid tert-butyl ester, EE-1a, as a white solid (66 mg, 86%): HPLC $R_t$ 18.9 min.; TLC $R_f$ 0.4 (2% methanol-dichloromethane); $^1$H NMR (DMSO-$d_6$, 300 MHz) δ10.44 (s, 1H), 8.96 (d, 1H, J=2.1 Hz), 8.62 (d, 1H, J=1.9 Hz), 8.19 (t, 1H, J=2.0 Hz), 8.14 (d, 1H, J =2.3 Hz), 8.03 (dd, 1H, J=8.6, 2.2 Hz), 7.89 (dd, 1H, J=8.3, 1.9 Hz), 7.86 (d, 1H, J=1.6 Hz), 7.69–7.65 (m, 1H), 7.60 (d, 1H, J=8.8 Hz), 7.44 (dd, 1H, J=11.0, 8.6 Hz), 7.16 (d, 1H, J=3.3 Hz), 6.67 (dd, 1H, J=3.4, 1.8 Hz), 5.38 (s, 2H), 3.44 (br. s, 4H), 2.80 (t, 4H, J=4.7 Hz), 1.43 (s, 9H); MS (ESI) m/z 641 (M+H)$^+$.

(b) 4-Fluoro-3-(5-furan-2-yl-pyridin-3-ylmethoxy)-N-(4-piperazin-1-yl-3-trifluoromethyl-phenyl)-benzamide dihydrochloride, EE-1, was prepared in the manner similar to that described in example AA-1, step (i), except 4-[({1-[4-fluoro-3-(5-furan-2-yl-pyridin-3-ylmethoxy)-phenyl]-methanoyl}-amino)-trifluoromethyl-phenyl]-piperazine-1-carboxylic acid tert-butyl ester, EE-1a, was used in place of 4-{[(1-{3-[2-(6-acetylamino-pyridin-3-yl)-ethyl]-phenyl}-methanoyl)-amino]-trifluoromethyl-phenyl}-piperazine-1-carboxylic acid tert-butyl ester, AA-1h: HPLC $R_t$ 14.2 min.; $^1$H NMR (DMSO-$d_6$, 300 MHz) δ10.66 (s, 1H), 9.16 (br. s, 2H), 9.03 (s, 1H), 8.70 (s, 1H), 8.37 (s, 1H), 8.21 (d, 1H, J=2.0 Hz), 8.14 (d, 1H, J=8.9 Hz), 7.99 (d, 1H, J=7.0 Hz), 7.89 (s, 1H), 7.72–7.69 (m, 1H), 7.56 (d, 1H, J=8.5 Hz), 7.44 (dd, 1H, J=10.8, 8.7 Hz), 7.24 (d, 1H, J=3.3 Hz), 6.69 (d, 1H, J=1.5 Hz), 5.45 (s, 2H), 3.17 (s, 4H), 3.07 (s, 4H); MS (ESI) m/z 541 (M+H)$^+$. Anal. calcd for $C_{28}H_{24}F_4N_4O_3 \times 2.0$ HCl× 1.0 $H_2O$: C, 53.26; H, 4.47; N, 8.87; Cl, 11.23. Found: C, 53.27; H, 4.25; N, 8.56; Cl, 11.48.

The exemplary compounds described above may be tested for their activity as described below.

Biological Testing

Enzyme Assays

The stimulation of cell proliferation by growth factors such as VEFG, FGF, and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

VEGF-R2 Construct for Assay

A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. See commonly assigned, co-pending U.S. patent application Ser. No. 09/390,326, filed Sep. 7, 1999, incorporated by reference herein, for discussion of VEGF constructs and expression systems. Autophosphorylation of the purified construct was performed by incubation of the enzyme at a concentration of 4 $\mu$M in the presence of 3 mM ATP and 40 mM MgCl$_2$ in 100 mM Hepes, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

FGF-R1 Construct for Assay

The intracellular kinase domain of human FGF-R1 was expressed using the baculovirus vector expression system starting from the endogenous methionine residue 456 to glutamate 766, according to the residue numbering system of Mohammadi et al., *Mol. Cell. Biol.*, 16, 977–989 (1996). In addition, the construct also has the following 3 amino acid substitutions: L457V, C488A, and C584S.

LCK Construct for Assay

The LCK tyrosine kinase was expressed in insect cells as an N-terminal deletion starting from amino acid residue 223 to the end of the protein at residue 509, with the following two amino acid substitutions at the N-terminus: P233M and C224D.

CHK-1 Construct for Assay

C-terminally His-tagged full-length human CHK-1 (FL-CHK-1) was expressed using the baculovirus/insect cell system. It contains 6 histidine residues (6×His-tag) at the C-terminus of the 476 amino acid human CHK-1. The protein was purified by conventional chromatographic techniques.

Catalytically active truncations of CHK-1 may be exchanged for the full length CHK-1 protein. A preferred truncation comprises the kinase domain of CHK-1, which begins between amino acid residues 1 and 16 and terminates between amino acid residues 265 and 291. See commonly assigned, co-pending U.S. patent application Ser. No. 09/460,421, filed Dec. 14, 1999, incorporated by reference herein, for discussion of such alternate CHK-1 constructs and expression systems.

CDK2/Cyclin A Construct for Assay

CDK2 was purified using published methodology (Rosenblatt et al., *J. Mol. Biol.*, 230, 1317–1319 (1993)) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., *Nature*, 376, 313–320 (1995)).

CDK4/Cyclin D Construct for Assay

A complex of human CDK4 and cyclin D3, or a complex of cyclin D1 and a fusion protein of human CDK4 and glutathione-S-transferase (GST-CDK4), was purified using traditional biochemical chromatographic techniques from insect cells that had been co-infected with the corresponding baculovirus expression vectors.

TEK Construct for Assay

The intracellular kinase domain (residues 775 to 1124, with methionine added at the N-terminus) of human TEK/Tie-2 was expressed using the baculovirus vector expression system. For assay purposes, the enzyme was autophosphorylated prior to use by incubation overnight at 4° C., at 10 $\mu$M enzyme concentration, with 4 mM ATP, 40 mM MgCl$_2$, and 5 mM DTT in 200 mM Hepes buffer at ph 7.5, in 90:10 water:glycerol.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 (indicated as FLVK-P in the tables below) were the following: 1 mM PEP; 250 $\mu$M NADH; 50 units of LDH/mL; 20 units of PK/mL; 5 mM DTT; 5.1 mM poly(E$_4$Y$_1$); 1 mM ATP; and 25 mM MgCl$_2$ in 200 mM Hepes, pH 7.5. Assay conditions for unphosphorylated VEGF-R2Δ50 (indicated as FLVK in the tables) were the following: 1 mM PEP; 250 $\mu$M NADH; 50 units of LDH/mL; 20 units of PK/mL; 5 mM DTT; 20 mM poly(E$_4$Y$_1$); 3 mM ATP; and 60 mM MgCl$_2$ and 2 mM MnCl$_2$ in 200 mM Hepes, pH 7.5. Assays were initiated with 5 to 40 nM of enzyme. K$_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1-17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azino-di-[3-ethylbenzathiazoline sulfonate(6)] diammonium salt (ABTS). Typical assay solutions contained: 2 $\mu$M biotinylated gastrin peptide; 5 mM DTT; 20 $\mu$M ATP; 26 mM MgCl$_2$; and 2 mM MnCl$_2$ in 200 mM Hepes, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid (H$_2$SO$_4$), followed by absorbance reading at 405 nm. K$_i$ values were determined by measuring enzyme activity in the presence of varying concentrations of test compounds. The data were analyzed using Enzyme Kinetic and Kaleidagraph software.

FGF-R Assay

The spectrophotometric assay was carried out as described above for VEGF-R2, except for the following changes in concentration: FGF-R=50 nM, ATP=2 mM, and poly(E4Y1)=15 mM.

LCK Assay

The spectrophotometric assay was carried out as described above for VEGF-R2, except for the following changes in concentration: LCK=60 nM, MgCl$_2$=40 nM, poly(E4Y1)=20 mM.

CHK-1 Assay

The production of ADP from ATP that accompanies phosphoryl transfer to the synthetic substrate peptide Syntide-2 (PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\epsilon 340=6.22$ cm$_{-1}$ mM$^{-1}$) using a HP8452 spectrophotometer. Typical reaction solutions contained: 4 mN PEP; 0.15 mM NADH; 28 units of LDH/ml; 16 units of PK/ml; 3 mM DTT; 0.125 mM Syntide-2; 0.15 mM ATP; 25 mM MgCl$_2$ in 50 mM TRIS, pH 7.5; and 400 mM NaCl. Assays were initiated with 10 nM of FL-CHK-1. K$_i$ values were determined by measuring initial enzyme activity in the presence of varying concentrations of test compounds. The data were analyzed using Enzyme Kinetic and Kaleidagraph software.

CDK2/Cyclin A and CDK4/Cyclin D Assays

Cyclin-dependent kinase activity was measured by quantifying the enzyme-catalyzed, time-dependent incorporation of radioactive phosphate from [$^{32}$P]ATP into a recombinant fragment of the retinoblastoma protein. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.2 μCi [$^{32}$P]ATP. The substrate (0.3–0.5 μg) was purified recombinant retinoblastoma protein fragment (Rb) (residues 386–928 of the native retinoblastoma protein; 62.3 kDa, containing the majority of the phosphorylation sites found in the native 106-kDa protein, as well as a tag of six histidine residues for ease of purification). Reactions were initiated with CDK2 (150 nM CDK2/Cyclin A complex) or CDK4 (50 nM CDK4/Cyclin D3 complex), incubated at 30° C., and terminated after 20 minutes by the addition of ethylenediaminetetraacetic acid (EDTA) to 250 mM. The phosphorylated substrate was then captured on a nitrocellulose membrane using a 96-well filtration manifold, and unincorporated radioactivity was removed by repeated washing with 0.85% phosphoric acid. Radioactivity was quantified by exposing the dried nitrocellulose membranes to a phosphorimager. Apparent K$_i$ values were measured by assaying enzyme activity in the presence of different compound concentrations and subtracting the background radioactivity measured in the absence of enzyme. The kinetic parameters (kcat, Km for ATP) were measured for each enzyme under the usual assay conditions by determining the dependence of initial rates on ATP concentration. The data were fit to an equation for competitive inhibition using Kaleidagraph (Synergy Software), or were fit to an equation for competitive tight-binding inhibition using the software KineTic (BioKin, Ltd.). Measured K$_i$ values for known inhibitors against CDK4 and CDK2 agreed with published IC$_{50}$ values. The specific activity of CDK4 was the same whether complexed to full-length cyclin D3 or the truncated Cyclin D3 construct; both complexes also yielded very similar K$_i$ values for selected inhibitors.

TEK/Tie-2 Assay

The spectrophotometric assay was carried out as described above for VEGF-R2, except for the following changes in concentration: TEK/Tie-2=200 nM, MgCl$_2$=40 mM, and ATP=2 mM.

HUVEC Proliferation Assay

This assay determines the ability of a test compound to inhibit the growth factor-stimulated proliferation of human umbilical vein endothelial cells ("HUVEC"). HUVEC cells (passage 3-4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 μg/ml endothelial cell growth supplement (ECGS), and 0.1 mg/ml heparin). Exponentially-growing HUVEC cells were used in experiments thereafter. Ten to twelve thousand HUVEC cells were plated in 96-well dishes in 100 μl of rich, culture medium (described above). The cells were allowed to attach for 24 hours in this medium. The medium was then removed by aspiration and 105 μl of starvation media (F12K+1% FBS) was added to each well. After 24 hours, 15 μl of test agent dissolved in 1% DMSO in starvation medium or this vehicle alone was added into each treatment well; the final DMSO concentration was 0.1%. One hour later, 30 μl of VEGF (30 ng/ml) in starvation media was added to all wells except those containing untreated controls; the final VEGF concentration was 6 ng/ml. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 λ was determined on a 96-well spectrophotometer plate reader.

Cancer Cell Proliferation (MV522) Assay

The protocol for assessing cellular proliferation in cancer cells is similar to that used for assessments in HUVEC cells. Two thousand lung cancer cells (line MV522, acquired from American Tissue Cultural Collection) were seeded in growth media (RPMI1640 medium supplemented with 2 mM glutamine and 10% FBS). Cells are allowed to attach for 1 day prior to addition of test agents and/or vehicles. Cells are treated simultaneously with the same test agents used in the HUVEC assay. Cellular proliferation is quantified by MTT dye reduction assay 72 hours after exposure to test agents. The total length of the assay is 4 days vs. 5 for HUVEC cells because MV522 cells are not exposed to starvation medium.

The results of the testing of the compounds using various assays are summarized in the table below, where a notation of "% @" indicates the percent inhibition at the stated concentration, "NI" indicates no inhibition, "slow-binding kinetics" indicates that curvature in the progress curves in the enzyme assay precluded the determination of rates, and "NT" indicates compounds "not tested" for a particular activity.

| EX # | FLVK-P Ki (nM) | FLVK Ki (nM) | LCK-P Ki (nM) | CHK-1 Ki (nM) | FGF-P Ki (nM) | CDK2 Ki (nM) | CDK4 Ki (nM) | HUVEC IC50 (nM) | Huvec + Albumin IC50 (nM) | MV522 IC50 (μM) | TEK-P (μM) |
|---|---|---|---|---|---|---|---|---|---|---|---|
| A-1 | 785 | NT | NT | NT | NT | NT | NT | NT | NT | NT | NT |
| A-2 | 100 μM | NT | NT | NT | NT | NT | NT | NT | NT | NT | NT |

-continued

| EX # | FLVK-P Ki (nM) | FLVK Ki (nM) | LCK-P Ki (nM) | CHK-1 Ki (nM) | FGF-P Ki (nM) | CDK2 Ki (nM) | CDK4 Ki (nM) | HUVEC IC50 (nM) | Huvec + Albumin IC50 (nM) | MV522 IC50 (μM) | TEK-P (μM) |
|---|---|---|---|---|---|---|---|---|---|---|---|
| A-3 | 32 | 4.5 | NT | NT | NT | NT | NT | 240 | NT | >10 | NT |
| A-4 | 13000 | NT | NT | NT | NT | NT | NT | NT | NT | NT | NT |
| A-5 | 8.64 | 1 | 37% @ 5 μM | NT | NT | NT | NT | 270 | NT | >10 | NT |
| A-6 | 1050 | NT | NT | NT | NT | NT | NT | NT | NT | NT | NT |
| A-7 | 26 | NT | NT | NT | NT | NT | NT | >700 | NT | NT | NT |
| A-8 | 3.36 | 1.9 | NT | NT | NT | NT | NT | 740 | NT | >10 | NT |
| B-1 | 111 | 25 | NT | NT | 87,000 | NT | NT | NT | NT | NT | NT |
| B-10 | NI @ 300 μM (ELISA) | NT | NT | NT | NT | NT | NT | NT | NT | NT | NT |
| B-11 | NI @ 300 μM (ELISA) | NT | NT | NT | NT | NT | NT | NT | NT | NT | NT |
| B-12 | 28 | NT | NT | NT | NT | NT | NT | 530 | NT | >10 | NT |
| B-13 | NI @ 1 mM (ELISA) | NT | NT | NT | NT | NT | NT | NT | NT | NT | NT |
| B-14 | NI @ 490 μM (ELISA) | NT | NT | NT | NT | NT | NT | NT | NT | NT | NT |
| B-15 | 15.7 | NT | NT | NT | NT | NT | NT | 120 | NT | >10 | NT |
| B-16 | 15 | NT | 9% @ 1 μM | NT | NT | NT | NT | 370 | NT | >10 | NT |
| B-17 | 6.95 | NT | NT | NT | NT | NT | NT | >700 | NT | >10 | NT |
| B-18 | 5.84 | NT | NT | NT | NT | NT | NT | 130 | NT | >10 | NT |
| B-19 | 42% @ 1 μM | NT | NT | NT | NT | NT | NT | NT | NT | NT | NT |
| B-2 | 1820 | NT | NT | NT | NT | NT | NT | NT | NT | NT | NT |
| B-20 | 26 | NT | NT | NT | NT | NT | NT | NT | NT | NT | NT |
| B-21 | 208 | NT | NT | NT | NT | NT | NT | NT | NT | NT | NT |
| B-22 | 32% @ 1 μM | NT | NT | NT | NT | NT | NT | NT | NT | NT | NT |
| B-23 | 17% @ 1 μM | NT | NT | NT | NT | NT | NT | NT | NT | NT | NT |
| B-24 | 37 | NT | NT | NT | NT | NT | NT | NT | NT | NT | NT |
| B-25 | 26% @ 1 μM | NT | NT | NT | NT | NT | NT | NT | NT | NT | NT |
| B-3 | 406 | NT | NT | NT | NT | NT | NT | NT | NT | NT | NT |
| B-4 | 35000 | NT | NT | NT | NT | NT | NT | NT | NT | NT | NT |
| B-5 | 11000 | NT | NT | NT | NT | NT | NT | NT | NT | NT | NT |
| B-6 | 62% @ 10 μM (ELISA) | NT | NT | NT | NT | NT | NT | NT | NT | NT | NT |
| B-7 | 3310 | NT | NT | NT | NT | NT | NT | NT | NT | NT | NT |
| B-8 | NI @ 1 mM (ELISA) | NT | NT | NT | NT | NT | NT | NT | NT | NT | NT |
| B-9 | 17000 | NT | NT | NT | NT | NT | NT | NT | NT | NT | NT |
| C-1 | NI @ 1 mM (ELISA) | NT | NT | NT | NT | NT | NT | NT | NT | NT | NT |
| C-2 | NI @ 50 μM (ELISA) | NT | NT | NT | NT | NT | NT | NT | NT | NT | NT |
| C-3 | NI @ 5 μM (ELISA) | NT | NT | NT | NT | NT | NT | NT | NT | NT | NT |
| D-1 | 28 | NT | NT | NT | NT | NT | NT | 520 | NT | >10 | NT |
| D-2 | 1640 | NT | NT | NT | NT | NT | NT | NT | NT | NT | NT |
| D-3 | 133 | NT | NT | NT | NT | NT | NT | NT | NT | NT | NT |
| E-1 | 2.21 | 1.4 | 85%@ 5 μM | NT | 36% at 5 μM | 23% @ 100 μM | 40% @ 100 μM | 170 | >1000 | >10 | NT |
| E-2 | 4.79 | 0.95 | NT | NT | NT | >100 μM | >100 μM | 55 | NT | >10 | NT |
| F-1 | 2.36 | NT | 22% @ 1 μM | NT | 11% @ 1 μM | NT | NT | 710 | NT | >10 | NT |
| F-2 | 14.7 | NT | NT | NT | NT | NT | NT | 650 | NT | >10 | NT |
| F-3 | 1.01 | 0.31 | 84% @ 1 μM | NT | 83% @ 1 μM | NT | NT | 10 | NT | >10 | NT |
| F-4 | slow-binding kinetics | slow-binding kinetics | 19% @ 1 μM | NT | 18% @ 1 μM | NT | NT | 63 | NT | 2.6 | NT |

-continued

| EX # | FLVK-P Ki (nM) | FLVK Ki (nM) | LCK-P Ki (nM) | CHK-1 Ki (nM) | FGF-P Ki (nM) | CDK2 Ki (nM) | CDK4 Ki (nM) | HUVEC IC50 (nM) | Huvec + Albumin IC50 (nM) | MV522 IC50 (μM) | TEK-P (μM) |
|---|---|---|---|---|---|---|---|---|---|---|---|
| F-5 | NT | 0.86 | 84% @ 1 μM | NT | 69% @ 1 μM | NT | NT | 4.1 | 17 | 1.4 | 56% @ 1 μM |
| G-1 | 0.592 | NT | 90 | NT | 81% @ 1 μM | NT | NT | 10 | 435 | >10 | NT |
| G-10 | 2.6 | 3 | 48% @ 1 μM | NT | 33% @ 1 μM | NT | NT | 5.7 | 180 | 5.1 | NT |
| G-11 | 0.17 | 0.11 | 2.5 | 7% @ 1 μM | 19 | NI @ 1 μM | 16% @ 1 μM | 4.4 | 64 | 5.6 | NT |
| G-2 | 1.78 | NT | NT | NT | NT | NT | NT | 120 | NT | >10 | NT |
| G-3 | 0.197 | NT | 11.2 | NT | 91% @ 1 μM | NT | NT | 9.8 | 280 | >10 | NT |
| G-4 | 0.79 | 0.1 | 72 | NT | 77% @ 1 μM | NT | NT | 16 | NT | >10 | NT |
| G-5 | 1.86 | 0.35 | 69 | NT | 68% @ 1 μM | NT | NT | 8.4 | NT | >10 | NT |
| G-6 | 1.98 | NT | 65 | NT | 74% @ 1 μM | NT | NT | 12 | 59 | 10 | NT |
| G-7 | 0.65 | 0.25 | 27 | NT | 23 | NT | NT | 17 | 190 | >10 | 14% @ 1 μM |
| G-8 | 0.73 | 0.035 | 5.8 | NT | 20 | NT | NT | 12 | 114 | 8.7 | 62% @ 1 μM |
| G-9 | NT | 2.5 | NT | NT | NT | NT | NT | NT | NT | NT | NT |
| H-1 | 1.19 | 0.19 | 41% @ 1 μM | NT | 83% @ 1 μM | NT | NT | 27 | NT | >10 | NT |
| I-1 | 8.84 | NT | NT | NT | NT | NT | NT | 220 | NT | >10 | NT |
| I-2 | 16% @ 1 μM | NT | NT | NT | NT | NT | NT |  | NT | NT | NT |
| J-1 | NT | 1.6 | 38% @ 1 μM | NT | 61% @ 1 μM | NT | NT | 37 | NT | NT | NT |
| J-2 | NT | 0.68 | 10.5 | NT | 57 | NT | NT | 26 | 180 | >10 | 17% @ 1 μM |
| J-3 | NT | 0.92 | 44% @ 1 μM | NT | 54% @ 1 μM | NT | NT | 50 | NT | NT | NT |
| K-1 | 1.46 | 1.6 | 59 | NT | 79% @ 1 μM | NT | NT | 40 | >1000 | 10 | NT |
| K-10 | 2.19 | 0.23 | 57.7 | 8% @ 1 μM | 26 | 12% @ 1 μM | 17% @ 1 μM | 12 | NT | 4.6 | NT |
| K-11 | 3.49 | NT | 82% @ 1 μM | NT | 59% @ 1 μM | NT | NT | 37 | NT | 8.1 | NT |
| K-12 | 2.96 | NT | 48% @ 1 μM | NT | 70% @ 1 μM | NT | NT | 27 | NT | 4.7 | NT |
| K-2 | 138 | NT | NT | NT | NT | NT | NT | NT | NT | NT | NT |
| K-3 | 1.66 | 3.4 | NT | 26,000 | NI @ 150 μM | NT | NT | 430 | NT | >10 | NT |
| K-4 | 64 | NT | NT | NT | NT | NT | NT | 380 | NT | >10 | NT |
| K-5 | 1270 | NT | NT | NT | NT | NT | NT | NT | NT | NT | NT |
| K-6 | 200 | NT | NT | NT | NI @ 1 mM | NT | NT | NT | NT | NT | NT |
| K-7 | 122 | NT | NT | NT | NT | NT | NT | NT | NT | NT | NT |
| K-8 | 707 | NT | NT | NT | NT | NT | NT | NT | NT | NT | NT |
| K-9 | 109 | 10 | NT | NT | NI @ 600 | NT | NT | NT | NT | NT | NT |
| L-1 | NT | 3% @ 50 nM | NT | NT | NT | NT | NT | NT | NT | NT | NT |
| M-1 | 52 | NT | NT | NT | NT | NT | NT | NT | NT | NT | NT |
| N-1 | 3.74 | 1.3 | 160 | 10% @ 1 μM | 12% @ 1 μM | 18% @ 1 μM | 19% @ 1 μM | 38 | >1000 | >10 | NT |
| N-2 | NT | 8% @ 50 nM | NT | NT | NT | NT | NT | >100 | NT | >10 | NT |
| O-1 | NT | 5.5 | NT | NT | NT | NT | NT | >300 | NT | <3 | NT |
| O-2 | NT | 13% @ 50 nM | NT | NT | NT | NT | NT | NT | NT | NT | NT |
| O-3 | NT | 5.8 | NT | NT | NT | NT | NT | NT | NT | NT | NT |
| P-1 | 4% @ 50 nM | NT | NT | NT | NT | NT | NT | NT | NT | NT | NT |
| Q-1 | 17% @ 50 nM | NT | NT | NT | NT | NT | NT | 100–300 | NT | NT | NT |
| R-1 | 49% @ 50 nM | NT | NT | NT | NT | NT | NT | NT | NT | NT | NT |
| R-10 | 12.1 | 6.9 | 23% @ 1 μM | NT | NT | NT | NT | 28 | NT | >10 | NT |
| R-11 | NT | slow binding 59% @ 50 nM | 59% @ 1 μM | NT | 30% @ 1 μM | NT | NT | 31 | NT | NT | NT |

-continued

| EX # | FLVK-P Ki (nM) | FLVK Ki (nM) | LCK-P Ki (nM) | CHK-1 Ki (nM) | FGF-P Ki (nM) | CDK2 Ki (nM) | CDK4 Ki (nM) | HUVEC IC50 (nM) | Huvec + Albumin IC50 (nM) | MV522 IC50 ($\mu$M) | TEK-P ($\mu$M) |
|---|---|---|---|---|---|---|---|---|---|---|---|
| R-12 | NT | 4.4 | 45% @ 1 $\mu$M | NT | 62% @ 1 $\mu$M | NT | NT | 15 | NT | 5.9 | NT |
| R-13 | NT | 16.5 | 5% @ 1 $\mu$M | NT | 7% @ 1 $\mu$M | NT | NT | 19 | 120 | 1.8 | NT |
| R-14 | NT | 3.4 | 87% @ 1 $\mu$M | NT | 96% @ 1 $\mu$M | NT | NT | 14 | 345 | 5.7 | NT |
| R-15 | NT | 8.8 | 26% @ 1 $\mu$M | NT | 41% @ 1 $\mu$M | NT | NT | 36 | 130 | 3.1 | NT |
| R-16 | NT | 2.3 | NT | NT | NT | NT | NT | 13 | NT | 5.6 | NT |
| R-17 | NT | 7.4 | NT | NT | NT | NT | NT | 32 | NT | | NT |
| R-18 | NT | 3.1 | NT | NT | NT | NT | NT | 18 | NT | >10 | NT |
| R-19 | NT | 13.9 | NT | NT | NT | NT | NT | 64 | NT | 1.7 | NT |
| R-2 | 2.53 | NT | NT | NT | NT | NT | NT | 110 | NT | 0.43 | NT |
| R-20 | NT | 19% @ 50 nM | NT | NT | NT | NT | NT | 155 | NT | 2.6 | NT |
| R-3 | 67% @ 5 $\mu$M | NT | NT | NT | NT | NT | NT | 50 | NT | 9.7 | NT |
| R-4 | 9.93 | 2.4 | 28% @ 1 $\mu$M | NT | NT | NT | NT | 88 | NT | 9.9 | NT |
| R-5 | 11.2 | 1.7 | | NT | NT | NT | NT | 89 | NT | 10 | NT |
| R-6 | 16% @ 5 $\mu$M | NT | NT | NT | NT | NT | NT | NT | NT | NT | NT |
| R-7 | 325 | NT | NT | NT | NT | NT | NT | NT | NT | NT | NT |
| R-8 | 4% @ 5 $\mu$M | NT | NT | NT | NT | NT | NT | NT | NT | NT | NT |
| R-9 | 9% @ 1 $\mu$M | NT | NT | NT | NT | NT | NT | NT | NT | NT | NT |
| R-21 | NT | 42% @ 50 nM | NT | NT | NT | NT | NT | NT | NT | NT | NT |
| R-22 | NT | 52% @ 50 nM | 13% @ 1 $\mu$M | NT | 21% @ 1 $\mu$M | NT | NT | NT | >100 | NT | NT |
| R-23 | NT | 50% @ 50 nM | NT | NT | NT | NT | NT | NT | NT | NT | NT |
| R-24 | NT | 62% @ 50 nM | NT | NT | NT | NT | NT | NT | NT | NT | NT |
| R-25 | NT | 6.6 | NT | NT | NT | NT | NT | NT | 155 | NT | NT |
| S-1 | 2% @ 1 $\mu$M | NT | NT | NT | NT | NT | NT | NT | NT | NT | NT |
| S-2 | 28% @ 1 $\mu$M | NT | NT | NT | NT | NT | NT | NT | NT | NT | NT |
| S-3 | 8.7 | 0.76 | NT | NT | NT | NT | NT | 180 | NT | NT | NT |
| S-4 | 20% @ 50 nM | NT | NT | NT | NT | NT | NT | >300 | NT | NT | NT |
| S-5 | 4.2 | NT | NT | NT | NT | NT | NT | >300 | NT | NT | NT |
| S-6 | 6% @ 50 nM | NT | NT | NT | NT | NT | NT | NT | NT | NT | NT |
| S-7 | NT | 19% @ 50 nM | NT | NT | NT | NT | NT | >300 | NT | NT | NT |
| S-8 | NT | 1.4 | NT | NT | NT | NT | NT | NT | NT | NT | NT |
| T-1 | 13.6 | NT | NT | NT | NT | NT | NT | NT | NT | NT | NT |
| U-1 | 68 | NT | NT | NT | NT | NT | NT | NT | NT | NT | NT |
| U-2 | 12.4 | NT | NT | NT | NT | NT | NT | 100 | NT | >10 | NT |
| V-1 | NT | 2 | NT | NT | NT | NT | NT | NT | NT | NT | NT |
| V-2 | 13 | NT | NT | NT | NT | NT | NT | 180 | NT | 10 | NT |
| V-3 | 42% @ 1 $\mu$M | NT | NT | NT | NT | NT | NT | NT | NT | NT | NT |
| V-4 | NT | 0.045 | 22% @ 1 $\mu$M | NT | 37% @ 1 $\mu$M | NT | NT | 27 | >1000 | NT | 40% @ 1 $\mu$M |
| V-5 | NT | 1.4 | NT | NT | NT | NT | NT | NT | NT | NT | NT |
| V-6 | NT | 12% @ 50 nM | NT | NT | NT | NT | NT | NT | NT | NT | NT |
| V-7 | NT | 2.6 | NT | NT | NT | NT | NT | NT | NT | NT | NT |
| V-8 | NT | 0% @ 50 nM | NT | NT | NT | NT | NT | NT | NT | NT | NT |
| V-9 | NT | 22 | NT | NT | NT | NT | NT | NT | NT | NT | NT |
| V-10 | NT | 16% @ 50 $\mu$M | NT | NT | NT | NT | NT | NT | NT | NT | NT |
| V-11 | NT | 18% @ 50 nM | NT | NT | NT | NT | NT | NT | NT | NT | NT |
| V-12 | NT | 18% @ 50 nM | NT | NT | NT | NT | NT | NT | NT | NT | NT |
| V-13 | NT | 17% @ 50 nM | NT | NT | NT | NT | NT | NT | NT | NT | NT |

-continued

| EX # | FLVK-P Ki (nM) | FLVK Ki (nM) | LCK-P Ki (nM) | CHK-1 Ki (nM) | FGF-P Ki (nM) | CDK2 Ki (nM) | CDK4 Ki (nM) | HUVEC IC50 (nM) | Huvec + Albumin IC50 (nM) | MV522 IC50 (μM) | TEK-P (μM) |
|---|---|---|---|---|---|---|---|---|---|---|---|
| V-15 | NT | 30% @ 50 nM | NT | NT | NT | NT | NT | NT | NT | NT | NT |
| W-1 | NT | 0.12 | 88% @ 1 μM | NT | 67% @ 1 μM | NT | NT | 23 | NT | NT | NT |
| W-2 | NT | 1.5 | 19% @ 1 μM | NT | 18% @ 1 μM | NT | NT | 120 | NT | NT | NT |
| W-3 | NT | 0.7 | 65% @ 1 μM | NT | 56% @ 1 μM | NT | NT | 220 | NT | NT | NT |
| X-1 | NT | 1.5 | 59% @ 1 μM | NT | 28% @ 1 μM | NT | NT | 27 | 330 | NT | NT |
| X-2 | NT | 9.1 | NT | NT | NT | NT | NT | NT | NT | NT | NT |
| X-3 | NT | 2.2 | NT | NT | NT | NT | NT | 30–100 | NT | 4.6 | NT |
| X-4 | NT | 4.1 | 11% @ 1 μM | NT | 11% @ 1 μM | NT | NT | 71 | >1000 | 6.1 | NT |
| X-5 | NT | 1.3 | NT | NT | NT | NT | NT | 29 | NT | 3.7 | NT |
| Y-1 | NT | 6% @ 50 nM | NT | NT | NT | NT | NT | >700 | NT | NT | NT |
| Y-2 | NT | NI @ 50 nM | NT | NT | NT | NT | NT | NT | NT | NT | NT |
| Z-1 | NI @ 5 μM | NT | NT | NT | NT | NT | NT | NT | NT | NT | NT |
| AA-1 | 59% @ 50 nM | 2.8 | 44% @ 1 μM | NT | 39% @ 1 μM | NT | NT | NT | 25 | NT | NT |
| AA-2 | NT | 25 | NT | NT | NT | NT | NT | NT | 80 | NT | NT |
| BB-1 | NT | 10.8 | NT | NT | NT | NT | NT | NT | 940 | NT | NT |
| CC-1 | NT | 20% @ 50 nM | NT | NT | NT | NT | NT | NT | NT | NT | NT |
| CC-2 | NT | 30% @ 50 nM | NT | NT | NT | NT | NT | NT | NT | NT | NT |
| DD-1 | NT | 5.6 | NT | NT | NT | NT | NT | NT | 700 | NT | NT |
| EE-1 | NT | 3.4 | 53% @ 1 μM | NT | 32% @ 1 μM | NT | NT | NT | 180 | NT | NT |

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

Example 3

Intraocular Composition

To prepare a sustained-release pharmaceutical for intraocular delivery, a compound of Formula I is suspended in a neutral, isotonic solution of hyaluronic acid (1.5% conc.) in phosphate buffer (pH 7.4) to form a 1% suspension.

It is to be understood that the foregoing description is exemplary and explanatory in nature, and is intended to illustrate the invention and its preferred embodiments. Thus, the scope of the invention should be understood to be defined not by the foregoing description, but by the following claims and their equivalents.

What is claimed:

1. A compound represented by the Formula I:

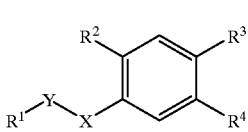

I wherein:

$R^1$ is a substituted or unsubstituted pyrazine;

X is selected from the group consisting of $CH_2$, O, S, and NH;

Y is selected from the group consisting of $CH_2$, O, and S, provided that at least one of X and Y is $CH_2$, or X and Y together with the bond there-between form a cyclopropyl;

$R^2$ and $R^3$ are independently selected from the group consisting of hydrogen, methyl, halogen, trifluoromethyl, and cyano; and

349

R⁴ is selected from the group consisting of

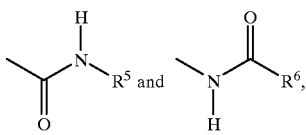

where R⁵ is selected from the group consisting of substituted and unsubstituted aryl, heteroaryl, cycloalkyl, heterocycloalkyl, O—R⁷, NR⁸R⁹, $C_1$–$C_8$ alkyl, and monocyclic heterocycloalkyl, R⁶ is selected from the group consisting of substituted and unsubstituted aryl, heteroaryl, cycloalkyl, heterocycloalkyl, alkenyl, O—R⁷, C(O)R⁷, NR⁸R⁹, $C_2$–$C_8$ alkyl, and monocyclic heterocycloalkyl, where R⁷ is selected from the group consisting of substituted and unsubstituted alkyl, cycloalkyl, heterocycloalkyl, aryl, and heteroaryl, R⁸ is selected from the group consisting of hydrogen, and substituted and unsubstituted alkyl, and R⁹ is selected from the group consisting of substituted and unsubstituted alkyl, aryl, heteroaryl, cycloalkyl, and heterocycloalkyl;
or a pharmaceutically acceptable prodrug, pharmaceutically active metabolite, or pharmaceutically acceptable salt thereof.

2. A compound according to claim 1, wherein R¹ is a substituted or unsubstituted pyrazine selected from the group consisting of:

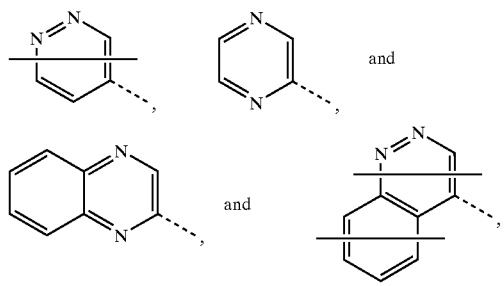

X is selected from the group consisting of $CH_2$, O, and S;
Y is selected from the group consisting of $CH_2$ and S, provided that at least one of X and Y is $CH_2$;
R² and R³ are independently selected from the group consisting of hydrogen, methyl, fluorine, and chlorine, and
R⁴ is selected from the group consisting of

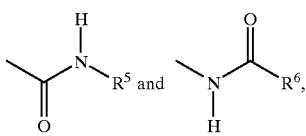

where R⁵ is selected from the group consisting of substituted and unsubstituted aryl, heteroaryl, cycloalkyl, heterocycloalkyl, O—R⁷, NR⁸R⁹, $C_1$–$C_8$ alkyl, and monocyclic heterocycloalkyl, R⁶ is selected from the group consisting of substituted and unsubstituted aryl, heteroaryl, cycloalkyl, heterocycloalkyl, alkenyl, O—R⁷, C(O)R⁷, NR⁸R⁹, $C_2$–$C_8$ alkyl, and monocyclic heterocycloalkyl, where R⁷ is selected from the group consisting of substituted and unsubstituted alkyl, cycloalkyl, heterocycloalkyl, aryl, and heteroaryl, R⁸ is selected from the group consisting of hydrogen and substituted and unsubstituted alkyl, and

350

R⁹ is selected from the group consisting of substituted and unsubstituted alkyl, aryl, heteroaryl, cycloalkyl, and heterocycloalkyl;
or a pharmaceutically acceptable prodrug, pharmaceutically active metabolite, or pharmaceutically acceptable salt thereof.

3. A compound selected from the group consisting of

N-(3,4,5-Trimethoxyphenyl)-3-[(pyrazin-2-yl)sulfanylmethyl]benzamide;
N-(4-Isopropyl-3-methylphenyl)-3-[(pyrazin-2-yl)sulfanylmethyl]benzamide;
N-(2-Methylquinolin-6-yl)-3-[(pyrazin-2-yl)sulfanylmethyl]benzamide;
N-(3-Isopropylphenyl)-3-[(pyrazin-2-yl)sulfanylmethyl]benzamide;
N-(3,5-Dibromo-4-methylphenyl)-3-[(pyrazin-2-yl)sulfanylmethyl]benzamide;
N-(4-Isopropyl-3-methylphenyl)-3-[(pyrazin-2-yl)methylsulfanyl]benzamide;
N-(2-Methylquinolin-6-yl)-3-[(pyrazin-2-yl)methylsulfanyl]benzamide;
3-[{6-Methoxy-7-(2-methoxyethoxy)cinnolin-4-yl}sulfanylmethyl]-N-phenyl-benzamide;

or a pharmaceutically acceptable salt, pharmaceutically acceptable prodrug, or pharmaceutically active metabolite thereof or a pharmaceutically acceptable salt of said metabolite.

4. A compound selected from the group consisting of the following compounds:

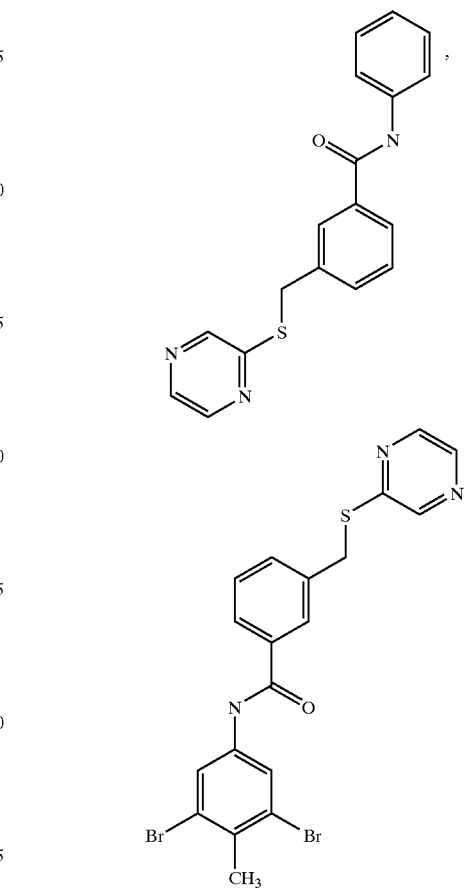

351
-continued
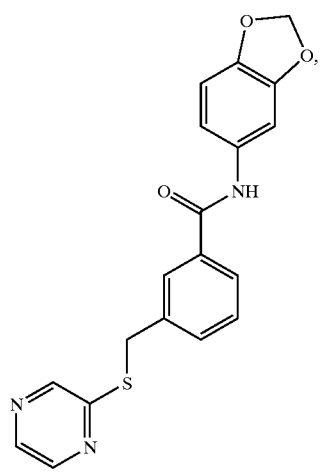
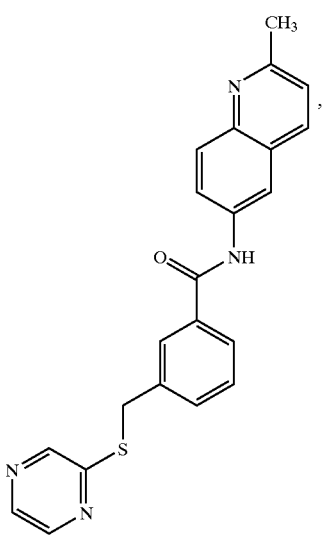
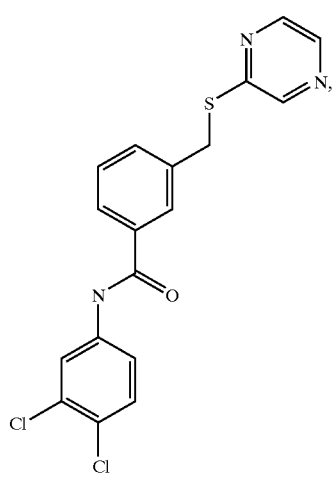
352
-continued
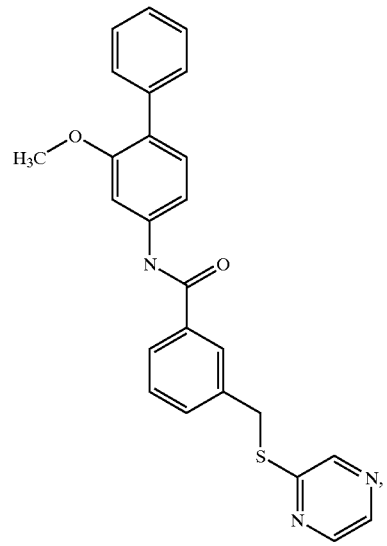
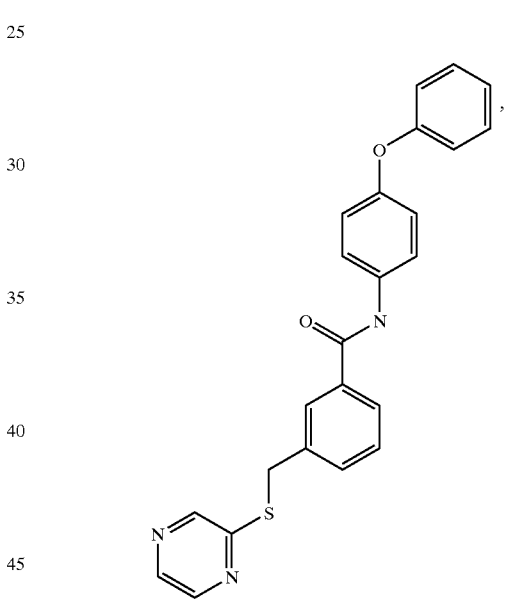
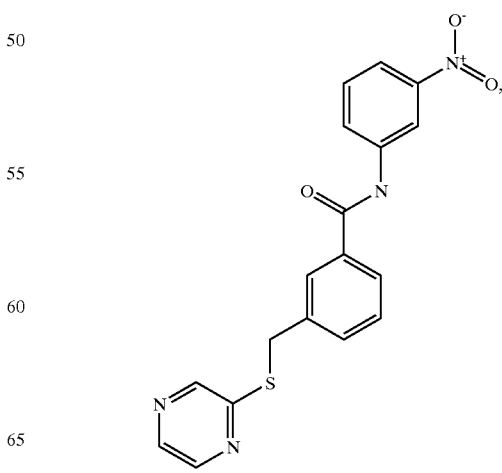

353                                                  354
-continued                                      -continued
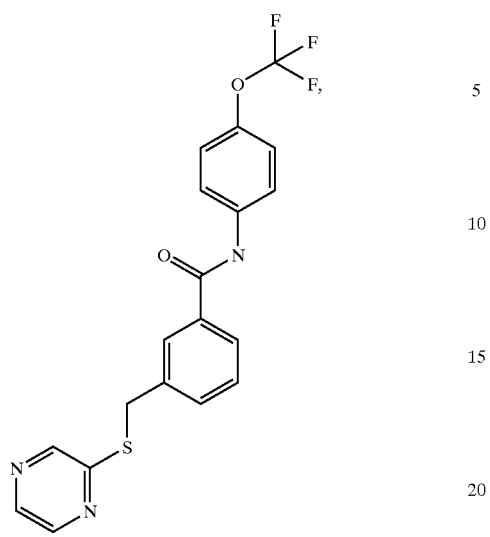
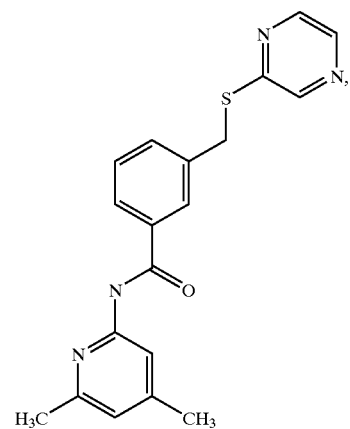
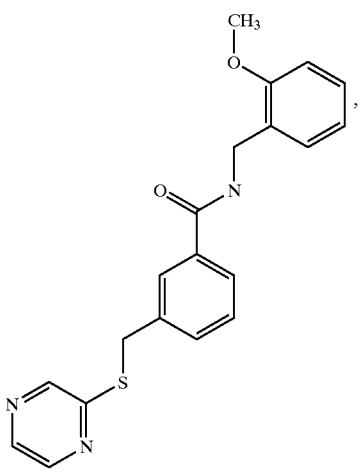
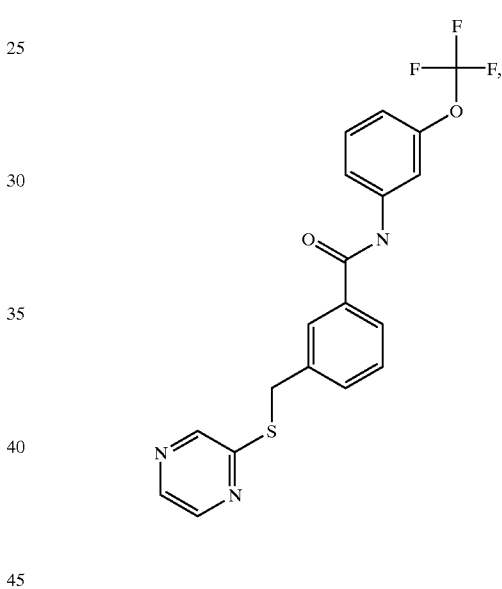
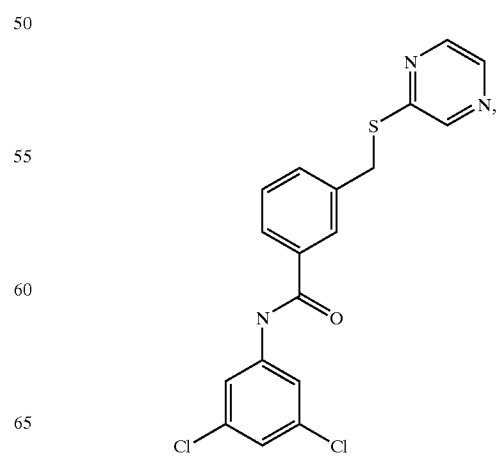

355
-continued
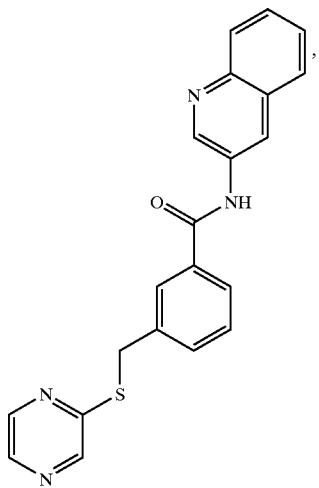
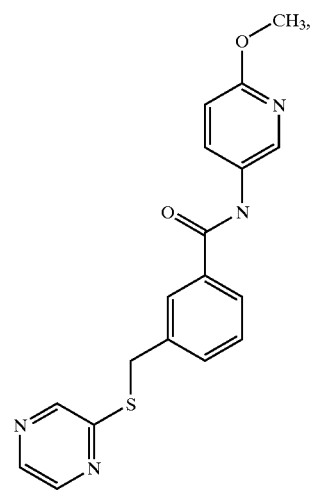
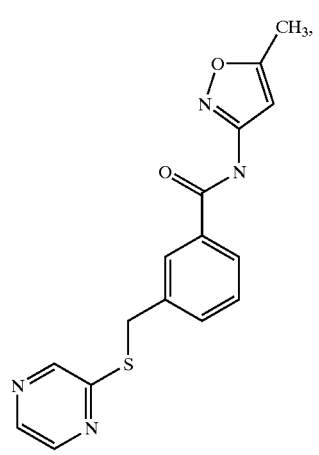
356
-continued
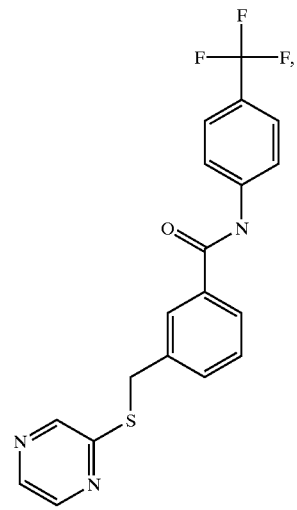
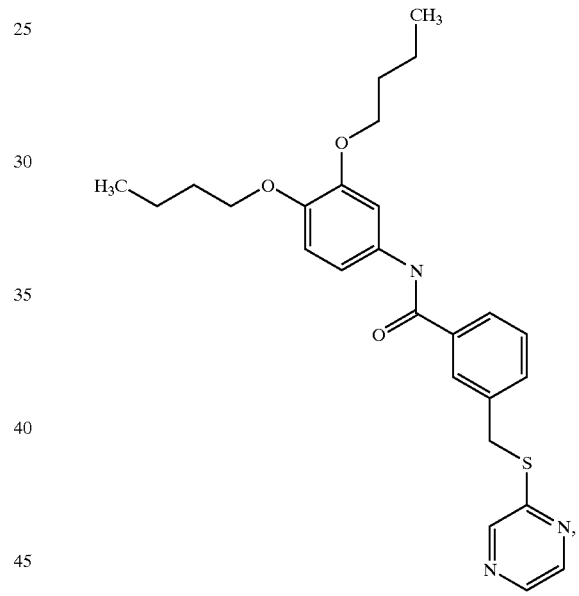
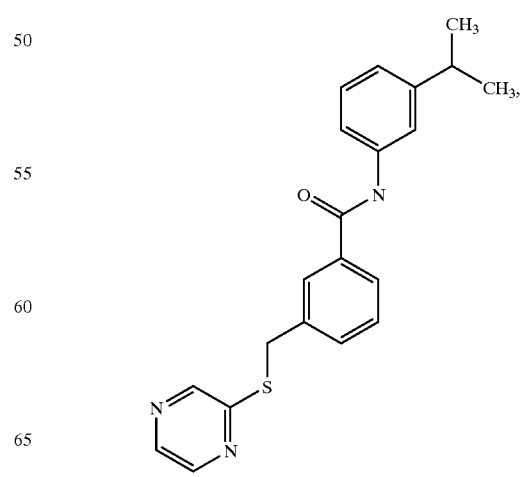

-continued
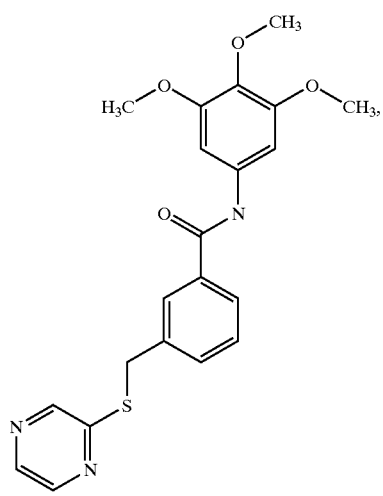
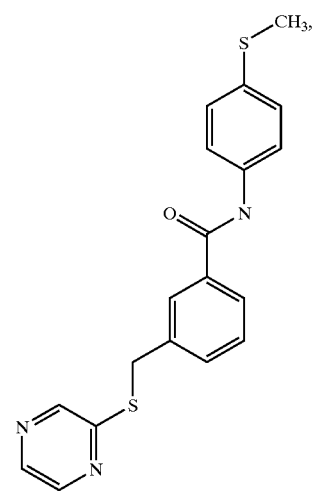
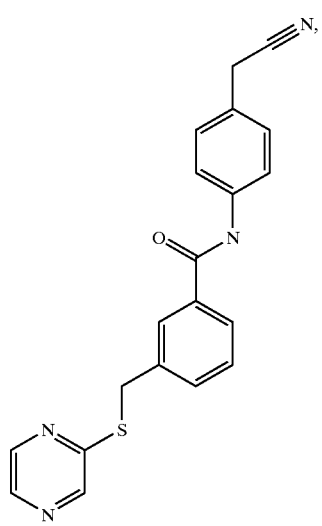
-continued
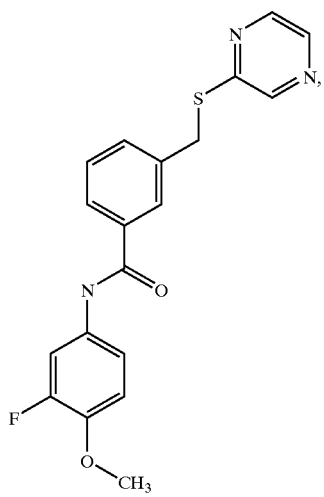
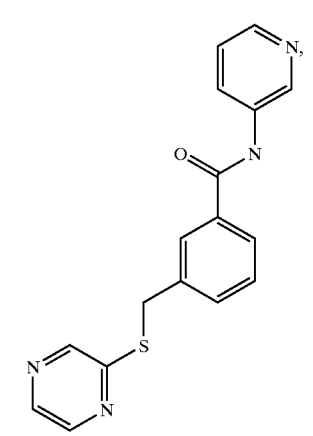

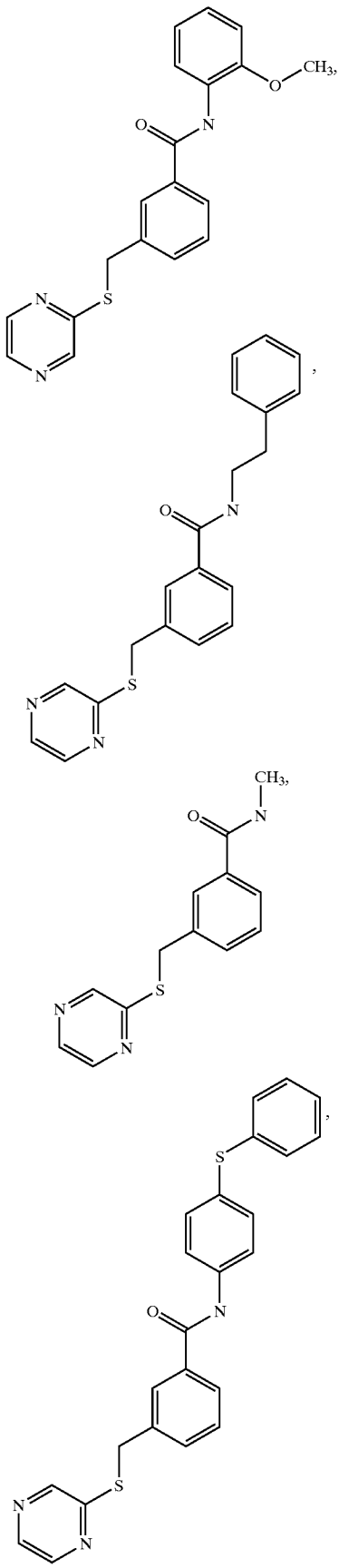
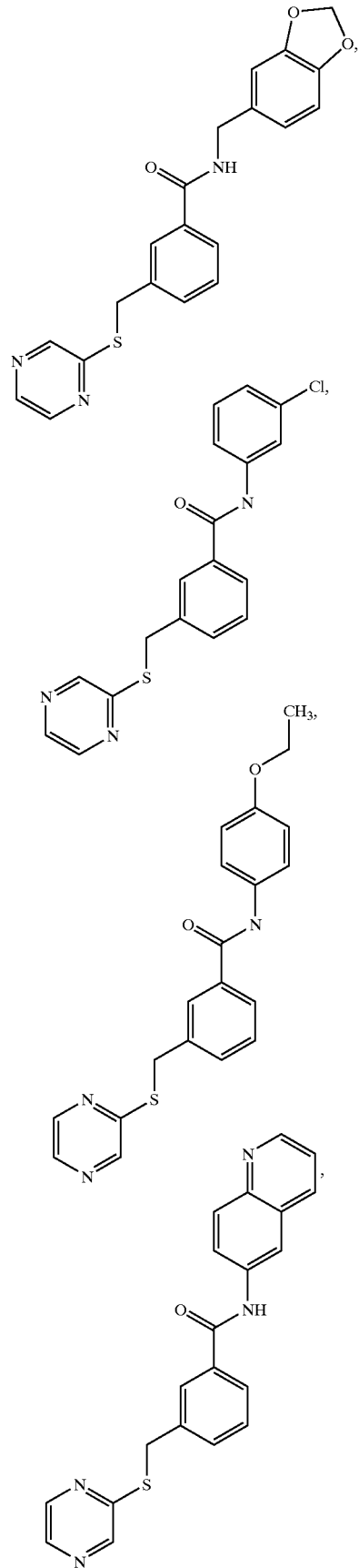

-continued
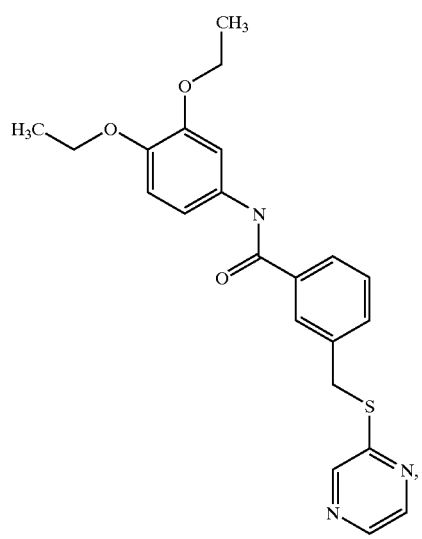
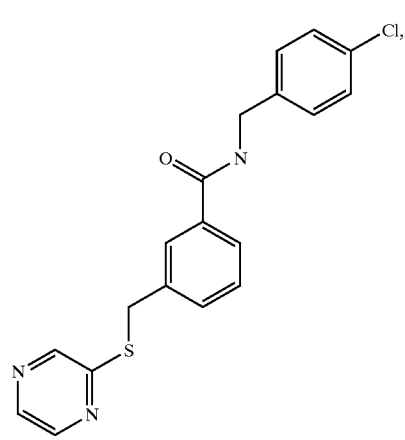
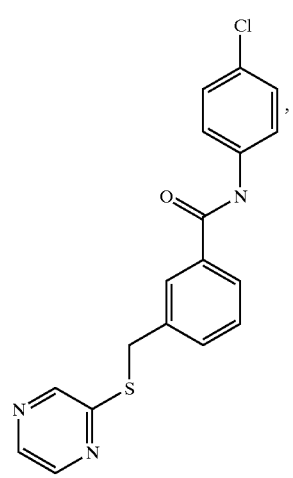
-continued
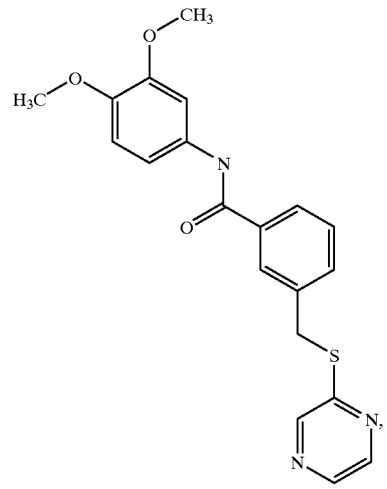
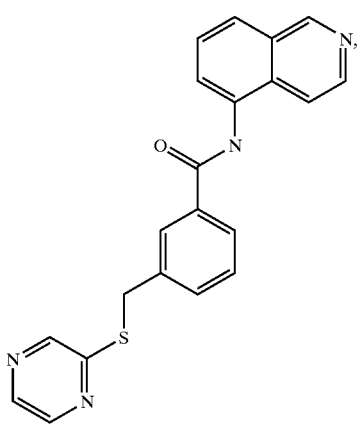
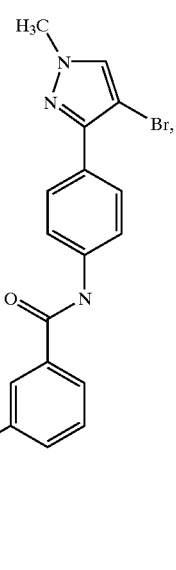

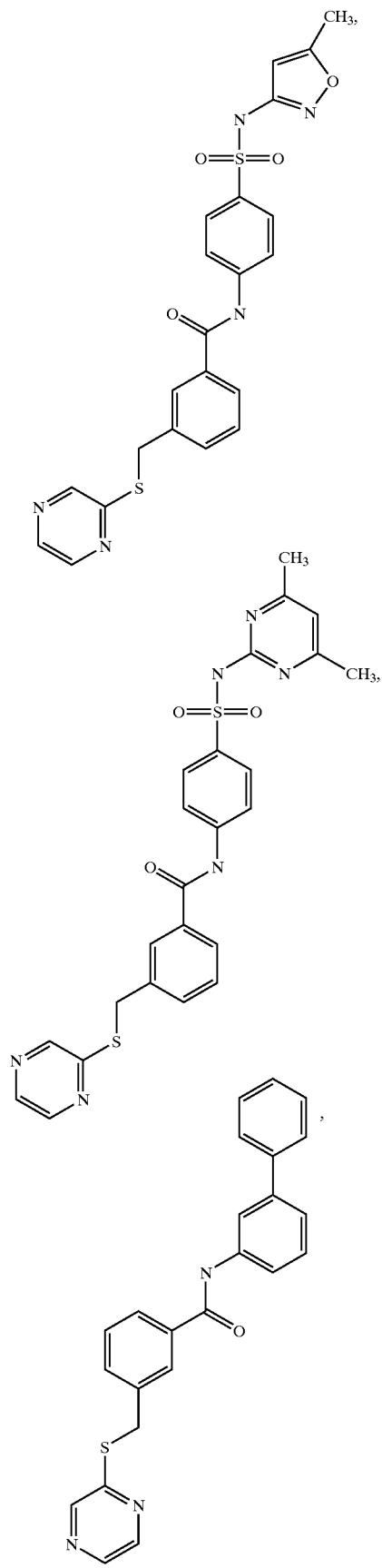
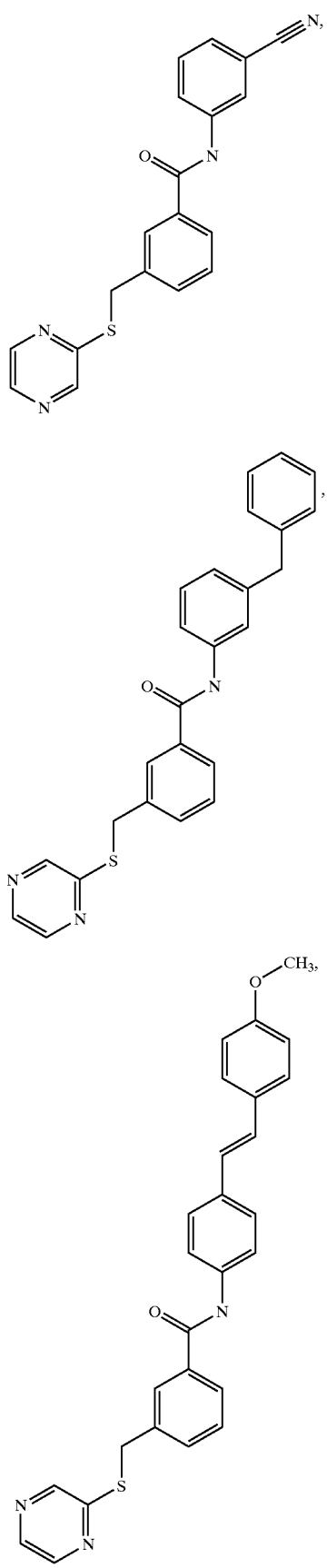

365
-continued
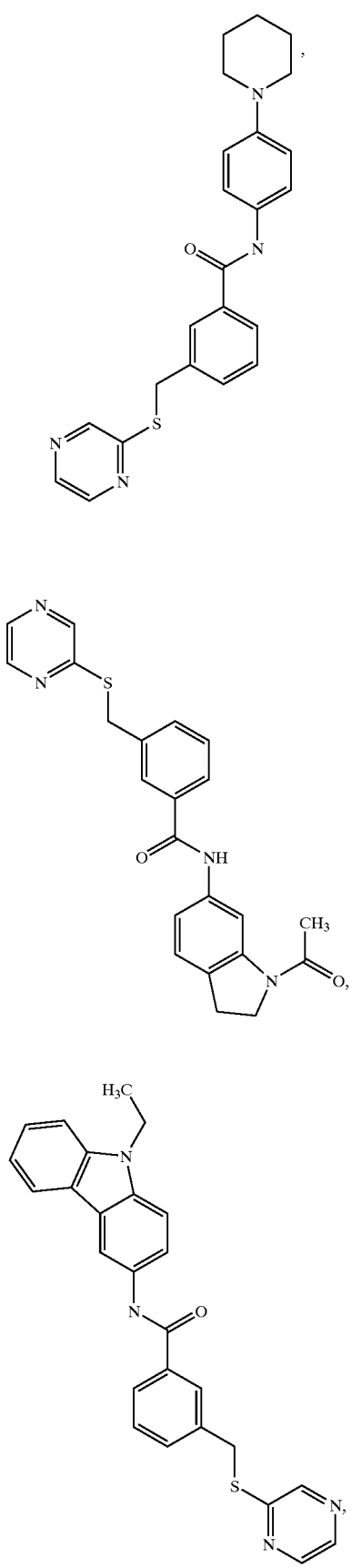
366
-continued
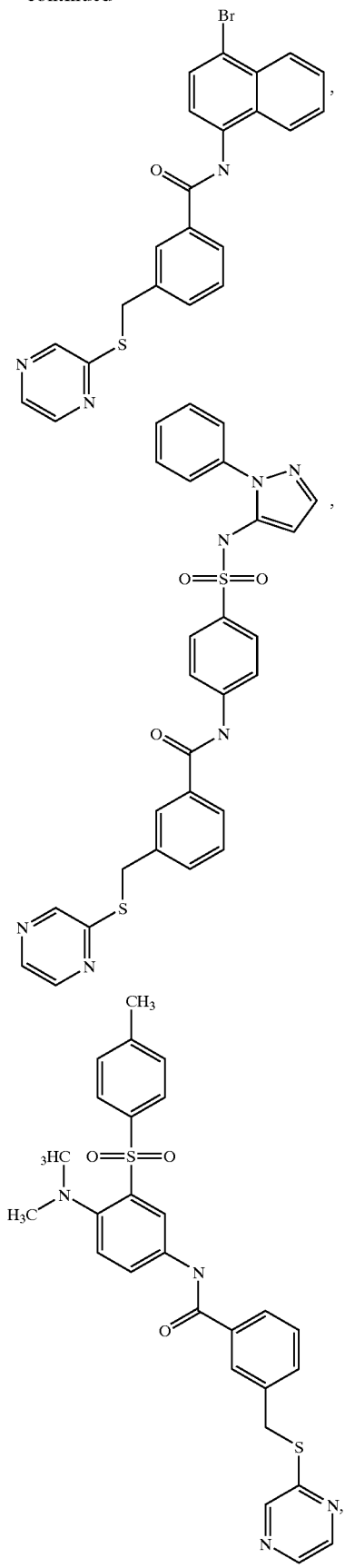

367
-continued
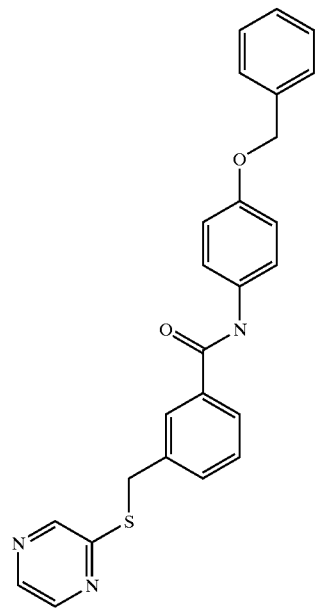
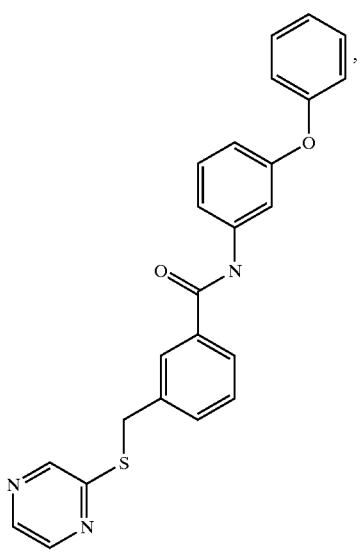
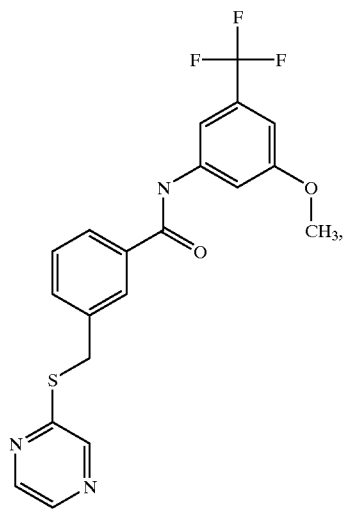
368
-continued
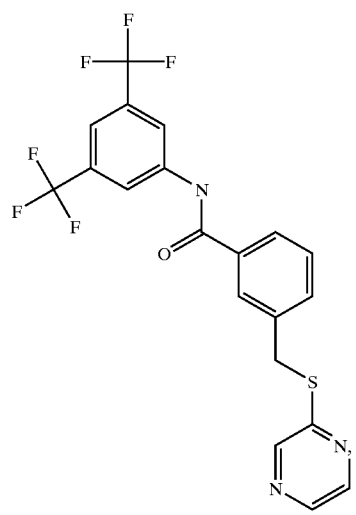
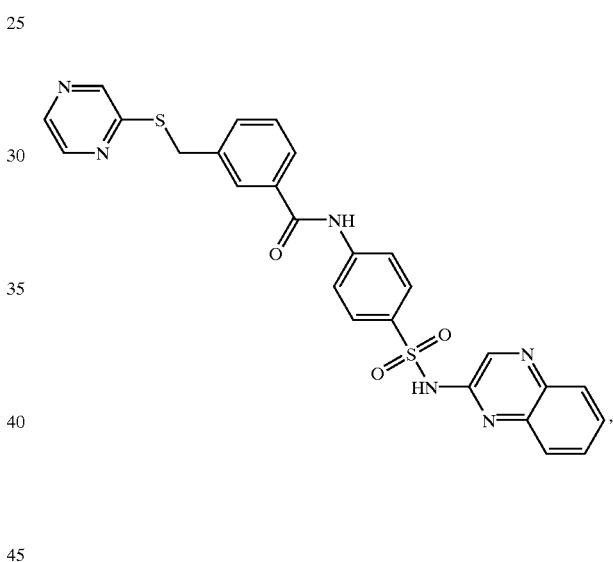
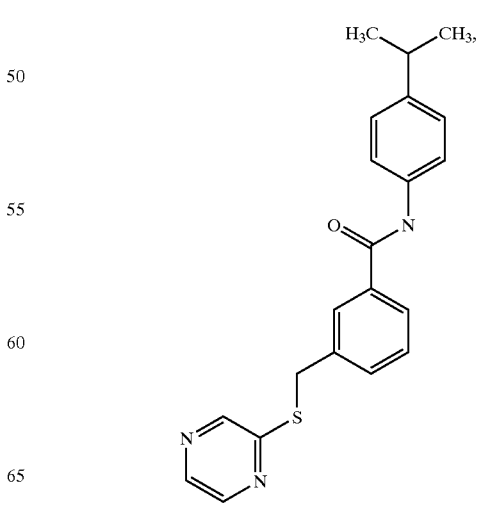

369
-continued
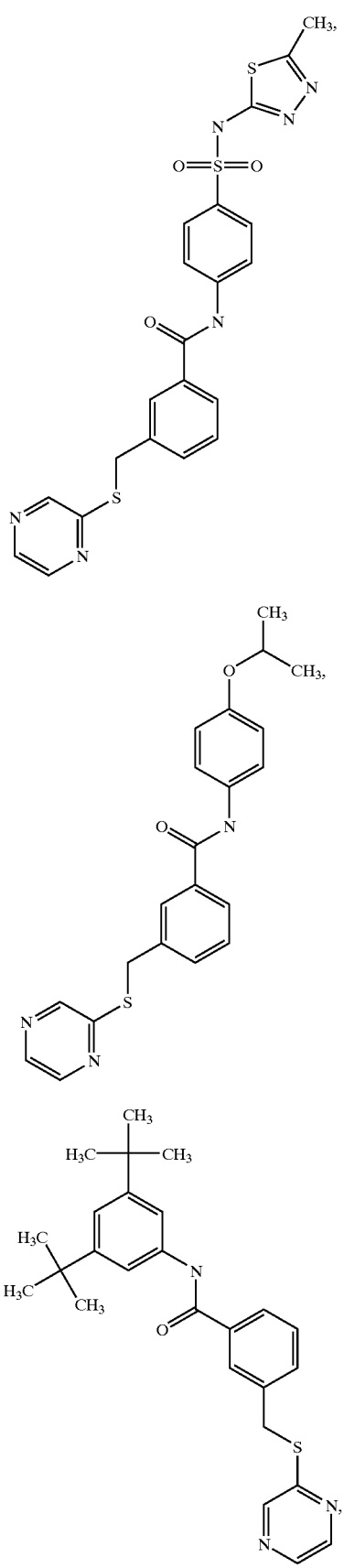
370
-continued
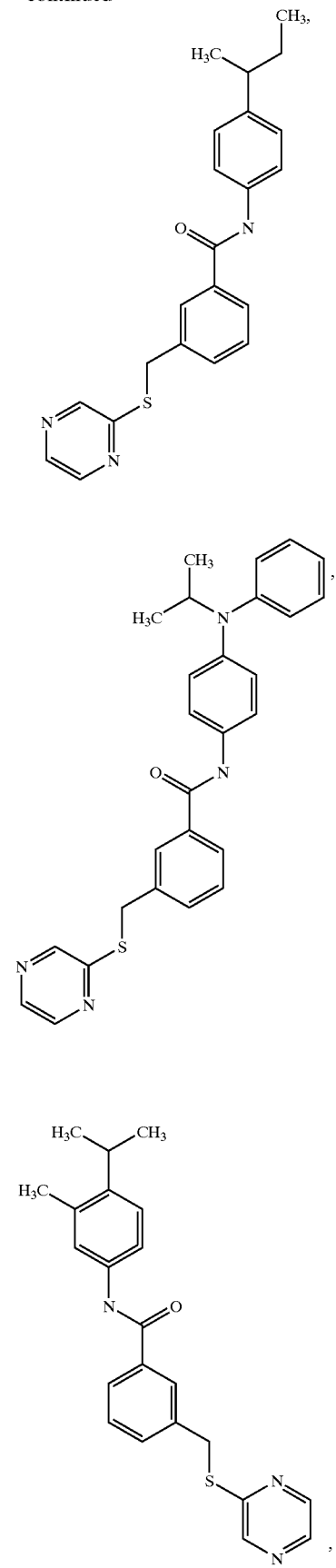

371
-continued
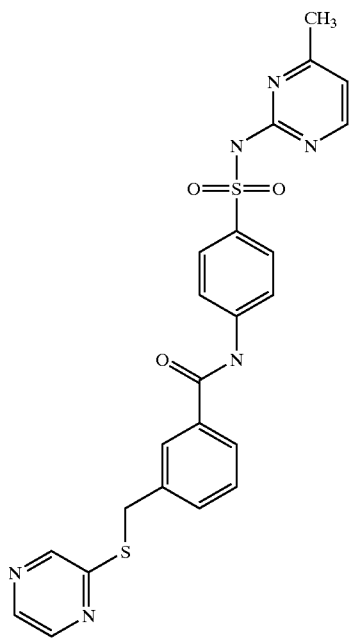
372
-continued
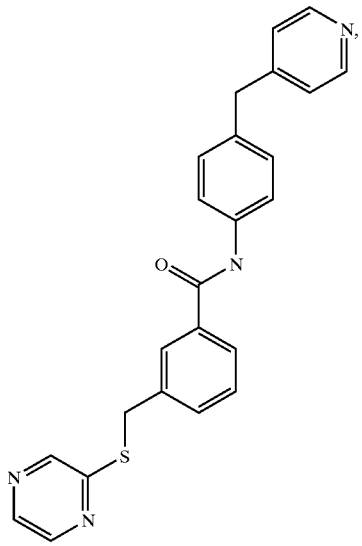
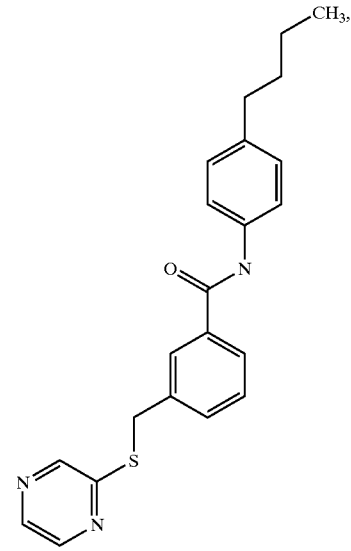
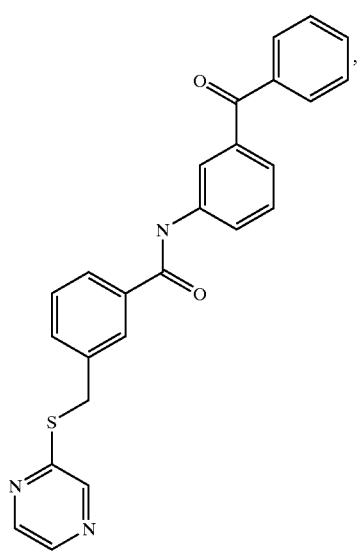

373
-continued
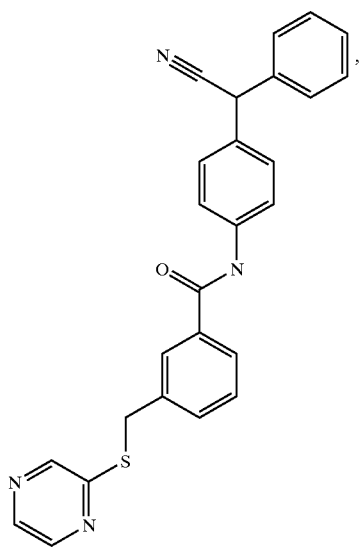
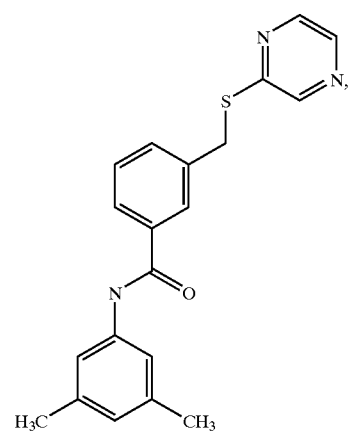
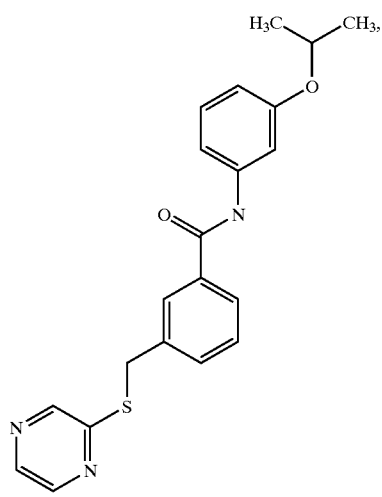
374
-continued
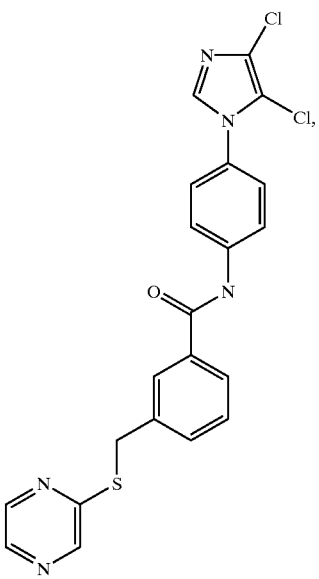
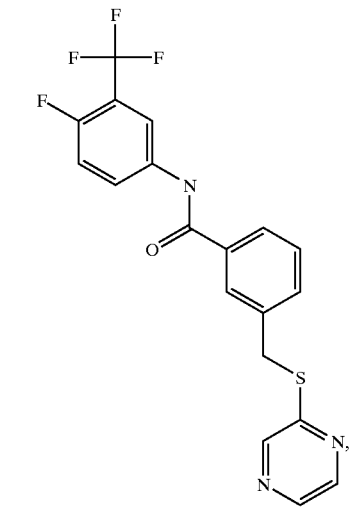
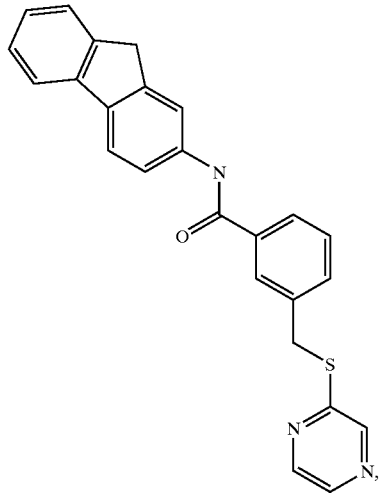

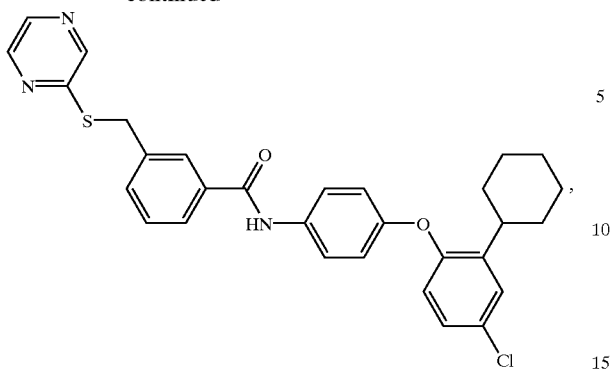
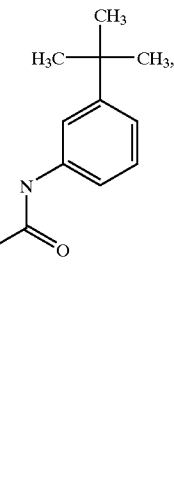
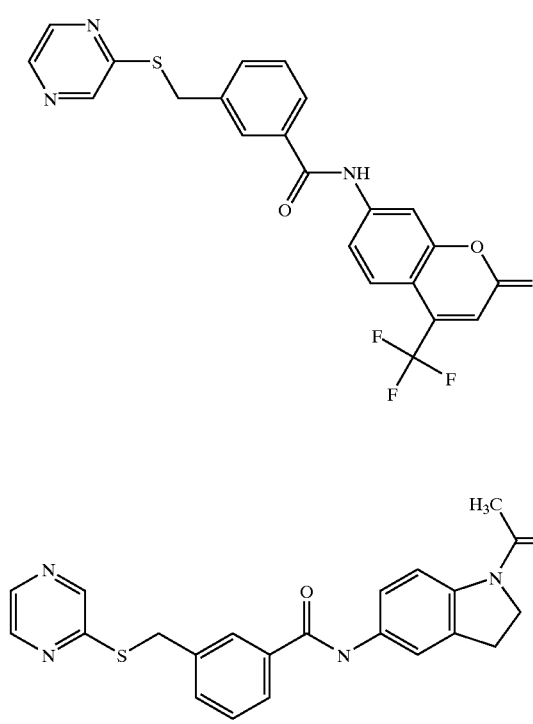
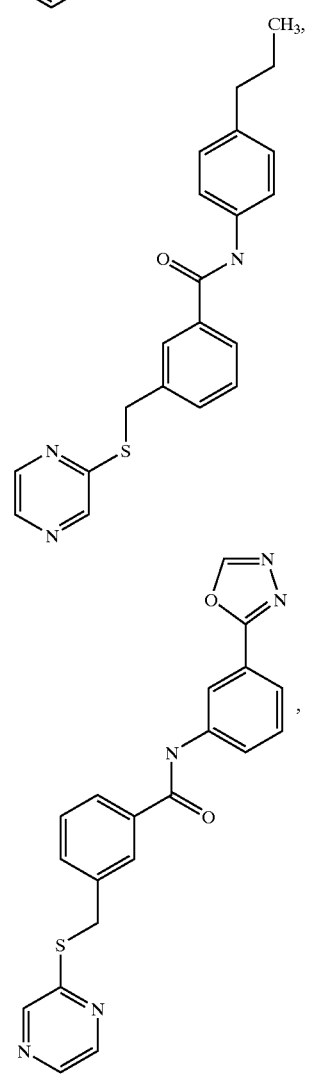
or a pharmaceutically acceptable salt, pharmaceutically acceptable prodrug, or pharmaceutically active metabolite thereof or a pharmaceutically acceptable salt of said metabolite.
5. A pharmaceutically acceptable salt of a pharmaceutically active metabolite of a compound according to claim 1.

6. A pharmaceutical composition for modulating or inhibiting the activity of a protein kinase receptor comprising:
  (a) a therapeutically effective amount of an agent selected from the group consisting of a compound according to claim 1, a pharmaceutically acceptable prodrug thereof, a pharmaceutically active metabolite thereof, and a pharmaceutically acceptable salt thereof; and
  (b) a pharmaceutically acceptable carrier, diluent, or vehicle therefor.

7. A pharmaceutical composition for modulating or inhibiting the activity of a protein kinase receptor comprising:
  (a) a therapeutically effective amount of a pharmaceutically acceptable salt of a pharmaceutically active metabolite of a compound according to claim 1;
  (b) a pharmaceutically acceptable carrier, diluent, or vehicle therefor.

8. A method of treating a mammalian disease condition mediated by protein kinase activity, comprising administering to a mammal in need thereof a therapeutically effective amount of an agent selected from the group consisting of a compound according to claim 1, a pharmaceutically acceptable prodrug thereof, a pharmaceutically active metabolite thereof, and a pharmaceutically acceptable salt thereof.

9. A method according to claim 8, wherein the mammalian disease condition is associated with tumor growth, cell proliferation, or angiogenesis.

10. A method of modulating or inhibiting the activity of a protein kinase receptor, comprising contacting the kinase receptor with an effective amount of an agent selected from the group consisting of a compound according to claim 1, a pharmaceutically acceptable prodrug thereof, a pharmaceutically active metabolite thereof, and a pharmaceutically acceptable salt thereof.

11. A method according to claim 10, wherein the protein kinase receptor is a VEGF receptor.

* * * * *